US010556907B2

(12) United States Patent
Lange et al.

(10) Patent No.: US 10,556,907 B2
(45) Date of Patent: Feb. 11, 2020

(54) FUSED HETEROCYCLIC COMPOUNDS AS S1P MODULATORS

(71) Applicants: AbbVie Inc., North Chicago, IL (US); AbbVie Deutschland GmbH & Co. KG, Wiesbaden (DE)

(72) Inventors: Udo Lange, Ludwigshafen (DE); Michael Ochse, Ludwigshafen (DE); Elizabeth van der Kam, Ludwigshafen (DE); Jeroen van Bergeijk, Ludwigshafen (DE); Sean Turner, Ludwigshafen (DE); Frank Oellien, Ludwigshafen (DE); Patrick Walleser, Ludwigshafen (DE); Wilhelm Amberg, Ludwigshafen (DE); Wilfried Hornberger, Ludwigshafen (DE); Herve Geneste, Ludwigshafen (DE); Mario Mezler, Ludwigshafen (DE); Charles Hutchins, North Chicago, IL (US)

(73) Assignees: ABBVIE DEUTSCHLAND GMBH & CO. KG, Wiesbaden (DE); ABBVIE INC., North Chicago, IL (US)

( * ) Notice: Subject to any disclaimer, the term of this patent is extended or adjusted under 35 U.S.C. 154(b) by 0 days.

(21) Appl. No.: 15/248,994

(22) Filed: Aug. 26, 2016

(65) Prior Publication Data
US 2017/0057966 A1    Mar. 2, 2017

Related U.S. Application Data

(63) Continuation of application No. PCT/CN2015/088447, filed on Aug. 28, 2015.

(60) Provisional application No. 62/242,558, filed on Oct. 16, 2015.

(51) Int. Cl.
C07D 487/04    (2006.01)
C07D 471/04    (2006.01)

(52) U.S. Cl.
CPC ......... *C07D 487/04* (2013.01); *C07D 471/04* (2013.01)

(58) Field of Classification Search
None
See application file for complete search history.

(56) References Cited

U.S. PATENT DOCUMENTS

| 7,662,828 B2 | 2/2010 | Oberboersch et al. | |
| 2009/0176811 A1* | 7/2009 | Oberborsch | C07D 239/84 514/264.11 |
| 2011/0082130 A1* | 4/2011 | Gao | C07D 217/04 514/215 |

FOREIGN PATENT DOCUMENTS

| EP | 2650284 A1 | | 10/2013 |
| WO | 200059510 A1 | | 10/2000 |
| WO | 2005105759 A1 | | 11/2005 |
| WO | 2012004373 | | 1/2012 |
| WO | WO2012/085167 | * | 6/2012 |
| WO | 2015095097 A2 | | 6/2015 |

OTHER PUBLICATIONS

Huwiler et al., New Players on the Center Stage: Sphingosine 1-Phosphate and Its Receptors as Drug Targets, 75(10) Biochemical Pharmacology 1893-1900 (2008).*

Written Opinion of the International Searching Authority issued in connection with International Patent Application No. PCT/CN2015/088447 dated Jun. 3, 2016. (14 pages).

* cited by examiner

*Primary Examiner* — Bong-Sook Baek
(74) *Attorney, Agent, or Firm* — Neal, Gerber & Eisenberg LLP

(57) ABSTRACT

The invention relates to heterocyclic compounds as S1P modulators, pharmaceutical compositions comprising such compounds, and uses thereof in the treatment, alleviation or prevention of diseases or disorders mediated by an S1P receptor.

12 Claims, No Drawings

FUSED HETEROCYCLIC COMPOUNDS AS S1P MODULATORS

CROSS-REFERENCE TO RELATED APPLICATIONS

This is a Continuation that claims priority to International Patent Application No. PCT/CN2015/088447 filed on Aug. 28, 2015, and U.S. Provisional Patent Application No. 62/242,558, filed on Oct. 16, 2015, the entire contents of all of which are fully incorporated herein by reference.

The invention relates to fused heterocyclic compounds with affinity to S1P receptors, pharmaceutical compositions comprising such compounds, the use of such compounds in the treatment, alleviation or prevention of diseases and conditions in which an S1P receptor is involved or in which modulation of the endogenous S1P signaling system via an S1P receptor is involved and the preparation of a medicament for treating, alleviating or preventing such diseases and conditions.

BACKGROUND OF THE INVENTION

Sphingosine-1-phosphate (S1P) is part of the sphingolipid class of molecules. S1P is a bioactive sphingolipid that mediates a wide variety of cellular responses, such as proliferation, autophagy, blockade of apoptosis, cell differentiation, blockade of cell senescence, cytoskeletal organization and migration, adherence- and tight junction assembly, and morphogenesis. Moreover, S1P is a modulator of APP processing via BACE1 regulation as well as lipid raft formation and can interact with ABC transporters thereby modulating cellular in-and efflux. S1P can bind with members of the endothelial cell differentiation gene family (EDG receptors) of plasma membrane-localized G protein-coupled receptors. To date, five members of this family have been identified as S1P receptors in different cell types, S1P1 (EDG-1), S1P2 (EDG-5), S1P3 (EDG-3), S1P4 (EDG-6) and S1P5 (EDG-8). S1P can produce cytoskeletal re-arrangements in many cell types to regulate immune cell trafficking, vascular homeostasis and cell communication in the central nervous system (CNS) and in peripheral organ systems. The above mentioned actions of S1P are mediated by interaction with its receptors. Therefore, S1P receptors are therapeutic targets for the treatment of, for example, neoplastic diseases, diseases of the central and peripheral nervous system, autoimmune disorders and tissue rejection in transplantation.

It is known that S1P is secreted by vascular endothelium and is present in blood at concentrations of 200-900 nanomolar and is bound by albumin and other plasma proteins. This provides both a stable reservoir in extracellular fluids and efficient delivery to high-affinity cell-surface receptors. S1P binds with low nanomolar affinity to the five receptors S1P1-5. In addition, platelets also contain S1P and may be locally released to cause e.g. vasoconstriction. The receptor subtypes S1P1, S1P2 and S1P3 are widely expressed and represent dominant receptors in the cardiovascular system. Further, S1P1 is also a receptor on lymphocytes. S1P4 receptors are almost exclusively in the haematopoietic and lymphoid system. S1P5 is primarily (though not exclusively) expressed in central nervous system (CNS; brain and spinal cord). Other tissues with S1P5 expression are skin and spleen. Moreover, S1P5 is expressed on NK cells. Early study showed that the CNS expression in mice appeared restricted to oligodendrocytes, while in men and rats expression was more diverse. Recent evidence has shown a broader distribution in all species: S1P5 expression is shown at the level of astrocytes, endothelial cells, glial cells, oligodendrocytes and to a lesser extent neurons.

The present invention relates to modulators of the S1P5 receptor, in particular agonists, and preferably to agonists with selectivity over S1P1, S1P3 and/or S1P4 receptors, in view of unwanted cardiovascular and/or peripheral immune-modulatory effects. It has now been found that S1P5 agonists can be used in the treatment of cognitive disorders, in particular age-related cognitive decline. Moreover, evidence has shown an impact on amyloid β (protein) processing, ABC transporter expression, blood-brain-barrier integrity, neuro-inflammatory processes, and (sphingo)lipid content in the CNS.

The latter is of high relevance as an altered sphingolipid metabolism is strongly implicated in several neurodegenerative and cognitive diseases. A comparison of CNS gene expression profiles of normal and Alzheimer's Disease (AD) patients indicated that genes responsible for S1P degradation were strongly upregulated, including the phosphatidic acid phosphatase PPAP2A and S1P lyase genes, while genes for ceramide production (apoptotic sphingolipid) were upregulated (Katsel et al, 2007, Neurochem Res, 32, 845-856). These gene expression data are predictive of actual changes in enzyme and lipid levels in the brain and cerebrospinal fluid (CSF): compared to normal subjects, AD brain are characterized by higher levels of ceramide and cholesterol as well as decreased levels of S1P. These changes also correlate with disease severity of the patients and are related to levels of Amyloid β and Tau, two hallmarks of Alzheimer's Disease (Cutler et al, 2004, PNAS, 101, 2070-2075; He et al, 2010, Neurobiol. Aging, 31, 398-408; Koal et al, 2015, J. Alz Disease, 44, 1193-1201). The same changes have been reported in brain tissues (and CSF) from patients suffering HIV dementia, Amyotrophic Lateral Sclerosis (ALS), Parkinson's Disease, Parkison's Disease with Lewy Bodies, Multiple Sclerosis, Huntington's Disease, and several sphingolipdidosis disorders (Lysosomal Storage Disorders) such as Niemann Pick Disease and Gauchers (Cutler et al, 2002, Ann Neurol, 52, 448-457; Haughey et al, 2004, Ann Neurol, 55, 257-267; Cutler et al, 2010, Neurol, 63, 636-630; Mielke et al, 2013, PLOS ONE, 8; Bras et al, 2008, FEBS Journal, 275, 5767-5773; Vidaurre et al, 2014, Brain, 137, 2271-2286; Fan et al, 2013, J Lipid Research, 54, 2800-2814). Modulating the activity of the S1P5 receptor in the central nervous system may be a therapeutic method for such neurodegenerative or cognitive disorders by shifting the ceramide/S1P balance towards S1P effects and away from ceramide-mediated cell death.

Soluble β-amyloid (Aβ) oligomers are considered the proximate effectors of synaptic injury and neuronal death occurring in AD. Aβ induces increased ceramide levels and oxidative stress in neuronal cultures, leading to apoptosis and cell death. S1P is a potent neuroprotective factor against this Aβ-induced damage, consistent with its role as ceramide's counterpart (Cutler et al, 2004, PNAS, 101, 2070-2075, Malaplate-Armand, 2006, Neurobiol. Dis, 23, 178-189). Aβ is also pro-inflammatory, inducing the migration of monocytes to sites of injury, and the S1P1, S1P3, S1P4, S1P5 agonist FTY720/FIngolimod inhibits such migration. Aβ is known to induce expression of S1P2 and S1P5, but not of S1P1, S1P3 and S1P4 (Kaneider et al, 2004, FASEB). The actions of FTY720/FIngolimod and those expressed by monocytes suggests these effects are mediated by the S1P5 receptor. The same applies to more recent findings that FTY720/FIngolimod is able to modulate Aβ-induced memory deficits (Fukumoto et al, 2014, Beh Brain Res, 268, 88-93).

Additional studies suggest a role for S1P in modulating pain signals. In example, S1P modulates action potentials in capsaicin-sensitive sensory neurons (Zhang et al, 2006, J Physiol, 575, 101-113) and S1P levels are known to be decreased in CSF in acute and inflammatory pain models (Coste et al, 2008, J Biol Chem, 283, 32442-32451). The S1P1, S1P3, S1P4, S1P5 receptor agonist FTY720/FIngolimod is indeed able to reduce nociceptive behavior in neuropathic pain models (Coste et al, 2008, 12, 995-1004), while the selective S1P1 agonist SEW2817 fails to have an effect. Given the high CNS expression of S1P5 and lack of effects of S1P1 agonism, the effects can be contributed to effects on the S1P5 receptor.

In summary, potent and selective agents that are agonists of the S1P5 receptor will be beneficial for the treatment of cognitive disorders, neurodegenerative disorders and pain. In particular, S1P5-selective ligands would be beneficial for these diseases by not engaging the S1P1, S1P3 and/or S1P4 receptor ensuring a lack of peripheral immune suppression and cardiovascular side-effects.

WO 2011/017561 describes S1P agonists containing a fused cyclic core wherein optionally one the rings is a heterocycle. The compounds therefore structurally differ from the compounds of the present invention.

WO 2012/004373 describes S1P receptor modulators containing a fused heterocyclic core. These fused heterocyclic core structurally differs from the compounds of the present invention in the size of the rings constituting the core and the type and number of heteroatoms present in the rings.

Currently, there is still a need for new, potent S1P receptor modulators, in particular selective S1P5 receptor modulators.

SUMMARY OF THE INVENTION

It is an object of the present invention to provide S1P5 receptor modulators, in particular agonists, preferably to agonists with selectivity over S1P1, S1P3 and/or S1P4 receptors to avoid unwanted cardiovascular and/or immunomodulatory effects. It is a further objection of the invention to provide a method for treatment or alleviation of a variety of CNS disorders, such as cognitive disorders, in particular age-related cognitive decline. The invention therefor provides a compound of formula (I):

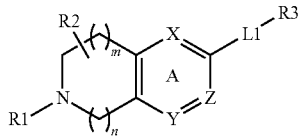

formula (I)

or a pharmaceutically acceptable salt, solvate, tautomer, stereoisomer or N-oxide thereof, wherein X, Y and Z are independently selected from the group consisting of N and CR5, with the proviso that at least one of X, Y and Z is N, and wherein each R5 is independently selected from the group consisting of hydrogen, a halogen atom, (C1-4)alkyl and (C1-4)alkyl substituted with one or more fluor atoms;

m is 0, 1 or 2 and n is 1, 2 or 3 with the proviso that m+n is 1, 2 or 3;

R1 is selected from the group consisting of
—(C1-6)alkylene-R6 wherein one or more carbon atoms in the alkylene group, each independently, are optionally substituted with one or more halogen atoms or with (CH$_2$)$_2$ to form a cyclopropyl moiety or with (CH$_2$)$_3$ to form a cyclobutyl moiety,
—(C3-6)cycloalkylene-R6 in which one carbon atom in the (C3-6)cycloalkylene can optionally be replaced by oxygen,
—(C1-3)alkylene-(C3-6)cycloalkylene-R6,
—(C3-6)cycloalkylene-(C1-3)alkylene-R6 and
—C(O)—(C1-4)alkylene-R6,
wherein R6 is selected from the group consisting of
—OH, —OPO$_3$H$_2$, —COOH, —COO(C1-4)alkyl and tetrazol-5-yl;

R2 is absent, one or more substituents independently selected from the group consisting of a halogen atom, oxo, (C1-4)alkyl optionally substituted with one or more halogen atoms and (C1-4)alkoxy optionally substituted with one or more halogen atoms or together with one of the carbon atoms in the N-containing ring forms a (C3-6)cycloalkyl;

L1 is absent or

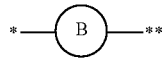

wherein
* indicates the bond to ring A and ** indicates the bond to R3; and
Ring B is selected from the group consisting of (C3-7) cycloalkyl, (C4-7)cycloalkenyl, phenyl, pyridyl, thienyl and thiazolyl, each optionally substituted with one or more substituents independently selected from the group consisting of
hydroxy,
cyano,
a halogen atom,
(C1-4)alkyl optionally substituted with one or more halogen atoms,
(C3-6)cycloalkyl optionally substituted with one or more halogen atoms,
(C1-4)alkoxy optionally substituted with one or more halogen atoms, and
phenyl optionally substituted with one or more substituents independently selected from the group consisting of a halogen atom, (C1-4)alkyl optionally substituted with one or more halogen atoms, and (C1-4)alkoxy optionally substituted with one or more halogen atoms; and R3 is L2-R4, wherein:
L2 is absent or a group —W—(CH$_2$)p-T- wherein:
W is attached to L1 and selected from the group consisting of a bond, —O—, —CO—, —S—, —SO—, —SO$_2$—, —NH—, —CH=CH—, —C(CF$_3$)=CH—, CH=C(CF$_3$)—, —CF$_2$—CH$_2$—, —CH$_2$—CF$_2$—, —CHF—CH$_2$—, —CH$_2$—CHF—, —C≡C—, —CH$_2$—O—, —O—CH$_2$—, —O—CO—, —CO—O—, —CO—NH—, —NH—CO— and cyclopropylene;
p is an integer from 0 to 10;
one or more C atoms of (CH$_2$)p are optionally substituted with one or two fluoro atoms, and
T is absent or attached to R4 and selected from the group consisting of a bond, —O—, —S—, —SO—, —SO$_2$—, —NH—, —CO—, —CH=CH—, —C≡C—, and cyclopropylene, R4 is selected from the group consisting of:
(C3-6)cycloalkyl, (C4-6)cycloalkenyl or an 8-10 membered bicyclic group, each optionally substituted with a substituent selected from the group consisting of a halogen atom, (C1-4)alkyl optionally substituted with one or more fluoro atoms and (C1-4)alkoxy optionally substituted with one or more fluoro atoms,
phenyl, biphenyl or naphthyl, pyridyl, thienyl, thiazolyl optionally substituted with one or more substituents independently selected from the group consisting of:
a halogen atom,
hydroxy,
cyano,
(C1-4)alkyl optionally substituted with one or more fluoro atoms,
(C1-4)alkoxy optionally substituted with one or more fluoro atoms,
—S—(C1-4)-alkyl,
—SF$_5$, and
(C3-6)cycloalkyl optionally substituted with phenyl whereby said phenyl is optionally substituted with a substituent selected from the group consisting of (C1-4)alkyl and a halogen atom, and
phenyl substituted with a substituent selected from the group consisting of phenoxy, benzyl, benzyloxy, phenylethyl and a monocyclic heterocycle, wherein each substituent is optionally substituted with one or more halogen atoms, (C1-4)alkyl, (C1-4)alkyl substituted with one or more fluoro atoms, (C1-4) alkoxy, or (C1-4)alkoxy substituted with one or more fluoro atoms.

Also provided is a compound of formula (I):

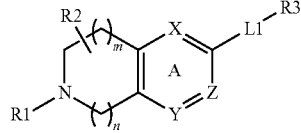

formula (I)

or a pharmaceutically acceptable salt, solvate, tautomer, stereoisomer or N-oxide thereof, wherein
X, Y and Z are independently selected from the group consisting of N and CR5, with the proviso that at least one of X, Y and Z is N, and wherein each R5 is independently selected from the group consisting of hydrogen, a halogen atom, (C1-4)alkyl and (C1-4)alkyl substituted with one or more fluor atoms;
m is 0, 1 or 2 and n is 1, 2 or 3 with the proviso that m+n is 1, 2 or 3;
R1 is selected from the group consisting of
—(C1-6)alkylene-R6 wherein one or more carbon atoms in the alkylene group, each independently, are optionally substituted with one or more halogen atoms or with (CH$_2$)$_2$ to form a cyclopropyl moiety or with (CH$_2$)$_3$ to form a cyclobutyl moiety,
—(C3-6)cycloalkylene-R6 in which one carbon atom in the (C3-6)cycloalkylene can optionally be replaced by oxygen,
—(C1-3)alkylene-(C3-6)cycloalkylene-R6,
—(C3-6)cycloalkylene-(C1-3)alkylene-R6 and
—C(O)—(C1-4)alkylene-R6, wherein R6 is selected from the group consisting of —OH, —OPO$_3$H$_2$, —COOH, —COO(C1-4)alkyl and tetrazol-5-yl;
R2 is absent or one or more substituents independently selected from the group consisting of a halogen atom, (C1-4)alkyl optionally substituted with one or more halogen atoms, and (C1-4)alkoxy optionally substituted with one or more halogen atoms;
L1 is absent or

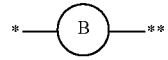

wherein
* indicates the bond to ring A and ** indicates the bond to R3; and
Ring B is selected from the group consisting of (C3-7) cycloalkyl, phenyl, pyridyl, thienyl and thiazolyl, each optionally substituted with one or more substituents independently selected from the group consisting of
hydroxy,
cyano,
a halogen atom,
(C1-4)alkyl optionally substituted with one or more halogen atoms,
(C3-6)cycloalkyl optionally substituted with one or more halogen atoms,
(C1-4)alkoxy optionally substituted with one or more halogen atoms, and
phenyl optionally substituted with one or more substituents independently selected from the group consisting of a halogen atom, (C1-4)alkyl optionally substituted with one or more halogen atoms, and (C1-4)alkoxy optionally substituted with one or more halogen atoms; and
R3 is L2-R4, wherein:
L2 is absent or a group —W—(CH$_2$)p-T- wherein:
W is attached to L1 and selected from the group consisting of a bond, —O—, —CO—, —S—, —SO—, —SO$_2$—, —NH—, —CH=CH—, —C(CF$_3$)=CH—, CH=C(CF$_3$)—, —CF$_2$—CH$_2$—, —CH$_2$—CF$_2$—, —CHF—CH$_2$—, —CH$_2$—CHF—, —C≡C—, —CH$_2$—O—, —O—CH$_2$—, —O—CO—, —CO—O—, —CO—NH—, —NH—CO— and cyclopropylene;
p is an integer from 0 to 10;
one or more C atoms of (CH$_2$)p are optionally substituted with one or two fluoro atoms, and
T is absent or attached to R4 and selected from the group consisting of a bond, —O—, —S—, —SO—, —SO$_2$—, —NH—, —CO—, —C≡C—, —C≡C—, and cyclopropylene,
R4 is selected from the group consisting of:
(C3-6)cycloalkyl, (C4-6)cycloalkenyl or an 8-10 membered bicyclic group, each optionally substituted with a substituent selected from the group consisting of a halogen atom, (C1-4)alkyl optionally substituted with one or more fluoro atoms and (C1-4)alkoxy optionally substituted with one or more fluoro atoms,
phenyl, biphenyl or naphthyl, pyridyl, thienyl, thiazolyl optionally substituted with one or more substituents independently selected from the group consisting of:
a halogen atom, cyano,
(C1-4)alkyl optionally substituted with one or more fluoro atoms,
(C1-4)alkoxy optionally substituted with one or more fluoro atoms,
—S—(C1-4)-alkyl,
—SF$_5$, and
(C3-6)cycloalkyl optionally substituted with phenyl whereby said phenyl is optionally substituted with a substituent selected from the group consisting of (C1-4)alkyl and a halogen atom, and
phenyl substituted with a substituent selected from the group consisting of phenoxy, benzyl, benzyloxy, phenylethyl and a monocyclic heterocycle, wherein each substituent is optionally substituted with one or more halogen atoms, (C1-4)alkyl, (C1-4)alkyl substituted with one or more fluoro atoms, (C1-4)alkoxy, or (C1-4)alkoxy substituted with one or more fluoro atoms.

In a further aspect the invention provides a pharmaceutical composition comprising a compound according to the invention or a pharmaceutically acceptable salt, solvate, tautomer, stereoisomer or N-oxide thereof and at least one pharmaceutically acceptable auxiliary.

In a still further aspect the invention provides a method of treatment, alleviation or prevention of a disease or condition in which an S1P receptor is involved or in which modulation of the endogenous S1P signaling system via an S1P receptor is involved, preferably S1P5, comprising administering to a patient in need thereof a compound according to the invention or a pharmaceutically acceptable salt, solvate, tautomer, stereoisomer or N-oxide thereof.

In a still further aspect the invention provides a use of a compound according to the invention or a pharmaceutically acceptable salt, solvate, tautomer, stereoisomer or N-oxide thereof for the manufacture of a medicament for the treatment, alleviation or prevention of a disease or condition in which an S1P receptor is involved or in which modulation of the endogenous S1P signaling system via an S1P receptor is involved, preferably S1P5 receptor.

In a still further aspect the invention provides a compound according to the invention or a pharmaceutically acceptable salt, solvate, tautomer, stereoisomer or N-oxide thereof for use in therapy.

In a still further aspect the invention provides a compound according to the invention or a pharmaceutically acceptable salt, solvate, tautomer, stereoisomer or N-oxide thereof for use in the treatment, alleviation or prevention of a disease or condition in which an S1P receptor is involved or in which modulation of the endogenous S1P signaling system via an S1P receptor is involved, preferably S1P5.

DETAILED DESCRIPTION OF THE INVENTION

The compounds of the invention are modulators of the S1P receptor, in particular of the S1P5 receptor. More specifically, the compounds of the invention are S1P5 receptor agonists. The compounds of the invention and their pharmaceutically acceptable salts, solvates, tautomers, stereoisomers and N-oxides are in particular suitable for agonizing S1P5 in a subject suffering from a disorder in which modulation of S1P5 activity and the subsequent ceramide/S1P axis is beneficial. Administration of such compound to a subject is preferably such that S1P5 activity in the subject is altered and treatment is achieved. The compounds of the present invention are particularly suitable to treat, alleviate or prevent diseases and conditions in which an S1P receptor is involved or in which modulation of the endogenous S1P signaling system via an S1P receptor is involved. In particular the compounds of the present invention are suitable to treat, alleviate or prevent a disorder or condition selected from the group consisting of Alzheimer's Disease (AD) and associated dementia's, amyloid β-associated disorders, Mild Cognitive Impairment (MCI), Parkinson's Disease (PD), Lewy Body Dementia (LBD), Progressive Supranuclear Palsy (PSP), Cerebral Palsy (CP), Amyotrophic Lateral Sclerosis (ALS), Frontal Temporal Lobe Dementia (FTLD), multiple sclerosis, Huntington's Disease, neurological symptoms of sphingolipidosis disorders, a lysosomal storage disorder including Tay Sachs Disease, Sandhoff Disease, Fabry's Disease, Krabbe Disease, Gaucher's Disease, Niemann Pick A, B or C, and Batten's Disease, stroke, HIV-associated Dementia (HAD), HIV-associate Neurocognitive Disorder (HAND), HIV-associated neuropathy, schizophrenia, cognitive deficits in Schizophrenia, an attention deficit disorder including Anxiety Attention Deficit Disorder and Attention Deficit Hyperactivity Disorder (ADHD), a bipolar disorder, Obsessive-Compulsive Behavior, pain including neuropathic, back pain and pain-associated with multiple sclerosis, spinal cord injury, Parkinson's Disease, epilepsy, diabetes and cancer, cancer-induced peripheral neuropathy (CIPN), depression, treatment-resistant depression, Creutzfeld-Jakob Disease and other Prion-related Disorders, Down's Syndrome, autism, age-related cognitive decline or memory impairment, cognitive deficits associated with diabetes, dementia, dementia associated with Down's Syndrome, cognitive deficits in psychiatric disorders, dementia associated with Lewy Body pathology, diminished CNS function associated with traumatic brain injury, Pick's Disease, spinal cord injury, a demyelinating disorder, a disorder of basal ganglia and AIDS-associated dementia. Given the neuro-inflammatory actions of S1P receptors, and S1P5 in specific, as well as the peripheral localization of S1P5 in skin tissue and a role in endothelial function and NK cells, the compounds of the invention are further suitable to treat, alleviate or prevent a disease with a neuro-inflammatory component, in particular a disease or condition selected from the group consisting of Psoriasis type 1 and type 2, atopic dermatitis, dermatitis scleroderma, insulin-dependent diabetes mellitus, ulcerative colitis, atherosclerosis, sepsis syndrome, septic shock, Dengue hemorrhagic fever, Dengue, atopic allergy, HIV/AIDS, barrier-integrity associated lung diseases, leukemia, contact dermatitis, encephalomyelitis, Epstein Barr virus infection and other virus infections requiring cell-cell fusion.

In formula (I), X, Y and Z are independently selected from the group consisting of N or CR5, with the proviso that at least one of X, Y and Z is N, and wherein each R5 is independently selected from the group consisting of hydrogen, a halogen atom, (C1-4)alkyl and (C1-4)alkyl substituted with one or more fluor atoms. Preferably one or two of X, Y and Z are N and at least one of X, Y and Z is CR5. R5 is preferably independently selected from the group consisting of hydrogen, methyl and a halogen atom. R5 is preferably independently selected from the group consisting of hydrogen, a fluoro atom, methyl optionally substituted with one or more fluoro atoms and ethyl optionally substituted with one or more fluoro atoms, more preferably from the group consisting of hydrogen and a fluoro atom. R5 is preferably fluor if one of X or Y is N and Z and the other of X and Y are C, most preferably if X is N, Z=CH and Y is CF.

In formula (I), m is 0, 1 or 2 and n is 1, 2 or 3 with the proviso that m+n is 1, 2 or 3. Preferably m is 0 or 1 and n is 1 or 2 with the proviso that m+n is 1 or 2.

Formula (I) is preferably selected from the group consisting of

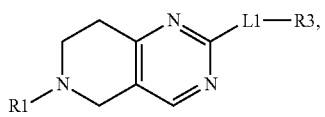

formula (Ia)

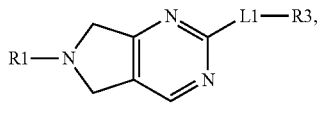

formula (Ib)

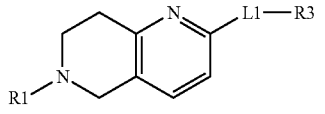

formula (Ic)

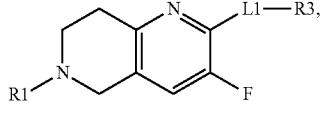

formula (Id)

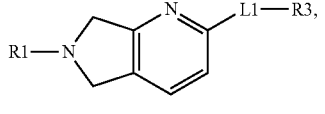

formula (Ie)

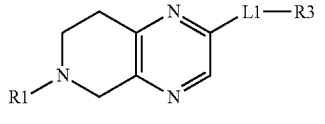

formula (If)

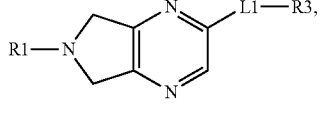

formula (Ig)

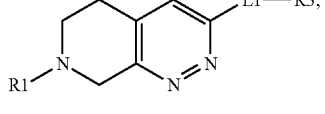

formula (Ih)

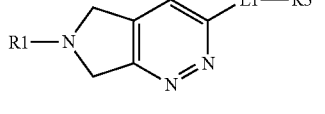

formula (Ii)

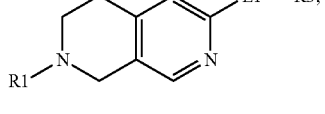

formula (Ij)

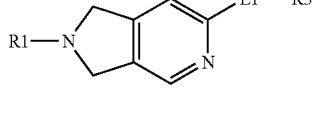

and

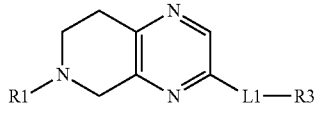

formula (Im)

More preferably, formula (I) is selected from the group consisting of

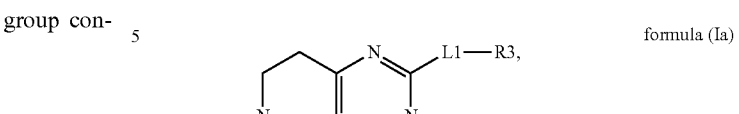

formula (Ia)

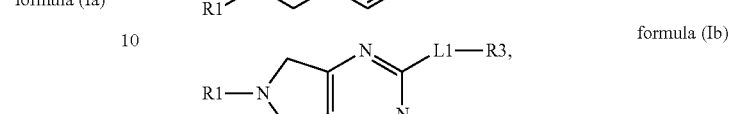

formula (Ib)

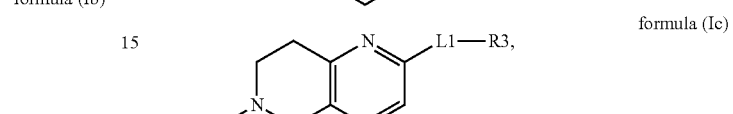

formula (Ic)

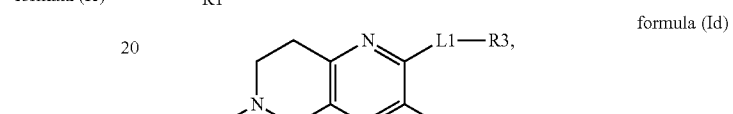

formula (Id)

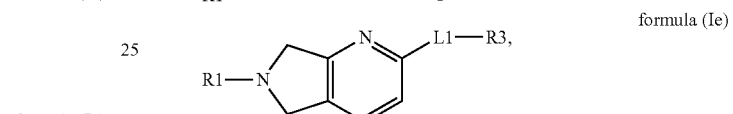

formula (Ie)

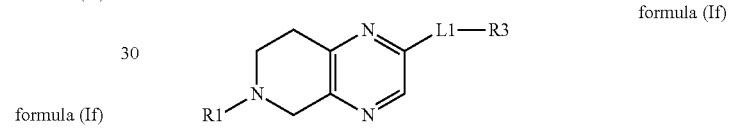

formula (If)

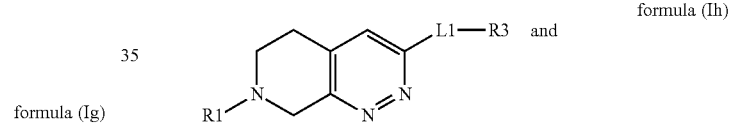

formula (Ih)

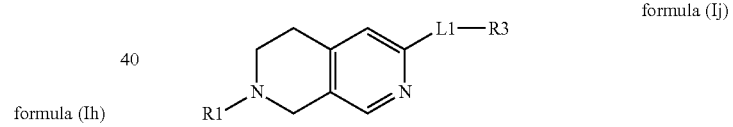

and formula (Ij)

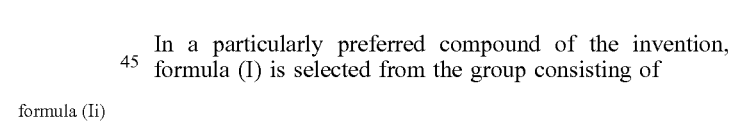

In a particularly preferred compound of the invention, formula (I) is selected from the group consisting of

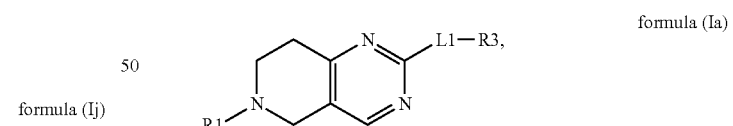

formula (Ia)

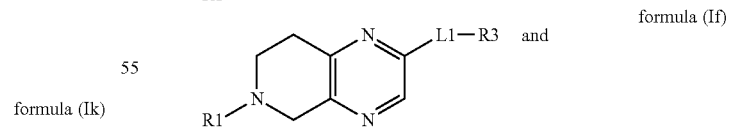

and formula (If)

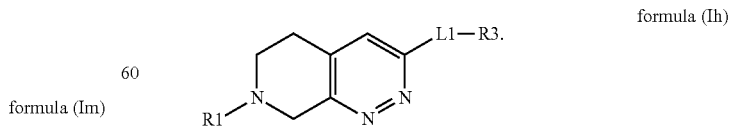

formula (Ih)

R2 is absent or one or more substituents independently selected from the group consisting of a halogen atom, oxo, (C1-4)alkyl optionally substituted with one or more halogen atoms and (C1-4)alkoxy optionally substituted with one or more halogen atoms or together with one of the carbon atoms in the N-containing ring forms a (C3-6)cycloalkyl. Said (C3-6)cycloalkyl is preferably cyclopropyl or cyclobutyl, more preferably cyclobutyl. Said carbon atom in the N-containing ring is preferably a carbon atom attached to the N atom, more preferably atom a in the formula Ii

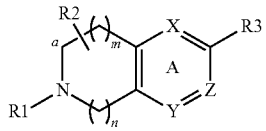

(formula Ii), wherein m is 1 or 2 and n is 1 or 2 with the proviso that m+n is 2 or 3.

R2 is preferably absent or 1, 2 or 3 substituents as defined herein, such as 0, 1, 2 or 3 substituents. Therefore, in one embodiment formula (I) is

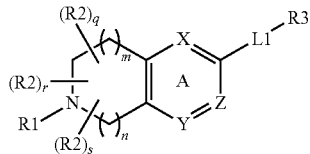

formula (II), wherein q is 0 or 1; r is 0 or 1 and s is 0 or 1 and each R2 is independently selected from the group consisting of a halogen atom, oxo, (C1-4)alkyl optionally substituted with one or more halogen atoms and (C1-4)alkoxy optionally substituted with one or more halogen atoms and (C3-6)cycloalkyl. In one embodiment at least one of q, r and s is 0. In another embodiment at least two of q, r and s are 0.

R2 is preferably absent or 1 or 2 substituents. More preferably R2 is absent, one substituent selected from the group consisting of oxo, methyl, ethyl, methoxy, a chloro atom and a fluoro atom, two methyl substituents or together with one of the carbon atoms in the N-containing ring forms a cyclopropyl, cyclobutyl or. More preferably R2 is absent, a fluoro atom, oxo, one or two methyl substituents or together with one of the carbon atoms in the N-containing ring forms a cyclobutyl. Said carbon atom in the N-containing ring is preferably a carbon atom attached to the N atom, more preferably atom a in the formula Ii

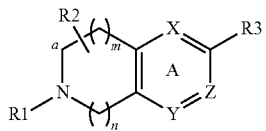

(formula Ii), wherein m is 1 or 2 and n is 1 or 2 with the proviso that m+n is 2 or 3.

In one embodiment, R2 is absent or one substituent independently selected from the group consisting of methyl, ethyl, methoxy, a chloro atom and a fluoro atom. More preferably R2 is absent or a fluoro atom, most preferably R2 is absent.

R1 is preferably selected from the group consisting of —(C1-5)alkylene-R6 wherein one or more carbon atoms in the alkylene group, each independently, are optionally substituted with one or more halogen atoms or with (CH₂)₂ to form a cyclopropyl moiety or with (CH₂)₃ to form a cyclobutyl moiety,
—(C3-6)cycloalkylene-R6,
—(C3-6)cycloalkylene-(C1-3)alkylene-R6 and
—C(O)—(C1-4)alkylene-R6,
wherein R6 is selected from the group consisting of —OH, —OPO₃H₂, —COOH and —COO(C1-4)alkyl, preferably from —OH, —COOH and —COO(C1-4) alkyl, more preferably from —COOH and —COO(C1-4)alkyl.

More preferably, R1 is selected from the group consisting of —CH₂—COOH, —CH₂—OH, —CHCH₃—COOH, —(CH₂)₂—OH, —(CH₂)₂—COOH, —(CH₂)₃—COOH, —(CH₂)₄—COOH, —(CH₂)₅—COOH, —CH₂—CHCH₃—COOH, —CHCH₃—CH₂—COOH, —CH₂—C(CH₃)₂—COOH, —C(CH₃)₂—CH₂—COOH, —CH₂—CHCH₃—CH₂—COOH, —CH₂—C(CH₃)₂—CH₂—COOH, —(CH₂)₂—CHCH₃—COOH, —(CH₂)₂—C(CH₃)₂—COOH, —C(CH₃)₂—(CH₂)₂—COOH, —CHCH₃—(CH₂)₂—COOH, —CH₂—CF₂—COOH, —(CH₂)₂—CF₂—COOH, —CO—CH₂—COOH, —CO—(CH₂)₂—COOH, —CH₂—COO(C1-4)alkyl, —(CH₂)₂—COO(C1-4)alkyl, —(CH₂)₃—COO(C1-4)alkyl, —CH₂—CHCH₃—CH₂—COO(C1-4)alkyl, —CH₂—C(CH₃)₂—CH₂—COO(C1-4)alkyl, —(CH₂)₂—CHCH₃—COO(C1-4)alkyl, —C(CH₃)₂—(CH₂)₂—COO(C1-4)alkyl,

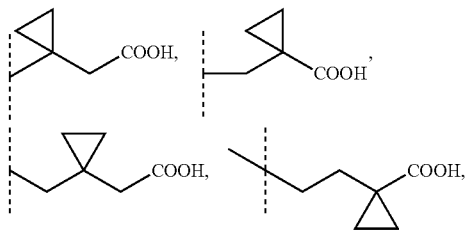

-1,3-cyclobutylene-COOH, -1,3-cyclobutylene-CH₂—COOH, —CH₂-1,3-cyclobutylene-COOH, -1,3-cyclobutylene-COO(C1-4)alkyl, -1,3-cyclobutylene-CH₂—COO(C1-4)alkyl, —CH₂-1,3-cyclobutylene-COO(C1-4)alkyl, C(O)—(C1-4)alkyl-OH, C(O)—(C1-4)alkyl-COOH, —(CH₂)₂—OPO₃H₂, —(CH₂)₃—OPO₃H₂, —CH₂—CHCH₃—CH₂—OPO₃H₂, —CH₂—C(CH₃)₂—CH₂—OPO₃H₂, —(CH₂)₂—CHCH₃—OPO₃H₂, —C(CH₃)₂—(CH₂)₂—OPO₃H₂, —CH₂-tetrazol-5-yl, —(CH₂)₂-tetrazol-5-yl, —(CH₂)₃-tetrazol, -5-yl-CH₂—CHCH₃—CH₂-tetrazol-5-yl, —CH₂—C(CH₃)₂—CH₂-tetrazol-5-yl, —(CH₂)₂—CHCH₃-tetrazol-5-yl and —C(CH₃)₂—(CH₂)₂-tetrazol-5-yl.

More preferably, R1 is selected from the group consisting of —CH₂—COOH, —CHCH₃—COOH, —(CH₂)₂—COOH, —(CH₂)₃—COOH, —(CH₂)₄—COOH, —(CH₂)₅—COOH, —CH₂—CHCH₃—COOH, —CHCH₃—CH₂—COOH, —CH₂—C(CH₃)₂—COOH, —C(CH₃)₂—CH₂—COOH, —CH₂—CHCH₃—CH₂—COOH, —CH₂—C(CH₃)₂—CH₂—COOH, —(CH₂)₂—CHCH₃—COOH, —(CH₂)₂—C(CH₃)₂—COOH, —C(CH₃)₂—(CH₂)₂—COOH, —CHCH₃—(CH₂)₂—COOH, —CH₂—COO(C1-4)alkyl, —(CH₂)₂—COO(C1-4)alkyl, —(CH₂)₃—COO(C1-4)alkyl, —CH₂—CHCH₃—CH₂—COO(C1-4)alkyl, —CH₂—C(CH₃)₂—CH₂—COO(C1-4)alkyl, —(CH₂)₂—CHCH₃—COO(C1-4)alkyl, —C(CH₃)₂—(CH₂)₂—COO(C1-4)alkyl, C(O)—(C1-4)alkyl-OH, C(O)—(C1-4)alkyl-COOH,

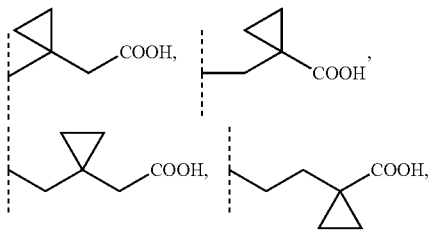

-1,3-cyclobutylene-COOH, -1,3-cyclobutylene-CH$_2$—COOH, —CH$_2$-1,3-cyclobutylene-COOH, -1,3-cyclobutylene-COO(C1-4)alkyl, -1,3-cyclobutylene-CH$_2$—COO(C1-4)alkyl and —CH$_2$-1,3-cyclobutylene-COO(C1-4)alkyl, wherein R2 is preferably absent, oxo or together with one of the carbon atoms in the N-containing ring forms a (C3-6) cycloalkyl.

More preferably, R1 is selected from the group consisting of —CH$_2$—COOH, —CHCH$_3$—COOH, —(CH$_2$)$_2$—COOH, —(CH$_2$)$_3$—COOH, —CH$_2$—CHCH$_3$—COOH, —CHCH$_3$—CH$_2$—COOH, —CH$_2$—CHCH$_3$—CH$_2$—COOH, —CH$_2$—C(CH$_3$)$_2$—CH$_2$—COOH, —(CH$_2$)$_2$—CHCH$_3$—COOH, —CHCH$_3$—(CH$_2$)$_2$—COOH, —CH$_2$—COOC(CH$_3$)$_3$, —(CH$_2$)$_2$—C(CH$_3$)$_2$—COOH, C(O)—CH$_2$—CH(CH$_3$)—CH$_2$—OH, C(O)—CH(CH$_3$)—CH$_2$—COOH,

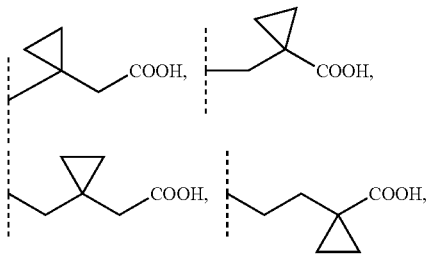

-1,3-cyclobutylene-COOH, -1,3-cyclobutylene-CH$_2$—COOH, -1,3-cyclobutylene-COOCH$_3$ and -1,3-cyclobutylene-COOC(CH$_3$)$_3$.

A particularly preferred R1 is —(C1-5)alkylene-R6, preferably —(CH$_2$)$_3$—R6, wherein one carbon atom in the alkylene group, preferably the carbon atom attached to R6, is substituted with (CH$_2$)$_2$ to form a cyclopropyl moiety. A particularly preferred R1 is

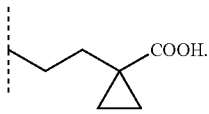

In one embodiment, R1 is —(CH$_2$)$_2$—C(CH$_3$)$_2$—COOH.

In one embodiment, R1 is selected from the group consisting of —CH$_2$—COOH, —CHCH$_3$—COOH, —(CH$_2$)$_2$—COOH, —(CH$_2$)$_3$—COOH, —CH$_2$—CHCH$_3$—COOH, —CHCH$_3$—CH$_2$—COOH, —CH$_2$—CHCH$_3$—CH$_2$—COOH, —CH$_2$—C(CH$_3$)$_2$—CH$_2$—COOH, —(CH$_2$)$_2$—CHCH$_3$—COOH, —CHCH$_3$—(CH$_2$)$_2$—COOH, —CH$_2$—COOC(CH$_3$)$_3$,

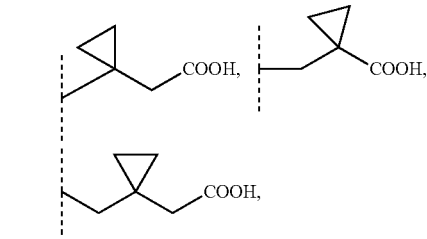

-1,3-cyclobutylene-COOH, -1,3-cyclobutylene-CH$_2$—COOH, -1,3-cyclobutylene-COOCH$_3$ and -1,3-cyclobutylene-COOC(CH$_3$)$_3$.

L1 is absent or

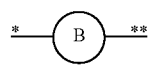

wherein * indicates the bond to ring A, ** indicates the bond to R3.

Ring B is preferably (C3-7)cycloalkyl, (C4-7)cycloalkenyl, phenyl or thienyl, more preferably (C3-7)cycloalkyl or phenyl, each optionally substituted with one or more of the substituents indicated above. If ring B is (C4-7)alkenyl, the alkenyl preferably has one carbon-carbon double bond, i.e. is cyclobutene, cyclopentene, cyclohexene and cycloheptene. Ring B is preferably selected from the group consisting of (C3-7)cycloalkyl, preferably cyclobutyl, phenyl and thienyl, more preferably (C3-7)cycloalkyl, preferably cyclobutyl, or phenyl most preferably phenyl, each optionally substituted with one or more substituents, preferably one or two substituents, independently selected from the group consisting of:
- a halogen atom, preferably F or Cl,
- (C1-4)alkyl optionally substituted with one or more halogen atoms, preferably F,
- (C1-4)alkoxy optionally substituted with one or more halogen atoms, preferably F, and
- phenyl optionally substituted with one or more substituents, preferably one or two substituents, independently selected from the group consisting of a halogen atom, preferably F or Cl, (C1-4)alkyl optionally substituted with one or more fluoro atoms, and (C1-4)alkoxy optionally substituted with one or more fluoro atoms.

Ring B is preferably selected from the group consisting of:

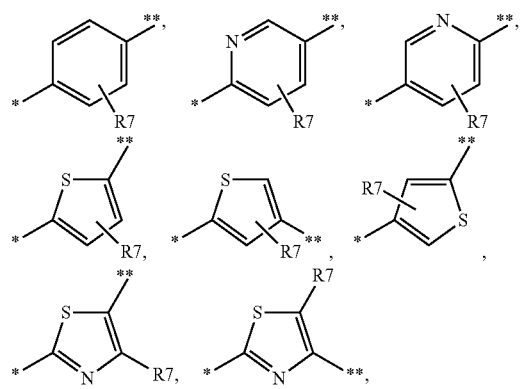

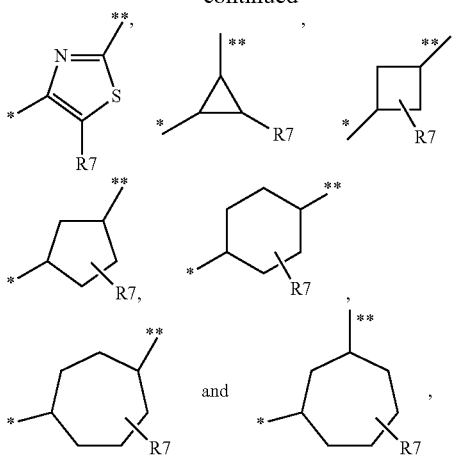

wherein
* indicates the bond to ring A, ** indicates the bond to R3 and R7 is hydrogen or one or more substituents of ring B as defined above.

More preferably, Ring B is selected from the group consisting of:

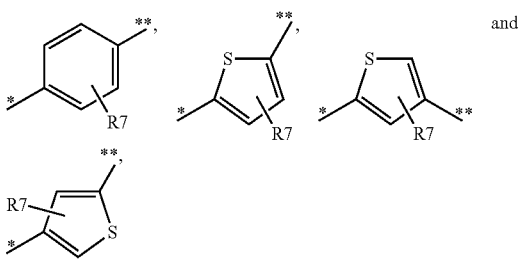

wherein * indicates the bond to ring A, ** indicates the bond to R3 and R7 is absent or one or more substituents of ring B as defined above. R7 is preferably a halogen atom or a (C1-4)alkyl, more preferably F, methyl or ethyl, most preferably methyl or F.

A particularly preferred ring B is phenyl, preferably

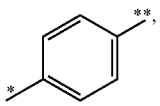

optionally substituted with one or more substituents, preferably one or two substituents, independently selected from the group consisting of:
a halogen atom, preferably F or Cl,
(C1-4)alkyl optionally substituted with one or more halogen atoms, preferably F, and
(C1-4)alkoxy optionally substituted with one or more halogen atoms, preferably F.

In a further embodiment ring B is (C3-7)cycloalkyl, preferably a (C3-6)cycloalkyl. Preferred is cyclobutyl, more preferably

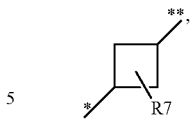

R7 is hydrogen or one or more substituents of ring B as defined above.

Most preferably, L1 is absent or Ring B is

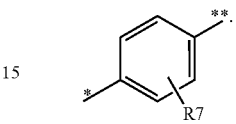

Herein, * indicates the bond to ring A, ** indicates the bond to R3 and R7 is absent or one or more substituents of ring B as defined above, preferably one or two substituents, preferably one or two substituents, independently selected from the group consisting of:
a halogen atom, preferably F or Cl,
(C1-4)alkyl optionally substituted with one or more halogen atoms, preferably F, and
(C1-4)alkoxy optionally substituted with one or more halogen atoms, preferably F.

L2 is preferably absent or W is selected from the group consisting of a bond, —$CH_2$—, —O—, —$CH_2$—O—, —O—$CH_2$—, —CO—, —S—, —SO—, —$SO_2$—, —NH—, —CH=CH—, —$CF_2$=CH—, —CH=$CF_2$—, —C≡C— and cyclopropylene, p is an integer from 0 to 4, and T is absent or a bond. More preferably, W is selected from the group consisting of a bond, —$CH_2$—, —O—, —CO—, —S—, —SO—, —$SO_2$—, —NH—, —O—$CH_2$—, —CH=CH— and —C≡C—, p is an integer from 0-2 and T is a bond. More preferably, L2 is absent or selected from the group consisting of —O—, —O—$CH_2$—, —$CH_2$—, —$CH_2$—O—, —$(CH_2)_2$—, —CH=CH—, and —C≡C—. Most preferably L2 is absent or selected from the group consisting of —O—$CH_2$—, —$CH_2$—, —CH=CH— and —C≡C—.

If both L1 and L2 are absent, R4 is directly attached to ring A via a single bond.

If L1 is ring B, preferably phenyl or cyclobutyl, L2 is preferably —O—$CH_2$—. If L1 is absent, L2 is preferably absent or selected from the group consisting of —O—$CH_2$—, —$CH_2$—, —CH=CH— and —C≡C—.

R4 is preferably selected from the group consisting of:
(C3-6)cycloalkyl or an 8-10 membered bicyclic group, each optionally substituted with a substituent selected from the group consisting of a halogen atom, preferably F or Cl, (C1-4)alkyl optionally substituted with one or more, preferably 2 or 3 fluoro atoms, and (C1-4)alkoxy optionally substituted with one or more fluoro atoms, preferably 2 or 3 fluoro atoms,
phenyl, optionally substituted with one or more substituents, preferably one or two, independently selected from the group consisting of:
a halogen atom, preferably F and/or Cl,
hydroxy,
(C1-4)alkyl group optionally substituted with one or more, preferably 2 or 3, fluoro atoms, and
(C1-4)alkoxy optionally substituted with one or more, preferably 2 or 3, fluoro atoms, and
phenyl substituted with —S—$CH_3$ or benzyloxy.

Said 8-10 membered bicyclic group preferably contains up to 2 heteroatoms. Preferably said 8-10 membered bicyclic group is preferably selected from the group consisting of indane, tetralin, dihydrobenzofuran, dihydroisobenzofuran, dihydroindole, dihydroisoindole, dihydrobenzopyran, dihydrobenzothiophene and dihydrobenzo[c]thiophene. Most preferably said 8-10 membered bicyclic group is indane.

More preferably, R4 is selected from the group consisting of:
- (C3-6)cycloalkyl, e.g. cyclohexyl,
- indanyl,
- phenyl, optionally substituted with:
  - one or two F or Cl atoms, or
  - hydroxy, or
  - a group selected from methyl, difluoromethyl, trifluoromethyl, ethyl, methoxy, difluoromethoxy, trifluoromethoxy, isopropoxy and ethoxy, or
  - a F or Cl atom and a group selected from methyl, difluoromethyl, trifluoromethyl, ethyl, methoxy, difluoromethoxy, trifluoromethoxy, isopropoxy and ethoxy, or
  - —S—CH₃, or
  - benzyloxy.

Particularly preferred compounds of the invention are compounds wherein
one or two of X, Y and Z are N and at least one of X, Y and Z is CR5, wherein R5 is independently selected from the group consisting of hydrogen, a fluoro atom, methyl optionally substituted with one or more fluoro atoms and ethyl optionally substituted with one or more fluoro atoms;
m is 0 or 1 and n is 1 or 2 with the proviso that m+n is 1 or 2;
R2 is absent, oxo or together with one of the carbon atoms in the N-containing ring forms a (C3-6)cycloalkyl;
R1 is selected from the group consisting of —CH₂—COOH, —CHCH₃—COOH, —(CH₂)₂—COOH, —(CH₂)₃—COOH, —(CH₂)₄—COOH, —(CH₂)₅—COOH, —CH₂—CHCH₃—COOH, —CHCH₃—CH₂—COOH, —CH₂—C(CH₃)₂—COOH, —C(CH₃)₂—CH₂—COOH, —CH₂—CHCH₃—CH₂—COOH, —CH₂—C(CH₃)₂—CH₂—COOH, —(CH₂)₂—CHCH₃—COOH, —(CH₂)₂—C(CH₃)₂—COOH, —C(CH₃)₂—(CH₂)₂—COOH, —CHCH₃—(CH₂)₂—COOH, —CH₂—COO(C1-4)alkyl, —(CH₂)₂—COO(C1-4)alkyl, —(CH₂)₃—COO(C1-4)alkyl, —CH₂—CHCH₃—CH₂—COO(C1-4)alkyl, —CH₂—C(CH₃)₂—CH₂—COO(C1-4)alkyl, —(CH₂)₂—CHCH₃—COO(C1-4)alkyl, —C(CH 3)₂—(CH₂)₂—COO(C1-4)alkyl, —C(O)—(C1-4)alkylene-OH, —C(O)—(C1-4)alkylene-COOH,

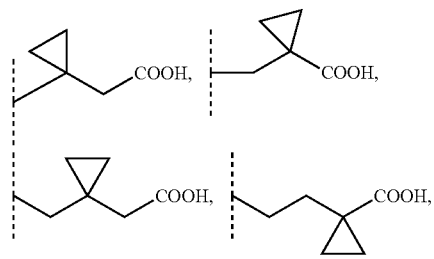

-1,3-cyclobutylene-COOH, -1,3-cyclobutylene-CH₂—COOH, —CH₂-1,3-cyclobutylene-COOH, -1,3-cyclobutylene-COO(C1-4)alkyl, -1,3-cyclobutylene-CH₂—COO(C1-4)alkyl and —CH₂-1,3-cyclobutylene-COO(C1-4)alkyl;

W is selected from the group consisting of a bond, CH₂, —O—, —CO—, —S—, —SO—, —SO₂—, —NH—, —O—CH₂—, —CH=CH— and —C≡C—;
p is an integer from 0-2; and
T is absent or a bond.

Also provided is a compound of formula (I):

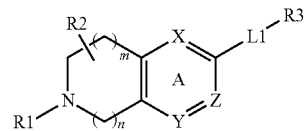

or a pharmaceutically acceptable salt, solvate, tautomer, stereoisomer or N-oxide thereof, wherein
X, Y and Z are independently selected from the group consisting of N and CR5, with the proviso that at least one of X, Y and Z is N, and wherein each R5 is independently selected from the group consisting of hydrogen, a halogen atom, (C1-4)alkyl and (C1-4)alkyl substituted with one or more fluor atoms;
m is 0, 1 or 2 and n is 1, 2 or 3 with the proviso that m+n is 1, 2 or 3;
R1 is selected from the group consisting of
- —(C1-6)alkylene-R6 wherein one or more carbon atoms in the alkylene group, each independently, are optionally substituted with one or more halogen atoms or with (CH₂)₂ to form a cyclopropyl moiety or with (CH₂)₃ to form a cyclobutyl moiety,
- —(C3-6)cycloalkylene-R6 in which one carbon atom in the (C3-6)cycloalkylene can optionally be replaced by oxygen,
- —(C1-3)alkylene-(C3-6)cycloalkylene-R6,
- —(C3-6)cycloalkylene-(C1-3)alkylene-R6 and
- —C(O)—(C1-4)alkylene-R6, wherein R6 is selected from the group consisting of —OH, —OPO₃H₂, —COOH, —COO(C1-4)alkyl and tetrazol-5-yl;
R2 is absent or one or more substituents independently selected from the group consisting of a halogen atom, (C1-4)alkyl optionally substituted with one or more halogen atoms, and (C1-4)alkoxy optionally substituted with one or more halogen atoms;
L1 is absent or

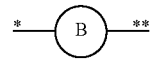

wherein
* indicates the bond to ring A and ** indicates the bond to R3; and
Ring B is selected from the group consisting of (C3-7)cycloalkyl, phenyl, pyridyl, thienyl and thiazolyl, each optionally substituted with one or more substituents independently selected from the group consisting of
- hydroxy,
- cyano,
- a halogen atom,
- (C1-4)alkyl optionally substituted with one or more halogen atoms,
- (C3-6)cycloalkyl optionally substituted with one or more halogen atoms,
- (C1-4)alkoxy optionally substituted with one or more halogen atoms, and phenyl optionally substituted with one or more substituents independently selected from the group consisting of a halogen atom, (C1-4)alkyl optionally substituted with one or more halogen atoms, and (C1-4)alkoxy optionally substituted with one or more halogen atoms; and R3 is L2-R4, wherein:
L2 is absent or a group —W—(CH$_2$)p-T- wherein:
W is attached to L1 and selected from the group consisting of a bond, —O—, —CO—, —S—, —SO—, —SO$_2$—, —NH—, —CH=CH—, —C(CF$_3$)=CH—, CH=C(CF$_3$)—, —CF$_2$—CH$_2$—, —CH$_2$—CF$_2$—, —CHF—CH$_2$—, —CH$_2$—CHF—, —C≡C—, —CH$_2$—O—, —O—CH$_2$—, —O—CO—, —CO—O—, —CO—NH—, —NH—CO— and cyclopropylene;
p is an integer from 0 to 10;
one or more C atoms of (CH$_2$)p are optionally substituted with one or two fluoro atoms, and
T is absent or attached to R4 and selected from the group consisting of a bond, —O—, —S—, —SO—, —SO$_2$—, —NH—, —CO—, —C≡C—, —C≡C—, and cyclopropylene,
R4 is selected from the group consisting of:
(C3-6)cycloalkyl, (C4-6)cycloalkenyl or an 8-10 membered bicyclic group, each optionally substituted with a substituent selected from the group consisting of a halogen atom and (C1-4)alkyl optionally substituted with one or more fluoro atoms,
phenyl, biphenyl or naphthyl, pyridyl, thienyl, thiazolyl optionally substituted with one or more substituents independently selected from the group consisting of:
a halogen atom,
cyano,
(C1-4)alkyl optionally substituted with one or more fluoro atoms,
(C1-4)alkoxy optionally substituted with one or more fluoro atoms,
—S—(C1-4)-alkyl,
—SF$_5$, and
(C3-6)cycloalkyl optionally substituted with phenyl whereby said
phenyl is optionally substituted with a substituent selected from the group consisting of (C1-4)alkyl and a halogen atom, and phenyl substituted with a substituent selected from the group consisting of phenoxy, benzyl, benzyloxy, phenylethyl and a monocyclic heterocycle, wherein each substituent is optionally substituted with one or more halogen atoms, (C1-4)alkyl, (C1-4)alkyl substituted with one or more fluoro atoms, (C1-4)alkoxy, or (C1-4)alkoxy substituted with one or more fluoro atoms.

Further particularly preferred compounds of the invention are compounds wherein compounds wherein formula (I) is selected from the group consisting of

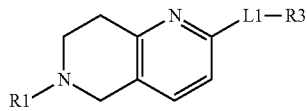

formula (Ia)

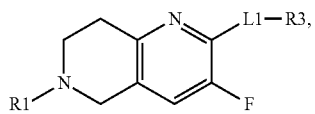

formula (Ib)

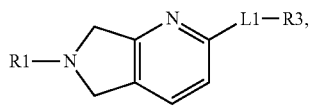

formula (Ic)

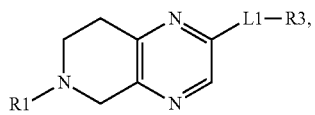

formula (Id)

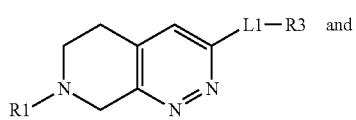

formula (Ie)

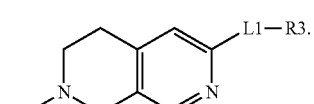

formula (If)

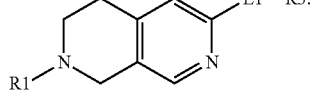

formula (Ih)

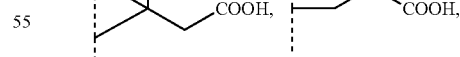

formula (Ij)

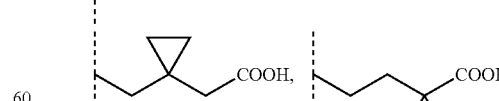

R1 is selected from the group consisting of —CH$_2$—COOH, —CHCH$_3$—COOH, —(CH$_2$)$_2$—COOH, —(CH$_2$)$_3$—COOH, —(CH$_2$)$_4$—COOH, —(CH$_2$)$_5$—COOH, —CH$_2$—CHCH$_3$—COOH, —CHCH$_3$—CH$_2$—COOH, —CH$_2$—C(CH$_3$)$_2$—COOH, —C(CH$_3$)$_2$—CH$_2$—COOH, —CH$_2$—CHCH$_3$—CH$_2$—COOH, —CH$_2$—C(CH$_3$)$_2$—CH$_2$—COOH, —(CH$_2$)$_2$—CHCH$_3$—COOH, —(CH$_2$)$_2$—C(CH$_3$)$_2$—COOH, —C(CH$_3$)$_2$—(CH$_2$)$_2$—COOH, —CHCH$_3$—(CH$_2$)$_2$—COOH, —CH$_2$—COO(C1-4)alkyl, —(CH$_2$)$_2$—COO(C1-4)alkyl, —(CH$_2$)$_3$—COO(C1-4)alkyl, —CH$_2$—CHCH$_3$—CH$_2$—COO(C1-4)alkyl, —CH$_2$—C(CH$_3$)$_2$—CH$_2$—COO(C1-4)alkyl, —(CH$_2$)$_2$—CHCH$_3$—COO(C1-4)alkyl, —C(CH$_3$)$_2$—(CH$_2$)$_2$—COO(C1-4)alkyl, —C(O)—(C1-4)alkylene-OH, —C(O)—(C1-4)alkylene-COOH

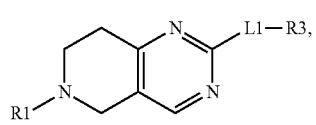

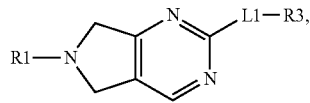

-1,3-cyclobutylene-COOH, -1,3-cyclobutylene-CH$_2$—COOH, —CH$_2$-1,3-cyclobutylene-COOH, -1,3-cyclobutylene-COO(C1-4)alkyl, -1,3-cyclobutylene-CH$_2$—COO(C1-4)alkyl and —CH$_2$-1,3-cyclobutylene-COO(C1-4)alkyl;

L1 is absent or

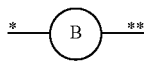

wherein
* indicates the bond to ring A and ** indicates the bond to R3; and

Ring B is selected from the group consisting of: (C3-7)cycloalkyl, (C4-7)cycloalkenyl, phenyl and thienyl each optionally substituted with one or more substituents independently selected from the group consisting of
a halogen atom,
(C1-4)alkyl optionally substituted with one or more halogen atoms, preferably F,
(C1-4)alkoxy optionally substituted with one or more halogen atoms, preferably F, and
phenyl optionally substituted with one or more substituents independently selected from the group consisting of a halogen atom, preferably F or Cl, (C1-4)alkyl optionally substituted with one or more halogen atoms, preferably F, and (C1-4)alkoxy optionally substituted with one or more halogen atoms, preferably F;

W is selected from the group consisting of a bond, $CH_2$, —O—, —CO—, —S—, —SO—, —SO$_2$—, —NH—, —O—CH$_2$—, —CH═CH— and —C≡C—;

p is an integer from 0-2;

T is absent or a bond; and

R4 is selected from the group consisting of:
(C3-6)cycloalkyl,
an 8-10 membered bicyclic group, and
phenyl, optionally substituted with one or more substituents, preferably one or two, independently selected from the group consisting of:
a halogen atoms, preferably F and/or Cl,
hydroxy,
a (C1-4)alkyl group optionally substituted with one or more, preferably 2 or 3, fluoro atoms,
(C1-4)alkoxy optionally substituted with one or more, preferably 2 or 3, fluoro atoms,
—S—CH$_3$.

Further particularly preferred compounds of the invention are compounds wherein
formula (I) is selected from the group consisting of

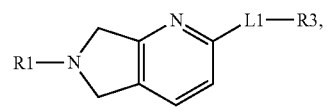

formula (Ia)

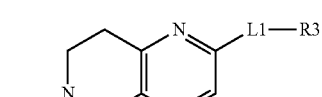

formula (Ib)

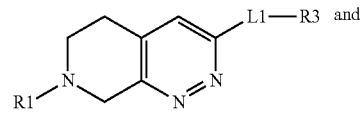

formula (Ic)

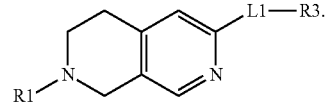

formula (Id)

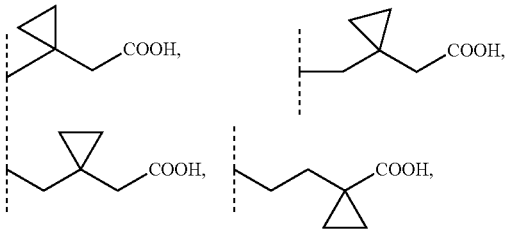

formula (Ie)

formula (If)

formula (Ih) and formula (Ij)

R1 is selected from the group consisting of —CH$_2$—COOH, —CHCH$_3$—COOH, —(CH$_2$)$_2$—COOH, —(CH$_2$)$_3$—COOH, —CH$_2$—CHCH$_3$—COOH, —CHCH$_3$—CH$_2$—COOH, —CH$_2$—CHCH$_3$—CH$_2$—COOH, —CH$_2$—C(CH$_3$)$_2$—CH$_2$—COOH, —(CH$_2$)$_2$—CHCH$_3$—COOH, —CHCH$_3$—(CH$_2$)$_2$—COOH, —CH$_2$—COOC(CH$_3$)$_3$, C(O)—CH$_2$—CH(CH$_3$)—CH$_2$—OH, C(O)—CH(CH$_3$)—CH$_2$—COOH,

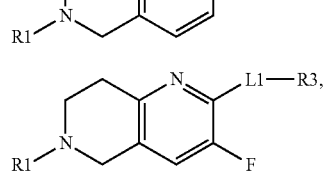

-1,3-cyclobutylene-COOH, -1,3-cyclobutylene-CH$_2$—COOH, -1,3-cyclobutylene-COOCH$_3$ and -1,3-cyclobutylene-COOC(CH$_3$)$_3$;

Ring B is

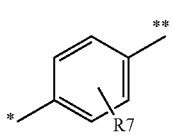 or 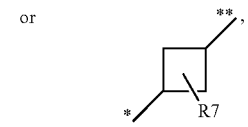

wherein R7 is absent or one or more substituents, preferably one or two substituents, independently selected from the group consisting of:
a halogen atom, preferably F or Cl,
(C1-4)alkyl, preferably methyl, optionally substituted with one or more halogen atoms, preferably F, and
(C1-4)alkoxy, preferably methoxy, optionally substituted with one or more halogen atoms, preferably F.

L2 is absent or selected from the group consisting of —O—CH$_2$—, —CH$_2$—, —CH=CH— and —C≡C—; and R4 is selected from the group consisting of:
(C3-6)cycloalkyl, e.g. cyclohexyl,
indanyl,
phenyl, optionally substituted with:
one or two F or Cl atoms, or
hydroxy, or
a group selected from methyl, difluoromethyl, trifluoromethyl, ethyl, methoxy, difluoromethoxy, trifluoromethoxy and ethoxy, or
a F or Cl atom and a group selected from methyl, difluoromethyl, trifluoromethyl, ethyl, methoxy, difluoromethoxy, trifluoromethoxy, isopropoxy and ethoxy, or
—S—CH$_3$.

Further particularly preferred compounds of the invention are depicted in table 1.

Particularly preferred compounds depicted in table 1 are compounds having a EC50 for the S1P5 receptor of 100 nM or less, as shown in table 1, i.e. compounds having an S1P5 EC50 range of A, B or E in table 1. Further particularly preferred compounds depicted in table 1 are compounds having a EC50 for the S1P5 receptor of 10 nM or less, as shown in table 1, i.e. compounds having an S1P5 EC50 range of A in table 1. Such compounds further preferably have an EC50 for at least one of the S1P1 receptor, the S1P3 receptor and the S1P4 receptor of more than 1 μM as shown in table 1, preferably an EC50 of more than 1 μM as shown in table 1 for the S1P1 receptor and/or the S1P3 receptor.

Hence, in a particularly preferred embodiment are provided compounds depicted in table 1 having an S1P5 EC50 of 100 nM or less (indicated with range A, B or E in table 1) and EC50 of more than 1 μM for at least one of the S1P1 receptor, the S1P3 receptor and the S1P4 receptor, preferably an EC50 of more than 1 μM as shown in table 1 for the S1P1 receptor and/or the S1P3 receptor. In a further particularly preferred embodiment are provided compounds depicted in table 1 having an S1P5 EC50 of 10 nM or less (indicated with range A in table 1) and EC50 of more than 1 μM for at least one of the S1P1 receptor, the S1P3 receptor and the S1P4 receptor, preferably an EC50 of more than 1 μM as shown in table 1 for the S1P1 receptor and/or the S1P3 receptor.

As used herein, the term "a halogen atom" refers to fluoro, chloro, bromo, or iodo. Preferred halogen atoms are fluoro and chloro.

As used herein, the term "(Cx-y)alkyl" refers to a branched or unbranched alkyl group having x-y carbon atoms. For instance, (C1-4)alkyl means a branched or unbranched alkyl group having 1-4 carbon atoms, for example methyl, ethyl, propyl, isopropyl and butyl. Similarly, the term "(C1-2) alkyl" refers to an alkyl group having 1 or 2 carbon atoms. Preferred alkyl groups are methyl and ethyl.

As used herein, the term (Cx-y)alkoxy refers to an alkoxy group having x-y carbon atoms, wherein the alkyl moiety is as defined above. For instance, the term (C1-4)alkoxy means an alkoxy group having 1-4 carbon atoms. Preferred alkoxy groups are methoxy and ethoxy.

As used herein, the term "(Cx-y)alkylene" refers to a branched or unbranched saturated alkylene group having x-y carbon atoms. For instance, the term "(C1-4)alkylene" means a saturated alkylene group having 1-4 carbon atoms, for example methylene, (CH$_2$)$_3$—CHCH$_3$—, —C(CH$_3$)$_2$—, —CHCH$_3$CH$_2$—. As another example, the term "(C1-6) alkylene means a saturated alkylene group having 1-6 carbon atoms". In the definition of R1 as —(C1-6)alkylene-R6, one or more carbon atoms in the alkylene group may independently be substituted with (CH$_2$)$_2$ to form a cyclopropyl moiety, for instance to form an R1 group

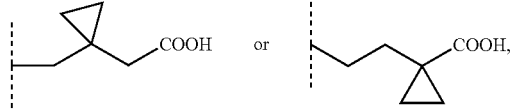

or with (CH$_2$)$_3$ to form a cyclobutyl moiety.

As used herein a dashed line in a partial structure, such as

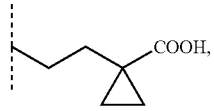

means that the partial structure is attached to the remainder of the structure at the site of the dashed line. For instance, if R1 is

the compound of formula (I) is

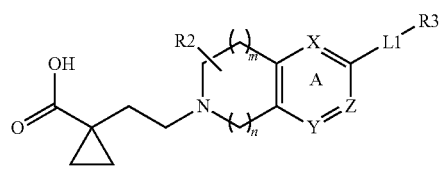

As used herein the term "(Cx-y)alkenyl" means a branched or unbranched alkenyl group having x-y carbon atoms, wherein the double bond may be present at various positions in the group. Examples are ethenyl, propenyl, 1-butenyl, 2-butenyl. For instance, the term "(C2-4)alkenyl" means a branched or unbranched alkenyl group having 2-4 carbon atoms.

As used herein, the term "(Cx-y)alkynyl" refers to a branched or unbranched alkynyl group having x-y carbon atoms, wherein the triple bond may be present at different positions in the group, for example ethynyl, propanyl, 1-butynyl, 2-butynyl. For instance, the term "(C2-4)alkynyl" refers to a branched or unbranched alkynyl group having 2-4 carbon atoms.

As used herein the term "(Cx-y)cycloalkyl" refers to a cyclic alkyl group having x-y carbon atoms. For instance, the term "(C3-6)cycloalkyl" refers to a cyclic alkyl group having 3-6 carbon atoms, i.e. cyclopropyl, cyclobutyl, cyclopentyl or cyclohexyl.

As used herein the term "(Cx-y)cycloalkenyl" means a cyclic alkenyl group having x-y carbon atoms. For instance, the term "(C4-6)cycloalkenyl" means a cyclic alkenyl group having 4-6 carbon atoms and comprising one or two double bonds, for example cyclohexenyl. Preferably a cycloalkenyl as used herein has one carbon-carbon double bond, e.g. cyclobutene, cyclopentene, cyclohexene and cycloheptene.

As used herein the term "(Cx-y)cycloalkylene" means a saturated cyclic group having x-y carbon atoms. For instance, the term "(C3-7)cycloalkylene" means a saturated cyclic group having 3-7 carbon atoms, e.g. cyclobutylene, cyclopentylene, cyclohexylene and cycloheptane.

As used herein the term "8-10 membered bicyclic group" for R4 means a fused ring system of two ring structures together having 8-10 atoms. The rings can be either aromatic or non-aromatic ring structures. Preferred 8-10 membered bicyclic groups contain up to two heteroatoms, preferably O, S or N. Particularly preferred 8-10 membered bicyclic groups for R4 are indane, tetralin, benzofuran, isobenzofuran, dihydrobenzofuran, dihydroisobenzofuran, tetrahydrobenzofuran, tetrahydroisobenzofuran, indoline, isoindoline, indole, isoindole, dihydroindole, dihydroisoindole, tetrahydroindole, tetrahydroisoindole, quinolone, isoquinoline, tetrahydroquinoline, tetrahydroisoquinoline, quinoxaline dihydroquinoxaline, tetrahydroquinoxaline, quinazoline, dihydroquinazoline, tetrahydroquinazoline, dihydrobenzopyran, benzothiophene, benzothiophene, dihydrobenzothiophene, dihydrobenzo[c]thiophene, tetrahydrobenzothiophene, tetrahydroquinoxaline, indazole, dihydroindazole, tetrahydroindazole, benzimidazole, dihydrobenzimidazole and tetrahydrobenzimidazole, benzoxazole, dihydrobenzoxazole, tetrahydrobenzoxazole, benzisoxazole, dihydrobenzisoxazole and tetrahydrobenzisoxazole. More preferred 8-10 membered bicyclic groups in the definition of R4 are indane, tetralin, dihydrobenzofuran, dihydroisobenzofuran, dihydroindole, dihydroisoindole, dihydrobenzopyran, dihydrobenzothiophene and dihydrobenzo[c]thiophene. A particularly preferred 8-10 membered bicyclic group for R4 is indane.

With respect to substituents, the term "optionally substituted" indicates a group may be unsubstituted or substituted with the indicated number and type of the substituent(s). The term "independently substituted" means that if a group that is substituted with more than one substituent, these substituents may be the same or different from each other. Similarly, if multiple atoms have one substituent selected from a group of substituents, such as X, Y and Z in present formula (I) which can be CR5, the term "independently substituted" means that each atom has a substituent that may be the same or different from the substituent of the other atom(s).

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the compound. Each such asymmetric center will independently produce two optical isomers and it is intended that all of the possible optical isomers and diastereomers in mixtures and as pure or partially purified compounds are included within the ambit of this invention. The present invention encompasses all such isomeric forms of these compounds. The independent syntheses of these diastereomers or their chromatographic separations may be achieved with any method known in the art, for instance as described in the Examples. The absolute stereochemistry of a compound may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as chiral HPLC or SFC (Supercritical Fluid Chromatography) techniques. In the Examples, two suitable SFC methods are described.

Salts of compounds according to the invention are also provided. Such salts include, but are not limited to, acid addition salts and base addition salts. The term "pharmaceutically acceptable salt" as used herein refers to those salts retain the pharmacological activity of the compounds and that are, within the scope of sound medical judgment, suitable for use in humans or animals without undue toxicity, irritation, allergic response, and the like, and are commensurate with a reasonable benefit/risk ratio. Pharmaceutically acceptable salts are well-known in the art. They can be prepared in situ when isolating and purifying the compounds of the invention, or separately by reacting them with pharmaceutically acceptable non-toxic bases or acids, including inorganic or organic bases and inorganic or organic acids, for instance by reacting the free acid or free base forms of the product with one or more equivalents of the appropriate acid or base in a solvent or medium in which the salt is insoluble, or in a solvent such as water or an organkic solvent which is then removed in vacuo or by freeze-drying, or by exchanging the cations of an existing salt for another cation on a suitable ion exchange resin. Examples of pharmaceutically acceptable acids and bases include organic and inorganic acids such as acetic acid, propionic acid, lactic acid, glycolic acid, oxalic acid, pyruvic acid, succinic acid, maleic acid, malonic acid, trifluoroacetic acid, cinnamic acid, sulfuric acid, hydrochloric acid, hydrobromic acid, nitric acid, perchloric acid and phosphoric acid, and bases such as ethylamine, methylamine, dimethylamine, triethylamine, isopropylamine, diisopropylamine, and other mono-, di- and trialkylamines, and arylamines.

Compounds may exist as polymorphs and as such are intended to be included in the present invention. In addition, compounds may form solvates with water (i.e., hydrates) or common organic solvents, and such solvates are also intended to be encompassed within the scope of this invention. Hydrates are a preferred type of solvate.

Isotopically-labeled compounds of formula (I) or pharmaceutically acceptable salts thereof, including compounds of formula (I) isotopically-labeled to be detectable by PET or SPECT, also fall within the scope of the invention. The same applies to compounds of formula (I) labeled with [13C]—, [14C]—, [3H]—, [18F]—, [125I]— or other isotopically enriched atoms, suitable for receptor binding or metabolism studies.

The compounds of the invention may be prepared by methods known in the art and to a skilled person. Suitable methods to prepare the compounds are described in the experimental section of this description.

Compounds according to the invention are useful in counteracting diseases or disorders mediated by an S1P receptor, preferably S1P5. They are preferably mixed with pharmaceutically suitable auxiliaries, e.g. as described in the standard reference "Remington, The Science and Practice of Pharmacy" (21st edition, Lippincott Williams & Wilkins, 2005, see especially Part 5: Pharmaceutical Manufacturing). The compounds together with pharmaceutically suitable auxiliaries may be compressed into solid dosage units, such as pills or tablets, or be processed into capsules or suppositories. By means of pharmaceutically suitable liquids the compounds can also be applied in the form of a solution, suspension or emulsion.

Provided is therefore a pharmaceutical composition comprising a compound according to the invention or a pharmaceutically acceptable salt, solvate, tautomer, stereoisomer or N-oxide thereof, and at least one pharmaceutically acceptable carrier, diluent and/or excipient. By "pharmaceutically acceptable" it is meant that the carrier, diluent or excipient must be compatible with the other ingredients of the formulation and not deleterious to the recipient thereof. In general, any pharmaceutically suitable additive which does not interfere with the function of the active compounds can be used. A pharmaceutical composition according to the invention is preferably suitable for human use.

Examples of suitable carriers comprise a solution, lactose, starch, cellulose derivatives and the like, or mixtures thereof. In a preferred embodiment said suitable carrier is a solution, for example saline. For making dosage units, e.g. tablets, the use of conventional additives such as fillers, colorants, polymeric binders and the like, is contemplated. Examples of excipients which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor. Compositions for intravenous administration may for example be solutions of the compounds of the invention in sterile isotonic aqueous buffer. Where necessary, the intravenous compositions may include for instance solubilizing agents, stabilizing agents and/or a local anesthetic to ease the pain at the site of the injection.

The compounds of the invention may be administered enterally or parenterally. The exact dose and regimen of these compounds and compositions thereof will be dependent on the biological activity of the compound per se, the age, weight and sex of the individual, the needs of the individual subject to whom the medicament is administered, the degree of affliction or need and the judgment of the medical practitioner. In general, parenteral administration requires lower dosages than other methods of administration which are more dependent upon adsorption. However, the dosages for humans are preferably 0.001-10 mg per kg body weight. In general, enteral and parenteral dosages will be in the range of 0.1 to 1,000 mg per day of total active ingredients.

In an embodiment of the invention, a pharmaceutical kit or kit of parts is provided comprising one or more containers filled with one or more pharmaceutical compositions of the invention and optionally one or more pharmaceutically acceptable excipients as described herein. Associated with such container(s) can be various written materials such as instructions for use, or a notice in the form prescribed by a governmental agency regulating the manufacture, use or sale of pharmaceuticals products, which notice reflects approval by the agency of manufacture, use, or sale for human or veterinary administration. Preferably, a pharmaceutical kit or kit of parts comprises instructions for use.

The compounds of the invention are modulators of the S1P receptor, in particular of the S1P5 receptor. More specifically, the compounds of the invention are S1P5 receptor agonists. The compounds are useful in the treatment, alleviation and/or prevention of diseases or disorders mediated by an S1P receptor, preferably S1P5. The compounds of the present invention are particularly suitable to treat, alleviate or prevent diseases and conditions in which an S1P receptor is involved or in which modulation of the endogenous S1P signaling system via an S1P receptor is involved, preferably S1P5.

Provided is therefore a method of treatment, alleviation or prevention of a disease or condition in which an S1P receptor is involved or in which modulation of the endogenous S1P signaling system via an S1P receptor is involved, preferably S1P5, comprising administering to a patient in need thereof a compound according to the invention or a pharmaceutically acceptable salt, solvate, tautomer, stereoisomer or N-oxide thereof. Said patient is preferably a human patient.

Further provided is a use of a compound according to the invention or a pharmaceutically acceptable salt, solvate, tautomer, stereoisomer or N-oxide thereof for the manufacture of a medicament for the treatment, alleviation or prevention of a disease or condition in which an S1P receptor is involved or in which modulation of the endogenous S1P signaling system via an S1P receptor is involved, preferably S1P5 receptor.

Further provided is a compound according to the invention, or a pharmaceutically acceptable salt, solvate, tautomer, stereoisomer or N-oxide thereof for use in therapy, preferably for use as a medicament.

Further provided is a compound according to the invention or a pharmaceutically acceptable salt, solvate, tautomer, stereoisomer or N-oxide thereof, or a pharmaceutical composition comprising such compound, or a pharmaceutically acceptable salt, solvate, tautomer, stereoisomer or N-oxide thereof, for use in the treatment, alleviation or prevention of a disease or condition in which an S1P receptor is involved or in which modulation of the endogenous S1P signaling system via an S1P receptor is involved, preferably S1P5.

Said diseases or condition is preferably selected from the group consisting of Alzheimer's Disease (AD) and associated dementia's, amyloid β-associated disorders, Mild Cognitive Impairment (MCI), Parkinson's Disease (PD), Lewy Body Dementia (LBD), Progressive Supranuclear Palsy (PSP), Cerebral Palsy (CP), Amyotrophic Lateral Sclerosis (ALS), Frontal Temporal Lobe Dementia (FTLD), multiple sclerosis, Huntington's Disease, neurological symptoms of sphingolipidosis disorders, a lysosomal storage disorder including Tay Sachs Disease, Sandhoff Disease, Fabry's Disease, Krabbe Disease, Gaucher's Disease, Niemann Pick A, B or C, and Batten's Disease, stroke, HIV-associated Dementia (HAD), HIV-associate Neurocognitive Disorder (HAND), HIV-associated neuropathy, schizophrenia, cognitive deficits in Schizophrenia, an attention deficit disorder including Anxiety Attention Deficit Disorder and Attention Deficit Hyperactivity Disorder (ADHD), a bipolar disorder, Obsessive-Compulsive Behavior, pain including neuropathic, back pain and pain-associated with multiple sclerosis, spinal cord injury, Parkinson's Disease, epilepsy, diabetes and cancer, cancer-induced peripheral neuropathy (CIPN), depression, treatment-resistant depression, Creutzfeld-Jakob Disease and other Prion-related Disorders, Down's Syndrome, autism, age-related cognitive decline or memory impairment, cognitive deficits associated with diabetes, dementia, dementia associated with Down's Syndrome, cognitive deficits in psychiatric disorders, dementia associated with Lewy Body pathology, diminished CNS function associated with traumatic brain injury, Pick's Disease, spinal cord injury, a demyelinating disorder, a disorder of basal ganglia, AIDS-associated dementia, Psoriasis type 1 and type 2, atopic dermatitis, dermatitis scleroderma, insulin-dependent diabetes mellitus, ulcerative colitis, atherosclerosis, sepsis syndrome, septic shock, Dengue hemorrhagic fever, Dengue, atopic allergy, HIV/AIDS, barrier-integrity associated lung diseases, leukemia, contact dermatitis, encephalomyelitis, Epstein Barr virus infection and other virus infections requiring cell-cell fusion.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described in this document.

Features may be described herein as part of the same or separate aspects or embodiments of the present invention for the purpose of clarity and a concise description. It will be appreciated by the skilled person that the scope of the invention may include embodiments having combinations of all or some of the features described herein as part of the same or separate embodiments.

References described herein are incorporated by reference. Neither these, nor any other documents or citations to any references, are admitted to be prior art documents or citations.

The invention will be explained in more detail in the following, non-limiting examples.

Examples

Abbreviations

AcOH acetic acid
ACN acetonitrile
DBU diazabicyclo[5.4.0]undec-7-ene
DCM dichloromethane
DIPEA N,N-Diisopropylethylamine
DMA N,N-dimethylacetamide
DMF N,N-dimethylformamide
DMSO dimethyl sulfoxide
EA ethyl acetate
Eq molar equivalent
$Et_3N$ triethylamine
EtOAc ethyl acetate
EtOH ethanol
KOH potassium hydroxyde
KOtBu potassium tert-butoxide
MeOH methanol
MTBE/MTB ether methyl tert-butyl ether
NaOH sodium hydroxide
NMP N-methyl-2-pyrrolidinone
Pd—C palladium-on-carbon
PE petroleum ether
RT room temperature
TLC thin layer chromatography
TFA trifluoroacetic acid
THF tetradydrofuran
TOTU O-[(ethoxycarbonyl)cyanomethylenamino]-N,N,N',N'-tetramethyluronium tetrafluoroborate
v/v volume/volume
XPHOS 2-Dicyclohexylphosphino-2',4',6'-triisopropylbiphenyl 1. Methods Liquid Chromatography-Mass Spectrometry (LC-MS)

Analytical samples were run on Agilent 1200 series instruments controlled by Agilent ChemStation Software. The system consists of an injector, a column compartment for 2 columns, a binary solvent pump, an UV-detector and a quadrupole mass spectrometer (Agilent 6100 series, ESI-ionization). If not stated otherwise, the mobile phase consisted of water and acetonitrile, both acidified with 0.1% formic acid. Separation was performed on YMC Meteoric Core C18 columns with 50 mm in length, 2.1 mm in diameter and packed with 2.7 μm material. Elution was done at 50° C. with a linear gradient ramping from 5 to 100% organic solvent over 1.8 min at a constant flow rate of 1 mL/min.

Nuclear Magnetic Resonance (NMR)

The compounds were either characterized via proton-NMR in d6-dimethylsulfoxide, d-chloroform, d-methanol or d-pyridine on a 400 MHz (Bruker) or 500 MHz NMR instrument (Bruker Avance 500 MHz with 5 mm BBFo-z-Grd) or a 600 MHz (Bruker Avance 600 MHz with 5 mm Cryoprobe CPTCI (1H-13C/15N z-Grd), and/or by mass spectrometry.

The magnetic nuclear resonance spectral properties (NMR) refer to the chemical shifts (δ) expressed in parts per million (ppm). The relative area of the shifts in the 1H-NMR spectrum corresponds to the number of hydrogen atoms for a particular functional type in the molecule. The nature of the shift, as regards multiplicity, is indicated as singlet (s), broad singlet (s. br.), doublet (d), broad doublet (d br.), triplet (t), broad triplet (t br.), quartet (q), quintet (quint.) and multiplet (m).

Separation of the Pure Enantiomers of Chiral Compounds.

Two Supercritical Fluid Chromatography (SFC) methods were used to separate enantiomers from racemates of chiral compounds, referred to as "analytical SFC" and "preparative SFC". The former is in particular suitable for small scale and the latter for larger scale.

Analytical SFC

Samples were run on an Agilent 1260 Infinity Hybrid SFC System, controlled by Agilent OpenLab CDS ChemStation Edition. The system consists of an injector, a heated column compartment including a switch for 15 columns, a $CO_2$-booster pump and a binary pump module for $CO_2$ and modifier flow. Detection was done with an UV-detector and Agilent 1100 series quadrupole mass spectrometer (ESI ionization). The backpressure regulator was set to 160 bar and heated to 60° C. If not stated otherwise, the columns were 100 mm in length, 4.6 mm in diameter and packed with 5 μm material. They were kept at RT during analysis. As mobile phase, a mixture of liquefied $CO_2$ and organic modifier with additive was used as indicated for each sample. The flow rate was kept at 3.5 mL/min.

Preparative SFC

Preparative separations were carried out on a Waters Prep 100q SFC System, controlled by Waters MassLynx Software. The system consists of an open bed injector/collector, a heated column compartment including a switch for 6 columns, a $CO_2$-booster pump, a pump module for modifier flow. Detection was done by UV and a quadrupole mass spectrometer (Waters Aquity QDa, ESI-ionization). To enable quantitative collection, the gas liquid separator was driven with a make-up flow of 30 mL/min methanol. The backpressure regulator was set to 120 bar and heated to 60° C. If not stated otherwise, the columns were 250 mm in length, 20 mm in diameter and packed with 5 μm material.

2. General Synthesis Methods

Suitable methods to synthesize compounds of the invention are described below.

Intermediate Compounds I and II

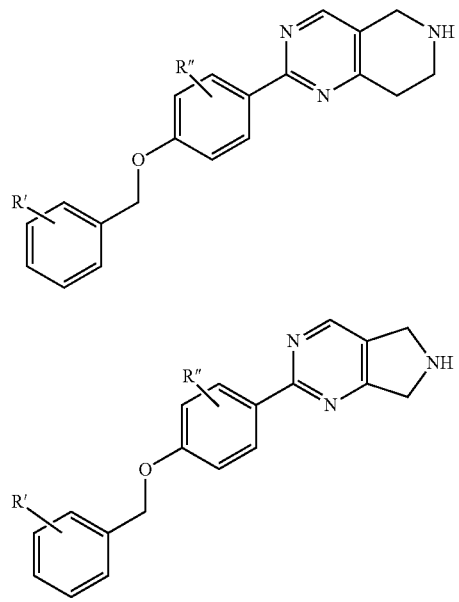

Intermediate compound I can be prepared from intermediate compound V, for which two synthesis routes are described in reaction schemes 1 and 2. For intermediate compound V, tert-butyl-2-choloro-7,8-dihydropyrido[4,3-d]pyrimidine-6(5H)-carboxylate can be reacted with a properly R' and/or R'' substituted potassium (4-benzyloxyphenyl) trifluoroborate compound or with a properly R' and/or R'' substituted benzyloxy-phenylboronic acid compound in a Suzuki reaction. Deprotection of compound V can be can be achieved using TFA. Alternatively, compound V can be converted in the corresponding carboxylic acid containing compound under the influence of NaOH, KOH or LiOH.

Scheme 1

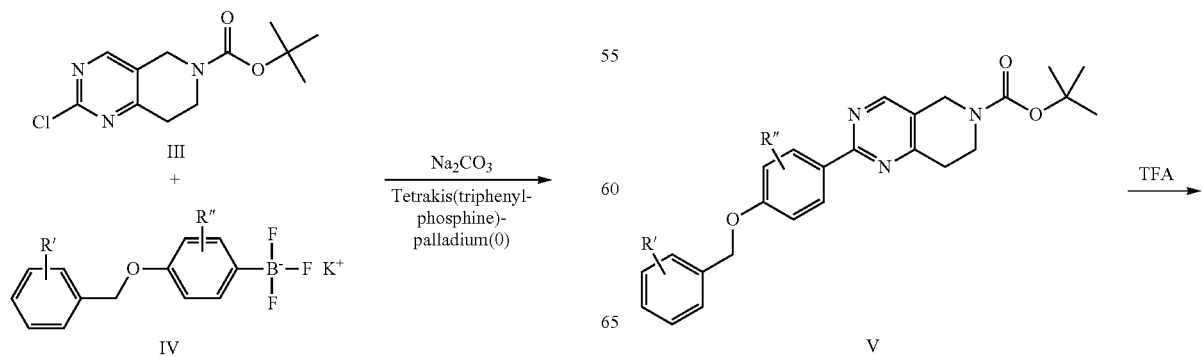

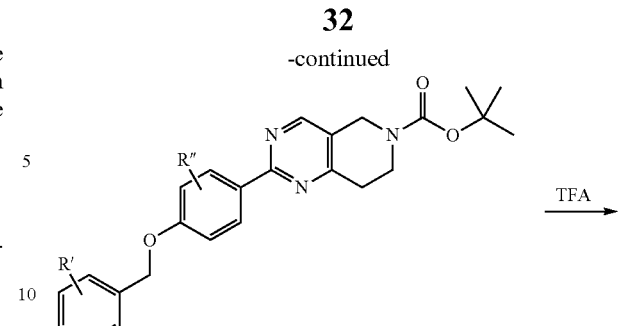

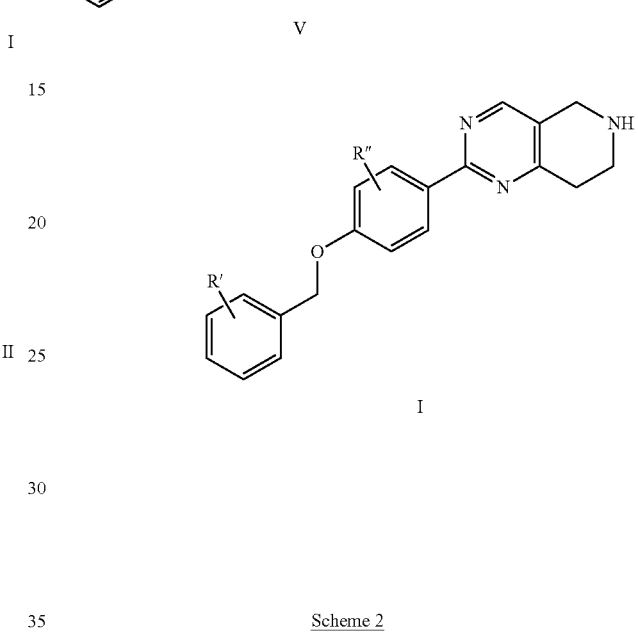

Scheme 2

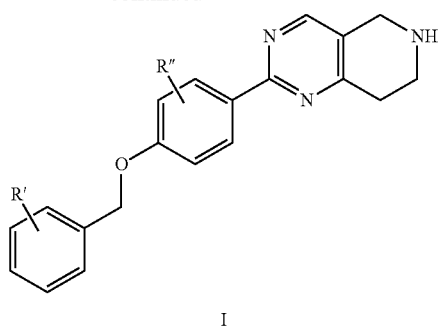

I

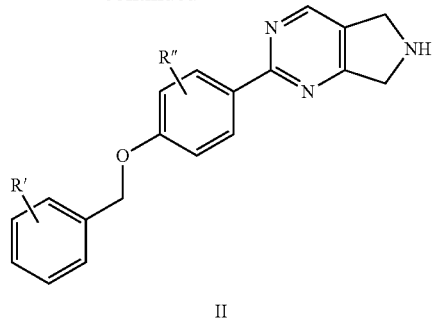

II

Intermediate compound I can be prepared in a similar way from intermediate compound VIII, for which two synthesis routes are described in reaction schemes 3 and 4. For intermediate compound VIII, tert-butyl-2-choloro-5H-pyrrolo[3,4-D]pyrimidine-6(7H)-carboxylate can be reacted with a properly R' and/or R" substituted potassium (4-benzyloxyphenyl)trifluoroborate compound or with a properly R' and/or R" substituted benzyloxy-phenylboronic acid compound in a Suzuki reaction. Deprotection of compound VIII can be can be achieved using TFA. Alternatively, compound VIII can be converted in the corresponding carboxylic acid containing compound under the influence of NaOH, KOH or LiOH.

Scheme 3

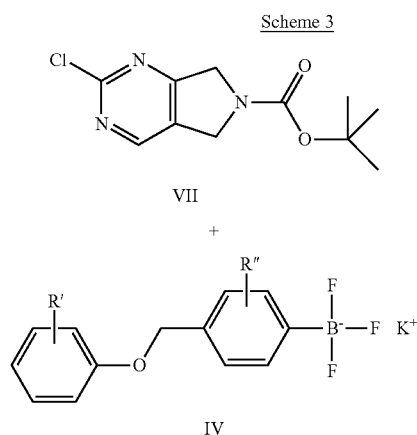

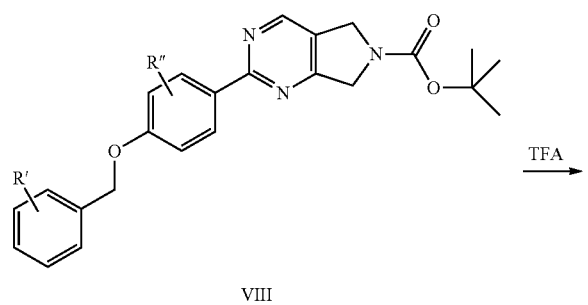

VIII

Scheme 4

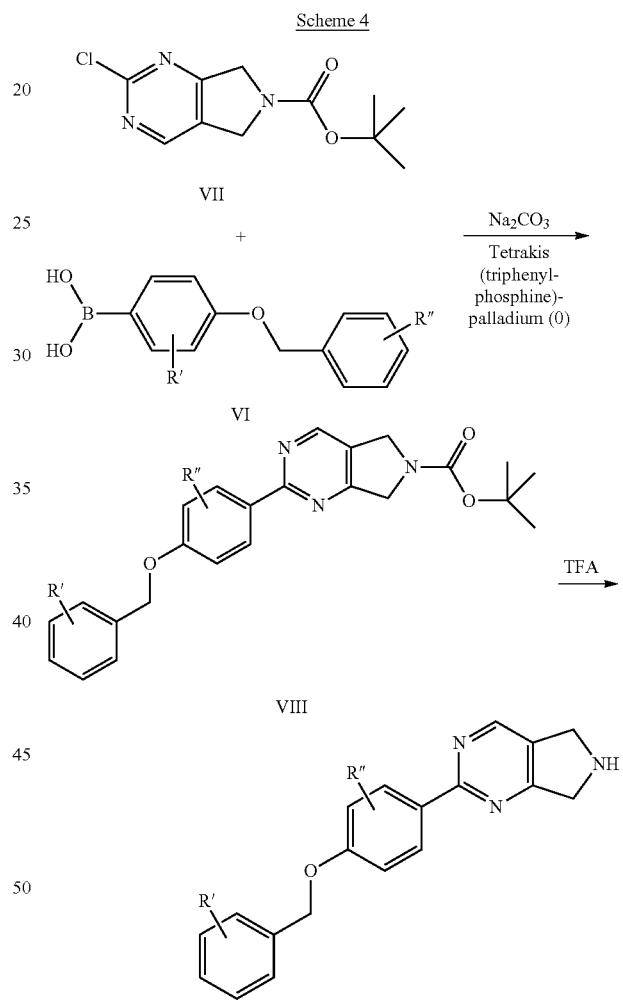

Intermediate Compounds IX-XVI

In a similar way as for pyrimidine compounds described in schemes 1-4, the corresponding pyridine compounds (compounds IX, X), pyrazine compounds (compounds XI, XII), pyridazine compounds (compounds XIII, XIV), triazine compounds (compounds XV, XVI) and the corresponding compounds having a 7-membered cyclic amine can be prepared from the properly R' and/or R" substituted potassium (4-benzyloxyphenyl)trifluoroborate compound or benzyloxy-phenylboronic acid compound.

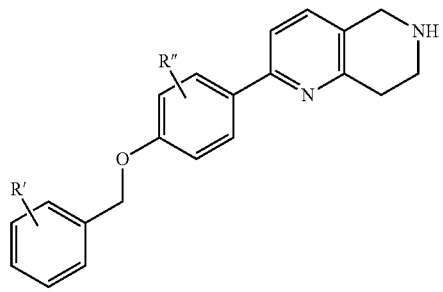 IXa
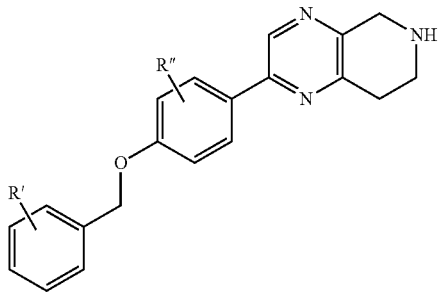 XI
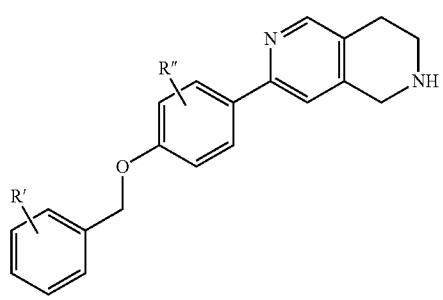 IXb
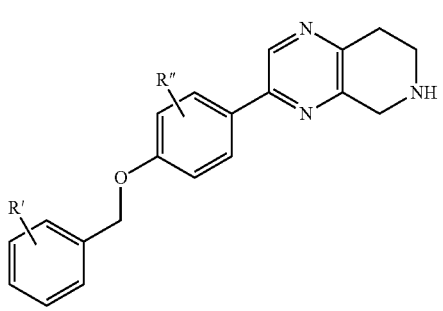 XIc
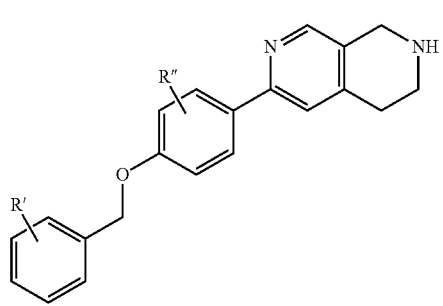 IXe
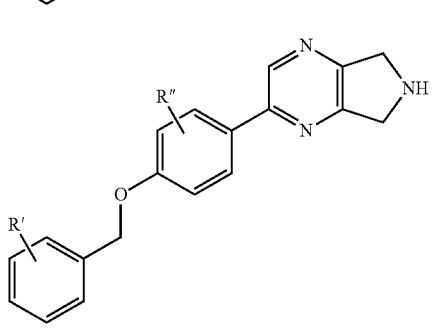 XII
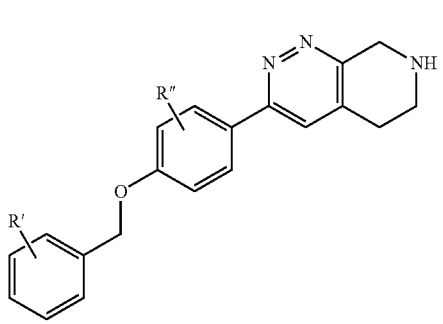 XIII
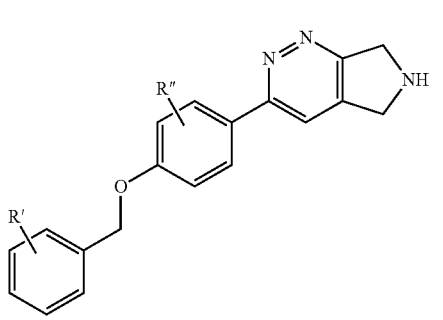 XIV
Xa
Xb

Benzylphenyl-Containing Derivatives

The synthesis routes described in schemes 1-4 are further suitable to prepare optionally substituted benzylphenyl-containing derivatives instead of optionally substituted benzyloxyphenyl-containing derivatives using the properly R' and/or R'' substituted potassium (4-benzylphenyl)trifluoroborate compound or benzylphenylboronic acid compound.

Introduction of R* Substituents

Method A.

The synthetic routes for the introduction of a variety of R* substituents in compounds I is shown in scheme 5 giving general compound XVII.

Compounds XVII can be prepared by Michael-Addition reactions starting from secondary amine I, the corresponding alpha,beta-unsaturated ester and a base like DBU (Scheme 5, XVIIa to XVIIc). Alternative compound XVII can be obtained from an N-alkylation using secondary amine I and the corresponding alkyl bromide (Scheme 5, XVIId) or in a reductive amination reaction using secondary amine I, the corresponding aldehyde or ketone and a reducing agent like sodium triacetyboro hydride (Scheme 5, XVIIe and XVIIf).

Scheme 5 shows a number of routes starting from compound I. It is clear to a person skilled in the art that these routes are suitable to introduce alternative substituents in compounds I using the appropriate reagent, as well as in compounds II and IX-XVI. Carboxylate containing R* substituents can be converted to the carboxylic acid under the influence of NaOH, KOH or LiOH.

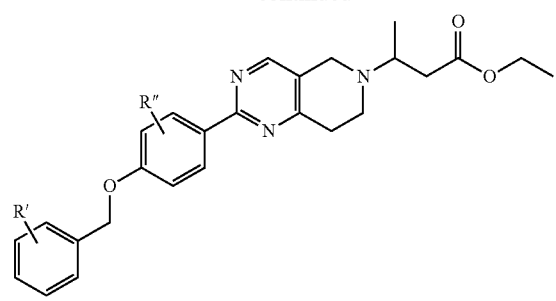

XVIIc

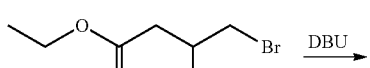

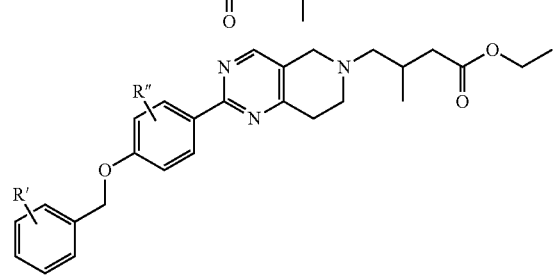

XVIId

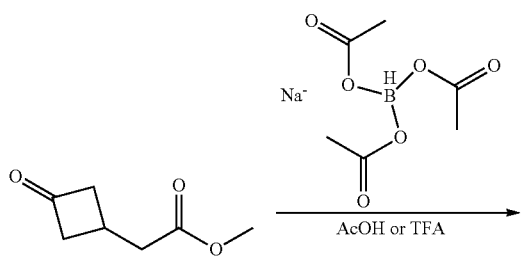

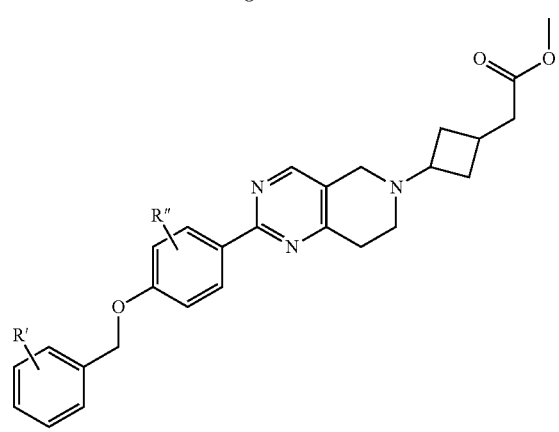

XVIIe

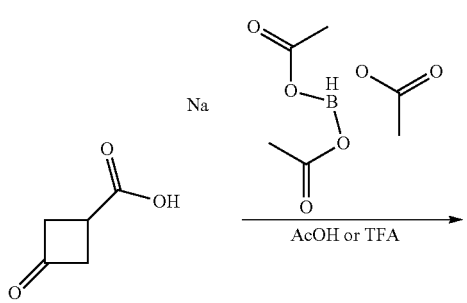

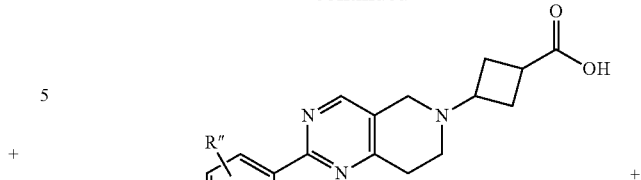

XVIIf

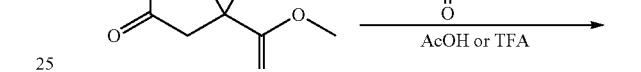

Method B.

Alternatively, R* substituents can be introduced into the compounds of the invention via the precursors tert-butyl-2-choloro-7,8-dihydropyrido[4,3-d]pyrimidine compounds (to provide compounds XX, starting from compound III), the corresponding pyridine compounds (to provide compounds XXI and XXII, starting from compounds XVIII and XIX, respectively) or tert-butyl-2-choloro-5H-pyrrolo[3,4-D]pyrimidine compounds (starting from compound VII). The general synthesis routes for the preparation of compounds XX-XXII with a variety of R* substituents is shown in reaction scheme 6. It is clear to a person skilled in the art that these routes are suitable to introduce alternative R* substituents in compounds III, XVIII and XIX, as well as in compounds VII and the corresponding pyrazine, pyridazine and triazine compounds, using the appropriate reagent.
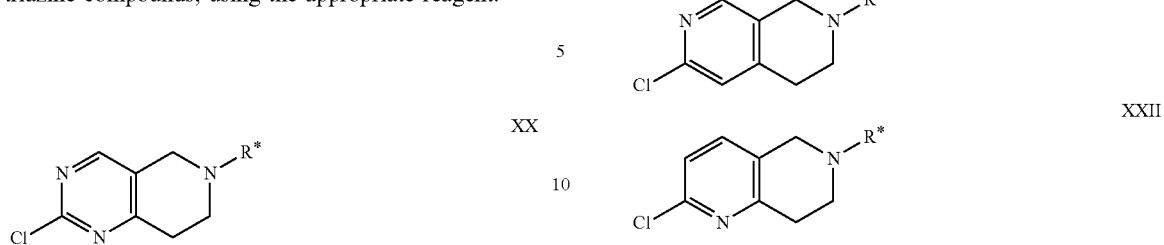
Scheme 6
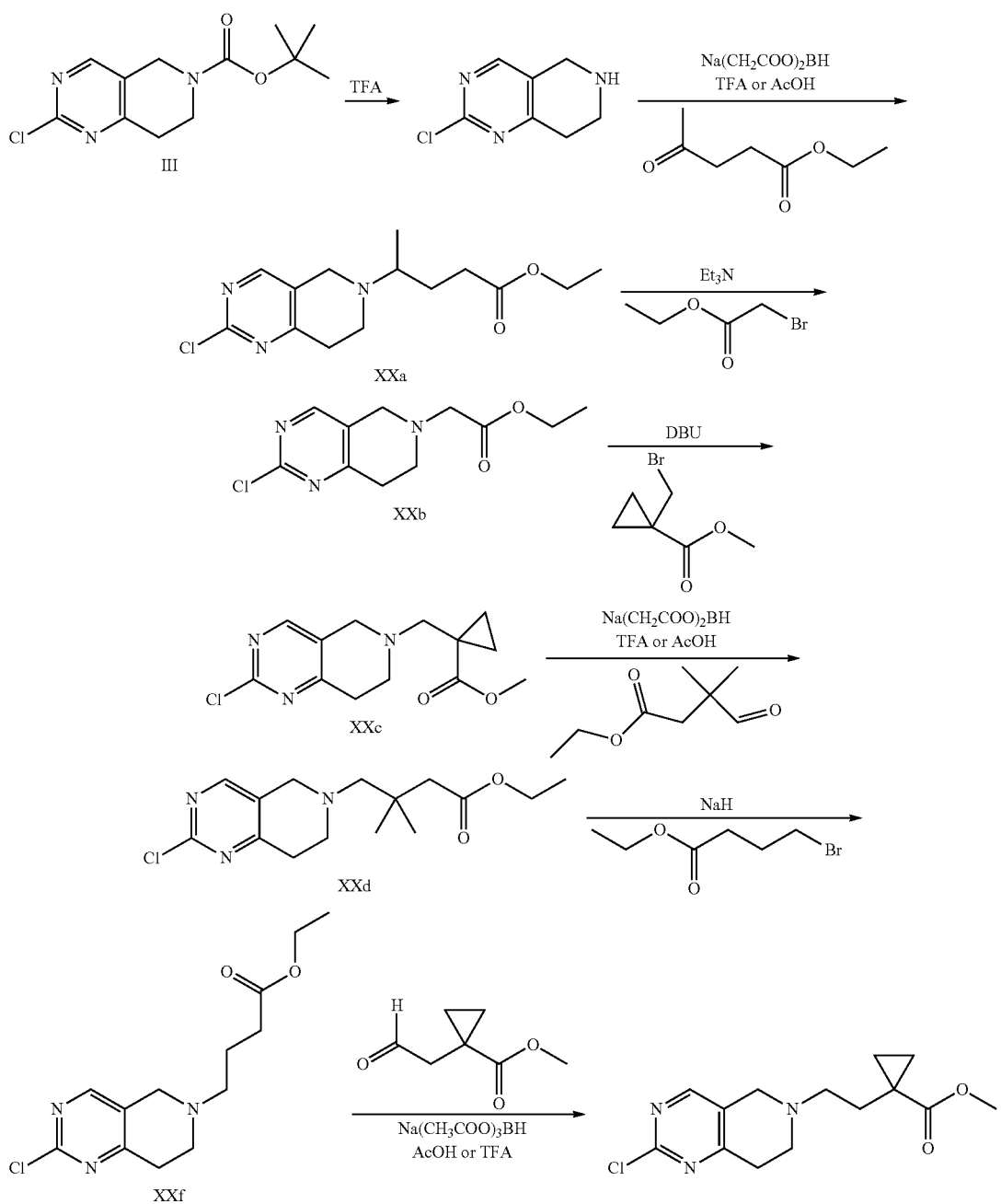

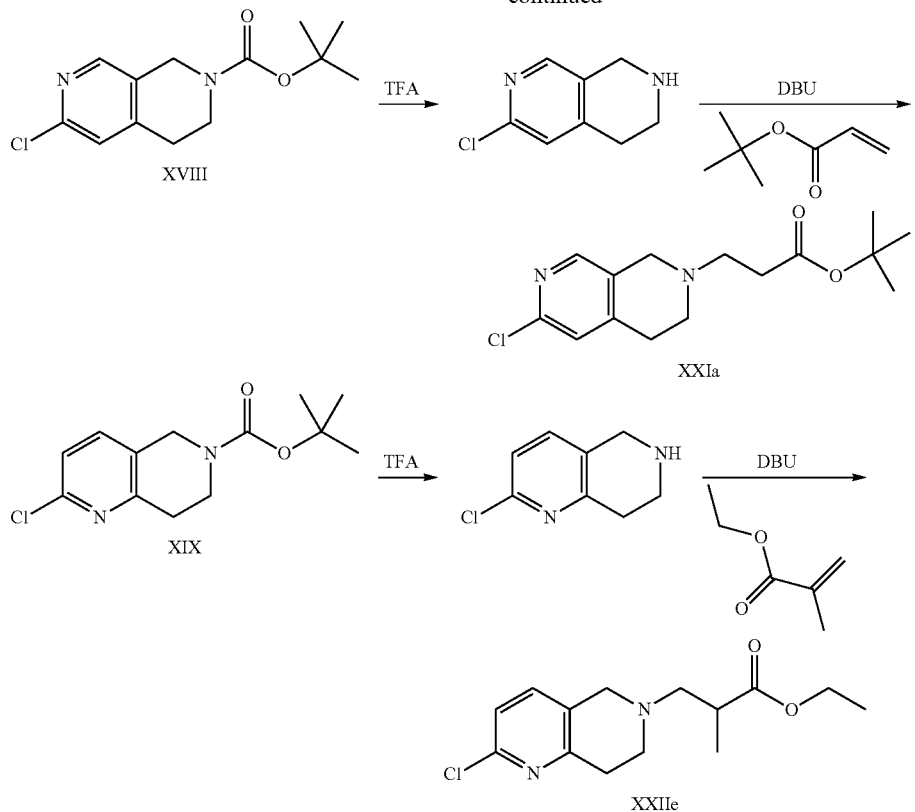

The resulting products can be further processed in a Suzuki reaction in accordance with reactions schemes 1-4, and optionally have alternative R' substituents introduced, e.g. in accordance with reaction scheme 7.

Introduction of Alternative R' Substituents

Method A. As is apparent from schemes 1-4, substituents R' can be introduced in compounds I, II and IX-XVI by using the appropriately substituted benzyloxy-phenylboronic acid compound in the synthesis.

Method B.

Alternatively, the synthesis route described in scheme 7 can be followed to introduce substituents in compounds I, II, IX-XVI and XVII, either before or after the introduction of R* substituents as described in scheme 5. Compounds I, II, IX-XVI and XVII can be converted to the phenol derivative XXIII derivative via a palladium mediated reaction via hydrogenation (e.g.: with palladium on carbon). Alternatively, compound XXIII can be prepared from 4-hydroxybenzamidine hydrochloride and tert-butyl 3-((dimethylamino)methylene)-4-oxopiperidine-1-carboxylate in a condensation reaction, whereby substituent R* can be varied after deprotection. Compound XXIII can be converted to the desired benzyl ether derivative XXIV with the properly R'''  substituted benzyl halide. Scheme 7 shows the synthesis for compounds XVII as an example. It is clear to a person skilled in the art that these routes are suitable to introduce alternative R''' substituents in compounds I, II and IX-XVI as well using the appropriately substituted benzyl halide.

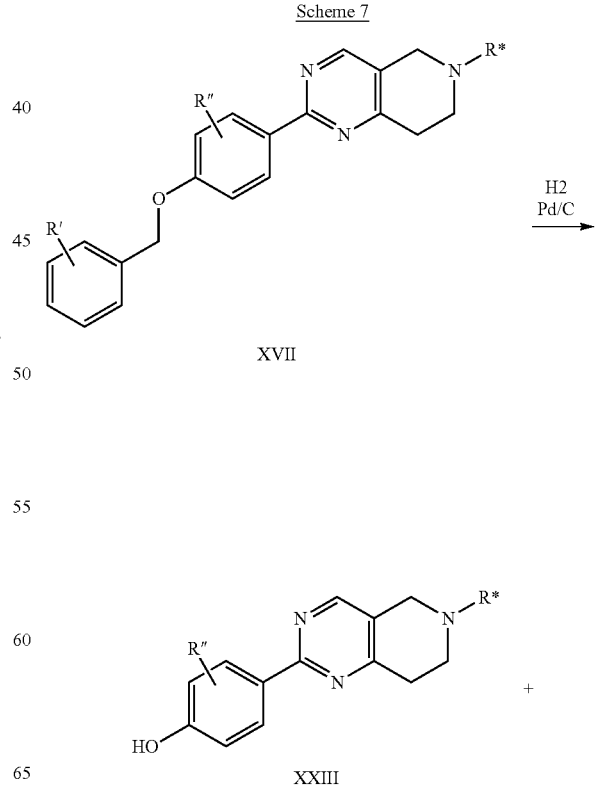

Scheme 7

-continued

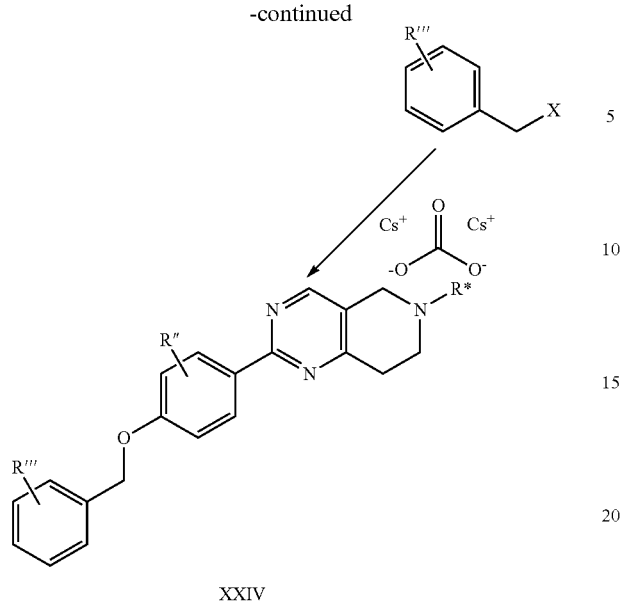

XXIV

Intermediate Compounds XXXIII and XXV

Scheme 8 shows the synthesis of intermediate compound XXV.

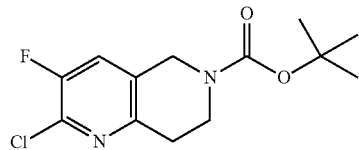

XXV 2,6-dichloro-5-fluoronicotinonitrile (compound XXVI) can be reacted with (4-methoxyphenyl)methanol to form compound XXVIII in a addition-elimination reaction, followed by Suzuki reaction with potassium trifluoro(vinyl)borate to provide compound XXIX. Compound XXX can be obtained from compound XXIX by reaction with benzyl amine. Reduction of the amide in compound XXX with borane will give compound XXXI. Reaction of benzyl ether derivative XXXI with phosphoryl chloride will give the corresponding chloro pyridine derivative XXXII. The benzyl group can be removed from compound XXII with 1-chloroethyl chloroformate. Finally, the piperidine of compound XXXIII can be protected with a BOC group.

Scheme 8

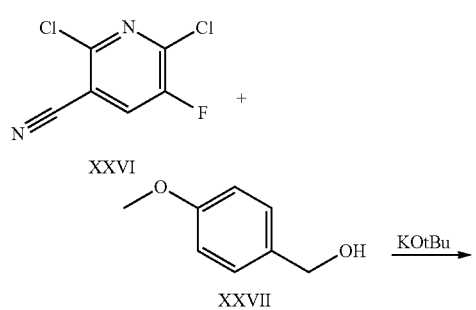

-continued

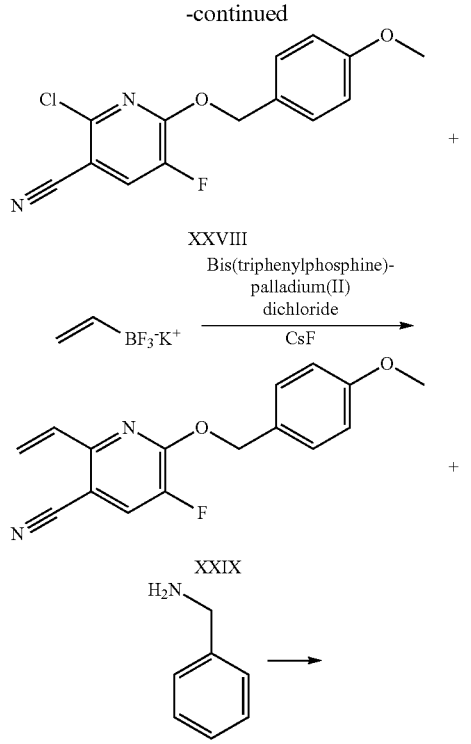

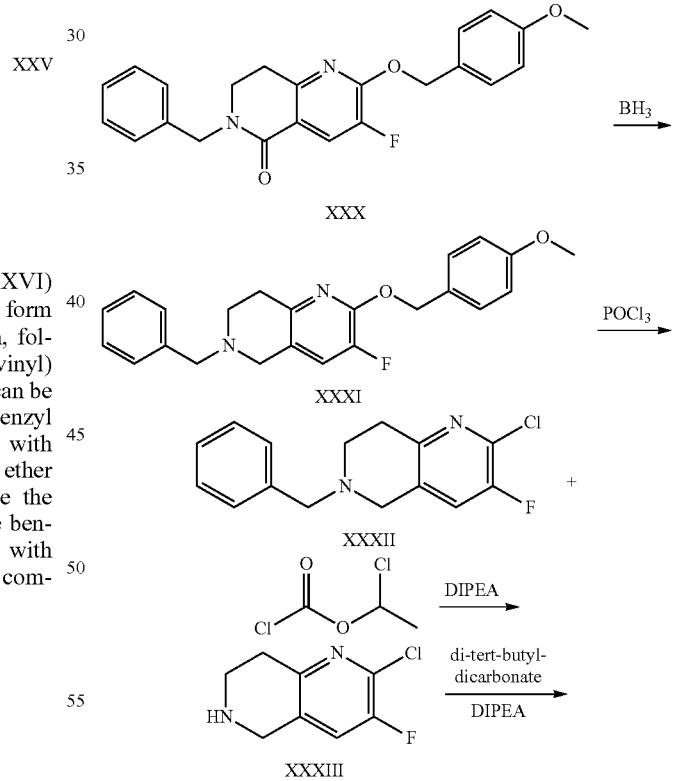

Compounds XXXIV

Scheme 9 shows the synthesis of compounds XXXIV. Compound XX can be converted to the desired ether intermediate XXXIV with the properly R''' substituted benzyl alcohol in a palladium mediated reaction.

Scheme 9

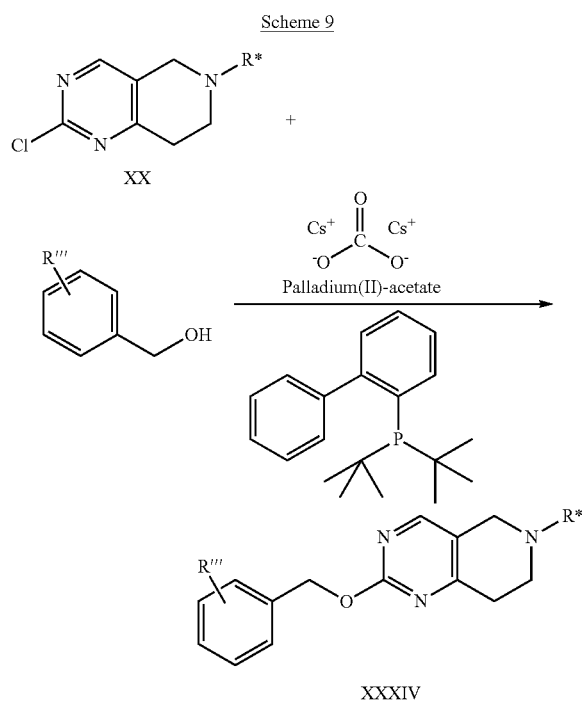

XXXIV

Scheme 9 shows the synthesis for compounds XXXIV as an example. It is clear to a person skilled in the art that this route is suitable to introduce alternative R* substituents in compounds III, XVIII and IX, as well as in compounds VII and the corresponding pyrazine, pyridazine and triazine compounds, as well as pyrrolidine containing compounds, using the appropriate starting compound and properly R''' substituted benzyl alcohol.

Compounds XXXV and XXXVI

The general synthesis of compound XXXV and XXXVI containing an ethynyl-linker is depicted in scheme 10. Compound III and compounds XX can be converted to the desired intermediates XXXV and XXXVI with the properly R''' substituted ethynylbenzene in a palladium and CuI mediated Sonogashira reaction.

Scheme 10

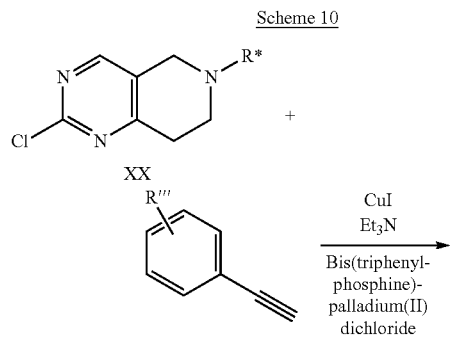

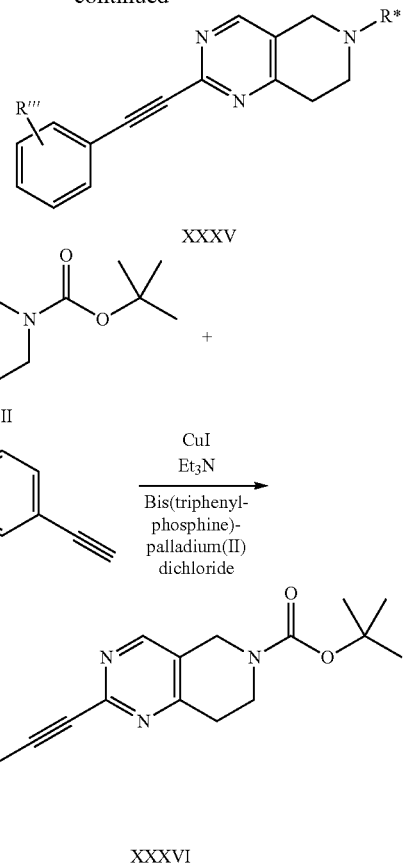

XXXV

XXXVI

Scheme 10 shows the synthesis for compounds XXXV and XXXVI starting from compound III and compounds XX as an example. It is clear to a person skilled in the art that this route is suitable starting from compounds XXI, XXII and XXV, as well as from other corresponding pyrazine, pyridazine and triazine compounds of the invention and pyrrolidine containing compounds, using the appropriate starting compound and properly R''' substituted ethynylbenzene.

Compounds XXXVII and XXXVIII

The general synthesis of compounds XXXVII containing a alkylene linker is depicted in scheme 11. Compound III can be converted to intermediate compounds XXXVII with the properly R''' substituted benzylzinc bromide in a palladium mediated Negishi reaction. Deprotection of compound VIII can be can be achieved using TFA. Alternatively, compound VIII can be converted in the corresponding carboxylic acid containing compound under the influence of NaOH, KOH or LiOH.

Scheme 11

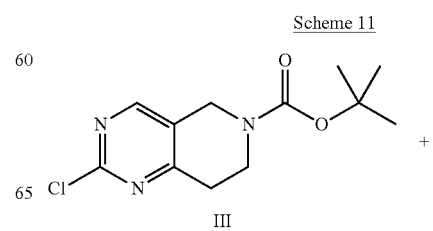

III

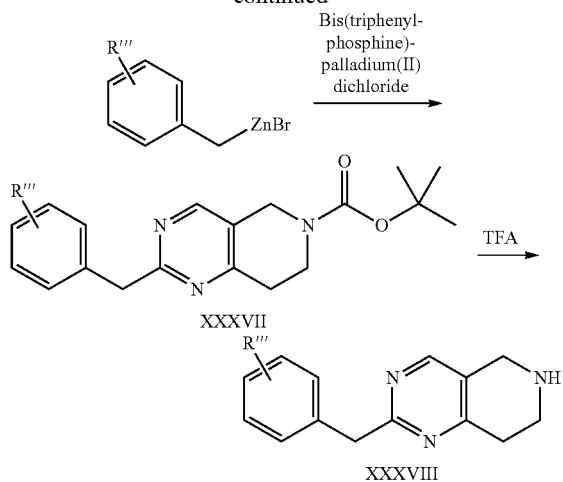

Scheme 11 shows the synthesis for compounds XXXVII and XXXVIII starting from compound III as an example. It is clear to a person skilled in the art that this route is suitable starting from compounds VII and XXV, as well as to prepare other corresponding pyrazine, pyridazine and triazine compounds of the invention and pyrrolidine containing compounds, using the appropriate starting compound and properly R''' substituted benzylzinc bromide. Optionally, R* can be subsequently introduced in accordance with scheme 5.

Compounds XXXIX and XL

The general synthesis of compounds XXXIX and XL is depicted in scheme 12. In a Suzuki reaction hetaryl chloride III can be converted to the corresponding benzaldehyde derivative. Addition of a substituted benzylzinc bromide will give the secondary alcohol. This can either be converted with diethylsulphur trifluoride to the corresponding fluoride (compounds XXXIX), with sodium borohydride to the saturated ethylene derivative (compounds V) or with methyl N-(triethylammoniumsulfonyl)carbamate (Burgess reagent) to the styryl derivative (compounds XLI), which in turn may be converted to the saturated ethylene derivative (compounds XL) via hydrogenation (e.g.: with palladium on carbon). Alternatively, oxidation followed by reaction with diethylsulphur trifluoride will give the corresponding ethylene difluoride derivative (compounds XL).

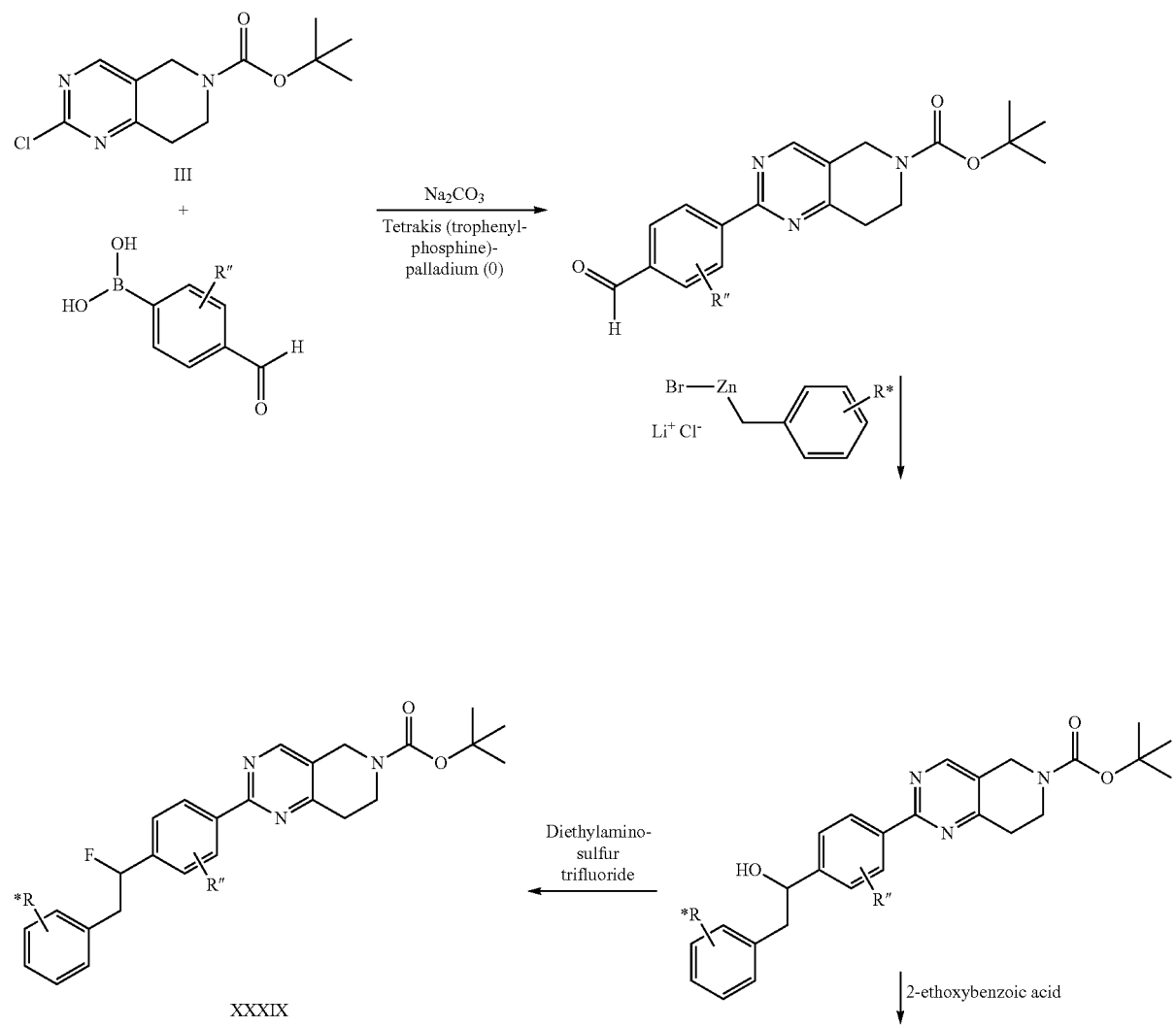

51
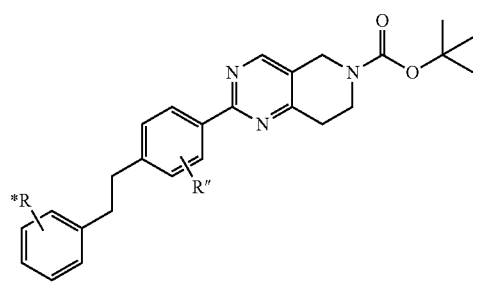
V
52
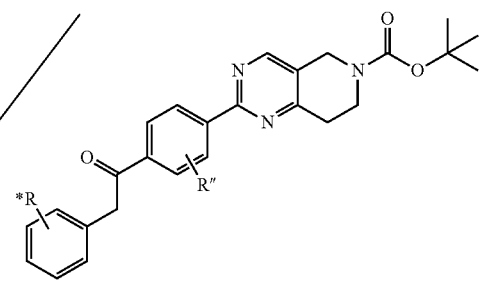
-continued
NaOH₄, Trifluoro acetic acid
Burgess reagent
Diethylamino-sulfur trifluoride
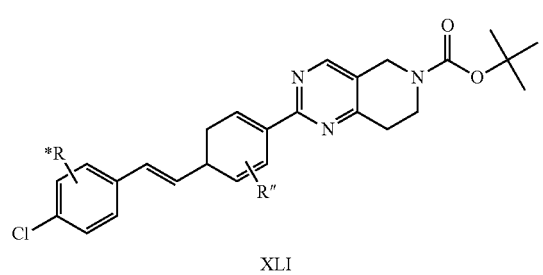
XLI
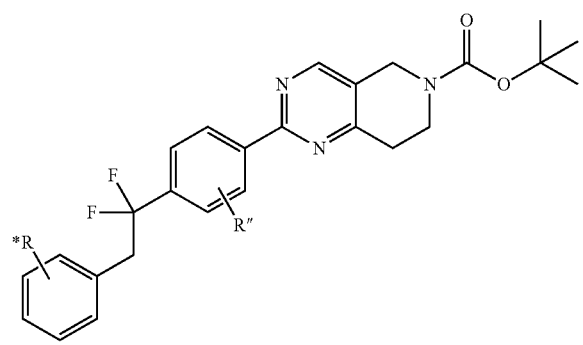
XL Deprotection is for instance done under acidic conditions. Alternative R* substituents can subsequently be introduced as described above. Alternatively, deprotection can be followed by reductive amination and saponification to give the compounds of formula (I).

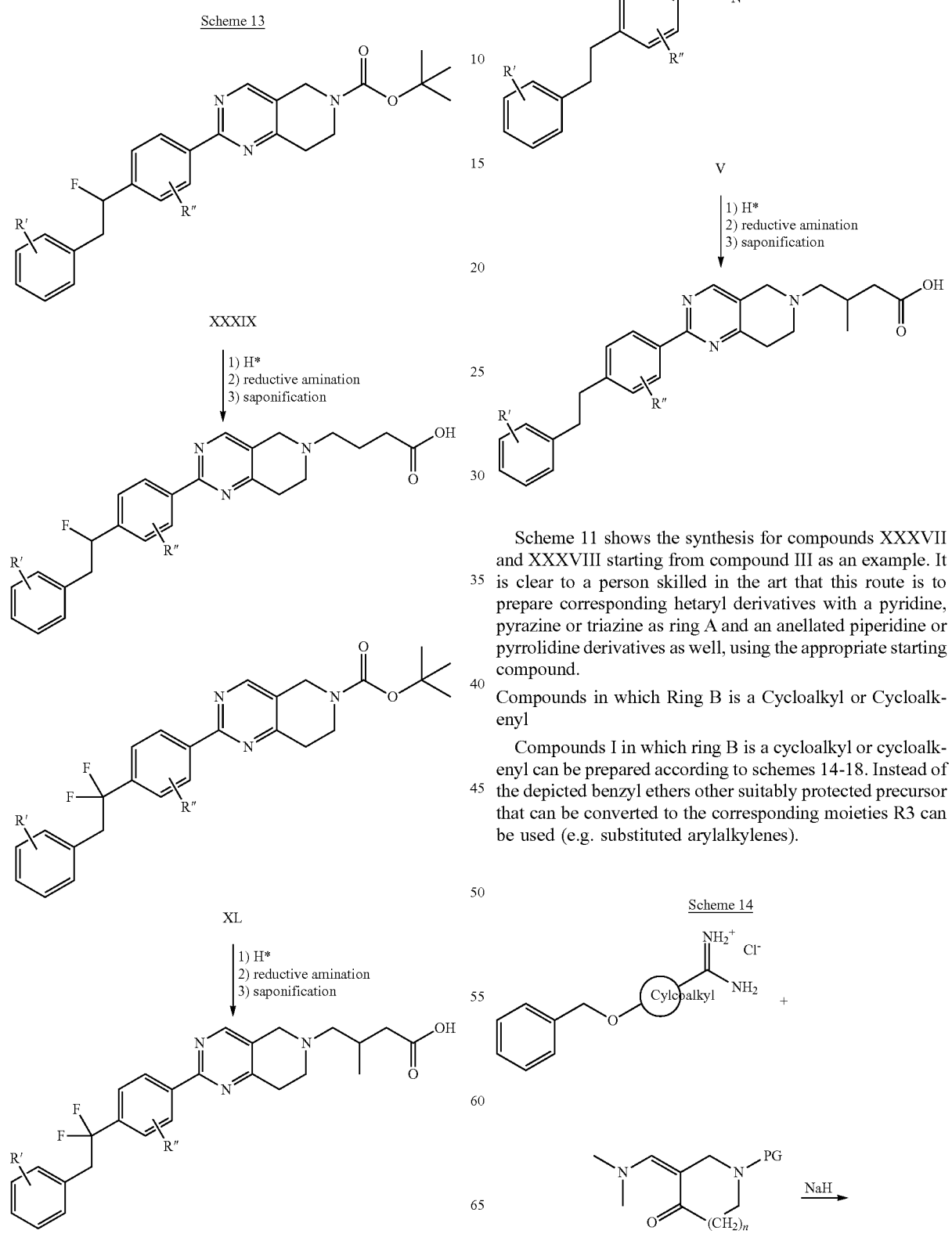

Scheme 11 shows the synthesis for compounds XXXVII and XXXVIII starting from compound III as an example. It is clear to a person skilled in the art that this route is to prepare corresponding hetaryl derivatives with a pyridine, pyrazine or triazine as ring A and an anellated piperidine or pyrrolidine derivatives as well, using the appropriate starting compound.

Compounds in which Ring B is a Cycloalkyl or Cycloalkenyl

Compounds I in which ring B is a cycloalkyl or cycloalkenyl can be prepared according to schemes 14-18. Instead of the depicted benzyl ethers other suitably protected precursor that can be converted to the corresponding moieties R3 can be used (e.g. substituted arylalkylenes).

Scheme 14

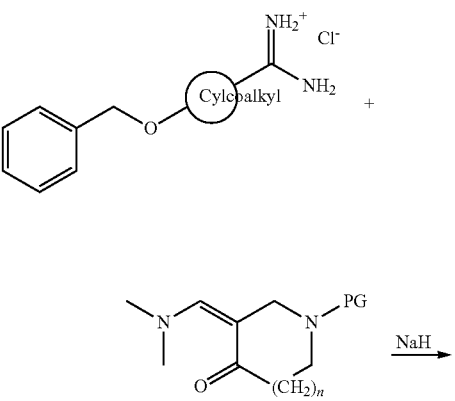

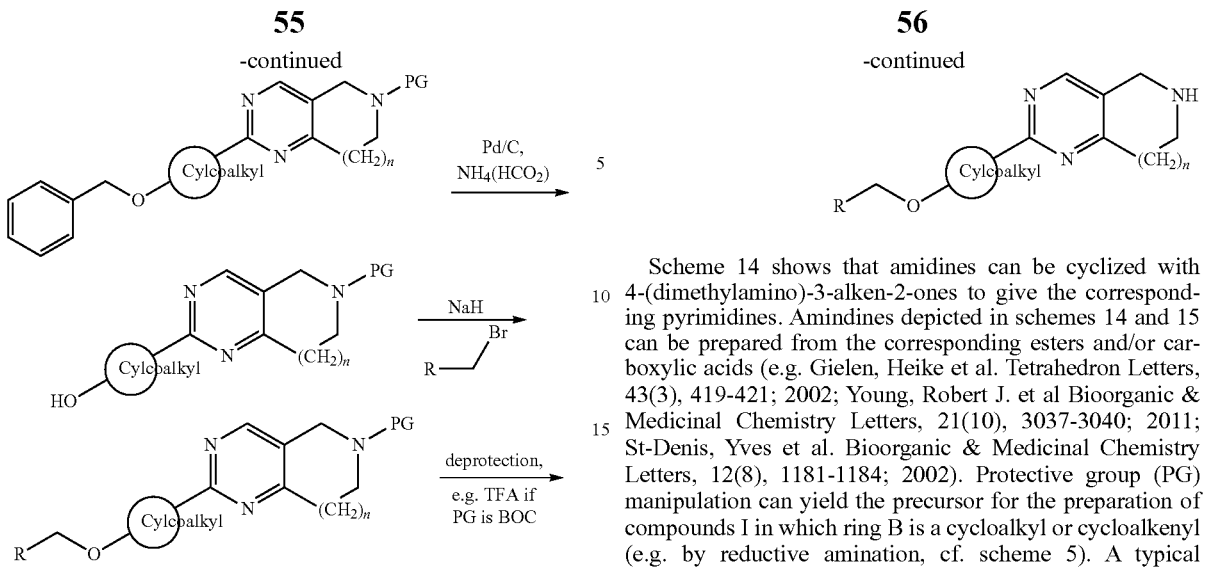

Scheme 14 shows that amidines can be cyclized with 4-(dimethylamino)-3-alken-2-ones to give the corresponding pyrimidines. Amindines depicted in schemes 14 and 15 can be prepared from the corresponding esters and/or carboxylic acids (e.g. Gielen, Heike et al. Tetrahedron Letters, 43(3), 419-421; 2002; Young, Robert J. et al Bioorganic & Medicinal Chemistry Letters, 21(10), 3037-3040; 2011; St-Denis, Yves et al. Bioorganic & Medicinal Chemistry Letters, 12(8), 1181-1184; 2002). Protective group (PG) manipulation can yield the precursor for the preparation of compounds I in which ring B is a cycloalkyl or cycloalkenyl (e.g. by reductive amination, cf. scheme 5). A typical example is shown in scheme 15:

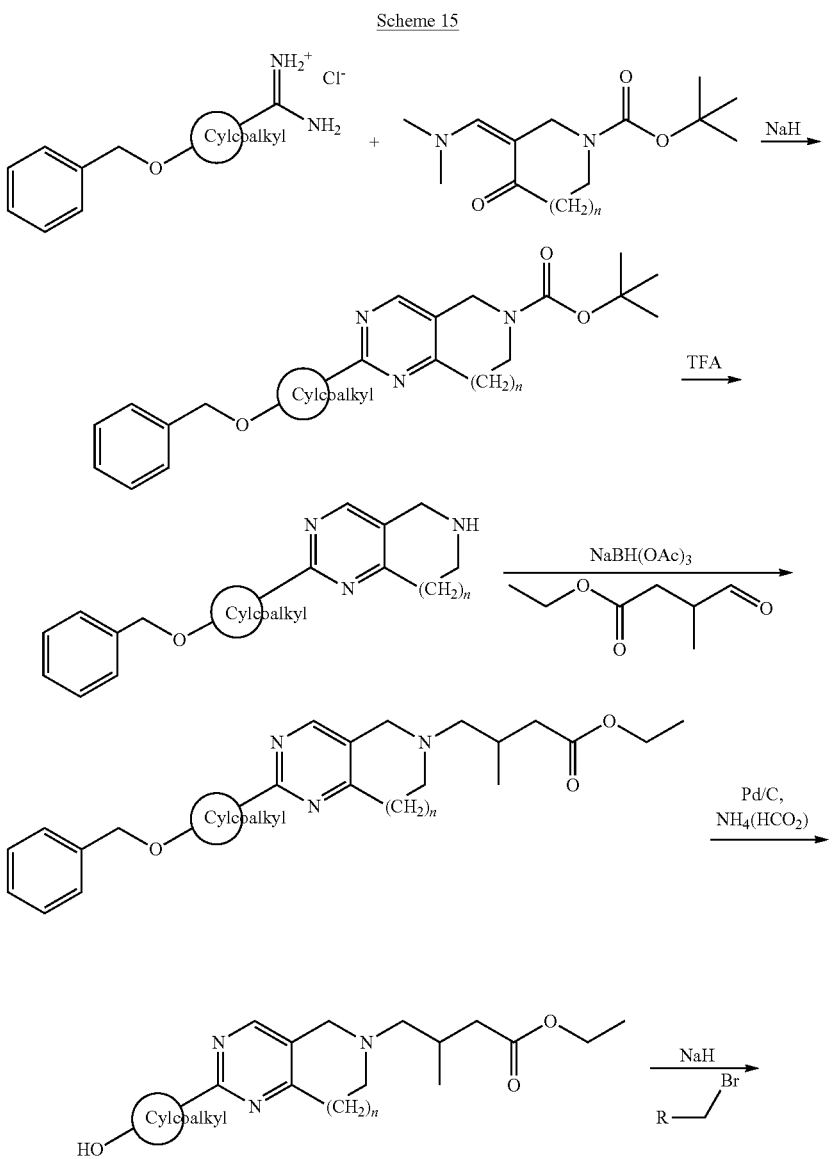

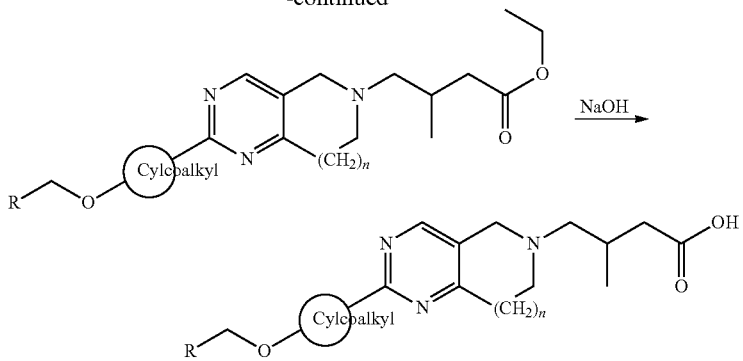

Alternatively Grignard reagents can be coupled with the corresponding hetaryl chlorides (e.g. as described in Qin, Jie et al Organic Letters, 13(24), 6568-6571; 2011), as shown in scheme 16:

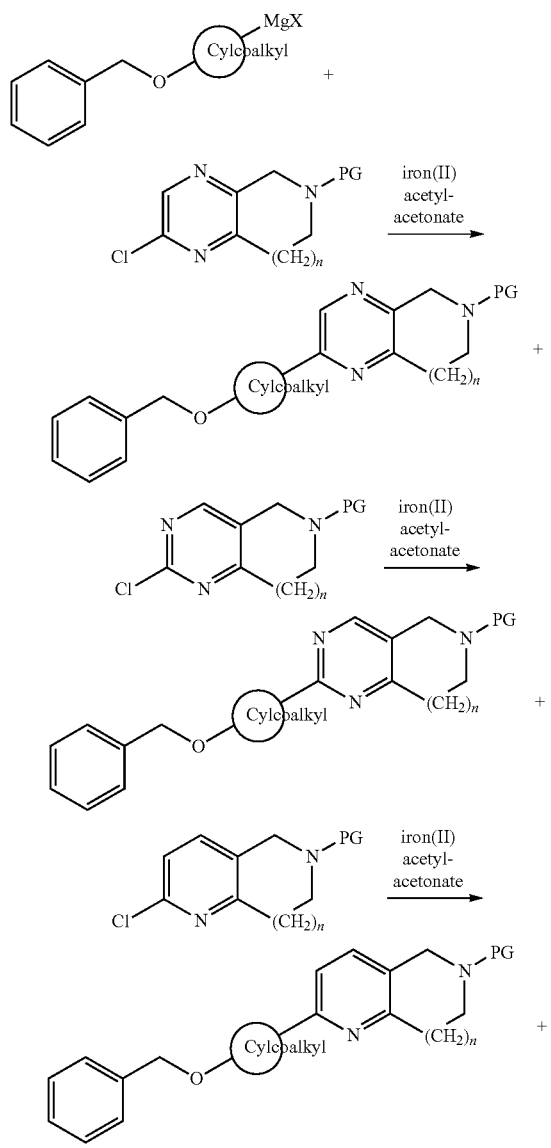

-continued

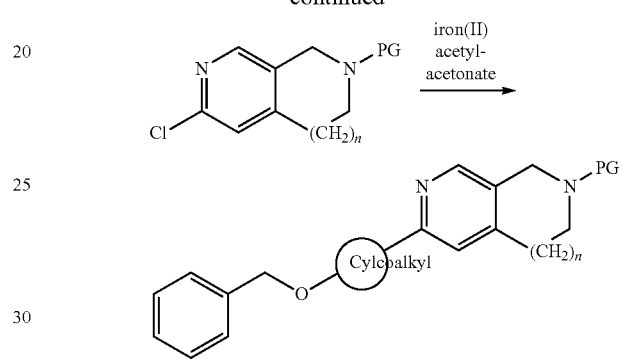

X is halogen, PG is protective group.

Instead of Grignard reagents zinc organyls can be used in palladium catalyzed reactions to prepare the corresponding building blocks containing a cycloalkyl or cycloalkenyl as ring B (e.g as described in Chekmarev, Dmitriy S. et al, Tetrahedron Letters, 46(8), 1303-1305; 2005 or WO2011131596), as shown in scheme 17.

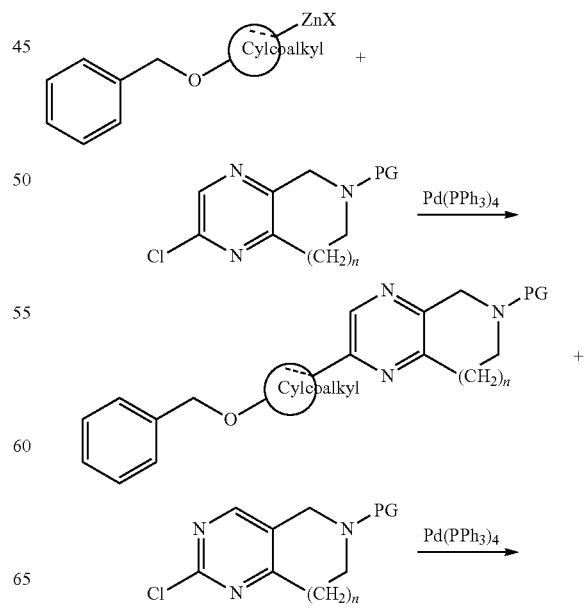

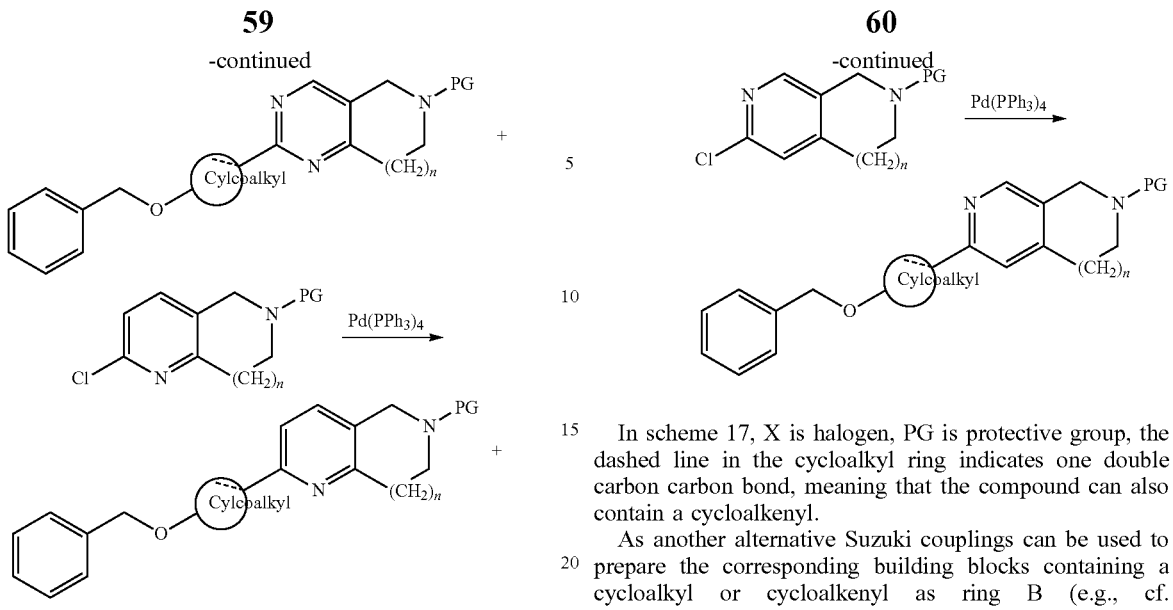
In scheme 17, X is halogen, PG is protective group, the dashed line in the cycloalkyl ring indicates one double carbon carbon bond, meaning that the compound can also contain a cycloalkenyl.
As another alternative Suzuki couplings can be used to prepare the corresponding building blocks containing a cycloalkyl or cycloalkenyl as ring B (e.g., cf. WO2011131596), as shown in scheme 18.

Scheme 18
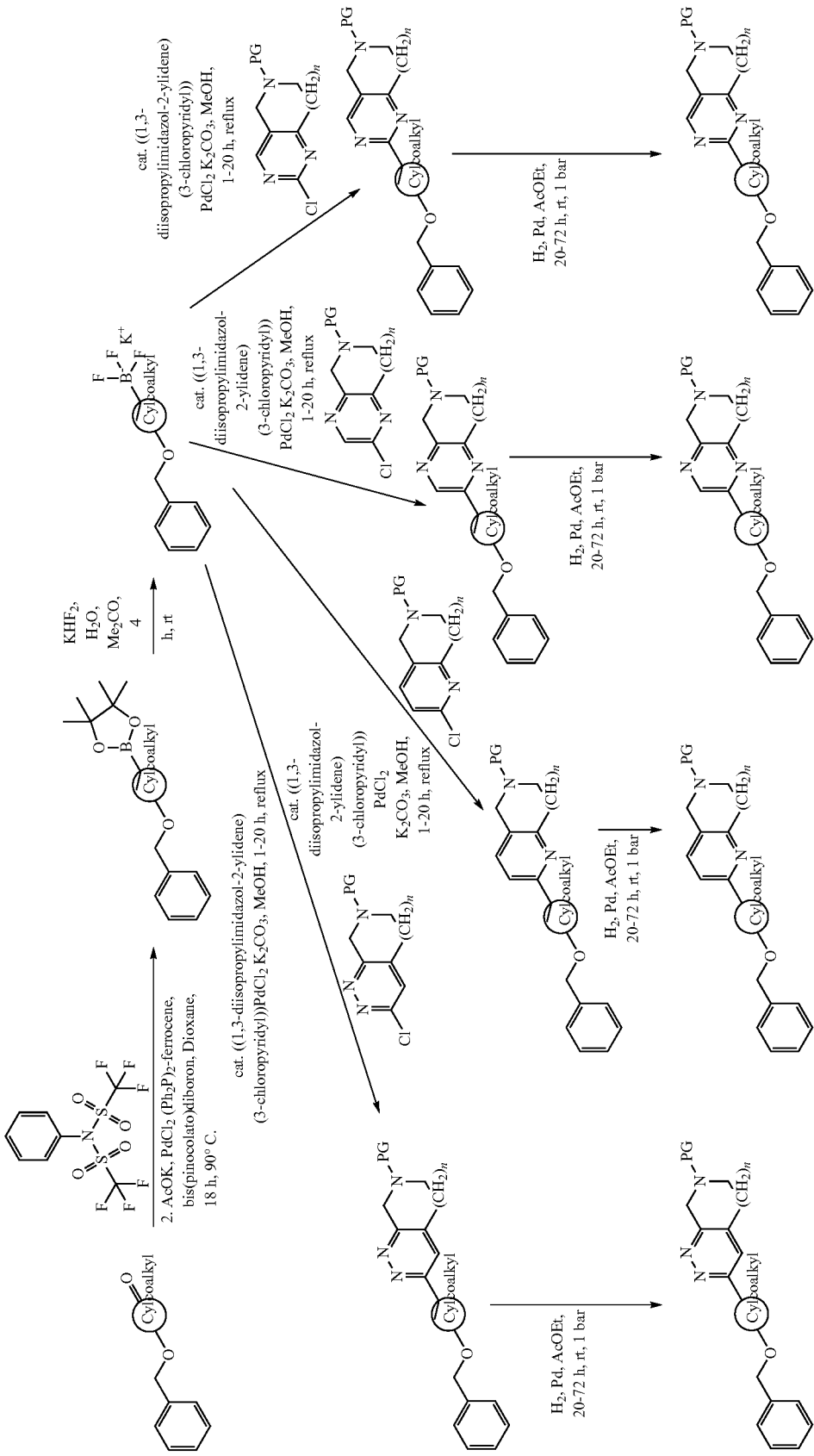

3. Synthesis of Intermediates

General Method for Synthesis of Intermediate Compounds I from Compounds III and IV (Scheme 1)

For the preparation of intermediate I, tert-butyl-2-choloro-7,8-dihydropyrido[4,3-d]pyrimidine-6(5H)-carboxylate (1 eq), $Na_2CO_3$ (2.1 eq) and a properly R'/R" substituted potassium (4-benzyloxyphenyl)trifluoroborate compound (1.2 eq) were dissolved in DMF to give a yellow solution. The solution was rinsed with Argon (5-30 min). Tetrakis(triphenylphosphine)palladium(0) (0.05 eq) was added and the mixture was heated for 60 min at 120° C. to yield a dark grey reaction mixture. The reaction mixture was evaporated, the residue was dissolved in $DCM/H_2O$. After phase separation, the organic layer was washed once with water and once with saturated NaCl solution, dried over $MgSO_4$, filtered and evaporated. The residue was purified using silica gel chromatography (MeOH:/DCM) giving intermediate compound V. Deprotection with acid (e.g. TFA) followed by aqueous work-up and chromatography gave compound I.

General Method for Synthesis of Intermediate Compounds I from Compounds III and VI (Scheme 2)

Tert-butyl-2-chloro-7,8-dihydropyrido[4,3-d]pyrimidine-6(5H)-carboxylate (1 eq) and a properly R'/R" substituted 4-(benzyloxy)phenylboronic acid (1.2 eq) were dissolved in DMF. $Na_2CO_3$ (10% in water; 2.1 eq) was added and the solution was rinsed with argon (3 min). Tetrakis(triphenylphosphine)palladium(0) (0.05 eq) was added and the mixture was heated for 30 min at 120° C. to yield a dark grey reaction mixture. The reaction mixture was evaporated and the residue dissolved in difluoromethane/$H_2O$. After phase separation, the organic layer was washed once with water, dried ($MgSO_4$) and evaporated overnight. The resulting white residue was purified in n-pentane with diethyl ether, washed again with n-pentane and dried to giving compound V. Deprotection with acid (e.g. TFA) followed by aqueous work-up and chromatography gave compound I.

General Method for Synthesis of Intermediate Compound II from Compounds IV and VII (Scheme 3)

Tert-butyl-2-choloro-5H-pyrrolo[4,3-d]pyrimidine-6(7H)-carboxylate (1 eq) was dissolved in DMF and under stirring a properly R' and/or R" substituted potassium (4-benzyloxyphenyl)trifluoroborate compound (1.2 eq) and $Na_2CO_3$ (10% in water, 2.1 eq) were added. The solution was rinsed by bubbling with Argon (3 min). Tetrakis(triphenylphosphine)palladium(0) (0.05 eq) was added and the mixture was heated for 30 min at 120° C. The reaction mixture was evaporated, the residue was dissolved in DCM/$H_2O$. After phase separation, the organic layer was washed once with water, dried over $MgSO_4$ and evaporated. The semi-solid black residue was purified using silica gel chromatography (MeOH:/DCM) giving intermediate compound VIII. Deprotection with acid (e.g. TFA) followed by aqueous work-up and chromatography gave compound II.

General Method for Synthesis of Intermediate Compound II from Compounds VI and VII (Scheme 4)

Intermediates compounds VIII are prepared analogues to intermediate V from compounds III and VI, with the exception that a tert-butyl-2-choloro-5H-pyrrolo[4,3-d]pyrimidine-6(7H)-carboxylate (compound vii) was used instead of tert-butyl-2-choloro-7,8-dihydropyrido[4,3-d]pyrimidine-6(5H)-carboxylate (compound III). Deprotection with acid (e.g. TFA) followed by aqueous work-up and chromatography gave compound II.

Deprotection of intermediate compounds V, VIII

Intermediate compounds V and VIII were dissolved in difluoromethane. TFA was added and the mixture was stirred for 20 h at RT. The reaction mixture was diluted with 10 times difluoromethane and neutralized with 1-2N NaOH to pH 9. After phase separation, the organic layer was dried over $MgSO_4$, filtered and evaporated, yielding intermediate compounds I or II.

General Methods for the Introduction of Carboxylic Acid in Compounds XXVII

Compounds XVIIa-XVIIe (1 eq) were dissolved in THF or in a 1:1 mixtures of THF and MeOH after which NaOH (±10-14.52 eq) was added. The mixture was stirred overnight at RT. HCl was added and the mixture was evaporated. The residue was dissolved in water/DCM, optionally with a small amount of MeOH. After phase separation, the aqueous phase was extracted with DCM, the (combined) organic phase was dried with $MgSO_4$, filtered, concentrated and purified by flash chromatography (silica gel, MeOH:/DCM) to provide the respective carboxylic acid derivative.

Alternatively, LiOH (1N, 5.18 eq) was added to a solution of compounds XVIIa-XVIIe in THF. The mixture was stirred for ±20 h at RT, after which the mixture was neutralized with 1-2N HCl and evaporated. The resulting yellow oil was crystallized with a glass stirring rod, washed with water and evaporated over $P_2O_5$.

General Method for Introduction of Alternative Substituents R'/R'" (Scheme 7)

Compound XVII (1 eq) was dissolved in 1:1 tetrahydrofuran/MeOH. Palladium-on-carbon (Pd—C; 0.83 eq) was added under argon atmosphere. The mixture was hydrogenated by stirring at RT under hydrogen atmosphere. The reaction mixture was filtered and the organic layer was evaporated to give compound XXIII. Alternatively, compound XVII was dissolved in MeOH and hydrogenated using Pd—C (hydrogen, 40° C., atmospheric pressure). The product was checked with LC/MS. The organic layer was evaporated to give compound XXIII.

Alternatively, compound XXIII was obtained from 4-hydroxybenzamidine hydrochloride and the appropriately substituted (dimethylamino)methylene)-oxopipideridine-carboxylate. The latter can be prepared from the appropriately substituted tert-butyl oxopiperidine-carboxylate and N,N-dimethylfomamide dimethyl acetal. The tert-butyl oxopiperidine-carboxylate (1 eq) was dissolved in DMF after which N,N-dimethylfomamide dimethyl acetal (1.1 eq) was added. The mixture was heated for 8 h at 90° C. and subsequently stirred at RT overnight. The mixture was then evaporated and the resulting yellow oil was extracted with ethanol acetate and saturated NaCl solution. The organic phase was washed with further saturated NaCl solution, dried over $MgSO_4$ and evaporated. Compound XXIII was prepared by adding, under stirring and under cooling and argon atmosphere, a 60% solution of sodium hydride to ethanol. Subsequently 4-hydroxybenzamidine hydrochloride (1 eq) was added, as well as a solution of tert-butyl 3-((dimethylamino)methylene)-4-oxopiperidine-1-carboxylate (1 eq) in ethanol slowly, and the mixture was heated under reflux for 5 h and incubated overnight. The resulting mixture was evaporated, stirred with water and neutralized with 1N AcOH to pH 6-7. The resulting gum-like product was crystallized with a glass stirring rod while stirring for several hours, filtered, washed with water and evaporated over $P_2O_5$ at 40° C.

Compound XXIII (1 eq) was used in the next step without purification. Compound XXIII was dissolved in DMF. Cesium carbonate (1.0 eq) and the properly substituted benzylbromide (1.1 eq) were added and the mixture was stirred overnight at RT. The reaction mixture was subsequently evaporated. The residue was dissolved in DCM and washed with water. After phase separation the organic layer was evaporated. The residue was purified by flash chromatography (silica gel, MeOH/DCM) giving compound XXIV. Compounds XXIV can be converted to the corresponding carboxylic acid as described for compounds XVII.

General Method for Synthesis of Intermediate Compounds XXXIV (Scheme 9)

Compound XX (1 eq) and the properly substituted benzyl alcohol (2 eq) were dissolved in toluene. The mixture was degassed with argon. [1,1'-biphenyl]-2-yldi-tert-butylphosphine (0.1 eq), Palladium(II) acetate (0.1 eq) and cesium carbonate (2 eq) were added and the mixture was stirred for approximately 4 h at 100° C. The mixture was evaporated, the residue was mixed with DCM and washed twice with water. The organic phase was dried with $MgSO_4$, filtered and evaporated. The residue was purified by flash chromatography (silica gel, DCM/MeOH) to give compound XXXIV.

General Method for Synthesis of Intermediate Compounds XXXV and XXXVI (Scheme 10)

Compound III or compounds XX (1 eq) and the properly substituted ethynylbenzene (1 eq) and ethyl 4-(2-chloro-7,8-dihydropyrido[4,3-d]pyrimidin-6(5H)-yl)butanoate (1 eq) were dissolved in DMF. Triethylamine (2 eq), copper(I) iodide (0.1 eq) and bis(triphenylphosphine) Pd (II) dichloride (0.1 eq) were added and the mixture was stirred for 10 min at 110° C. The product was checked by LC/MS. The reaction mixture was evaporated. The residue was dissolved in ethylacetate, washed twice with a saturated $NH_4Cl$-solution and once with a saturated NaCl solution, dried over $MgSO_4$, filtered and evaporated. The residue was purified by flash chromatography (silica gel, MeOH/DCM) giving products XXXV and XXXVI.

General Method for Synthesis of Intermediate Compounds XXXVII (Scheme 11)

Compound III (1 eq) was dissolved in THF and under stirring degassed with argon at RT for 2 min. Bis(triphenylphosphine) Pd (II) dichloride (0.05 eq) and the properly R''' substituted benzylzinc bromide (1.2 eq) were added and heated for ±1 h to reflux. The mixture was cooled to RT and water and EtOAc were added. The mixture was stirred and filtered over a clarifying filter. After phase separation, the organic phase was dried with $MgSO_4$, filtered and evaporated. The oily residue was dissolved in DCM and purified by flash chromatography (silica gel, MeOH/DCM 98:2)

General Method for Synthesis of Dioxaborolane Intermediates

Dioxaborolane intermediates can be prepared from the appropriately substituted and bromobenzene compounds, e.g. 1-bromo-4-(2-(4-chlorophenyl)-1,1-difluoroethyl)benzene, 1-bromo-4-(2-(3-chlorophenyl)-1,1-difluoroethyl)benzene, 1-bromo-4-(2-(4-chlorophenyl)-cyclopropyl)benzene and 1-bromo-4-(2-(4-chlorophenyl)-ethyl)benzene, in a [1,1'-Bis(diphenylphosphino)ferrocene]dichloropalladium (II) mediated reaction. The appropriate bromobenzene compound is dissolved in dioxane and 4,4,4',4',5,5,5',5'-octamethyl-2,2'-bi(1,3,2-dioxaborolane) (e.g. 1.1-1.5 eq), potassium acetate (e.g. 2-2.5 eq) and [1,1'-Bis(diphenylphosphino)ferrocene]dichloropalladium(II) (e.g. 0.1-0.02 eq) are added. The mixture is stirred at 100° C. overnight before being cooled to RT and filtered. The filtrate is concentrated to dryness and the residue taken up in ethyl acetate washed with saturated NaCl, dried over $Na_2SO_4$, filtered and concentrated under reduced pressure. The crude product is purified by chromatography (silica; ethyl acetate/petroleum ether 1:50) to give the dioxaborolane intermediate.

Tert-butyl 2-(4-(benzyloxy)phenyl)-7,8-dihydropyrido[4,3-d]pyrimidine-6(5H)-carboxylate (compound Va; R'=H, R''=H) and 2-(4-(benzyloxy)phenyl)-5,6,7,8-tetrahydropyrido[4,3-d]pyrimidine (compound Ia; R'=H, R''=H)

A solution of compound III (1 g; 3.71 mmol; 1 eq), potassium (4-benzyloxyphenyl)-trifluoroborate (compound IV with R'=H and R''=H; 1.291 g; 4.45 mmol; 1.2 eq) and sodium carbonate (7.5 mL; 8.25 g; 7.78 mmol; 2.1 eq) in DMF (20 mL) was degassed for 30 min with argon. Tetrakis (triphenylphosphine)-palladium(0) (0.214 g; 0.185 mmol; 0.05 eq) was added and the mixture was stirred for 60 min at 120° C. The reaction mixture was evaporated, the residue was dissolved in $DCM/H_2O$. After phase separation, the organic layer was washed once with water and once with saturated NaCl solution, dried over $MgSO_4$, filtered and evaporated. The residue was purified by flash chromatography (40 g silica gel; 0-10% MeOH in DCM) giving compound Va (R'=H and R''=H).

Compound Va was converted to the corresponding compound Ia (R'=H and R''=H) with TFA. Compound Va (900 mg; 2.156 mmol; 1 eq) was dissolved in DCM (10 mL). TFA (1.5 mL; 19.47 mmol; 9 eq) was added and the mixture was stirred at RT. The reaction mixture was diluted with 100 mL DCM and neutralized with 2N NaOH to pH 9. After phase separation the organic layer was dried over $MgSO_4$, filtered and evaporated yielding compound Ia.

Tert-butyl 2-((4(2,6-dichloro-benzyl)oxy)phenyl)-7,8-dihydropyrido[4,3-d]pyrimidine-6(5H)-carboxylate (compound Vb; R'=2,6-diCl, R'') and 2-(4-((2,6-dichlorobenzyl)oxy)phenyl)-5,6,7,8-tetrahydropyrido[4,3-d]pyrimidine (compound Ib; R'=2,6-diCl, R''=H)

Compound Vb was prepared in the same way as compound Va with the exception that potassium (4-[2,6-dichlorobenzyloxy]phenyl)-trifluoroborate instead of potassium (4-benzyloxyphenyl)-trifluoroborate was used in the synthesis. Compound Vb was converted to the corresponding compound Ib (R'=2,6-diCl and R''=H) as described for the deprotection of intermediate compound Vb with TFA.

Tert-butyl 2-(4-((3-fluorobenzyl)oxy)phenyl)-7,8-dihydropyrido[4,3-d]pyrimidine-6(5H)-carboxylate (compound Vc; R'=3F, R''=H) and 2-(4-((3-fluorobenzyl)oxy)phenyl)-5,6,7,8-tetrahydropyrido[4,3-d]pyrimidine (compound Ic; R'=3-F, R''=H)

4-(3'-fluorobenzyloxy)phenylboronic acid (compound VI with R'=3F, R''=H; 296 mg; 1.2 mmol; 1.2 eq) and compound III (270 mg; 1 mmol; 1 eq) were dissolved in DMF. 10% $Na_2CO_3$ (265 mg; 2.5 mmol; 2.5 eq) in water was added and the solution was rinsed with argon for 3 min. Tetrakis(triphenylphosphine)-palladium(0) (57.8 mg; 0.05 mmol; 0.05 eq) was added and the mixture was heated for 30 min at 120° C. The reaction mixture was evaporated and the residue was dissolved in $DCM/H_2O$. After phase separation, the organic layer was washed once with water and dried with $MgSO_4$ overnight giving white crystals. These were stirred with n-pentane and a small amount of diethyl ether, extracted and washed with n-pentane giving compound Vc. Compound Vc was converted to the corresponding compound Ic as described for the deprotection of intermediate compounds V and VIII with TFA.

Methyl 3-(2-(4-(benzyloxy)phenyl)-7,8-dihydropyrido[4,3-d]pyrimidin-6(5H)-yl)-2-methylpropanoate (compound XVIIa; R'=H, R"=H)

Compound Ia (900 mg; 2.55 mmol; 1 eq) was suspended in MeOH (15 mL), giving a white suspension. DBU (1.16 g; 7.66 mol; 3 eq) and ethyl methacrylate (2.9 g; 25.5 mmol; 10 eq) were added and the reaction mixture was stirred at 130° C. for 10 min. The reaction mixture was evaporated and purified by flash chromatography (12 g silica gel, 0-10% MeOH in DCM) giving compound XVIIa (R'=H, R"=H) with a yield of 610 mg (1.461 mmol; 57.2%).

Tert-butyl 3-(2-(4-(benzyloxy)phenyl)-7,8-dihydropyrido[4,3-d]pyrimidin-6(5H)-yl)propanoate (compound XVIIb; R'=H, R"=H)

Compound Ia (122 mg; 0.38 mmol; 1 eq) was suspended in 6 mL MeOH, giving a white suspension. DBU (46.8 mg; 0.31 mmol; 0.8 eq) and tert-butylacrylate (148 mg; 1.15 mmol; 3 eq) were added and the reaction mixture was stirred under argon at RT for 20 h. The reaction mixture was evaporated, dissolved in DCM and purified by flash chromatography (silica gel, n-heptane/EtOAc gradient) giving compound XVIIb with a yield of 130 mg (0.292 mmol; 76%).

Ethyl 3-(2-(4-(benzyloxy)phenyl)-7,8-dihydropyrido[4,3-d]pyrimidin-6(5H)-yl)butanoate (compound XVIIc; R'=H, R"=H)

Compound Ia (1.6 g; 5 mmol; 1 eq) was dissolved in NMP (13). DBU (1.5 g; 10 mmol; 2 eq) and ethylcrotonate (2.85 g; 25 mmol; 5 eq) were added and the reaction mixture was stirred for 1 h at 140° C. The reaction mixture was evaporated, dissolved in DCM and washed three times with water. After phase separation, the organic phase was dried with $MgSO_4$, evaporated and purified by flash chromatography (silica gel, 5% MeOH in DCM) giving compound XVIIc with a yield of 2.1 g (4.87 mmol; 97%).

Ethyl 4-(2-(4-(benzyloxy)phenyl)-7,8-dihydropyrido[4,3-d]pyrimidin-6(5H)-yl)-3-methylbutanoate (compound XVIId; R'=H, R"=H)

Compound Ia (150 mg; 0.473 mmol; 1 eq) was suspended in DMF (5 mL). Under stirring and argon, 50% NaH in oil (34 mg; 0.709 mmol; 1.5 eq) was added. The mixture was stirred for 1 h at RT after which ethyl 4-bromo-3-methylbutanoate (198 mg; 0.945 mmol; 2 eq) was added. The reaction mixture was heated under stirring to 50° C. for 1 h, followed by 3 h at 80° C., 20 h at RT, 3 h at 80° C., 1 h at 120° C. and 1 h at 140° C. The reaction mixture was evaporated and the residue was reconstituted in water/DCM. After phase separation, the organic layer was washed once with water, dried ($MgSO_4$) and evaporated. The reaction mixture was dissolved in DCM and purified by flash chromatography (silica gel, 5% MeOH in DCM) giving compound XVIId (R'=H, R"=H) with a yield of 55 mg (0.123 mmol; 26.1%).

Methyl 2-(3-(2-(4-(benzyloxy)phenyl)-7,8-dihydropyrido[4,3-d]pyrimidin-6(5H)-yl)cyclobutyl)acetate (compound XVIIe with R'=H, R"=H, R*=methyl cyclobutylacetate)

To a solution of compound Ia (R'=H and R"=H; 226 mg, 0,712 mmol; 1 eq) in THF was added methyl 2-(3-oxocyclobutyl)acetate (101 mg; 0.712 mmol; 1 eq). The mixture was stirred at RT for 10 min. Sodium triacetoxyborohydride (226 mg; 1.068 mmol; 1.5 eq) was added and the mixture was stirred at RT for 5 h. The reaction mixture was diluted with ethylacetate and poured into water. After phase separation, the organic layer was washed once with water and once with saturated NaCl solution, dried over $MgSO_4$, filtered and evaporated. The residue was purified by flash chromatography (12 g silica gel, 0-10% MeOH in DCM) giving product XVIIe with a yield of 250 mg (0.564 mmol; 79%).

Ethyl 3-(2-(4-(benzyloxy)phenyl)-7,8-dihydropyrido[4,3-d]pyrimidin-6(5H)-yl)-2-methylpropanoate (compound XVIIg, with R'=H, R"=H, R*=ethyl 2-methylpropanoate)

A solution of compound Ia (R'=H and R"=H; 63 mg; 0.198 mmol; 1 eq) in MeOH (3 mL) was stirred under argon. Ethyl methacrylate (45 mg; 0.397 mmol; 2 eq) and DBU (15 mg; 0.099 mmol; 0.5 eq) were added at RT. The mixture was stirred for 20 h at RT and subsequently for 1 h at 100° C. The mixture was evaporated and the residue was dissolved in 3 mL NMP. A further 350 µL ethylmethacrylate and 180 µL DBU were added and the mixture was heated at 120° C. for 1 h and 140° C. for 2 h. The mixture was evaporated at 65° C. and the oily residue was dissolved in DCM. The mixture was purified by flash chromatography (silica gel, n-heptane/ 30% EtOAc). The purified product was reconstituted in n-Heptan/EtOAc 1:1 after TLC check, and concentrated giving compound XVIIg with a yield of 52 mg (0.121 mmol; 60.7%).

Ethyl 3-(2-(4-((2,6-dichlorobenzyl)oxy)phenyl)-7,8-dihydropyrido[4,3-d]pyrimidin-6(5H)-yl)-2-methylpropanoate (compound XVIIh with R'=2,6-diCl, R"=H, R*=ethyl 2-methylpropanoate)

Compound XVIIh was prepared in the same way as compound XVIIg with the exception that compound Ib (R'=2,6-diCl, R"=H) instead of 2-(4-(benzyloxy)phenyl)-5,6,7,8-tetrahydropyrido[4,3-d]pyrimidine (compound Ia) was used in the synthesis.

Methyl 3-(2-(4-((3-fluorobenzyl)oxy)phenyl)-7,8-dihydropyrido[4,3-d]pyrimidin-6(5H)-yl)-2-methylpropanoate (compound XVIIi; R'=3-F, R"=H, R*=methyl 2-methylproponate)

Compound Ic (78 mg; 0.233 mmol; 1 eq) was mixed with MeOH (4 mL) to give a white suspension. DBU (80 µL; 0.531 mmo; 2.28 eq) and ethyl methacrylate (160 µL; 1.285 mmol; 5.5 eq) were added. The reaction mixture was stirred at 120° C. for 1 h and checked with LC/MS. Further DBU (0.08 mL) and ethyl methacrylate (0.16 mL) were added and the mixture was stirred at 120° C. for a further 2.5 h. The reaction mixture was evaporated and purified by flash chromatography (12 g silica gel, 0-5% MeOH in DCM) giving product XVIIi with a yield of 60 mg (0.138 mmol; 59.2%).

Methyl 3-(2-(4-((3,4-dichlorobenzyl)oxy)phenyl)-7,8-dihydropyrido[4,3-d]pyrimidin-6(5H)-yl)-2-methylpropanoate (compound XXIVa; R"=H, R'''=3,4-diCl, R*=methyl 2-methylpropanoate)

To a solution of compound XVIIa (R'=H and R"=H; 610 mg; 1.461 mmol; 1 eq) in MeOH (20 mL) and THF (20 mL) was added Pd—C (100 mg; 0.940 mmol) under argon. The reaction mixture was stirred at RT under hydrogen atmosphere. The reaction mixture was filtered and evaporated, providing methyl 3-(2-(4-hydroxyphenyl)-7,8-dihydropyrido[4,3-d]pyrimidin-6(5H)-yl)-2-methylpropanoate (compound XXIIIa; R"=H, R*=methyl 2-methylpropanoate) with a yield of 463 mg (1.414 mmol; 97%).

To a solution of compound XXIIIa (80 mg; 0.244 mmol; 1 eq) in DMF (5 mL) were added cesium carbonate (120 mg; 0.368 mmol; 1.5 eq) and 3,4-dichlorobenzyl bromide (0.039 mL; 0.271 mmol; 1.1 eq). The mixture was stirred overnight at RT. The reaction mixture was evaporated. The residue was dissolved in DCM and washed once with water. After phase separation, the organic layer was evaporated. The residue was purified by flash chromatography (4 g silica gel, 0-10% MeOH in DCM) giving compound XXIVa with a yield of 76 mg (0.156 mmol; 63.9%).

Tert-butyl 2-(4-hydroxyphenyl)-7,8-dihydropyrido [4,3-d]pyrimidine-6(5H)-carboxylate (compound XXIIIb) and tert-butyl 2-(4-((4-chlorobenzyl)oxy) phenyl)-7,8-dihydropyrido[4,3-d]pyrimidine-6(5H)-carboxylate (compound XXIVb)

Tert-Butyl 4-oxo-1-piperidinecarboxylate (39.8 g; 0.2 mol; 1 eq) was dissolved in DMF (300 ml) after which N,N-dimethylfomamide dimethyl acetal (26.2 g; 0.22 mol; 1.1 eq) was added under stirring. The mixture was heated for 8 h at 90° C. and subsequently stirred at RT overnight. The mixture was then evaporated and the resulting yellow oil was extracted with ethanol acetate and saturated NaCl solution. The organic phase was washed with further saturated NaCl solution, dried over $MgSO_4$ and evaporated. Tert-butyl 3-((dimethylamino)methylene)-4-oxopiperidine-1-carboxylate was obtained with a yield of 50.6 g (0.199 mol; 99%). Under stirring and under cooling and argon atmosphere, a 60% solution of sodium hydride (16.8 g; 420 mmol; 2.1 eq) was added to 800 ml ethanol. 4-hydroxybenzamidine hydrochloride (34.5 g; 200 mmol; 1 eq) was added as well as a solution of 50.9 g tert-butyl 3-((dimethylamino)methylene)-4-oxopiperidine-1-carboxylate (200 mmol; 1 eq) in 200 ml ethanol, which was added slowly. The mixture was heated under reflux for 5 h and incubated overnight. The resulting mixture was evaporated, stirred with water and neutralized with 400 ml 1N AcOH to pH 6-7. The resulting gum-like product was crystallized with a glass stirring rod while stirring for several hours, filtered, washed with water and evaporated over $P_2O_5$ at 40° C. giving compound XXIIIb with a yield of 62.5 g (191 mmol; 95%). Compound XXIVb was prepared in accordance with the second step of scheme 7. Compound XXIIIb (62.5 g; 191 mmol; 1 eq) was dissolved in DMF (800 ml). Cesium carbonate (71.5 g; 220 mmol; 1.15 eq) and 4-chlorobenzylbromide (43.2 g; 210 mmol; 1.1 eq) were added under stirring and the mixture was stirred for 2 h at RT. The mixture was evaporated and the residue was extracted with DCM and water. The organic phase was washed twice with water, evaporated and dried over $MgSO_4$. The yellow residue (93 g) was recrystallized in 900 ml ethylacetate with activated charcoal, cooled and the precipitated crystals were obtained, washed with cold ethylacetate and n-pentane and dried under vacuum at 40° C. Compound XXIVb was obtained with a yield of 57 g (126 mmol; 66.1%).

Tert-butyl 2-(4-hydroxyphenyl)-7,7-dimethyl-7,8-dihydropyrido[4,3-d]pyrimidine-6(5H)-carboxylate (compound XXIIIc) and tert-butyl 2-(4-((4-chlorobenzyl)oxy)phenyl)-7,7-dimethyl-7,8-dihydropyrido[4,3-d]pyrimidine-6(5H)-carboxylate (compound XXIVc)

Compound XXIIIc was prepared in the same way as compound XXIIIb using tert-butyl 2,2-dimethyl-4-oxopiperidine-1-carboxylate instead of tert-Butyl 4-oxo-1-piperidinecarboxylate.

Compound XXIIIc (200 mg; 0.563 mmol; 1 eq) was dissolved in 5 ml DMF to give a colorless solution. 4-chlorobenzylbromide (127 mg; 0.619 mmol; 1.1 eq) and cesium carbonate (202 mg; 0.619 mmol; 1.1 eq) were added and the mixture was stirred.

The reaction mixture was evaporated and the residue was extracted with DCM, water and NaCl. After phase separation, the organic layer was evaporated and the residue was purified by flash chromatography (4 g; 0-15% MeOH in DCM) giving compound XXIVc with a yield of 120 mg (0.250 mmol; 44.4%).

Tert-butyl 2'-(4-hydroxyphenyl)-5'H-spiro[cyclobutane-1,7'-pyrido[4,3-d]pyrimidine]-6'(8'H)-carboxylate (compound XXIIId) and tert-butyl 2'-(4-((4-chlorobenzyl)oxy)phenyl)-5'H-spiro[cyclobutane-1, 7'-pyrido[4,3-d]pyrimidine]-6'(8'H)-carboxylate (compound XXIVd)

Tert-butyl 7-((dimethylamino)methylene)-8-oxo-5-azaspiro[3.5]nonane-5-carboxylate was prepared in the same way as tert-butyl 3-((dimethylamino)methylene)-4-oxopiperidine-1-carboxylate described above for the preparation of compound XXIIIb using tert-butyl 8-oxo-5-azaspiro[3.5]nonane-5-carboxylate instead of tert-Butyl 4-oxo-1-piperidinecarboxylate.

Under stirring and under cooling and argon atmosphere, a 60% solution of sodium hydride (371 mg; 9.27 mmol; 2.1 eq) was added to 15 ml ethanol. 4-hydroxybenzamidine hydrochloride (762 mg; 4.41 mmol; 1 eq) was added as well as a solution of 1.3 g tert-butyl 7-((dimethylamino)methylene)-8-oxo-5-azaspiro[3.5]nonane-5-carboxylate (4.42 mmol; 1 eq) in 7 ml ethanol. The mixture was heated under reflux for 5 h and incubated overnight. The resulting mixture was evaporated, stirred with 50 ml water and neutralized with 5 ml 1N AcOH to pH 6-7. The resulting gum-like product was extracted with DCM, the organic phase was washed with water, evaporated and dried over $MgSO_4$. The residue was dissolved in DCM with a little MeOH and filtered through a Chromabond-PTS-cartridge. The residue was purified by flash chromatography (4 g silica gel, 98:2 DCM/MeOH) giving compound XXIIId with a yield of 660 mg (1.796 mmol; 40.7%). Compound XXIVd was prepared in accordance with the second step of scheme 7. Compound XXIIId (300 mg; 0.816 mmol; 1 eq) was dissolved in DMF (5 ml). Cesium carbonate (319 mg; 0.98 mmol; 1.2 eq) and 4-chlorobenzylbromide (185 mg; 0.898 mmol; 1.1 eq) were added under stirring and the mixture was stirred for 2 h at RT. The mixture was evaporated and the residue was extracted with DCM and water. The organic phase was washed with water, evaporated and dried over $MgSO_4$, giving compound XXIVd with a yield of 400 mg (0.813 mmol; 100%).

Tert-butyl 2-(2-fluoro-4-hydroxyphenyl)-7,8-dihydropyrido[4,3-d]pyrimidine-6(5H)-carboxylate (compound XXIIIf)

2-fluoro-4-hydroxyphenylboronic acid (347 mg; 2.224 mmol; 1.2 eq) and tert-butyl 2-chloro-7,8-dihydropyrido[4,3-D]pyrimidine-6(5H)-carboxylate (500 mg; 1.854 mmol; 1 eq) were dissolved in 10 ml DMF to give a yellow solution. Sodium carbonate (3.30 g; 3.11 mmol; 1.68 eq) was added and the mixture was degassed with Argon for 30 min. Tetrakis(triphenylphosphine)palladium(0) (107 mg; 0.093 mmol; 0.05 eq) was added and the mixture was stirred for 1 h at 100° C. The reaction mixture was evaporated and the residue was dissolved in DCM and washed twice with water and once with saturated NaCl solution. The organic layer was dried over MgSO$_4$, filtered and evaporated. the residue was purified by flash chromatography (12 g silica gel; 0-10% MeOH in DCM, giving 520 mg of compound XXIIIf (1.506 mmol; 81%).

Methyl 2-(3-(2-(4-((3-chlorobenzyl)oxy)phenyl)-7,8-dihydropyrido[4,3-d]pyrimidin-6(5H)-yl)cyclobutyl)acetate (compound XXIVe with R″=H, R*=cyclobutylacetate, R‴=3Cl)

To a solution of compound XVIIe (250 mg; 0.56 mmol; 1 eq) in THF (3 mL) and MeOH (3 mL) was added Pd—C under argon atmosphere. The mixture was stirred at RT under hydrogen atmosphere. The reaction mixture was filtered and the organic layer was evaporated giving compound XXIIIe (R″=H, R*=cyclobutylacetate) with a yield of 190 mg (0.538 mmol; 95%).

To a solution of compound XXIIIe (95 mg; 0.269 mmol; 1 eq) in 5 mL DMF were added cesium carbonate (90 mg; 0.276 mmol; 1.03 eq) and 3-chlorobenzyl bromide (60 mg; 0.292 mmol; 1.09 eq). The mixture was stirred overnight at RT. The reaction mixture was evaporated. The residue was dissolved in DCM and washed once with water. After phase separation, the organic layer was evaporated. The residue was purified by flash chromatography (4 g silica gel, 0-10% MeOH in DCM) giving compound XXIVe with a yield of 75 mg (0.157 mmol; 58.4%).

Methyl 2-(3-(2-(4-((4-chlorobenzyl)oxy)phenyl)-7,8-dihydropyrido[4,3-d]pyrimidin-6(5H)-yl)cyclobutyl)acetate (compound XXIVf with R″=H, R*=cyclobutylacetate, R‴=4C-1)

Compound XXIVf was prepared in the same way as compound XXIVe whereby 4-chlorobenzyl bromide was used instead of 3-chlorobenzyl bromide in the synthesis.

Methyl 2-(3-(2-(4-((3,5-dichlorobenzyl)oxy)phenyl)-7,8-dihydropyrido[4,3-d]pyrimidin-6(5H)-yl)cyclobutyl)acetate (compound XXIVg with (R″=H, R*=cyclobutylacetate, R‴=3,5-diCl)

To a solution of compound XXIIIe (0.042 mL; 0.184 mmol; 1 eq) in 3 mL DMF were added cesium carbonate (70 mg; 0.215 mmol; 1.2 eq) and 1-(bromomethyl)-3,5-dichlorobenzene (45 mg; 0.188 mmol; 1.02 eq). The mixture was stirred for 2 h at RT. The reaction mixture was evaporated. The residue was dissolved in DCM and washed once with water. After phase separation, the organic layer was evaporated. The residue was purified by flash chromatography (4 g silica gel, 0-10% MeOH in DCM) giving compound XXIVg (R′=H, R*=cyclobutylacetate, R‴=3,5diCl) with a yield of 56 mg (0.109 mmol; 59.4%).

Methyl 2-(3-(2-(4-((3,4-dichlorobenzyl)oxy)phenyl)-7,8-dihydropyrido[4,3-d]pyrimidin-6(5H)-yl) cyclobutyl)acetate (compound XXIVh with R″=H, R*=cyclobutylacetate, R‴=3,4-diCl)

Compound XXIVh was prepared in the same way as compound XXIVg whereby 1-(bromomethyl)-3,4-dichlorobenzene was used instead of 1-(bromomethyl)-3,5-dichlorobenzene in the synthesis.

Methyl 3-(2-(4-((3,5-difluorobenzyl)oxy)phenyl)-7,8-dihydropyrido[4,3-d]pyrimidin-6(5H)-yl)-2-methylpropanoate (compound XXIVi)

This compound was prepared from compound XVIIi in accordance with scheme 7. Methyl 3-(2-(4-((3-fluorobenzyl)oxy)phenyl)-7,8-dihydropyrido[4,3-d]pyrimidin-6(5H)-yl)-2-methylpropanoate (30 mg; 0.069 mmol; 1 eq) was dissolved in MeOH (4 mL). The mixture was hydrogenated using Pd—C(hydrogen, 40° C., atmospheric pressure) and the product was checked by LC/MS, which showed product mass and a small amount of reactant mass and side product (hydrogenated pyrimidine). The organic layer was evaporated and the crude product (methyl 3-(2-(4-hydroxyphenyl)-7,8-dihydropyrido[4,3-d]pyrimidin-6(5H)-yl)-2-methylpropanoate) was directly used in the next stage. Compound XXIVi was prepared as described for compound XXIVa starting from methyl 3-(2-(4-hydroxyphenyl)-7,8-dihydropyrido[4,3-d]pyrimidin-6(5H)-yl)-2-methylpropanoate instead compound XXIIIe of and using 3,5-difluorobenzyl bromide instead of 3,4-dichlorobenzyl bromide.

2-chloro-5,6,7,8-tetrahydropyrido[4,3-d]pyrimidine (compound IIIa)

TFA (12.68 g; 111 mmol; 10 eq) was added to a solution of compound III (3 g; 10.58 mmol; 1 eq) in 80 mL DCM under stirring. The mixture was stirred for 20 h at RT, evaporated, and dissolved in 20 mL DCM. 10 mL MTB ether was added slowly under stirring. The product precipitated as TFA salt. The crystallized product was washed with n-pentane and dried at 40° C. under reduced pressure, and obtained with a yield of 3 g (10.58 mmol; 95%).

Ethyl 4-(2-chloro-7,8-dihydropyrido[4,3-d]pyrimidin-6(5H)-yl)pentanoate (compound XXa)

Compound XXa was prepared from compound Ma in accordance with scheme 6. 2-chloro-5,6,7,8-tetrahydropyrido[4,3-D]pyrimidin (compound Ma) 2,2,2-trifluoroacetate (654 mg; 2.29 mmol; 1 eq) was dissolved in 30 mL 1,2-dichloroethane and stirred at RT. Ethyl levulinate (1.65 g; 11.76 mmol; 5 eq) was added and the mixture was stirred for 1 h at RT. The mixture was added to sodium triacetoxyborohydride (996 mg; 4.71 mmol; 2 eq) and the reaction mixture was stirred over the weekend at RT. The turbid solution was diluted with DCM and stirred with about 50 mL water. After phase separation, the organic phase was dried with MgSO$_4$ and evaporated. The residue was dissolved in DCM and purified by flash chromatography (silica gel, 98:2 DCM:MeOH) giving product XXa with a yield of 608 mg (2.04 mmol; 89%).

Ethyl 2-(2-chloro-7,8-dihydropyrido[4,3-d]pyrimidin-6 (5H)-yl)acetate (compound XXb)

This compound was prepared in accordance with scheme 6. To a solution of compound Ma (2 g; 7.05 mmol; 1 eq)) in DMF (10 mL) was added triethylamine (1.8 g; 17.9 mmol; 2.5 eq). Subsequently ethyl bromoacetate (1.7 g; 10.6 mmol; 1.5 eq) was added dropwise. The mixture was stirred at RT for 2 h after which the product was checked with LC/MS. The reaction mixture was evaporated. The residue was dissolved in ethylacetate, washed once with water and once with saturated NaCl solution. The mixture was dried over $MgSO_4$, filtered and evaporated. The product was purified by flash chromatography (silica gel, 0-10% MeOH in DCM), giving product 20b with a yield of 1.3 g (5.08 mmol; 72%).

Methyl 1-((2-chloro-7,8-dihydropyrido[4,3-d]pyrimidin-6(5H)-yl)methyl)cyclopropanecarboxylate (compound XXc)

This compound was prepared in accordance with scheme 6. 2-chloro-5,6,7,8-tetrahydropyrido[4,3-d]pyrimidine (compound Ma; 248 mg; 0.87 mmol; 1 eq) and DBU (333 mg; 2.2 mmol; 2.5 eq) were dissolved in DMF (3 mL). Methyl 1-(bromomethyl)cyclopropanecarboxylate (253 mg; 1.3 mmol; 1.5 eq) was added at RT. The solution was stirred overnight at RT, followed by stirring at 50° C. for 2 h. The solution was evaporated and water (10 mL) and diethyl ether (50 mL) were added. After phase separation, the organic phase was dried with $MgSO_4$, filtered and evaporated. The residue was dissolved in DCM and purified by flash chromatography (silica gel, 98:2 DCM:MeOH), giving compound XXc with a yield of 113 mg (0.401 mmol; 45.9%).

Ethyl 4-(2-chloro-7,8-dihydropyrido[4,3-d]pyrimidin-6(5H)-yl)-3,3-dimethylbutanoate (compound XXd)

This compound was prepared in accordance with scheme 6. 2-chloro-5,6,7,8-tetrahydropyrido[4,3-d]pyrimidine 2,2,2 trifluoroacetate (compound Ma; 284 mg; 1.00 mmol; 1 eq) was dissolved in 10 mL THF. Ethyl 3,3-dimethyl-4-oxobutanoate (317 mg; 2.00 mmol; 2 eq) was added and the mixture was stirred for 1 h at RT. Sodium triacetoxyborohydride (424 mg; 2.00 mmol; 2 eq) was added and the mixture was stirred for 4 h at RT. The mixture was stirred with 10 mL water and 30 mL EtOAc for 15 min. After phase separation, the aqueous phase was extracted once with EtOAc. The combined organic phases were dried with $MgSO_4$, filtered and evaporated. The oily residue was dissolved in DCM and purified by flash chromatography (98:2 DCM:MeOH) giving compound XXc with a yield of 292 mg (00.936 mmol; 94%).

Tert-butyl 3-(2-chloro-7,8-dihydropyrido[4,3-d]pyrimidin-6(5H)-yl)propanoate (compound XXe)

This compound was prepared from compound Ma in accordance with scheme 6. Compound IIIa (3.15 g; 11.1 mmol; 1 eq) and DBU (6.76 g; 44.4 mmol; 4 eq) were dissolved in 45 mL MeOH. Tert-butyl acrylate (4.27 g; 33.3 mmol; 3 eq) dissolved in 5 mL MeOH was added. The mixture was stirred overnight at RT. The mixture was evaporated, 70 mL ethyl acetate was added and washed three times with 30 mL of a saturated $NH_4Cl$ solution. The organic phase was dried with $MgSO_4$, filtered and evaporated. The residue was purified by flash chromatography (silica gel, DCM:MeOH) giving the product with a total yield of 758 mg (2.55 mmol; 22.9%).

Ethyl 4-(2-chloro-7,8-dihydropyrido[4,3-d]pyrimidin-6(5H)-yl)butanoate (compound XXf)

To a suspension of NaH (550 mg; 11.46 mmol; 2.1 eq) in DMF (5 mL) was added dropwise 2-chloro-5,6,7,8-tetrahydropyrido[4,3-d]pyrimidine (920 mg; 5.42 mmol; 1 eq) dissolved in DMF (5 mL). The mixture was stirred for 1 h at RT. Ethyl 4-bromoburytate (3.4 g; 17.47 mmol; 3.2 eq), dissolved in DMF (5 mL) was added dropwise. The reaction mixture was poured into ice-water and extracted 3 times with ethylacetate. The combined organic layers were washed with saturated NaCl solution, dried over $MgSO_4$, filtered and evaporated. The residue was purified by the flash chromatography (40 g silica gel, 0-15% MeOH in DCM) giving compound XXf with a yield of 860 mg (3.03 mmol; 55.9%).

Ethyl 4-(2-chloro-7,8-dihydropyrido[4,3-d]pyrimidin-6 (5H)-yl)-3-methylbutanoate (compound XXg)

This compound was prepared in accordance with scheme 6. 2-chloro-5,6,7,8-tetrahydropyrido[4,3-d]pyrimidine hydrochloride (3 g; 14.56 mmol; 1 eq), trimethylamine (1.826 ml; 13.10 mmol; 0.9 eq) and ethyl 3-methyl-4-oxobutanoate (2.52 g; 17.47 mmol; 1.2 eq) were dissolved in 100 ml THF and stirred for 3 h at RT. Sodium triacetoxyborohydride (4.63 g; 21.84 mmol; 1.5 eq) was added and the mixture was stirred for 30 min at RT. The mixture was extracted with 150 mL EtOAc and 60 mL $H_2O$. The $H_2O$ layer was extracted again with EtOAc. The mixture color turned to orange. The organic layer was washed with NaCl-solution and dried over $MgSO_4$. The residue was filtered and evaporated. The residue was purified by flash chromatography (40 g silica gel, 0-10% MeOH in DCM) giving compound XXg with a yield of 4.02 mg (13.5 mmol; 93%).

Methyl 3-(2-chloro-7,8-dihydropyrido[4,3-d]pyrimidin-6(5H)-yl)cyclopentanecarboxylate (compound XXh)

This compound was prepared in accordance with scheme 6. 2-chloro-5,6,7,8-tetrahydropyrido[4,3-d]pyrimidine 2,2,2-trifluoroacetate (500 mg; 1.763 mmol; 1 eq) was dissolved in THF (20 ml) to give an orange solution. Triethylamine (161 mg; 1.597 mmol; 0.9 eq) and methyl 3-oxocyclopentanecarboxylate (276 mg; 1.939 mmol; 1.1 eq) were added and the mixture was stirred for 10 min at RT. Sodium triacetoxyborohydride (560 mg; 2.64 mmol; 1.5 eq) was added and the mixture was stirred for another 1 h. The mixture was evaporated, the residue was dissolved in DCM and water and 10 ml saturated $NH_4Cl$ solution was added. After phase separation, the organic layer was washed with saturated NaCl solution, dried over $MgSO_4$, filtered and evaporated. The residue was purified by flash chromatography (12 g silica gel, 0-10% MeOH in DCM) giving product XXh with a yield of 418 mg (1.413 mmol; 80%).

Ethyl 2-(2-chloro-7,8-dihydropyrido[4,3-d]pyrimidin-6(5H)-yl)propanoate (compound XXi)

This compound was prepared in accordance with scheme 6. 2-chloro-5,6,7,8-tetrahydropyrido[4,3-d]pyrimidine 2,2,2-trifluoroacetate (600 mg; 2.115 mmol; 1 eq) was dissolved in DMF (10 ml) to give a orange solution. DBU (800 μL;

5.31 mmol; 2.51 eq) was added. Ethyl 2-bromopropionate (400 µL; 3.08 mmol; 1.46 eq) was added and the mixture was stirred at RT overnight. The reaction mixture was evaporated, the residue was dissolved in DCM and washed 2× with sat. NH$_4$Cl-solution and 1× with saturated NaCl solution. The organic layer was dried over MgSO$_4$, filtered and evaporated. The residue was purified by flash chromatography (12 g silica gel, 0-10% MeOH in DMC) giving compound XXi with a yield of 398 mg (1.476 mmol; 69.8%).

Tert-butyl 3-(6-chloro-3,4-dihydro-2,7-naphthyridin-2(1H)-yl)propanoate (compound XXIa)

6-chloro-1,2,3,4-tetrahydro-[2,7]naphthyridine hydrochloride (1 g; 4.88 mmol; 1 eq) is dissolved in 30 mL MeOH. DBU (1.49 g; 9.75 mmol; 2 eq) and tert-butylacrylate (1.89 g; 14.6 mmol; 3 eq) were added under stirring and the mixture was subsequently stirred for 20 h at RT. The mixture was evaporated and the residue was dissolved in DCM. The mixture was washed once with a saturated NaHCO$_3$ solution, once with a 10% NH$_4$Cl solution and extracted once with water. The mixture was dried with MgSO$_4$ and evaporated. The residue was dissolved in DCM and purified by flash chromatography (silica gel, 95:5 DCM/MeOH) giving the product with a yield of 922 mg (3.11 mmol; 63.7%).

Ethyl 3-(2-chloro-7,8-dihydro-1,6-naphthyridin-6 (5H)-yl)-2-methylpropanoate (compound XXIIa, R*=ethyl methylpropanoate)

Ethyl 3-(2-chloro-7,8-dihydro-1,6-naphthyridin-6(5H)-yl)-2-methylpropanoate was prepared starting from tert-butyl 2-chloro-7,8-dihydro-1,6-naphthyridine-6(5H)-carboxylate in accordance with scheme 6. Tert-butyl 2-chloro-7,8-dihydro-1,6-naphthyridine-6(5H)-carboxylate (3.22 g; 12 mmol; 1 eq) was dissolved in DCM (100 mL). TFA (13.7 g; 120 mmol; 10 eq) was added under stirring at RT. The mixture was stirred for 20 h at RT. 50 mL of a saturated NaHCO$_3$ solution was added followed by the addition of solid NaHCO$_3$ while stirring until the pH of the aqueous phase was 7. After phase separation, the organic phase was dried with MgSO$_4$ and evaporated. The aqueous phase was saturated with NaCl under stirring followed by addition of 200 mL DCM and stirring for 30 min. After phase separation, the organic phase was dried with MgSO$_4$ and evaporated. The yield of the combined product 2-chloro-5,6,7,8-tetrahydro-1,6-naphthyridine was 2.01 g (11.92 mmol; 99%).

2-chloro-5,6,7,8-tetrahydro-1,6-naphthyridine (2.01 g; 11.92 mmol; 1 eq) was dissolved in 12 mL NMP. DBU (3.6 g; 23.8 mmol; 2 eq) and ethyl methacrylate (6.8 g; 59.6 mmol; 5 eq) were added and the mixture was heated for 1 h at 140° C. The mixture was evaporated at 70° C. to remove NMP. The oily residue was dissolved in DCM and eluted by flash chromatography (silica gel, 95:5 DCM/MeOH). The purified residue (2 g) was dissolved in DCM, washed one with a 10% NH$_4$Cl solution and extracted twice with water. After phase separation, the organic phase was dried with MgSO$_4$, and evaporated giving product XXIIa with a yield of 2.74 g (9.69 mmol; 81%).

Methyl 3-(2-chloro-7,8-dihydro-1,6-naphthyridin-6 (5H)-yl)cyclobutanecarboxylate (compound XXIIb; R*=methylcyclobutanecarboxylate)

This compound was prepared from 2-chloro-5,6,7,8-tetrahydro-1,6-naphthyridine, prepared as described for compound XXIIa, in accordance with scheme 6. 2-chloro-5,6,7,8-tetrahydro-1,6-naphthyridine (725 mg; 4.30 mmol; 1 eq) was dissolved in 10 mL THF. Methyl 3-oxocyclobutanecarboxylate (551 mg; 4.30 mmol; 1 eq) was added and the mixture was stirred at RT for 10 min. Sodium triacetoxyborohydride (1367 mg; 6.45 mmol; 1.5 eq) was added and the mixture was stirred at RT. The reaction mixture was diluted with ethylacetate and poured into water. After phase separation, the organic layer was washed once with water and once with saturated NaCl solution, dried over MgSO$_4$, filtered and evaporated. The residue was purified by flash chromatography twice (12 g silica gel, 0-15% MeOH in DCM) giving compound XXIIb with a yield of 790 mg (2.81 mmol; 65.4%).

Tert-butyl 2-(4-(benzyloxy)phenyl)-5H-pyrrolo[3,4-d]pyrimidine-6(7H)-carboxylate (compound VIIIa; R'=H, R"=H) and 2-(4-(benzyloxy)phenyl)-6,7-dihydro-5H-pyrrolo[3,4-d]pyrimidine (compound IIa; R'=H, R"=H)

A solution of compound VII (1 g; 3.95 mmol; 1 eq), potassium (4-benzyloxyphenyl)-trifluoroborate (compound IV with R'=H, R"=H; 1.38 g; 4.74 mmol; 1.2 eq) and 10% sodium carbonate (10.5 g; 9.87 mmol; 2.5 eq) in DMF (30 mL) was degassed for 3 min with argon. Tetrakis(triphenylphosphine)-palladium(0) (0.228 g; 0.197 mmol; 0.05 eq) was added and the mixture was stirred for 30 min at 120° C. This was repeated twice with 480 mg of compound VII each time. The combined reaction mixtures were evaporated, the residue was dissolved in DCM/H$_2$O. After phase separation, the organic layer was washed once with water, dried with MgSO$_4$, filtered and evaporated. The residue was dissolved in DCM/MeOH, concentrated and purified by flash chromatography (silica gel, DCM/MeOH 98:2) giving compound VIIIa with a yield of 1.42 g (3.52 mmol; 89%).

Compound VIIIa was converted to the corresponding compound IIa (R'=H and R"=H) with TFA. Compound VIIIa (1.42 g; 3.52 mmol; 1 eq) was dissolved in DCM. TFA (4.01 g; 35.2 mmol; 10 eq) was added under stirring at RT. The mixture was stirred for 24 h at RT. 50 mL saturated NaHCO$_3$ solution was added resulting in a white emulsion. This was diluted with DCM but the product was poorly soluble. DCM was evaporated and the product was stirred until the product crystallized. The crystals were washed with water and dried under vacuum at 40° C. giving compound IIa with a yield of 1.05 g (3.46 mmol; 98%).

2-(4-(benzyloxy)phenyl)-5,6,7,8-tetrahydro-1,6-naphthyridine (compound IXa; R'=H, R"=H)

Compound IXa was prepared in accordance with scheme 1 starting from tert-butyl 2-chloro-7,8-dihydro-1,6-naphthyridine-6(5H)-carboxylate instead of compound III. To a solution of tert-butyl 2-chloro-7,8-dihydro-1,6-naphthyridine-6(5H)-carboxylate (500 mg; 1.86 mmol, 1 eq) in 15 mL DMF was added potassium (4-benzyloxyphenyl)-trifluoroborate (648 mg; 2.23 mmol; 1.2 eq) and sodium carbonate (493 mg; 4.65 mmol; 2.5 eq). The mixture was degassed with argon for 10 min. Tetrakis(triphenylphosphine)-palladium(0) (107 mg; 0.093 mmol; 0.05 eq) was added and the mixture was stirred for 1 h at 120° C. The reaction mixture was evaporated, the residue was dissolved in DCM/water. After phase separation, the organic phase was washed once with a saturated NaCl solution, dried with MgSO$_4$, filtered and evaporated. The residue was purified by flash chromatography (silica gel, 0-5% MeOH in DCM) giving tert-butyl 2-(4-(benzyloxy)phenyl)-7,8-dihydro-1,6-naphthyridine-6 (5H)-carboxylate with a yield of 600 mg (1.441 mmol; 77%). Tert-butyl 2-(4-(benzyloxy)phenyl)-7,8-dihydro-1,6-naphthyridine-6(5H)-carboxylate (600 mg; 1.44 mmol; 1 eq) was dissolved in DCM (13 mL). TFA (1 mL; 1.48 g; 12.98 mmol; 9 eq) was added and the mixture was stirred overnight at RT. The mixture was evaporated, and reconstituted in DCM with a little MeOH and washed once with a saturated NaHCO$_3$ solution. After phase separation, the aqueous phase was washed twice with DCM with a little MeOH. The combined organic phases were dried with MgSO$_4$, filtered and evaporated, giving compound IXa (with R'=H, R"=H) with a yield of 585 mg (1.359 mmol; 94%).

2-(4-(benzyloxy)-3-methylphenyl)-5,6,7,8-tetra-hydro-1,6-naphthyridine (compound IXc; R'=H, R"=3-CH$_3$)

Compound IXc was prepared in accordance with scheme 2 starting from tert-butyl 2-chloro-7,8-dihydro-1,6-naphthyridine-6(5H)-carboxylate instead of compound III using (4-(benzyloxy)-3-methylphenyl)boronic acid (compound VI with R'=H, R"=CH$_3$). Tert-butyl 2-chloro-7,8-dihydro-1,6-naphthyridine-6(5H)-carboxylate (500 mg; 1.86 mmol; 1 eq) and (4-(benzyloxy)-3-methylphenyl)boronic acid (540 mg; 2.233 mmol; 1.2 eq) were dissolved in DMF (15 mL) to give a yellow solution. Sodium carbonate (493 mg; 4.65 mmol; 2.5 eq) was added and the mixtures was degassed with argon for 30 min.

Tetrakis(triphenylphosphine)-palladium(0) (107 mg; 0.093 mmol; 0.05 eq) was added and the mixture was stirred for 1 h at 120° C. The reaction mixture was evaporated and the residue was dissolved in DCM. The crude product was subsequently washed with water and a saturated NaCl solution. The organic phase was dried over MgSO$_4$, filtered and evaporated. The residue was absorbed on Celite XTR and purified by flash chromatography (12 g silica gel, 0-10% MeOH in DCM) giving tert-butyl 2-(4-(benzyloxy)-3-methylphenyl)-7,8-dihydro-1,6-naphthyridine-6(5H)-carboxylate with a yield of 320 mg (0.743 mmol; 39.9%).

Tert-butyl 2-(4-(benzyloxy)-3-methylphenyl)-7,8-dihydro-1,6-naphthyridine-6(5H)-carboxylate (320 mg; 0.74 mmol; 1 eq) was dissolved in DCM (5 mL). TFA (1.48 g; 13 mmol; 17.5 eq) was added and the mixture was stirred overnight at RT. The reaction mixture was neutralized with 2N NaOH (pH 10) and extracted with DCM. The organic phase was dried over MgSO$_4$, filtered and evaporated to give compound IXc with a yield of 222 mg (0.672 mmol; 90%).

2-(4-(benzyloxy)phenyl)-6,7-dihydro-5H-pyrrolo[3, 4-b]pyridine (compound Xa; R'=H, R"=H)

Compound Xa was prepared in accordance with scheme 3 starting from tert-butyl 2-chloro-5H-pyrrolo[3,4-b]pyridine-6(7H)-carboxylate instead of compound VII.

Tert-butyl 2-chloro-5H-pyrrolo[3,4-b]pyridine-6 (7H)-carboxylate

To a suspension of 2-chloro-6,7-dihydro-5H-pyrrolo[3,4-b]pyridine (500 mg; 3.23 mmol; 1 eq) in THF (10 mL) was added Et$_3$N (726 mg; 7.17 mmol; 2.2 eq). BOC-anhydride (710 mg; 3.25 mmol; 1.0 eq) was added to give a brown solution. The mixture was stirred at RT for 2 h until the reaction was finished. The reaction mixture was evaporated. The residue was dissolved in DCM, extracted twice with a saturated NH$_4$Cl-solution, washed once with saturated NaCl solution, dried with MgSO$_4$, filtered and evaporated giving the product with a yield of 800 mg (3.14 mmol; 97%).

2-(4-(benzyloxy)phenyl)-6,7-dihydro-5H-pyrrolo[3, 4-b]pyridine (compound Xa; R'=H, R"=H)

Tert-butyl 2-chloro-5H-pyrrolo[3,4-b]pyridine-6(7H)-carboxylate (750 mg; 2.94 mmol; 1 eq), sodium carbonate (7.802 g; 7.36 mmol; 2.5 eq) and potassium 4-benzyloxy-phenyl)trifluoroborate (1.025 g; 3.53 mmol; 1.2 eq) were dissolved in 20 mL DMF. The solution was degassed with argon for 10 min. Tetrakis(triphenylphosphine)-palladium (0) (170 mg; 0.147 mmol; 0.05 eq) was added and the mixture was stirred for 1 h at 120° C. The reaction mixture was evaporated, the residue was dissolved in DCM/water with saturated NaCl solution. After phase separation, the organic phase was washed once with a saturated NaCl solution, dried with MgSO$_4$, filtered and evaporated. The crude product was purified by flash chromatography (40 g silica gel; 0-5% MeOH in DCM). The purified product was crystallized with tert-butyl methyl ether, filtered and dried under vacuum giving tert-butyl 2-(4-(benzyloxy)phenyl)-5H-pyrrolo[3,4-b]pyridine-6(7H)-carboxylate with a yield of 790 mg (1.963 mmol; 67%). 355 mg thereof (0.88 mmol; 1 eq) was dissolved in 5 mL DCM. TFA (1.48 g; 13.0 mmol; 14.7 eq) was added and the mixture was stirred overnight at RT. To the reaction mixture were added 10 mL of a saturated NaHCO$_3$-solution. The mixture was stirred for 10 min at RT. A white solid appeared. The mixture was diluted with DCM. The pH was adjusted to pH 4 with 2N HCl. After phase separation, the aqueous layer was extracted twice with DCM. The combined organic layers were dried over MgSO$_4$, filtered and evaporated. The aqueous layer contains a white solid, the solid was filtered off, dissolved in a mixture of MeOH/DCM and evaporated. 2-(4-(benzyloxy) phenyl)-6,7-dihydro-5H-pyrrolo[3,4-b]pyridine (compound Xa; R'=H, R"=H) was obtained with a yield of 300 mg (0.893 mmol; 90%).

2-(4-(benzyloxy)phenyl)-5,6,7,8-tetrahydropyrido[3, 4-b]pyrazine (compound XIa; R'=H, R"=H)

Compound XIa was prepared in accordance with scheme 1 starting from ethyl 2-chloro-7,8-dihydropyrido[3,4-B] pyrazine-6(5H)-carboxylate instead of compound III. To a solution of ethyl 2-chloro-7,8-dihydropyrido[3,4-B]pyrazine-6(5H)-carboxylate (2.8 g; 11.6 mmol; 1 eq) in 90 mL DMF was added potassium (4-benzyloxyphenyl)-trifluoroborate (4.03 g; 13.9 mmol; 1.2 eq) and Na$_2$CO$_3$ (30.7 g; 29 mmol; 2.5 eq) under stirring. The mixture was degassed with argon for 5 min. Tetrakis(triphenylphosphine)-palladium(0) (0.536 g; 0.46 mmol; 0.04 eq) was added and the mixture was heated for 30 min at 120° C. The reaction mixture was evaporated and the residue was extracted with DCM/water. The organic phase was washed twice with water, dried with MgSO$_4$, filtered and evaporated. The residue was dissolved in DCM and purified by flash chromatography (silica gel, DCM/MeOH) giving ethyl 2-(4-(benzyloxy)phenyl)-7,8-dihydropyrido[3,4-b]pyrazine-6(5H)-carboxylate (fraction 1) with a yield of 2.2 g (5.65 mmol; 48.8%) and ethyl 3-(4-(benzyloxy)phenyl)-7,8-dihydropyrido[3,4-b]pyrazine-6 (5H)-carboxylate (fraction 2) with a yield of 1.8 g (4.62 mmol; 39.9%).

Ethyl 2-(4-(benzyloxy)phenyl)-7,8-dihydropyrido[3,4-b] pyrazine-6(5H)-carboxylate (1 g; 2.57 mmol; 1 eq) was suspended in a 20% solution of KOH in ethanol (2.8 g; 51.4 mmol; 20 eq). The mixture was heated for 1 h at 90° C. 250 mL water and 250 mL DCM were then added to the reaction mixture. After phase separation, the organic phase was washed once with water, dried with MgSO$_4$ and evaporated giving compound XIa with a crude yield of 870 mg. The crude product was used in subsequent reactions without further purification.

2-(4-((3-chlorobenzyl)oxy)phenyl)-5,6,7,8-tetrahydropyrido[3,4-b]pyrazine (compound XIb, R'=3-Cl, R"=H)

Compound XIb was prepared in accordance with scheme 2 starting from ethyl 2-chloro-7,8-dihydropyrido[3,4-b]pyrazine-6(5H)-carboxylate instead of compound III. Ethyl 2-chloro-7,8-dihydropyrido[3,4-b]pyrazine-6(5H)-carboxylate (660 mg; 2.73 mmol; 1 eq) and (4-((3-chlorobenzyl)oxy)phenyl)boronic acid (1.08 g; 4.10 mmol; 1.5 eq) were dissolved in 4 mL DMF. Sodium carbonate (724 mg; 6.83 mmol; 2.5 eq) was added at RT. The mixture was degassed with argon form 20 min. Tetrakis(triphenylphosphine)-palladium(0) (158 mg; 0.137 mmol; 0.05 eq) was added and the mixture was heated for 60 min at 125° C. The reaction mixture was evaporated and the residue was extracted with 40 mL ethyl acetate and 20 mL water. The organic phase was washed once with 10 mL water, dried with MgSO$_4$, filtered and evaporated. The oily residue was purified by flash chromatography (silica gel, DCM:MeOH) giving ethyl 2-(4-((3-chlorobenzyl)oxy)phenyl)-7,8-dihydropyrido[3,4-b]pyrazine-6(5H)-carboxylate with a yield of 829 mg (1.956 mmol; 71.6%).

Ethyl 2-(4-((3-chlorobenzyl)oxy)phenyl)-7,8-dihydropyrido[3,4-b]pyrazine-6(5H)-carboxylate (710 mg; 1.68 mmol; 1 eq) was suspended in a solution of KOH (112; 2.0 mmol; 1.19 eq) in MeOH. The mixture was heated for 1 h at 90° C. 250 mL water and 250 mL DCM were then added to the reaction mixture. After phase separation, the organic phase was washed once with water, dried with MgSO$_4$ and evaporated giving compound XIb with a yield of 531 mg (1.509 mmol; 90%).

3-(4-(benzyloxy)phenyl)-5,6,7,8-tetrahydropyrido[3,4-c]pyridazine (compound XIIIa, R'=H, R"=H)

Compound XIIIa was prepared in accordance with scheme 1 starting from tert-butyl 3-chloro-5,6-dihydropyrido[3,4-c]pyridazine-7(8H)-carboxylate instead of compound III. To a solution of tert-butyl 3-chloro-5,6-dihydropyrido[3,4-c]pyridazine-7(8H)-carboxylate (637 mg; 2.36 mmol; 1 eq) and potassium (4-benzyloxyphenyl)trifluoroborate (822 mg; 2.83 mmol; 1.2 eq) in 12 mL DMF was added sodium carbonate 10% in water (626 mg; 5.9 mmol; 2.5 eq). The solution was rinsed with argon for 3 min. Tetrakis(triphenylphosphine)-palladium(0) (82 mg; 0.071 mmol; 0.03 eq) was added and the mixture was heated for 30 min at 120° C. The reaction mixture was evaporated and the residue was extracted with DCM/water. The organic phase was washed once with water, dried with MgSO$_4$, filtered and evaporated. The oily residue was dissolved in DCM, Celite XTR (kieselguhr) was added and the residue was purified by flash chromatography (silica gel, DCM/MeOH) giving tert-butyl 3-(4-(benzyloxy)phenyl)-5,6-dihydropyrido[3,4-c]pyridazine-7(8H)-carboxylate with a yield of 200 mg (0.479 mmol; 20.28%).

Tert-butyl 3-(4-(benzyloxy)phenyl)-5,6-dihydropyrido[3,4-c]pyridazine-7(8H)-carboxylate (200 mg; 0.48 mmol; 1 eq) was dissolved in 10 mL DCM. TFA (546 mg; 4.79 mmol; 10 eq) was added at RT. The mixture was stirred for 4 h at RT. The mixture was evaporated, 10 mL water was added and the pH was brought to pH 9 with a saturated NaHCO$_3$ solution. The mixture was extracted twice with 20 mL ethyl acetate. The combined ethyl acetate phase was dried with MgSO$_4$, filtered and evaporated giving compound XIIIa with a crude yield of 170 mg. The crude product was used without purification in subsequent reactions.

Tert-butyl 2-chloro-3-fluoro-7,8-dihydro-1,6-naphthyridine-6(5H)-carboxylate (compound XXV)

2-chloro-5-fluoro-6-((4-methoxybenzyl)oxy)nicotinonitrile (compound XXVIII)

To a solution of (4-methoxyphenyl)methanol (182 g; 1317 mmol; 1 eq) in 1 L THF was added potassium 2-methylpropan-2-olate (162 g; 1440 mmol; 1.1 eq) dropwise at −78° C. The reaction mixture was stirred for 30 min at −10° C. 2,6-dichloro-5-fluoronicotinonitrile (250 g; 1309 mmol; 1 eq) was added dropwise at −78° C. The solution was stirred overnight at RT while being monitored by TLC. The reaction mixture was concentrated under vacuum and the aqueous layer was extracted with ethyl acetate (3×800 mL). The solution was dried with Na$_2$SO$_4$ and concentrated under vacuum giving compound XXVIII with a yield of 213 g (728 mmol; 55.6%).

5-fluoro-6-((4-methoxybenzyl)oxy)-2-vinylnicotinonitrile (compound XXIX)

A solution maintained with an inert atmosphere of nitrogen of compound XXVIII (220 g; 752 mmol; 1 eq), potassium trifluoro(vinyl)borate (201 g; 1503 mmol; 2 eq), bis(triphenylphosphine)-palladium(II) dichloride (10.6 g; 15 mmol; 0.02 eq) and cesium fluoride (228 g; 1503 mmol; 2 eq) in 100 mL water with 1 L 1,4-dioxane was stirred overnight at 80° C., while being monitored by TLC. The reaction mixture was cooled to RT and concentrated under vacuum. 800 mL water was added and the aqueous layer was extracted with ethyl acetate (3×800 mL). The solution was dried with Na$_2$SO$_4$ and concentrated under vacuum. The solution was applied onto a silica gel column with EA/PE= (1/100-1/20), giving compound XXIX with a yield of 70 g (246 mmol; 32.8%).

6-benzyl-3-fluoro-2-((4-methoxybenzyl)oxy)-7,8-dihydro-1,6-naphthyridin-5(6H)-one (compound XXX)

Compound XXIX (70 g; 246 mmol; 1 eq) was dissolved in water (160 mL) in methanol (800 mL). The solution was stirred overnight at 80° C. while the reaction progress was monitored by LCMS. The reaction mixture was concentrated under vacuum, then 800 mL EA/PE (1/10) (1 v/v) was added and the solution was filtrated. Compound XXX was obtained with a yield of 55 g (140 mmol; 56.9%).

6-benzyl-3-fluoro-2-((4-methoxybenzyloxy)-5,6,7,8-tetrahydro-1,6-naphthyridine (compound XXXI)

To a solution of compound XXX (55 g; 140 mmol; 1 eq) in 500 mL THF was added borane (7.76 g; 561 mmol; 4 eq) at RT. The solution was stirred overnight at 70° C. while the reaction progress was monitored by TLC. MeOH was added to the reaction mixture which was then concentrated under vacuum. The solution was applied onto a silica gel column with EA/PE (1/100-1/5), providing compound XXXI with a yield of 40 g (106 mmol; 75%).

6-benzyl-2-chloro-3-fluoro-5,6,7,8-tetrahydro-1,6-naphthyridine (compound XXXII)

A solution of compound XXXI (40 g; 106 mmol; 1 eq) and phosphoryl trichloride (16.2 g; 106 mmol; 1 eq) was stirred overnight at 100° C. The reaction progress was monitored by LCMS. The reaction mixture was concentrated under vacuum and the resulting thick oil was poured into crashed ice. Solid $Na_2CO_3$ was added upon stirring to the suspension until pH>7. The aqueous layer was extracted with ethyl acetate (3×500 mL), the solution was dried with $Na_2SO_4$ and concentrated under vacuum giving compound XXXII with a crude yield of 30 g. The crude product was used in subsequent reactions without further purification.
Compound XXV To a solution of compound XXXII (30 g; 108 mmol; 1 eq) in 500 mL 1,2-Dichloroethane were added N-ethyl-N-isopropylpropan-2-amine (28 g; 325 mmol; 2 eq) and 1-chloroethyl carbonochloridate (46.5 g; 325 mmol; 3 eq) dropwise at 0° C. The solution was stirred for 10 min at 0° C. and 2 h at reflux. The reaction mixture was concentrated under vacuum and 500 mL methanol was added. The solution was stirred overnight at RT, while the reaction progress was monitored by LCMS. The reaction mixture was then concentrated under vacuum and the product containing 2-chloro-3-fluoro-5,6,7,8-tetrahydro-1,6-naphthyridine (compound XXXIII) was used directly in the next step. In the next step a solution of compound XXXIII (10 g; 53.6 mmol; 1 eq), 2-((((tert-butoxycarbonyl)oxy)carbonyl)oxy)-2-methylpropan-1-ylium (23.3 g; 107 mmol; 2 eq) and N-ethyl-N-isopropylpropan-2-amine (20.8 g; 161 mmol; 3 eq) in 500 mL methanol was stirred overnight at RT while the reaction progress was monitored by LCMS. The solution was concentrated under vacuum and applied onto a silica gel column with EA/PE (1/100-1/20) providing compound XXV with a yield of 7.90 g (27.6 mmol; 51.4%).

Tert-butyl 3-(2-chloro-3-fluoro-7,8-dihydro-1,6-naphthyridin-6(5H)-yl)propanoate (compound XXVb)

This compound was prepared starting from compound XXXIII using tert-butylacrylate as described for compound XXIa in accordance with scheme 6.

Tert-butyl 2-benzyl-7,8-dihydropyrido[4,3-d]pyrimidine-6 (5H)-carboxylate (compound XXXVIIa, with R'''=H) and 2-benzyl-5,6,7,8-tetrahydropyrido[4,3-d]pyrimidine (compound XXXVIIIa, with R'''=H)

Compound III (2 g; 7.41 mmol; 1 eq) was dissolved in THF and under stirring degassed with argon at RT for 2 min. Bis(triphenylphosphine) Pd (II) dichloride (195 mg; 0.278 mmol; 0.05 eq) and benzylzinc bromide (2.1 g; 8.9 mmol; 1.2 eq) were added and heated for 1 h to reflux. The mixture was cooled to RT and 80 mL water and 80 mL EtOAc were added. The mixture was stirred and filtered over a clarifying filter. After phase separation, the organic phase was dried with $MgSO_4$, filtered and evaporated. The oily residue was dissolved in a little DCM and purified by flash chromatography (silica gel, MeOH/DCM 98:2) giving product XXXVIIa with a yield of 2.35 g (7.22 mmol; 97%).

Compound XXXVIIa was converted to compound XXXVIIIa using TFA giving the product with a yield of 903 mg (4.01 mmol; 52.2%).

2-(2,6-difluorobenzyl)-5,6,7,8-tetrahydropyrido[4,3-d]pyrimidine (compound XXXVIIIb, with R'''=2,6-diFl)

This compound was prepared in the same way as compound XXXVIIIa using (2,6-difluorobenzyl)zinc bromide instead of benzylzinc bromide.

Tert-butyl 2-(4-(2-(4-chloro-2-fluorophenyl)-1-fluoroethyl)phenyl)-7,8-dihydropyrido[4,3-d]pyrimidine-6(5H)-carboxylate (compound XXXIXa)

This compound was prepared in accordance with scheme 12. Compound III (4.05 g; 15 mmol; 1 eq) is dissolved in DMF (80 ml) and under stirring at RT 4-formylphenylboronic acid (2.70 g; 18.0 mmol; 1.2 eq) and sodium carbonate (39.7 g; 37.5 mmol; 2.5 eq) are added. The mixture is degassed with Argon for 5 min and tetrakis(triphenylphosphine)palladium(0) (520 mg; 0.450 mmol; 0.03 eq) is added. The mixture is heated for 1 h at 120° C. The mixtures is evaporated, and the residue is extracted with water and DCM. The organic phase is washed with water, dried over $MgSO_4$ and evaporated. The oily product is dissolved in DCM and purified by flash chromatography (DCM/MeOH 98:2) giving 3.68 g tert-butyl 2-(4-formylphenyl)-7,8-dihydropyrido[4,3-d]pyrimidine-6(5H)-carboxylate (10.84 mmol; 72.3%).

4-chloro-2-fluorobenzylzinc bromide (6.93 g; 24.00 mmol; 4 eq) is dissolved in THF (5 ml) and 1.017 g (24.00 mmol; 4 eq) lithium chloride is added under stirring. The mixture is stirred for 1 h at RT. A solution of the product (2.036 g; 6 mmol; 1 eq) of the previous step in 5 ml THF was added and the mixture was stirred overnight at RT. The mixture was diluted with 30 ml ethylacetate and extracted with 30 ml water. The insoluble zinc salt is removed and the organic phase is obtained, dried over $MgSO_4$ and evaporated. The oily residue is dissolved in 20 ml DCM and purified by flash chromatography (DCM/MeOH 98:2) giving 2.15 g tert-butyl 2-(4-(2-(4-chloro-2-fluorophenyl)-1-hydroxyethyl)phenyl)-7,8-dihydropyrido[4,3-d]pyrimidine-6(5H)-carboxylate (4.44 mmol; 74%). 440 mg thereof (0.909 mmol; 1 eq) is dissolved in DCM (8 ml) and under stirring and at 0° C. diethylaminosulphur trifluoride (293 mg; 1.818 mmol; 2 eq) is added. The mixture is stirred for a further 2 h at RT. The solution is diluted with DCM and 50 ml saturated $NaHCO_3$ is added and stirred for 15 min. After phase separation, the organic phase is washed with water, dried over $MgSO_4$ and evaporated. The oily residue is dissolved in DCM and purified by flash chromatography (n-haptane/ethylacetate 2:1) giving the tert-butyl 2-(4-(2-(4-chloro-2-fluorophenyl)-1-fluoroethyl)phenyl)-7,8-dihydropyrido[4,3-d]pyrimidine-6(5H)-carboxylate with a yield of 81% (360 mg; 0.741 mmol).

Tert-butyl 2-(4-(4-chlorostyryl)phenyl)-7,8-dihydropyrido[4,3-d]pyrimidine-6(5H)-carboxylate (compound XLIa)

This compound was prepared in accordance with scheme 12.
To prepare (4-chlorobenzyl)zinc(II) bromide, zinc powder (0.850 g; 13 mmol; 1.3 eq) was suspended in 6 ml DMA in a preheated flask and, under stirring and Argon atmosphere, added to a solution of 1,2-dibromomethane (0.376 g; 2.00 mmol; 0.2 eq) and 1M chlorotrimethylsilane (0.217 g; 2.00 mmol; 0.2 eq) in 2 ml THF at 65° C. The mixture is stirred for 30 min at 65° C. A solution of 4-chlorobenzyl bromide (2.055 g; 10 mmol; 1 eq) in 4 ml DMA was added during 15 min to the mixture whereby the temperature was maintained at 65° C. The mixture was allowed to cool to RT and stirred for a further 3 h at RT. The solution is directly used in the next step.

Compound XLIa was prepared in accordance with scheme 12. Compound III (4.05 g; 15 mmol; 1 eq) was dissolved in 80 ml DMF. 4-formylphenylboronic acid (2.70 g; 18.00 mmol; 1.2 eq) and sodium carbonate (39.7 g; 37.5 mmol; 2.5 eq) solution were added under stirring at RT. The mixture is degassed with argon for 5 min and tetrakis(triphenylphosphine)palladium(0) (520 mg; 0.450 mmol; 0.03 eq) as added, followed by stirring for 1 h at 120° C. The mixture is evaporated and the residue is extracted with water and DCM. The organic phase was washed with water, dried over MgSO$_4$ and evaporated. The oily residue was dissolved in 15 ml DCM and purified by flash chromatography (n-heptane/ethylacetate 2:1) giving 3.5 g tert-butyl 2-(4-formylphenyl)-7,8-dihydropyrido[4,3-d]pyrimidine-6(5H)-carboxylate (10.31 mmol; 68.8%).

The solution containing (4-chlorobenzyl)zinc(II) bromide (0.83M in DMA; 2.7 g; 9.99 mmol; 4 eq) was dissolved in 10 ml THF at RT. Lithium chloride (424 mg; 9.99 mmol; 4 eq) was added under stirring and Argon atmosphere, followed by stirring for 1 h at RT. A solution of the tert-butyl 2-(4-formylphenyl)-7,8-dihydropyrido[4,3-d]pyrimidine-6(5H)-carboxylate (848 mg; 2.499 mmol; 1 eq) in 10 ml THF is added slowly followed by overnight stirring at RT. The mixture is diluted with 50 ml ethylacetate and extracted with 50 ml water. The insoluble zinc salts are removed and the organic phase is dried over MgSO$_4$ and evaporated. The semi-solid residue was dissolved in 15 ml DCM and purified by flash chromatography (n-heptane/ethylacetate 2:1) giving tert-butyl 2-(4-(2-(4-chlorophenyl)-1-hydroxyethyl)phenyl)-7,8-dihydropyrido[4,3-d]pyrimidine-6(5H)-carboxylate with a yield of 85%.

1.2 g tert-butyl 2-(4-(2-(4-chlorophenyl)-1-hydroxyethyl)phenyl)-7,8-dihydropyrido[4,3-d]pyrimidine-6(5H)-carboxylate (2.58 mmol; 1 eq) is dissolved in DMF (35 ml) and methyl N-(triethylammoniumsulfonyl)carbamate (3.68 g; 15.45 mmol; 6 eq) was added under stirring. The mixture is heated for 1 h at 90° C. The mixture is evaporated and the residue is extracted with 200 ml water. The solid product is removed, dried over P$_2$O$_5$ at 50° C. under vacuum. The residue is dissolved in 10 ml DCM and purified by flash chromatography (n-heptane/ethylacetate 2:1) giving compound XLIa with a yield of 48.5% (560 mg; 1.250 mmol).

Tert-butyl 2-(4-(2-fluoro-4-chlorostyryl)phenyl)-7,8-dihydropyrido[4,3-d]pyrimidine-6(5H)-carboxylate (compound XLIb)

This compound was prepared as described for compound XLIa starting from 2-fluoro-4-chlorobenzyl bromide instead of 4-chlorobenzyl bromide.

Tert-butyl 2-(4-(4-chlorostyryl)-2-fluorophenyl)-7,8-dihydropyrido[4,3-d]pyrimidine-6(5H)-carboxylate (compound XLIc)

This compound was prepared as described for compound XLIa using 2-fluoro-4-formylphenylboronic acid instead of 4-formylphenylboronic acid.

Tert-butyl 2-(4-(styryl)-2-fluorophenyl)-7,8-dihydropyrido[4,3-d]pyrimidine-6(5H)-carboxylate (compound XLId)

This compound was prepared as described for compound XLIa starting from benzyl bromide instead of 4-chlorobenzyl bromide and using 2-fluoro-4-formylphenylboronic acid instead of 4-formylphenylboronic acid.

Tert-butyl 2-(4-(3-chlorostyryl)-2-fluorophenyl)-7,8-dihydropyrido[4,3-d]pyrimidine-6(5H)-carboxylate (compound XLIe)

This compound was prepared as described for compound XLIa starting from 3-chlorobenzyl bromide instead of 4-chlorobenzyl bromide and using 2-fluoro-4-formylphenylboronic acid instead of 4-formylphenylboronic acid.

Tert-butyl 2-(4-(2-(4-chloro-2-fluorophenyl)acetyl)phenyl)-7,8-dihydropyrido[4,3-d]pyrimidine-6(5H)-carboxylate (compound XLa)

This compound was prepared in accordance with scheme 12.

Tert-butyl 2-(4-(2-(4-chloro-2-fluorophenyl)-1-hydroxyethyl)phenyl)-7,8-dihydropyrido[4,3-d]pyrimidine-6(5H)-carboxylate was prepared as in the same way as tert-butyl 2-(4-(2-(4-chlorophenyl)-1-hydroxyethyl)phenyl)-7,8-dihydropyrido[4,3-d]pyrimidine-6(5H)-carboxylate, described above for compound XLIa using 4-chloro-2-benzylzinc bromide instead of 4-chloro-benzylzinc bromide. 1.67 g thereof (3.45 mmol; 1 eq) was dissolved in DCM (20 ml)/DMSO (20 ml). 2-iodoxybenzoic acid (1.932 g; 6.90 mmol; 2 eq) was added under stirring and the mixture was stirred for 20 h at RT. The mixture was diluted with a further 150 DCM and extracted with 100 ml saturated NaHCO$_3$ solution. The insoluble residue between the two phases was removed. The organic phase was washed three times with water, dried over MgSO$_4$ and evaporated. The oily residue was dissolved in 10 ml DCM and purified by flash chromatograph (n-heptane/ethylacetate 2:1) giving 1.29 g tert-butyl 2-(4-(2-(4-chloro-2-fluorophenyl)acetyl)phenyl)-7,8-dihydropyrido[4,3-d]pyrimidine-6(5H)-carboxylate (2.68 mmol; 78%). 482 mg thereof (1.00 mmol; 1 eq) was dissolved in toluene (10 ml). Bis(2-methoxyethyl)aminosulfur trifluoride (DeoxoFluor®) 50% in toluene (443 mg; 2.00 mmol; 2 eq) was added under stirring and cooling to 0° C. The mixture is stirred for 5 h at RT, followed by heating for 2 h at 60° C. and further stirring for 20 h at RT. The mixture was evaporated and the residue was dissolved in 10 ml DCM. Diethylaminosulfur trifluoride (8.06 g; 50.0 mmol; 50 eq) was added under stirring at RT and the mixture was stirred for 2 days at RT. The reaction mixture was diluted with 10 ml DCM and slowly dripped into 200 ml saturated NaHCO$_3$ solution, followed by stirring for 30 min. 50 ml DCM was added and the organic phase was obtained, washed with water, dried over MgSO$_4$ and evaporated. The oily residue was dissolved in 2 ml DCM and purified by flash chromatograph (n-heptane/ethylacetate 2:1) giving compound XLa with a yield of 39.7% (200 mg; 0.397 mmol).

Methyl 1-(2-oxoethyl)cyclopropanecarboxylate 1-(2-hydroxyethyl)cyclopropane-1-carboxylic acid (500 mg; 3.84 mmol; 1 eq) was dissolved in DCM (40 ml). 6.22 ml MeOH and a solution of 2M(trimethylsilyl)diazomethane (570 mg; 4.99 mmol; 1.3 eq) in hexane (2.50 ml) were added and stirred for 3 h. 2 ml glacial acetic acid was added and the excess of the diazomethane is removed. The mixture was diluted with 50 ml DCM and stirred for 20 min with a 50 ml saturated NaHCO$_3$ solution. The organic phase was obtained and subjected to an additional extraction with 30 ml DCM. The organic phase was subsequently dried over MgSO$_4$ and evaporated. Of the resulting methyl 1-(2-hydroxyethyl)cyclopropanecarboxylate 300 mg (2.081 mmol; 1 eq) was used without purification in the next step. The material was dissolved in DMSO (40 ml) and triethylamine (842 mg; 8.32 mmol; 4 eq) and sulfur trioxide pyridine complex (662 mg; 4.16 mmol; 2 eq) were added stepwise under stirring. The mixture was stirred for a further 2 h at RT. The mixture was extracted with a saturated NaHCO$_3$ solution and DCM and the organic phase was subsequently washed three times with saturated NaHCO$_3$ solution. The organic phase was then dried over MgSO$_4$ and evaporated giving 500 mg methyl 1-(2-oxoethyl)cyclopropanecarboxylate containing traces of DMSO, which was used without further purification, e.g. for the preparation of compound 335.

2-(3-(benzyloxy)cyclobutyl)-5,6,7,8-tetrahydropyrido[4,3-d]pyrimidine

50% NaH in mineral oil (1.209 g; 25.2 mmol; 2.1 eq) was added gradually to 50 ml EtOH under cooling and Argon atmosphere. The mixture was stirred for 15 min and 3-(benzyloxy)cyclobutanecarboximidamide hydrochloride (3.30 g; 12.6 mmol; 1.05 eq) and tert-butyl 3-((dimethylamino)methylene)-4-oxopiperidine-1-carboxylate in 10 ml EtOH (prepared as described for compound XXIIIb; 3.05 g; 12 mmol; 1 eq) were added gradually. The mixture was heated for 5 h and subsequently evaporated. The residue was stirred with 80 ml water, adjusted to pH 5-6 with 30 ml 1N AcOH and extracted twice with EtOAc. The organic phase was obtained, washed twice with water, dried over MgSO$_4$ and evaporated. The oily residue was dissolved in 10 ml DCM and purified by flash chromatograph (40 g silica gel, n-heptane/ethyl acetate) giving tert-butyl 2-(3-(benzyloxy)cyclobutyl)-7,8-dihydropyrido[4,3-d]pyrimidine-6(5H)-carboxylate with a yield of 47.4% (2.25 g; 5.69 mmol). The whole product was converted to 2-(3-(benzyloxy)cyclobutyl)-5,6,7,8-tetrahydropyrido[4,3-d]pyrimidine using TFA as described elsewhere with a yield of 92% (1.55 g; 5.25 mmol).

2-(4-(2-(4-chlorophenyl)-1,1-difluoroethyl)phenyl)-4,4,5,5-tetramethyl-1,3,2-dioxaborolane 2-(4-chlorophenyl)acetic acid (17 g; 100 mmol; 1 eq) was heated with SOCl$_2$ (14.55 ml; 23.71 g; 199 mmol; 2 eq) for 3 hour, then the rest of the SOCl$_2$ was evaporated under vacuum. This mixture was added to a mixture of bromobenzene (94 g; 598 mmol; 6 eq) and aluminum trichloride (19.93 g; 149 mmol; 1.5 eq) at 0° C. The reaction mixture was stirred at RT for 0.75 h. The reaction mixture was poured onto ice/concentrated hydrochloric acid [(300 mL)] and stirred for 1 hour before extracting with chloroform (3×200 ml). The organic layer was washed with NaOH (2×200 ml) and water (2×200 ml) and then dried over Na$_2$SO$_4$. The chloroform and any remaining bromobenzene was removed in vacuo. The residue was applied on a silica gel column and eluted with ethyl acetate/hexane (1/20) to give 1-(4-bromophenyl)-2-(4-chlorophenyl)ethanone (22 g, 71.1%) as a colorless solid.

To a solution of 1-(4-bromophenyl)-2-(4-chlorophenyl)ethanone (20 g; 64.6 mmol; 1 eq) in dry DCM (200 ml) was added ethane-1,2-dithiol (7.30 g; 78 mmol; 1.2 eq) and BF$_3$.OEt$_2$ (4.09 ml; 4.58 g; 32.3 mmol; 0.5 eq) at 0° C. The resulting reaction mixture is stirred at RT for 96 h. After completion of reaction, the mixture is neutralized with 10M NaOH and extracted with DCM (3×150 ml). The combined organic layers are washed with water (300 mL), saturated NaCl (300 ml), dried over Na$_2$SO$_4$ and evaporated in vacuo to get the crude product, which is purified by column chromatograph (silica gel, 5% EA/PE) to yield 2-(4-bromophenyl)-2-(4-chlorobenzyl)-1,3-dithiolane (25 g; 64.8 mmol; 100% yield) as a colorless oil.

To a solution of N-iodosuccinimide (29.2 g; 130 mmol; 2 eq) in dry DCM (200 ml) was added HF-Pyridine (32.1 g; 324 mmol; 5 eq) at −78° C., followed by the addition of 2-(4-bromophenyl)-2-(4-chlorobenzyl)-1,3-dithiolane (25 g; 64.8 mmol; 1 eq) in dry DCM (100 ml) at the same temperature. The reaction mixture was stirred at −78° C. for 1.5 h and then allowed to warm to RT over a period of 1 h. After completion of reaction, the mixture was neutralized with saturated NaHCO$_3$ and the aqueous layer was extracted with DCM (3*200 ml), the organic layer is washed with 20% HCl (500 mL), water (500 mL), saturated NaCl (500 ml), dried over anhydrous Na$_2$SO$_4$ and evaporated in vacuo to yield 1-bromo-4-(2-(4-chlorophenyl)-1,1-difluoroethyl)benzene (9.1 g; 27.4 mmol; 42.3% yield) as white solid.

To a solution of 1-bromo-4-(2-(4-chlorophenyl)-1,1-difluoroethyl)benzene (4.0 g; 12.06 mmol; 1 eq) in dioxane (30 ml) was added 4,4,4',4',5,5,5',5'-octamethyl-2,2'-bi(1,3,2-dioxaborolane) (4.60 g; 18.10 mmol; 1.5 eq), potassium acetate (2.368 g; 24.13 mmol; 2 eq) and [1,1'-Bis(diphenylphosphino)ferrocene]dichloropalladium(II) (0.197 g; 0.241 mmol; 0.02 eq). The reaction mixture was stirred overnight at 100° C. before being cooled to RT and filtered. The filtrate was then concentrated to dryness and the residue was taken up in ethyl acetate, washed with NaCl, dried over Na$_2$SO$_4$, filtered and concentrated under reduced pressure. The crude product was applied onto a silica gel column with ethyl acetate/petroleum ether (1:50) to give 2-(4-(2-(4-chlorophenyl)-1,1-difluoroethyl)phenyl)-4,4,5,5-tetramethyl-1,3,2-dioxaborolane (3.2 g; 8.45 mmol; 70.1% yield) as a white solid.

2-(4-(2-(4-chlorophenyl)cyclopropyl)phenyl)-4,4,5,5-tetramethyl-1,3,2-dioxaborolane To a solution of 4-bromobenzaldehyde (5 g; 27.0 mmol; 1 eq) in 30 MeOH was added 4-methylbenzenesulfonohydrazide (5.54 g; 29.7 mmol; 1.1 eq) at RT. The mixture was stirred for 1 h at RT followed by cooling to 0° C. The precipitate was collected by filtration and washed twice with cooled MeOH (10 ml). The solid residue was dried in an oven to yield (Z)—N'-(4-bromobenzylidene)-4-methylbenzenesulfonohydrazide (9 g; 23.7 mmol; 88%).

6 g thereof (16.99 mmol; 1 eq) was dissolved in 12 ml 1,4-dioxane together with K$^2$CO$^3$ (3.52 g; 25.5 mmol; 1.5 eq) and 1-chloro-4-vinylbenzene (4.24 g; 30.6 mmol; 1.8 eq). The mixture was stirred for 6 h at 110° C., followed by concentration under vacuum. The residue was purified by chromatograph resulting in 3 g 1-bromo-4-(2-(4-chlorophenyl)cyclopropyl)benzene (8.78 mmol; 51.7%).

4,4,4',4',5,5,5',5'-octamethyl-2,2'-bi(1,3,2-dioxaborolane) (2.468 g; 9.72 mmol; 1.15 eq), 1-bromo-4-(2-(4-chlorophenyl)cyclopropyl)benzene (2.6 g; 8.45 mmol; 1 eq), potassium acetate (2.074 g; 21.13 mmol; 2.5 eq) and [1,1'-Bis(diphenylphosphino)ferrocene]dichloropalladium(II) (0.690 g; 0.845 mmol; 0.1 eq) were dissolved in 5 ml dioxane. The reaction mixture was stirred for 15 h at 80° C. before being cooled to RT and filtered. The residue was extracted with water and ethyl acetate. The aqueous phase was washed once with ethyl acetate. The combined organic phases were washed with saturated NaCl, dried and concentrated. The residue was purified by chromatography (hexane:ethyl acetate 8:1) to give 2.61 g 2-(4-(2-(4-chlorophenyl)cyclopropyl)phenyl)-4,4,5,5-tetramethyl-1,3,2-dioxaborolane (6.63 mmol; 78%).

4. Synthesis of Compounds According to the Invention

1-((2-(4-((3-chlorobenzyl)oxy)phenyl)-7,8-dihydropyrido[4,3-d]pyrimidin-6(5H)-yl)methyl)cyclopropanecarboxylic acid (compound 1)

This compound was prepared in accordance with scheme 2. Compound XXc (105 mg; 0.37 mmol; 1 eq) and (4-((3-chlorobenzyl)oxy)phenyl)boronic acid (compound VI with R'=3Cl, R"=H; 147 mg; 0.56 mmol; 1.5 eq) were dissolved in 4 mL DMF. $Na_2CO_3$ (988 mg; 0.93 mmol; 2.5 eq) was added at RT and the solution was rinsed with argon (20 min). Tetrakis(triphenylphosphine)-palladium(0) (21.53 mg; 0.019 mmol; 0.05 eq) was added and the mixture was heated and stirred for 60 min at 125° C. to yield a black suspension. The reaction mixture was evaporated and water (20 mL) and ethyl acetate (30 mL) were added to the residue. After phase separation, the organic layer was washed once with 10 mL water, dried with $MgSO_4$ and evaporated overnight. The residue was dissolved in DCM and purified by flash chromatography (silica gel, 98:2 DCM:MeOH), giving methyl 1-((2-(4-((3-chlorobenzyl)oxy)phenyl)-7,8-dihydropyrido[4,3-d]pyrimidin-6(5H)-yl)methyl)cyclopropanecarboxylate with a yield of 95 mg (0.205 mmol; 54.9%). This compound was dissolved in MeOH (3 mL) and THF (3 mL). NaOH (120 mg; 3.0 mmol) was added and the mixture was stirred overnight at RT. The mixture was evaporated, 5 mL water was added and 2N HCl was added until pH 1. The solution was extracted twice with 50 mL ethyl acetate. The combined organic phase is dried with $MgSO_4$, filtered and evaporated giving compound 1 (12 mg; 0.025 mmol; 12.3%). $^1$H NMR (600 MHz, DMSO-$d_6$) δ 8.59 (s, 1H), 8.31 (d, J=8.8 Hz, 2H), 7.56 (s, 1H), 7.52-7.36 (m, 3H), 7.14 (d, J=8.8 Hz, 2H), 5.21 (s, 2H), 3.78 (s, 2H), 2.97 (dp, J=9.2, 5.1, 4.1 Hz, 4H), 2.83 (s, 2H), 1.23 (s, 1H), 1.14 (q, J=3.7 Hz, 2H), 0.85 (q, J=3.8 Hz, 2H). M+H+ 450.25

1-((2-(4-((4-chlorobenzyl)oxy)phenyl)-7,8-dihydropyrido[4,3-d]pyrimidin-6(5H)-yl)methyl)cyclopropanecarboxylic acid (compound 215)

Compound 215 was prepared from compound XXc in the same way as described for compound 1 with the exception that (4-((4-chlorobenzyl)oxy)phenyl)boronic acid (compound VI with R'=3Cl, R"=H) was used instead of (44(3-chlorobenzyl)oxy)phenyl)boronic acid. Calculated mass (C25H24ClN3O3): 449.15 g/mol. $^1$H NMR (600 MHz, DMSO-$d_6$) δ 8.65 (s, 1H), 8.37 (d, J=8.6 Hz, 2H), 7.62-7.49 (m, 4H), 7.19 (d, J=8.7 Hz, 2H), 5.25 (s, 2H), 3.84 (s, 2H), 3.03 (dp, J=9.1, 5.0, 4.0 Hz, 4H), 2.89 (s, 2H), 1.20 (q, J=3.8 Hz, 2H), 0.91 (q, J=3.9 Hz, 2H). M+H+ 450.2

2-(3-(2-(4-((3-chlorobenzyl)oxy)phenyl)-7,8-dihydropyrido[4,3-d]pyrimidin-6(5H)-yl)cyclobutyl) acetic acid (compound 3)

Compound 3 was prepared from methyl 2-(3-(2-(4-((3-chlorobenzyl)oxy)phenyl)-7,8-dihydropyrido[4,3-d]pyrimidin-6(5H)-yl)cyclobutyl)acetate (compound XXIVe with R'=H, R*=cyclobutylacetate, R'''=3-Cl) using NaOH. Compound XXIVe (R'=H, R*=cyclobutylacetate, R'''=3-Cl; 75 mg; 0,157 mmol) was dissolved in MeOH (2 mL) and THF (2 mL) to give a yellow solution. NaOH (0.4 mL; 0.800 mmol) was added. The mixture was stirred at overnight at RT. The reaction mixture was evaporated. The residue was dissolved in water. 0.5 mL 2N HCl were added dropwise (pH value was between 1-2). The solid was filtered, washed once with 0.5 mL water and dried under vacuum at 40° C. giving the product with yield of 65 mg (0.130 mmol; 83%). Calculated mass (C26H26ClN3O3) 463.17 g/mol. $^1$H NMR (600 MHz, DMSO-$d_6$) δ 12.20 (s, 1H), 11.25 (d, J=35.5 Hz, 1H), 8.72 (d, J=2.4 Hz, 1H), 8.37-8.30 (m, 2H), 7.56 (dt, J=2.0, 1.0 Hz, 1H), 7.48-7.39 (m, 3H), 7.21-7.14 (m, 2H), 5.22 (s, 2H), 4.63-4.54 (m, 1H), 4.21-4.11 (m, 1H), 3.76 (q, J=8.2 Hz, 1H), 3.67 (s, 1H), 3.16 (d, J=15.6 Hz, 1H), 2.58 (dd, J=16.7, 8.7 Hz, 1H), 2.43 (d, J=7.5 Hz, 2H), 2.33 (dh, J=15.1, 8.0 Hz, 1H), 2.11 (h, J=8.9 Hz, 2H). M+H+ 464

The following compounds were prepared in the same way as compound 3:

2-(3-(2-(4-((4-chlorobenzyl)oxy)phenyl)-7,8-dihydropyrido[4,3-d]pyrimidin-6(5H)-yl)cyclobutyl) acetic acid (compound 2)

Using compound XXIVf instead of compound XXIVe. Calculated mass (C26H26ClN3O3) 463.17 g/mol. $^1$H NMR (600 MHz, DMSO-$d_6$) δ 12.19 (s, 1H), 8.71 (d, J=2.6 Hz, 1H), 8.42-8.17 (m, 2H), 7.62-7.42 (m, 4H), 7.29-7.05 (m, 2H), 5.20 (s, 2H), 4.58 (s, 1H), 3.67 (s, 1H), 3.16 (d, J=14.6 Hz, 1H), 2.12 (d, J=9.1 Hz, 1H). M+H+ 464

2-(3-(2-(4-((3,4-dichlorobenzyl)oxy)phenyl)-7,8-dihydropyrido[4,3-d]pyrimidin-6(5H)-yl)cyclobutyl) acetic acid (compound 4)

Using compound XXIVh instead of compound XXIVe. Calculated mass (C26H25Cl2N3O3) 497.13 g/mol. $^1$H NMR (600 MHz, DMSO-$d_6$) δ 8.72 (s, 1H), 8.39-8.31 (m, 2H), 7.82-7.62 (m, 2H), 7.49 (dd, J=8.3, 2.1 Hz, 1H), 7.24-7.06 (m, 2H), 5.23 (d, J=6.2 Hz, 2H). M+H+ 498

2-(3-(2-(4-((3,5-dichlorobenzyl)oxy)phenyl)-7,8-dihydropyrido[4,3-d]pyrimidin-6(5H)-yl)cyclobutyl) acetic acid (compound 5)

Using compound XXIVg instead of XXIVe. Calculated mass (C26H25Cl2N3O3) 497.13 g/mol. $^1$H NMR (600 MHz, DMSO-$d_6$) δ 8.72 (s, 1H), 8.35 (dd, J=8.9, 1.5 Hz, 2H), 7.58 (dd, J=35.6, 2.0 Hz, 3H), 7.23-7.07 (m, 2H), 5.23 (s, 2H), 4.61 (t, J=17.8 Hz, 1H), 4.29-3.95 (m, 1H), 3.73 (d, J=55.9 Hz, 1H), 2.18-1.93 (m, 2H). M+H+ 498

3-(2-(4-(benzyloxy)phenyl)-7,8-dihydropyrido[4,3-d]pyrimidin-6(5H)-yl)-2-methylpropanoic acid (compound 6)

Compound XVIIg (R'=H, R"=H, R*=ethyl 2-methylpropanoate; 50 mg; 0.116 mmol) was dissolved in THF. 1N LiOH (600 µL) was added under stirring at RT. The reaction mixture was neutralized with 1N HCl (600 µL) and subsequently evaporated. The resulting yellow oil was crystallized with a glass stirring rod, washed with water and evaporated over $P_2O_5$. Compound 6 was obtained with a yield of 39 mg (0.097 mmol; 83%). Calculated mass (C24H25N3O3): 403.47 g/mol. $^1$H NMR (DMSO-d6, 600

MHz): δ=10.38 (d, J=10.7 Hz, 1H), 8.71 (s, 1H), 8.32-8.35 (m, 2H), 7.48 (d, J=7.2 Hz, 2H), 7.42 (t, J=7.5 Hz, 2H), 7.34-7.37 (m, 1H), 7.15-7.18 (m, 2H), 5.20 (s, 2H), 4.66 (br. s., 1H), 4.42 (br. s., 1H), 3.57 (s, 1H), 3.30 (br. s., 2H), 3.22 (br. s., 1H), 3.18 (br. s., 1H), 3.07-3.11 (m, 1H), 1.27 (d, J=7.2 Hz, 2H), 1.22-1.30 (m, 1H). M+H=404

3-(2-(4-(2,6-dichlorobenzyloxy)phenyl)-7,8-dihydropyrido[4,3-d]pyrimidin-6(5H)-yl)-2-methylpropanoic acid (compound 7)

Compound 7 was prepared in the same way as described for compound 6 with the exception that compound XVIIh was used instead of compound XVIIg. Calculated mass: ($C_{24}H_{23}Cl_2N_3O_3$): 472.36 g/mol. $^1$H NMR (DMSO-d6, 600 MHz): δ=12.97 (br. s., 1H), 10.35 (br. s., 1H), 8.72 (s, 1H), 8.35-8.39 (m, 2H), 7.58-7.62 (m, 2H), 7.49-7.52 (m, 1H), 7.30-7.32 (m, 1H), 7.18-7.25 (m, 2H), 5.32 (s, 2H), 4.66 (br. s., 1H), 4.49 (s, 1H), 4.43 (br. s., 1H), 3.84 (br. s., 1H), 3.70-3.73 (m, 1H), 3.63-3.69 (m, 1H), 3.54-3.62 (m, 4H, 3.29 (br. s., 2H), 3.06-3.12 (m, 1H), 1.35 (s, 1H), 1.27 (d, J=7.0 Hz, 3H). M+H=472/474/476

3-(2-(4-((3-fluorobenzyl)oxy)phenyl)-7,8-dihydropyrido[4,3-d]pyrimidin-6(5H)-yl)-2-methylpropanoic acid (compound 8)

Compound XVIIi (30 mg; 0.069 mmol) was dissolved in THF (2 mL). Sodium hydroxide (0.5 mL; 1.000 mmol) was added and the reaction mixture was stirred overnight at RT. 500 μL 2 N HCl was added to the reaction mixture, which was subsequently evaporated. The residue was dissolved in water/DCM with a small amount of MeOH.

After phase separation, the aqueous phase was extracted once with DCM, the combined organic phase was dried with $MgSO_4$, filtered and concentrated. The product was absorbed on kieselguhr and purified by flash chromatography (4 g silica gel, 0-20% MeOH in DCM). Compound 8 was obtained with a yield of 14 mg (0.033 mmol; 48.2%). Calculated mass ($C_{24}H_{24}FN_3O_3$): 421.464 g/mol. $^1$H NMR (600 MHz, DMSO-$d_6$) δ 8.55 (s, 1H), 8.31 (d, J=8.9 Hz, 2H), 7.46 (td, J=8.0, 6.0 Hz, 1H), 7.36-7.28 (m, 2H), 7.22-7.16 (m, 1H), 7.15-7.11 (m, 2H), 5.21 (s, 2H), 3.65 (q, J=15.3 Hz, 2H), 2.99-2.84 (m, 3H), 1.09 (d, J=6.6 Hz, 3H). M+H+ 422

3-(2-(4-((3,4-dichlorobenzyl)oxy)phenyl)-7,8-dihydropyrido[4,3-d]pyrimidin-6(5H)-yl)-2-methylpropanoic acid (compound 14)

Compound XXIVa (76 mg; 0.156 mmol; 1 eq) was dissolved in MeOH (2 mL) and THF (2 mL) to give a yellow solution. NaOH (1 mL; 2 mmol) was added. The mixture was stirred overnight at RT. The reaction mixture was evaporated. The residue was dissolved in water. 0.5 mL 2N HCl was added dropwise (pH value between 1-2). The solid was filtered, washed once with 0.5 mL water and dried under vacuum at 40° C. giving the product with a yield of 75 mg (0.115 mmol; 73.7%). Calculated mass ($C_{24}H_{23}Cl_2N_3O_3$) 471.11 g/mol. $^1$H NMR (600 MHz, DMSO-$d_6$) δ 8.70 (s, 1H), 8.38-8.29 (m, 2H), 7.76 (d, J=2.0 Hz, 1H), 7.69 (d, J=8.2 Hz, 1H), 7.48 (dd, J=8.3, 2.0 Hz, 1H), 7.24-7.08 (m, 2H), 5.22 (s, 2H), 3.22 (s, 3H), 3.04 (s, 1H), 1.23 (d, J=7.1 Hz, 3H). M+H+ 472

The following compounds were made in the same way as compound 14:

3-(2-(4-((3,5-difluorobenzyl)oxy)phenyl)-7,8-dihydropyrido[4,3-d]pyrimidin-6(5H)-yl)-2-methylpropanoic acid (compound 9)

from compound XXIVi instead of compound XXIVa. Calculated mass ($C_{24}H_{23}F_2N_3O_3$): 439.17 g/mol. $^1$H NMR (600 MHz, Chloroform-d) δ 8.48 (s, 1H), 8.46-8.27 (m, 1H), 7.10-7.02 (m, 1H), 7.02-6.92 (m, 2H), 6.83-6.74 (m, OH), 5.13 (d, J=10.0 Hz, 2H), 1.26 (d, J=6.4 Hz, 5H). M+H+ 440

3-(2-(4-((3-chlorobenzyl)oxy)phenyl)-7,8-dihydropyrido[4,3-d]pyrimidin-6(5H)-yl)-2-methylpropanoic acid (compound 10)

from intermediate methyl 3-(2-(4-((3-chlorobenzyl)oxy)phenyl)-7,8-dihydropyrido[4,3-d]pyrimidin-6(5H)-yl)-2-methylpropanoate instead of compound XXIVa. Calculated mass ($C_{24}H_{24}ClN_3O_3$) 437.15 g/mol. $^1$H NMR (600 MHz, DMSO-$d_6$) δ 12.98 (s, 1H), 10.36 (s, 1H), 8.70 (s, 1H), 8.34 (d, J=8.5 Hz, 2H), 7.56 (s, 1H), 7.44 (dd, J=17.7, 4.5 Hz, 3H), 7.17 (d, J=8.6 Hz, 2H), 5.22 (s, 2H), 4.43 (s, 1H), 3.07 (s, 1H), 1.35 (s, 1H), 1.30-1.21 (m, 4H). M+H+ 438

3-(2-(4-((3,4-difluorobenzyl)oxy)phenyl)-7,8-dihydropyrido[4,3-d]pyrimidin-6(5H)-yl)-2-methylpropanoic acid (compound 11)

Using intermediate methyl 3-(2-(4-((3,4-difluorobenzyl)oxy)phenyl)-7,8-dihydropyrido[4,3-d]pyrimidin-6(5H)-yl)-2-methylpropanoate instead of compound XXIVa. Calculated mass ($C_{24}H_{23}F_2N_3O_3$) 439.17 g/mol. $^1$H NMR (600 MHz, DMSO-$d_6$) δ 12.99 (s, 1H), 10.46 (s, 1H), 8.71 (s, 1H), 8.42-8.25 (m, 2H), 7.58 (ddd, J=10.6, 7.9, 2.1 Hz, 1H), 7.49 (dt, J=10.9, 8.4 Hz, 1H), 7.36 (t, J=4.8 Hz, 1H), 7.17 (d, J=9.1 Hz, 2H), 5.19 (s, 2H), 4.66 (s, 1H), 3.84 (s, 1H), 3.09 (h, J=7.1 Hz, 1H), 1.27 (d, J=7.1 Hz, 3H). M+H+ 440

3-(2-(4-((4-chlorobenzyl)oxy)phenyl)-7,8-dihydropyrido[4,3-d]pyrimidin-6(5H)-yl)-2-methylpropanoic acid (compound 12)

Using intermediate methyl 3-(2-(4-((4-chlorobenzyl)oxy)phenyl)-7,8-dihydropyrido[4,3-d]pyrimidin-6(5H)-yl)-2-methylpropanoate instead of compound XXIVa. Calculated mass ($C_{24}H_{24}ClN_3O_3$) 437.15 g/mol. $^1$H NMR (600 MHz, DMSO-$d_6$) δ 8.71 (s, 1H), 8.45-8.26 (m, 2H), 7.62-7.40 (m, 4H), 7.25-7.10 (m, 2H), 5.20 (s, 2H), 3.10 (td, J=7.4, 5.6 Hz, 1H), 1.27 (d, J=7.2 Hz, 3H). M+H+ 438

3-(2-(4-((2,6-dimethylbenzyl)oxy)phenyl)-7,8-dihydropyrido[4,3-d]pyrimidin-6(5H)-yl)-2-methylpropanoic acid (compound 15)

Using intermediate methyl 3-(2-(4-((2,6-dimethylbenzyl)oxy)phenyl)-7,8-dihydropyrido[4,3-d]pyrimidin-6(5H)-yl)-2-methylpropanoate instead of compound XXIVa. Calculated mass ($C_{26}H_{29}N_3O_3$) 431.22 g/mol. $^1$H NMR (500 MHz, DMSO-$d_6$) δ 8.69 (s, 1H), 8.40-8.30 (m, 2H), 7.26-7.14 (m, 3H), 7.09 (d, J=7.5 Hz, 2H), 5.14 (s, 2H), 3.19 (dd, J=15.0, 8.3 Hz, 3H), 2.35 (s, 6H), 1.23 (d, J=7.1 Hz, 3H). M+H+ 432

3-(2-(4-((2,3-difluorobenzyl)oxy)phenyl)-7,8-dihydropyrido[4,3-d]pyrimidin-6(5H)-yl)-2-methylpropanoic acid (compound 16)

Using intermediate methyl 3-(2-(4-((2,3-difluorobenzyl)oxy)phenyl)-7,8-dihydropyrido[4,3-d]pyrimidin-6(5H)-yl)-

2-methylpropanoate instead of compound XXIVa. calculated mass (C24H23F2N3O3) 439.17 g/mol. ¹H NMR (500 MHz, DMSO-d₆) δ 8.70 (s, 1H), 8.45-8.27 (m, 2H), 7.52-7.36 (m, 2H), 7.33-7.22 (m, 1H), 7.23-7.14 (m, 2H), 5.29 (s, 2H), 3.21 (t, J=6.5 Hz, 3H), 3.03 (q, J=7.0 Hz, 1H), 1.23 (d, J=7.2 Hz, 3H). M+H+ 440

3-(2-(4-((3,5-dichlorobenzyl)oxy)phenyl)-7,8-dihydropyrido[4,3-d]pyrimidin-6(5H)-yl)-2-methylpropanoic acid (compound 17)

Using intermediate methyl 3-(2-(4-((3,5-dichlorobenzyl)oxy)phenyl)-7,8-dihydropyrido[4,3-d]pyrimidin-6(5H)-yl)-2-methylpropanoate instead of compound XXIVa. Calculated mass (C24H23Cl2N3O3) 471.11 g/mol. ¹H NMR (500 MHz, DMSO-d₆) δ 8.69 (s, 1H), 8.39-8.29 (m, 2H), 7.61 (t, J=2.0 Hz, 1H), 7.55 (d, J=1.9 Hz, 2H), 7.25-7.13 (m, 2H), 5.23 (s, 2H), 3.19 (d, J=20.1 Hz, 3H), 1.23 (d, J=7.1 Hz, 3H). M+H+ 472

3-(2-(4-((2-chloro-6-ethylbenzyl)oxy)phenyl)-7,8-dihydropyrido[4,3-d]pyrimidin-6(5H)-yl)-2-methylpropanoic acid (compound 18)

Using intermediate methyl 3-(2-(4-((3-chloro,6-ethylbenzyl)oxy)phenyl)-7,8-dihydropyrido[4,3-d]pyrimidin-6(5H)-yl)-2-methylpropanoate instead of compound XXIVa. Calculated mass (C26H28ClN3O3) 465.18 g/mol. ¹H NMR (500 MHz, DMSO-d₆) δ 8.70 (s, 1H), 8.42-8.32 (m, 2H), 7.44-7.35 (m, 2H), 7.31 (dd, J=5.5, 3.5 Hz, 1H), 7.27-7.15 (m, 2H), 5.26 (s, 2H), 3.17 (s, 7H), 2.74 (t, J=7.5 Hz, 2H), 1.20 (dt, J=15.0, 7.3 Hz, 7H). M+H+ 466

Pure enantiomers of 3-(2-(4-((3,5-dichlorobenzyl)oxy)phenyl)-7,8-dihydropyrido[4,3-d]pyrimidin-6(5H)-yl)-2-methylpropanoic acid (compounds 19 and 20)

Compounds 19 and 20 are the pure enantiomers of compound 17.
Analytical SFC:
Two peaks were separated on a Phenomenex LUX Amylose-2 column (250×4.6 mm, 5 µm) (t_R [min]=4.3, 4.8). The mobile phase consisted of 50% CO₂ and 50% modifier. As modifier MeOH with addition of 0.1% diethylamine was used.
Preparatory SFC:
Two peaks were separated on a Phenomenex LUX Amylose-2 column (250×21.2 mm, 5 µm) (t_R [min]=4.8, 5.5). The mobile phase consisted of 60% CO₂ and 40% modifier. As modifier MeOH with addition of 0.2% aqueous ammonia solution was used.
Enantiomer 1 (Peak a, Compound 19):
¹H NMR (DMSO-d6, 500 MHz): δ=8.54 (s, 1H), 8.30-8.32 (m, J=8.8 Hz, 2H), 7.59 (s, 1H), 7.55 (s, 2H), 7.12-7.15 (m, J=8.8 Hz, 2H), 5.21 (s, 2H), 3.64 (d, J=3.1 Hz, 1H), 2.89 (d, J=5.2 Hz, 2H), 2.84 (d, J=5.2 Hz, 1H), 2.81 (d, J=6.1 Hz, 1H), 2.64 (br. s., 1H), 2.46 (d, J=6.7 Hz, 1H), 1.24 (br. s., 1H), 1.06 (d, J=6.7 Hz, 3H)
Enantiomer 2 (Peak B, Compound 20):
1H NMR (DMSO-d6, 500 MHz): δ=8.54 (s, 1H), 8.31 (d, J=8.8 Hz, 2H), 7.59 (t, J=1.8 Hz, 1H), 7.55 (d, J=1.5 Hz, 2H), 7.13 (d, J=9.2 Hz, 2H), 5.21 (s, 2H), 3.64 (d, J=4.9 Hz, 1H), 2.89 (q, J=5.9 Hz, 2H), 2.85 (d, J=5.2 Hz, 1H), 2.81 (t, J=5.8 Hz, 1H), 2.75 (d, J=3.7 Hz, 1H), 2.73 (s, 1H), 1.23 (br. s., 1H), 1.07 (d, J=7.0 Hz, 3H)

4-(2-(4-(benzyloxy)phenyl)-7,8-dihydropyrido[4,3-d]pyrimidin-6(5H)-yl)-3-methylbutanoic acid (compound 21)

Compound XVIId (R'=H, R"=H; 55 mg; 0.123 mmol) was dissolved in THF (1.5 mL) and MeOH (1.5 mL). 1N NaOH (0.5 mL) was added and the reaction mixture was stirred 20 h at RT. The reaction mixture was neutralized with 1.5 mL 1N HCl and was subsequently evaporated. The residue was washed with water and evaporated over P2O5 at 40° C. The residue was dissolved in DCM with a small amount of MeOH and purified by flash chromatography (silica gel, 5% MeOH in DCM). Compound 21 was obtained with a yield of 32 mg (0.077 mmol; 62.1%). Calculated Mass: (C25H27N3O3): 417.50 g/mol. ¹H NMR (DMSO-d6, 600 MHz): δ=8.55 (s, 1H), 8.29-8.32 (m, 2H), 7.48 (d, J=7.3 Hz, 2H), 7.41 (t, J=7.5 Hz, 2H), 7.33-7.37 (m, 1H), 7.11-7.15 (m, 2H), 5.18 (s, 2H), 3.56-3.62 (m, 2H), 3.41-3.48 (m, 1H), 2.88-2.95 (m, 2H), 2.82 (dt, J=11.6, 5.7 Hz, 1H), 2.74 (dt, J=11.8, 5.9 Hz, 1H), 2.31-2.39 (m, 3H), 2.20 (dq, J=13.9, 7.0 Hz, 1H), 2.02 (dd, J=15.3, 7.6 Hz, 1H), 0.93 (d, J=6.6 Hz, 3H). M+H=418
The following compounds were made in the same way as compound 21:

4-(2-(4-((4-chlorobenzyl)oxy)phenyl)-7,8-dihydropyrido[4,3-d]pyrimidin-6(5H)-yl)-3-methylbutanoic acid (compound 23)

Using intermediate ethyl 4-(2-(4-((4-chlorobenzyl)oxy)phenyl)-7,8-dihydropyrido[4,3-d]pyrimidin-6 (5H)-yl)-3-methylbutanoate instead of compound XVIId. Calculated Mass: (C25H26ClN3O3): 451.94 g/mol. Calculated mass: (C25H26ClN3O3): 451.945 g/mol. ¹H NMR (500 MHz, DMSO-d₆) δ 8.56 (s, 1H), 8.34-8.26 (m, 2H), 7.54-7.43 (m, 5H), 7.16-7.08 (m, 2H), 5.18 (s, 2H), 3.62 (s, 2H), 2.92 (s, 2H), 2.81 (d, J=36.7 Hz, 2H), 2.37 (dd, J=15.3, 5.7 Hz, 2H), 2.26-2.15 (m, 1H), 2.03 (dd, J=15.3, 7.6 Hz, 1H), 0.93 (d, J=6.4 Hz, 3H). M+H=452/454

(+)-4-(2-(4-((4-chlorobenzyl)oxy)phenyl)-7,8-dihydropyrido[4,3-d]pyrimidin-6(5H)-yl)-3-methylbutanoic acid (compound 212) and (−)-4-(2-(4-((4-chlorobenzyl)oxy)phenyl)-7,8-dihydropyrido[4,3-d]pyrimidin-6(5H)-yl)-3-methylbutanoic acid (compound 213)

Compounds 212 and 213 are the pure enantiomers of compound 23. Racemic 6-(3-carboxy-2-methylpropyl)-2-(4-((4-chlorobenzyl)oxy)phenyl)-5,6,7,8-tetrahydropyrido[4,3-d]pyrimidin-6-ium chloride (12 mg, 0.0246 mmol) was separated into its pure enantiomers by SFC using the "preparative SFC" method. Two peaks were separated on a Daicel Chiralpak® IA for SFC column (250×20 mm, 5 µm, flow rate 30 mL/min) (t_R [min]=4.5, 5.7). The mobile phase consisted of 50% CO₂ and 50% modifier. As modifier, a mixture (by volume) of 99.8% MeOH and 0.2% concentrated aqueous ammonia (25%) was used. (+)-4-(2-(4-((4-chlorobenzyl)oxy)phenyl)-7,8-dihydropyrido[4,3-d]pyrimidin-6(5H)-yl)-3-methylbutanoic acid (compound 212), enantiomer 1 (3.7 mg, 0.0082 mmol, peak 1) and (−)-4-(2-(4-((4-chlorobenzyl)oxy)phenyl)-7,8-dihydropyrido[4,3-d]pyrimidin-6(5H)-yl)-3-methylbutanoic acid (compound 213), enantiomer 2 (3.0 mg, 0.0066 mmol, peak 2) were obtained.

(+)-4-(2-(4-((4-chlorobenzyl)oxy)phenyl)-7,8-dihydropyrido[4,3-d]pyrimidin-6(5H)-yl)-3-methylbutanoic acid (compound 212)

$[\alpha]_D^{20}$=+16.8° (c=1, THF); Calculated mass: (C25H26ClN3O3): 451.945 g/mol. $^1$H NMR (600 MHz, DMSO-d$_6$) δ 12.12 (s, 1H), 8.55 (s, 1H), 8.34-8.27 (m, 2H), 7.54-7.44 (m, 4H), 7.16-7.09 (m, 2H), 5.18 (s, 2H), 3.59 (s, 2H), 2.97-2.86 (m, 2H), 2.82 (dt, J=11.5, 5.7 Hz, 1H), 2.74 (dt, J=11.8, 6.0 Hz, 1H), 2.40-2.30 (m, 3H), 2.20 (dq, J=14.1, 7.0 Hz, 1H), 2.02 (dd, J=15.3, 7.6 Hz, 1H), 0.93 (d, J=6.6 Hz, 3H). M+H=452/454

(−)-4-(2-(4-((4-chlorobenzyl)oxy)phenyl)-7,8-dihydropyrido[4,3-d]pyrimidin-6(5H)-yl)-3-methylbutanoic acid (compound 213)

$[\alpha]_D^{20}$=−16.0° (c=1, THF). Calculated mass: (C25H26ClN3O3): 451.945 g/mol. $^1$H NMR (600 MHz, DMSO-d$_6$) δ 12.13 (s, 1H), 8.55 (s, 1H), 8.34-8.27 (m, 2H), 7.54-7.44 (m, 4H), 7.16-7.09 (m, 2H), 5.18 (s, 2H), 3.59 (s, 2H), 2.91 (d, J=12.5 Hz, 1H), 2.91 (s, 1H), 2.82 (dt, J=11.5, 5.8 Hz, 1H), 2.74 (dt, J=11.7, 6.0 Hz, 1H), 2.40-2.30 (m, 3H), 2.20 (dq, J=14.0, 7.0 Hz, 1H), 2.10-1.98 (m, 1H), 0.93 (d, J=6.5 Hz, 3H). M+H=452/454

4-(2-(4-((3-chlorobenzyl)oxy)phenyl)-7,8-dihydropyrido[4,3-d]pyrimidin-6(5H)-yl)-3-methylbutanoic acid (compound 22)

Compound 22 was prepared starting from compound XXg in a palladium mediated reaction using 4-(3-chlorophenylmethoxy)phenylboronic acid as compound VI in scheme 2. Compound XXg (200 mg; 0.672 mmol; 1 eq) and 4-(3-chlorophenylmethoxy)phenylboronic acid (176 mg; 0.672 mmol; 1 eq) were dissolved in DMF (5 mL) to give a yellow solution. Sodium carbonate (1.10 g; 1.038 mmol; 1.5 eq) was added. The mixture was degassed with Argon for 30 min. Tetrakis(triphenylphosphine)palladium(0) (40 mg; 0.035 mmol; 0.05 eq) was added. The reaction was stirred for 30 min at 120° C. The reaction mixture was evaporated. The residue was dissolved in ethylacetate and washed 1× with water and 1× with brine. The organic layer was dried over MgSO$_4$, filtered and evaporated. The residue was purified using flash chromatography (12 g silica gel, 0-15% MeOH in DCM) giving ethyl 4-(2-(4-((3-chlorobenzyl)oxy)phenyl)-7,8-dihydropyrido[4,3-d]pyrimidin-6(5H)-yl)-3-methylbutanoate with a yield of 100 mg (0.208 mmol; 31.0%).

Tthyl 4-(2-(4-((3-chlorobenzyl)oxy)phenyl)-7,8-dihydropyrido[4,3-d]pyrimidin-6(5H)-yl)-3-methylbutanoate (100 mg; 0.208 mmol; 1 eq)) was dissolved in MeOH (2 ml) and THF (2 ml) to give a yellow solution. NaOH (41.7 mg; 1.042 mmol; 5 eq) was added and the mixture was stirred overnight. The reaction mixture was evaporated. The residue was dissolved in H$_2$O and neutralized with 2N HCl to pH 7. The aqueous layer was extracted 3× with DCM. The combined organic layers were dried over MgSO$_4$, filtered and evaporated. The residue was absorbed on Celite XTR and purified by flash chromatography (4 g silica gel, 0-25% MeOH in DCM). Compound 22 was obtained with a yield of 80 mg (0.177 mmol; 85%). Calculated mass (C25H26ClN3O3) 451.17 g/mol. 1H NMR (600 MHz, DMSO-d$_6$) δ 12.12 (s, 1H), 8.55 (s, 1H), 8.34-8.27 (m, 2H), 7.55 (t, J=1.4 Hz, 1H), 7.48-7.38 (m, 3H), 7.17-7.10 (m, 2H), 5.20 (s, 2H), 3.60 (s, 2H), 2.92 (d, J=12.4 Hz, 1H), 2.92 (s, 1H), 2.83 (dt, J=11.5, 5.8 Hz, 1H), 2.74 (dt, J=11.7, 5.9 Hz, 1H), 2.40-2.30 (m, 3H), 2.20 (dq, J=14.0, 7.1 Hz, 1H), 2.02 (dd, J=15.4, 7.6 Hz, 1H), 0.93 (d, J=6.6 Hz, 3H). M+H+ 452

The following compounds were made in the same way as compound 22:

4-(2-(4-((4-fluorobenzyl)oxy)phenyl)-7,8-dihydropyrido[4,3-d]pyrimidin-6(5H)-yl)-3-methylbutanoic acid (compound 225)

Using 4-(4-fluorophenylmethoxy)phenylboronic acid instead of 4-(3-chlorophenylmethoxy)phenylboronic acid. Calculated mass (C25H26ClN3O3) 435.491 g/mol. $^1$H NMR (500 MHz, DMSO-d$_6$) δ 12.38 (s, 1H), 8.72 (s, 1H), 8.37-8.30 (m, 2H), 7.60-7.50 (m, 2H), 7.29-7.20 (m, 3H), 7.19-7.12 (m, 2H), 5.18 (s, 2H), 3.80 (s, 3H), 3.21 (s, 3H), 3.12 (s, 1H), 2.28-2.20 (m, 1H), 1.04 (dd, J=14.9, 6.4 Hz, 3H). M+H+ 436

4-(2-(4-((3-fluorobenzyl)oxy)phenyl)-7,8-dihydropyrido[4,3-d]pyrimidin-6(5H)-yl)-3-methylbutanoic acid (compound 227)

Using 4-(3-fluorophenylmethoxy)phenylboronic acid instead of 4-(3-chlorophenylmethoxy)phenylboronic acid. Calculated mass (C25H26FN3O3) 435.491 g/mol. $^1$H NMR (500 MHz, DMSO-d$_6$) δ 12.35 (s, 1H), 8.70 (s, 1H), 8.36-8.31 (m, 2H), 7.47 (tt, J=8.0, 5.6 Hz, 1H), 7.36-7.28 (m, 3H), 7.22-7.13 (m, 3H), 5.23 (s, 2H), 3.44-3.35 (m, 1H), 3.30 (s, 1H), 3.10 (s, 2H), 2.49-2.40 (m, 1H), 2.22 (s, 2H), 1.04 (s, 3H), 1.02 (dd, J=12.9, 6.6 Hz, 1H). M+H+ 436

4-(2-(4-((3,4-difluorobenzyl)oxy)phenyl)-7,8-dihydropyrido[4,3-d]pyrimidin-6(5H)-yl)-3-methylbutanoic acid (compound 228)

Using 4-(3,4-difluorophenylmethoxy)phenylboronic acid instead of 4-(3-chlorophenylmethoxy)phenylboronic acid. Calculated mass (C25H25F2N3O3) 453.481 g/mol. $^1$H NMR (600 MHz, DMSO-d$_6$) δ 12.41 (s, 1H), 10.10 (s, 1H), 8.72 (s, 1H), 8.37-8.31 (m, 2H), 7.58 (ddd, J=11.5, 7.9, 2.1 Hz, 1H), 7.49 (dt, J=10.8, 8.4 Hz, 1H), 7.36 (ddd, J=8.8, 4.2, 1.9 Hz, 1H), 7.19-7.13 (m, 2H), 5.19 (s, 2H), 4.70 (s, 1H), 4.36 (s, 1H), 3.83 (s, 1H), 3.52 (s, 2H), 3.19 (s, 4H), 2.24 (s, 1H), 1.07 (d, J=6.3 Hz, 3H). M+H+ 454

3-methyl-4-(2-(4-((3-methylbenzyl)oxy)phenyl)-7,8-dihydropyrido[4,3-d]pyrimidin-6(5H)-yl)butanoic acid (compound 230)

Using 4-(3-methylphenylmethoxy)phenylboronic acid instead of 4-(3-chlorophenylmethoxy)phenylboronic acid. Calculated mass (C26H29N3O3) 431.527 g/mol. $^1$H NMR (500 MHz, DMSO-d$_6$) δ 8.71 (s, 1H), 8.36-8.30 (m, 2H), 7.34-7.21 (m, 5H), 7.16 (dd, J=7.7, 5.5 Hz, 3H), 5.15 (s, 2H), 3.43-3.34 (m, 2H), 3.31 (dd, J=5.4, 2.7 Hz, 2H), 2.54 (d, J=1.5 Hz, 1H), 2.49-2.44 (m, 1H), 2.33 (s, 4H), 2.24 (s, 2H), 1.03 (dd, J=18.4, 11.6 Hz, 3H). M+H+ 432

3-methyl-4-(2-(4-((4-(trifluoromethyl)benzyl)oxy)phenyl)-7,8-dihydropyrido[4,3-d]pyrimidin-6(5H)-yl)butanoic acid (compound 233)

Using 4-(4-fluorophenylmethoxy)phenylboronic acid instead of 4-(3-trifluoromethylphenylmethoxy)phenylboronic acid. Calculated mass (C26H26F3N3O3) 485.498 g/mol. $^1$H NMR (500 MHz, DMSO-d$_6$) δ 8.71 (s, 1H), 8.37-8.31 (m, 2H), 7.79 (d, J=8.1 Hz, 3H), 7.70 (d, J=8.0 Hz, 3H), 7.20-7.14 (m, 2H), 5.33 (s, 2H), 3.37 (s, 1H), 3.14 (s, 5H), 2.23 (s, 2H), 1.07-0.99 (m, 3H), 0.93 (s, 1H). M+H+ 486

3-methyl-4-(2-(4-((3-(trifluoromethyl)benzyl)oxy) phenyl)-7,8-dihydropyrido[4,3-d]pyrimidin-6(5H)-yl)butanoic acid (compound 238)

Using 4-(3-fluorophenylmethoxy)phenylboronic acid instead of 4-(3-trifluoromethylphenylmethoxy)phenylboronic acid. Calculated mass (C26H26F3N3O3) 485.498 g/mol. $^1$H NMR (500 MHz, DMSO-d$_6$) δ 8.69 (s, 1H), 8.34 (d, J=8.8 Hz, 2H), 7.87-7.77 (m, 3H), 7.73 (d, J=7.9 Hz, 1H), 7.67 (t, J=7.7 Hz, 1H), 7.21-7.15 (m, 2H), 5.31 (s, 2H), 3.47-3.35 (m, 1H), 3.37 (s, 1H), 2.89 (s, 1H), 2.73 (s, 1H), 2.21 (s, 7H), 1.03 (s, 3H). M+H+ 486

3-methyl-4-(2-(4-((4-methylbenzyl)oxy)phenyl)-7,8-dihydropyrido[4,3-d]pyrimidin-6(5H)-yl)butanoic acid (compound 248)

Using 4-(4-methylphenylmethoxy)phenylboronic acid instead of 4-(3-chlorophenylmethoxy)phenylboronic acid. Calculated mass (C26H29N3O3) 431.527 g/mol. $^1$H NMR (500 MHz, DMSO-d$_6$) δ 8.69 (s, 1H), 8.35-8.29 (m, 2H), 7.36 (d, J=8.0 Hz, 2H), 7.21 (d, J=8.1 Hz, 2H), 7.17-7.10 (m, 2H), 5.14 (s, 2H), 3.30 (d, J=3.0 Hz, 1H), 2.50-2.41 (m, 1H), 2.31 (s, 3H), 2.22 (s, 1H), 2.17 (s, 1H), 1.04 (d, J=6.0 Hz, 3H). M+H+ 432

2-(2-(4-((2,6-dichlorobenzyl)oxy)phenyl)-7,8-dihydropyrido[4,3-d]pyrimidin-6(5H)-yl)acetic acid (compound 34)

Compound 34 was prepared starting from compound XXb in a palladium mediated reaction using 4-hydroxyphenylboronic acid instead of compound VI as indicated in scheme 2. Compound XXb (500 mg; 1.955 mmol; 1 eq), sodium carbonate (5.1 g; 4.89 mmol; 2.5 eq) and 4-hydroxyphenylboronic acid (270 mg; 1.955 mmol; 1 eq) were dissolved in DMF (5 mL) to give a brown solution. The solution was degassed with Argon for 10 min. Tetrakis(triphenylphosphine)palladium(0) (113 mg; 0.098 mmol; 0.05 eq) was added and the reaction mixture was stirred for 60 min at 120° C. The reaction mixture was evaporated. The residue was dissolved in DCM, washed once with water, once with saturated NaCl solution, dried over MgSO$_4$, filtered and evaporated. The brown oil was purified by flash chromatography (12 g silica gel, 0-10% MeOH in DCM) giving ethyl 2-(2-(4-hydroxyphenyl)-7,8-dihydropyrido[4,3-d]pyrimidin-6(5H)-yl)acetate with a yield of 160 mg (0.511 mmol; 26.1%).

ethyl 2-(2-(4-hydroxyphenyl)-7,8-dihydropyrido[4,3-d]pyrimidin-6(5H)-yl)acetate (70 mg; 0.223 mmol; 1 eq) was dissolved in DMF (3 mL) to give a yellow solution. Cesium carbonate (80 mg; 0.246 mmol; 1.1 eq) and 2,6-dichlorobenzylbromide (53.6 mg; 0.223 mmol; 1 eq) were added. The mixture was stirred overnight at RT. The reaction mixture was evaporated. The residue was dissolved in DCM and washed once with water. After phase separation, the organic layer was evaporated. The residue was purified by flash chromatography (4 g silica gel, 0-10% MeOH in DCM) giving methyl 2-(2-(4-((2,6-dichlorobenzyl)oxy)phenyl)-7,8-dihydropyrido[4,3-d]pyrimidin-6(5H)-yl)acetate with a yield of 54 mg (0.118 mmol; 52.7%).

Methyl 2-(2-(4-((2,6-dichlorobenzyl)oxy)phenyl)-7,8-dihydropyrido[4,3-d]pyrimidin-6(5H)-yl)acetate (54 mg; 0.118 mmol; 1 eq) was dissolved in MeOH (2 mL) and THF (2 mL) to give a yellow solution. NaOH (0.25 mL; 0.500 mmol) was added and the reaction mixture was stirred overnight at RT. The reaction mixture was evaporated and the residue was suspended in water. 0.5 mL 2N HCl was added. The mixture was stirred for 1 h at RT, the precipitate was filtered, washed once with water and dried under vacuum giving compound 34 with a yield of 25 mg (0.052 mmol; 44.1%). Calculated mass (C22H19Cl2N3O3) 443.08 g/mol. $^1$H NMR (600 MHz, DMSO-d$_6$) δ 8.61 (s, 1H), 8.39-8.29 (m, 2H), 7.65-7.55 (m, 2H), 7.56-7.44 (m, 1H), 7.31-7.12 (m, 2H), 5.31 (s, 2H), 3.05-2.92 (m, 3H). M+H+ 444

The following compounds were made in the same way as compound 34:

2-(2-(4-(benzyloxy)phenyl)-7,8-dihydropyrido[4,3-d]pyrimidin-6(5H)-yl)acetic acid (compound 25)

Using intermediate benzylbromide instead of 2,6-dichlorobenzylbromide. Calculated mass (C22H21N3O3) 375.42 g/mol. $^1$H NMR (600 MHz, DMSO-d$_6$) δ 8.50 (s, 1H), 8.38-8.23 (m, 2H), 7.56-7.44 (m, 2H), 7.41 (t, J=7.6 Hz, 2H), 7.39-7.29 (m, 1H), 7.22-7.04 (m, 2H), 5.18 (s, 2H), 2.87 (q, J=3.4 Hz, 4H). M+H+ 376

2-(2-(4-((3-fluorobenzyl)oxy)phenyl)-7,8-dihydropyrido[4,3-d]pyrimidin-6(5H)-yl)acetic acid (compound 27)

Using intermediate 3-fluorobenzylbromide instead of 2,6-dichlorobenzylbromide. Calculated mass (C22H20FN3O3) 393.411 g/mol. $^1$H NMR (600 MHz, DMSO-d$_6$) δ 8.69 (s, 1H), 8.42-8.25 (m, 2H), 7.46 (td, J=8.0, 6.0 Hz, 1H), 7.37-7.26 (m, 2H), 7.25-7.11 (m, 3H), 5.22 (s, 2H), 3.16 (d, J=9.2 Hz, 3H). M+H+ 394

2-(2-(4-((2,3-difluorobenzyl)oxy)phenyl)-7,8-dihydropyrido[4,3-d]pyrimidin-6(5H)-yl)acetic acid (compound 28)

Using intermediate 2,3-difluorobenzylbromide instead of 2,6-dichlorobenzylbromide. $^1$H NMR (600 MHz, DMSO-d$_6$) δ 8.64 (s, 1H), 8.34 (d, J=8.9 Hz, 2H), 7.56-7.06 (m, 5H), 6.93-6.59 (m, 1H), 5.28 (s, 2H). M+H+ 412

2-(2-(4-((4-chlorobenzyl)oxy)phenyl)-7,8-dihydropyrido[4,3-d]pyrimidin-6(5H)-yl)acetic acid (compound 29)

Using intermediate 4-chlorobenzylbromide instead of 2,6-dichlorobenzylbromide. Calculated mass (C22H19F2N3O3) 411.401 g/mol. Calculated mass (C22H20ClN3O3) 409.12 g/mol. $^1$H NMR (600 MHz, DMSO-d$_6$) δ 8.63 (s, 1H), 8.36-8.25 (m, 2H), 7.55-7.44 (m, 4H), 7.20-7.07 (m, 2H), 5.20 (s, 2H), 4.08 (s, 2H), 3.05 (s, 3H). M+H+ 410

2-(2-(4-((3,4-dichlorobenzyl)oxy)phenyl)-7,8-dihydropyrido[4,3-d]pyrimidin-6(5H)-yl)acetic acid (compound 30)

Using intermediate 3,4-dichlorobenzylbromide instead of 2,6-dichlorobenzylbromide. Calculated mass (C22H19Cl2N3O3) 443.08 g/mol. $^1$H NMR (600 MHz, DMSO-d$_6$) δ 8.60 (s, 1H), 8.38-8.25 (m, 2H), 7.76 (d, J=2.1

Hz, 1H), 7.69 (d, J=8.3 Hz, 1H), 7.48 (dd, J=8.3, 2.0 Hz, 1H), 7.25-7.04 (m, 2H), 5.21 (s, 2H), 3.00 (s, 2H). M+H+ 444

2-(2-(4-((3,5-difluorobenzyl)oxy)phenyl)-7,8-dihydropyrido[4,3-d]pyrimidin-6(5H)-yl)acetic acid (compound 31)

Using intermediate 3,5-difluorobenzylbromide instead of 2,6-dichlorobenzylbromide. Calculated mass (C22H19F2N3O3) 411.14 g/mol. $^1$H NMR (600 MHz, DMSO-d$_6$) δ 8.57 (s, 1H), 8.32 (d, J=8.8 Hz, 2H), 7.23 (dd, J=7.1, 3.0 Hz, 3H), 7.14 (d, J=8.8 Hz, 2H), 5.23 (s, 2H), 3.81 (s, 2H), 3.07-2.87 (m, 4H). M+H+ 412

2-(2-(4-((3-chlorobenzyl)oxy)phenyl)-7,8-dihydropyrido[4,3-d]pyrimidin-6(5H)-yl)acetic acid (compound 32)

Using intermediate 3-chlorobenzylbromide instead of 2,6-dichlorobenzylbromide. Calculated mass (C22H20ClN3O3) 409.12 g/mol. $^1$H NMR (500 MHz, DMSO-d$_6$) δ 8.55 (s, 1H), 8.38-8.21 (m, 2H), 7.55 (t, J=1.5 Hz, 1H), 7.48-7.34 (m, 3H), 7.23-7.08 (m, 2H), 5.21 (s, 2H), 3.78 (s, 2H), 2.94 (dd, J=11.6, 4.6 Hz, 4H). M+H+ 410

2-(2-(4-((2,6-dimethylbenzyl)oxy)phenyl)-7,8-dihydropyrido[4,3-d]pyrimidin-6(5H)-yl)acetic acid (compound 33)

Using intermediate 2,6-dimethylbenzylbromide instead of 2,6-dichlorobenzylbromide. Calculated mass (C24H25N3O3) 403.19 g/mol. $^1$H NMR (600 MHz, DMSO-d$_6$) δ 8.58 (s, 1H), 8.38-8.27 (m, 2H), 7.25-7.12 (m, 3H), 7.09 (d, J=7.6 Hz, 2H), 5.13 (s, 2H), 3.84 (s, 2H), 2.97 (d, J=5.4 Hz, 2H), 2.35 (s, 6H). M+H+ 404

2-(2-(4-((2-chloro-6-ethylbenzyl)oxy)phenyl)-7,8-dihydropyrido[4,3-d]pyrimidin-6(5H)-yl)acetic acid (compound 35)

Using intermediate 2-chloro-6-ethylbenzylbromide instead of 2,6-dichlorobenzylbromide. Calculated mass (C24H24ClN3O3) 437.15 g/mol. $^1$H NMR (600 MHz, DMSO-d$_6$) δ 8.64 (s, 1H), 8.42-8.28 (m, 2H), 7.39 (q, J=2.8 Hz, 2H), 7.31 (dd, J=6.0, 3.0 Hz, 1H), 7.26-7.12 (m, 2H), 5.25 (s, 2H), 3.08 (d, J=28.6 Hz, 2H), 2.75 (qd, J=7.6, 2.4 Hz, 3H), 1.22-1.11 (m, 4H). M+H+ 438

3-(2-(4-(benzyloxy)phenyl)-7,8-dihydropyrido[4,3-d]pyrimidin-6(5H)-yl)butanoic acid (compound 36)

Compound XVIIc (R'=H, R"=H; 86 mg; 0.199 mmol) was dissolved in THF (2.5 mL) and MeOH (2.5 mL). 1N Sodium hydroxide (2 mL) was added and the reaction mixture was stirred for 20 h at RT. The reaction mixture was neutralized with 2 mL 1N HCl and was subsequently evaporated. The residue was washed with water and evaporated over P2O5 at 40° C. Compound 36 was obtained with a yield of 65 mg (0.161 mmol; 81%). Calculated Mass: (C24H25N3O3): 403.47 g/mol. $^1$H NMR (DMSO-d6, 600 MHz): δ=10.92 (br. s., 1H), 8.70 (s, 1H), 8.32-8.35 (m, 2H), 7.47-7.50 (m, 2H), 7.40-7.43 (m, 2H), 7.34-7.37 (m, 1H), 7.15-7.18 (m, 2H), 5.20 (s, 2H), 4.50 (br. s., 2H), 3.92 (br. s., 1H), 3.83 (br. s., 1H), 3.77 (br. s., 1H), 3.52-3.60 (m, 1H), 3.17 (d, J=6.6 Hz, 2H), 3.10-3.16 (m, 1H), 2.68 (d, J=10.9 Hz, 1H), 1.41 (d, J=6.6 Hz, 3H). M+H=404

The following compounds were made in the same way as compound 36:

3-(2-(4-((3-fluorobenzyl)oxy)phenyl)-7,8-dihydropyrido[4,3-d]pyrimidin-6(5H)-yl)butanoic acid (compound 41)

Using ethyl 3-(2-(4-((3-fluorobenzyl)oxy)phenyl)-7,8-dihydropyrido[4,3-d]pyrimidin-6(5H)-yl)butanoate instead of compound XVIIc. Calculated Mass: (C24H24FN3O3): 421.46 g/mol. $^1$H NMR (DMSO-d6, 600 MHz): δ=11.17 (br. s., 1H), 8.70 (s, 1H), 8.33-8.36 (m, 2H), 7.44-7.48 (m, 1H), 7.34 (s, 1H), 7.31-7.33 (m, 1H), 7.15-7.21 (m, 3H), 5.23 (s, 2H), 4.47-4.55 (m, 2H), 4.09 (br. s., 1H), 4.02 (br. s., 1H), 3.58-3.62 (m, 1H), 3.57 (s, 1H), 3.47-3.54 (m, 1H), 3.47-3.54 (m, 1H), 3.41-3.45 (m, 1H), 2.66-2.74 (m, 1H), 2.64 (br. s., 1H), 1.42 (d, J=6.2 Hz, 3H). M+H=422

3-(2-(4-((3,4-difluorobenzyl)oxy)phenyl)-7,8-dihydropyrido[4,3-d]pyrimidin-6(5H)-yl)butanoic acid (compound 42)

Using ethyl 3-(2-(4-((3,4-difluorobenzyl)oxy)phenyl)-7,8-dihydropyrido[4,3-d]pyrimidin-6(5H)-yl)butanoate instead of compound XVIIc. Calculated Mass: (C24H23F2N3O3): 439.45 g/mol. $^1$H NMR (DMSO-d6, 600 MHz): δ=11.19 (br. s., 1H), 8.70 (s, 1H), 8.33-8.37 (m, 2H), 7.56-7.61 (m, 1H), 7.46-7.51 (m, 1H), 7.35-7.38 (m, 1H), 7.35 (br. s., 1H), 7.15-7.19 (m, 2H), 5.19 (s, 2H), 4.47-4.55 (m, 2H), 3.91 (br. s., 1H), 3.83 (br. s., 1H), 3.76 (br. s., 1H), 3.72 (td, J=5.9, 1.9 Hz, 1H), 3.63-3.69 (m, 1H), 3.15 (d, J=15.6 Hz, 2H), 2.66-2.74 (m, 1H), 2.65 (br. s., 1H), 1.42 (d, J=6.4 Hz, 3H). M+H=440

3-(2-(4-((3-chlorobenzyl)oxy)phenyl)-7,8-dihydropyrido[4,3-d]pyrimidin-6(5H)-yl)butanoic acid (compound 43)

Using ethyl 3-(2-(4-((3-chlorobenzyl)oxy)phenyl)-7,8-dihydropyrido[4,3-d]pyrimidin-6(5H)-yl)butanoate instead of compound XVIIc. Calculated Mass: (C24H24ClN3O3): 437.92. $^1$H NMR (DMSO-d6, 600 MHz): δ=11.21 (br. s., 1H), 8.70 (s, 1H), 8.33-8.36 (m, 2H), 7.55-7.57 (m, 1H), 7.40-7.47 (m, 4H), 7.15-7.20 (m, 2H), 5.22 (s, 2H), 4.47-4.55 (m, 2H), 3.91 (br. s., 1H), 3.83 (br. s., 1H), 3.76 (br. s., 1H), 3.37-3.45 (m, 2H), 3.12-3.19 (m, 2H), 2.66-2.74 (m, 1H), 1.42 (d, J=6.2 Hz, 3H). M+H=438/440

3-(2-(4-((4-chlorobenzyl)oxy)phenyl)-7,8-dihydropyrido[4,3-d]pyrimidin-6(5H)-yl)butanoic acid (compound 44)

Using ethyl 3-(2-(4-((4-chlorobenzyl)oxy)phenyl)-7,8-dihydropyrido[4,3-d]pyrimidin-6(5H)-yl)butanoate instead of compound XVIIc. Calculated Mass: (C24H24ClN3O3): 437.92. $^1$H NMR (DMSO-d6, 600 MHz): δ=11.10 (br. s., 1H), 8.70 (s, 1H), 8.32-8.35 (m, 2H), 7.47-7.53 (m, 4H), 7.14-7.18 (m, 2H), 5.20 (s, 2H), 4.47-4.56 (m, 2H), 3.91 (br. s., 1H), 3.83 (br. s., 1H), 3.77 (br. s., 1H), 3.64-3.69 (m, 1H), 3.58-3.64 (m, 1H), 3.40 (br. s., 1H), 3.31 (d, J=8.3 Hz, 1H), 3.15 (d, J=15.6 Hz, 2H), 2.66-2.74 (m, 1H), 1.42 (d, J=6.4 Hz, 3H). M+H=438/440

3-(2-(4-((3,4-dichlorobenzyl)oxy)phenyl)-7,8-dihydropyrido[4,3-d]pyrimidin-6(5H)-yl)butanoic acid (compound 45)

Using ethyl 3-(2-(4-((3,4-dichlorobenzyl)oxy)phenyl)-7,8-dihydropyrido[4,3-d]pyrimidin-6(5H)-yl)butanoate instead of compound XVIIc. Calculated Mass: (C24H23Cl2N3O3): 472.36 g/mol. $^1$H NMR (DMSO-d6, 600 MHz): δ=8.70 (s, 1H), 8.33-8.36 (m, 2H), 7.77 (d, J=1.9 Hz, 1H), 7.69 (d, J=8.3 Hz, 1H), 7.49 (dd, J=8.3, 2.1 Hz, 1H), 7.14-7.18 (m, 2H), 5.22 (s, 2H), 4.50 (br. s., 2H), 3.91 (br. s., 1H), 3.76-3.83 (m, 1H), 3.47-3.55 (m, 1H), 3.26-3.34 (m, 3H), 3.16-3.22 (m, 1H), 3.10 (d, J=16.4 Hz, 1H), 2.69 (br. s., 1H), 1.41 (d, J=6.4 Hz, 3H). M+H=472/474

4-(2-(4-isopropoxyphenyl)-7,8-dihydropyrido[4,3-d]pyrimidin-6(5H)-yl)butanoic acid (compound 46)

Compound 46 was prepared starting from compound III in a palladium mediated reaction using 4-isopropoxyphenylboronic acid instead of compound VI as indicated in scheme 2. Compound III (500 mg; 1.854 mmol; 1 eq) and 4-isopropoxyphenylboronic acid (334 mg; 1.854 mmol; 1 eq) were dissolved in 12 mL DMF. Sodium carbonate (491 mg; 4.63 mmol; 2.5 eq) was added at RT and the mixture was rinsed with argon for 20 min.

Tetrakis(triphenylphosphine)palladium(0) (107 mg; 0.098 mmol; 0.05 eq) was added and the reaction mixture was stirred for 35 min at 125° C. The reaction mixture was evaporated and water (40 mL) and ethyl acetate (60 mL) were added to the residue. After phase separation, the ethyl acetate layer was washed once with 30 mL water, dried with MgSO$_4$, filtered and evaporated overnight giving tert-butyl 2-(4-isopropoxyphenyl)-7,8-dihydropyrido[4,3-d]pyrimidine-6(5H)-carboxylate.

Tert-butyl 2-(4-isopropoxyphenyl)-7,8-dihydropyrido[4,3-d]pyrimidine-6(5H)-carboxylate (915 mg; 2.48 mmol; 1 eq) was dissolved in 15 mL DCM. TFA (1.7 g; 14.86 mmol; 6 eq) was added at RT. The mixture was stirred for 5 h at RT and subsequently evaporated. 30 mL saturated NaCl solution was added and the pH of the mixture was adjusted to pH 9 with a saturated NaHCO$_3$ solution. The mixture was extracted twice with 50 mL DCM while checking the pH of the aqueous phase. The combined organic phases were dried with MgSO$_4$, filtered and evaporated giving 2-(4-isopropoxyphenyl)-5,6,7,8-tetrahydropyrido[4,3-d]pyrimidine. To a solution of 2-(4-isopropoxyphenyl)-5,6,7,8-tetrahydropyrido[4,3-d]pyrimidine (100 mg; 0.371 mmol; 1 eq) in 35 mL MeOH was added sodium hydride (40.1 mg; 1.0 mmol; 2.7 eq) after which the temperature was slightly elevated. Ethyl 4-bromobutanoate (145 mg; 0.743 mmol; 2 eq) was added and the mixture was stirred overnight at RT. The mixture was evaporated, dissolved in 50 mL ethyl acetate and washed twice with 20 mL of a saturated ammoniumchloride solution. The ethyl acetate phase was dried with MgSOH, filtered and evaporated giving compound 46 as the 6-(3-carboxypropyl)-2-(4-isopropoxyphenyl)-5,6,7,8-tetrahydropyrido[4,3-d]pyrimidin-6-ium chloride. Calculated mass (C20H25N3O3): 355.19 g/mol. NMR (600 MHz, DMSO-d$_6$) δ 10.81 (s, 1H), 8.71 (s, 1H), 8.44-8.17 (m, 2H), 7.16-6.92 (m, 2H), 4.73 (h, J=6.1 Hz, 1H), 4.70-4.60 (m, 1H), 4.35 (dd, J=16.0, 6.9 Hz, 1H), 3.31-3.23 (m, 1H), 3.21-3.12 (m, 1H), 2.47-2.35 (m, 3H), 2.08-1.95 (m, 2H), 1.31 (d, J=6.0 Hz, 6H), 0.80 (dt, J=8.0, 2.9 Hz, 1H), 0.77 (dt, J=4.6, 2.9 Hz, 1H). M+H+ 356.3

The following compounds were prepared in the same way as compound 46:

4-(2-(3-chloro-4-isopropoxyphenyl)-7,8-dihydropyrido[4,3-d]pyrimidin-6(5H)-yl)butanoic acid (compound 47)

Using 2-(3-chloro-4-isopropoxyphenyl)-5,6,7,8-tetrahydropyrido[4,3-d]pyrimidine. This compound was prepared in the same way as 2-(4-isopropoxyphenyl)-5,6,7,8-tetrahydropyrido[4,3-d]pyrimidine used in the preparation of compound 46, but starting from 3-chloro-4-isopropoxyphenyl)boronic acid instead of 4-isopropoxyphenyl)boronic acid. Calculated mass (C20H24ClN3O3): 389.15 g/mol. $^1$H NMR (600 MHz, DMSO-d$_6$) δ 12.34 (s, 1H), 10.70 (s, 1H), 8.74 (s, 1H), 8.36 (d, J=2.2 Hz, 1H), 8.33-8.26 (m, 1H), 7.33 (d, J=8.9 Hz, 1H), 4.80 (hept, J=6.1 Hz, 1H), 4.36 (s, 1H), 3.81 (s, 1H), 3.51 (s, 2H), 3.25 (s, 4H), 2.40 (t, J=7.3 Hz, 2H), 2.00 (p, J=7.5 Hz, 2H), 1.34 (d, J=6.0 Hz, 6H). M+H+ 390.1

4-(2-((2,5-difluorophenyl)ethynyl)-7,8-dihydropyrido[4,3-d]pyrimidin-6(5H)-yl)butanoic acid (compound 49)

Ethyl 4-(2-((2,5-difluorophenyl)ethynyl)-7,8-dihydropyrido[4,3-d]pyrimidin-6(5H)-yl)butanoate This compound was prepared from compound XXf in accordance with scheme 10. To a solution of 2-ethynyl-1,4-difluorobenzene (48.7 mg; 0.352 mmol; 1 eq) and ethyl 4-(2-chloro-7,8-dihydropyrido[4,3-d]pyrimidin-6(5H)-yl)butanoate (100 mg; 0.352 mmol; 1 eq) in DMF (2 mL) were added triethylamine (72.6 mg; 0.717 mmol; 2 eq), copper(I) iodide (7 mg; 0.037 mmol; 0.1 eq) and bis(triphenylphosphine) Pd (II) dichloride (25 mg; 0.036 mmol; 0.1 eq). The mixture was stirred for 10 min at 110° C. The product was checked by LC/MS. The reaction mixture was evaporated. The residue was dissolved in ethylacetate, washed twice with a saturated NH$_4$Cl-solution and once with saturated NaCl solution, dried over MgSO$_4$, filtered and evaporated. The residue was purified by flash chromatography (12 g silica gel, 0-15% MeOH in DCM). The product was obtained with a yield of 78 mg (0.202 mmol; 57.4%). The crude oil product was used directly in the next step.

Compound 49

Ethyl 4-(2-((2,5-difluorophenyl)ethynyl)-7,8-dihydropyrido[4,3-d]pyrimidin-6(5H)-yl)butanoate (78 mg; 0.202 mmol; eq) was dissolved in MeOH (1 mL) and THF (1 mL). 2N NaOH (40 mg; 1.0 mmol) was added and the mixture was stirred overnight at RT. The pH was brought to pH 1 with 2N HCl. The residue was evaporated, washed with water and dried overnight at 40° C. under vacuum. 2 mL Ethyl acetate was added and the mixtures was stirred for 20 min at RT. The residue was evaporated and dried overnight at 40° C. under vacuum giving compound 49 with a yield of 7.8 mg (0.022 mmol; 10.8%). Calculated mass (C19H17F2N3O2) 357.354 g/mol. $^1$H NMR (DMSO-d$_6$, 500 MHz): d=8.76 (s, 1H), 7.67-7.70 (m, 1H), 7.48 (td, J=6.4, 1.8 Hz, 2H), 3.63 (br. s., 3H), 3.27 (br. s., 2H), 3.19-3.24 (m, 2H), 2.39 (t, J=7.2 Hz, 2H), 1.94-1.98 (m, 2H). M+H+ 358

The following compound was prepared in the same way as compound 49:

4-(2-(phenylethynyl)-7,8-dihydropyrido[4,3-d]pyrimidin-6(5H)-yl)butanoic acid (compound 48)

Using ethynylbenzene instead of 2-ethynyl-1,4-difluorobenzene. Calculated mass (C19H19N3O2) 321.373 g/mol. $^1$H NMR (500 MHz, DMSO-d$_6$) δ 8.70 (s, 2H), 7.71-7.63

(m, 3H), 7.50 (d, J=7.9 Hz, 3H), 3.16 (d, J=7.2 Hz, 3H), 2.37 (s, 2H), 1.93 (s, 4H). M+H+ 322

4-(2-benzyl-7,8-dihydropyrido[4,3-d]pyrimidin-6 (5H)-yl)butanoic acid (compound 50)

Ethyl 4-(2-benzyl-7,8-dihydropyrido[4,3-d]pyrimidin-6(5H)-yl)butanoate

This compound was prepared from compound XXXVIIIa in accordance with scheme 5. Compound XXXVIIIa (278 mg; 1.234; 1 eq) was dissolved in 8 mL DMF. Under stirring and argon atmosphere, NaH (50% in oil; 118 mg; 2.47 mmol; 2 eq) was added. The mixture was stirred for 1 h at RT. Ethyl-4-bromobutyrate (722 mg; 3.7 mmol; 3 eq) was added and the mixture was heat for 2 h at 60° C. under stirring. The solution is colled, 0.5 mL water was added and the mixture was evaporated. The residue was extracted with DCM and water, the organic phase was washed once with water, dried over MgSO$_4$, filtered and evaporated. The oily residue was purified by flash chromatography (silica gel, DCM/MeOH 95:). The purified product was evaporated giving the product with a yield of 209 mg (0.616 mmol; 49.9%).
Compound 50
Ethyl 4-(2-benzyl-7,8-dihydropyrido[4,3-d]pyrimidin-6 (5H)-yl)butanoate (209 mg; 0.62 mmol; 1 eq) was dissolved in THF (6 mL) and MeOH (6 mL). Under stirring at RT, NaOH (240 mg; 6 mmol; 9.7 eq) was added and the mixture was stirred overnight at RT. The solution was neutralized with 6 mL 1N HCl and the THF and
MeOH were evaporated. The solution was then freeze dried and the residue was suspended in 3 mL MeOH and 320 μL THF. DCM and MeOH were added and the residue was obtained. The solution was neutralized with 1N NaOH, evaporated, dried with MgSO$_4$ and filtered. The residue was dissolved in DCM with a little MeOH and purified by flash chromatography (silica gel, DCM/MeOH 95:5). The purified product was stirred with diethylether and evaporated giving the product with a yield of 33 mg (0.106 mmol; 17.2%). Calculated Mass: (C18H21N3O2): 311.38 g/mol. $^1$H NMR (600 MHz, DMSO-d$_6$) δ 12.08 (s, 1H), 8.43 (s, 1H), 7.27 (d, J=4.4 Hz, 4H), 7.19 (h, J=4.1 Hz, 1H), 4.11 (s, 2H), 3.53 (s, 2H), 2.82 (t, J=5.9 Hz, 2H), 2.72 (t, J=5.9 Hz, 2H), 2.48 (t, J=7.1 Hz, 2H), 2.25 (t, J=7.2 Hz, 2H), 1.73 (p, J=7.2 Hz, 2H). M+H=312

The following compounds were prepared in the same way as compound 50:

4-(2-(2,6-difluorobenzyl)-7,8-dihydropyrido[4,3-d] pyrimidin-6(5H)-yl)butanoic acid (compound 51)

starting from compound XXXVIIIb instead of XXXVIIIa. Calculated Mass: (C18H19F2N3O2): 347.36 g/mol. $^1$H NMR (600 MHz, DMSO-d$_6$) δ 12.05 (s, 1H), 8.38 (s, 1H), 7.36 (tt, J=8.4, 6.6 Hz, 1H), 7.13-7.03 (m, 2H), 4.20 (s, 2H), 3.52 (s, 2H), 2.79 (t, J=5.9 Hz, 2H), 2.72 (t, J=5.9 Hz, 2H), 2.48 (t, J=7.0 Hz, 2H), 2.26 (t, J=7.2 Hz, 2H), 1.73 (p, J=7.2 Hz, 2H). M+H=348

2-(2-benzyl-7,8-dihydropyrido[4,3-d]pyrimidin-6 (5H)-yl)acetic acid (compound 24)

Using ethyl 2-bromoacetate instead of ethyl-4-bromobutyrate. Calculated Mass: (C16H17N3O2): 283.33 g/mol. $^1$H NMR (600 MHz, DMSO-d$_6$) δ 8.41 (s, 1H), 7.27 (d, J=4.5 Hz, 4H), 7.23-7.15 (m, 1H), 4.12 (s, 2H), 3.69 (s, 2H), 3.18 (s, 2H), 2.86 (t, J=5.9 Hz, 2H), 2.81 (t, J=5.6 Hz, 2H). M+H=284

2-(2-(2,6-difluorobenzyl)-7,8-dihydropyrido[4,3-d] pyrimidin-6(5H)-yl)acetic acid (compound 26)

starting from compound XXXVIIIb instead of XXXVIIIa and using ethyl 2-bromoacetate instead of ethyl-4-bromobutyrate. Calculated Mass: (C16H15F2N3O2): 319.31 g/mol. $^1$H NMR (600 MHz, DMSO-d$_6$) δ 8.39 (s, 1H), 7.36 (tt, J=8.3, 6.6 Hz, 1H), 7.14-7.04 (m, 2H), 4.21 (s, 2H), 3.71 (s, 2H), 3.37 (s, 2H), 2.90 (t, J=5.9 Hz, 2H), 2.81 (t, J=5.9 Hz, 2H). M+H=320

3-(2-(4-((3-fluorobenzyl)oxy)phenyl)-7,8-dihydropyrido[4,3-d]pyrimidin-6(5H)-yl)cyclobutanecarboxylic acid (compound 52)

Compound 52 was prepared from compound Ic as described in scheme 3. Compound Ic (50 mg; 0.15 mmol) was dissolved in 3 mL 1,2 dichloroethane. 3-oxocyclobutanecarboxylic acid (34 mg; 0.30 mmol) is added under stirring at RT. Stirring was continued for 5 min to obtain a white suspension. Sodium triacetoxyborohydride (63.2 mg; 0.30 mmol) was added and the mixtures was stirred for 30 min at RT. 10 mL water was added and the mixture was stirred for 30 min at RT. The 1,2 dichloroethane was evaporated resulting in a white solid residue. This was washed with water, dried overnight at 40° C. under vacuum. The residue was mixed with n-pentane and white crystals were obtained and dried giving compound 52 with a yield of 57 mg (0.131 mmol; 88%). Calculated mass: (C25H24FN3O3): 433.48 g/mol. $^1$H NMR (DMSO-d6, 600 MHz): δ=12.53-12.61 (m, 1H), 11.45 (br. s., 1H), 10.97 (br. s., 1H), 8.72 (br. s., 1H), 8.34 (d, J=8.7 Hz, 2H), 7.44-7.48 (m, 1H), 7.30-7.34 (m, 2H), 7.17 (d, J=8.8 Hz, 2H), 7.15-7.21 (m, 1H), 5.23 (s, 2H), 4.61 (d, J=14.9 Hz, 1H), 4.21-4.25 (m, 1H), 4.20 (br. s., 1H), 4.04 (d, J=7.7 Hz, 1H), 3.82 (br. s., 1H), 3.69 (d, J=18.1 Hz, 1H), 3.17 (d, J=13.2 Hz, 1H), 3.04-3.09 (m, 1H), 2.88-2.92 (m, 1H), 2.73 (d, J=8.8 Hz, 1H), 2.62 (dt, J=3.6, 1.8 Hz, 1H). M+H=434

3-(2-(2,6-difluorobenzyl)-7,8-dihydropyrido[4,3-d] pyrimidin-6(5H)-yl)cyclobutanecarboxylic acid (compound 53)

Methyl 3-(2-(2,6-difluorobenzyl)-7,8-dihydropyrido[4,3-d]pyrimidin-6(5H)-yl)cyclobutanecarboxylate was prepared form compound XXXVIIIb in accordance with scheme 5. Compound XXXVIIIb (200 mg; 0.53 mmol; 1 eq) was dissolved in 5 mL THF. Methyl 3-oxocyclobutanecarboxylate (205 mg; 1.60 mmo; 3 eq) was added and the mixture was stirred for 1 h at RT. Sodium triacetoxyborohydride (248 mg; 1.17 mmol; 2.2 eq) was added and the mixture was stirred for 3 h at RT. 20 mL water was added, stirred for 15 min at RT. The mixture was extracted twice with DCM and the combined organic phase was washed with water, dried with MgSO$_4$, and evaporated. The residue was dissolved in DCM and purified by flash chromatography (DCM/MeOH 95:5) giving methyl 3-(2-(2,6-difluorobenzyl)-7,8-dihydropyrido[4,3-d]pyrimidin-6(5H)-yl)cyclobutanecarboxylate with a yield of 158 mg (0.423 mmol; 79%). 158 mg (0.42 mmol; 1 eq) thereof was dissolved in 4 mL THF with 4 mL MeOH. Under stirring 4.5 mL 1N NaOH was added and the mixture was stirred for 20 h at RT. The solution was neutralized with 4.5 mL 1N HCl, evaporated until the THF and MeOH were absent. The resulting solution was freeze dried and the residue was stirred with 30 mL DCM/MeOH 2:1. The insoluble residue was obtained and the solution was evaporated. The residue was dissolved in DCM and purified by flash chromatography (silica gel, DCM/MeOH 9:1). The purified product was evaporated and crystallized in diethylether, the crystals were washed in n-pentane and dried at 45° C. giving compound 53 with a yield of 69 mg (0.192 mmol; 45.4%). Calculated Mass: (C19H19F2N3O2): 359.37 g/mol. $^1$H NMR (600 MHz, DMSO-$d_6$) δ 12.16 (s, 1H), 8.39 (s, 1H), 7.40-7.32 (m, 1H), 7.08 (t, J=7.8 Hz, 2H), 4.20 (s, 2H), 3.42 (s, 2H), 2.91-2.70 (m, 5H), 2.60 (t, J=6.0 Hz, 2H), 2.35-2.23 (m, 2H), 1.99 (qd, J=9.0, 2.6 Hz, 2H). M+H=360

3-(2-((4-chlorophenyl)ethynyl)-7,8-dihydropyrido[4,3-d]pyrimidin-6(5H)-yl)cyclobutanecarboxylic acid (compound 54)

A 4 mL vial containing a stir bar and 1-chloro-4-ethynylbenzene (31.1 mg; 0.23 mmol; 1.5 eq), along with another 4 mL vial containing a stir bar and methyl 3-(2-chloro-7,8-dihydropyrido[4,3-d]pyrimidin-6(5H)-yl)cyclobutanecarboxylate (42.7 mg; 0.15 mmol; 1 eq), prepared from compound Ma in accordance with scheme 6, were capped with septa caps and flushed with N2 for 5 minutes. A microwave vial containing $K_3PO_4$ and a stir bar, was capped with a septa cap and flushed with $N_2$. The flushed and prepared vials containing starting material were introduced to the dry-box. The microwave vial had the cap removed, and to it dry $PdCl_2(MeCN)_2$ (5.11 mg; 0.02 mmol; 0.13 eq) along with XPHOS (17.4 mg; 0.04 mmol; 0.24 eq) were added. Dry acetonitrile was added to the vials containing the starting material (250 μL each) via syringe. The starting material solutions were then added to the microwave vial containing the base, catalyst, and ligand. This was then capped and placed to heat/stir at 90° C. overnight. The crude material was then passed through a filter cartridge containing Celite using MeOH to wash 2 times (3500 μL total). This was then concentrated to dryness. An aqueous 1M solution of LiOH in 75% MeOH was added (1000 μL). The vial was capped and placed to heat at 60° C. for 1 hour. The compound was then filtered using a Biotage empty filter cartridge washing with 500 μL of MeOH. The crude material was concentrated to dryness and re-dissolved in 1400 μL of a 1:1 v/v solution of DMSO/MeOH. This was reverse phase HPLC purified to obtain 3-(2-((4-chlorophenyl)ethynyl)-7,8-dihydropyrido[4,3-d]pyrimidin-6(5H)-yl)cyclobutanecarboxylic acid with a yield of 17.7 mg (26.07%). $^1$H NMR (400 MHz, Pyridine-$d_5$) δ ppm 8.51 (s, 1H), 7.56 (d, J=1.9 Hz, 2H), 7.34 (d, J=8.3 Hz, 2H), 3.42 (s, 2H), 2.97 (t, J=5.8 Hz, 2H), 2.58-2.53 (m, 2H), 2.52-2.45 (m, 4H), 2.41-2.27 (m, 2H). MS (APCI$^+$) m/z 367.9 (M+H)$^+$.

The following compound were prepared in the same way as compound 54:

3-(2-(o-tolylethynyl)-7,8-dihydropyrido[4,3-d]pyrimidin-6(5H)-yl)cyclobutanecarboxylic acid (compound 55)

Using o-ethynyltoluene instead of 1-chloro-4-ethynylbenzene. $^1$H NMR (400 MHz, Pyridine-$d_5$) δ ppm 8.51 (d, J=3.3 Hz, 1H), 7.68 (d, J=7.5 Hz, 1H), 7.30-7.24 (m, 1H), 7.20-7.13 (m, 2H), 3.42 (s, 2H), 3.08 (t, J=8.9 Hz, 1H), 2.96 (t, J=6.1 Hz, 2H), 2.81 (p, J=7.9 Hz, 1H), 2.57-2.52 (m, 5H), 2.51-2.45 (m, 4H). MS (APCI$^+$) m/z 348.0 (M+H)$^+$. (31.1 mg, 45.3%)

3-(2-((4-ethoxyphenyl)ethynyl)-7,8-dihydropyrido[4,3-d]pyrimidin-6(5H)-yl)cyclobutanecarboxylic acid (compound 56)

Using 1-ethoxy-4-ethynylbenzene instead of 1-chloro-4-ethynylbenzene. $^1$H NMR (400 MHz, Pyridine-$d_5$) δ ppm 8.51 (s, 1H), 8.49 (d, J=3.1 Hz, 1H), 7.70-7.65 (m, 2H), 6.97-6.92 (m, 2H), 3.87 (q, J=7.0 Hz, 2H), 3.41 (s, 2H), 3.08 (p, J=9.1 Hz, 1H), 2.96 (t, J=6.1 Hz, 2H), 2.80 (q, J=7.9 Hz, 1H), 2.55 (t, J=5.9 Hz, 2H), 2.52-2.45 (m, 3H), 1.23 (t, J=7.0 Hz, 3H). MS (APCI$^+$) m/z 378.0 (M+H)$^+$. (43.8 mg, 64.8%)

3-(2-((4-fluorophenyl)ethynyl)-7,8-dihydropyrido[4,3-d]pyrimidin-6(5H)-yl)cyclobutanecarboxylic acid (compound 57)

Using 1-fluoro-4-ethynylbenzene instead of 1-chloro-4-ethynylbenzene. $^1$H NMR (400 MHz, Pyridine-$d_5$) δ ppm 8.51 (d, J=3.1 Hz, 1H), 7.68-7.62 (m, 2H), 7.14-7.07 (m, 2H), 3.42 (s, 2H), 3.09 (t, J=8.9 Hz, 1H), 2.97 (t, J=6.0 Hz, 2H), 2.82 (t, J=7.8 Hz, 1H), 2.55 (td, J=5.9, 3.8 Hz, 2H), 2.52-2.45 (m, 4H). MS (APCI$^+$) m/z 351.9 (M+H)$^+$. (35.0 mg, 51.1%)

3-(2-((4-isopropylphenyl)ethynyl)-7,8-dihydropyrido[4,3-d]pyrimidin-6(5H)-yl)cyclobutanecarboxylic acid (compound 58)

Using 1-isopropyl-4-ethynylbenzene instead of 1-chloro-4-ethynylbenzene. $^1$H NMR (400 MHz, Pyridine-$d_5$) δ ppm 8.51 (d, J=3.1 Hz, 1H), 7.68-7.62 (m, 2H), 7.14-7.07 (m, 2H), 3.42 (s, 2H), 3.09 (t, J=8.9 Hz, 1H), 2.97 (t, J=6.0 Hz, 2H), 2.82 (t, J=7.8 Hz, 1H), 2.55 (td, J=5.9, 3.8 Hz, 2H), 2.52-2.45 (m, 4H). MS (APCI$^+$) m/z 376.0 (M+H)$^+$. (29.2 mg, 43.2%)

3-(2-((4-(benzyloxy)phenyl)ethynyl)-7,8-dihydropyrido[4,3-d]pyrimidin-6(5H)-yl)cyclobutanecarboxylic acid (compound 59)

Using (p-(benzyloxy)phenyl)ethyne instead of 1-chloro-4-ethynylbenzene. $^1$H NMR (400 MHz, Pyridine-$d_5$) δ ppm 8.51 (s, 1H), 8.49 (d, J=3.0 Hz, 1H), 7.68 (d, J=8.9 Hz, 2H), 7.53-7.48 (m, 2H), 7.44-7.37 (m, 2H), 7.36-7.30 (m, 1H), 7.07 (d, J=8.8 Hz, 2H), 5.08 (s, 2H), 3.41 (s, 2H), 3.09 (p, J=9.0 Hz, 1H), 2.97 (q, J=6.4, 6.0 Hz, 2H), 2.81 (p, J=7.9 Hz, 1H), 2.55 (t, J=6.0 Hz, 2H), 2.48 (t, J=8.4 Hz, 4H). MS (APCI$^+$) m/z 440.0 (M+H)$^+$. (14.0 mg, 21.3%)

3-(2-((2-chlorophenyl)ethynyl)-7,8-dihydropyrido[4,3-d]pyrimidin-6(5H)-yl)cyclobutanecarboxylic acid (compound 60)

Using 1-chloro-2-ethynylbenzene instead of 1-chloro-4-ethynylbenzene. $^1$H NMR (400 MHz, Pyridine-$d_5$) δ ppm 8.51 (d, J=3.6 Hz, 1H), 7.68 (dd, J=7.6, 1.8 Hz, 1H), 7.46 (dd, J=8.0, 1.3 Hz, 1H), 7.26 (td, J=7.7, 1.8 Hz, 1H), 7.19 (dd, J=7.4, 1.3 Hz, 1H), 3.42 (s, 2H), 3.08 (p, J=9.1 Hz, 1H), 2.96 (t, J=6.2 Hz, 2H), 2.81 (p, J=8.0 Hz, 1H), 2.54 (td, J=5.9, 3.1 Hz, 2H), 2.51-2.45 (m, 4H). MS (APCI$^+$) m/z 368.0 (M+H)$^+$. (24.8 mg, 36.5%)

3-(2-((3,5-difluorophenyl)ethynyl)-7,8-dihydropyrido[4,3-d]pyrimidin-6(5H)-yl)cyclobutanecarboxylic acid (compound 61)

Using 1,5-difluoro-3-ethynylbenzene instead of 1-chloro-4-ethynylbenzene. $^1$H NMR (400 MHz, Pyridine-$d_5$) δ ppm 8.54 (d, J=5.7 Hz, 1H), 7.24 (dd, J=6.0, 1.9 Hz, 2H), 7.08 (tt, J=9.2, 2.4 Hz, 1H), 3.43 (d, J=6.2 Hz, 2H), 3.09 (p, J=9.0 Hz, 1H), 2.98 (t, J=6.0 Hz, 2H), 2.83 (p, J=8.0 Hz, 1H), 2.61-2.54 (m, 2H), 2.49 (td, J=8.3, 2.8 Hz, 4H). MS (APCI$^+$) m/z 369.9 (M+H)$^+$. (15.0 mg, 22.1%)

3-(2-((3-chlorophenyl)ethynyl)-7,8-dihydropyrido[4,3-d]pyrimidin-6(5H)-yl)cyclobutanecarboxylic acid (compound 62)

Using 1-chloro-3-ethynylbenzene instead of 1-chloro-4-ethynylbenzene. $^1$H NMR (400 MHz, Pyridine-d$_5$) δ ppm 8.51 (s, 1H), 7.68 (t, J=1.9 Hz, 1H), 7.51 (dt, J=7.4, 1.3 Hz, 1H), 7.38-7.34 (m, 1H), 7.23 (d, J=7.9 Hz, 1H), 3.43 (s, 2H), 3.09 (p, J=9.0 Hz, 1H), 2.97 (t, J=6.0 Hz, 1H), 2.82 (p, J=8.0 Hz, 1H), 2.61-2.54 (m, 2H), 2.52-2.46 (m, 4H).). MS (APCI$^+$) m/z 367.9 (M+H)$^+$. (16.6 mg, 24.5%)

4-(2-(4-((4-chlorobenzyl)oxy)phenyl)-7,8-dihydropyrido[4,3-d]pyrimidin-6(5H)-yl)pentanoic acid (compound 66)

Compound 66 was prepared starting from compound XXa using 4-(4'-chlorobenzyloxy)phenylboronic acid (compound VI with R'=4Cl, R''=H) as indicated in scheme 2. Compound XXa (200 mg; 0.67 mmol; 1 eq) was dissolved in 5 mL DMF. 4-(4'-chlorobenzyloxy)phenylboronic acid (212 mg; 0.806 mmol; 1.2 eq) and a 10% Na$_2$CO$_3$ solution (1.78 g; 1.68 mmol; 2.5 eq) were added under stirring. The solution was degassed with Argon for 5 min.

Tetrakis(triphenylphosphine)palladium(0) (38.8 mg; 0.034 mmol; 0.05 eq) was added and the reaction mixture was stirred for 30 min at 120° C. The mixture was evaporated. The residue was extracted with DCM/water and the organic phase was washed once with water, dried with MgSO$_4$ and evaporated. The resulting oily product was dissolved in DCM and purified by flash chromatography (silica gel, DCM/MeOH 98:2 giving ethyl 4-(2-(4-((4-chlorobenzyl)oxy)phenyl)-7,8-dihydropyrido[4,3-d]pyrimidin-6(5H)-yl)pentanoate with a yield of 182 mg (0.379 mmol; 56.5%).

Ethyl 4-(2-(4-((4-chlorobenzyl)oxy)phenyl)-7,8-dihydropyrido[4,3-d]pyrimidin-6(5H)-yl)pentanoate (182 mg; 0.38 mmol; 1 eq) was dissolved in MeOH (4 mL) and THF (4 mL). 1N NaOH (160 mg; 4 mmol; 10.5 eq) was added under stirring at RT. The mixture was stirred for 20 h at RT and subsequently neutralized with 4 mL 1N HCl. The mixture was evaporated and the resulting crystals were washed with water and evaporated over P2O5 at 40° C. The residue was dissolved in DCM with a small amount of MeOH and purified by flash chromatography (silica gel, DCM/MeOH 9:1) giving compound 66 with a yield of 98 mg (0.217 mmol; 57.2%). Calculated Mass: (C25H26ClN3O3): 451.95 g/mol. $^1$H NMR (600 MHz, DMSO-d$_6$) δ 12.37 (s, 1H), 10.78 (s, 1H), 8.72 (d, J=2.8 Hz, 1H), 8.38-8.31 (m, 2H), 7.56-7.44 (m, 4H), 7.20-7.13 (m, 2H), 5.20 (s, 2H), 4.48 (q, J=15.5, 13.2 Hz, 2H), 3.73 (s, 1H), 3.63-3.50 (m, 3H), 3.18-3.11 (m, 1H), 2.50-2.42 (m, 1H), 2.37 (ddd, J=16.5, 8.9, 6.6 Hz, 1H), 2.23-2.17 (m, 1H), 1.82-1.74 (m, 1H), 1.40-1.34 (m, 3H). M+H=452/454

The following compounds were made in the same way as compound 66:

4-(2-(4-(benzyloxy)phenyl)-7,8-dihydropyrido[4,3-d]pyrimidin-6(5H)-yl)pentanoic acid (compound 64)

Using 4-benzyloxy-phenylboronic acid (compound VI with R'=H, R''=H). Calculated Mass: (C25H27N3O3): 417.60 g/mol. $^1$H NMR (600 MHz, DMSO-d$_6$) δ 12.38 (s, 1H), 10.71 (s, 1H), 8.72 (d, J=2.1 Hz, 1H), 8.37-8.31 (m, 2H), 7.51-7.46 (m, 2H), 7.44-7.39 (m, 2H), 7.38-7.32 (m, 1H), 7.21-7.13 (m, 2H), 5.20 (s, 2H), 4.50 (t, J=9.7 Hz, 2H), 3.75 (d, J=14.0 Hz, 1H), 3.63-3.50 (m, 3H), 3.15 (d, J=20.7 Hz, 1H), 2.46 (dt, J=9.1, 6.3 Hz, 1H), 2.37 (ddd, J=16.4, 8.8, 6.6 Hz, 1H), 2.20 (s, 1H), 1.82-1.74 (m, 1H), 1.36 (s, 2H). M+H=418

4-(2-(4-((3-chlorobenzyl)oxy)phenyl)-7,8-dihydropyrido[4,3-d]pyrimidin-6(5H)-yl)pentanoic acid (compound 65)

Using 4-(3'-chlorobenzyloxy)phenylboronic acid (compound VI with R'=3Cl, R''=H). Calculated Mass: (C25H26ClN3O3): 451.95 g/mol. $^1$H NMR (600 MHz, DMSO-d$_6$) δ 10.67 (s, 1H), 8.72 (d, J=2.1 Hz, 1H), 8.38-8.32 (m, 2H), 7.56 (t, J=1.6 Hz, 1H), 7.50-7.39 (m, 3H), 7.21-7.14 (m, 2H), 5.22 (s, 2H), 4.50 (dd, J=11.9, 7.8 Hz, 2H), 3.76 (s, 1H), 3.63-3.52 (m, 1H), 3.53 (s, 1H), 3.44 (d, J=5.5 Hz, 1H), 3.15 (dd, J=18.1, 3.8 Hz, 1H), 2.50-2.42 (m, 1H), 2.37 (ddd, J=16.4, 8.9, 6.7 Hz, 1H), 2.21 (d, J=10.7 Hz, 1H), 1.80 (s, 1H), 1.76 (td, J=6.9, 3.6 Hz, 1H), 1.39-1.33 (m, 2H). M+H=452/454

3-(2-(4-(benzyloxy)phenyl)-7,8-dihydropyrido[4,3-d]pyrimidin-6(5H)-yl)propanoic acid (compound 67)

Compound XVIIb (R'=H, R''=H; 128 mg; 0.29 mmol; 1 eq) was dissolved in MeOH (5 mL) and THF (2.5 mL). 1N NaOH (120 mg; 3 mmol; 10.4 eq) was added under stirring at RT. The mixture was stirred for 20 h at RT and subsequently neutralized with 3 mL 1N HCl. The mixture was evaporated and 30 mL water was added to the resulting white residue. The residue was then extracted and washed with water and evaporated over P2O5 at 40° C. giving compound 67 with a yield of 102 mg (0.262 mmol; 91%). Calculated mass (C23H23N3O3): 389.45 g/mol. $^1$H NMR (DMSO-d6, 600 MHz): δ=8.70 (s, 1H), 8.32-8.35 (m, 2H), 7.47-7.50 (m, 2H), 7.39-7.43 (m, 2H), 7.34-7.37 (m, 1H), 7.14-7.18 (m, 2H), 5.20 (s, 2H), 4.43 (br. s., 1H), 3.56-3.62 (m, 1H), 3.47 (br. s., 3H), 3.30 (br. s., 1H), 3.24 (br. s., 2H), 3.17 (br. s., 1H), 2.90 (t, J=7.4 Hz, 2H), 1.75-1.77 (m, 1H) M+H=390/391

The following compounds were made in the same way as compound 67:

3-(2-(4-((3-fluorobenzyl)oxy)phenyl)-7,8-dihydropyrido[4,3-d]pyrimidin-6(5H)-yl)propanoic acid (compound 68)

Using tert-butyl 3-(2-(4-((3-fluorobenzyl)oxy)phenyl)-7,8-dihydropyrido[4,3-d]pyrimidin-6(5H)-yl)propanoate instead of compound XVIIb. Calculated mass: (C23H22FN3O3): 407.44 g/mol. $^1$H NMR (DMSO-d6, 600 MHz): δ=10.81 (br. s., 1H), 8.70 (s, 1H), 8.32-8.36 (m, 2H), 7.44-7.48 (m, 1H), 7.33 (s, 1H), 7.32 (dd, J=5.8, 2.4 Hz, 1H), 7.15-7.21 (m, 3H), 5.23 (s, 2H), 4.55-4.61 (m, 1H), 4.42 (br. s., 1H), 3.56-3.62 (m, 1H), 3.47 (br. s., 2H), 3.23 (br. s., 1H), 3.17 (s, 1H), 2.90 (t, J=7.2 Hz, 2H). M+H=408

3-(2-(4-((2,3-difluorobenzyl)oxy)phenyl)-7,8-dihydropyrido[4,3-d]pyrimidin-6(5H)-yl)propanoic acid (compound 69)

tert-butyl 3-(2-(4-((2,3-difluorobenzyl)oxy)phenyl)-7,8-dihydropyrido[4,3-d]pyrimidin-6(5H)-yl)propanoate instead of compound XVIIb. Calculated mass: (C23H21F2N3O3): 425.43 g/mol. ¹H NMR (DMSO-d6, 600 MHz): δ=12.8 (br. S., 1H), 10.9 (br. S., 1H), 8.71 (s, 1H), 8.34-8.37 (m, 2H), 7.45-7.50 (m, 1H), 7.41-7.44 (m, 1H), 7.25-7.30 (m, 1H), 7.18-7.21 (m, 2H), 5.29 (s, 2H), 4.62 (br. s., 1H), 4.42 (br. s., 1H), 3.78-3.86 (m, 1H), 3.72-3.78 (m, 1H), 3.70 (d, J=7.9 Hz, 1H), 3.49-3.57 (m, 1H), 3.47 (br. s., 2H), 3.41 (d, J=5.3 Hz, 1H), 3.24 (br. s., 1H). M+H=426

3-(2-(4-((2,6-dichlorobenzyl)oxy)phenyl)-7,8-dihydropyrido[4,3-d]pyrimidin-6(5H)-yl)propanoic acid (compound 70)

tert-butyl 3-(2-(4-((2,6-dichlorobenzyl)oxy)phenyl)-7,8-dihydropyrido[4,3-d]pyrimidin-6(5H)-yl)propanoate instead of compound XVIIb. Calculated mass: (C23H21Cl2N3O3): 458.34 g/mol. ¹H NMR (DMSO-d6, 600 MHz): δ=12.83 (br. s., 1H), 10.66 (br. s., 1H), 8.72 (s, 1H), 8.35-8.39 (m, 2H), 7.60 (d, J=8.1 Hz, 2H), 7.50 (dd, J=8.7, 7.5 Hz, 1H), 7.21-7.25 (m, 2H), 5.33 (s, 2H), 4.67 (d, J=14.7 Hz, 1H), 4.42 (br. s., 1H), 3.85 (br. s., 1H), 3.54-3.62 (m, 3H), 3.47-3.54 (m, 3H), 3.23 (br. s., 1H), 2.91 (t, J=7.4 Hz, 2H), M+H=458/460

3-(2-(4-((3,4-difluorobenzyl)oxy)phenyl)-7,8-dihydropyrido[4,3-d]pyrimidin-6(5H)-yl)propanoic acid (compound 71)

tert-butyl 3-(2-(4-((3,4-difluorobenzyl)oxy)phenyl)-7,8-dihydropyrido[4,3-d]pyrimidin-6(5H)-yl)propanoate instead of compound XVIIb. Calculated mass: (C23H21F2N3O3): 425.43 g/mol. ¹H NMR (DMSO-d6, 600 MHz): δ=8.65 (s, 1H), 8.31-8.35 (m, 2H), 7.58 (ddd, J=11.5, 7.9, 2.1 Hz, 1H), 7.48 (dt, J=10.8, 8.4 Hz, 1H), 7.34-7.37 (m, 1H), 7.14-7.17 (m, 2H), 5.18 (s, 2H), 4.25 (br. s., 1H), 3.11-3.19 (m, 3H), 2.78 (br. s., 2H). M+H=426

3-(2-(4-((3-chlorobenzyl)oxy)phenyl)-7,8-dihydropyrido[4,3-d]pyrimidin-6(5H)-yl)propanoic acid (compound 72)

tert-butyl 3-(2-(4-((3-chlorobenzyl)oxy)phenyl)-7,8-dihydropyrido[4,3-d]pyrimidin-6(5H)-yl)propanoate instead of compound XVIIb. Calculated Mass: (C23H22ClN3O3): 423.89. ¹H NMR (DMSO-d6, 500 MHz): δ=8.70 (s, 1H), 8.32-8.36 (m, 2H), 7.55 (s, 1H), 7.40-7.47 (m, 3H), 7.15-7.18 (m, 2H), 5.22 (s, 2H), 4.48 (br. s., 1H), 3.59-3.68 (m, 1H), 3.47 (t, J=7.3 Hz, 3H), 3.25 (br. s., 2H), 2.92 (t, J=7.5 Hz, 2H). M+H=424/426

3-(2-(4-((3,4-dichlorobenzyl)oxy)phenyl)-7,8-dihydropyrido[4,3-d]pyrimidin-6(5H)-yl)propanoic acid (compound 73)

tert-butyl 3-(2-(4-((3,4-dichlorobenzyl)oxy)phenyl)-7,8-dihydropyrido[4,3-d]pyrimidin-6(5H)-yl)propanoate instead of compound XVIIb. Calculated Mass: (C23H21Cl2N3O3): 458.34. ¹H NMR (DMSO-d6, 500 MHz): δ=8.55 (s, 1H), 8.29-8.32 (m, 2H), 7.76 (d, J=2.1 Hz, 1H), 7.69 (s, 1H), 7.67 (s, 1H), 7.48 (dd, J=8.2, 1.8 Hz, 1H), 7.11-7.15 (m, 2H), 5.20 (s, 2H), 3.67 (br. s., 2H), 3.57 (br. s., 1H), 2.90-2.94 (m, 2H), 2.79-2.88 (m, 4H). M+H=458/460/462

3-(2-(4-((4-chlorobenzyl)oxy)phenyl)-7,8-dihydropyrido[4,3-d]pyrimidin-6(5H)-yl)propanoic acid (compound 74)

tert-butyl 3-(2-(4-((4-chlorobenzyl)oxy)phenyl)-7,8-dihydropyrido[4,3-d]pyrimidin-6(5H)-yl)propanoate instead of compound XVIIb. Calculated Mass: (C23H22ClN3O3): 423.89 g/mol. ¹H NMR (DMSO-d6, 600 MHz): δ=8.66 (s, 1H), 8.31-8.34 (m, 2H), 7.46-7.53 (m, 4H), 7.13-7.16 (m, 2H), 5.20 (s, 2H), 4.27 (br. s., 1H), 3.51 (br. s., 1H), 3.15 (br. s., 2H), 2.78 (br. s., 2H). M+H=424/426

3-(2-(4-((3-difluoromethylbenzyl)oxy)phenyl)-7,8-dihydropyrido[4,3-d]pyrimidin-6(5H)-yl)propanoic acid (compound 76)

tert-butyl 3-(2-(4-((3-difluoromethylbenzyl)oxy)phenyl)-7,8-dihydropyrido[4,3-d]pyrimidin-6(5H)-yl)propanoate instead of compound XVIIb. Calculated Mass: (C24H23F2N3O3): 439.46 g/mol. ¹H NMR (DMSO-d6, 600 MHz): δ=10.88 (br. s., 1H), 8.70 (s, 1H), 8.33-8.36 (m, 2H), 7.65-7.70 (m, 2H), 7.55-7.59 (m, 2H), 7.18 (d, J=9.0 Hz, 2H), 7.08 (s, 1H), 5.27 (s, 2H), 4.66 (d, J=14.7 Hz, 1H), 4.37-4.43 (m, 1H), 3.85 (br. s., 1H), 3.60 (dd, J=11.6, 9.7 Hz, 1H), 3.57 (br. s., 1H), 3.18-3.24 (m, 1H), 2.92 (t, J=7.3 Hz, 2H) M+H=440

3-(2-(4-((4-difluoromethylbenzyl)oxy)phenyl)-7,8-dihydropyrido[4,3-d]pyrimidin-6(5H)-yl)propanoic acid (compound 77)

tert-butyl 3-(2-(4-((4-difluoromethylbenzyl)oxy)phenyl)-7,8-dihydropyrido[4,3-d]pyrimidin-6(5H)-yl)propanoate instead of compound XVIIb. Calculated Mass: (C24H23F2N3O3): 439.46 g/mol. ¹H NMR (DMSO-d6, 600 MHz): δ=10.98 (br. s., 1H), 8.70 (s, 1H), 8.32-8.36 (m, 2H), 7.60-7.64 (m, 4H), 7.14-7.19 (m, 2H), 7.06 (s, 1H), 5.28 (s, 2H), 4.64 (br. s., 1H), 4.41 (br. s., 1H), 3.84 (br. s., 1H), 3.58-3.62 (m, 1H), 3.49 (br. s., 2H), 3.21 (br. s., 1H), 3.14 (d, J=6.2 Hz, 1H), 2.92 (t, J=7.3 Hz, 2H). M+H=440

3-(2-(4-((2-difluoromethylbenzyl)oxy)phenyl)-7,8-dihydropyrido[4,3-d]pyrimidin-6(5H)-yl)propanoic acid (compound 78)

tert-butyl 3-(2-(4-((2-difluoromethylbenzyl)oxy)phenyl)-7,8-dihydropyrido[4,3-d]pyrimidin-6(5H)-yl)propanoate instead of compound XVIIb. Calculated Mass: (C24H23F2N3O3): 439.46 g/mol. ¹H NMR (DMSO-d6, 600 MHz): δ=12.81 (br. s., 1H), 10.90 (br. s., 1H), 8.71 (s, 1H), 8.33-8.37 (m, 2H), 7.68 (t, J=7.4 Hz, 2H), 7.60 (t, J=7.3 Hz, 1H), 7.58 (s, 1H), 7.52-7.56 (m, 1H), 7.38 (s, 1H), 7.29 (s, 1H), 7.17-7.22 (m, 2H), 5.36 (s, 2H), 4.62-4.69 (m, 1H), 4.41 (br. s., 1H), 3.84 (br. s., 1H), 3.31 (br. s., 1H), 3.21 (br. s., 1H), 3.15 (d, J=7.0 Hz, 1H), 2.92 (t, J=7.3 Hz, 2H) M+H=440

3-(2-(4-isopropoxyphenyl)-7,8-dihydropyrido[4,3-d]pyrimidin-6(5H)-yl)propanoic acid (compound 75)

2-(4-isopropoxyphenyl)-5,6,7,8-tetrahydropyrido[4,3-d]pyrimidine was prepared as described for compound 46. 110 mg (0.408 mmol; 1 eq) thereof was dissolved in 5 mL MeOH. DBU (187 mg; 1.23 mmol; 3 eq) was added followed by ethyl acylate (102 mg; 1.02 mmol; 2.5 eq). The mixture was stirred overnight at RT. The mixture was then evaporated, dissolved in 30 mL ethyl acetate and washed twice with 20 mL of a saturated ammoniumchloride solution. The ethyl acetate phase was dried with MgSOH, filtered and evaporated giving methyl 3-(2-(4-isopropoxyphenyl)-7,8-dihydropyrido[4,3-d]pyrimidin-6(5H)-yl)propanoate.

Methyl 3-(2-(4-isopropoxyphenyl)-7,8-dihydropyrido[4,3-d]pyrimidin-6(5H)-yl)propanoate (93 mg; 0.26 mmol; 1 eq) was dissolved in 5 mL MeOH. 2N NaOH (157 mg; 3.92 mmol; 15 eq) was added and the mixture was stirred overnight at RT. The pH was brought to pH 1 with 2N HCl. 10 mL Ethyl acetate was added, followed by stirring for 5 min at RT. The acidic water-phase was mixed with some NaCl resulting in a slightly pale yellow residue. The residue was evaporated, washed with water and ethyl acetate and dried overnight at 40° C. under vacuum giving compound 75 with a yield of 57 mg (0.151 mmol; 57.7%) as the 6-(2-carboxyethyl)-2-(4-isopropoxyphenyl)-5,6,7,8-tetrahydropyrido[4,3-d]pyrimidin-6-ium chloride. Calculated mass (C19H23N3O3): 341.17 g/mol. $^1$H NMR (600 MHz, DMSO-d$_6$) δ 12.79 (s, 1H), 11.10 (s, 1H), 8.69 (s, 1H), 8.44-8.19 (m, 2H), 7.18-6.92 (m, 2H), 4.72 (hept, J=6.0 Hz, 1H), 4.43 (s, 1H), 3.52-3.42 (m, 2H), 3.24 (s, 2H), 2.92 (t, J=7.5 Hz, 2H), 1.31 (d, J=6.0 Hz, 6H). M+H+ 342.2

The following compound was prepared in the same way as compound 75:

3-(2-(3-chloro-4-isopropoxyphenyl)-7,8-dihydropyrido[4,3-d]pyrimidin-6(5H)-yl)propanoic acid (compound 79)

Using 2-(3-chloro-4-isopropoxyphenyl)-5,6,7,8-tetrahydropyrido[4,3-d]pyrimidine instead of 2-(4-isopropoxyphenyl)-5,6,7,8-tetrahydropyrido[4,3-d]pyrimidine. Calculated mass (C19H22ClN3O3): 375.13 g/mol. $^1$H NMR (600 MHz, DMSO-d$_6$) δ 12.02 (s, 2H), 8.68 (s, 1H), 8.29 (dd, J=8.7, 2.1 Hz, 1H), 7.32 (d, J=9.0 Hz, 1H), 4.80 (p, J=6.0 Hz, 1H), 4.28 (s, 2H), 3.17 (s, 2H), 2.80 (s, 2H), 1.34 (d, J=6.0 Hz, 6H). M+H+ 376.1

3-(2-(4-((4-(trifluoromethoxy)benzyl)oxy)phenyl)-7,8-dihydropyrido[4,3-d]pyrimidin-6(5H)-yl)propanoic acid (compound 85)

To a 4 mL vial a solution of tert-butyl 3-(2-(4-hydroxyphenyl)-7,8-dihydropyrido[4,3-d]pyrimidin-6(5H)-yl)propanoate (compound XXIIIf with R"=H; R*=tert-butyl propanoate; 41 mg; 0.12 mmol) dissolved in DMF (0.5 mL) was added, followed by a solution of sodium hydride (16.6 mg; 0.69 mmol) dissolved in DMF (0.5 mL). The reaction was let shake for 15 minutes at RT. Then a solution of 1-(bromomethyl)-4-(trifluoromethoxy)benzene (58 mg; 0.23 mmol) dissolved in DMF (0.4 mL) was added and the reaction was shaken at RT of 2 h. The crude material was then passed through a filter cartridge and concentrated to dryness. An aqueous 1M solution of LiOH in 75% MeOH was added (1000 μL), and the vial was capped and placed to stir at RT for 2 h. The reaction was filtered, and concentrated to dryness. Then it was re-dissolved in 1800 μL of a 1:1 v/v solution of DMSO/MeOH, checked by LC/MS and purified by reverse phase HPLC (TTA method) to provide compound 85. $^1$H NMR (400 MHz, Pyridine-d$_5$, Temp=25° C.) δ: 8.80 (d, J=8.8 Hz, 2H), 8.49 (s, 1H), 7.97 (d, J=8.7 Hz, 1H), 7.35-7.32 (m, 3H), 7.29 (d, J=8.9 Hz, 2H), 5.30 (s, 2H), 3.61 (s, 2H), 3.07-3.02 (m, 4H), 2.85 (t, J=7.1 Hz, 2H), 2.80 (t, J=5.9 Hz, 2H); (APCI+) m/z 474 (M+H)+.

The following compounds were prepared in the same way as compound 85:

3-(2-(4-((4-(methylthio)benzyl)oxy)phenyl)-7,8-dihydropyrido[4,3-d]pyrimidin-6(5H)-yl)propanoic acid (compound 80)

Using 1-(bromomethyl)-4-(methylthio)benzene instead of 1-(bromomethyl)-4-(trifluoromethoxy)benzene. $^1$H NMR (400 MHz, Pyridine-d$_5$, Temp=25° C.) δ: 8.83-8.77 (m, 2H), 8.49 (s, 1H), 7.48 (d, J=8.0 Hz, 2H), 7.39-7.34 (m, 2H), 7.31-7.27 (m, 2H), 5.13 (s, 2H), 3.60 (s, 2H), 3.05 (t, J=7.0 Hz, 4H), 2.85 (t, J=7.1 Hz, 2H), 2.80 (t, J=5.9 Hz, 2H), 2.40 (s, 3H); MS (APCI+) m/z 436 (M+H)+

3-(2-(4-((4-(trifluoromethyl)benzyl)oxy)phenyl)-7,8-dihydropyrido[4,3-d]pyrimidin-6(5H)-yl)propanoic acid (compound 81)

Using 1-(bromomethyl)-4-(trifluoromethyl)benzene instead of 1-(bromomethyl)-4-(trifluoromethoxy)benzene. $^1$H NMR (400 MHz, Pyridine-d$_5$, Temp=25° C.) δ: 8.81 (d, J=8.9 Hz, 2H), 8.49 (s, 1H), 7.71 (d, J=8.2 Hz, 2H), 7.65 (d, J=8.2 Hz, 2H), 7.31-7.28 (m, 2H), 5.23 (s, 2H), 3.60 (s, 2H), 3.07-3.03 (m, 4H), 2.85 (t, J=7.1 Hz, 2H), 2.80 (t, J=5.9 Hz, 2H); MS (APCI+) m/z 458 (M+H)+.

3-(2-(4-((3-(trifluoromethoxy)benzyl)oxy)phenyl)-7,8-dihydropyrido[4,3-d]pyrimidin-6(5H)-yl)propanoic acid (compound 82)

Using 1-(bromomethyl)-3-(trifluoromethoxy)benzene instead of 1-(bromomethyl)-4-(trifluoromethoxy)benzene. $^1$H NMR (400 MHz, Pyridine-d$_5$, Temp=25° C.) δ: 8.81-8.78 (m, 2H), 8.49 (s, 1H), 7.54 (s, 1H), 7.49-7.46 (m, 1H), 7.45-7.38 (m, 1H), 7.31-7.27 (m, 3H), 5.38 (s, 2H), 3.61 (s, 2H), 3.06-3.02 (m, 4H), 2.90-2.84 (m, 2H), 2.80 (t, J=5.9 Hz, 2H); MS (APCI+) m/z 474 (M+H)+.

3-(2-(4-((4-(difluoromethoxy)benzyl)oxy)phenyl)-7,8-dihydropyrido[4,3-d]pyrimidin-6(5H)-yl)propanoic acid (compound 83)

Using 1-(bromomethyl)-4-(difluoromethoxy)benzene instead of 1-(bromomethyl)-4-(trifluoromethoxy)benzene. $^1$H NMR (400 MHz, Pyridine-d$_5$, Temp=25° C.) δ: 8.80 (d, J=8.8 Hz, 2H), 8.49 (s, 1H), 7.56-7.52 (m, 2H), 7.32-7.28 (m, 5H), 5.14 (s, 2H), 3.61 (s, 2H), 3.09-3.00 (m, 4H), 2.85 (t, J=7.1 Hz, 2H), 2.80 (t, J=5.9 Hz, 2H); MS (APCI+) m/z 456 (M+H)+.

3-(2-(4-((2-(trifluoromethoxy)benzyl)oxy)phenyl)-7,8-dihydropyrido[4,3-d]pyrimidin-6(5H)-yl)propanoic acid (compound 84)

Using 1-(bromomethyl)-2-(trifluoromethoxy)benzene instead of 1-(bromomethyl)-4-(trifluoromethoxy)benzene. $^1$H NMR (400 MHz, Pyridine-d$_5$, Temp=25° C.) δ: 8.80 (d, J=8.8 Hz, 2H), 8.48 (s, 1H), 7.72-7.69 (m, 1H), 7.39-7.36 (m, 2H), 7.34-7.30 (m, 3H), 5.32 (s, 2H), 3.60 (s, 2H), 3.08-3.00 (m, 4H), 2.85 (t, J=7.1 Hz, 2H), 2.79 (t, J=5.9 Hz, 2H); MS (APCI+) m/z 474 (M+H)+.

3-(2-(4-((3-(trifluoromethyl)benzyl)oxy)phenyl)-7,8-dihydropyrido[4,3-d]pyrimidin-6(5H)-yl)propanoic acid (compound 86)

Using 1-(bromomethyl)-3-(trifluoromethyl)benzene instead of 1-(bromomethyl)-4-(trifluoromethoxy)benzene.

¹H NMR (400 MHz, Pyridine-d₅, Temp=25° C.) δ: 8.81 (d, J=8.9 Hz, 2H), 8.49 (s, 1H), 7.91 (s, 1H), 7.71 (d, J=7.7 Hz, 1H), 7.64 (d, J=7.9 Hz, 1H), 7.50 (t, J=7.8 Hz, 1H), 7.32-7.28 (m, 2H), 5.22 (s, 2H), 3.61 (s, 2H), 3.08-3.02 (m, 4H), 2.85 (t, J=7.1 Hz, 2H), 2.80 (t, J=5.9 Hz, 2H); (APCI+) m/z 458 (M+H)+.

3-(2-(4-((4-(tert-butyl)benzyl)oxy)phenyl)-7,8-dihydropyrido[4,3-d]pyrimidin-6(5H)-yl)propanoic acid (compound 87)

Using 1-(bromomethyl)-4-(tert-butyl)benzene instead of 1-(bromomethyl)-4-(trifluoromethoxy)benzene. ¹H NMR (400 MHz, Pyridine-d₅, Temp=25° C.) δ: 8.80 (d, J=8.7 Hz, 2H), 8.48 (s, 1H), 7.55-7.52 (m, 1H), 7.48-7.45 (m, 2H), 7.33-7.29 (m, 2H), 5.19 (s, 2H), 3.60 (s, 2H), 3.04 (t, J=6.7 Hz, 4H), 2.85 (t, J=7.1 Hz, 2H), 2.79 (t, J=5.9 Hz, 2H), 1.27 (s, 9H); (APCI+) m/z 446 (M+H)+.

3-(2-(4-((2-methyl-5-(trifluoromethyl)benzyl)oxy)phenyl)-7,8-dihydropyrido[4,3-d]pyrimidin-6(5H)-yl)propanoic acid (compound 88)

Using 1-(bromomethyl)-2-methyl-5-(trifluoromethyl)benzene instead of 1-(bromomethyl)-4-(trifluoromethoxy)benzene. ¹H NMR (400 MHz, Pyridine-d₅, Temp=25° C.) δ: 8.83 (d, 2H), 8.50 (s, 1H), 7.94 (d, J=1.8 Hz, 1H), 7.56 (s, 1H), 7.34 (d, 2H), 7.29 (d, J=8.0 Hz, 1H), 5.19 (s, 2H), 3.61 (s, 2H), 3.09-3.02 (m, 4H), 2.85 (t, J=7.0 Hz, 2H), 2.80 (t, J=6.0 Hz, 2H), 2.33 (s, 3H); (APCI+) m/z 472 (M+H)+.

3-(2-(4-((4-methyl-3-(trifluoromethyl)benzyl)oxy)phenyl)-7,8-dihydropyrido[4,3-d]pyrimidin-6(5H)-yl)propanoic acid (compound 89)

Using 1-(bromomethyl)-4-methyl-2-(trifluoromethyl)benzene instead of 1-(bromomethyl)-4-(trifluoromethoxy)benzene. ¹H NMR (400 MHz, Pyridine-d₅, Temp=25° C.) δ: 8.82 (d, 2H), 8.49 (s, 1H), 7.85 (s, 1H), 7.60 (s, 1H), 7.34-7.29 (m, 2H), 7.27 (s, 1H), 5.18 (s, 2H), 3.60 (s, 2H), 3.08-3.02 (m, 4H), 2.85 (t, J=7.1 Hz, 2H), 2.79 (t, J=6.0 Hz, 2H), 2.39 (s, 3H); (APCI+) m/z 472 (M+H)+.

3-(2-(4-((2-(difluoromethoxy)benzyl)oxy)phenyl)-7,8-dihydropyrido[4,3-d]pyrimidin-6(5H)-yl)propanoic acid (compound 90)

Using 1-(bromomethyl)-2-(difluoromethoxy)benzene instead of 1-(bromomethyl)-4-(trifluoromethoxy)benzene. ¹H NMR (400 MHz, Pyridine-d₅, Temp=25° C.) δ: 8.81-8.76 (m, 2H), 8.47 (s, 1H), 7.68 (d, J=7.5 Hz, 1H), 7.37-7.34 (m, 2H), 7.31-7.28 (m, 2H), 7.27-7.23 (m, 1H), 5.32 (s, 2H), 3.60 (s, 2H), 3.06-3.01 (m, 4H), 2.85 (t, J=7.0 Hz, 2H), 2.79 (t, J=5.9 Hz, 2H); (APCI+) m/z 456 (M+H)+.

3-(2-(4-((5-methyl-2-(trifluoromethyl)benzyl)oxy)phenyl)-7,8-dihydropyrido[4,3-d]pyrimidin-6(5H)-yl)propanoic acid (compound 91)

Using 1-(bromomethyl)-5-methyl-2-(trifluoromethyl)benzene instead of 1-(bromomethyl)-4-(trifluoromethoxy)benzene. ¹H NMR (400 MHz, Pyridine-d₅, Temp=25° C.) δ: 8.82 (d, J=8.9 Hz, 2H), 8.48 (s, 1H), 7.63-7.60 (m, 2H), 7.38-7.30 (m, 2H), 7.17 (d, 1H), 5.40 (s, 2H), 3.60 (s, 2H), 3.06-3.00 (m, 4H), 2.85 (t, J=7.1 Hz, 2H), 2.79 (t, J=6.0 Hz, 2H), 2.23 (s, 3H); (APCI+) m/z 472 (M+H)+.

3-(2-(4-((3-(difluoromethoxy)benzyl)oxy)phenyl)-7,8-dihydropyrido[4,3-d]pyrimidin-6(5H)-yl)propanoic acid (compound 92)

Using 1-(bromomethyl)-3-(difluoromethoxy)benzene instead of 1-(bromomethyl)-4-(trifluoromethoxy)benzene. ¹H NMR (400 MHz, Pyridine-d₅, Temp=25° C.) δ: 8.81-8.78 (m, 2H), 8.49 (s, 1H), 7.49 (s, 1H), 7.41-7.36 (m, 2H), 7.30-7.24 (m, 3H), 5.17 (s, 2H), 3.60 (s, 2H), 3.07-3.03 (m, 4H), 2.85 (t, J=7.1 Hz, 2H), 2.80 (t, J=5.9 Hz, 2H); (APCI+) m/z 456 (M+H)+.

3-(2-(4-((2-methyl-4-(trifluoromethoxy)benzyl)oxy)phenyl)-7,8-dihydropyrido[4,3-d]pyrimidin-6(5H)-yl)propanoic acid (compound 93)

Using 1-(bromomethyl)-2-methyl-4-(trifluoromethoxy)benzene instead of 1-(bromomethyl)-4-(trifluoromethoxy)benzene. ¹H NMR (400 MHz, Pyridine-d₅, Temp=25° C.) δ: 8.85-8.79 (m, 2H), 8.49 (s, 1H), 7.56 (s, 1H), 7.34-7.30 (m, 2H), 7.21-7.14 (m, 2H), 5.14 (s, 2H), 3.61 (s, 2H), 3.07-3.01 (m, 4H), 2.88-2.77 (m, 4H), 2.30 (s, 3H); (APCI+) m/z 488 (M+H)+.

3-(2-(4-((2-methyl-3-(trifluoromethyl)benzyl)oxy)phenyl)-7,8-dihydropyrido[4,3-d]pyrimidin-6(5H)-yl)propanoic acid (compound 94)

Using 1-(bromomethyl)-2-methyl-3-(trifluoromethyl)benzene instead of 1-(bromomethyl)-4-(trifluoromethoxy)benzene. ¹H NMR (400 MHz, Pyridine-d₅, Temp=25° C.) δ: 8.87-8.80 (m, 2H), 8.49 (s, 1H), 7.74 (d, J=7.5 Hz, 1H), 7.65 (d, J=7.8 Hz, 1H), 7.37-7.29 (m, 3H), 5.21 (s, 2H), 3.60 (s, 2H), 3.07-3.01 (m, 4H), 2.90-2.78 (m, 4H), 2.46 (s, 3H); (APCI+) m/z 472 (M+H)+.

3-(2-(4-((3-methyl-5-(trifluoromethoxy)benzyl)oxy)phenyl)-7,8-dihydropyrido[4,3-d]pyrimidin-6(5H)-yl)propanoic acid (compound 95)

Using 1-(bromomethyl)-3-methyl-5-(trifluoromethoxy)benzene instead of 1-(bromomethyl)-4-(trifluoromethoxy)benzene. ¹H NMR (400 MHz, Pyridine-d₅, Temp=25° C.) δ: 8.81 (d, J=8.9 Hz, 2H), 8.49 (s, 1H), 7.36 (s, 1H), 7.31 (d, J=8.5 Hz, 2H), 7.24 (s, 1H), 7.08 (s, 1H), 5.17 (s, 2H), 3.60 (s, 2H), 3.05 (t, J=6.8 Hz, 4H), 2.85 (t, J=7.0 Hz, 2H), 2.80 (t, J=5.9 Hz, 2H), 2.23 (s, 3H); (APCI+) m/z 488 (M+H)+.

3-(2-((2-chloro-6-ethylbenzyl)oxy)-7,8-dihydropyrido[4,3-d]pyrimidin-6(5H)-yl)propanoic acid (compound 96)

Tert-butyl 3-(2-((2-chloro-6-ethylbenzyl)oxy)-7,8-dihydropyrido[4,3-d]pyrimidin-6(5H)-yl)propanoate This compound was prepared from compound XXe in accordance with scheme 9. Compound XXe (130 mg; 0.35 mmol; 1 eq) and (2-chloro-6-ethylphenyl)methanol (160 mg; 0.94 mmol; 2 eq) were dissolved in 5 mL toluene. The mixture was degassed with argon for 15 min. [1, F-biphenyl]-2-yldi-tert-butylphosphine (10.4 mg; 0.035 mmol; 0.1 eq), Palladium(11)acetate (7.84 g; 0.035 mmol; 0.1 eq) and cesium carbonate (228 mg; 0.70 mmol; 2 eq) were added and the mixture was stirred for 4 h at 100° C. The mixture is evaporated, the residue is mixed with 30 mL DCM and washed twice with 20 mL water. The organic phase is dried with MgSO₄, filtered and evaporated. The residue was purified by flash chromatography (silica gel, DCM/MeOH) giving the product with a yield of 78 mg (0.181 mmol; 51.7%).

Compound 96

Tert-butyl 3-(2-((2-chloro-6-ethylbenzyl)oxy)-7,8-dihydropyrido[4,3-d]pyrimidin-6(5H)-yl)propanoate (70 mg; 0.15 mmol; 1 eq) was dissolved in MeOH (3 mL) and THF (3 mL). 2N NaOH (97 mg; 2.4 mmol; 15 eq) was added and the mixture was stirred overnight at RT. The pH was brought to pH 1 with 2N HCl. The oily residue was extracted once with 100 mL DCM and the DCM phase was dried with MgSO$_4$, filtered, evaporated. The residue was purified by flash chromatography (silica gel, DCM/MeOH) giving compound 96 with a yield of 35 mg (0.085 mmol; 52.4%). Calculated mass (C19H22ClN3O3): 375.13 g/mol. $^1$H NMR (600 MHz, DMSO-d$_6$) δ 11.91 (s, 1H), 8.43 (s, 1H), 7.43-7.34 (m, 2H), 7.29 (dd, J=5.7, 3.3 Hz, 1H), 5.45 (s, 2H), 4.08-3.84 (m, 2H), 3.16 (s, 1H), 3.08 (s, 1H), 2.97 (d, J=6.2 Hz, 2H), 2.76 (q, J=7.5 Hz, 2H), 2.67 (q, J=8.6, 7.2 Hz, 2H), 1.16 (t, J=7.6 Hz, 3H). M+H+ 376.2

The following compound was prepared in the same way as compound 96:

3-(2-((2-chloro-6-ethylbenzyl)oxy)-7,8-dihydro-1,6-naphthyridin-6(5H)-yl)cyclobutanecarboxylic acid (compound 118)

Using compound XXIIb instead of compound XXe. Calculated mass (C22H25ClN2O3): 400.16 g/mol. $^1$H NMR (600 MHz, DMSO-d$_6$) δ 7.37-7.34 (m, 2H), 7.27 (dd, J=6.2, 2.8 Hz, 1H), 5.39 (s, 2H), 2.74 (q, J=7.6 Hz, 2H), 1.16 (t, J=7.5 Hz, 4H). M+H+ 401.2

4-(2-(4-(benzyloxy)phenyl)-5H-pyrrolo[3,4-d]pyrimidin-6(7H)-yl)butanoic acid (compound 99)

Ethyl 4-(2-(4-(benzyloxy)phenyl)-5H-pyrrolo[3,4-d]pyrimidin-6(7H)-yl)butanoate

Ethyl 4-(2-(4-(benzyloxy)phenyl)-5H-pyrrolo[3,4-d]pyrimidin-6(7H)-yl)butanoate was prepared from compound IIa (compound II with R'=H, r"=H) in accordance with scheme 5. Compound IIa (500 mg; 1.65 mmol; 1 eq) was dissolved in 20 mL DMF. 50% NaH in oil (158 mg; 3.30 mmol; 2 eq) was added under stirring and argon atmosphere at RT. The mixture is stirred for 1 h at 50° C. Ethyl 4-bromobuyrate (964 mg; 4.94 mmol; 3 eq) was added and the mixture was stirred for 2 h at 50° C., followed by 1 h at 85° C. to obtain a dark solution. DMF is evaporated and the residue was extracted with DCM/water. After phase separation, the organic phase was washed twice with water, dried with MgSO$_4$ and evaporated. The residue was dissolved in DCM and purified by flash chromatography (silica gel, DCM/MeOH). The purified product was evaporated to give a brown oil. CH$_3$CN was added to the product, which was then evaporated and freeze dried giving ethyl 4-(2-(4-(benzyloxy)phenyl)-5H-pyrrolo[3,4-d]pyrimidin-6(7H)-yl)butanoate with a yield of 142 mg (0.340 mmol; 20.6%).

Compound 99

Ethyl 4-(2-(4-(benzyloxy)phenyl)-5H-pyrrolo[3,4-d]pyrimidin-6(7H)-yl)butanoate (71 mg; 0.17 mmol; 1 eq) was dissolved in MeOH (3 mL) and THF (3 mL). 1N NaOH (80 mg; 2 mmol; 11.8 eq) was added under stirring at RT. The mixture was stirred for 3 h at RT and subsequently neutralized with 2 mL 1N HCl. The mixture was evaporated and the residue was then extracted, washed with water and evaporated over P2O5 at 40° C. The resulting product was stirred with 3 mL MeOH, extracted and washed with MeOH, pentane and dried giving compound 99 with a yield of 50 mg (0.128 mmol; 75%). Calculated Mass: (C23H23N3O3): 389.45 g/mol. $^1$H NMR (DMSO-d6, 600 MHz): δ=12.34 (br. s., 1H), 11.65 (br. s., 1H), 8.88 (s, 1H), 8.33-8.37 (m, 2H), 7.47-7.50 (m, 2H), 7.42 (t, J=7.4 Hz, 2H), 7.34-7.37 (m, 1H), 7.16-7.20 (m, 2H), 5.21 (s, 2H), 4.69 (br. s., 4H), 3.41 (br. s., 2H), 2.40 (t, J=7.2 Hz, 2H), 1.97 (qd, J=7.6, 7.3 Hz, 2H), M+H=390

The following compounds were made in the same way as compound 99:

3-(2-(4-(benzyloxy)phenyl)-5H-pyrrolo[3,4-d]pyrimidin-6(7H)-yl)propanoic acid (compound 100)

Tert-butyl 3-(2-(4-(benzyloxy)phenyl)-5H-pyrrolo[3,4-d]pyrimidin-6(7H)-yl)propanoate Tert-butyl 3-(2-(4-(benzyloxy)phenyl)-5H-pyrrolo[3,4-d]pyrimidin-6(7H)-yl)propanoate was prepared from compound IIa in accordance with scheme 5. Compound IIa (500 mg; 1.65 mmol; 1 eq) was suspended in MeOH (10 mL) and THF (10 mL). DBU (201 mg; 1.32 mmol; 0.8 eq) and tert-butylacrylate were added under stirring at RT. The mixture was stirred for 4 h at RT. 10 mL DMF and 724 µL tert-butylacrylate (0.875 g/mL) were added and the mixture was stirred overnight at RT. LCMS showed a conversion of 30%. MeOH and THF were evaporated and 20 mL DMF was added, as well as a further 1.5 mL tert-butylacrylate (0.875 g/mL) and 0.4 mL DBU (1.02 g/mL). The mixture was heated for 1 h at 90° C., followed by 1 h at 100° C. DMF was evaporated and the residue was dissolved in 70 mL DCM/MeOH 1:1. The mixture was evaporated and eluted by flash chromatography (silica gel, DCM/MeOH 98:2) giving tert-butyl 34244-(benzyloxy)phenyl)-5H-pyrrolo[3,4-d]pyrimidin-6(7H)-yl)propanoate with a yield of 397 mg (0.920 mmol; 55.8%).

Compound 100

Tert-butyl 3-(2-(4-(benzyloxy)phenyl)-5H-pyrrolo[3,4-d]pyrimidin-6(7H)-yl)propanoate (100 mg; 0.23 mmol; 1 eq) was dissolved in MeOH (4 mL) and THF (4 mL). 1N NaOH (100 mg; 2.5 mmol; 10.8 eq) was added under stirring at RT. The mixture was stirred for 20 h at RT and subsequently neutralized with 2.5 mL 1N HCl. The mixture was evaporated. The resulting residue was then extracted and washed with water and evaporated over P2O5 at 40° C. The product was dissolved in DCM/MeOH and purified by flash chromatography (silica gel, DCM/MeOH 98:2) giving compound 100 with a yield of 68 mg (0.181 mmol; 78%). Calculated Mass: (C22H21N3O3): 375.42 g/mol. $^1$H NMR (DMSO-d6, 600 MHz): δ=8.88 (s, 1H), 8.33-8.36 (m, 2H), 7.47-7.50 (m, 2H), 7.39-7.44 (m, 2H), 7.34-7.37 (m, 1H), 7.16-7.19 (m, 2H), 5.21 (s, 2H), 4.74 (br. s., 2H), 3.63 (t, J=7.1 Hz, 2H), 3.58-3.66 (m, 2H), 2.88 (t, J=7.5 Hz, 2H) M+H=376

3-(2-(4-(benzyloxy)phenyl)-7,8-dihydro-1,6-naphthyridin-6(5H)-yl)-2-methylpropanoic acid (compound 101)

Methyl 3-(2-(4-(benzyloxy)phenyl)-7,8-dihydro-1,6-naphthyridin-6(5H)-yl)-2-methylpropanoate Methyl 3-(2-(4-(benzyloxy)phenyl)-7,8-dihydro-1,6-naphthyridin-6(5H)-yl)-2-methylpropanoate was prepared from 2-(4-(benzyloxy)phenyl)-5,6,7,8-tetrahydro-1,6-naphthyridine (compound IXa; R'=H, R"=H) in accordance with scheme 5. Compound IXa (290 mg; 0.92 mmol; 1 eq) was suspended in MeOH (4 mL). DBU (558 mg; 3.67 mmol; 4 eq) and ethyl methacrylate (1.05 g; 9.17 mmol; 10 eq) were added. The reaction mixture was stirred at 120° C. for 2 h. The reaction mixture was evaporated and purified by flash chromatography (12 g silica gel, 0-5% MeOH in DCM) giving methyl 3-(2-(4-(benzyloxy)phenyl)-7,8-dihydro-1,6-naphthyridin-6(5H)-yl)-2-methylpropanoate with a yield of 220 mg (0.528 mmol; 57.6%).

Compound 101

Methyl 3-(2-(4-(benzyloxy)phenyl)-7,8-dihydro-1,6-naphthyridin-6(5H)-yl)-2-methylpropanoate (30 mg; 0.072 mmol; 1 eq) was dissolved in 2 mL THF. 2N NaOH (40 mg; 1 mmol; 13.9 eq) was added and the mixture was stirred overnight at RT. 2N HCl (500 µL) was added to the mixture, which was then evaporated. Water and DCM with a little MeOH was added and after phase separation the aqueous phase was extracted once with DCM. The combined organic phases were eluted by flash chromatography (4 g silica gel, 0-10% MeOH in DCM). The purified product was dried under vacuum overnight at 40° C. giving compound 101 with a yield of 17 mg (0.042 mmol; 58.6%). Calculated mass (C25H26N2O3): 402.486 g/mol. $^1$H NMR (600 MHz, DMSO-d$_6$) δ 8.04-7.95 (m, 2H), 7.66 (d, J=8.0 Hz, 1H), 7.51 (d, J=8.2 Hz, 1H), 7.50-7.46 (m, 2H), 7.41 (dd, J=8.4, 6.8 Hz, 2H), 7.35 (d, J=7.4 Hz, 1H), 7.15-7.02 (m, 2H), 5.16 (s, 2H), 3.78-3.54 (m, 2H), 2.98-2.86 (m, 3H), 2.86-2.67 (m, 3H), 1.09 (d, J=6.6 Hz, 3H). M+H+ 403

3-(2-(4-(benzyloxy)-2-fluorophenyl)-7,8-dihydro-1,6-naphthyridin-6(5H)-yl)-2-methylpropanoic acid (compound 102)

Compound 102 was prepared from ethyl 3-(2-chloro-7,8-dihydro-1,6-naphthyridin-6(5H)-yl)-2-methylpropanoate (compound XXIIa) in accordance with scheme 2 using 4-benzyloxy-2-fluorophenylboronic acid.

Ethyl 3-(2-(4-(benzyloxy)-2-fluorophenyl)-7,8-dihydro-1,6-naphthyridin-6(5H)-yl)-2-methylpropanoate Compound XXIIa (130 mg; 0.46 mmol; 1 eq) was dissolved in DMF (5 mL). 4-benzyloxy-2-fluorophenylboronic acid (136 mg; 0.55 mmol; 1.2 eq) and sodium carbonate (122 mg; 1.15 mmol; 2.5 eq) as a 10% solution were added under stirring, followed by degassing with argon for 3 min. Tetrakis(triphenylphosphine)-palladium(0) (26.6 mg, 0.023 mmol; 0.05 eq) was added and the mixture was stirred for 30 min at 120° C. The mixture was evaporated until the DMF was removed. The residue was extracted with DCM/water. After phase separation, the organic phase was washed one with water, dried with MgSO$_4$ and evaporated. The oily residue was purified by flash chromatography (silica gel, DMC/MeOH 98:2 giving ethyl 3-(2-(4-(benzyloxy)-2-fluorophenyl)-7,8-dihydro-1,6-naphthyridin-6(5H)-yl)-2-methylpropanoate with a yield of 113 mg (0.252 mmol; 54.8%).

Compound 102

Ethyl 3-(2-(4-(benzyloxy)-2-fluorophenyl)-7,8-dihydro-1,6-naphthyridin-6(5H)-yl)-2-methylpropanoate (113 mg; 0.25 mmol; 7.9 eq) was dissolved in MeOH (3 mL) and THF (3 mL). 1N NaOH (80 mg; 2 mmol; 7.9 eq) was added under stirring at RT. The mixture was stirred for 20 h at RT and subsequently neutralized with 2 mL 1N HCl. The mixture was evaporated until the THF and MeOH were removed. The resulting mixture was saturated with NaCl and stirred with 30 mL DCM/MeOH 9:1. The organic phase was separated and the aqueous phase extracted once with DCM/MeOH 9:1. The combined organic phases were dried with MgSO$_4$ and evaporated. The residue was dissolved in DCM and purified by flash chromatography (silica gel, DMC/MeOH 95:5) giving compound 102 with a yield of 52 mg (0.124 mmol; 49.1%). Calculated mass: (C25H25FN2O3): 420.48 g/mol. $^1$H NMR (DMSO-d6, 600 MHz): δ=10.40 (br. s., 1H), 10.35 (br. s., 1H), 7.89 (t, J=9.0 Hz, 1H), 7.73 (d, J=8.3 Hz, 1H), 7.66 (dd, J=8.1, 1.7 Hz, 1H), 7.46-7.51 (m, 2H), 7.40-7.45 (m, 2H), 7.34-7.38 (m, 1H), 7.00-7.08 (m, 2H), 5.20 (s, 2H), 4.60-4.67 (m, 1H), 4.46 (d, J=18.3 Hz, 1H), 3.96-4.03 (m, 1H), 3.57 (s, 2H), 3.53-3.61 (m, 1H), 3.50-3.52 (m, 1H), 3.40-3.42 (m, 1H), 3.34 (br. s., 1H), 3.30-3.33 (m, 1H), 3.18-3.22 (m, 1H), 3.08-3.15 (m, 1H), 1.22-1.30 (m, 4H). M+H=421

The following compounds were made in the same way as compound 102:

3-(2-(4-(benzyloxy)-3-fluorophenyl)-7,8-dihydro-1,6-naphthyridin-6(5H)-yl)-2-methylpropanoic acid (compound 103)

Using 4-benzyloxy-3-fluorophenylboronic acid instead of 4-benzyloxy-3-fluorophenylboronic acid. Calculated mass: (C25H25FN2O3): 420.48 g/mol. $^1$H NMR (DMSO-d6, 600 MHz): δ=10.25 (br. s., 1H), 10.20 (br. s., 1H), 7.97 (dd, J=12.8, 2.1 Hz, 1H), 7.89-7.91 (m, 1H), 7.89 (s, 1H), 7.71 (d, J=8.3 Hz, 1H), 7.49 (d, J=7.2 Hz, 2H), 7.42 (t, J=7.4 Hz, 2H), 7.35-7.39 (m, 2H), 5.26 (s, 2H), 4.62 (br. s., 1H), 4.43 (br. s., 1H), 3.84 (br. s., 1H), 3.57 (s, 2H), 3.31 (br. s., 1H), 3.23-3.29 (m, 1H), 3.21 (br. s., 1H), 3.17 (br.s., 1H), 3.06-3.12 (m, 1H), 1.26 (d, J=6.8 Hz, 3H). M+H=421

3-(2-(4-((4-fluorobenzyl)oxy)-3-chlorophenyl)-7,8-dihydro-1,6-naphthyridin-6(5H)-yl)-2-methylpropanoic acid (compound 104)

Using 4-(4'-fluorobenzyloxy)-3-chlorophenylboronic acid instead of 4-benzyloxy-3-fluorophenylboronic acid. Calculated mass: (C25H24ClFN2O3): 454.92 g/mol. $^1$H NMR (DMSO-d6, 600 MHz): δ=8.20 (d, J=2.1 Hz, 1H), 8.05 (dd, J=8.7, 2.3 Hz, 1H), 7.92 (d, J=8.3 Hz, 1H), 7.72 (d, J=8.3 Hz, 1H), 7.53-7.58 (m, 2H), 7.37 (d, J=8.8 Hz, 1H), 7.27 (t, J=8.8 Hz, 1H), 7.24-7.30 (m, 1H), 5.28 (s, 2H), 4.59-4.66 (m, 1H), 4.45 (d, J=15.4 Hz, 1H), 3.84 (br. s., 1H), 3.62-3.70 (m, 1H), 3.30-3.35 (m, 1H), 3.26 (br. s., 1H), 3.17-3.24 (m, 1H), 3.07-3.13 (m, 1H), 1.27 (br. s., 2H), 1.23 (d, J=7.3 Hz, 1H). M+H=455

3-(2-(4-((2-fluorobenzyl)oxy)-3-chlorophenyl)-7,8-dihydro-1,6-naphthyridin-6(5H)-yl)-2-methylpropanoic acid (compound 105)

Using 4-(2'-fluorobenzyloxy)-3-chlorophenylboronic acid instead of 4-benzyloxy-2-fluorophenylboronic acid. Calculated mass: (C25H24ClFN2O3): 454.92 g/mol. $^1$H NMR (DMSO-d6, 600 MHz): δ=10.25 (d, J=17.3 Hz, 1H), 10.20 (br. s., 1H), 8.20 (d, J=2.3 Hz, 1H), 8.07 (dd, J=8.7, 2.3 Hz, 1H), 7.93 (d, J=8.3 Hz, 1H), 7.72 (d, J=8.3 Hz, 1H), 7.60-7.64 (m, 1H), 7.42-7.48 (m, 2H), 7.26-7.32 (m, 2H), 5.33 (s, 2H), 4.59-4.66 (m, 1H), 4.44 (t, J=15.4 Hz, 1H), 3.85 (br. s., 1H), 3.59-3.60 (m, 1H), 3.57 (s, 1H), 3.32-3.34 (m, 1H), 3.22-3.25 (m, 1H), 3.17-3.21 (m, 1H), 3.06-3.12 (m, 1H), 1.75-1.77 (m, 1H), 1.22-1.30 (m, 4H). M+H=455/457

3-(2-(4-(benzyloxy)-3-chlorophenyl)-7,8-dihydro-1, 6-naphthyridin-6(5H)-yl)-2-methylpropanoic acid (compound 106)

Using 4-benzyloxy-3-chlorophenylboronic acid instead of 4-benzyloxy-2-fluorophenylboronic acid. Calculated mass: (C25H25ClN2O3): 436.93 g/mol. $^1$H NMR (DMSO-d6, 600 MHz): δ=10.26 (br. s., 1H), 10.20 (br. s., 1H), 8.20 (d, J=2.3 Hz, 1H), 8.04 (dd, J=8.8, 2.2 Hz, 1H), 7.91 (d, J=8.1 Hz, 1H), 7.72 (d, J=8.5 Hz, 1H), 7.48-7.52 (m, 2H), 7.43 (t, J=7.5 Hz, 2H), 7.33-7.39 (m, 2H), 5.30 (s, 2H), 4.59-4.66 (m, 1H), 4.45 (d, J=16.0 Hz, 1H), 3.84 (br. s., 1H), 3.59-3.61 (m, 1H), 3.41 (d, J=5.5 Hz, 2H), 3.28-3.36 (m, 2H), 3.21-3.27 (m, 1H), 3.07-3.12 (m, 1H), 1.22-1.30 (m, 4H). M+H=437/439

3-(2-(4-(benzyloxyphenyl)-7,8-dihydro-1,6-naphthyridin-6(5H)-yl)-2-methylpropanoic acid (compound 107)

Using 4-benzyloxyphenylboronic acid instead of 4-benzyloxy-2-fluorophenylboronic acid. Calculated mass: (C25H26N2O3): 402.49 g/mol. $^1$H NMR (DMSO-d6, 600 MHz): δ=10.31 (br. s., 1H), 10.25 (br. s., 1H), 7.92 (d, J=8.1 Hz, 1H), 7.74 (d, J=8.3 Hz, 1H), 7.71-7.73 (m, 1H), 7.67 (d, J=7.0 Hz, 1H), 7.66-7.67 (m, 1H), 7.48-7.52 (m, 2H), 7.39-7.45 (m, 3H), 7.33-7.37 (m, 1H), 7.12 (ddd, J=8.2, 2.5, 0.8 Hz, 1H), 5.19 (s, 2H), 4.61-4.67 (m, 1H), 4.46 (d, J=16.9 Hz, 1H), 3.85 (br. s., 1H), 3.54-3.58 (m, 1H), 3.17-3.25 (m, 1H), 3.07-3.13 (m, 1H), 1.22-1.30 (m, 3H). M+H=403

3-(2-(4-(benzyloxy)-2-chlorophenyl)-7,8-dihydro-1, 6-naphthyridin-6(5H)-yl)-2-methylpropanoic acid (compound 108)

Using 4-benzyloxy-2-chlorophenylboronic acid instead of 4-benzyloxy-2-fluorophenylboronic acid. Calculated mass: (C25H25ClN2O3): 436.93 g/mol. $^1$H NMR (DMSO-d6, 600 MHz): δ=7.73 (d, J=8.1 Hz, 1H), 7.57 (d, J=8.1 Hz, 1H), 7.46-7.52 (m, 3H), 7.40-7.44 (m, 2H), 7.34-7.37 (m, 1H), 7.25 (d, J=2.4 Hz, 1H), 7.13 (dd, J=8.7, 2.4 Hz, 1H), 5.21 (s, 2H), 4.63-4.69 (m, 1H), 4.47 (br. s., 1H), 3.85 (br. s., 1H), 3.59-3.61 (m, 1H), 3.57 (s, 1H), 3.40-3.48 (m, 3H), 3.32 (br. s., 2H), 3.24 (br. s., 1H), 3.18 (d, J=13.7 Hz, 1H), 3.07-3.13 (m, 1H), 1.22-1.30 (m, 3H). M+H=437

3-(2-(4-((3-fluorobenzyl)oxy)phenyl)-7,8-dihydro-1, 6-naphthyridin-6(5H)-yl)-2-methylpropanoic acid (compound 109)

Using 4-benzyloxy-3-fluorophenylboronic acid instead of 4-benzyloxy-2-fluorophenylboronic acid. Calculated mass: (C25H25FN2O3): 420.48 g/mol. $^1$H NMR (DMSO-d6, 600 MHz): δ=10.30 (br. s., 1H), 10.25 (br. s., 1H), 8.04-8.07 (m, 2H), 7.84 (d, J=8.3 Hz, 1H), 7.70 (d, J=8.3 Hz, 1H), 7.44-7.48 (m, 1H), 7.30-7.34 (m, 2H), 7.12-7.20 (m, 3H), 5.21 (s, 2H), 4.61 (br. s., 1H), 4.43 (br. s., 1H), 3.84 (br. s., 1H), 3.58-3.64 (m, 1H), 3.57 (s, 2H), 3.20 (br. s., 1H), 3.06-3.13 (m, 1H), 1.75-1.77 (m, 1H), 1.27 (d, J=6.6 Hz, 3H). M+H=421

2-(2-(4-(benzyloxy)-3-methylphenyl)-7,8-dihydro-1, 6-naphthyridin-6(5H)-yl)acetic acid (compound 111)

Methyl 2-(2-(4-(benzyloxy)-3-methylphenyl)-7,8-dihydro-1,6-naphthyridin-6(5H)-yl)acetate Compound IXc (110 mg; 0.33 mmol; 1 eq) was dissolved in acetonitrile (5 mL). K$_2$CO$_3$ (46 mg; 0.33 mmol; 1 eq) and methyl bromoacetate (50.9 mg; 0.33 mmol; 1 eq) were added and the mixture was stirred for 3 h at RT. The reaction mixture was evaporated. The residue was dissolved in DCM and washed once with water. After phase separation, the organic layer was evaporated and the residue was absorbed on Celite XTR and purified by flash chromatography (4 g silica gel, 0-90% MeOH in DCM) giving the product with a yield of 129 mg (0.321 mmol; 96%).

Compound 111

Methyl 2-(2-(4-(benzyloxy)-3-methylphenyl)-7,8-dihydro-1,6-naphthyridin-6(5H)-yl)acetate (40 mg; 0.10 mmol; 1 eq) was dissolved in MeOH (4 mL). 2N NaOH (60 mg; 1.5 mmol; 15 eq) was added under stirring at RT. The mixture was stirred for overnight at RT. The MeOH was evaporated. The resulting suspension was brought to pH 1 with 2N HCl. The mixture was stirred for 15 min at RT. The resulting suspension was extracted twice with 60 mL DCM. The combined organic phases were separated, dried with MgSO$_4$, filtered and evaporated. The residue was purified by flash chromatography (silica gel, DCM:MeOH 98:2) giving compound 111 with a yield of 13 mg (0.031 mmol; 30.8%). Calculated mass (C24H24N2O3): 388.18 g/mol. $^1$H NMR (600 MHz, DMSO-d$_6$) δ 7.90 (d, J=2.4 Hz, 1H), 7.85 (dd, J=8.5, 2.3 Hz, 1H), 7.67 (d, J=8.1 Hz, 1H), 7.52 (d, J=8.1 Hz, 1H), 7.51-7.47 (m, 2H), 7.44-7.39 (m, 2H), 7.36-7.31 (m, 1H), 7.10 (d, J=8.7 Hz, 1H), 5.19 (s, 2H), 3.84 (s, 2H), 3.44 (s, 2H), 3.02 (t, J=6.0 Hz, 2H), 2.97 (t, J=5.9 Hz, 2H), 2.27 (s, 3H). M+H+ 389.2

2-(2-(3-methyl-4-((4-(trifluoromethyl)benzyl)oxy) phenyl)-7,8-dihydro-1,6-naphthyridin-6(5H)-yl)acetic acid (compound 112)

Methyl 2-(2-(4-(benzyloxy)-3-methylphenyl)-7,8-dihydro-1,6-naphthyridin-6(5H)-yl)acetate was prepared as described for compound 111 and processed in accordance with scheme 7.

Methyl 2-(2-(4-hydroxy-3-methylphenyl)-7,8-dihydro-1,6-naphthyridin-6(5H)-yl)acetate Methyl 2-(2-(4-(benzyloxy)-3-methylphenyl)-7,8-dihydro-1,6-naphthyridin-6(5H)-yl)acetate (75 mg; 0.186 mmol; 1 eq) thereof was dissolved in 10 mL MeOH. Pd—C (27 mg; 0.025 mmol; 0.14 eq) was added under N2. The mixture was stirred under an atmosphere of hydrogen over night at RT. Pd—C was removed, the resulting product washed with MeOH and evaporated.

Compound 112

To a solution of methyl 2-(2-(4-hydroxy-3-methylphenyl)-7,8-dihydro-1,6-naphthyridin-6(5H)-yl)acetate (65 mg; 0.21 mmol; 1 eq) and 1-(bromomethyl)-4-(trifluoromethyl) benzene (60 mg; 0.25 mmol; 1.2 eq) in 2 mL DMF. Cesium carbonate (81 mg; 0.25 mmol; 1.2 eq) was added at RT resulting in a suspension. The mixture was stirred for 3 h at RT. The mixture was evaporated and 5 mL water and 20 mL ethyl acetate were added. After phase separation, the organic phase was dried with MgSO$_4$, filtered and evaporated. The residue was purified by flash chromatography (silica gel, DCM:MeOH 98:2) giving compound 112 with a yield of 39 mg (0.083 mmol; 39.8%). Calculated mass (C25H23F3N2O3): 456.17 g/mol. $^1$H NMR (600 MHz, DMSO-d$_6$) δ 7.91 (d, J=2.4 Hz, 1H), 7.85 (dd, J=8.5, 2.4 Hz, 1H), 7.79 (d, J=8.1 Hz, 2H), 7.71 (d, J=8.1 Hz, 2H), 7.67 (d, J=8.1 Hz, 1H), 7.52 (d, J=8.2 Hz, 1H), 7.08 (d, J=8.6 Hz, 1H), 5.31 (s, 2H), 4.03 (s, 1H), 3.81 (s, 2H), 3.04-2.90 (m, 4H), 2.31 (s, 3H), 1.23 (s, 1H), 1.21-1.13 (m, 3H). M+H+ 457.3

3-(2-(4-(benzyloxy)phenyl)-7,8-dihydro-1,6-naphthyridin-6(5H)-yl)butanoic acid (compound 113)

Methyl 3-(2-(4-(benzyloxy)phenyl)-7,8-dihydro-1,6-naphthyridin-6(5H)-yl)butanoate This compound was prepared from 2-(4-(benzyloxy)phenyl)-5,6,7,8-tetrahydro-1,6-naphthyridine (compound IXa; R'=H, R''=H) in accordance with scheme 5. Compound IXa with R'=H, R''=H (290 mg; 0.92 mmol; 1 eq) was suspended in MeOH (4 mL). DBU (558 mg; 3.67 mmol; 4 eq) and ethyl crotonate (1.05 g; 9.17 mmol; 10 eq) were added. The reaction mixture was stirred at 120° C. for 2 h and the product was checked with LC/MS. The reaction mixture was evaporated and purified by flash chromatography (12 g silica gel, 0-10% MeOH in DCM) giving methyl 3-(2-(4-(benzyloxy)phenyl)-7,8-dihydro-1,6-naphthyridin-6(5H)-yl)butanoate with a yield of 176 mg (0.423 mmol; 46.1%).

Compound 113

Methyl 3-(2-(4-(benzyloxy)phenyl)-7,8-dihydro-1,6-naphthyridin-6(5H)-yl)butanoate (30 mg; 0.072 mmol; 1 eq) was dissolved in 2 mL THF. 2N NaOH (40 mg; 1.0 mmol; 13.9 eq) were added and the mixture was stirred overnight at RT. 500 µL 2N HCl was added and the mixture was evaporated. The residue was dissolved in water/DCM with a little MeOH. After phase separation, the aqueous phase is extracted once with DCM. The combined organic phases are evaporated and eluted by flash chromatography (4 g silica gel, 0-20% MeOH in DCM) giving compound 113 with a yield of 17 mg (0.042 mmol; 58.6%). Calculated mass (C25H26N2O3): 402.486 g/mol. $^1$H NMR (600 MHz, DMSO-d$_6$) δ 8.04-7.94 (m, 2H), 7.66 (d, J=8.1 Hz, 1H), 7.52 (d, J=8.1 Hz, 1H), 7.50-7.43 (m, 2H), 7.41 (dd, J=8.4, 6.8 Hz, 2H), 7.37-7.29 (m, 1H), 7.14-7.05 (m, 2H), 5.16 (s, 2H), 3.86-3.67 (m, 2H), 3.00-2.87 (m, 3H), 2.85-2.76 (m, 1H), 2.56 (dd, J=15.2, 7.6 Hz, 1H), 2.27 (dd, J=15.2, 7.0 Hz, 1H), 1.09 (d, J=6.7 Hz, 3H). M+H+ 403

4-(2-(4-(benzyloxy)-3-methylphenyl)-7,8-dihydro-1,6-naphthyridin-6(5H)-yl)butanoic acid (compound 114)

Tert-butyl 4-(2-(4-(benzyloxy)-3-methylphenyl)-7,8-dihydro-1,6-naphthyridin-6(5H)-yl)butanoate Compound IXc (56 mg; 0.169 mmol; 1 eq) was dissolved in DMF (2 mL). NaH (9.76 mg; 0.20 mmol; 1.2 eq; 50% in oil) was added under stirring and argon. The mixture was stirred for 1 h at RT. Tert-butyl 4-bromobutanoate (56.7 mg; 0.254 mmol; 1.5 eq) was added and the mixture was stirred for 20 h at RT during which half of the starting materials were reacted. A further 10 mg naH (50% in oil), followed by stirring at RT for 30 min and addition of a further 60 mg tert-butyl 4-bromobutanoate. The mixture was stirred for 5 h at 50° C. The DMF was evaporated and the residue was extracted with water and DCM. The organic phase was washed twice with water, dried with MgSO$_4$ and evaporated. The residue was purified by flash chromatography (silica gel, DCM/MeOH 95:5) giving the product with a yield of 63 mg (0.133 mmol; 79%).

Compound 114

Tert-butyl 4-(2-(4-(benzyloxy)-3-methylphenyl)-7,8-dihydro-1,6-naphthyridin-6(5H)-yl)butanoate (63 mg; 0.13 mmol; 1 eq) was dissolved in THF (2 mL) and MeOH (2 mL). 1N NaOH (60 mg; 1.5 mmol; 11.25 eq) was added under stirring and the mixture was stirred for 20 h at RT. The solution was neutralized with 1N HCl to pH5 and evaporated, resulting in precipitation of the carboxylic acid. The residue was extracted with DCM/MeOH 9:1, the organic phase was dried with MgSO$_4$, filtered and evaporated. The residue is dissolved in DCM/MeOH 9:1 and chromatographed over 5 g SiOH column giving compound 114 with a yield of 35 mg (0.084 mmol; 63%). Calculated Mass: (C26H28N2O3): 416.51 g/mol. $^1$H NMR (DMSO-d6, 600 MHz): δ=10.91 (br. s., 1H), 7.92-7.95 (m, 1H), 7.88-7.91 (m, 1H), 7.85 (d, J=8.1 Hz, 1H), 7.73 (d, J=8.1 Hz, 1H), 7.49 (d, J=7.2 Hz, 2H), 7.42 (t, J=7.6 Hz, 2H), 7.33-7.36 (m, 1H), 7.14 (d, J=8.8 Hz, 1H), 5.21 (s, 2H), 4.61 (d, J=15.2 Hz, 1H), 4.35 (dd, J=15.4, 7.9 Hz, 1H), 4.08-4.14 (m, 1H), 3.46-3.54 (m, 1H), 3.34-3.41 (m, 1H), 3.21-3.29 (m, 2H), 3.17 (d, J=17.9 Hz, 1H), 2.41 (br. s., 1H), 2.38-2.41 (m, 2H), 2.27-2.31 (m, 3H), 2.03 (qd, J=7.7, 7.5 Hz, 2H). M+H=417

4-(2-(4-((3-fluorobenzyl)oxy)phenyl)-7,8-dihydro-1,6-naphthyridin-6(5H)-yl)butanoic acid (compound 116)

Ethyl 4-(2-(4-(benzyloxy)phenyl)-7,8-dihydro-1,6-naphthyridin-6(5H)-yl)butanoate This compound was prepared from 2-(4-(benzyloxy)phenyl)-5,6,7,8-tetrahydro-1,6-naphthyridine (compound IXa; R'=H, R''=H) in accordance with scheme 5. Compound IXa with R'=H, R''=H (200 mg; 0.63 mmol; 1 eq) was dissolved in 5 mL DMF. This solution was added dropwise to a suspension of NaH (60 mg; 1.25 mmol; 2 eq) in 2 mL DMF. The mixture was stirred at RT for 1 h. Ethyl 4-bromoburate (341 mg; 1.75 mmol; 2.8 eq) dissolved in 2 mL DMF was added dropwise. The reaction mixture was stirred for 3 h at 60° C. and overnight at RT and the product was checked by LC/MS showing 50% conversion. A further 60 mg NaH and 250 µL ethyl 4-bromoburate (1.36 g/mL) were added and the reaction mixture was heated to 60° C. for 4 h, followed by stirring for 2 days at RT. The reaction mixture was poured into ice-water and extracted with ethylacetate. The organic layer was separated, washed once with saturated NaCl solution, dried over MgSO$_4$, filtered and evaporated. The reaction mixture purified by flash chromatography (12 g silica gel, 0-20% MeOH in DCM) giving ethyl 4-(2-(4-(benzyloxy)phenyl)-7,8-dihydro-1,6-naphthyridin-6(5H)-yl)butanoate with a yield of 280 mg (0.585 mmol; 93%).

Ethyl 4-(2-(4-hydroxyphenyl)-7,8-dihydro-1,6-naphthyridin-6(5H)-yl)butanoate This compound was prepared from ethyl 4-(2-(4-(benzyloxy)phenyl)-7,8-dihydro-1,6-naphthyridin-6(5H)-yl)butanoate in a palladium mediated reaction in accordance with scheme 7. Ethyl 4-(2-(4-(benzyloxy)phenyl)-7,8-dihydro-1,6-naphthyridin-6(5H)-yl)butanoate (200 mg; 0.465 mmol; 1 eq) was dissolved in MeOH (6 mL). Pd—C (49.4 mg; 0.47 mmol; 1 eq) was added under argon atmosphere. The mixture was stirred at RT under hydrogen atmosphere. The reaction mixture was filtered and evaporated giving the product with a yield of 147 mg (0.432 mmol; 93%).

Ethyl 4-(2-(4-((3-fluorobenzyl)oxy)phenyl)-7,8-dihydro-1,6-naphthyridin-6(5H)-yl)butanoate Ethyl 4-(2-(4-hydroxyphenyl)-7,8-dihydro-1,6-naphthyridin-6(5H)-yl)butanoate (70 mg; 0.21 mmol; 1 eq) was dissolved in 4 mL acetonitrile. K$_2$CO$_3$ (35 mg; 0.25 mmol; 1.2 eq) and 3-fluorobenzylbromide (46.2 mg; 0.45 mmol; 1.2 eq) were added and the mixture was stirred at 150° C. for 15 min. The reaction mixture was evaporated and the residue was dissolved in DCM and water. The phases were separated and the organic layer was evaporated. The residue was purified by flash chromatography (4 g silica gel, 0-10% MeOH in DCM) giving the product with a yield of 40 mg (0.089 mmol; 43.4%).

Compound 116

Ethyl 4-(2-(4-((3-fluorobenzyl)oxy)phenyl)-7,8-dihydro-1,6-naphthyridin-6(5H)-yl)butanoate (40 mg; 0.089 mmol; 1 eq) was dissolved in MeOH (2 mL) to give a yellow solution. 2N NaOH (40 mg; 1.0 mmol; 11.2 eq) was added and the mixture was stirred overnight at RT. The reaction mixture was evaporated. The residue was purified by flash chromatography (4 g silica gel, 5-30% MeOH in DCM) giving compound 116 with a yield of 20 mg (0.048 mmol; 53.3%). Calculated mass (C25H25FN2O3): 420.476 g/mol. $^1$H NMR (600 MHz, DMSO-d$_6$) δ 8.01 (d, J=8.4 Hz, 2H), 7.67 (d, J=8.1 Hz, 1H), 7.53 (d, J=8.1 Hz, 1H), 7.49-7.41 (m, 1H), 7.31 (dd, J=10.4, 4.4 Hz, 2H), 7.17 (td, J=8.7, 2.7 Hz, 1H), 7.10 (d, J=8.4 Hz, 2H), 5.20 (s, 2H), 3.65 (s, 2H), 2.94 (t, J=5.9 Hz, 2H), 2.83 (s, 2H), 2.55 (s, 2H), 2.30 (t, J=7.2 Hz, 2H), 2.23 (t, J=7.5 Hz, 1H), 1.78 (p, J=7.2 Hz, 2H), 1.63 (p, J=6.9 Hz, 1H). M+H+ 421

The following compounds were made in the same way as compound 116:

4-(2-(4-(benzyloxy)phenyl)-7,8-dihydro-dihydropyrido[4,3-d]pyrimidin-6(5H)-yl)butanoic acid (compound 37)

starting from compound Ia instead of compound IXa and wherein compound 37 was prepared directly from 4-(2-(4-(benzyloxy)phenyl)-7,8-dihydro-dihydropyrido[4,3-d]pyrimidin-6(5H)-yl)butanoate using NaOH. Calculated mass (C24H25N3O3): 403.474 g/mol. $^1$H NMR (500 MHz, DMSO-d$_6$) δ 8.55 (s, 1H), 8.37-8.22 (m, 2H), 7.48 (d, J=6.8 Hz, 2H), 7.41 (dd, J=8.3, 6.6 Hz, 2H), 7.37-7.30 (m, 1H), 7.22-7.00 (m, 2H), 5.18 (s, 2H), 3.59 (s, 2H), 2.91 (q, J=6.0 Hz, 2H), 2.78 (t, J=5.9 Hz, 2H), 2.28 (t, J=7.3 Hz, 2H), 1.81-1.71 (m, 2H). M+H+ 404

4-(2-(4-((3-chlorobenzyl)oxy)phenyl)-7,8-dihydropyrido[4,3-d]pyrimidin-6(5H)-yl)butanoic acid (compound 38)

starting from compound Ia instead of compound IXa and using 3-chlorobenzylbromide instead of 3-fluorobenzylbromide. Calculated mass (C24H24ClN3O3): 437.15 g/mol. $^1$H NMR (600 MHz, DMSO-d$_6$) δ 8.55 (s, 1H), 8.31 (d, J=8.7 Hz, 2H), 7.55 (s, 1H), 7.54-7.32 (m, 3H), 7.28-6.95 (m, 2H), 5.20 (s, 2H), 3.60 (s, 2H), 2.92 (t, J=5.9 Hz, 2H), 2.78 (t, J=5.9 Hz, 2H), 2.28 (t, J=7.2 Hz, 2H), 1.77 (p, J=7.2 Hz, 2H). M+H+ 438

4-(2-(4-((4-chlorobenzyl)oxy)phenyl)-7,8-dihydropyrido[4,3-d]pyrimidin-6(5H)-yl)butanoic acid (compound 40)

starting from compound Ia instead of compound IXa and using 4-chlorobenzylbromide instead of 3-fluorobenzylbromide. Calculated mass (C24H24ClN3O3): 437.15 g/mol. $^1$H NMR (600 MHz, DMSO-d$_6$) δ 8.55 (s, 1H), 8.35-8.19 (m, 2H), 7.57-7.39 (m, 3H), 7.12 (d, J=8.9 Hz, 2H), 5.18 (s, 2H), 3.60 (s, 2H), 2.91 (t, J=6.0 Hz, 2H), 2.79 (d, J=6.0 Hz, 2H), 2.28 (t, J=7.2 Hz, 2H), 1.82-1.71 (m, 2H). M+H+ 438

4-(2-(4-(benzyloxy)phenyl)-7,8-dihydro-1,6-naphthyridin-6(5H)-yl)butanoic acid (compound 115)

whereby compound 115 was prepared directly from ethyl 4-(2-(4-(benzyloxy)phenyl)-7,8-dihydro-1,6-naphthyridin-6(5H)-yl)butanoate using NaOH. Calculated mass (C25H26N2O3): 402.486 g/mol. $^1$H NMR (600 MHz, DMSO-d6) δ 8.02 (d, J=8.4 Hz, 2H), 7.73 (d, J=8.1 Hz, 1H), 7.59 (d, J=8.2 Hz, 1H), 7.48 (d, J=7.5 Hz, 2H), 7.41 (t, J=7.5 Hz, 2H), 7.34 (t, J=7.3 Hz, 1H), 7.11 (d, J=8.4 Hz, 2H), 5.17 (s, 2H), 3.94 (s, 2H), 3.04 (s, 2H), 2.80 (s, 2H), 2.33 (t, J=7.2 Hz, 2H), 1.85 (p, J=7.1 Hz, 2H). M+H+ 403

3-(2-(4-(benzyloxy)-3-methylphenyl)-7,8-dihydro-1,6-naphthyridin-6(5H)-yl)cyclobutanecarboxylic acid (compound 117)

Compound 117 was prepared from compound IXc (R'=H, R"=3-CH$_3$ in accordance with scheme 5. Compound IXc (58 mg; 0.18 mmol; 1 eq) was dissolved in 1,2-dichloroethane (3 mL). 3-oxocyclobutanecarboxylic acid (40.1 mg; 0.35 mmol; 2 eq) was added under stirring at RT. The mixture was stirred for 5 min at RT after which sodium triacetoxyborohydride (74.4 mg; 0.35 mmol; 2 eq) was added. The mixture was stirred for 1 h at RT. 5 mL water was added to the solution which was then stirred for 30 min at RT and evaporated until the dichloroethane was gone. The residue was extracted, washed with water and evaporated over P2O5 at 40° C. under vacuum giving product 117 with a yield of 63 mg (0.147 mmol; 84%). Calculated Mass: (C27H28N2O3): 428.52 g/mol. $^1$H NMR (DMSO-d6, 600 MHz): δ=10.98 (br. s., 1H), 7.94 (d, J=1.7 Hz, 1H), 7.89 (dd, J=8.6, 2.2 Hz, 1H), 7.85 (d, J=8.1 Hz, 1H), 7.71 (dd, J=8.3, 2.8 Hz, 1H), 7.49 (d, J=7.2 Hz, 2H), 7.40-7.44 (m, 2H), 7.32-7.36 (m, 1H), 7.13 (d, J=8.7 Hz, 1H), 5.21 (s, 2H), 4.54 (d, J=15.6 Hz, 1H), 4.21 (dd, J=14.9, 7.5 Hz, 1H), 0.99-4.04 (m, 1H), 3.75-3.82 (m, 1H), 3.66-3.71 (m, 1H), 3.33-3.39 (m, 2H), 3.31 (br. s., 1H), 3.17 (s, 1H), 3.06 (tt, J=10.0, 3.2 Hz, 1H), 2.89-2.93 (m, 1H), 2.76 (q, J=9.9 Hz, 1H), 2.27-2.30 (m, 3H). M+H=429

3-(2-(phenylethynyl)-7,8-dihydro-1,6-naphthyridin-6(5H)-yl)cyclobutanecarboxylic acid (compound 119)

To a 4 mL vial containing a stir bar was added methyl 3-(2-chloro-7,8-dihydro-1,6-naphthyridin-6(5H)-yl)cyclobutanecarboxylate (40 mg; 0.14 mmol), prepared from 2-chloro-1,6-diaza-5,6,7,8-tetrahydronaphthalene in accordance with scheme 6, followed by ethynylbenzene (29 mg; 0.28 mmol) and K$_3$PO$_4$ (75 mg; 0.35 mmol) and was capped with septa caps and flushed with N2 for 5 minutes. The septa vial was introduced to the dry-box and PdCl$_2$(MeCN)$_2$ dry (3.7 mg; 0.014 mmol) was added, followed by XPHOS (16.3 mg; 0.03 mmol). Acetonitrile (purged with N2) was added to the vial containing the starting materials (500 µl, each) via syringe, capped and placed to heat/stir at 90° C. for 4 hours. The crude material was then passed through a filter cartridge containing Celite using MeOH to wash, and then concentrated to dryness. An aqueous 1M solution of LiOH in 75% MeOH was added (1000 µL), and the vial was capped and heated at 50° C. for 1 hour. The reaction was filtered, and concentrated to dryness. Then it was re-dissolved in 1800 µl, of a 1:1 v/v solution of DMSO/MeOH, checked by LC/MS and purified by reverse phase HPLC (TFA method) to provide the title compound. $^1$H NMR (400 MHz, Pyridine-d$_5$, Temp=90° C.) δ: 7.63-7.56 (m, 2H), 7.37-7.23 (m, 5H), 3.51 (s, 2H), 3.09-3.02 (m, 2H), 3.02-2.94 (m, 1H), 2.93-2.83 (m, 1H), 2.69-2.62 (m, 2H), 2.50-2.42 (m, 4H); MS (APCI+) m/z 333 (M+H)+.

The following compounds were made in the same way as compound 119:

3-(2-((4-chlorophenyl)ethynyl)-7,8-dihydro-1,6-naphthyridin-6(5H)-yl)cyclobutanecarboxylic acid (compound 120)

Using 1-chloro-4-ethynylbenzene instead of ethynylbenzene. $^1$H NMR (400 MHz, Pyridine-d$_5$, Temp=90° C.) δ: 7.50-7.47 (m, 2H), 7.37-7.26 (m, 4H), 3.51 (s, 2H), 3.09-2.96 (m, 3H), 2.88 (t, J=7.7 Hz, 1H), 2.66 (t, J=6.1 Hz, 2H), 2.50-2.40 (m, 4H); MS (APCI+) m/z 367 (M+H)+.

3-(2-(o-tolylethynyl)-7,8-dihydro-1,6-naphthyridin-6(5H)-yl)cyclobutanecarboxylic acid (compound 121)

Using o-ethynyltoluene instead of ethynylbenzene. $^1$H NMR (400 MHz, Pyridine-d$_5$, Temp=90° C.) δ: 7.58 (d, 1H), 7.36 (d, J=7.7 Hz, 1H), 7.31-7.25 (m, 1H), 7.23-7.16 (m, 2H), 7.14-7.10 (m, 1H), 3.52 (s, 2H), 3.10-3.02 (m, 2H), 3.02-2.94 (m, 1H), 2.93-2.82 (m, 1H), 2.70-2.63 (m, 2H), 2.50 (s, 3H), 2.48-2.40 (m, 4H); MS (APCI+) m/z 347 (M+H)+.

3-(2-((4-ethoxyphenyl)ethynyl)-7,8-dihydro-1,6-naphthyridin-6(5H)-yl)cyclobutanecarboxylic acid (compound 122)

Using 1-ethoxy-4-ethynylbenzene instead of ethynylbenzene.

3-(2-((4-fluorophenyl)ethynyl)-7,8-dihydro-1,6-naphthyridin-6(5H)-yl)cyclobutanecarboxylic acid (compound 123)

Using 1-fluoro-4-ethynylbenzene instead of ethynylbenzene. $^1$H NMR (400 MHz, Pyridine-d$_5$, Temp=90° C.) δ: 7.58-7.52 (m, 2H), 7.37-7.24 (m, 2H), 7.04 (t, J=8.7 Hz, 2H), 3.50 (s, 2H), 3.09-2.94 (m, 3H), 2.93-2.82 (m, 1H), 2.69-2.62 (m, 2H), 2.50-2.40 (m, 4H); MS (APCI+) m/z 351 (M+H)+.

3-(2-((4-isopropylphenyl)ethynyl)-7,8-dihydro-1,6-naphthyridin-6(5H)-yl)cyclobutanecarboxylic acid (compound 124)

Using 1-isopropyl-4-ethynylbenzene instead of ethynylbenzene. $^1$H NMR (400 MHz, Pyridine-d$_5$, Temp=90° C.) δ: 7.57 (d, J=8.0 Hz, 2H), 7.35 (d, J=7.8 Hz, 1H), 7.28-7.23 (m, 1H), 7.19 (d, J=7.9 Hz, 2H), 3.50 (s, 2H), 3.10-2.93 (m, 3H), 2.93-2.76 (m, 2H), 2.69-2.58 (m, 2H), 2.50-2.37 (m, 4H), 1.15 (d, J=7.0 Hz, 6H); (APCI+) m/z 375 (M+H)+.

3-(2-((4-(benzyloxy)phenyl)ethynyl)-7,8-dihydro-1,6-naphthyridin-6(5H)-yl)cyclobutanecarboxylic acid (compound 125)

Using 1(p-(benzyloxy)phenyl)ethyne instead of ethynylbenzene. $^1$H NMR (Pyridine-d$_5$) δ: 7.60-7.55 (m, 2H), 7.44 (d, J=7.6 Hz, 2H), 7.38-7.23 (m, 5H), 7.05-7.00 (m, 2H), 5.08 (s, 2H), 3.50 (s, 2H), 3.11-2.96 (m, 3H), 2.91-2.84 (m, 1H), 2.65 (t, J=6.1 Hz, 2H), 2.45 (t, J=8.3 Hz, 4H); (APCI+) m/z 439 (M+H)+.

3-(2-((2-chlorophenyl)ethynyl)-7,8-dihydro-1,6-naphthyridin-6(5H)-yl)cyclobutanecarboxylic acid (compound 126)

Using 1-chloro-2-ethynylbenzene instead of ethynylbenzene. $^1$H NMR (400 MHz, Pyridine-d$_5$, Temp=90° C.) δ: 7.61-7.57 (m, 1H), 7.43-7.38 (m, 2H), 7.30-7.25 (m, 1H), 7.22-7.15 (m, 2H), 3.50 (s, 2H), 3.08-2.93 (m, 3H), 2.92-2.82 (m, 1H), 2.65 (t, J=6.0 Hz, 2H), 2.49-2.40 (m, 4iiH); (APCI+) m/z 367 (M+H)+.

3-(2-((3,5-difluorophenyl)ethynyl)-7,8-dihydro-1,6-naphthyridin-6(5H)-yl)cyclobutanecarboxylic acid (compound 127)

Using 1,5-difluoro-3-ethynylbenzene instead of ethynylbenzene. $^1$H NMR (400 MHz, Pyridine-d$_5$, Temp=90° C.) δ: 7.50-7.45 (m, 1H), 7.42-7.33 (m, 2H), 7.26-7.23 (m, 1H), 7.11-7.03 (m, 1H), 3.47 (s, 2H), 3.15-3.04 (m, 3H), 2.85-2.77 (m, 1H), 2.63-2.56 (m, 2H), 2.52-2.46 (m, 4H); (APCI+) m/z 369 (M+H)+.

3-(2-((3-chlorophenyl)ethynyl)-7,8-dihydro-1,6-naphthyridin-6(5H)-yl)cyclobutanecarboxylic acid (compound 128)

Using 1-chloro-3-ethynylbenzene instead of ethynylbenzene. $^1$H NMR (400 MHz, Pyridine-d$_5$, Temp=90° C.) δ: 7.67 (t, J=1.8 Hz, 1H), 7.53-7.44 (m, 2H), 7.39-7.31 (m, 2H), 7.28-7.24 (m, 1H), 3.46 (s, 2H), 3.14-3.04 (m, 3H), 2.85-2.75 (m, 1H), 2.59 (t, J=5.8 Hz, 2H), 2.52-2.44 (m, 4H); (APCI+) m/z 367 (M+H)+.

3-(3-fluoro-2-(phenylethynyl)-7,8-dihydro-1,6-naphthyridin-6(5H)-yl)cyclobutanecarboxylic acid (compound 184)

starting from methyl 3-(2-chloro-3-fluoro-1,6-diaza-5,6,7,8-tetrahydronaphth-6-yl)cyclobutanecarboxylate instead of methyl 3-(2-chloro-3-fluoro-7,8-dihydro-1,6-naphthyridin-6(5H)-yl)cyclobutanecarboxylate. $^1$H NMR (400 MHz, Pyridine-d$_5$, Temp=27° C.) δ: 7.65-7.59 (m, 2H), 7.29-7.24 (m, 3H), 7.18 (d, J=9.4 Hz, 1H), 3.42 (s, 2H), 3.07-2.93 (m, 3H), 2.74 (q, J=7.9 Hz, 1H), 2.52 (t, J=6.0 Hz, 2H), 2.46-2.37 (m, 4H); (APCI+) m/z 351 (M+H)+.

3-(2-(4-(benzyloxy)phenyl)-7,8-dihydro-1,6-naphthyridin-6(5H)-yl)propanoic acid (compound 129)

Tert-butyl 3-(2-(4-(benzyloxy)phenyl)-7,8-dihydro-1,6-naphthyridin-6(5H)-yl)propanoate This compound was prepared from compound IXa (R'=H, R''=H) in accordance with scheme 5. Compound IXa (590 mg; 1389 mmol; 1 eq) was dissolved in MeOH (3 mL) and THF (3 mL). DBU (227 mg; 1.49 mmol; 0.8 eq) and tert-burylacrylate (717; 5.59 mmol; 3 eq) were added and the mixture was stirred for 20 h at RT. The mixture was evaporated and the residue was dissolved in DCM and purified by flash chromatography (silica gel, DCM/MeOH gradient) giving the product with a yield of 739 mg (1.662 mmol; 89%).

Compound 129

Tert-butyl 3-(2-(4-(benzyloxy)phenyl)-7,8-dihydro-1,6-naphthyridin-6(5H)-yl)propanoate (89 mg; 0.20 mmol; 1 eq) was dissolved in MeOH (3 mL) and THF (3 mL). 1N NaOH (80 mg; 2.0 mmol; 10 eq) was added under stirring at RT and the mixture was subsequently stirred for 20 h at RT. The reaction mixture was neutralized with 2 mL 1N HCl and the THF/MeOH was evaporated. 5 mL water was added and the residue was obtained and dried under vacuum at 40° giving compound 129 with a yield of 69.2 mg (0.178 mmol; 89%). Calculated mass: (C24H24N2O3): 388.46 g/mol. $^1$H NMR (DMSO-d6, 600 MHz): δ=8.03-8.06 (m, 2H), 7.81-7.84 (m, J=8.1 Hz, 1H), 7.65-7.68 (m, J=8.3 Hz, 1H), 7.46-7.49 (m, 2H), 7.41 (t, J=7.5 Hz, 2H), 7.33-7.36 (m, 1H), 7.11-7.14 (m, 2H), 5.18 (s, 2H), 4.44 (br. s., 1H), 3.69-3.77 (m, 1H), 3.68 (br. s., 1H), 3.59-3.61 (m, 1H), 3.45 (br. s., 2H), 3.24 (br. s., 1H), 3.17 (s, 1H), 2.91 (t, J=7.4 Hz, 2H). M+H=389

The following compounds were made in the same way as compound 129:

3-(2-(4-((2,6-dichlorobenzyl)oxy)phenyl)-7,8-dihydro-1,6-naphthyridin-6(5H)-yl)propanoic acid (compound 130)

Using 2-(4-((2,6-dichlorobenzyl)oxy)phenyl)-5,6,7,8-tetrahydro-1,6-naphthyridine prepared in accordance with scheme 1 instead of compound IXa. Calculated mass: (C24H22Cl2N2O3): 457.35 g/mol. $^1$H NMR (DMSO-d6, 600 MHz): δ=10.82 (br. s., 1H), 8.06-8.10 (m, 2H), 7.86 (d, J=8.3 Hz, 1H), 7.69 (d, J=8.3 Hz, 1H), 7.58-7.61 (m, 2H), 7.48-7.51 (m, 1H), 7.17-7.22 (m, 2H), 5.31 (s, 2H), 4.61 (d, J=16.2 Hz, 1H), 4.41 (br. s., 1H), 3.84 (br. s., 1H), 3.60 (d, J=8.7 Hz, 1H), 3.45-3.52 (m, 4H), 3.28 (br. s., 1H), 3.17 (s, 1H), 2.93 (t, J=6.8 Hz, 2H). M+H=457/459

3-(2-(4-((2,3-difluorobenzyl)oxy)phenyl)-7,8-dihydro-1,6-naphthyridin-6(5H)-yl)propanoic acid (compound 131)

Using 2-(4-((2,3-difluorobenzyl)oxy)phenyl)-5,6,7,8-tetrahydro-1,6-naphthyridine prepared in accordance with scheme 1 instead of compound IXa. Calculated mass: (C24H22F2N2O3): 424.44 g/mol. $^1$H NMR (DMSO-d6, 600 MHz): δ=12.80 (br. s., 1H), 10.86 (br. s., 1H), 8.05-8.08 (m, 2H), 7.85 (d, J=8.3 Hz, 1H), 7.68 (d, J=8.3 Hz, 1H), 7.44-7.50 (m, 1H), 7.40-7.43 (m, 1H), 7.25-7.29 (m, 1H), 7.15-7.18 (m, 2H), 5.27 (s, 2H), 4.60 (d, J=15.6 Hz, 1H), 4.37-4.43 (m, 1H), 3.83 (br. s., 1H), 3.57-3.61 (m, 1H), 3.57 (br. s., 1H), 3.50-3.51 (m, 1H), 3.39-3.47 (m, 3H), 3.34 (br. s., 2H), 3.14-3.22 (m, 1H), 2.90-2.96 (m, 2H). M+H=425

3-(2-(4-((2-fluorobenzyl)oxy)phenyl)-7,8-dihydro-1,6-naphthyridin-6(5H)-yl)propanoic acid (compound 132)

Using 2-((4(2-fluorobenzyl)oxy)phenyl)-5,6,7,8-tetrahydro-1,6-naphthyridine prepared in accordance with scheme 1 instead of compound IXa. Calculated mass: (C24H23FN2O3): 406.45 g/mol. $^1$H NMR (DMSO-d6, 600 MHz): δ=12.80 (br. s., 1H), 10.86 (br. s., 1H), 8.04-8.08 (m, 2H), 7.85 (d, J=8.3 Hz, 1H), 7.69 (d, J=8.3 Hz, 1H), 7.59 (td, J=7.5, 1.5 Hz, 1H), 7.42-7.47 (m, 1H), 7.24-7.30 (m, 2H), 7.15 (d, J=9.0 Hz, 2H), 5.22 (s, 2H), 4.60 (d, J=15.8 Hz, 1H), 4.40 (dd, J=15.0, 6.7 Hz, 1H), 3.83 (br. s., 1H), 3.66 (br. s., 1H), 3.31-3.39 (m, 1H), 3.14-3.21 (m, 1H), 2.90-2.96 (m, 2H). M+H=407

3-(2-(4-((3-fluorobenzyl)oxy)phenyl)-7,8-dihydro-1,6-naphthyridin-6(5H)-yl)propanoic acid (compound 133)

Using 2-(4-((3-fluorobenzyl)oxy)phenyl)-5,6,7,8-tetrahydro-1,6-naphthyridine prepared in accordance with scheme 1 instead of compound IXa. Calculated mass: (C24H23FN2O3): 406.45 g/mol. $^1$H NMR (DMSO-d6, 600 MHz): δ=12.76-12.84 (m, 1H), 10.87 (br. s., 1H), 8.03-8.07 (m, 2H), 7.82-7.85 (m, J=8.1 Hz, 1H), 7.67-7.70 (m, J=8.3 Hz, 1H), 7.44-7.48 (m, 1H), 7.30-7.34 (m, 2H), 7.18 (td, J=8.6, 2.0 Hz, 1H), 7.12-7.16 (m, 2H), 5.21 (s, 2H), 4.60 (d, J=15.4 Hz, 1H), 4.39 (dd, J=14.4, 5.7 Hz, 1H), 3.83 (br. s., 1H), 3.57 (br. s., 1H), 3.32-3.37 (m, 1H), 3.13-3.21 (m, 1H), 2.90-2.96 (m, 2H). M+H=407

3-(2-(4-(benzyloxy)-2-fluorophenyl)-7,8-dihydro-1,6-naphthyridin-6(5H)-yl)propanoic acid (compound 134)

Using 2-(4-(benzyloxy)-2-fluorophenyl)-5,6,7,8-tetrahydro-1,6-naphthyridine prepared in accordance with scheme 1 instead of compound IXa. Calculated mass: (C24H23FN2O3): 406.45 g/mol. $^1$H NMR (DMSO-d6, 600 MHz): δ=12.81 (br. s., 1H), 10.68 (br. s., 1H), 7.90 (t, J=9.0 Hz, 1H), 7.69-7.72 (m, 1H), 7.64-7.68 (m, 1H), 7.48 (d, J=7.2 Hz, 2H), 7.42 (t, J=7.5 Hz, 2H), 7.34-7.38 (m, 1H), 7.06 (dd, J=13.4, 2.3 Hz, 1H), 7.01 (dd, J=8.8, 2.4 Hz, 1H), 5.20 (s, 2H), 4.61 (br. s., 1H), 4.43 (br. s., 1H), 3.84 (br. s., 1H), 3.48 (br. s., 3H), 3.20 (br. s., 1H), 2.92 (t, J=7.4 Hz, 2H). M+H=407

3-(2-(4-(benzyloxy)-2-methylphenyl)-7,8-dihydro-1,6-naphthyridin-6(5H)-yl)propanoic acid (compound 135)

Using 2-(4-(benzyloxy)-2-methylphenyl)-5,6,7,8-tetrahydro-1,6-naphthyridine prepared in accordance with scheme 1 instead of compound IXa. Calculated mass: (C25H26N2O3): 402.49 g/mol. $^1$H NMR (DMSO-d6, 600 MHz): δ=12.80 (br. s., 1H), 10.78 (br. s., 1H), 7.71 (d, J=7.9 Hz, 1H), 7.44-7.48 (m, 3H), 7.39-7.43 (m, 2H), 7.32-7.36 (m, 2H), 6.98 (d, J=2.4 Hz, 1H), 6.94 (dd, J=8.5, 2.4 Hz, 1H), 5.16 (s, 2H), 4.63 (d, J=15.1 Hz, 1H), 4.39-4.47 (m, 1H), 3.83 (br. s., 1H), 3.54-3.62 (m, 1H), 3.50-3.51 (m, 1H), 3.24 (br. s., 1H), 3.13-3.21 (m, 1H), 2.93 (t, J=7.5 Hz, 2H), 2.33 (s, 3H). M+H=403

3-(2-(4-(benzyloxy)-2-trifluoromethylphenyl)-7,8-dihydro-1,6-naphthyridin-6(5H)-yl)propanoic acid (compound 136)

Using 2-(4-(benzyloxy)-2-trifluoromethylphenyl)-5,6,7,8-tetrahydro-1,6-naphthyridine prepared in accordance with scheme 1 instead of compound IXa. Calculated mass: (C25H23F3N2O3): 456.46 g/mol. $^1$H NMR (DMSO-d6, 600 MHz): δ=12.83 (br. s. 1H), 10.84 (br. s., 1H), 7.73 (d, J=8.1 Hz, 1H), 7.46-7.51 (m, 3H), 7.38-7.44 (m, 5H), 7.34-7.38 (m, 1H), 5.27 (s, 2H), 4.66 (d, J=15.4 Hz, 1H), 4.46 (dd, J=15.2, 7.1 Hz, 1H), 3.83 (br. s., 1H), 3.63-3.69 (m, 1H), 3.53-3.61 (m, 2H), 3.37-3.45 (m, 1H), 3.27-3.36 (m, 1H), 3.12 (d, J=17.5 Hz, 1H), 2.93 (t, J=7.2 Hz, 2H). M+H=457

3-(2-(4-(benzyloxy)-3-fluorophenyl)-7,8-dihydro-1,6-naphthyridin-6(5H)-yl)propanoic acid (compound 137)

Using 2-(4-(benzyloxy)-3-fluorophenyl)-5,6,7,8-tetrahydro-1,6-naphthyridine prepared in accordance with scheme 1 instead of compound IXa. Calculated mass: (C24H23FN2O3): 406.45 g/mol. ¹H NMR (DMSO-d6, 600 MHz): δ=12.73 (br.s., 1H), 11.06 (br. s., 1H), 7.95-7.99 (m, 1H), 7.90 (t, J=4.3 Hz, 1H), 7.89 (s, 1H), 7.71 (d, J=8.3 Hz, 1H), 7.48-7.51 (m, 2H), 7.42 (t, J=7.4 Hz, 2H), 7.35-7.40 (m, 2H), 5.26 (s, 2H), 4.60 (d, J=15.8 Hz, 1H), 4.40 (dd, J=15.3, 7.6 Hz, 1H), 4.28 (d, J=8.7 Hz, 1H), 3.81-3.87 (m, 1H), 3.66-3.73 (m, 1H), 3.57 (s, 1H), 3.44-3.52 (m, 4H), 3.36 (ddd, J=17.4, 10.8, 6.5 Hz, 1H), 3.13-3.20 (m, 1H), 2.90-2.98 (m, 2H). M+H=407

3-(2-(4-(benzyloxy)-2-methoxyphenyl)-7,8-dihydro-1,6-naphthyridin-6(5H)-yl)propanoic acid (compound 138)

Using 2-(4-(benzyloxy)-2-methoxyphenyl)-5,6,7,8-tetrahydro-1,6-naphthyridine prepared in accordance with scheme 1 instead of compound IXa. Calculated mass: (C25H26N2O4): 418.49 g/mol. ¹H NMR (DMSO-d6, 600 MHz): δ=11.15 (br. s., 1H), 7.78-7.83 (m, 1H), 7.76 (br. s., 1H), 7.72 (br. s., 1H), 7.70 (d, J=8.5 Hz, 1H), 7.47-7.51 (m, 2H), 7.42 (t, J=7.4 Hz, 2H), 7.34-7.38 (m, 1H), 6.82 (d, J=2.1 Hz, 1H), 6.77 (dd, J=8.7, 2.3 Hz, 1H), 5.20 (s, 2H), 4.62 (d, J=15.4 Hz, 1H), 4.38-4.45 (m, 1H), 3.95 (s, 1H), 3.91 (d, J=3.4 Hz, 1H), 3.84 (s, 4H), 3.80 (br. s., 2H), 3.57 (s, 1H), 3.45-3.53 (m, 3H), 3.34-3.41 (m, 2H), 3.16-3.24 (m, 1H), 2.91-2.98 (m, 2H). M+H=419

3-(2-(4-(benzyloxy)-3-methylphenyl)-7,8-dihydro-1,6-naphthyridin-6(5H)-yl)propanoic acid (compound 139)

Using 2-(4-(benzyloxy)-3-methylphenyl)-5,6,7,8-tetrahydro-1,6-naphthyridine prepared in accordance with scheme 1 instead of compound IXa. Calculated mass: (C25H26N2O3): 402.49 g/mol. ¹H NMR (DMSO-d6, 600 MHz): δ=12.80 (br. s., 1H), 10.72 (br. s., 1H), 7.93 (s, 1H), 7.89 (dd, J=8.6, 1.8 Hz, 1H), 7.83 (d, J=8.3 Hz, 1H), 7.67 (d, J=8.1 Hz, 1H), 7.49 (d, J=7.3 Hz, 2H), 7.42 (t, J=7.6 Hz, 2H), 7.32-7.36 (m, 1H), 7.13 (d, J=8.7 Hz, 1H), 5.21 (s, 2H), 4.60 (d, J=15.4 Hz, 1H), 4.39 (dd, J=14.4, 6.7 Hz, 1H), 3.83 (br. s., 1H), 3.67 (d, J=5.5 Hz, 1H), 3.29-3.38 (m, 1H), 3.18 (d, J=14.1 Hz, 1H), 2.92 (t, J=6.9 Hz, 2H), 2.28 (s, 3H). M+H=403

3-(2-(3-chloro-4-((4-fluorobenzyl)oxy)phenyl)-7,8-dihydro-1,6-naphthyridin-6(5H)-yl)propanoic acid (compound 140)

Using 2-(3-chloro-4-((4-fluorobenzyl)oxy)phenyl)-5,6,7,8-tetrahydro-1,6-naphthyridine prepared in accordance with scheme 1 instead of compound IXa. Calculated mass: (C24H22ClFN2O3): 440.89 g/mol. ¹H NMR (DMSO-d6, 600 MHz): δ=10.83 (br. s., 1H), 8.19 (d, J=2.3 Hz, 1H), 8.05 (dd, J=8.7, 2.3 Hz, 1H), 7.91 (d, J=8.1 Hz, 1H), 7.71 (d, J=8.3 Hz, 1H), 7.52-7.58 (m, 2H), 7.37 (d, J=8.8 Hz, 1H), 7.26 (t, J=8.8 Hz, 1H), 7.24-7.29 (m, 1H), 5.28 (s, 2H), 4.61 (d, J=15.4 Hz, 1H), 4.41 (dd, J=15.1, 6.8 Hz, 1H), 3.84 (br. s., 1H), 3.61-3.68 (m, 1H), 3.57 (br. s., 3H), 3.40-3.46 (m, 2H), 3.31-3.39 (m, 1H), 3.15-3.23 (m, 1H), 2.93 (td, J=7.6, 2.5 Hz, 2H). M+H=441/443

3-(2-(3-chloro-44(2-fluorobenzyl)oxy)phenyl)-7,8-dihydro-1,6-naphthyridin-6(5H)-yl)propanoic acid (compound 141)

Using 2-(3-chloro-4-((2-fluorobenzyl)oxy)phenyl)-5,6,7,8-tetrahydro-1,6-naphthyridine prepared in accordance with scheme 1 instead of compound IXa. Calculated mass: (C24H22ClFN2O3): 440.89 g/mol. ¹H NMR (DMSO-d6, 600 MHz): δ=10.69 (br. s., 1H), 8.20 (d, J=2.3 Hz, 1H), 8.07 (dd, J=8.7, 2.3 Hz, 1H), 7.92 (d, J=8.3 Hz, 1H), 7.71 (d, J=8.3 Hz, 1H), 7.62 (td, J=7.7, 1.6 Hz, 1H), 7.42-7.48 (m, 2H), 7.26-7.31 (m, 2H), 5.33 (s, 2H), 4.62 (d, J=15.4 Hz, 1H), 4.41 (dd, J=14.7, 6.0 Hz, 1H), 3.85 (br. s., 1H), 3.54-3.62 (m, 1H), 3.49-3.54 (m, 6H), 3.41 (d, J=5.5 Hz, 2H), 3.40 (br. s., 1H), 2.89-2.94 (m, 2H). M+H=441/443

3-(2-(4-(benzyloxy)-3-methoxyphenyl)-7,8-dihydro-1,6-naphthyridin-6(5H)-yl)propanoic acid (compound 142)

Using 2-(4-(benzyloxy)-3-methoxyphenyl)-5,6,7,8-tetrahydro-1,6-naphthyridine prepared in accordance with scheme 1 instead of compound IXa. Calculated mass: (C25H26N2O4): 418.49 g/mol. ¹H NMR (DMSO-d6, 600 MHz): δ=10.72 (br. s., 1H), 7.88 (d, J=8.3 Hz, 1H), 7.69 (d, J=1.9 Hz, 1H), 7.68 (s, 1H), 7.64 (dd, J=8.5, 2.1 Hz, 1H), 7.46-7.49 (m, 2H), 7.41 (t, J=7.5 Hz, 2H), 7.39-7.43 (m, 1H), 7.33-7.37 (m, 1H), 7.15 (d, J=8.7 Hz, 1H), 5.16 (s, 2H), 4.61 (d, J=15.8 Hz, 1H), 4.40 (dd, J=15.2, 7.4 Hz, 1H), 3.87 (s, 4H), 3.81-3.89 (m, 1H), 3.67 (br. s., 2H), 3.30-3.38 (m, 1H), 3.16-3.22 (m, 1H), 2.90-2.94 (m, 2H). M+H=419

3-(2-(4-(benzyloxy)-3-trifluoromethylphenyl)-7,8-dihydro-1,6-naphthyridin-6(5H)-yl)propanoic acid (compound 143)

Using 2-(4-(benzyloxy)-3-trifluoromethylphenyl)-5,6,7,8-tetrahydro-1,6-naphthyridine prepared in accordance with scheme 1 instead of compound IXa. Calculated mass: (C25H23F3N2O3): 456.46 g/mol. ¹H NMR (DMSO-d6, 600 MHz): δ=10.67 (br. s., 1H), 8.33-8.37 (m, 2H), 7.97 (d, J=8.3 Hz, 1H), 7.73 (d, J=8.3 Hz, 1H), 7.46-7.50 (m, 3H), 7.43 (t, J=7.6 Hz, 2H), 7.34-7.37 (m, 1H), 5.37 (s, 2H), 4.63 (d, J=15.6 Hz, 1H), 4.42 (d, J=9.2 Hz, 1H), 3.85 (br. s., 1H), 3.57 (s, 1H), 3.47 (br. s., 1H), 3.30-3.38 (m, 2H), 3.18-3.25 (m, 1H), 2.90-2.94 (m, 2H), 2.90 (br. s., 1H). M+H=458

3-(2-(4-(benzyloxy)-3-chlorophenyl)-7,8-dihydro-1,6-naphthyridin-6(5H)-yl)propanoic acid (compound 144)

Using 2-(4-(benzyloxy)-3-chlorophenyl)-5,6,7,8-tetrahydro-1,6-naphthyridine prepared in accordance with scheme 1 instead of compound IXa. Calculated mass: (C24H23ClN2O3): 422.90 g/mol. ¹H NMR (DMSO-d6, 600 MHz): δ=10.69 (br. s., 1H), 8.20 (d, J=2.3 Hz, 1H), 8.04 (dd, J=8.7, 2.3 Hz, 1H), 7.91 (d, J=8.3 Hz, 1H), 7.71 (d, J=8.3 Hz, 1H), 7.49-7.51 (m, 2H), 7.41-7.44 (m, 2H), 7.36 (d, J=8.7 Hz, 2H), 5.30 (s, 2H), 4.62 (d, J=15.8 Hz, 1H), 4.41 (dd, J=15.2, 7.5 Hz, 1H), 3.84 (br. s., 1H), 3.62-3.70 (m, 3H), 3.33 (ddd, J=17.5, 10.7, 6.2 Hz, 1H), 3.19 (d, J=17.1 Hz, 1H), 2.89-2.94 (m, 2H). M+H=423

Tert-butyl 3-(2-(4-(benzyloxy)phenyl)-7,8-dihydro-1,6-naphthyridin-6(5H)-yl)propanoate (intermediate in the synthesis of compound 129). Calculated mass: (C28H32N2O3): 444.57 g/mol. ¹H NMR (DMSO-d6, 600 MHz): δ=7.98-8.01 (m, 2 H), 7.66 (d, J=7.9 Hz, 1H), 7.50 (d, J=8.1 Hz, 1H), 7.46-7.49 (m, 2H), 7.41 (t, J=7.4 Hz, 2H), 7.32-7.36 (m, 1H), 7.08-7.11 (m, 2H), 5.16 (s, 2H), 3.57-3.65 (m, 2H), 3.47-3.55 (m, 1H), 2.88-2.94 (m, 2H), 2.80 (br. s., 2H), 2.75 (br. s., 2H), 1.39 (s, 9H). M+H=445

3-(2-(2-fluoro-4-((3-fluorobenzyl)oxy)phenyl)-7,8-dihydro-1,6-naphthyridin-6(5H)-yl)propanoic acid (compound 145)

Tert-butyl 3-(2-(4-(benzyloxy)-2-fluorophenyl)-7,8-dihydro-1,6-naphthyridin-6(5H)-yl)propanoate This compound was prepared in accordance with scheme 2 from tert-butyl 3-(2-chloro-7,8-dihydro-1,6-naphthyridin-6(5H)-yl)propanoate. 275 mg thereof (0.927 mmol; 1 eq) was dissolved in 8 mL DMF. 4-benzyloxy-2-fluorophenylboronic acid (274 mg; 1.11 mmol; 1.2 eq) and sodium carbonate (246 mg; 2.32 mmol; 2.5 eq) are added under stirring and the mixture is degassed with argon for 3 min. Tetrakis(triphenylphosphine)-palladium(0) (53.5 mg; 0.046 mmol; 0.05 eq) was added and the mixture was stirred for 30 min at 120° C. The mixture was evaporated until the DMF was removed. The residue was extracted with DCM/water. After phase separation, the organic phase was washed one with water, dried with $MgSO_4$ and evaporated. The oily residue was dissolved in a little DCM and purified by flash chromatography (silica gel, DMC/MeOH 98:2) giving the product with a yield of 411 mg (0.889 mmol; 96%).

Tert-butyl 3-(2-(2-fluoro-4-((3-fluorobenzyl)oxy)phenyl)-7,8-dihydro-1,6-naphthyridin-6(5H)-yl)propanoate This compound was prepared in accordance with scheme 7. Tert-butyl 3-(2-(4-(benzyloxy)-2-fluorophenyl)-7,8-dihydro-1,6-naphthyridin-6(5H)-yl)propanoate (260 mg; 0.56 mmol; 1 eq) was dissolved in MeOH (15 mL) and THF (15 mL). Pd—C (59.8 mg; 0.56 mmol; 1 eq) was added under stirring under argon atmosphere. The mixture was hydrogenated by adding H2 (1.13 mg; 0.56 mmol; 1 eq) and stirred for 20 h at RT under hydrogen atmosphere. Pd—C was removed, the resulting product washed with MeOH/THF 1:1 and evaporated giving tert-butyl 3-(2-(2-fluoro-4-hydroxyphenyl)-7,8-dihydro-1,6-naphthyridin-6(5H)-yl)propanoate with a yield of 200 mg (0.537 mmol; 96%). The product (0.54 mmol; 1 eq) was dissolved in 5 mL DMF. Under stirring and argon cesium carbonate (192 mg; 0.59 mmol; 1.1. eq) and 3-fluorobenzylbromide (111 mg; 0.59 mmol; 1.1. eq) were added. DMF was evaporated and the DCM and water were added to the residue. After phase separation, the organic phase was washed twice with water, dried with $MgSO_4$ and evaporated. The residue was purified by flash chromatography (silica gel, DMC/MeOH 98:2) giving the product with a yield of 151 mg (0.314 mmol; 58.5%).
Compound 145
Tert-butyl 3-(2-(2-fluoro-4-((3-fluorobenzyl)oxy)phenyl)-7,8-dihydro-1,6-naphthyridin-6(5H)-yl)propanoate (151 mg; 0.31 mmol; 1 eq) was dissolved in MeOH (3 mL) and THF (3 mL). 1N NaOH (120 mg; 3.0 mmol; 10 eq) was added under stirring at RT and the mixture was subsequently stirred for 20 h at RT. The reaction mixture was neutralized with 2 mL 1N HCl and the THF/MeOH was evaporated. 5 mL water was added and the residue was obtained and dried under vacuum at 40° C. with a yield of 42.9 mg (0.101 mmol; 32.3%). Calculated mass (C24H22F2N2O3): 424.16 g/mol. $^1$H NMR (600 MHz, DMSO-$d_6$) δ 12.80 (s, 1H), 10.89 (s, 1H), 7.90 (t, J=9.0 Hz, 1H), 7.74-7.60 (m, 2H), 7.47 (td, J=7.8, 5.9 Hz, 1H), 7.39-7.27 (m, 2H), 7.19 (td, J=8.9, 2.2 Hz, 1H), 7.12-6.98 (m, 2H), 5.23 (s, 2H), 4.52 (d, J=115.2 Hz, 2H), 3.84 (s, 1H), 3.51-3.45 (m, 3H), 2.93 (t, J=7.6 Hz, 2H). M+H+ 425

The following compounds were prepared in the same way as compound 145 using 4-benzyloxy-phenylboronic acid (compound VI) instead of 4-benzyloxy-2-fluorophenylboronic acid:

3-(2-(4-((4-methylthiobenzyl)oxy)phenyl)-7,8-dihydro-1,6-naphthyridin-6(5H)-yl)propanoic acid (compound 146)

further using 4-methylthiobenzylbromide instead of 3-fluorobenzylbromide. $^1$H NMR (400 MHz, Pyridine-$d_5$, Temp=90° C.) δ: 8.00-7.95 (m, 2H), 7.72 (d, J=8.2 Hz, 1H), 7.64 (d, J=8.2 Hz, 1H), 7.42-7.38 (m, 2H), 7.32-7.27 (m, 2H), 7.13-7.07 (m, 2H), 5.13 (s, 2H), 4.37 (s, 2H), 3.57 (t, J=6.5 Hz, 2H), 3.41 (t, J=7.2 Hz, 2H), 3.22-3.17 (m, 2H), 2.82 (t, J=7.2 Hz, 2H), 2.47 (s, 3H); MS (APCI+) m/z 435 (M+H)+.

3-(2-(4-((2-methyl-3-(trifluoromethyl)benzyl)oxy)phenyl)-7,8-dihydro-1,6-naphthyridin-6(5H)-yl)propanoic acid (compound 147)

further using 2-methyl-3-(trifluoromethyl)benzylbromide instead of 3-fluorobenzylbromide. $^1$H NMR (400 MHz, Pyridine-$d_5$, Temp=90° C.) δ: 8.04-7.97 (m, 2H), 7.79-7.72 (m, 2H), 7.70-7.65 (m, 2H), 7.42 (t, J=7.8 Hz, 1H), 7.19-7.14 (m, 2H), 5.26 (s, 2H), 4.50 (s, 2H), 3.70 (t, J=6.4 Hz, 2H), 3.52 (t, J=7.2 Hz, 2H), 3.26-3.24 (m, 2H), 2.88 (t, J=7.2 Hz, 2H), 2.48-2.45 (m, 3H); MS (APCI+) m/z 471 (M+H)+.

3-(2-(4-((4-difluoromethoxybenzyl)oxy)phenyl)-7,8-dihydro-1,6-naphthyridin-6(5H)-yl)propanoic acid (compound 148)

further using 4-difluoromethoxybenzylbromide instead of 3-fluorobenzylbromide. $^1$H NMR (400 MHz, Pyridine-$d_5$, Temp=90° C.) δ: 8.03-7.96 (m, 2H), 7.75 (d, J=8.2 Hz, 1H), 7.67 (d, J=8.2 Hz, 1H), 7.51 (d, J=8.6 Hz, 2H), 7.22-7.17 (m, 2H), 7.15-7.09 (m, 2H), 7.07 (s, 1H), 5.17 (s, 2H), 4.48 (s, 2H), 3.68 (t, J=6.4 Hz, 2H), 3.51 (t, J=7.3 Hz, 2H), 3.26-3.23 (m, 2H), 2.87 (t, J=7.2 Hz, 2H); MS (APCI+) m/z 455 (M+H)+.

3-(2-(4-((2-trifluoromethyl-5-(methyl)benzyl)oxy)phenyl)-7,8-dihydro-1,6-naphthyridin-6(5H)-yl)propanoic acid (compound 149)

further using 2-trifluoromethyl-5-(methyl)benzylbromide instead of 3-fluorobenzylbromide. $^1$H NMR (400 MHz, Pyridine-$d_5$, Temp=90° C.) δ: 8.08-7.96 (m, 2H), 7.76 (d, J=8.2 Hz, 1H), 7.70-7.62 (m, 2H), 7.57 (s, 1H), 7.39 (d, J=7.8 Hz, 1H), 7.12 (d, J=8.8 Hz, 2H), 5.26 (s, 2H), 4.50 (s, 2H), 3.70 (t, J=6.5 Hz, 2H), 3.52 (t, J=7.2 Hz, 2H), 3.27-3.25 (m, 2H), 2.88 (t, J=7.2 Hz, 2H), 2.41 (s, 3H); MS (APCI+) m/z 471 (M+H)+.

3-(2-(4-((2-trifluoromethylbenzyl)oxy)phenyl)-7,8-dihydro-1,6-naphthyridin-6(5H)-yl)propanoic acid (compound 150)

further using 2-trifluoromethylbenzylbromide instead of 3-fluorobenzylbromide. $^1$H NMR (400 MHz, Pyridine-$d_5$, Temp=90° C.) δ: 8.02 (d, J=8.8 Hz, 2H), 7.82-7.72 (m, 3H), 7.69 (t, J=7.4 Hz, 1H), 7.59 (t, J=7.6 Hz, 1H), 7.12 (d, J=8.8 Hz, 2H), 5.31 (s, 2H), 4.51 (s, 2H), 3.71 (t, J=6.5 Hz, 2H), 3.53 (t, J=7.3 Hz, 2H), 3.28-3.25 (m, 2H), 2.88 (t, J=7.2 Hz, 2H); MS (APCI+) m/z 457 (M+H)+.

3-(2-(4-((3-trifluoromethoxybenzyl)oxy)phenyl)-7,8-dihydro-1,6-naphthyridin-6(5H)-yl)propanoic acid (compound 151)

further using 3-trifluoromethoxybenzylbromide instead of 3-fluorobenzylbromide. $^1$H NMR (400 MHz, Pyridine-$d_5$, Temp=90° C.) δ: 8.07-7.95 (m, 2H), 7.76 (d, J=8.1 Hz, 1H), 7.68 (d, J=8.2 Hz, 1H), 7.56-7.47 (m, 2H), 7.40 (s, 1H), 7.28 (d, J=7.6 Hz, 1H), 7.20-7.08 (m, 2H), 5.24 (s, 2H), 4.50 (s, 2H), 3.70 (t, J=6.4 Hz, 2H), 3.52 (t, J=7.2 Hz, 2H), 3.27-3.24 (m, 2H), 2.87 (t, J=7.2 Hz, 2H); MS (APCI+) m/z 473 (M+H)+.

3-(2-(4-((4-trifluoromethylbenzyl)oxy)phenyl)-7,8-dihydro-1,6-naphthyridin-6(5H)-yl)propanoic acid (compound 152)

further using 4-trifluoromethylbenzylbromide instead of 3-fluorobenzylbromide. $^1$H NMR (400 MHz, Pyridine-$d_5$, Temp=90° C.) δ: 8.06-7.94 (m, 2H), 7.81-7.62 (m, 6H), 7.19-7.09 (m, 2H), 5.28 (s, 2H), 4.48 (s, 2H), 3.69 (t, J=6.5 Hz, 2H), 3.51 (t, J=7.2 Hz, 2H), 3.26 (s, 2H), 2.87 (t, J=7.2 Hz, 2H); MS (APCI+) m/z 457 (M+H)+.

3-(2-(4-((4-trifluoromethoxybenzyl)oxy)phenyl)-7,8-dihydro-1,6-naphthyridin-6(5H)-yl)propanoic acid (compound 153)

further using 4-trifluoromethoxybenzylbromide instead of 3-fluorobenzylbromide. $^1$H NMR (400 MHz, Pyridine-$d_5$, Temp=90° C.) δ: 8.06-7.94 (m, 2H), 7.76 (d, J=8.2 Hz, 1H), 7.67 (d, J=8.2 Hz, 1H), 7.62-7.56 (m, 2H), 7.34 (d, J=8.3 Hz, 2H), 7.19-7.07 (m, 2H), 5.21 (s, 2H), 4.49 (s, 2H), 3.69 (t, J=6.4 Hz, 2H), 3.52 (t, J=7.2 Hz, 2H), 3.27-3.24 (m, 2H), 2.87 (t, J=7.2 Hz, 2H); MS (APCI+) m/z 473 (M+H)+.

3-(2-(4-((3-trifluoromethyl-4-(methyl)benzyl)oxy)phenyl)-7,8-dihydro-1,6-naphthyridin-6(5H)-yl)propanoic acid (compound 154)

further using 3-trifluoromethyl-4-(methyl)benzylbromide instead of 3-fluorobenzylbromide. $^1$H NMR (400 MHz, Pyridine-$d_5$, Temp=90° C.) δ: 8.06-7.94 (m, 2H), 7.81-7.66 (m, 3H), 7.62 (d, J=7.5 Hz, 1H), 7.45 (d, J=7.9 Hz, 1H), 7.18-7.08 (m, 2H), 5.22 (s, 2H), 4.50 (s, 2H), 3.70 (t, J=6.4 Hz, 2H), 3.52 (t, J=7.2 Hz, 2H), 3.27-3.24 (m, 2H), 2.88 (t, J=7.2 Hz, 2H), 2.47-2.42 (m, 3H); MS (APCI+) m/z 471 (M+H)+.

3-(2-(4-((2-trifluoromethoxybenzyl)oxy)phenyl)-7,8-dihydro-1,6-naphthyridin-6(5H)-yl)propanoic acid (compound 155)

further using 2-trifluoromethoxybenzylbromide instead of 3-fluorobenzylbromide. $^1$H NMR (400 MHz, Pyridine-$d_5$, Temp=90° C.) δ: 8.07-7.95 (m, 2H), 7.76 (d, J=8.2 Hz, 1H), 7.71-7.63 (m, 2H), 7.58-7.48 (m, 1H), 7.46-7.36 (m, 2H), 7.18-7.07 (m, 2H), 5.21 (s, 2H), 4.50 (s, 2H), 3.70 (t, J=6.4 Hz, 2H), 3.52 (t, J=7.2 Hz, 2H), 3.27-3.25 (m, 2H), 2.88 (t, J=7.2 Hz, 2H); MS (APCI+) m/z 473 (M+H)+.

3-(2-(4-((4-(tert-butyl)benzyl)oxy)phenyl)-7,8-dihydro-1,6-naphthyridin-6(5H)-yl)propanoic acid (compound 156)

further using 4-(tert-butyl)benzylbromide instead of 3-fluorobenzylbromide. $^1$H NMR (400 MHz, Pyridine-d5, Temp=90° C.) δ: 8.05-7.93 (m, 2H), 7.79-7.61 (m, 2H), 7.47-7.32 (m, 4H), 7.17-7.06 (m, 2H), 5.13 (s, 2H), 4.46 (s, 2H), 3.66 (t, J=6.4 Hz, 2H), 3.49 (t, J=7.3 Hz, 2H), 3.23 (s, 2H), 2.86 (t, J=7.2 Hz, 2H), 1.29 (s, 9H); MS (APCI+) m/z 445 (M+H)+.

3-(2-(4-((3-trifluoromethylbenzyl)oxy)phenyl)-7,8-dihydro-1,6-naphthyridin-6(5H)-yl)propanoic acid (compound 157)

further using 3-trifluoromethyl benzylbromide instead of 3-fluorobenzylbromide. $^1$H NMR (400 MHz, Pyridine-$d_5$, Temp=90° C.) δ: 8.07-7.95 (m, 2H), 7.82-7.74 (m, 3H), 7.71-7.61 (m, 3H), 7.21-7.09 (m, 2H), 5.28 (s, 2H), 4.50 (s, 2H), 3.70 (t, J=6.4 Hz, 2H), 3.53 (t, J=7.2 Hz, 2H), 3.27-3.24 (m, 2H), 2.88 (t, J=7.2 Hz, 2H); MS (APCI+) m/z 457 (M+H)+.

3-(2-(4-((2-methyl-5-(trifluoromethyl)benzyl)oxy)phenyl)-7,8-dihydro-1,6-naphthyridin-6(5H)-yl)propanoic acid (compound 158)

further using 2-methyl-5-(trifluoromethyl)benzylbromide instead of 3-fluorobenzylbromide. $^1$H NMR (400 MHz, Pyridine-$d_5$, Temp=90° C.) δ: 8.02 (d, J=8.8 Hz, 2H), 7.82-7.72 (m, 2H), 7.68 (d, J=8.2 Hz, 1H), 7.61-7.56 (m, 1H), 7.47 (d, J=8.1 Hz, 1H), 7.17 (d, J=8.9 Hz, 2H), 5.25 (s, 2H), 4.49 (s, 2H), 3.69 (t, J=6.4 Hz, 2H), 3.52 (t, J=7.2 Hz, 2H), 3.27 (s, 2H), 2.87 (t, J=7.2 Hz, 2H), 2.44 (s, 3H); MS (APCI+) m/z 471 (M+H)+.

3-(2-(4-((3-difluoromethylbenzyl)oxy)phenyl)-7,8-dihydro-1,6-naphthyridin-6(5H)-yl)propanoic acid (compound 159)

further using 3-difluoromethylbenzylbromide instead of 3-fluorobenzylbromide. $^1$H NMR (400 MHz, Pyridine-$d_5$, Temp=90° C.) δ: 8.07-7.94 (m, 2H), 7.79-7.73 (m, 1H), 7.70-7.61 (m, 3H), 7.59-7.49 (m, 2H), 7.18-7.11 (m, 2H), 7.11-6.80 (m, 1H), 5.25 (s, 2H), 4.50 (s, 2H), 3.70 (t, J=6.4 Hz, 2H), 3.52 (t, J=7.2 Hz, 2H), 3.25 (s, 2H), 2.88 (t, J=7.2 Hz, 2H); MS (APCI+) m/z 439 (M+H)+.

3-(2-(4-((3-trifluoromethoxy-5-(methyl)benzyl)oxy)phenyl)-7,8-dihydro-1,6-naphthyridin-6(5H)-yl)propanoic acid (compound 160)

further using 3-trifluoromethoxy-5-(methyl)benzylbromide instead of 3-fluorobenzylbromide. $^1$H NMR (400 MHz, Pyridine-$d_5$, Temp=90° C.) δ: 8.07-7.94 (m, 2H), 7.76 (d, J=8.2 Hz, 1H), 7.68 (d, J=8.2 Hz, 1H), 7.30 (s, 1H), 7.21-7.05 (m, 4H), 5.19 (s, 2H), 4.50 (s, 2H), 3.70 (t, J=6.4 Hz, 2H), 3.52 (t, J=7.3 Hz, 2H), 3.27 (m, 2H), 2.88 (t, J=7.3 Hz, 2H), 2.37 (s, 3H); MS (APCI+) m/z 487 (M+H)+.

3-(2-(4-((2-methyl-4-(trifluoromethoxy)benzyl)oxy)phenyl)-7,8-dihydro-1,6-naphthyridin-6(5H)-yl)propanoic acid (compound 161)

further using 2-methyl-4-(trifluoromethoxy)benzylbromide instead of 3-fluorobenzylbromide. $^1$H NMR (400 MHz, Pyridine-$d_5$, Temp=90° C.) δ: 8.07-7.95 (m, 2H), 7.76 (d, J=8.2 Hz, 1H), 7.68 (d, J=8.2 Hz, 1H), 7.54 (d, J=8.4 Hz, 1H), 7.24-7.10 (m, 4H), 5.18 (s, 2H), 4.50 (s, 2H), 3.70 (t, J=6.5 Hz, 2H), 3.53 (t, J=7.2 Hz, 2H), 3.27-3.25 (m, 2H), 2.88 (t, J=7.2 Hz, 2H), 2.40 (s, 3H); MS (APCI+) m/z 487 (M+H)+.

3-(2-(4-((5-indanyl)methoxy)phenyl)-7,8-dihydro-1,6-naphthyridin-6(5H)-yl)propanoic acid (compound 162)

further using 5-indanylmethylbromide instead of 3-fluorobenzylbromide. $^1$H NMR (400 MHz, Pyridine-d$_5$, Temp=90° C.) δ: 8.05-7.94 (m, 2H), 7.75 (d, J=8.2 Hz, 1H), 7.67 (d, J=8.3 Hz, 1H), 7.30 (s, 1H), 7.24-7.16 (m, 2H), 7.13-7.07 (m, 2H), 5.12 (s, 2H), 4.49 (s, 2H), 3.69 (t, J=6.5 Hz, 2H), 3.52 (t, J=7.2 Hz, 2H), 3.26-3.24 (m, 2H), 2.93-2.80 (m, 6H), 2.03 (p, J=7.4 Hz, 2H); MS (APCI+) m/z 429 (M+H)+.

3-(2-(4-((2-difluoromethoxybenzyl)oxy)phenyl)-7,8-dihydro-1,6-naphthyridin-6(5H)-yl)propanoic acid (compound 163)

further using 2-difluoromethoxybenzylbromide instead of 3-fluorobenzylbromide. $^1$H NMR (400 MHz, Pyridine-d$_5$, Temp=90° C.) δ: 8.04-7.98 (m, 2H), 7.76 (d, J=8.1 Hz, 1H), 7.68 (d, J=8.2 Hz, 1H), 7.59-7.53 (m, 1H), 7.48-7.41 (m, 1H), 7.33-7.23 (m, 2H), 7.15-7.10 (m, 2H), 7.09-6.88 (m, 1H), 5.19 (s, 2H), 4.50 (s, 2H), 3.70 (t, J=6.5 Hz, 2H), 3.52 (t, J=7.2 Hz, 2H), 3.25 (s, 2H), 2.87 (t, J=7.2 Hz, 2H); MS (APCI+) m/z 455 (M+H)+.

3-(2-(4-((3-difluoromethoxybenzyl)oxy)phenyl)-7,8-dihydro-1,6-naphthyridin-6(5H)-yl)propanoic acid (compound 164)

further using 3-difluoromethoxybenzylbromide instead of 3-fluorobenzylbromide. $^1$H NMR (400 MHz, Pyridine-d$_5$, Temp=90° C.) δ: 8.06-7.94 (m, 2H), 7.76 (d, J=8.1 Hz, 1H), 7.68 (d, J=8.2 Hz, 1H), 7.45 (t, J=7.9 Hz, 1H), 7.34 (d, J=7.7 Hz, 1H), 7.27-7.22 (m, 1H), 7.18-7.11 (m, 3H), 7.09-6.85 (m, 1H), 5.20 (s, 2H), 4.50 (s, 2H), 3.70 (t, J=6.4 Hz, 2H), 3.52 (t, J=7.3 Hz, 2H), 3.27-3.24 (m, 2H), 2.88 (t, J=7.2 Hz, 2H); MS (APCI+) m/z 455 (M+H)+.

3-(2-(4-((2-difluoromethylbenzyl)oxy)phenyl)-7,8-dihydro-1,6-naphthyridin-6(5H)-yl)propanoic acid (compound 165)

further using 2-difluoromethylbenzylbromide instead of 3-fluorobenzylbromide. $^1$H NMR (400 MHz, Pyridine-d$_5$, Temp=90° C.) δ: 8.07-7.95 (m, 2H), 7.76 (d, J=8.2 Hz, 1H), 7.71-7.62 (m, 3H), 7.60-7.47 (m, 2H), 7.36-6.97 (m, 3H), 5.33 (s, 2H), 4.51 (s, 2H), 3.71 (t, J=6.4 Hz, 2H), 3.53 (t, J=7.3 Hz, 2H), 3.28-3.25 (m, 2H), 2.88 (t, J=7.2 Hz, 2H); MS (APCI+) m/z 439 (M+H)+.

3-(2-(4-((4-difluoromethylbenzyl)oxy)phenyl)-7,8-dihydro-1,6-naphthyridin-6(5H)-yl)propanoic acid (compound 166)

further using 4-difluoromethylbenzylbromide instead of 3-fluorobenzylbromide. $^1$H NMR (400 MHz, Pyridine-d$_5$, Temp=90° C.) δ: 8.06-7.94 (m, 2H), 7.75 (d, J=8.2 Hz, 1H), 7.67 (d, J=8.3 Hz, 1H), 7.59 (s, 4H), 7.19-7.10 (m, 2H), 7.09-6.76 (m, 1H), 5.25 (s, 2H), 4.49 (s, 2H), 3.69 (t, J=6.5 Hz, 2H), 3.51 (t, J=7.2 Hz, 2H), 3.25-3.24 (m, 2H), 2.87 (t, J=7.2 Hz, 2H); MS (APCI+) m/z 439 (M+H)+.

3-(2-(3-methyl-4-((4-(trifluoromethyl)benzyl)oxy)phenyl)-7,8-dihydro-1,6-naphthyridin-6(5H)-yl)propanoic acid (compound 167)

Tert-butyl 3-(2-(4-(benzyloxy)-3-methylphenyl)-7,8-dihydro-1,6-naphthyridin-6(5H)-yl)propanoate This compound was prepared from compound IXc (R'=H, R"=3-CH$_3$ in accordance with scheme 5. Compound IXc (520 mg; 1.57 mmol; 1 eq) and DBU (479 mg; 0.47 mmol; 2 eq) were dissolved in MeOH (23 mL). Tert-butyl acrylate (504 mg; 3.93 mmol; 2.5 eq) was added and the mixture was stirred overnight at RT. The mixture was evaporated, the residue was dissolved in 50 mL ethyl acetate and washed twice with 20 mL of a saturated ammonium chloride solution. The ethyl acetate phase was dried with MgSOH, filtered and evaporated. The residue was purified by flash chromatography (silica gel, DMC/MeOH 20:1) giving the product with a yield of 454 mg (0.990 mmol; 62.9%).

Tert-butyl 3-(2-(3-methyl-4-((4-(trifluoromethyl)benzyl)oxy)phenyl)-7,8-dihydro-1,6-naphthyridin-6(5H)-yl)propanoate This compound was prepared in accordance with scheme 7. Tert-butyl 3-(2-(4-(benzyloxy)-3-methylphenyl)-7,8-dihydro-1,6-naphthyridin-6(5H)-yl)propanoate (450 mg; 0.98 mmol; 1 eq) was dissolved in 25 mL MeOH. Pd—C (142 mg; 0.133 mmol; 0.14 eq) was added under N2. The mixture was hydrogenated by adding H2 (1.98 mg; 0.98 mmol; 1 eq) and stirred overnight at RT under hydrogen atmosphere. Pd—C was removed, the resulting product washed with MeOH and evaporated giving tert-butyl 3-(2-(4-hydroxy-3-methylphenyl)-7,8-dihydro-1,6-naphthyridin-6(5H)-yl)propanoate with a yield of 363 ml (0.985 mmol). 124 mg thereof (0.34 mmol; 1 eq) was dissolved in 4 mL DMF. Cesium carbonate (132 mg; 0.40 mmol; 1.2 eq) was added at RT giving a yellow suspension. 1-(bromomethyl)-4-(trifluoromethyl)benzene (97 mg; 0.40 mmol; 1.2 eq) was added and the mixture was stirred for 3 h at RT. The mixture was evaporated, 15 mL water and 30 mL ethyl acetate were added. The ethyl acetate phase was obtained, dried with MgSO$_4$, filtered and evaporated. The residue was purified by flash chromatography (silica gel, DMC/MeOH) giving the product with a yield of 173 mg (0.329 mmol; 98%).

Compound 167

Tert-butyl 3-(2-(3-methyl-4-((4-(trifluoromethyl)benzyl)oxy)phenyl)-7,8-dihydro-1,6-naphthyridin-6(5H)-yl)propanoate (165 mg; 0.31 mmol; 1 eq) was dissolved in 10 mL MeOH. 2N NaOH (188 mg; 4.7 mmol; 15 eq) was added and the mixture was stirred overnight at RT. The MeOH was evaporated. 3 mL water was added and the pH was brought to 1 with 2N HCl. 20 mL ethyl acetate was added and the mixture was stirred for 15 min at RT. The residue was obtained, washed with water and dried overnight at 40° C. under vacuum giving compound 167 with a yield of 64 mg (0.126 mmol; 40.3%) as the 6-(2-carboxyethyl)-2-(3-methyl-4-((4-(trifluoromethyl)benzyl)oxy)phenyl)-5,6,7,8-tetrahydro-1,6-naphthyridin-6-ium chloride. Calculated mass (C26H25F3N2O3): 470.18 g/mol. $^1$H NMR (600 MHz, DMSO-d$_6$) δ 12.80 (s, 1H), 10.82 (s, 1H), 7.95 (d, J=2.2 Hz, 1H), 7.90 (dd, J=8.5, 2.3 Hz, 1H), 7.84 (d, J=8.2 Hz, 1H), 7.79 (d, J=8.1 Hz, 2H), 7.71 (d, J=8.1 Hz, 2H), 7.68 (d, J=8.3 Hz, 1H), 7.12 (d, J=8.7 Hz, 1H), 5.33 (s, 2H), 4.60 (d, J=15.6 Hz, 1H), 4.39 (dd, J=15.9, 7.3 Hz, 1H), 3.83 (d, J=9.5 Hz, 1H), 3.34 (td, J=14.3, 11.0, 6.4 Hz, 1H), 3.17 (d, J=18.0 Hz, 1H), 2.93 (td, J=7.8, 2.4 Hz, 2H), 2.32 (s, 3H). M+H+ 471.2

The following compounds were prepared in the same way as compound 167:

3-(2-(4-((4-fluorobenzyl)oxy)-3-methylphenyl)-7,8-dihydro-1,6-naphthyridin-6(5H)-yl)propanoic acid (compound 168)

Using 1-(bromomethyl)-4-fluorobenzene instead of 1-(bromomethyl)-4-(trifluoromethyl)benzene. Calculated mass (C25H25FN2O3): 420.18 g/mol. $^1$H NMR (600 MHz, DMSO-d$_6$) δ 12.80 (s, 1H), 10.73 (s, 1H), 7.95-7.92 (m, 1H), 7.90 (dd, J=8.5, 2.3 Hz, 1H), 7.83 (d, J=8.2 Hz, 1H), 7.68 (d, J=8.3 Hz, 1H), 7.57-7.51 (m, 2H), 7.28-7.21 (m, 2H), 7.13 (d, J=8.6 Hz, 1H), 5.18 (s, 2H), 4.60 (d, J=15.6 Hz, 1H), 4.39 (dd, J=15.4, 7.6 Hz, 1H), 3.84 (s, 1H), 3.38-3.28 (m, 1H), 3.18 (d, J=18.1 Hz, 1H), 2.92 (td, J=7.7, 2.1 Hz, 2H), 2.27 (s, 3H). M+H+ 421.3

3-(2-(4-((4-chlorobenzyl)oxy)-3-methylphenyl)-7,8-dihydro-1,6-naphthyridin-6(5H)-yl)propanoic acid (compound 169)

Using 1-(bromomethyl)-4-chlorobenzene instead of 1-(bromomethyl)-4-(trifluoromethyl)benzene. Calculated mass (C25H25ClN2O3): 436.16 g/mol. 41 NMR (600 MHz, DMSO-d$_6$) δ 7.89 (d, J=2.3 Hz, 1H), 7.83 (dd, J=8.5, 2.3 Hz, 1H), 7.65 (d, J=8.0 Hz, 1H), 7.53-7.50 (m, 3H), 7.49-7.46 (m, 3H), 7.07 (d, J=8.6 Hz, 1H), 5.19 (s, 2H), 3.63 (s, 2H), 2.92 (t, J=6.0 Hz, 2H), 2.82 (t, J=5.9 Hz, 2H), 2.77 (t, J=7.1 Hz, 2H), 2.27 (s, 3H). M+H+ 437.3

3-(6-(4-((4-chlorobenzyl)oxy)-3-methylphenyl)-3,4-dihydro-2,7-naphthyridin-2(1H)-yl)propanoic acid (compound 172)

Tert-butyl 3-(6-(4-(benzyloxy)-3-methylphenyl)-3,4-dihydro-2,7-naphthyridin-2(1H)-yl)propanoate This compound was prepared from compound XXIa in accordance with scheme 2 using 4-benzyloxy-3-methylphenylboronic acid (compound VI with R'=H, R"=3-CH$_3$). Compound XXIa (445 mg; 1.50 mmol; 1 eq) was dissolved in 10 mL DMF. 4-benzyloxy-3-methylphenylboronic acid (436 mg; 1.80 mmol; 1.2 eq) and sodium carbonate (397 mg; 3.75 mmol; 2.5 eq) were added under stirring and the mixtures was degassed with argon for 5 min. Tetrakis(triphenylphosphine)-palladium(0) (87 mg; 0.075 mmol; 0.05 eq) was added and the mixture was stirred for 30 min at 120° C. The mixture was evaporated. The residue was extracted with DCM/water. After phase separation, the organic phase was washed one with water, dried with MgSO$_4$ and evaporated. The oily residue was dissolved in DCM and purified by flash chromatography (silica gel, DMC/MeOH 95:5 giving the product with a yield of 470 mg (1.025 mmol; 68.4%).

Tert-butyl 3-(6-(4-((4-chlorobenzyl)oxy)-3-methylphenyl)-3,4-dihydro-2,7-naphthyridin-2(1H)-yl)propanoate This compound was prepared in accordance with scheme 7. Tert-butyl 3-(6-(4-(benzyloxy)-3-methylphenyl)-3,4-dihydro-2,7-naphthyridin-2(1H)-yl)propanoate (395 mg; 0.86 mmol; 1 eq) was dissolved in 40 mL MeOH. Pd—C (0.14 eq) was added and the mixture was hydrogenated by adding H2 (1.74 mg; 0.86 mmol; 1 eq) and stirred overnight at RT under hydrogen atmosphere. Pd—C was removed, the resulting product washed with MeOH and evaporated giving tert-butyl 3-(6-(4-hydroxy-3-methylphenyl)-3,4-dihydro-2,7-naphthyridin-2(1H)-yl)propanoate with a yield of 275 mg (0.746 mmol; 87%). 139 mg thereof (0.38 mmol; 1 eq) was dissolved in 5 mL DMF. Cesium carbonate (147 mg; 0.453 mmol; 1.2 eq) and 4-chlorobenzylbromide (85 mg; 0.42 mmol; 1.1 eq) were added under stirring. The mixture was stirred for 20 h at RT. The DMF was evaporated and the residue was extracted with DCM/water. After phase separation, the organic phase was washed with water, dried with MgSO$_4$ and evaporated. The oily residue was dissolved in DCM and purified by flash chromatography (silica gel, DMC/MeOH 95:5) giving the product with a yield of 115 mg (0.233 mmol; 61.8%).

Compound 172

Tert-butyl 3-(6-(4-((4-chlorobenzyl)oxy)-3-methylphenyl)-3,4-dihydro-2,7-naphthyridin-2(1H)-yl)propanoate (115 mg; 0.23 mmol; 1 eq) was dissolved in MeOH (2.5 mL) and THF (2.5 mL). 1N NaOH (100 mg; 2.5 mmol; 10.7 eq) was added under stirring. The mixture was stirred for 20 h at RT. The mixture was neutralized with 2.5 mL 1N HCl and evaporated until the THF and MeOH were removed. The residue was extracted twice with DCM. The organic phase was dried with MgSO$_4$ and evaporated. The residue was dissolved in DCM with a little MeOH and purified by flash chromatography (silica gel, DMC/MeOH 9:1) giving compound 172 with a yield of 54 mg (0.124 mmol; 53%). Calculated Mass: (C25H25ClN2O3): 436.93 g/mol. $^1$H NMR (DMSO-d6, 600 MHz): δ=12.81 (br. s., 1H), 10.75 (br. s., 1H), 8.46 (s, 1H), 7.93-7.95 (m, 1H), 7.90 (dd, J=8.7, 2.1 Hz, 1H), 7.85 (s, 1H), 7.47-7.53 (m, 4H), 7.12 (d, J=8.7 Hz, 1H), 5.21 (s, 2H), 4.65 (d, J=15.4 Hz, 1H), 4.33-4.40 (m, 1H), 3.76 (br. s., 1H), 3.68 (d, J=5.6 Hz, 1H), 3.57 (br. s., 1H), 3.21-3.29 (m, 1H), 3.12-3.20 (m, 1H), 2.92 (t, J=7.5 Hz, 2H), 2.28 (s, 3H). M+H=437/439

The following compounds were made in the same way as compound 172:

3-(6-(4-(benzyloxy)-3-methylphenyl)-3,4-dihydro-2,7-naphthyridin-2(1H)-yl)propanoic acid (compound 171)

Using benzylbromide instead of 4-chlorobenzylbromide. Calculated Mass: (C25H26N2O3): 402.49 g/mol. $^1$H NMR (DMSO-d6, 600 MHz): δ=11.18 (br. s., 1H), 8.51 (s, 1H), 7.90-7.97 (m, 3H), 7.47-7.51 (m, 2H), 7.42 (t, J=7.6 Hz, 2H), 7.31-7.36 (m, 1H), 7.17 (d, J=8.7 Hz, 1H), 5.22 (s, 2H), 4.67 (d, J=15.4 Hz, 1H), 4.38 (d, J=10.4 Hz, 1H), 3.46 (d, J=7.2 Hz, 3H), 3.36-3.43 (m, 2H), 3.29-3.35 (m, 1H), 3.16-3.24 (m, 1H), 2.90-2.98 (m, 2H), 2.29 (s, 3H), 1.35 (s, 1H). M+H=403

3-(6-((4(4-trifluoromethylbenzyl)oxy)-3-methylphenyl)-3,4-dihydro-2,7-naphthyridin-2(1H)-yl)propanoic acid (compound 173)

Using 4-trifluoromethylbenzylbromide instead of 4-chlorobenzylbromide. Calculated Mass: (C26H25F3N2O3): 470.48 g/mol. $^1$H NMR (DMSO-d6, 600 MHz): δ=10.92 (br. s., 1H), 8.48 (s, 1H), 7.96 (d, J=1.7 Hz, 1H), 7.86-7.93 (m, 2H), 7.80 (d, J=8.3 Hz, 2H), 7.72 (d, J=8.1 Hz, 2H), 7.14 (d, J=8.7 Hz, 1H), 5.34 (s, 2H), 4.65 (d, J=15.4 Hz, 1H), 4.37 (d, J=9.6 Hz, 1H), 3.76 (br. s., 1H), 3.24-3.31 (m, 2H), 3.12-3.20 (m, 1H), 2.93 (t, J=7.6 Hz, 2H), 2.37-2.39 (m, 1H), 2.32 (s, 3H). M+H=471

3-(6-((4(4-chlorobenzyl)oxy)phenyl)-3,4-dihydro-2,7-naphthyridin-2(1H)-yl)propanoic acid (compound 174)

Using 4-benzyloxyphenylboronic acid (compound VI with R'=H, R"=H) instead of 4-benzyloxy-3-methylphenylboronic acid (compound VI with R'=H, R"=3-CH₃). Calculated Mass: (C24H23ClN2O3): 422.90 g/mol. ¹H NMR (600 MHz, DMSO-d₆) δ 12.80 (s, 1H), 11.00 (s, 1H), 8.48 (s, 1H), 8.08-8.02 (m, 2H), 7.87 (s, 1H), 7.54-7.45 (m, 4H), 7.18-7.12 (m, 2H), 5.19 (s, 2H), 4.65 (d, J=15.6 Hz, 1H), 4.37 (s, 1H), 3.38 (s, 1H), 3.27 (d, J=9.0 Hz, 1H), 2.93 (t, J=7.7 Hz, 2H). M+H=423/425

3-(6-(4-((3-chlorobenzyl)oxy)phenyl)-3,4-dihydro-2,7-naphthyridin-2(1H)-yl)propanoic acid (compound 175)

Using 4-benzyloxyphenylboronic acid (compound VI with R'=H, R"=H) instead of 4-benzyloxy-3-methylphenylboronic acid (compound VI with R'=H, R"=3-CH₃) and 3-chlorobenzylbromide instead of 4-chlorobenzylbromide. Calculated Mass: (C24H23ClN2O3): 422.90 g/mol. ¹H NMR (600 MHz, DMSO-d₆) δ 12.79 (s, 1H), 10.99 (s, 1H), 8.48 (s, 1H), 8.05 (d, J=8.8 Hz, 2H), 7.87 (s, 1H), 7.55 (s, 1H), 7.45 (d, J=5.0 Hz, 3H), 7.15 (d, J=9.0 Hz, 2H), 5.21 (s, 3H), 4.65 (d, J=15.6 Hz, 1H), 4.45-4.27 (m, 1H), 3.76 (s, 1H), 2.93 (s, 1H). M+H=423/425

3-(6-(4-((3-fluorobenzyl)oxy)phenyl)-3,4-dihydro-2,7-naphthyridin-2(1H)-yl)propanoic acid (compound 176)

Using 4-benzyloxyphenylboronic acid (compound VI with R'=H, R"=H) instead of 4-benzyloxy-3-methylphenylboronic acid (compound VI with R'=H, R"=3-CH₃) and 3-fluorobenzylbromide instead of 4-chlorobenzylbromide. Calculated Mass: (C24H23FN2O3): 406.45 g/mol. ¹H NMR (600 MHz, DMSO-d₆) δ 12.81 (s, 1H), 10.96 (s, 1H), 8.48 (s, 1H), 8.08-8.02 (m, 2H), 7.88 (s, 1H), 7.46 (td, J=8.1, 6.0 Hz, 1H), 7.35-7.29 (m, 2H), 7.21-7.12 (m, 3H), 5.22 (s, 2H), 4.64 (s, 1H), 4.45-4.29 (m, 1H), 3.76 (s, 1H), 3.29-3.23 (m, 1H), 3.18 (s, 1H), 2.93 (t, J=7.6 Hz, 2H). M+H=407

3-(2-(4-(benzyloxy)phenyl)-7,8-dihydropyrido[3,4-b]pyrazin-6(5H)-yl)propanoic acid (compound 177)

Tert-butyl 3-(2-(4-(benzyloxy)phenyl)-7,8-dihydropyrido[3,4-b]pyrazin-6(5H)-yl)propanoate Tert-butyl 3-(2-(4-(benzyloxy)phenyl)-7,8-dihydropyrido[3,4-b]pyrazin-6(5H)-yl)propanoate was prepared from 2-(4-(benzyloxy)phenyl)-5,6,7,8-tetrahydropyrido[3,4-b]pyrazine (compound XIa; R'=H, R"=H) in accordance with scheme 5. Compound XIa (870 mg; 2.74 mmol; 1 eq) was dissolved in MeOH (40 mL). DBU (334 mg; 2.19 mmol; 0.8 eq) and tert-butylacrylate (1.05 g; 8.22 mmol; 3 eq) were added under stirring and the mixture was stirred for 20 h at RT. The mixture is evaporated and the residue is dissolved in DCM, washed once with a 10% NH₄Cl solution and extracted once with water. The organic phase was dried with MgSO₄ and evaporated. The resulting oily residue was dissolved in a little DCM and purified by flash chromatography (silica gel, DCM/MeOH 95:5) giving the product with a yield of 1.2 g (2.69 mmol; 98%).
Compound 177
Tert-butyl 3-(2-(4-(benzyloxy)phenyl)-7,8-dihydropyrido[3,4-b]pyrazin-6(5H)-yl)propanoate (110 mg; 0.247 mmol; 1 eq) was dissolved in MeOH (2.5 mL) and THF (2.5 mL). 1 N NaOH (100 mg; 2.5 mmol; 10.1 eq) was added under stirring.
The mixture was stirred for 20 h at RT. The mixture was neutralized with 2.5 mL 1N HCl and evaporated until the THF and MeOH were removed. The residue was obtained and washed with water and dried over P2O5 at 40° C. under vacuum. The residue was dissolved in DCM with a little MeOH and purified by flash chromatography (silica gel, DMC/MeOH 9:1) giving compound 177 with a yield of 74 mg (0.190 mmol; 77%). Calculated Mass: (C23H23N3O3): 389.45 g/mol. ¹H NMR (DMSO-d6, 600 MHz): δ=9.11 (s, 1H), 8.10-8.14 (m, 2H), 7.47-7.50 (m, 2H), 7.39-7.43 (m, 2H), 7.34-7.37 (m, 1H), 7.34 (t, J=1.3 Hz, 1H), 7.15-7.20 (m, 2H), 5.20 (s, 2H), 4.53 (br. s., 2H), 3.54-3.62 (m, 1H), 3.46-3.54 (m, 2H), 3.48 (d, J=5.5 Hz, 1H), 2.94 (t, J=7.2 Hz, 2H). M+H=390

The following compounds were made in the same way as compound 177:

3-(2-(4-((4-chlorobenzyl)oxy)phenyl)-7,8-dihydropyrido[3,4-b]pyrazin-6(5H)-yl)propanoic acid (compound 178)

Using 2-(4-((4-chlorobenzyl)oxy)phenyl)-5,6,7,8-tetrahydropyrido[3,4-b]pyrazine prepared in accordance with scheme 1 instead of compound XIa. Calculated Mass: (C23H23N3O3): 423.89 g/mol. ¹H NMR (DMSO-d6, 600 MHz): δ=9.11 (s, 1H), 8.10-8.14 (m, 2H), 7.46-7.53 (m, 4H), 7.16-7.19 (m, 2H), 5.21 (s, 2H), 4.54 (br. s., 1H), 3.84 (br. s., 1H), 3.54-3.62 (m, 1H), 3.52 (br. s., 2H), 3.42 (br. s., 1H), 3.28 (dd, J=17.8, 3.1 Hz, 2H), 2.94 (t, J=7.2 Hz, 2H). M+H=424

3-(2-(4-((3-chlorobenzyl)oxy)phenyl)-7,8-dihydropyrido[3,4-b]pyrazin-6(5H)-yl)propanoic acid (compound 179)

Using 2-(4-((3-chlorobenzyl)oxy)phenyl)-5,6,7,8-tetrahydropyrido[3,4-b]pyrazine (compound XIb) prepared in accordance with scheme 1 instead of compound XIa. Calculated Mass: (C23H22ClN3O3): 423.89 g/mol. ¹H NMR (DMSO-d6, 600 MHz): δ=12.81 (br. s., 1H), 11.11 (br. s., 1H), 9.12 (s, 1H), 8.11-8.15 (m, 2H), 7.55-7.58 (m, 1H), 7.40-7.47 (m, 3H), 7.17-7.21 (m, 2H), 5.23 (s, 2H), 4.59 (br. s., 1H), 4.54 (br. s., 1H), 3.88 (br. s., 1H), 3.52-3.59 (m, 3H), 3.19-3.27 (m, 1H), 3.17 (s, 1H), 2.96 (t, J=7.6 Hz, 2H). M+H=424/426

4-(2-(4-((3-chlorobenzyl)oxy)phenyl)-3-fluoro-7,8-dihydro-1,6-naphthyridin-6(5H)-yl)-2-methylbutanoic acid (compound 182)

2-(4-(benzyloxy)phenyl)-3-fluoro-5,6,7,8-tetrahydro-1,6-naphthyridine

This compound was prepared starting from compound XXV instead of compound III in a palladium mediated reaction as indicated in scheme 1. Compound XXV (1 g; 3.49 mmol; 1 eq), sodium carbonate (7.7 g; 7.26 mmol; 2.1 eq) and potassium (4-beznyloxyphenyl)trifluoroborate (1.21 g; 4.19 mmol; 1.2 eq) were dissolved in DMF (20 mL). The solution was degassed with argon for 10 min. Tetrakis (triphenylphosphine)-palladium(0) (0.202 g; 0.174 mmol; 0.05 eq) was added and the mixture was stirred for 1 h at 120° C. The reaction mixture was evaporated, the residue was dissolved in DCM/water. After phase separation, the organic layer was washed once with water and once with saturated NaCl solution, dried over MgSO₄, filtered and evaporated. The residue was purified by flash chromatography (40 g silica gel; 0-10% MeOH in CH2Cl2) giving tert-butyl 2-(4-(benzyloxy)phenyl)-3-fluoro-7,8-dihydro-1, 6-naphthyridine-6(5H)-carboxylate. 1.85 g thereof (4.25 mmol; 1 eq) was dissolved in DCM (50 mL). TFA (7.4 g; 64.9 mmol; 15.3 eq) was added and the mixture was stirred overnight at RT. The reaction mixture was evaporated, the residue was dissolved in DCM and H$_2$O. To the mixture was added 2 NaOH until the pH was 10. The phases were separated, the organic layer was washed once with saturated NaCl solution, dried over MgSO$_4$, filtered and evaporated. The product was obtained with a yield of 1.26 g (3.77 mmol; 89%).

Ethyl 4-(2-(4-(benzyloxy)phenyl)-3-fluoro-7,8-dihydro-1,6-naphthyridin-6(5H)-yl)butanoate This compound was prepared in accordance with scheme 5. 2-(4-(benzyloxy)phenyl)-3-fluoro-5,6,7,8-tetrahydro-1,6-naphthyridine (700 mg; 2.09 mmol; 1 eq) dissolved in 10 mL DMF was added dropwise to a suspension of NaH (201 mg; 4.19 mmol; 2 eq) in DMF (5 mL). The mixture was stirred for 1 h at RT. Ethyl 4-bromobutyrate (1.23 g; 6.28 mmol; 3 eq) dissolved in 5 mL DMF was added dropwise. The mixture was heated to 60° C. for 2 h. The mixture was evaporated. The residue was dissolved in ethylacetate and washed once with water and once with saturated NaCl solution. The organic layer was dried over MgSO$_4$, filtered and evaporated. The residue was purified by flash chromatography twice (40 g silica gel, 0-20% MeOH in DCM and 0-10% MeOH in DCM, respectively) giving the product with a yield of 539 mg (1.202 mmol; 57.4%).

Ethyl 4-(2-(4-(benzyloxy)phenyl)-3-fluoro-7,8-dihydro-1,6-naphthyridin-6(5H)-yl)-2-methylbutanoate Ethyl 4-(2-(4-(benzyloxy)phenyl)-3-fluoro-7,8-dihydro-1,6-naphthyridin-6(5H)-yl)butanoate (340 mg; 0.758 mmol; 1 eq) was dissolved in 7 mL THF. At −70° C. lithium bis(trimethylsilyl)amide (184 mg; 1.10 mmol; 1.5 eq) was added dropwise under argon atmosphere. The mixture was stirred for 45 min at −70° C. Methyl iodide (1.08 g; 7.58 mmol; 10 eq) dissolved in THF (3 mL) was added dropwise at −50° C. under argon atmosphere. After 2 h during which the temperature was raised slowly to −10° C. the reaction was finished, as observed by TLC. To the reaction mixture was added 3 mL of a saturated NH$_4$Cl-solution after which the mixture was diluted with ethylacetate. After phase separation, the organic layer was washed once with saturated NaCl solution, dried over MgSO$_4$, filtered and evaporated. The residue was purified by flash chromatography (12 g silica gel, 10-30% ethylacetate in n-Heptane) giving the product with a yield of 103 mg (0.223 mmol; 29.4%).

Ethyl 4-(2-(4-((3-chlorobenzyl)oxy)phenyl)-3-fluoro-7,8-dihydro-1,6-naphthyridin-6(5H)-yl)-2-methylbutanoate This product was prepared in accordance with scheme 7. Ethyl 4-(2-(4-(benzyloxy)phenyl)-3-fluoro-7,8-dihydro-1,6-naphthyridin-6(5H)-yl)-2-methylbutanoate (100 mg; 0.216 mmol; 1 eq) was dissolved in THF (3 mL) and MeOH (3 mL). Under Argon atmosphere Pd—C (23.01 mg; 0.216 mmol; 1 eq) was added. The mixture was stirred at RT under hydrogen atmosphere. The reaction mixture was filtered and the organic layer was evaporated giving ethyl 4-(3-fluoro-2-(4-hydroxyphenyl)-7,8-dihydro-1,6-naphthyridin-6(5H)-yl)-2-methylbutanoate with a yield of 78 mg (0.209 mmol; 97%). 40 mg thereof (0.107 mmol; 1 eq) was dissolved in 3 mL DMF. Cesium carbonate (35.0 mg; 0.107 mmol; 1 eq) and 3-chlorobenzyl bromide (23 mg; 0.112 mmol; 1.04 eq) were added under stirring at RT. The reaction mixture was evaporated. The residue was dissolved in DCM and washed once with water. After phase separation with a Chromabond PTS-cartridge, the organic layer was evaporated. The residue was purified by flash chromatography (4 g silica gel, 0-10% MeOH in DCM giving the product with a yield of 24 mg (0.048 mmol; 45%).

Compound 182

Ethyl 4-(2-(4-((3-chlorobenzyl)oxy)phenyl)-3-fluoro-7,8-dihydro-1,6-naphthyridin-6(5H)-yl)-2-methylbutanoate (24 mg; 0.048 mmol; 1 eq) was dissolved in MeOH (0.5 mL) and THF (0.5 mL). 2N NaOH (100 µL; 0.200 mmol; 4.1 eq) was added and the mixture was stirred at RT overnight. LC/MS showed that the reaction wasn't finished. A further 100 µL 2N NaOH was added and the mixture was stirred for a further 4 h. The reaction mixture was neutralized with 200 µL 2N HCl and evaporated. The residue was dissolved in DCM and washed once with water and once with saturated NaCl solution. The organic layer was dried over MgSO$_4$, filtered and evaporated. The residue was purified by flash chromatography (4 g silica gel, 0-20% MeOH in DCM) giving compound 182 with a yield of 12.2 mg (0.026 mmol; 53.9%). Calculated mass (C26H26ClFN2O3) 468.16 g/mol. $^1$H NMR (500 MHz, Chloroform-d) δ 7.98-7.81 (m, 2H), 7.46 (d, J=1.9 Hz, 1H), 7.36-7.28 (m, 3H), 7.15 (d, J=10.9 Hz, 1H), 7.09-6.97 (m, 2H), 5.10 (s, 2H), 3.88 (d, J=15.4 Hz, 2H), 3.24-3.00 (m, 3H), 2.61 (dd, J=8.2, 5.3 Hz, 1H), 1.90-1.77 (m, 1H), 1.28 (d, J=7.1 Hz, 4H). M+H+ 469

The following compounds were prepared in the same way as compound 182:

4-(2-(4-(benzyloxy)phenyl)-3-fluoro-7,8-dihydro-1,6-naphthyridin-6(5H)-yl)-2-methylbutanoic acid (compound 180)

by converting ethyl 44244-(benzyloxy)phenyl)-3-fluoro-7,8-dihydro-1,6-naphthyridin-6(5H)-yl)-2-methylbutanoate directly into compound 180 using NaOH. Calculated mass (C26H27FN2O3) 434.20 g/mol. $^1$H NMR (500 MHz, DMSO-d$_6$) δ 7.98-7.82 (m, 2H), 7.70 (d, J=11.6 Hz, 1H), 7.54-7.44 (m, 2H), 7.46-7.30 (m, 3H), 7.26-7.10 (m, 2H), 5.19 (s, 2H), 2.06 (d, J=22.6 Hz, 1H), 1.81 (s, 1H), 1.16 (d, J=7.1 Hz, 3H). M+H+ 435

4-(2-(4-((4-chlorobenzyl)oxy)phenyl)-3-fluoro-7,8-dihydro-1,6-naphthyridin-6(5H)—O-2-methylbutanoic acid (compound 181)

Using 4-chlorobenzyl bromide instead of 3-chlorobenzyl bromide. Calculated mass (C26H26ClFN2O3) 468.16 g/mol. $^1$H NMR (600 MHz, DMSO-d$_6$) δ 7.93-7.85 (m, 2H), 7.71 (d, J=11.4 Hz, 1H), 7.57-7.43 (m, 5H), 7.21-7.07 (m, 2H), 5.20 (d, J=5.6 Hz, 2H), 2.06 (s, 1H), 1.83 (s, 1H), 1.14 (dd, J=16.5, 7.1 Hz, 3H). M+H+ 469

3-(2-((2-chloro-6-ethylbenzyl)oxy)-3-fluoro-7,8-dihydro-1,6-naphthyridin-6(5H)-yl)cyclobutanecarboxylic acid (compound 183)

Methyl 3-(2-chloro-3-fluoro-7,8-dihydro-1,6-naphthyridin-6(5H)-yl)cyclobutanecarboxylate This compound was prepared from compound XXV in accordance with scheme 6. Compound XXV (5.1 g; 17.0 mmol; 1 eq) was suspended in 25 mL THF. Triethylamine (1.55 g; 15.3 mmol; 0.9 eq) was added at RT, followed by methyl 3-oxocyclobutanecarboxylate (3.26 g; 25.4 mmol; 1.5 eq). The mixture was stirred for 30 min at RT. Sodium triacetoxyhydroborate (5.39 g; 25.4 mmol; 1.5 eq) was added in portions and the mixture was evaporated.

Methyl 3-(2-((2-chloro-6-ethylbenzyl)oxy)-3-fluoro-7,8-dihydro-1,6-naphthyridin-6(5H)-yl)cyclobutanecarboxylate This compound was prepared in accordance with scheme 9. Methyl 3-(2-chloro-3-fluoro-7,8-dihydro-1,6-naphthyridin-6(5H)-yl)cyclobutanecarboxylate (17 mg; 0.59 mmol; 1 eq) and (2-chloro-6-ethylphenyl)methanol (202 mg; 1.19 mmol; 2 eq) were suspended in 10 mL toluene. The mixture was degassed with argon for 15 min. [1,1'-biphenyl]-2-yldi-tert-butylphosphine (17.7 mg; 0.059 mmol; 0.1 eq), Palladium(II)acetate (13.3 g; 0.059 mmol; 0.1 eq) and cesium carbonate (386 mg; 1.19 mmol; 2 eq) were added and the mixture was stirred for 5 h at 100° C. The mixture is evaporated, the residue is mixed with 40 mL DCM. The DCM phase is dried with $MgSO_4$, filtered and evaporated. The residue was purified by flash chromatography (silica gel, DCM/MeOH) giving the product with a yield of 160 mg (0.370 mmol; 62.4%).

Compound 183

Methyl 3-(2-((2-chloro-6-ethylbenzyl)oxy)-3-fluoro-7,8-dihydro-1,6-naphthyridin-6(5H)-yl)cyclobutanecarboxylate (155 mg; 0.36 mmol; 1 eq) was dissolved in MeOH (3 mL) and THF (3 mL). 2N NaOH (215 mg; 5.4 mmol; 15 eq) was added and the mixture was stirred overnight at RT. MeOH and THF were evaporated, the pH was brought to pH 1 with 2N HCl and the mixture was stirred for 15 in at RT. The residue was washed with water and a little ethyl acetate. The residue was dried overnight at 40° C. under vacuum, giving compound 183 with a yield of 52 mg (0.114 mmol; 31.9%). Calculated mass (C22H24ClFN2O3): 418.15 g/mol. $^1$H NMR (500 MHz, DMSO-$d_6$) δ 11.96 (s, 2H), 7.55 (d, J=10.7 Hz, 1H), 7.44-7.34 (m, 2H), 7.29 (q, J=4.5 Hz, 1H), 5.49 (s, 2H), 2.99 (s, 2H), 2.84 (p, J=9.1 Hz, 1H), 2.76 (q, J=7.6 Hz, 2H), 2.44 (d, J=8.7 Hz, 3H), 2.34 (s, 2H), 1.17 (d, J=7.6 Hz, 2H). M+H+ 419.2

3-(2-(4-((3,4-difluorobenzyl)oxy)phenyl)-3-fluoro-7,8-dihydro-1,6-naphthyridin-6(5H)-yl)propanoic acid (compound 198)

Tert-butyl 2-(4-(benzyloxy)phenyl)-3-fluoro-7,8-dihydro-1,6-naphthyridine-6(5H)-propanoate This compound was prepared from compound XXVb instead of compound III in accordance with scheme 2. Compound XXVb (6 g; 19.1 mmol; 1 eq), (4-(benzyloxy)phenyl)boronic acid (4.35 g; 19.1 mmol; 1 eq) and tetrakis(triphenylphosphine)-palladium(0) (0.44 g; 0.38 mmol; 0.02 eq) were dissolved in a mixture of water (20 mL) in 1,4-dioxane (200 mL) and maintained with an inert atmosphere of nitrogen. The solution was stirred overnight at 80° C. and the reaction progress was monitored by LCMS. The reaction was concentrated under vacuum, and extracted 3 times with 200 mL ethylacetate. The combined organic layer was washed twice with 200 mL water and twice with 200 mL saturated NaCl solution. The solution was eluted by flash chromatography (silica gel, MeOH/DCM=(1/100-1/5)) giving the product with a yield of 7 g (15.13 mmol; 79%).

Tert-butyl 3-(3-fluoro-2-(4-hydroxyphenyl)-7,8-dihydro-1,6-naphthyridin-6(5H)-yl)propanoate This compound was prepared in accordance with scheme 7. Tert-butyl 2-(4-(benzyloxy)phenyl)-3-fluoro-7,8-dihydro-1,6-naphthyridine-6(5H)-propanoate (7 g; 15.13 mmol; 1 eq) was dissolved in 100 mL MeOH. Pd—C (1 g; 15.13 mmol; 1 eq) was added under N2 (~1 atm.). The solution was stirred for overnight at 80° C. and the reaction progress was monitored by LCMS. The reaction was filtered and concentrated under vacuum. The solution was eluted by flash chromatography (silica gel, EA/PE=(1/100-1/2)) giving the product with a yield of 3.7 g (9.89 mmol; 65.4%).

Tert-butyl 3-(2-(4-((3,4-difluorobenzyl)oxy)phenyl)-3-fluoro-7,8-dihydro-1,6-naphthyridin-6(5H)-yl)propanoate Tert-butyl 3-(3-fluoro-2-(4-hydroxyphenyl)-7,8-dihydro-1,6-naphthyridin-6(5H)-yl)propanoate (60 mg; 0.16 mmol; 1 eq) was dissolved in DMF (3 mL). Cesium carbonate (80 mg; 0.25 mmol; 1.5 eq) and 3,4-difluorobenzyl bromide (0.025 mL; 0.18 mmol; 1.1 eq) were added. The mixture was stirred at RT overnight. The reaction mixture was evaporated. The residue was dissolved in DCM and washed with water. After phase separation with a Chromabond PTS-cartridge, the organic layer was evaporated. The residue was purified by flash chromatography (4 g silica gel, 0-10% MeOH in DCM giving the product with a yield of 51 mg (0.102 mmol; 63.5%).

Compound 198

Tert-butyl 3-(2-(4-((3,4-difluorobenzyl)oxy)phenyl)-3-fluoro-7,8-dihydro-1,6-naphthyridin-6(5H)-yl)propanoate (51 mg; 0.10 mmol; 1 eq) was dissolved in MeOH (1 mL) and THF (1 mL). 2N NaOH (40 mg; 1.0 mmol; 9.8 eq) was added and the mixture was stirred overnight at RT. The pH was brought to pH 1 with 2N HCl. The residue was evaporated, washed with water and dried overnight at 40° C. under vacuum. 2 mL Ethyl acetate was added and the mixtures was stirred for 20 min at RT. The residue was evaporated and dried overnight at 40° C. under vacuum giving compound 198 with a yield of 43 mg (0.078 mmol; 76%). Calculated mass (C24H21F3N2O3) 442.15 g/mol. $^1$H NMR (500 MHz, DMSO-$d_6$) δ 7.93-7.87 (m, 2H), 7.69 (d, J=11.9 Hz, 1H), 7.56 (ddd, J=11.6, 7.9, 2.2 Hz, 1H), 7.48 (dt, J=10.8, 8.4 Hz, 1H), 7.20-7.13 (m, 2H), 5.18 (s, 2H), 4.47 (s, 2H), 3.18 (s, 3H), 2.82 (s, 2H). M+H+ 443

The following compounds were prepared in the same way as compound 198:

3-(2-(4-(benzyloxy)phenyl)-3-fluoro-7,8-dihydro-1,6-naphthyridin-6(5H)-yl)propanoic acid (compound 186)

Using benzylbromide instead of 3,4-difluorobenzyl bromide. Calculated mass (C24H23FN2O3) 406.449 g/mol. $^1$H NMR (500 MHz, DMSO-$d_6$) δ 7.93-7.83 (m, 2H), 7.71 (d, J=11.6 Hz, 1H), 7.51-7.45 (m, 2H), 7.45-7.38 (m, 2H), 7.39-7.29 (m, 1H), 7.17 (d, J=8.9 Hz, 2H), 5.19 (s, 2H), 3.51 (t, J=7.3 Hz, 2H), 3.21 (s, 2H), 2.86 (t, J=7.4 Hz, 2H). M+H+ 407

3-(2-(4-((4-chlorobenzyl)oxy)phenyl)-3-fluoro-7,8-dihydro-1,6-naphthyridin-6(5H)-yl)propanoic acid (compound 187)

Using 4-chlorobenzyl bromide instead of 3,4-difluorobenzyl bromide. Calculated mass (C24H22ClFN2O3) 440.894 g/mol. $^1$H NMR (500 MHz, DMSO-$d_6$) δ 7.98-7.82 (m, 2H), 7.68 (d, J=11.8 Hz, 1H), 7.49 (q, J=8.6 Hz, 4H), 7.23-7.11 (m, 2H), 5.19 (s, 2H), 3.17 (t, J=6.2 Hz, 2H), 2.81 (s, 1H). M+H+ 441

3-(2-(4-((3-chlorobenzyl)oxy)phenyl)-3-fluoro-7,8-dihydro-1,6-naphthyridin-6(5H)-yl)propanoic acid (compound 189)

Using 3-chlorobenzyl bromide instead of 3-chlorobenzyl bromide. Calculated mass (C24H22ClFN2O3) 440.13 g/mol. $^1$H NMR (500 MHz, DMSO-$d_6$) δ 7.97-7.84 (m, 2H), 7.70 (d, J=11.8 Hz, 1H), 7.55 (d, J=2.1 Hz, 1H), 7.48-7.34 (m, 3H), 7.22-7.09 (m, 2H), 5.22 (s, 2H), 3.18 (d, J=10.4 Hz, 3H), 2.83 (t, J=7.3 Hz, 2H). M+H+ 441

3-(2-(4-((4-fluorobenzyl)oxy)phenyl)-3-fluoro-7,8-dihydro-1,6-naphthyridin-6(5H)-yl)propanoic acid (compound 190)

Using 4-fluorobenzyl bromide instead of 3,4-difluorobenzyl bromide. Calculated mass (C24H22F2N2O3) 424.440 g/mol. $^1$H NMR (500 MHz, DMSO-$d_6$) δ 7.95-7.83 (m, 2H), 7.70 (d, J=11.7 Hz, 1H), 7.58-7.46 (m, 2H), 7.31-7.18 (m, 2H), 7.21-7.10 (m, 2H), 5.17 (s, 2H), 3.18 (d, J=12.0 Hz, 2H), 2.84 (s, 1H). M+H+ 425

3-(2-(4-((4-trifluoromethylbenzyl)oxy)phenyl)-3-fluoro-7,8-dihydro-1,6-naphthyridin-6(5H)-yl)propanoic acid (compound 191)

Using 4-trifluoromethylbenzyl bromide instead of 3,4-difluorobenzyl bromide. Calculated mass (C25H22F4N2O3) 474.447 g/mol. $^1$H NMR (500 MHz, DMSO-$d_6$) δ 7.90 (d, J=8.1 Hz, 2H), 7.79 (d, J=8.2 Hz, 2H), 7.74-7.62 (m, 3H), 7.25-7.09 (m, 2H), 5.32 (s, 2H), 4.51 (s, 2H), 3.20 (d, J=6.6 Hz, 2H), 2.85 (t, J=7.4 Hz, 2H). M+H+ 475

3-(2-(4-((2,6-dichlorobenzyl)oxy)phenyl)-3-fluoro-7,8-dihydro-1,6-naphthyridin-6(5H)-yl)propanoic acid (compound 192)

Using 2,6-dichloromethylbenzyl bromide instead of 3,4-difluorobenzyl bromide. Calculated mass (C24H21Cl2FN2O3) 474.09 g/mol. $^1$H NMR (500 MHz, DMSO-$d_6$) δ 7.93 (d, J=8.1 Hz, 2H), 7.72 (d, J=11.7 Hz, 1H), 7.59 (d, J=8.0 Hz, 2H), 7.50 (dd, J=8.8, 7.4 Hz, 1H), 7.29-7.18 (m, 2H), 5.32 (s, 2H), 3.21 (d, J=6.6 Hz, 2H), 2.85 (t, J=7.3 Hz, 2H). M+H+ 475

3-(2-(4-((3-fluorobenzyl)oxy)phenyl)-3-fluoro-7,8-dihydro-1,6-naphthyridin-6(5H)-yl)propanoic acid (compound 193)

Using 3-fluorobenzyl bromide instead of 3,4-difluorobenzyl bromide. Calculated mass (C24H22F2N2O3) 424.44 g/mol. $^1$H NMR (500 MHz, DMSO-$d_6$) δ 7.98-7.83 (m, 2H), 7.71 (d, J=11.7 Hz, 1H), 7.46 (td, J=8.0, 6.0 Hz, 1H), 7.31 (dd, J=10.3, 4.5 Hz, 2H), 7.27-7.13 (m, 3H), 5.22 (s, 2H), 3.21 (t, J=6.4 Hz, 2H), 2.86 (t, J=7.3 Hz, 2H). M+H+ 425

3-(2-(4-((3-trifluoromethylbenzyl)oxy)phenyl)-3-fluoro-7,8-dihydro-1,6-naphthyridin-6(5H)-yl)propanoic acid (compound 194)

Using 3-trifluoromethylbenzyl bromide instead of 3-chlorobenzyl bromide. Calculated mass (C25H22F4N2O3) 474.447 g/mol. $^1$H NMR (500 MHz, DMSO-$d_6$) δ 7.96-7.87 (m, 2H), 7.85 (s, 1H), 7.80 (d, J=7.5 Hz, 1H), 7.75-7.61 (m, 3H), 7.26-7.12 (m, 2H), 5.31 (s, 2H), 4.78-4.23 (m, 2H), 3.85 (s, 1H), 3.49 (s, 3H), 2.90 (dd, J=9.1, 6.1 Hz, 2H). M+H+ 475

3-(2-(4-((2-chloro-6-ethylbenzyl)oxy)phenyl)-3-fluoro-7,8-dihydro-1,6-naphthyridin-6(5H)-yl)propanoic acid (compound 196)

Using 2-chloro-6-ethylbenzyl bromide instead of 3,4-difluorobenzyl bromide. Calculated mass (C26H26ClFN2O3) 468.16 g/mol. $^1$H NMR (500 MHz, DMSO-$d_6$) δ 8.01-7.85 (m, 2H), 7.72 (d, J=11.7 Hz, 1H), 7.48-7.36 (m, 2H), 7.31 (dd, J=5.6, 3.3 Hz, 1H), 7.22 (d, J=8.9 Hz, 2H), 5.25 (s, 2H), 2.85 (t, J=7.3 Hz, 2H), 2.75 (q, J=7.6 Hz, 2H), 1.19 (t, J=7.5 Hz, 3H). M+H+ 469

3-(2-(4-((2-chloro-6-ethylbenzyl)oxy)phenyl)-3-fluoro-7,8-dihydro-1,6-naphthyridin-6(5H)-yl)propanoic acid (compound 197)

Using 2-chloro-6-ethylbenzyl bromide instead of 3,4-difluorobenzyl bromide. Calculated mass (C24H21F3N2O3) 442.15 g/mol. $^1$H NMR (500 MHz, DMSO-$d_6$) δ 8.01-7.84 (m, 2H), 7.70 (d, J=11.6 Hz, 1H), 7.52-7.22 (m, 4H), 7.20 (d, J=9.0 Hz, 2H), 5.28 (s, 2H), 3.19 (s, 3H), 2.83 (s, 3H). M+H+ 443

3-(2-(4-(benzyloxy)phenyl)-5H-pyrrolo[3,4-b]pyridin-6(7H)-yl)-2-methylpropanoic acid (compound 199)

Methyl 3-(2-(4-(benzyloxy)phenyl)-5H-pyrrolo[3,4-b]pyridin-6(7H)-yl)-2-methylpropanoate Methyl 3-(2-(4-(benzyloxy)phenyl)-5H-pyrrolo[3,4-b]pyridin-6(7H)-yl)-2-methylpropanoate was prepared from 2-(4-(benzyloxy)phenyl)-6,7-dihydro-5H-pyrrolo[3,4-b]pyridine (compound Xa; R'=H, R"=H) in accordance with scheme 5. To a suspension of compound Xa (with R'=H, R"=H; 100 mg; 0.33 mmol; 1 eq) in MeOH (2 mL) was added DBU (101 mg; 0.66 mmol; 2 eq) and ethylmethacrylate (189 mg; 1.65 mmol; 5 eq). The reaction mixture was stirred at 120° C. for 1 h. A further 0.1 mL (1.01 g/mL) DBU and 0.2 mL (0.97 g/mL) ethylmethacrylate were added and the mixture was stirred again at 120° C. for 1 h. The reaction mixture was evaporated and the residue was purified by flash chromatography (12 g silica gel, 0-5% MeOH in DCM) giving the product with a yield of 82 mg (0.204 mmol; 61.6%).

Compound 199

Methyl 3-(2-(4-(benzyloxy)phenyl)-5H-pyrrolo[3,4-b]pyridin-6(7H)-yl)-2-methylpropanoate (30 mg; 0.075 mmol; 1 eq) was dissolved in MeOH (0.5 mL) and THF (2 mL). 2N NaOH (40 mg; 1 mmol; 13.4 eq) was added and the mixture was stirred overnight at RT. 2N HCl (500 μL) was added to the mixture, which was then evaporated. The residue was dissolved in H$_2$O/DCM with a small amount of MeOH. After phase separation, the aqueous layer was extracted once with DCM. The combined organic layer was dried with MgSO$_4$, filtered and evaporated. The residue was dissolved in DCM/MeOH and Celite XTR (Kieselguhr) was added. The mixture was evaporated and the residue was purified by flash chromatography (4 g silica gel, 0-15% MeOH in DCM) giving compound 199 with a yield of 19 mg (0.049 mmol; 65.6%). Calculated mass (C24H24N2O3): 388.18 g/mol. $^1$H NMR (600 MHz, DMSO-$d_6$) δ 8.13-7.89 (m, 2H), 7.69 (q, J=8.0 Hz, 2H), 7.51-7.45 (m, 2H), 7.41 (dd, J=8.4, 6.8 Hz, 2H), 7.38-7.28 (m, 1H), 7.15-7.01 (m, 2H), 5.17 (s, 2H), 4.11-3.66 (m, 5H), 2.95 (dd, J=11.7, 8.7 Hz, 1H), 2.72 (dd, J=11.7, 6.5 Hz, 1H), 2.64 (dt, J=8.5, 6.5 Hz, 1H), 1.12 (d, J=6.8 Hz, 3H). M+H+ 389

The following compound were prepared in the same way as compound 199:

3-(2-(4-(benzyloxy)phenyl)-5H-pyrrolo[3,4-b]pyridin-6(7H)-yl)butanoic acid (compound 200)

Using ethyl crotonate instead of ethylmethacrylate. Calculated mass (C24H24N2O3): 388.18 g/mol. $^1$H NMR (600 MHz, DMSO-d$_6$) δ 8.06-7.91 (m, 2H), 7.70 (q, J=8.0 Hz, 2H), 7.51-7.46 (m, 2H), 7.41 (t, J=7.5 Hz, 2H), 7.38-7.26 (m, 2H), 7.16-7.00 (m, 2H), 5.17 (s, 2H), 4.22-3.76 (m, 3H), 2.30 (dd, J=15.0, 7.8 Hz, 1H), 1.16 (d, J=6.4 Hz, 3H). M+H+ 389

3-(2-(4-(benzyloxy)phenyl)-5H-pyrrolo[3,4-b]pyridin-6(7H)-yl)propanoic acid (compound 202)

Using tert-butyl acrylate under argon atmosphere instead of ethylmethacrylate. Calculated mass (C23H22N2O3): 374.16 g/mol. $^1$H NMR (600 MHz, DMSO-d$_6$) δ 8.05-7.95 (m, 2H), 7.73 (q, J=8.1 Hz, 2H), 7.50-7.45 (m, 2H), 7.41 (dd, J=8.4, 6.8 Hz, 2H), 7.37-7.30 (m, 1H), 7.15-7.03 (m, 2H), 5.17 (s, 2H), 4.07 (d, J=12.4 Hz, 4H), 3.09 (t, J=6.9 Hz, 2H), 2.56 (t, J=7.2 Hz, 2H). M+H+ 375.

3-(2-(4-((2,6-dichlorobenzyl)oxy)phenyl)-5H-pyrrolo[3,4-b]pyridin-6(7H)-yl)butanoic acid (compound 201)

Methyl 3-(2-(4-(benzyloxy)phenyl)-5H-pyrrolo[3,4-b]pyridin-6(7H)-yl)butanoate

This compound was prepared from 2-(4-(benzyloxy)phenyl)-6,7-dihydro-5H-pyrrolo[3,4-b]pyridine (compound Xa; R'=H, R"=H) in accordance with scheme 5. To a suspension of compound Xa (100 mg; 0.33 mmol; 1 eq) in MeOH (4 mL) was added DBU (100 mg; 0.66 mmol; 2 eq) and ethyl crotonate (189 mg; 1.65 mmol; 5 eq). The reaction mixture was stirred at 120° C. for 1 h. A further 0.1 mL (1.01 g/mL) DBU and 0.2 mL (0.97 g/mL) ethyl crotonate were added and the mixture was stirred again at 120° C. for 2 h. The reaction mixture was evaporated and the residue was purified by flash chromatography (12 g silica gel, 0-5% MeOH in DCM) giving the product with a yield of 86 mg (0.214 mmol; 64.6%).

Methyl 3-(2-(4-((2,6-dichlorobenzyl)oxy)phenyl)-5H-pyrrolo[3,4-b]pyridin-6(7H)-yl)butanoate This compound was prepared in accordance with scheme 7 To a solution of methyl 3-(2-(4-(benzyloxy)phenyl)-5H-pyrrolo[3,4-b]pyridin-6(7H)-yl)butanoate (86 mg; 0.214 mmol; 1 eq) in MeOH (2 mL) was added Pd—C (2.274 mg; 0.021 mmol; 0.1 eq) and hydrogenated at RT overnight. The mixture was filtrated and evaporated to obtain methyl 3-(2-(4-hydroxyphenyl)-5H-pyrrolo[3,4-b]pyridin-6(7H)-yl)butanoate with a yield of 27.6 mg (0.088 mmol; 41.4%), which product (0.088 mmol; 1 eq) was dissolved in DMF (1 mL) and cooled down to 0° C. Potassium tert-butoxide 1.6M in THF (11.9 mg; 0.106 mmol; 0.066 mL; 1.2 eq) was added (instead of cesium carbonate) and stirred for 1 h. 2-(bromomethyl)-1,3-dichlorobenzene (23.32 mg; 0.097 mmol; 1.1 eq) was added and the reaction mixture was stirred for 1 h, allowing the temperature to warm up to RT. The mixture was poured into cold 0.5 M HCl and extracted three-times with EtOAc. The organic phases were combined and washed with water three times and dried over Na$_2$SO$_4$, filtrated and evaporated to obtain the crude product with a yield of 50.8 mg (0.086 mmol; 98%), which was used as it is for the next step.

Compound 201

To methyl 3-(2-(4-((2,6-dichlorobenzyl)oxy)phenyl)-5H-pyrrolo[3,4-b]pyridin-6(7H)-yl)butanoate (50.8 mg; 0.108 mmol; 1 eq) was added KOH 2N in MeOH (1 mL, 2.0 mmol) and stirred at RT over night. The mixture was evaporated and purified by LCMS giving compound 201 with a yield of 3.4 mg (7.43 μmol; 6.9%). Calculated mass (C24H22Cl2N2O3) 456.10 g/mol. $^1$H NMR (600 MHz, Methanol-d$_4$) δ 8.06-8.02 (m, 2H), 7.89-7.84 (m, 2H), 7.50-7.46 (m, 2H), 7.38 (dd, J=8.7, 7.5 Hz, 1H), 7.18-7.14 (m, 2H), 5.37 (s, 2H), 4.87 (s, 2H), 4.81 (s, 2H), 4.05 (pd, J=6.6, 4.6 Hz, 1H), 3.01-2.86 (m, 2H), 1.55 (d, J=6.6 Hz, 3H). M+H+ 457

3-(2-(3-(benzyloxy)phenyl)-5H-pyrrolo[3,4-b]pyridin-6(7H)-yl)propanoic acid (compound 204)

Tert-butyl 3-(2-chloro-5H-pyrrolo[3,4-b]pyridin-6(7H)-yl)propanoate

This compound was prepared from 2-chloro-6,7-dihydro-5H-pyrrolo[3,4-b]pyridin-6-ium 2,2,2-trifluoroacetate as described in scheme 6. 2-chloro-6,7-dihydro-5H-pyrrolo[3,4-b]pyridin-6-ium 2,2,2-trifluoroacetate (280 mg; 1.04 mmol; 1 eq) was dissolved in 12 mL MeOH. DBU (317 mg; 2.09 mmol; 2 eq) was added, followed by tert-butyl acrylate (334 mg; 2.61 mmol; 2.5 eq). The mixture was stirred overnight at RT. The mixture was evaporated and the resulting oil was dissolved in 30 ethyl acetate and washed with 20 mL of a saturated ammonium chloride solution and 10 mL water. The ethyl acetate phase was dried with MgSO$_4$, filtered and evaporated. The oily residue was purified by flash chromatography (silica gel, DCM:MeOH giving the product with a yield of 268 mg (0.948 mmol; 91%).

Tert-butyl 3-(2-(3-(benzyloxy)phenyl)-5H-Pyrrolo[3,4-b]pyridin-6(7H)-yl)propanoate This compound was prepared in accordance with scheme 4 from tert-butyl 3-(2-chloro-5H-pyrrolo[3,4-b]pyridin-6(7H)-yl)propanoate instead of compound VII. To a solution of tert-butyl 3-(2-chloro-5H-pyrrolo[3,4-b]pyridin-6(7H)-yl)propanoate (120 mg; 0.42 mmol; 1 eq) and (3-(benzyloxy)phenyl)boronic acid (116 mg; 0.51 mmol; 1.2 eq) in 3 mL DMF was added sodium carbonate (112 mg; 1.06 mmol; 2.5 eq). The mixture was degassed with argon for 20 min. Tetrakis(triphenylphosphine)-palladium(0) (24.5 mg; 0.021 mmol; 0.05 eq) was added and the mixture was stirred for 1 h at 120° C. The reaction mixture was evaporated and 40 mL ethyl acetate and 30 mL water was added. The ethyl acetate was separated and washed once with 30 mL water, dried with MgSO$_4$, filtered and evaporated. The oily residue was purified by flash chromatography (silica gel, DCM:MeOH) giving the product with a yield of 155 mg (0.360 mmol; 85%).

Compound 204

Tert-butyl 3-(2-(3-(benzyloxy)phenyl)-5H-pyrrolo[3,4-b]pyridin-6(7H)-yl)propanoate (150 mg; 0.35 mmol; 1 eq) was dissolved in 12 mL MeOH.2N NaOH (209 mg; 5.23 mmol; 15 eq) was added and the mixture was stirred overnight at RT. The MeOH was evaporated and the resulting suspension was brought to pH 1 with 2N HCl. The mixture was stirred for 15 min at RT. The residue was obtained and washed with water. The residue was dissolved in 5 mL acetone/1 mL DCM and stirred for 10 min at RT. The residue was obtained and dried overnight at 40° C. under vacuum giving compound 204 with a yield of 96 mg (0.234 mmol; 67.1%). Calculated mass (C23H22N2O3): 374.16 g/mol. $^1$H NMR (600 MHz, DMSO-d$_6$) δ 12.81 (s, 1H), 10.90 (s, 1H), 8.11-7.85 (m, 2H), 7.81-7.58 (m, 2H), 7.52-7.47 (m, 2H), 7.42 (td, J=8.6, 7.9, 7.1 Hz, 3H), 7.38-7.32 (m, 1H), 7.12 (dd, J=8.0, 2.6 Hz, 1H), 5.19 (s, 2H), 4.67 (s, 4H), 3.61 (s, 2H), 2.82 (s, 2H). M+H+ 375.1

The following compounds were prepared in the same way as compound 204:

3-(2-(3-((3-fluorobenzyl)oxy)phenyl)-5H-pyrrolo[3,4-b]pyridin-6(7H)-yl)propanoic acid (compound 203)

Using (3-((3-fluorobenzyl)oxy)phenyl)boronic acid instead of (3-(benzyloxy)phenyl)boronic acid. Calculated mass (C23H21FN2O3): 392.15 g/mol. $^1$H NMR (600 MHz, DMSO-d$_6$) δ 12.79 (s, 1H), 11.65 (s, 1H), 8.11-7.87 (m, 2H), 7.85-7.60 (m, 2H), 7.49-7.42 (m, 2H), 7.36-7.30 (m, 2H), 7.18 (td, J=8.6, 2.6 Hz, 1H), 7.13 (dd, J=8.1, 2.5 Hz, 1H), 5.23 (s, 2H), 4.71 (s, 4H), 3.64 (t, J=7.6 Hz, 2H), 2.89 (t, J=7.6 Hz, 2H). M+H+ 393.2

3-(2-(3-((2,6-dichlorobenzyl)oxy)phenyl)-5H-pyrrolo[3,4-b]pyridin-6(7H)-yl)propanoic acid (compound 205)

Using (3-((2,6-dichloro benzyl)oxy)phenyl)boronic acid instead of (3-(benzyloxy)phenyl)boronic acid. $^1$H NMR (600 MHz, Methanol-d$_4$) δ 8.05-8.01 (m, 2H), 7.89-7.84 (m, 2H), 7.50-7.46 (m, 2H), 7.38 (dd, J=8.7, 7.5 Hz, 1H), 7.17-7.13 (m, 2H), 5.37 (s, 2H), 4.87 (s, 2H), 4.81 (s, 2H), 3.79 (t, J=6.7 Hz, 2H), 2.96 (t, J=6.7 Hz, 2H).

3-(3-(4-(benzyloxy)phenyl)-5,6-dihydropyrido[3,4-c]pyridazin-7(8H)-yl)-2-methylpropanoic acid (compound 206)

Methyl 3-(3-(4-(benzyloxy)phenyl)-5,6-dihydropyrido[3,4-c]pyridazin-7(8H)—O-2-methylpropanoate Methyl 3-(3-(4-(benzyloxy)phenyl)-5,6-dihydropyrido[3,4-c]pyridazin-7(8H)-yl)-2-methylpropanoate was prepared from 3-(4-(benzyloxy)phenyl)-5,6,7,8-tetrahydropyrido[3,4-c]pyridazine (compound XIIIa; R'=H, R"=H) in accordance with scheme 5. Compound XIIIa (80 mg; 0.25 mmol; 1 eq) was dissolved in MeOH (4 mL). DBU (153 mg; 1.01 mmol; 4 eq) and ethyl metacrylate (288 mg; 2.52 mmol; 10 eq) were added under stirring and the mixture was stirred for 2 h at 120° C. The mixture was evaporated and the residue is dissolved in 30 mL ethyl acetate and washed twice with 15 mL of a saturated NH$_4$Cl solution. The organic phase was dried with MgSOH, filtered and evaporated. The resulting residue was purified by flash chromatography (silica gel, DCM/MeOH 95:5) giving the product with a yield of 59 mg (0.141 mmol; 56.1%).
Compound 206

Methyl 3-(3-(4-(benzyloxy)phenyl)-5,6-dihydropyrido[3,4-c]pyridazin-7(8H)-yl)-2-methylpropanoate (53 mg; 0.127 mmol; 1 eq) was dissolved in MeOH (4 mL). 2N NaOH (76 mg; 1.9 mmol; 15 eq) was added under stirring. The mixture was stirred for overnight at RT. The MeOH was evaporated and the resulting suspension was brought to pH 1 with 2N HCl. The mixture was stirred for 15 min at RT. The residue was obtained and washed with water. The residue was dissolved in 40 mL DCM/2 mL MeOH. The organic phase was dried with MgSO$_4$, filtered and evaporated. The residue was obtained mixed with 2 mL DCM/MTBE, dried overnight at 40° C. under vacuum giving compound 206 as the 3-(4-(benzyloxy)phenyl)-7-(2-carboxypropyl)-5,6,7,8-tetrahydropyrido[3,4-c]pyridazin-7-ium chloride with a yield of 39 mg (0.089 mmol; 69.8%). Calculated mass (C24H25N3O3): 403.19 g/mol. $^1$H NMR (600 MHz, DMSO-d$_6$) δ 8.17-8.04 (m, 3H), 7.51-7.46 (m, 2H), 7.45-7.39 (m, 2H), 7.39-7.32 (m, 1H), 7.26-7.14 (m, 2H), 5.21 (s, 2H), 4.63 (s, 2H), 3.19 (s, 1H), 1.24 (d, J=7.0 Hz, 3H). M+H+ 404.4

The following compound was prepared in the same way as compound 206:

3-(3-(4-(benzyloxy)phenyl)-5,6-dihydropyrido[3,4-c]pyridazin-7(8H)-yl)propanoic acid (compound 207)

Using tert-butyl acrylate instead of ethyl metacrylate. Calculated mass (C23H23N3O3): 389.17 g/mol. $^1$H NMR (600 MHz, DMSO-d$_6$) δ 8.11 (dd, J=7.1, 5.0 Hz, 1H), 7.52-7.47 (m, 1H), 7.42 (t, J=7.6 Hz, 1H), 7.38-7.32 (m, 1H), 7.24-7.17 (m, 1H), 5.21 (s, 1H), 4.58 (s, 1H), 3.24-3.11 (m, 1H), 2.87 (s, 1H). M+H+ 390.4

3-(2-(3-(benzyloxy)phenyl)-7,8-dihydropyrido[3,4-b]pyrazin-6(5H)-yl)cyclobutanecarboxylic acid (compound 208)

This compound was prepared from 2-(4-(benzyloxy)phenyl)-5,6,7,8-tetrahydropyrido[3,4-b]pyrazine (compound XIa; R'=H, R"=H) in accordance with scheme 5. Compound XIa (379 mg; 1.19 mmol; 1 eq) was dissolved in THF (10 mL). 3-oxocyclobutanecarboxylic acid (150 mg; 1.31 mmol; 1.1 eq) was added under stirring and the mixture was stirred for 1 at RT. Sodium triacetoxyborhydride (380 mg; 1.79 mmol; 1.5 eq) was added and the mixture was stirred for 3 h at RT. 20 mL water was added and the mixture was stirred for 15 min and extracted with EtOAc. The organic phase was washed with water, dried with MgSO$_4$, filtered and evaporated. The oily residue was dissolved in DCM and purified by flash chromatography (silica gel, DCM/MeOH). The purified product was dissolved in DCM with a little MeOH and purified again by flash chromatography (silica gel, EtOAc/MeOH 9:1). The purified product was mixed with acetone, isolated, washed with acetone and pentane and dried at 45° C. under vacuum giving compound 208 with a yield of 40 mg (0.096 mmol; 8.06%). Calculated mass: (C25H25N3O3): 415.484 g/mol. $^1$H NMR (600 MHz, DMSO-d$_6$) δ 12.21 (s, 1H), 9.00 (s, 1H), 7.74 (dd, J=2.5, 1.7 Hz, 1H), 7.69 (dt, J=7.8, 1.2 Hz, 1H), 7.53-7.47 (m, 2H), 7.48-7.38 (m, 4H), 7.39-7.31 (m, 1H), 7.13 (ddd, J=8.2, 2.7, 0.9 Hz, 1H), 5.20 (s, 2H), 3.59 (s, 2H), 3.14 (dd, J=7.6, 1.2 Hz, 1H), 3.00 (t, J=6.0 Hz, 2H), 2.98-2.87 (m, 1H), 2.71 (t, J=5.9 Hz, 2H), 2.31 (dddd, J=10.0, 7.5, 3.7, 2.4 Hz, 2H), 2.21 (tdd, J=9.9, 7.6, 2.5 Hz, 2H). M+H=416

4-(2-(4-((3-chlorobenzyl)oxy)phenyl)-7,8-dihydropyrido[3,4-b]pyrazin-6(5H)-yl)-3-methylbutanoic acid (compound 209)

2-(4-((3-chlorobenzyl)oxy)phenyl)-5,6,7,8-tetrahydropyrido[3,4-b]pyrazine (45 mg; 10.047 mmol; 1 eq) was dissolved in MeOH (3 mL) and THF (3 mL). 2N NaOH (28.1 mg; 0.703 mmol; 15 eq) was added under stirring. The mixture was stirred for overnight at RT. The mixture was evaporated and the resulting solution was brought to pH 1 with 2N HCl resulting in the precipitation of an oily residue. The residue was obtained and washed with water. The residue was extracted with 100 mL DCM, dried with MgSO$_4$, filtered and evaporated giving compound 209 with a yield of 59 mg. Calculated mass (C25H26ClN3O3): 451.17 g/mol. $^1$H NMR (600 MHz, DMSO-d$_6$) δ 12.09 (s, 1H), 8.93 (s, 1H), 8.17-8.03 (m, 2H), 7.66-7.50 (m, 1H), 7.52-7.36 (m, 3H), 7.30-7.06 (m, 2H), 5.21 (s, 2H), 3.67 (q, J=16.1 Hz, 2H), 2.98 (t, J=5.9 Hz, 2H), 2.86 (dt, J=11.6, 5.8 Hz, 1H), 2.79 (dt, J=11.7, 6.0 Hz, 1H), 2.43-2.34 (m, 3H), 2.26-2.12 (m, 1H), 2.02 (dd, J=15.3, 7.6 Hz, 1H), 0.93 (d, J=6.6 Hz, 3H). M+H+ 452.1

4-(2-(4-((3-chlorobenzyl)oxy)phenyl)-7,8-dihydropyrido[4,3-d]pyrimidin-6(5H)-yl)-3,3-dimethylbutanoic acid (compound 216)

Ethyl 4-(2-chloro-7,8-dihydropyrido[4,3-d]Pyrimidin-6(5H)-yl)-3,3-dimethylbutanoate This compound was prepared in accordance with scheme 2. Compound XXd (145 mg; 0.47 mmol; 1 eq) were dissolved in 5 mL DMF. Na$_2$CO$_3$ (123 mg; 1.16 mmol; 2.5 eq) and 4-(3'-chlorobenzyloxy)phenylboronic acid (compound VI with R'=3-Cl, R"=H; 146 mg; 0.56 mmol; 1.2 eq) were added at RT and the solution was rinsed with argon for 5 min. Tetrakis(triphenylphosphine)-palladium(0) (37.1 mg; 0.032 mmol; 0.05 eq) was added and the mixture was heated and stirred for 30 min at 120° C. The reaction mixture was evaporated and extracted with DCM/water. After phase separation, the organic layer was washed once with water, dried with MgSO$_4$ and evaporated. The residue was dissolved in DCM and purified by flash chromatography (silica gel, 98:2 DCM:MeOH) giving the product with a yield of 130 mg (0.263 mmol; 56.6%).
Compound 216
Ethyl 4-(2-chloro-7,8-dihydropyrido[4,3-d]pyrimidin-6(5H)-yl)-3,3-dimethylbutanoate (130 mg; 0.26 mmol; 1 eq) was dissolved in MeOH (3 mL) and THF (3 mL). NaOH (120 mg; 3.0 mmol; 11.4 eq) was added and the mixture was stirred for 20 h at RT. The mixture was neutralized with 3 mL 1N HCl. The MeOH/THF was evaporated and mixture was extracted with DCM twice. The combined organic phase was dried with MgSO$_4$, filtered and evaporated. The residue was dissolved in DCM and purified by flash chromatography (silica gel, 95:5 DCM:MeOH). The residue was dissolved in DCM with a little MeOH and again chromatographed giving compound 216 with a yield of 48 mng (0.103 mmol; 39.1%). Calculated mass: (C26H28ClN3O3): 465.972 g/mol. $^1$H NMR (600 MHz, DMSO-d$_6$) δ 12.45 (s, 1H), 10.13 (s, 1H), 8.73 (s, 1H), 8.37-8.32 (m, 2H), 7.56 (s, 1H), 7.50-7.40 (m, 4H), 7.22-7.14 (m, 2H), 5.22 (s, 2H), 4.50 (s, 1H), 3.85-3.62 (m, 2H), 1.20 (s, 7H). M+H=466/468
The following compounds were prepared in the same way as compound 216:

4-(2-(4-((4-chlorobenzyl)oxy)phenyl)-7,8-dihydropyrido[4,3-d]pyrimidin-6(5H)-yl)-3,3-dimethylbutanoic acid (compound 210)

Using (4-((4-chlorobenzyl)oxy)phenyl)boronic acid instead of 4-(3'-chlorobenzyloxy)phenylboronic acid. Calculated mass (C26H28ClN3O3) 465.18 g/mol. $^1$H NMR (600 MHz, Chloroform-d) δ 8.45 (s, 1H), 8.37-8.31 (m, 2H), 7.42-7.35 (m, 4H), 7.07-7.02 (m, 2H), 5.10 (s, 2H), 3.96 (s, 2H), 3.19 (d, J=25.7 Hz, 4H), 2.72 (s, 2H), 2.60 (s, 2H), 1.16 (s, 6H). M+H+ 466

4-(2-(4-((3,4-dichlorobenzyl)oxy)phenyl)-7,8-dihydropyrido[4,3-d]pyrimidin-6(5H)-yl)-3,3-dimethylbutanoic acid (compound 217)

Using 4-(3,4'-dichlorobenzyloxy)phenylboronic acid instead of 4-(3'-chlorobenzyloxy)phenylboronic acid. Calculated mass: (C26H27Cl2N3O3): 500.417 g/mol. $^1$H NMR (600 MHz, DMSO-d$_6$) δ 12.47 (s, 1H), 10.11 (s, 1H), 8.73 (s, 1H), 8.35 (d, J=8.5 Hz, 2H), 7.77 (d, J=2.0 Hz, 1H), 7.69 (d, J=8.3 Hz, 1H), 7.49 (dd, J=8.3, 2.0 Hz, 1H), 7.17 (d, J=8.5 Hz, 2H), 5.22 (s, 2H), 1.19 (s, 7H). M+H=500/502

4-(2-(4-((3-chlorobenzyl)oxy)phenyl)-7,8-dihydropyrido[3,4-b]pyrazin-6(5H)-yl)-3,3-dimethylbutanoic acid (compound 211)

Ethyl 4-(2-(4-((3-chlorobenzyl)oxy)phenyl)-7,8-dihydropyrido[3,4-b]pyrazin-6(5H)-yl)-3,3-dimethylbutanoate This compound was prepared from compound XIb in accordance with scheme 5. Compound XIb (90 mg; 0.26 mmol; 1 eq) was dissolved in THF (3 mL). Ethyl 3,3-dimethyl-4-oxobutanoate (81 mg; 0.51 mmol; 2 eq) was added at RT and the mixture was stirred for a further 30 min at RT. Sodium triacetoxyhydroborate (108 mg; 0.51 mmol) was added in portions under stirring and the mixture was stirred for 2 h at RT. The mixture is evaporated and extracted with 40 mL ethyl acetate and 10 mL of a saturated NaCl solution. The organic phase was obtained, dried with MgSO$_4$, filtered and evaporated. The resulting oily residue was purified by flash chromatography (silica gel, DCM/MeOH) giving the product with a yield of 110 mg (0.223 mmol; 87%).
Compound 211
Ethyl 4-(2-(4-((3-chlorobenzyl)oxy)phenyl)-7,8-dihydropyrido[3,4-b]pyrazin-6(5H)-yl)-3,3-dimethylbutanoate (105 mg; 0.213 mmol; 1 eq) was dissolved in MeOH (3 mL) and THF (3 mL). 2N NaOH (128 mg; 3.19 mmol; 15 eq) was added under stirring. The mixture was stirred overnight at RT. The pH was brought to pH1 with 1N HCl. The mixture was extracted with 100 mL DCM. The organic phase was dried with MgSO$_4$, filtered and evaporated. The residue was dissolved in 1 mL acetone and 1 mL MeOH, stirred for 15 min at RT and the residue was dried at 40° C. under giving compound 211 with a yield of 26 mg (0.052 mmol; 24.4%). Calculated mass (C26H28ClN3O3): 465.18 g/mol. $^1$H NMR (600 MHz, DMSO-d$_6$) δ 9.11 (d, J=15.1 Hz, 1H), 8.12 (d, J=8.4 Hz, 2H), 7.56 (s, 1H), 7.44 (dd, J=17.8, 5.3 Hz, 3H), 7.19 (d, J=8.5 Hz, 2H), 5.23 (s, 2H), 4.56 (s, 1H), 1.18 (s, 6H). M+H+ 466.3

1-((2-(4-benzylphenyl)-7,8-dihydropyrido[4,3-d]pyrimidin-6(5H)-yl)methyl)cyclopropanecarboxylic acid (compound 218)

Methyl 1-((2-(4-benzylphenyl)-7,8-dihydropyrido[4,3-d]pyrimidin-6(5H)-yl)methyl)cyclopropanecarboxylate This compound was prepared from compound XXc in a palladium mediated reaction as described in scheme 2, using (4-benzylphenyl)boronic acid instead of compound VI. Compound XXc (87 mg; 0.31 mmol; 1 eq) and (4-benzylphenyl)boronic acid (98 mg; 0.46 mmol; 1.5 eq) were dissolved in 4 mL DMF. Sodium carbonate (82 mg; 0.77 mmol; 2.5 eq) was added at RT and the mixture was degassed with argon (20 min). Tetrakis(triphenylphosphine)-palladium(0) (17.8 mg; 0.015 mmol; 0.05 eq) was added and the mixture was stirred for 1 h at 125° C. The reaction mixture was evaporated, the residue was mixed with 40 mL ethyl acetate and 20 mL water. After phase separation, the ethyl acetate phase was washed once with 10 mL water, dried with MgSO$_4$, filtered and evaporated. The residue was purified by flash chromatography (silica gel, DCM:MeOH) giving the product with a yield of 112 mg (0.295 mmol; 96%).

Compound 218

Methyl 1-((2-(4-benzylphenyl)-7,8-dihydropyrido[4,3-d]pyrimidin-6(5H)-yl)methyl)cyclopropanecarboxylate (115 mg; 0.28 mmol; 1 eq) was dissolved in MeOH (3 mL) and THF (3 mL). 2N NaOH (167 mg; 4.17 mmol; 15 eq) was added under stirring. The mixture was stirred overnight at RT. The pH was brought to pH1 with 2N HCl. MeOH/THF were evaporated and the oily residue was extracted once with 100 mL DCM. The organic phase was dried with MgSO$_4$, filtered and evaporated. The residue was purified by flash chromatography (silica gel, DCM:MeOH) giving compound 218 with a yield of 46 mg (0.106 mmol; 37.9%). Calculated mass (C25H25N3O2): 399.19 g/mol. $^1$H NMR (600 MHz, DMSO-d$_6$) δ 8.61 (s, 1H), 8.32-8.24 (m, 2H), 7.36 (d, J=8.2 Hz, 2H), 7.33-7.29 (m, 2H), 7.29-7.25 (m, 2H), 7.23-7.17 (m, 1H), 4.01 (s, 2H), 3.79 (s, 2H), 2.97 (s, 4H), 2.82 (s, 2H), 1.14 (q, J=3.7 Hz, 2H), 0.85 (q, J=3.8 Hz, 2H). M+H+ 400.3

The following compounds were prepared in the same way as compound 218:

4-(2-(4-benzylphenyl)-7,8-dihydropyrido[4,3-d]pyrimidin-6(5H)-yl)pentanoic acid (compound 214)

Using ethyl 4-(2-chloro-7,8-dihydropyrido[4,3-d]pyrimidin-6(5H)-yl)pentanoate instead of methyl 1-((2-(4-benzylphenyl)-7,8-dihydropyrido[4,3-d]pyrimidin-6(5H)-yl)methyl)cyclopropanecarboxylate. Calculated mass: (C25H27N3O2): 401.501 g/mol. $^1$H NMR (600 MHz, DMSO-d$_6$) δ 12.42 (s, 1H), 10.67 (s, 1H), 8.75 (d, J=2.3 Hz, 1H), 8.33-8.28 (m, 2H), 7.40 (d, J=8.2 Hz, 2H), 7.34-7.25 (m, 4H), 7.25-7.18 (m, 1H), 4.50 (td, J=15.2, 13.4, 7.7 Hz, 2H), 4.03 (s, 2H), 3.75 (d, J=7.1 Hz, 1H), 3.63-3.50 (m, 2H), 3.24-3.10 (m, OH), 2.50-2.42 (m, 1H), 2.36 (ddd, J=16.6, 8.8, 6.6 Hz, 1H), 2.24-2.16 (m, 1H), 1.84-1.72 (m, 2H), 1.36 (s, 2H). M+H=402

3-(6-((2,6-dichlorobenzyl)oxy)-3,4-dihydro-2,7-naphthyridin-2(1H)-yl)propanoic acid hydrochloride (compound 219)

6-((2,6-dichlorobenzyl)oxy)-1,2,3,4-tetrahydro-2,7-naphthyridine

To solution of 6-chloro-1,2,3,4-tetrahydro-2,7-naphthyridine hydrochloride (500 mg; 2.44 mmol; 1 eq) in 30 mL toluene were added (2,6-dichlorophenyl)methanol (518 mg; 2.93 mmol; 1.2 eq), 1,4,7,10,13,16-hexaoxacyclooctadecane (18-Crown-6; 64.4 mg; 0.244 mmol; 1.1 eq) and KOH (547 mg; 9.75 mmol; 4 eq). The mixture was stirred for 3 h at RT. The mixture was evaporated and the residue was purified by flash chromatography (silica gel, DCM:MeOH 9:1) giving the product with a yield of 710 mg (1.378 mmol; 47%).

Tert-butyl 3-(6-((2,6-dichlorobenzyl)oxy)-3,4-dihydro-2,7-naphthyridin-2(1H)-yl)propanoate Preparation in accordance with scheme 6. To a solution of 6-((2,6-dichlorobenzyl)oxy)-1,2,3,4-tetrahydro-2,7-naphthyridine (80 mg; 0.259 mmol; 1 eq) in 10 mL acetonitrile were added tert-butyl 3-bromopropanoate (56.8 mg; 0.272 mmol; 1.05 eq) and triethylamine (131 mg; 1.29 mmol; 5 eq). The mixture was stirred at RT overnight. The mixture was extracted with water/ethylacetate. The organic phase was washed with water, dried with MgSO$_4$, and evaporated. The residue was purified by flash chromatography (4 g silica gel; 3-10% MeOH in DCM) giving the product with a yield of 40 mg (0.091 mmol; 35.3%).

Compound 219

Tert-butyl 3-(6-((2,6-dichlorobenzyl)oxy)-3,4-dihydro-2,7-naphthyridin-2(1H)-yl)propanoate (40 mg; 0.091 mmol; 1 eq) was dissolved in DCM and HCl in dioxin (600 mg; 2 mmol; 22 eq; 500 µL) was added. The HCl salt of the compound precipitates after a short period of time. 0.2 mL water was added and the mixture was stirred overnight at RT. The water phase was discarded and acetonitrile was added to the remaining phase. The precipitate containing the HCl salt was dried overnight under vacuum, giving compound 219 with a yield of 3.6 mg (3.59 mob 3.93%). Calculated mass (C18H18Cl2N2O3) 380.07 g/mol. $^1$H NMR (600 MHz, DMSO-d$_6$) δ 8.09 (s, 1H), 7.57 (d, J=8.1 Hz, 2H), 7.47 (dd, J=8.7, 7.5 Hz, 1H), 6.77 (s, 1H), 5.48 (s, 2H), 3.07 (t, J=6.2 Hz, 2H), 2.86 (t, J=7.5 Hz, 2H). M+H=381.1

3-(3-(4-(benzyloxy)phenyl)-7,8-dihydropyrido[3,4-b]pyrazin-6(5H)-yl)propanoic acid (compound 221)

3-(4-(benzyloxy)phenyl)-5,6,7,8-tetrahydropyrido[3,4-b]pyrazine

This compound was prepared from ethyl 3-(4-(benzyloxy)phenyl)-7,8-dihydropyrido[3,4-b]pyrazine-6(5H)-carboxylate, obtained as fraction 2 in the first step of the synthesis of compound XIa. Ethyl 3-(4-(benzyloxy)phenyl)-7,8-dihydropyrido[3,4-b]pyrazine-6(5H)-carboxylate (0.91 g; 2.34 mmol; 1 eq) was suspended in a 20% solution of KOH (2.62 g; 46.8 mmol; 20 eq) in EtOH. The mixture was heated for 30 min at 80° C., for a further 1 h at 90° C. 200 mL water and 200 mL DCM were then added to the reaction mixture. After phase separation, the organic phase was washed once with water, dried with MgSO$_4$ and evaporated giving the product with a yield of 0.75 g (2.363 mmol).

Tert-butyl 3-(3-(4-(benzyloxy)phenyl)-7,8-dihydropyrido[3,4-b]pyrazin-6(5H)-yl)propanoate 3-(4-(benzyloxy)phenyl)-5,6,7,8-tetrahydropyrido[3,4-b]pyrazine (300 mg; 0.95 mmol; 1 eq) was dissolved in MeOH. DBU (115 mg; 0.76 mmol; 0.8 mmol) and tert-butyl acrylate (363 mg; 2.84 mmol; 3 eq) were added under stirring at RT. The solution was evaporated. The residue was dissolve din DCM, washed once with a 10% NH$_4$Cl solution, extracted once with water, dried with MgSO$_4$ and evaporated. The oily residue was dissolve din a little DCM and purified by flash chromatography (silica gel, DCM/MeOH 95:5) giving the product with a yield of 406 mg (0.911 mmol; 96%).

Compound 221

Tert-butyl 3-(3-(4-(benzyloxy)phenyl)-7,8-dihydropyrido[3,4-b]pyrazin-6(5H)-yl)propanoate (75 mg; 0.17 mmol; 1 eq) was dissolved in MeOH (2 mL) and THF (2 mL). 1N NaOH (80 mg; 2 mmol; 11.9 eq) was added under stirring. The mixture was stirred 20 h at RT. The mixture was neutralized with 1 mL 1N HCl. The mixture was evaporated, washed with water and dried over P2O5 at 40° C. under vacuum, giving compound 221 with a yield of 56 mg (0.144 mmol; 85%). Calculated mass: (C23H23N3O3): 389.447 g/mol. $^1$H NMR (DMSO-d6, 600 MHz): δ=12.79 (d, J=8.3 Hz, 1H), 11.12-11.20 (m, 1H), 9.15 (s, 1H), 8.08-8.12 (m, 2H), 7.47-7.50 (m, 2H), 7.39-7.44 (m, 2H), 7.34-7.37 (m, 1H), 7.34 (t, J=1.2 Hz, 1H), 7.17-7.20 (m, 2H), 5.20 (s, 2H), 4.56 (br. s., 2H), 3.81 (br. s., 1H), 3.70-3.78 (m, 1H), 3.68 (br. s., 1H), 3.54-3.62 (m, 1H), 3.52 (br. s., 2H), 3.17 (br. s., 1H), 2.96 (t, J=7.4 Hz, 2H). M+H=390

The following compounds were prepared in the same way as compound 221

3-(3-(4-((3-chlorobenzyl)oxy)phenyl)-7,8-dihydropyrido[3,4-b]pyrazin-6(5H)-yl)propanoic acid (compound 222)

Using ethyl 3-(4-((3-chlorobenzyl)oxy)phenyl)-7,8-dihydropyrido[3,4-b]pyrazine-6(5H)-carboxylate instead of ethyl 3-(4-(benzyloxy)phenyl)-7,8-dihydropyrido[3,4-b]pyrazine-6(5H)-carboxylate. Calculated mass: (C23H22ClN3O3): 423.892 g/mol. $^1$H NMR (DMSO-d6, 600 MHz): δ=12.81 (br. s., 1H), 11.11 (br. s., 1H), 9.16 (s, 1H), 8.09-8.12 (m, 2H), 7.56 (s, 1H), 7.40-7.47 (m, 3H), 7.17-7.21 (m, 2H), 5.23 (s, 2H), 4.58 (br. s., 2H), 3.87 (br. s., 1H), 3.74 (dd, J=15.0, 7.1 Hz, 1H), 3.59-3.60 (m, 1H), 3.50-3.58 (m, 3H), 3.19 (dd, J=13.8, 7.1 Hz, 1H), 2.96 (t, J=7.5 Hz, 2H). M+H=424/426

3-(3-(4-((4-chlorobenzyl)oxy)phenyl)-7,8-dihydropyrido[3,4-b]pyrazin-6(5H)-yl)propanoic acid (compound 223)

ethyl 3-(4-((4-chlorobenzyl)oxy)phenyl)-7,8-dihydropyrido[3,4-b]pyrazine-6(5H)-carboxylate instead of ethyl 3-(4-(benzyloxy)phenyl)-7,8-dihydropyrido[3,4-b]pyrazine-6(5H)-carboxylate. Calculated mass: (C23H22ClN3O3): 423.892 g/mol. $^1$H NMR (500 MHz, DMSO-d$_6$) δ 8.95 (s, 1H), 8.25-7.79 (m, 2H), 7.70-7.33 (m, 4H), 7.21-6.88 (m, 2H), 5.19 (s, 2H), 3.74 (s, 2H), 3.09-2.75 (m, 6H). M+H=424/426

4-(2-(4-((3-chlorobenzyl)oxy)-2-fluorophenyl)-7,8-dihydropyrido[4,3-d]pyrimidin-6(5H)-yl)-3-methylbutanoic acid (compound 232)

Compound XXIIIf was converted to the corresponding pyrimidine (3-fluoro-4-(5,6,7,8-tetrahydropyrido[4,3-d]pyrimidin-2-yl)phenol) with TFA as described herein elsewhere, and was subsequently substituted in accordance with scheme 6: 393 mg 3-fluoro-4-(5,6,7,8-tetrahydropyrido[4,3-d]pyrimidin-2-yl)phenol 2,2,2 trifluoroacetate (1.094 mmol; 1 eq) was suspended in 10 ml THF to give a brown suspension. Triethylamine (100 mg; 0.984 mmol; 0.9 eq) was added to give a yellow solution. Ethyl 3-methyl-4-oxobutanoate (189 mg; 1.313 mmol; 1.2 eq) was added and the mixture was stirred at RT for 1 h, after which sodium triacetoxyborohydride (348 mg; 1.641 mmol; 1.5 eq) was added. 2 ml water was added to the reaction mixture, which was stirred for 5 min and concentrated under vacuum. DCM was added and after phase separation, the organic layer was washed twice with water, filtered and evaporated to give 394 mg ethyl 4-(2-(2-fluoro-4-hydroxyphenyl)-7,8-dihydropyrido[4,3-d]pyrimidin-6(5H)-yl)-3-methylbutanoate (1.055 mmol; 96%).

In accordance with scheme 7, step 2, 190 mg of this product (0.509 mmol; 1 eq) was dissolved in 5 ml DMF to give a colorless solution. Cesium carbonate (249 mg; 0.763 mmol; 1.5 eq) and 3-chlorobenzyl bromide (125 mg; 0.611 mmol; 1.2 eq) were added. The reaction mixture was stirred at RT overnight. The mixture was subsequently evaporated and the residue was dissolved in DCM and washed once with water. After phase separation, the organic layer was evaporated and the residue was purified by flash chromatography (4 g silica gel, 0-10% MeOH in DCM) to give 198 mg ethyl 4-(2-(4-((3-chlorobenzyl)oxy)-2-fluorophenyl)-7,8-dihydropyrido[4,3-d]pyrimidin-6(5H)-yl)-3-methylbutanoate (0.398 mmol; 78%). This product was converted to the corresponding carboxylic acid with NaOH as described herein elsewhere to give compound 232 with a yield of 86% (161 mg; 0.343 mmol). Calculated mass (C25H25ClFN3O3) 469.936 g/mol. $^1$H NMR (600 MHz, DMSO-d$_6$) δ 12.42 (s, 1H), 10.00 (s, 1H), 8.77 (s, 1H), 8.01 (t, J=8.8 Hz, 1H), 7.56 (d, J=1.9 Hz, 1H), 7.49-7.40 (m, 3H), 7.09-7.00 (m, 2H), 5.24 (s, 2H), 4.72 (s, 1H), 4.39 (s, 1H), 3.84 (s, 1H), 3.36-3.28 (m, 1H), 2.46 (d, J=19.4 Hz, 2H), 2.37 (s, 2H), 2.24 (s, 2H), 1.06 (s, 3H). M+H+ 470

The following compound was prepared in the same way as compound 232:

4-(2-(4-((4-chlorobenzyl)oxy)-2-fluorophenyl)-7,8-dihydropyrido[4,3-d]pyrimidin-6(5H)-yl)-3-methylbutanoic acid (compound 236)

Using 4-chlorobenzyl bromide instead of 3-chlorobenzyl bromide. Calculated mass (C25H25ClFN3O3) 469.936 g/mol. $^1$H NMR (600 MHz, DMSO-d$_6$) δ 12.41 (s, 1H), 9.81 (s, 1H), 8.76 (s, 1H), 8.00 (t, J=8.9 Hz, 1H), 7.54-7.46 (m, 4H), 7.07-6.98 (m, 2H), 5.22 (s, 2H), 4.72 (s, 1H), 4.39 (s, 1H), 3.84 (s, 1H), 3.55 (s, 1H), 3.36-3.29 (m, 1H), 2.23 (s, 2H), 1.06 (s, 3H). M+H+ 470

3-methyl-4-(2-(3-methyl-44(2-methylbenzyl)oxy)phenyl)-7,8-dihydropyrido[4,3-d]pyrimidin-6(5H)-yl)butanoic acid (compound 239)

Compound 239 was prepared starting from compound XXg in a palladium mediated reaction using (4-hydroxy-3-methylphenyl)boronic acid instead of compound VI as indicated in scheme 2. Compound XXg (2.13 g; 7.15 mmol; 1 eq), sodium carbonate (16.5 g; 15.57 mmol; 2.2 eq) and (4-hydroxy-3-methylphenyl)boronic acid (1.30 g; 8.58 mmol; 1.2 eq) were suspended in DMF (50 mL) to give a black suspension. The solution was stirred under Argon for 30 min. Tetrakis(triphenylphosphine)palladium(0) (248 mg; 0.215 mmol; 0.03 eq) was added and the reaction mixture was heated with a pre-heated oil-bath to 125° C. The reaction mixture was stirred for 2.5 h at 125° C. and evaporated. The residue was diluted in 125 ml water and neutralized to pH 5-6 with 15 ml 2N HCl and extracted with DCM. The organic layer was washed with a NaCl solution, dried over MgSO$_4$, and evaporated. The residue was purified by flash chromatography (40 g silica gel, 30% EtOAc/n-heptane) giving ethyl 4-(2-(4-hydroxy-3-methylphenyl)-7,8-dihydropyrido[4,3-d]pyrimidin-6(5H)-yl)-3-methylbutanoate with a yield of 1.59 g (4.30 mmol; 60.1%).

Ethyl 4-(2-(4-hydroxy-3-methylphenyl)-7,8-dihydropyrido[4,3-d]pyrimidin-6(5H)-yl)-3-methylbutanoate (100 mg; 0.271 mmol; 1 eq) was dissolved in DMF (5 mL) to give an orange solution. Cesium carbonate (132 mg; 0.406 mmol; 1.5 eq) and 2-methylbenzylbromide (60.1 mg; 0.325 mmol; 1.2 eq) were added. The mixture was stirred overnight at RT. The reaction mixture was extracted with DCM and H$_2$O. The organic layer was washed with NaCl, dried over MgSO$_4$, and evaporated. The residue was purified by flash chromatography (4 g silica gel, 0-10% MeOH in DCM) giving ethyl 3-methyl-4-(2-(3-methyl-4-((2-methylbenzyl)oxy)phenyl)-7,8-dihydropyrido[4,3-d]pyrimidin-6(5H)-yl)butanoate with a yield of 72 mg (0.152 mmol; 56.2%).

Ethyl 3-methyl-4-(2-(3-methyl-4-((2-methylbenzyl)oxy)phenyl)-7,8-dihydropyrido[4,3-d]pyrimidin-6(5H)-yl)butanoate (72.4 mg; 0.153 mmol; 1 eq) was dissolved in MeOH (1 mL) and THF (1 mL) to give a colorless solution. NaOH (0.382 mL; 0.764 mmol) was added and the reaction mixture was stirred overnight at RT. The reaction mixture was evaporated and the residue was diluted in water and neutralized with HCl and NaHCO$_3$. The mixture was extracted with DCM and the H2O layer was extracted again. The mixture was dried over MgSO$_4$, and evaporated. The precipitate was filtered, washed with 0.5 ml acetone and dried under vacuum at 40° C. giving compound 239 with a yield of 32.5 mg (0.073 mmol; 47.7%). Calculated mass (C27H31N3O3) 445.553 g/mol. $^1$H NMR (600 MHz, DMSO-d$_6$) δ 8.54 (s, 1H), 8.22-8.16 (m, 2H), 7.47 (d, J=7.2 Hz, 1H), 7.30-7.18 (m, 4H), 5.17 (s, 2H), 3.59 (s, 2H), 2.92 (d, J=12.5 Hz, 1H), 2.92 (s, 1H), 2.82 (dt, J=11.4, 5.7 Hz, 1H), 2.74 (dt, J=11.8, 6.0 Hz, 1H), 2.40-2.30 (m, 3H), 2.36 (s, 3H), 2.25 (s, 3H), 2.20 (dq, J=14.0, 7.0 Hz, 1H), 2.02 (dd, J=15.4, 7.7 Hz, 1H), 1.20 (s, 1H), 0.93 (d, J=6.6 Hz, 3H). M+H+ 446

The following compounds were made in the same way as compound 239:

(S)-3-methyl-4-(2-(3-methyl-44(2-methylbenzyl)oxy)phenyl)-7,8-dihydropyrido[4,3-d]pyrimidin-6(5H)-yl)butanoic acid (compound 249)

Calculated mass (C27H31N3O3) 445.553 g/mol. $^1$H NMR (500 MHz, DMSO-d$_6$) δ 8.69 (s, 1H), 8.35-8.29 (m, 2H), 7.36 (d, J=8.0 Hz, 2H), 7.21 (d, J=8.1 Hz, 2H), 7.17-7.10 (m, 2H), 5.14 (s, 2H), 3.30 (d, J=3.0 Hz, 1H), 2.50-2.41 (m, 1H), 2.31 (s, 3H), 2.22 (s, 1H), 2.17 (s, 1H), 1.04 (d, J=6.0 Hz, 3H). M+H+ 446

4-(2-(4-(benzyloxy)-3-methylphenyl)-7,8-dihydropyrido[4,3-d]pyrimidin-6(5H)-yl)-3-methylbutanoic acid (compound 251)

Using intermediate benzylbromide instead of 2-methylbenzylbromide. Calculated mass (C26H29N3O3) 431.527 g/mol. $^1$H NMR (600 MHz, DMSO-d$_6$) δ 12.43 (s, 1H), 9.89 (s, 1H), 8.71 (s, 1H), 8.21 (dq, J=4.8, 2.3 Hz, 2H), 7.53-7.48 (m, 2H), 7.43 (t, J=7.6 Hz, 2H), 7.39-7.32 (m, 1H), 7.20-7.14 (m, 1H), 5.23 (s, 2H), 4.71 (s, 1H), 4.37 (s, 1H), 3.84 (s, 2H), 3.46-3.38 (m, 2H), 3.37-3.28 (m, 1H), 2.29 (s, 4H), 1.07 (d, J=6.4 Hz, 3H). M+H+ 432

4-(2-(4-((3-chlorobenzyl)oxy)-3-methylphenyl)-7,8-dihydropyrido[4,3-d]pyrimidin-6(5H)-yl)-3-methylbutanoic acid (compound 252)

Using intermediate 2-chlorobenzylbromide instead of 2-methylbenzylbromide. Calculated mass (C26H28ClN3O3) 465.18 g/mol. $^1$H NMR (600 MHz, DMSO-d$_6$) δ 12.39 (s, 1H), 8.71 (s, 1H), 8.24-8.19 (m, 2H), 7.56 (q, J=1.3 Hz, 1H), 7.49-7.39 (m, 3H), 7.19-7.13 (m, 1H), 5.24 (s, 2H), 4.69 (s, 1H), 4.36 (s, 1H), 3.82 (s, 1H), 3.53 (s, 1H), 3.19 (s, 4H), 2.30 (s, 3H), 2.27-2.21 (m, 1H), 1.07 (d, J=6.4 Hz, 3H). M+H+ 466

4-(2-(4-((2,3-difluorobenzyl)oxy)-3-methylphenyl)-7,8-dihydropyrido[4,3-d]pyrimidin-6(5H)-yl)-3-methylbutanoic acid (compound 256)

Using intermediate 2,3-difluorobenzylbromide instead of 2-methylbenzylbromide. Calculated mass (C26H27F2N3O3) 467.508 g/mol. $^1$H NMR (600 MHz, Methanol-d$_4$) δ 8.58 (s, 1H), 8.25-8.19 (m, 2H), 7.36 (tt, J=6.0, 1.7 Hz, 1H), 7.31-7.23 (m, 1H), 7.20 (tdd, J=8.2, 4.8, 1.6 Hz, 1H), 7.12 (d, J=8.5 Hz, 1H), 5.28 (d, J=1.2 Hz, 2H), 4.25 (q, J=15.4 Hz, 2H), 3.31-3.18 (m, 2H), 3.04-2.95 (m, 2H), 2.53-2.45 (m, 2H), 2.43-2.35 (m, 1H), 2.30 (s, 3H), 1.10 (d, J=6.3 Hz, 3H). M+H+ 468

4-(2-(4-((4-chlorobenzyl)oxy)-3-methylphenyl)-7,8-dihydropyrido[4,3-d]pyrimidin-6(5H)-yl)-3-methylbutanoic acid (compound 258)

Using intermediate 4-chlorobenzylbromide instead of 2-methylbenzylbromide. Calculated mass (C26H28ClN3O3) 465.972 g/mol. $^1$H NMR (600 MHz, DMSO-d$_6$) δ 8.54 (s, 1H), 8.18 (s, 1H), 7.56-7.45 (m, 5H), 7.14-7.09 (m, 1H), 5.20 (s, 2H), 3.59 (s, 2H), 2.91 (d, J=12.6 Hz, 1H), 2.91 (s, 1H), 2.82 (dt, J=11.4, 5.6 Hz, 1H), 2.74 (dt, J=11.8, 6.0 Hz, 1H), 2.39-2.30 (m, 3H), 2.27 (s, 3H), 2.20 (dq, J=13.9, 7.1 Hz, 1H), 2.02 (dd, J=15.4, 7.6 Hz, 1H), 1.11 (s, 1H), 0.93 (d, J=6.6 Hz, 3H). M+H+ 466

4-(2-(4-((2-chlorobenzyl)oxy)-3-methylphenyl)-7,8-dihydropyrido[4,3-d]pyrimidin-6(5H)-yl)-3-methylbutanoic acid (compound 262)

Using intermediate 2-chlorobenzylbromide instead of 2-methylbenzylbromide. Calculated mass (C26H28ClN3O3) 465.972 g/mol. $^1$H NMR (600 MHz, DMSO-d$_6$) δ 8.54 (s, 1H), 8.19 (s, 1H), 7.69-7.64 (m, 1H), 7.58-7.52 (m, 1H), 7.46-7.38 (m, 2H), 7.16 (d, J=8.4 Hz, 1H), 5.25 (s, 2H), 3.60 (d, J=15.4 Hz, 1H), 3.53 (d, J=15.4 Hz, 1H), 2.92 (q, J=5.3, 4.9 Hz, 2H), 2.76 (hept, J=5.7 Hz, 2H), 2.36 (dd, J=11.8, 6.6 Hz, 1H), 2.28 (s, 3H), 2.24 (dd, J=11.8, 8.1 Hz, 1H), 2.17 (p, J=6.7 Hz, 1H), 2.08 (dd, J=14.5, 5.2 Hz, 1H), 1.75 (dd, J=14.4, 7.9 Hz, 1H), 0.89 (d, J=6.4 Hz, 3H). M+H+ 466

(S)-4-(2-(4-((4-chlorobenzyl)oxy)-3-methylphenyl)-7,8-dihydropyrido[4,3-d]pyrimidin-6(5H)-yl)-3-methylbutanoic acid (compound 270)

Using intermediate 4-chlorobenzylbromide instead of 2-methylbenzylbromide. Calculated mass (C26H28ClN3O3) 465.972 g/mol. $^1$H NMR (600 MHz, DMSO-d$_6$) δ 8.54 (s, 1H), 8.17 (d, J=7.5 Hz, 2H), 7.56-7.45 (m, 5H), 7.14-7.09 (m, 1H), 5.20 (s, 2H), 3.59 (s, 2H), 2.91 (d, J=12.5 Hz, 1H), 2.91 (s, 1H), 2.82 (dt, J=11.4, 5.7 Hz, 1H), 2.74 (dt, J=11.7, 5.9 Hz, 1H), 2.39-2.31 (m, 3H), 2.27 (s, 3H), 2.20 (dq, J=13.7, 7.0 Hz, 1H), 2.02 (dd, J=15.3, 7.6 Hz, 1H), 0.93 (d, J=6.6 Hz, 3H). M+H+ 466

3-methyl-4-(2-(3-methyl-4-((2-methyl-3-(trifluoromethyl)benzyl)oxy)phenyl)-7,8-dihydropyrido[4,3-d]pyrimidin-6(5H)-yl)butanoic acid (compound 273)

Using intermediate (2-methyl-3-trifluoromethyl)benzylbromide instead of 2-methylbenzylbromide. Calculated mass (C28H30F3N3O3) 513.551 g/mol. $^1$H NMR (600 MHz, DMSO-d$_6$) δ 12.12 (s, 1H), 8.55 (s, 1H), 8.23-8.18 (m, 2H), 7.81 (d, J=7.4 Hz, 1H), 7.70 (dd, J=8.1, 1.2 Hz, 1H), 7.46 (t, J=7.8 Hz, 1H), 7.23 (d, J=8.6 Hz, 1H), 5.29 (s, 2H), 3.60 (s, 2H), 2.92 (d, J=12.3 Hz, 1H), 2.92 (s, 1H), 2.83 (dt, J=11.5, 5.7 Hz, 1H), 2.75 (dt, J=11.7, 6.0 Hz, 1H), 2.39-2.31 (m, 3H), 2.27 (s, 3H), 2.23-2.17 (m, 1H), 2.03 (dd, J=15.3, 7.6 Hz, 1H), 0.93 (d, J=6.6 Hz, 3H). M+H+ 514

(R)-3-methyl-4-(2-(3-methyl-44(2-methylbenzyl)oxy)phenyl)-7,8-dihydropyrido[4,3-d]pyrimidin-6(5H)-yl)butanoic acid (compound 303)

Calculated mass (C27H31N3O3) 445.553 g/mol. $^1$H NMR (600 MHz, DMSO-d$_6$) δ 8.55 (s, 1H), 8.22-8.16 (m, 2H), 7.49-7.45 (m, 1H), 7.30-7.18 (m, 5H), 5.18 (s, 2H), 3.60 (s, 2H), 2.93 (s, 2H), 2.83 (s, 1H), 2.75 (s, 1H), 2.47 (h, J=1.5 Hz, 1H), 2.39-2.31 (m, 1H), 2.36 (s, 4H), 2.25 (s, 3H), 2.20 (d, J=13.2 Hz, 1H), 2.03 (dd, J=15.5, 7.5 Hz, 1H), 0.93 (d, J=6.6 Hz, 3H). M+H+ 446

(R)-4-(2-(4-((4-chlorobenzyl)oxy)-3-methylphenyl)-7,8-dihydropyrido[4,3-d]pyrimidin-6(5H)-yl)-3-methylbutanoic acid (compound 318)

Using intermediate 4-chlorobenzylbromide instead of 2-methylbenzylbromide. Calculated mass (C26H28ClN3O3) 465.972 g/mol. $^1$H NMR (600 MHz, DMSO-d$_6$) δ 12.15 (s, 1H), 8.54 (s, 1H), 8.17 (d, J=7.5 Hz, 2H), 7.56-7.45 (m, 4H), 7.14-7.09 (m, 1H), 5.20 (s, 2H), 3.59 (s, 2H), 2.91 (d, J=12.5 Hz, 1H), 2.91 (s, 1H), 2.82 (dt, J=11.4, 5.7 Hz, 1H), 2.74 (dt, J=11.7, 5.9 Hz, 1H), 2.39-2.31 (m, 3H), 2.33-2.27 (m, OH), 2.27 (s, 3H), 2.20 (dq, J=13.7, 7.0 Hz, 1H), 2.02 (dd, J=15.3, 7.6 Hz, 1H), 0.93 (d, J=6.6 Hz, 3H). M+H+ 466

(S)-4-(2-(4-(benzyloxy)-3-methylphenyl)-7,8-dihydropyrido[4,3-d]pyrimidin-6(5H)-yl)-3-methylbutanoic acid (compound 261) and (R)-4-(2-(4-(benzyloxy)-3-methylphenyl)-7,8-dihydropyrido[4,3-d]pyrimidin-6(5H)-yl)-3-methylbutanoic acid (compound 319)

are the pure enantiomers of compound 251 and were obtained by enantiomer separation as described for compounds 212 and 213.
Compound 261:
Calculated mass (C26H29N3O3) 431.527 g/mol. $^1$H NMR (600 MHz, Methanol-d$_4$) δ 8.51 (s, 1H), 8.19-8.13 (m, 2H), 7.50-7.45 (m, 2H), 7.42-7.36 (m, 2H), 7.35-7.28 (m, 1H), 7.06 (d, J=8.4 Hz, 1H), 5.18 (s, 2H), 4.02 (d, J=15.3 Hz, 1H), 3.94 (d, J=15.3 Hz, 1H), 3.28 (s, 1H), 3.11 (dp, J=19.7, 6.6, 6.2 Hz, 3H), 2.77-2.69 (m, 2H), 2.51-2.27 (m, 3H), 2.32 (s, 3H), 1.03 (d, J=6.7 Hz, 3H). M+H+ 432
Compound 319:
Calculated mass (C26H29N3O3) 431.527 g/mol. $^1$H NMR (600 MHz, DMSO-d$_6$) δ 8.54 (s, 1H), 8.20-8.15 (m, 2H), 7.53-7.47 (m, 2H), 7.42 (dd, J=8.4, 6.8 Hz, 2H), 7.34 (t, J=7.3 Hz, 1H), 7.14 (d, J=9.4 Hz, 1H), 5.20 (s, 2H), 3.59 (s, 2H), 2.92 (d, J=12.3 Hz, 1H), 2.92 (s, 1H), 2.82 (s, 1H), 2.75 (s, 1H), 2.54 (q, J=1.8 Hz, 1H), 2.36 (d, J=15.6 Hz, 1H), 2.35 (s, 2H), 2.28 (s, 3H), 2.23-2.17 (m, 1H), 2.03 (dd, J=15.4, 7.6 Hz, 1H), 0.93 (d, J=6.6 Hz, 3H). M+H+ 432

4-(2-(4-(4-chlorophenethyl)phenyl)-7,8-dihydropyrido[4,3-d]pyrimidin-6(5H)-yl)-3-methylbutanoic acid (compound 244)

Compound XLIa was converted to the corresponding pyrimidine ((E)-2-(4-(4-chlorostyryl)phenyl)-5,6,7,8-tetrahydropyrido[4,3-d]pyrimidine) with TFA as described herein elsewhere, and was subsequently substituted in accordance with scheme 5: 337 mg of the pyrimidine (0.969 mmol; 1 eq) was suspended in 10 ml THF and 10 ml MeOH. Ethyl 3-methyl-4-oxobutanoate (419 mg; 2.91 mmol; 3 eq) was added under stirring and Argon atmosphere at RT. 100 µl acetic acid was added (pH 3). The mixture was stirred for 1 h at RT and subsequently sodium triacetoxyborohydride (657 mg; 3.10 mmol; 3.2 eq) was added followed by a further stirring for 2 h at RT. The mixture was evaporated and the residue was extracted with 30 ml DCM and 30 ml water for 1 h. The organic phase was washed with water, dried over MgSO$_4$ and evaporated. The solid residue was dissolved in DCM and purified flash chromatography (n-heptane/ethylacetate 2:1) giving 400 mg (E)-ethyl 4-(2-(4-(4-chlorostyryl)phenyl)-7,8-dihydropyrido[4,3-d]pyrimidin-6(5H)-yl)-3-methylbutanoate (0.840 mmol; 87%).

350 mg thereof (0.735 mmol; 1 eq) was dissolved in 30 ml THF/30 ml MeOH. Pd—C (50 mg; 0.470 mmol; 0.64 eq) was added under argon atmosphere. The mixture was hydrogenated by stirring at RT for 1 h. The reaction mixture was filtered to remove Pd—C and evaporated. HPLC chromatography was performed on the semi-solid residue to separate by-product ethyl 3-methyl-4-(2-(4-phenethylphenyl)-7,8-dihydropyrido[4,3-d]pyrimidin-6(5H)-yl)butanoate. The remaining residue was evaporated giving ethyl 4-(2-(4-(4-chlorophenethyl)phenyl)-7,8-dihydropyrido[4,3-d]pyrimidin-6(5H)-yl)-3-methylbutanoate with a yield of 85% (300 mg; 0.628 mmol).

This product was converted to the corresponding butanoic acid with NaOH as described herein elsewhere to give compound 244 with a yield of 49.2% (139 mg; 0.309 mmol). Calculated mass (C26H28ClN3O2) 449.972 g/mol. 1H NMR (600 MHz, DMSO-d$_6$) δ 12.11 (s, 1H), 8.61 (s, 1H), 8.29-8.23 (m, 2H), 7.37-7.27 (m, 4H), 7.31-7.23 (m, 2H), 2.93 (d, J=3.0 Hz, 8H), 2.44-2.30 (m, 2H), 2.25 (d, J=12.4 Hz, 1H), 2.10-2.03 (m, 1H), 0.95 (d, J=6.4 Hz, 3H). M+H+ 450

(R)-4-(2-(4-(4-chlorophenethyl)phenyl)-7,8-dihydropyrido[4,3-d]pyrimidin-6(5H)-yl)-3-methylbutanoic acid (compound 237) and (S)-4-(2-(4-(4-chlorophenethyl)phenyl)-7,8-dihydropyrido[4,3-d]pyrimidin-6(5H)-yl)-3-methylbutanoic acid (compound 278)

Compounds 237 and 278 are the pure enantiomers of compound 244 and were obtained by enantiomer separation as described for compounds 212 and 213.

(R)-4-(2-(4-(4-chlorophenethyl)phenyl)-7,8-dihydropyrido[4,3-d]pyrimidin-6(5H)-yl)-3-methylbutanoic acid (compound 237)

Calculated mass (C26H28ClN3O2) 449.972 g/mol. 1H NMR (600 MHz, DMSO-d$_6$) δ 12.08 (s, 1H), 8.59 (s, 1H), 8.28-8.22 (m, 2H), 7.37-7.29 (m, 4H), 7.29-7.23 (m, 2H), 3.61 (s, 2H), 2.92 (q, J=2.5 Hz, 6H), 2.84 (dd, J=11.7, 5.7

Hz, 1H), 2.75 (dt, J=11.9, 6.0 Hz, 1H), 2.40-2.31 (m, 3H), 2.20 (dq, J=13.9, 7.0 Hz, 1H), 2.03 (dd, J=15.4, 7.6 Hz, 1H), 0.93 (d, J=6.6 Hz, 3H). M+H+ 450

(S)-4-(2-(4-(4-chlorophenethyl)phenyl)-7,8-dihydropyrido[4,3-d]pyrimidin-6(5H)-yl)-3-methylbutanoic acid (compound 278)

Calculated mass (C26H28ClN3O2) 449.972 g/mol. M+H+ 450

The following compounds were prepared in the same way as compound 244:

4-(2-(4-(4-chloro-2-fluorophenethyl)phenyl)-7,8-dihydropyrido[4,3-d]pyrimidin-6(5H)-yl)-3-methylbutanoic acid (compound 250)

Using compound XLIb instead of compound XLIa. Calculated mass (C26H27ClFN3O2) 467.963 g/mol. 1H NMR (500 MHz, DMSO-d$_6$) δ 12.06 (s, 1H), 8.58 (s, 1H), 8.29-8.22 (m, 2H), 7.39-7.28 (m, 4H), 7.19 (dd, J=8.2, 2.1 Hz, 1H), 3.62 (s, 2H), 2.93 (s, 6H), 2.84 (d, J=7.5 Hz, 1H), 2.77 (s, 1H), 2.36 (dd, J=15.1, 5.9 Hz, 2H), 2.20 (dq, J=14.0, 7.0 Hz, 1H), 2.03 (dd, J=15.3, 7.6 Hz, 1H), 0.93 (d, J=6.6 Hz, 3H). M+H+ 468

4-(2-(4-(4-chlorophenethyl)-2-fluorophenyl)-7,8-dihydropyrido[4,3-d]pyrimidin-6(5H)-yl)-3-methylbutanoic acid (compound 255)

Using compound XLIc instead of compound XLIa. Calculated mass (C26H27ClFN3O2) 467.963 g/mol. 1H NMR (600 MHz, DMSO-d$_6$) δ 12.09 (s, 1H), 8.63 (s, 1H), 7.85 (t, J=8.1 Hz, 1H), 7.34 (d, J=8.0 Hz, 2H), 7.28 (d, J=8.0 Hz, 2H), 7.17 (dd, J=18.5, 10.0 Hz, 2H), 3.65 (s, 2H), 2.94 (d, J=9.6 Hz, 6H), 2.90-2.82 (m, 1H), 2.77 (s, 1H), 2.38 (dq, J=15.3, 9.0, 5.9 Hz, 1H), 2.21 (h, J=6.9 Hz, 1H), 2.04 (dd, J=15.3, 7.6 Hz, 1H), 0.94 (d, J=6.5 Hz, 3H). M+H+ 468

4-(2-(2-fluoro-4-phenethylphenyl)-7,8-dihydropyrido[4,3-d]pyrimidin-6(5H)-yl)-3-methylbutanoic acid (compound 280)

Using compound XLId instead of compound XLIa. Calculated mass (C26H28FN3O2) 433.518 g/mol. 1H NMR (600 MHz, DMSO-d$_6$) δ 12.07 (s, 1H), 8.62 (s, 1H), 7.85 (t, J=8.1 Hz, 1H), 7.38-7.22 (m, 4H), 7.25-7.11 (m, 3H), 3.63 (s, 2H), 2.95 (tt, J=16.1, 6.3 Hz, 6H), 2.84 (dt, J=11.4, 5.7 Hz, 1H), 2.75 (dt, J=11.7, 5.9 Hz, 1H), 2.37 (ddd, J=10.5, 6.1, 3.9 Hz, 3H), 2.21 (dq, J=14.0, 7.0 Hz, 1H), 2.08-1.99 (m, 1H), 0.93 (d, J=6.6 Hz, 3H). M+H+ 434

4-(2-(4-(4-chloro-2-fluorostyryl)phenyl)-7,8-dihydropyrido[4,3-d]pyrimidin-6(5H)—O-3-methylbutanoic acid (compound 282)

Using compound XLIb instead of compound XLIa. Further, instead of hydrogenation using Pd—C, the (E)-ethyl 4-(2-(4-(2-fluoro-4-chlorostyryl)phenyl)-7,8-dihydropyrido[4,3-d]pyrimidin-6(5H)-yl)-3-methylbutanoate is directly converted to the butanoic acid derivative using NaOH. Calculated mass (C26H25ClFN3O2) 465.947 g/mol. 1H NMR (600 MHz, DMSO-d$_6$) δ 12.10 (s, 1H), 8.62 (s, 1H), 8.41-8.35 (m, 2H), 7.88 (t, J=8.5 Hz, 1H), 7.80-7.74 (m, 2H), 7.55-7.29 (m, 4H), 3.63 (s, 2H), 2.95 (t, J=6.1 Hz, 2H), 2.84 (dt, J=11.5, 5.8 Hz, 1H), 2.76 (dt, J=11.8, 6.0 Hz, 1H), 2.48-2.31 (m, 3H), 2.21 (h, J=7.1 Hz, 1H), 2.03 (dd, J=15.3, 7.6 Hz, 1H), 0.93 (d, J=6.6 Hz, 3H). M+H+ 466

4-(2-(4-(3-chlorophenethyl)-2-fluorophenyl)-7,8-dihydropyrido[4,3-d]pyrimidin-6(5H)-yl)-3-methylbutanoic acid (compound 292)

Using compound XLIe instead of compound XLIa. Calculated mass (C26H27ClFN3O2) 467.963 g/mol. 1H NMR (600 MHz, DMSO-d$_6$) δ 12.15 (s, 1H), 8.63 (s, 1H), 7.86 (t, J=8.0 Hz, 1H), 7.37 (s, 1H), 7.32 (t, J=7.8 Hz, 1H), 7.30-7.13 (m, 4H), 3.63 (s, 2H), 3.01-2.87 (m, 6H), 2.84 (dt, J=11.4, 5.7 Hz, 1H), 2.75 (dt, J=11.7, 6.0 Hz, 1H), 2.37 (ddd, J=10.4, 5.9, 3.7 Hz, 3H), 2.21 (dq, J=14.0, 7.0 Hz, 1H), 2.03 (dd, J=15.4, 7.6 Hz, 1H), 0.93 (d, J=6.6 Hz, 3H). M+H+ 468

4-(2-(4-(4-chlorostyryl)phenyl)-7,8-dihydropyrido[4,3-d]pyrimidin-6(5H)-yl)-3-methylbutanoic acid (compound 297)

whereby (E)-ethyl 4-(2-(4-(4-chlorostyryl)phenyl)-7,8-dihydropyrido[4,3-d]pyrimidin-6(5H)-yl)-3-methylbutanoate is directly converted to the butanoic acid derivative using NaOH instead of hydrogenated using Pd—C. Calculated mass (C26H26ClN3O2) 447.957 g/mol. 1H NMR (600 MHz, DMSO-d6) δ 12.10 (s, 1H), 8.62 (s, 1H), 8.40-8.34 (m, 2H), 7.77-7.69 (m, 2H), 7.73-7.63 (m, 2H), 7.51-7.42 (m, 2H), 7.38 (d, J=1.3 Hz, 2H), 3.64 (s, 2H), 2.96 (d, J=12.2 Hz, 1H), 2.96 (s, 1H), 2.86 (s, 1H), 2.78 (s, 1H), 2.42-2.33 (m, 3H), 2.21 (h, J=7.0 Hz, 1H), 2.04 (dd, J=15.4, 7.6 Hz, 1H), 0.94 (d, J=6.5 Hz, 3H). M+H+ 448

4-(2-(4-(2-(4-chloro-2-fluorophenyl)-1-fluoroethyl)phenyl)-7,8-dihydropyrido[4,3-d]pyrimidin-6(5H)—O-3-methylbutanoic acid (compound 253)

Tert-butyl 2-(4-(2-(4-chloro-2-fluorophenyl)-1-fluoroethyl)phenyl)-7,8-dihydropyrido[4,3-d]pyrimidine-6(5H)-carboxylate was converted to the corresponding pyrimidine (2-(4-(2-(4-chloro-2-fluorophenyl)-1-fluoroethyl)phenyl)-5,6,7,8-tetrahydropyrido[4,3-d]pyrimidine) with TFA as described herein elsewhere, and was subsequently substituted in accordance with scheme 5 using ethyl 3-methyl-4-oxobutanoate in the presence of sodium triacetoxyborohydride as described herein elsewhere, e.g. for compound 244, resulting in 359 mg ethyl 4-(2-(4-(2-(4-chloro-2-fluorophenyl)-1-fluoroethyl)phenyl)-7,8-dihydropyrido[4,3-d]pyrimidin-6(5H)-yl)-3-methylbutanoate (0.698 mmol; 93%).

The whole product (358 mg; 0.698 mmol; 1 eq) was converted into the corresponding carboxylic acid with 2N NaOH (3.5 ml; 7 mmol; 10.05 eq) as described herein elsewhere to give compound 253 with a yield of 264 mg (0.543 mmol; 78%). Calculated mass (C26H26ClF2N3O2) 485.953 g/mol. 1H NMR (600 MHz, DMSO-d6) δ 12.39 (s, 1H), 10.43 (s, 1H), 8.80 (s, 1H), 8.40 (d, J=8.0 Hz, 2H), 7.54 (d, J=8.3 Hz, 2H), 7.51-7.30 (m, 2H), 7.26 (dd, J=8.2, 2.1 Hz, 1H), 5.88 (ddd, J=47.2, 8.1, 4.7 Hz, 1H), 4.71 (s, 1H), 4.39 (s, 1H), 3.83 (s, 1H), 3.54 (s, 1H), 3.45-3.12 (m, 3H), 2.44 (s, 1H), 2.24 (dd, J=16.4, 7.6 Hz, 1H), 1.09 (d, J=6.4 Hz, 3H). M+H+ 486

4-(2-(4-((4-chlorobenzyl)oxy)phenyl)-7,8-dihydropyrido[4,3-d]pyrimidin-6(5H)-yl)-3-methylbutanoic acid (compound 259)

Calculated mass (C25H26ClN3O3) 451.945 g/mol. 1H NMR (600 MHz, DMSO-d$_6$) δ 12.38 (s, 1H), 10.69 (d, J=42.8 Hz, 1H), 8.73 (s, 1H), 8.34 (d, J=8.5 Hz, 2H), 7.68-7.33 (m, 4H), 7.16 (d, J=8.6 Hz, 2H), 5.20 (s, 2H), 4.68 (t, J=16.8 Hz, 1H), 4.41-4.31 (m, 1H), 3.77 (s, 1H), 3.52 (d, J=12.3 Hz, 1H), 3.41 (dd, J=20.5, 9.0 Hz, 1H), 3.28-3.17 (m, 2H), 2.25 (dt, J=15.4, 6.4 Hz, 1H), 1.13-1.07 (m, 3H). M+H+ 452

4-(2-(4-(2-(4-chlorophenyl)-1,1-difluoroethyl)phenyl)-7,8-dihydropyrido[4,3-d]pyrimidin-6(5H)-yl)-3-methylbutanoic acid (compound 265)

Ethyl 4-(2-chloro-7,8-dihydropyrido[4,3-d]pyrimidin-6(5H)-yl)-3-methylbutanoate (compound XXg; 200 mg; 0.672 mmol; 1 eq) was dissolved in 4 ml DMF. 2-(4-(2-(4-chlorophenyl)-1,1-difluoroethyl)phenyl)-4,4,5,5-tetramethyl-1,3,2-dioxaborolane (305 mg; 0.806 mmol; 1.2 eq) and sodium carbonate (1.78 g; 1.679 mmol; 2.5 eq) were added under stirring and the mixture was degassed with Argon for 5 min. Tetrakis(triphenylphosphine)palladium(0) (31.0 mg; 0.027 mmol; 0.04 eq) was added and the mixture was heated for 30 min at 120° C. The mixture was evaporated and the residue was extracted with DCM and water. The organic phase was washed once with water, dried over MgSO$_4$ and evaporated. The oily residue was dissolved in DCM and purified by flash chromatography (n-heptane/ethylacetate 2:1) giving 233 mg ethyl 4-(2-(4-(2-(4-chlorophenyl)-1,1-difluoroethyl)phenyl)-7,8-dihydropyrido[4,3-d]pyrimidin-6(5H)-yl)-3-methylbutanoate (0.453 mmol; 67.5%).

The whole product (233 mg; 0.453 mmol; 1 eq) was dissolved in 4 ml THF/4 ml MeOH. 1N NaOH (180 mg; 4.50 mmol; 9.93 eq) was added under stirring and the mixture was stirred for a further 20 h at RT. The reaction mixture was neutralized with 4.5 ml 1N HCl and evaporated. The residue was diluted with a little water and extracted twice with DCM. The organic phase dried over MgSO$_4$ and evaporated. The residue was dissolved in 2 ml DCM and purified by flash chromatography (DCM/MeOH 95:5) giving 4-(2-(4-(2-(4-chlorophenyl)-1,1-difluoroethyl)phenyl)-7,8-dihydropyrido[4,3-d]pyrimidin-6(5H)-yl)-3-methylbutanoic acid with a yield of 100% (220 mg; 0.453 mmol). The product (215 mg; 0.442 mmol) was purified dissolving in 4 ml THF/4 ml MeOH and adding 4M HCl in dioxane. The mixture was evaporated and the residue taken up in pentane. This was evaporated and dried at 50° C. under vacuum giving compound 265 with a yield of 78% (180 mg; 0.345 mmol). Calculated mass (C26H26ClF2N3O2) 485.953 g/mol. 1H NMR (600 MHz, DMSO-d$_6$) δ 12.39 (s, 1H), 10.57-10.06 (m, 1H), 8.82 (s, 1H), 8.44 (d, J=8.3 Hz, 2H), 7.63 (d, J=8.6 Hz, 2H), 7.38-7.32 (m, 2H), 7.24-7.18 (m, 2H), 4.73 (s, 1H), 3.65 (d, J=16.8 Hz, 2H), 2.45 (s, 2H), 2.29-2.20 (m, 1H), 1.09 (d, J=6.4 Hz, 3H). M+H+ 486

4-(2-(4-(2-(4-chlorophenyl)-1,1-difluoroethyl)phenyl)-7,8-dihydropyrido[4,3-d]pyrimidin-6(5H)-yl)-3-methylbutanoic acid, enantiomer 1 and 2 (compounds 266 and 294)

Compounds 266 and 294 are the pure enantiomers of compound 265 and were obtained by enantiomer separation as described for compounds 212 and 213.

4-(2-(4-(2-(4-chlorophenyl)-1,1-difluoroethyl)phenyl)-7,8-dihydropyrido[4,3-d]pyrimidin-6(5H)-yl)-3-methylbutanoic acid, enantiomer 1 (compound 266)

Calculated mass (C26H26ClF2N3O2) 485.953 g/mol. M+H+ 486

4-(2-(4-(2-(4-chlorophenyl)-1,1-difluoroethyl)phenyl)-7,8-dihydropyrido[4,3-d]pyrimidin-6(5H)-yl)-3-methylbutanoic acid, enantiomer 2 (compound 294)

Calculated mass (C26H26ClF2N3O2) 485.953 g/mol. M+H+ 486

The following compounds were prepared in the same way as compound 265:

4-(2-(4-(2-(3-chlorophenyl)-1,1-difluoroethyl)phenyl)-7,8-dihydropyrido[4,3-d]pyrimidin-6(5H)-yl)-3-methylbutanoic acid (compound 328)

Using 2-(4-(2-(3-chlorophenyl)-1,1-difluoroethyl)phenyl)-4,4,5,5-tetramethyl-1,3,2-dioxaborolane instead of 2-(4-(2-(4-chlorophenyl)-1,1-difluoroethyl)phenyl)-4,4,5,5-tetramethyl-1,3,2-dioxaborolane. Calculated mass (C26H26ClF2N3O2) 485,953 g/mol. 1H NMR (600 MHz, DMSO-d6) δ 12.39 (s, 1H), 10.29 (s, 1H), 8.83 (s, 1H), 8.46 (d, J=8.4 Hz, 2H), 7.73-7.63 (m, 2H), 7.38-7.26 (m, 3H), 7.21-7.14 (m, 1H), 4.74 (s, 1H), 4.41 (s, 1H), 3.85 (s, 1H), 3.68 (d, J=17.0 Hz, 2H), 2.25 (dd, J=16.1, 7.4 Hz, 1H), 1.15-1.03 (m, 3H). M+H+ 486

4-(2-(4-(2-(4-chlorophenyl)cyclopropyl)phenyl)-7,8-dihydropyrido[4,3-d]pyrimidin-6(5H)-yl)-3-methylbutanoic acid (compound 323)

Using 2-(4-(2-(4-chlorophenyl)cyclopropyl)phenyl)-4,4,5,5-tetramethyl-1,3,2-dioxaborolane instead of 2-(4-(2-(4-chlorophenyl)-1,1-difluoroethyl)phenyl)-4,4,5,5-tetramethyl-1,3,2-dioxaborolane. Calculated mass (C27H28ClN3O2) 461.983 g/mol. 1H NMR (600 MHz, DMSO-d$_6$) δ 12.11 (s, 1H), 8.54 (s, 1H), 8.10-8.04 (m, 2H), 7.17-7.08 (m, 4H), 7.07-7.00 (m, 2H), 3.58 (s, 2H), 2.89 (d, J=12.2 Hz, 1H), 2.80 (dt, J=11.5, 5.7 Hz, 1H), 2.72 (dt, J=11.7, 5.9 Hz, 1H), 2.63-2.51 (m, 2H), 2.39-2.29 (m, 3H), 2.18 (h, J=7.0 Hz, 1H), 2.01 (dd, J=15.3, 7.6 Hz, 1H), 1.64 (q, J=6.1 Hz, 1H), 1.46 (td, J=8.5, 5.5 Hz, 1H), 0.92 (d, J=6.6 Hz, 3H). M+H+ 462

4-(2-(4-(2-(3-chlorophenyl)cyclopropyl)phenyl)-7,8-dihydropyrido[4,3-d]pyrimidin-6(5H)-yl)-3-methylbutanoic acid (compound 293)

Using 2-(4-(2-(3-chlorophenyl)cyclopropyl)phenyl)-4,4,5,5-tetramethyl-1,3,2-dioxaborolane instead of 2-(4-(2-(4-chlorophenyl)-1,1-difluoroethyl)phenyl)-4,4,5,5-tetramethyl-1,3,2-dioxaborolane. Calculated mass (C27H28ClN3O2) 461.983 g/mol. 1H NMR (600 MHz, DMSO-d6) δ 12.38 (s, 1H), 10.33 (s, 1H), 8.75 (d, J=27.3 Hz, 1H), 8.33-8.28 (m, 2H), 7.43-6.95 (m, 6H), 4.71 (s, 1H), 4.37 (s, 1H), 3.83 (s, 1H), 3.32-3.08 (m, 3H), 2.68-2.56 (m, 1H), 2.40-2.31 (m, 2H), 2.25 (s, 1H), 1.63-1.55 (m, 2H), 1.13-1.05 (m, 4H). M+H+ 462

(S)-4-(2-(4-((4-chlorobenzyl)oxy)phenyl)-5-oxo-7,8-dihydropyrido[4,3-d]pyrimidin-6(5H)-yl)-3-methylbutanoic acid (compound 267)

Calculated mass (C25H24ClN3O4) 465.929 g/mol. 1H NMR (600 MHz, DMSO-d$_6$) δ 12.11 (s, 1H), 9.06 (s, 1H), 8.46-8.38 (m, 2H), 7.56-7.48 (m, 2H), 7.52-7.45 (m, 2H), 7.23-7.14 (m, 2H), 5.21 (s, 2H), 3.68 (s, 2H), 3.39 (d, J=7.2 Hz, 2H), 3.17 (dd, J=7.3, 6.1 Hz, 2H), 2.37-2.24 (m, 2H), 2.13-2.03 (m, 1H), 0.93 (d, J=6.5 Hz, 3H). M+H+ 466

4-(2-(4-(2-(4-chloro-2-fluorophenyl)-1,1-difluoroethyl)phenyl)-7,8-dihydropyrido[4,3-d]pyrimidin-6(5H))—O-3-methylbutanoic acid (compound 277)

Compound XLa was converted into the corresponding pyrimidine (2-(4-(2-(4-chloro-2-fluorophenyl)-1,1-difluoroethyl)phenyl)-5,6,7,8-tetrahydropyrido[4,3-d]pyrimidine) with TFA as described herein elsewhere, which was subsequently substituted in accordance with scheme 5 using ethyl 3-methyl-4-oxobutanoate in the presence of sodium triacetoxyboronhydride as described herein elsewhere, e.g. for compound 244, resulting in ethyl 4-(2-(4-(2-(4-chloro-2-fluorophenyl)-1,1-difluoroethyl)phenyl)-7,8-dihydropyrido[4,3-d]pyrimidin-6(5H)-yl)-3-methylbutanoate (123 mg; 0.231 mmol; 43.6%). This compound was converted to the butanoic acid using NaOH as described herein elsewhere giving 98 mg of compound 277 (0.194 mmol; 84%). Calculated mass (C26H25ClF3N3O2) 503.944 g/mol. 1H NMR (600 MHz, DMSO-d$_6$) δ 12.39 (s, 1H), 10.37 (s, 1H), 10.30 (s, 1H), 8.83 (s, 1H), 8.46 (d, J=8.3 Hz, 2H), 7.67-7.61 (m, 2H), 7.41 (dd, J=9.7, 2.1 Hz, 1H), 7.33 (t, J=8.1 Hz, 1H), 7.27 (dd, J=8.2, 2.1 Hz, 1H), 4.74 (s, 1H), 4.41 (s, 1H), 3.68-3.54 (m, 2H), 3.24 (s, 1H), 2.50-2.42 (m, 2H), 2.25 (dd, J=16.4, 7.5 Hz, 1H), 1.12-1.06 (m, 4H). M+H+ 504

2-((4(2-(4-((4-chlorobenzyl)oxy)phenyl)-7,8-dihydropyrido[4,3-d]pyrimidin-6(5H)-yl)methyl)cyclopropyl)acetic acid (compounds 281 and 286)

compound 281: Calculated mass (C26H26ClN3O3) 463.956 g/mol. 1H NMR (600 MHz, DMSO-d$_6$) δ 12.33 (s, 1H), 10.28 (s, 1H), 8.76 (s, 1H), 8.37-8.31 (m, 2H), 7.54-7.45 (m, 4H), 7.19-7.13 (m, 2H), 5.20 (s, 2H), 4.71 (s, 1H), 4.38 (s, 1H), 3.91 (s, 1H), 3.47 (s, 2H), 3.28 (s, 2H), 3.19 (s, 1H), 2.63 (s, 1H), 0.76 (s, 2H), 0.67 (s, 2H). M+H+ 464 compound 286: Calculated mass (C26H26ClN3O3) 463.956 g/mol. 1H NMR (600 MHz, DMSO-d$_6$) δ 8.56 (s, 1H), 8.34-8.27 (m, 2H), 7.54-7.44 (m, 5H), 7.16-7.09 (m, 2H), 5.19 (s, 2H), 3.65 (s, 2H), 2.93 (t, J=5.9 Hz, 2H), 2.86 (t, J=5.9 Hz, 2H), 2.49 (s, 1H), 2.30 (s, 2H), 0.55-0.47 (m, 2H), 0.46-0.40 (m, 2H). M+H+ 464

2-((4(2-(4-((3-chlorobenzyl)oxy)phenyl)-7,8-dihydropyrido[4,3-d]pyrimidin-6(5H)-yl)methyl)cyclopropyl)acetic acid (compound 285 and 327)

compound 285: Calculated mass (C26H26ClN3O3) 463.956 g/mol. 1H NMR (600 MHz, DMSO-d$_6$) δ 12.33 (s, 1H), 10.27 (s, 1H), 8.76 (s, 1H), 8.37-8.32 (m, 2H), 7.56 (t, J=1.2 Hz, 1H), 7.49-7.39 (m, 3H), 7.21-7.14 (m, 2H), 5.22 (s, 2H), 4.71 (s, 1H), 4.38 (s, 1H), 3.92 (s, 1H), 3.47 (s, 2H), 3.28 (s, 2H), 3.19 (s, 1H), 2.72-2.56 (m, 1H), 0.76 (s, 2H), 0.67 (s, 2H). M+H+ 464 compound 327: Calculated mass (C26H26ClN3O3) 463.956 g/mol. 1H NMR (600 MHz, DMSO-d$_6$) δ 12.26 (s, 1H), 8.57 (s, 1H), 8.35-8.28 (m, 2H), 7.58-7.53 (m, 1H), 7.48-7.38 (m, 3H), 7.17-7.10 (m, 2H), 5.21 (s, 2H), 3.65 (s, 2H), 2.93 (t, J=5.9 Hz, 2H), 2.86 (t, J=5.9 Hz, 2H), 2.49 (s, 1H), 2.30 (s, 2H), 0.56-0.49 (m, 2H), 0.46-0.40 (m, 2H). M+H+ 464

3-(2-(4-((4-chlorobenzyl)oxy)phenyl)-7,8-dihydropyrido[4,3-d]pyrimidin-6(5H)-yl)cyclobutanecarboxylic acid (Compound 287)

Compound XXIVb was converted to the corresponding pyrimidine (2-(4-((4-chlorobenzyl)oxy)phenyl)-5,6,7,8-tetrahydropyrido[4,3-d]pyrimidine) with TFA with a yield of 99% as described herein elsewhere, and was subsequently substituted in accordance with scheme 5: 100 mg of the pyrimidine (0.284 mmol; 1 eq) was suspended in 5 ml THF to give a yellow suspension. Methyl 3-cyclobutanecarboxylate (72.8 mg; 0.568 mmol; 2 eq) was added and the mixture was stirred for 30 min at RT. Sodium triacetoxyborohydride (120 mg; 0.568 mmol; 2 eq) was added and the reaction was finished after 5 h. The mixture was diluted with DCM and water and stirred for 10 min. After phase separation the organic layer was evaporated and the residue was purified by flash chromatography (4 g silica gel; 0-10% MeOH in DCM). Methyl 3-(2-(4-((4-chlorobenzyl)oxy)phenyl)-7,8-dihydropyrido[4,3-d]pyrimidin-6(5H)-yl)cyclobutanecarboxylate was obtained with a yield of 119 mg (0.256 mmol; 90%). The whole product (119 mg; 0.256 mmol; 1 eq) was converted into the corresponding carboxylic acid using NaOH (1 ml; 2 mmol; 7.8 eq) as described herein elsewhere to give compound 287 with a yield of 98 mg (0.218 mmol; 85%). Calculated mass (C25H24ClN3O3) 449.929 g/mol. 1H NMR (500 MHz, DMSO-d$_6$) δ 12.14 (s, 1H), 8.56 (s, 1H), 8.34-8.26 (m, 2H), 7.54-7.43 (m, 4H), 7.16-7.08 (m, 2H), 5.19 (s, 2H), 3.49 (s, 2H), 3.01-2.72 (m, 4H), 2.72-2.61 (m, 2H), 2.41-1.92 (m, 4H). M+H+ 450

3-(2-(4-((3-chlorobenzyl)oxy)phenyl)-7,8-dihydropyrido[4,3-d]pyrimidin-6(5H)-yl)cyclopentanecarboxylic acid hydrochloride (compound 288)

Compound 288 was prepared from compound XXh in a palladium mediated reaction using 4-(3-chlorophenylmethoxy)phenylboronic acid as compound VI in scheme 2. Compound XXh (200 mg; 0.676 mmol; 1 eq) was dissolved in DMF (5 ml) to give a yellow solution. Sodium carbonate (179 mg; 1.691 mmol; 2.5 eq) and 4-(3-chlorophenylmethoxy)phenylboronic acid (213 mg; 0.811 mmol; 1.2 eq) were added under argon and the mixture was stirred for 30 min. Tetrakis(triphenylphosphine)palladium(0) (39.1 mg; 0.034 mmol; 0.05 eq) was added and the mixture was stirred for 60 min at 120° C. The reaction mixture was evaporated. The residue was dissolved in DCM and washed once with water and once with saturated NaCl solution. The organic layer was dried over MgSO$_4$, filtered and evaporated. The residue was purified by flash chromatography (12 g silica gel, 0-10% MeOH in DCM) giving 250 mg methyl 3-(2-(4-((3-chlorobenzyl)oxy)phenyl)-7,8-dihydropyrido[4,3-d]pyrimidin-6(5H)-yl)cyclopentanecarboxylate (0.523 mmol; 77% yield).

The whole product (1 eq) was converted into the corresponding carboxylic acid with 1N NaOH (120 mg; 3.00 mmol; 5.74 eq) as described herein elsewhere to give compound 288 with a yield of 130 mg (0.260 mmol; 49.7%). Calculated mass (C26H26ClN3O3) 463.956 g/mol. 1H NMR (500 MHz, Methanol-d4) δ 8.66 (s, 1H), 8.42-8.35 (m, 2H), 7.49 (d, J=1.8 Hz, 1H), 7.43-7.30 (m, 3H), 7.15-7.07 (m, 2H), 5.18 (s, 2H), 4.60 (s, 2H), 3.90 (dp, J=38.5, 8.3 Hz, 1H), 3.80 (s, 2H), 3.34 (d, J=6.4 Hz, 2H), 3.01 (ddd, J=16.2, 8.9, 7.3 Hz, 1H), 2.65-2.55 (m, 1H), 2.47-2.30 (m, 1H), 2.32-2.04 (m, 3H), 2.04-1.89 (m, 1H). M+H+ 464

The following compound was prepared in the same way as compound 288:

3-(2-(4-((4-chlorobenzyl)oxy)phenyl)-7,8-dihydropyrido[4,3-d]pyrimidin-6(5H)-yl)cyclopentanecarboxylic acid (compound 295)

Using 4-(4-chlorophenylmethoxy)phenylboronic acid instead of 4-(3-chlorophenylmethoxy)phenylboronic acid.

Calculated mass (C26H26ClN3O3) 463.956 g/mol. $^1$H NMR (600 MHz, DMSO-d$_6$) δ 12.43 (s, 1H), 8.72 (s, 1H), 8.37-8.31 (m, 2H), 7.54-7.46 (m, 4H), 7.20-7.13 (m, 2H), 5.20 (s, 2H), 4.73 (d, J=17.7 Hz, 1H), 4.40 (s, 1H), 3.85 (s, 1H), 3.77 (s, 1H), 3.53 (s, 1H), 3.20 (d, J=16.5 Hz, 1H), 2.88-2.82 (m, 1H), 1.92 (s, 2H). M+H+ 464

4-(2-(4-(4-chlorophenethyl)-3-methylphenyl)-7,8-dihydropyrido[4,3-d]pyrimidin-6(5H)-yl)-3-methylbutanoic acid (compound 291)

Ethyl 4-(2-(4-hydroxy-3-methylphenyl)-7,8-dihydropyrido[4,3-d]pyrimidin-6(5H)-yl)-3-methylbutanoate was prepared as described for compound 239. To 544.1 mg thereof (1.473 mmol; 1 eq) in DCM (15 ml) was added pyridine (293 mg; 3.71 mmol; 2.52 eq) and trifluoroemthanesulfonic anhydride (457 mg; 1.62 mmol; 1.1 eq) at 0° C. The reaction was finished after 1 h. A NH$_4$Cl was added to stop the reaction and extraction was performed with DCM followed by washing with water. The residue was filtered, evaporated and purified by flash chromatography (4 g silica gel, 0-10% MeOH in DCM). Ethyl 3-methyl-4-(2-(3-methyl-4-(((trifluoromethyl)sulfonyl)oxy)phenyl)-7,8-dihydropyrido[4,3-d]pyrimidin-6(5H)-yl)butanoate was obtained with a yield of 600 mg (1.196 mmol; 81%).

Ethyl 3-methyl-4-(2-(3-methyl-4-(((trifluoromethyl)sulfonyl)oxy)phenyl)-7,8-dihydropyrido[4,3-d]pyrimidin-6(5H)-yl)butanoate (80 mg; 0.160 mmol; 1 eq) was dissolved in DMF (4 ml). 2-(4-chlorophenyl)ethylboronic acid pinacol ester (50 mg; 0.188 mmol; 1.176 eq) and sodium carbonate (440 mg; 0.415 mmol; 2.6 eq) were added under argon to give a yellow suspension. This was stirred for 30 min under argon atmosphere. Tetrakis(triphenylphosphine)palladium(0) (6 mg; 5.19 μmol; 0.033 eq) was added and the mixture was stirred for 30 min at 120° C. The mixture was evaporated. The residue was dissolved in DCM and H2O. After phase separation with a Chromabond PTS-cartridge the organic layer was evaporated. The residue was purified by flash chromatography (4 g silica gel, 0-10% MeOH in DCM). Ethyl 4-(2-(4-(4-chlorophenethyl)-3-methylphenyl)-7,8-dihydropyrido[4,3-d]pyrimidin-6(5H)-yl)-3-methylbutanoate was obtained with a yield of 48 mg (0.098 mmol; 61.2%).

The whole product was dissolved in MeOh (1 ml) and THF (aml) to give a colorless solution. NaOH (20 mg; 0.50 mmol; 5.13 eq) was added and the mixture was stirred at RT overnight. The mixture was evaporated and the residue was dissolved in H$_2$O and neutralized with 0.25 ml 2N HCl. The precipitate was filtered, washed with 1 ml water and dried under vacuum at 40° C. to give a yellow solid, which was purified by flash chromatography (4 g silica gel, 0-20% MeOH in DCM). Compound 291 was obtained with a yield of 11 mg (0.024 mmol; 24.3%). Calculated mass (C27H30ClN3O2) 463.20 g/mol. $^1$H NMR (600 MHz, DMSO-d$_6$) δ 12.11 (s, 1H), 8.58 (s, 1H), 8.14 (d, J=1.8 Hz, 1H), 8.09 (dd, J=7.9, 1.8 Hz, 1H), 7.34 (d, J=8.3 Hz, 2H), 7.27 (dd, J=8.1, 5.7 Hz, 3H), 3.61 (s, 2H), 2.96-2.80 (m, 7H), 2.79-2.72 (m, 1H), 2.42-2.31 (m, 3H), 2.34 (s, 3H), 2.21 (dt, J=13.7, 6.9 Hz, 1H), 2.03 (dd, J=15.4, 7.6 Hz, 1H), 0.93 (d, J=6.6 Hz, 4H). M+H+ 464

The following compound was prepared in the same way as compound 291:

4-(2-(4-(3-chlorophenethyl)-3-methylphenyl)-7,8-dihydropyrido[4,3-d]pyrimidin-6(5H)-yl)-3-methylbutanoic acid (compound 331)

Using 2-(3-chlorophenyl)ethylboronic acid pinacol ester instead of 2-(4-chlorophenyl)ethylboronic acid pinacol ester. Calculated mass (C27H30ClN3O2) 463.999 g/mol. $^1$H NMR (600 MHz, Methanol-d$_4$) δ 8.56 (s, 1H), 8.14 (d, J=1.8 Hz, 1H), 8.07 (dd, J=7.8, 1.9 Hz, 1H), 7.27-7.15 (m, 4H), 7.10 (dt, J=7.5, 1.4 Hz, 1H), 4.88 (s, 1H), 4.08 (d, J=15.3 Hz, 1H), 3.99 (d, J=15.3 Hz, 1H), 3.36-3.30 (m, 1H), 3.23-3.11 (m, 3H), 3.04-2.93 (m, 2H), 2.95-2.87 (m, 2H), 2.78 (d, J=6.9 Hz, 2H), 2.48 (dd, J=15.5, 8.0 Hz, 1H), 2.42 (q, J=7.6 Hz, 1H), 2.35 (s, 3H), 2.39-2.29 (m, 1H), 1.05 (d, J=6.7 Hz, 3H). M+H+ 464

2-(2-(4-((3,5-difluorobenzyl)oxy)phenyl)-7,8-dihydropyrido[4,3-d]pyrimidin-6(5H)-yl)propanoic acid (compound 299)

Compound 299 was prepared starting from compound XXi in a palladium mediated reaction using potassium (4-benzyloxyphenyl)trifluoroborate as compound IV in scheme 1. Compound XXi (398 mg; 1.476 mmol; 1 eq), sodium carbonate (3 g; 2.83 mmol; 192 eq) and potassium (4-benzyloxyphenyl)trifluoroborate (514 mg; 1.771 mmol; 1.2 eq) were dissolved in DMF (15 mol) to give a brown solution, which was degassed with argon. Tetrakis(triphenylphosphine)palladium(0) (85 mg; 0.074 mmol; 0.05 eq) was added and the mixture was stirred for 60 min at 120° C. The reaction mixture was evaporated. The residue was dissolved in diethyl ether. The organic layer was washed 2× with water and 1× with saturated NaCl solution, dried over MgSO$_4$, filtered and evaporated. The residue was purified by flash chromatography (12 g silica gel, 0-10% MeOH in DCM) giving ethyl 2-(2-(4-(benzyloxy)phenyl)-7,8-dihydropyrido[4,3-d]pyrimidin-6(5H)-yl)propanoate with a yield of 430 mg (1.030 mmol; 69.8%).

Ethyl 2-(2-(4-((3,5-difluorobenzyl)oxy)phenyl)-7,8-dihydropyrido[4,3-d]pyrimidin-6(5H)-yl)propanoate was prepared from this product in accordance with scheme 7. 370 mg ethyl 2-(2-(4-(benzyloxy)phenyl)-7,8-dihydropyrido[4,3-d]pyrimidin-6(5H)-yl)propanoate (0.886 mmol; 1 eq) was dissolved in MeOH (5 ml) and THF (5 ml) to give a yellow solution. Under Argon atmosphere Pd—C (100 mg; 0.940 mmol; 1.06 eq) was added. The mixture was stirred overnight under H2-atmosphere. The reaction mixture was filtered and the organic layer was evaporated. The residue was dissolved in 50 mL MeOH and 50 mL THF. The reaction mixture was filtered and the organic layer was evaporated. The residue was purified by flash chromatography (4 g silica gel, 0-10% MeOH in DCM). Ethyl 2-(2-(4-hydroxyphenyl)-7,8-dihydropyrido[4,3-d]pyrimidin-6 (5H)-yl)propanoate was obtained with a yield of 180 g (0.55 mmol; 62.0%). 60 mg thereof (0.183 mmol; 1 eq) was dissolved in DMF (3 ml) to give a colorless solution. Cesium carbonate (90 mg; 0.275 mmol; 1.5 eq) and 3,5-difluorobenzyl bromide (41.7 mg; 0.202 mmol; 1.1 eq) were added. The reaction mixture was stirred for 2 days at RT. The reaction mixtures was evaporated, the residue was dissolved in DCM and water and filtered through a Chromabond-PTS-cartridge. The organic layer was evaporated and the residue was purified by flash chromatography (4 g silica gel, 0-10% MeOH in DCM) giving ethyl 2-(2-(4-((3,5-difluorobenzyl)oxy)phenyl)-7,8-dihydropyrido[4,3-d]pyrimidin-6(5H)-yl)propanoate with a yield of 72 mg (0.159 mmol; 87%).

72 mg thereof (0.159 mmol; 1 eq) was converted into the corresponding carboxylic acid with 1N NaOH as described elsewhere to give compound 299 with a yield of 61 mg (0.143 mmol; 90%). Calculated mass (C23H21F2N3O3) 425.428 g/mol. $^1$H NMR (600 MHz, DMSO-d$_6$) δ 8.57 (s, 1H), 8.34-8.29 (m, 2H), 7.23 (td, J=7.7, 2.9 Hz, 3H), 7.16-7.11 (m, 2H), 5.22 (s, 2H), 3.86 (d, J=15.3 Hz, 1H), 3.81 (d, J=15.3 Hz, 1H), 3.52 (q, J=7.0 Hz, 1H), 3.06-2.98 (m, 1H), 2.98-2.85 (m, 3H), 1.29 (d, J=7.1 Hz, 3H). M+H+ 426

The following compounds were made in the same way as compound 299:

2-(2-(4-((4-chlorobenzyl)oxy)phenyl)-7,8-dihydropyrido[4,3-d]pyrimidin-6(5H)-yl)propanoic acid (compound 312)

Using 4-chlorobenzyl bromide instead of 3,5-difluorobenzyl bromide. Calculated mass (C23H22ClN3O3) 423.892 g/mol. $^1$H NMR (600 MHz, DMSO-$d_6$) δ 8.58 (s, 1H), 8.34-8.28 (m, 2H), 7.54-7.45 (m, 4H), 7.16-7.10 (m, 2H), 5.19 (s, 2H), 3.91 (s, 2H), 3.61 (s, 2H), 3.11-3.07 (m, 1H), 2.97-2.93 (m, 3H), 1.33 (d, J=6.9 Hz, 3H). M+H+ 424

2-(2-(4-((3-chlorobenzyl)oxy)phenyl)-7,8-dihydropyrido[4,3-d]pyrimidin-6(5H)-yl)propanoic acid (compound 317)

Using 3-chlorobenzyl bromide instead of 3,5-difluorobenzyl bromide. Calculated mass (C23H22ClN3O3) 423.892 g/mol. $^1$H NMR (600 MHz, DMSO-$d_6$) δ 8.62 (s, 1H), 8.34-8.29 (m, 2H), 7.55 (t, J=1.6 Hz, 1H), 7.49-7.38 (m, 4H), 7.17-7.12 (m, 2H), 5.21 (s, 2H), 4.01 (s, 3H), 3.00 (s, 2H), 1.38 (s, 3H). M+H+ 424

2-(2-(4-(benzyloxy)phenyl)-7,8-dihydropyrido[4,3-d]pyrimidin-6(5H)-yl)propanoic acid (compound 322)

Using benzyl bromide instead of 3,5-difluorobenzyl bromide. Calculated mass (C23H23N3O3) 389.17 g/mol. $^1$H NMR (600 MHz, DMSO-$d_6$) δ 12.47 (s, 1H), 8.57 (s, 1H), 8.33-8.28 (m, 2H), 7.51-7.46 (m, 2H), 7.41 (t, J=7.5 Hz, 2H), 7.39-7.32 (m, 1H), 7.15-7.11 (m, 2H), 5.18 (s, 2H), 3.87 (s, 2H), 3.56 (s, 1H), 3.05 (s, 1H), 2.93 (s, 3H), 1.31 (d, J=7.0 Hz, 3H). M+H+ 390

(R)-4-(2-(4-((4-chlorobenzyl)oxy)phenyl)-7,8-dihydropyrido[4,3-d]pyrimidin-6(5H)-yl)-3-methylbutan-1-ol (compound 315)

Compound XXIVb was converted to the corresponding pyrimidine (2-(4-((4-chlorobenzyl)oxy)phenyl)-5,6,7,8-tetrahydropyrido[4,3-d]pyrimidine) with TFA with a yield of 100% as described herein elsewhere, and was subsequently substituted in accordance with scheme 5: 2-(4-((4-chlorobenzyl)oxy)phenyl)-5,6,7,8-tetrahydropyrido[4,3-d]pyrimidine (10.2 g; 29.0 mmol; 1 eq) was suspended in 250 ml DMF. (R)-(+)-3-methylsuccinic acid 1-monomethyl ester (4.24 g; 29.0 mmol; 1 eq), O-[(ethoxycarbonyl)cyanomethylenamino]-N, N, N',N'-tetramethyluronium tetrafluoroborate (TOTU; 9.51 g; 29.0 mmol; 1 eq) and triethylamine (2.93 g; 29.0 mmol; 1 eq) were added and the mixture was stirred for 2 h at RT. The DMF was evaporated, the residue was dissolved in 250 ml DCM and extracted twice with 200 ml saturated NaHCO$_3$ and twice with 200 ml water. The organic phase was obtained and evaporated. The residue was dissolved in 30 ml DCM followed by flash chromatography (120 g silica gel, EtOAc/n-heptane 2:1). The resulting oily residue was crystallized in n-pentane yielding 12.5 g (R)-methyl 442444(4-chlorobenzyl)oxy)phenyl)-7,8-dihydropyrido[4,3-d]pyrimidin-6(5H)-yl)-3-methyl-4-oxobutanoate (26.0 mmol; 90%).

7.7 g thereof (16.04 mmol; 1 eq) was dissolved in 200 ml THF. Zinc acetate (0.589 g; 3.21 mmol; 0.2 eq) and diethoxymethylsilane (10.77 g; 80 mmol; 5 eq) were added under argon atmosphere. The mixture was heated for 48 h at 80° C. and evaporated. The residues was stirred with 200 ml water and the solid residue was obtained washed with water and dried over P2O5 at 40° C. under vacuum. A mixture of (R)-4-(2-(4-((4-chlorobenzyl)oxy)phenyl)-7,8-dihydropyrido[4,3-d]pyrimidin-6(5H)-yl)-3-methylbutanoic acid (40%), (R)-methyl 4-(2-(4-((4-chlorobenzyl)oxy)phenyl)-7, 8-dihydropyrido[4,3-d]pyrimidin-6(5H)-yl)-3-methylbutanoate (40%) and (R)-4-(2-(4-((4-chlorobenzyl)oxy)phenyl)-7,8-dihydropyrido[4,3-d]pyrimidin-6(5H)-yl)-3-methylbutan-1-ol (20%) was obtained. The whole product (10.3 g; assumed 16 mmol) was suspended in THF/MeOH (100 ml each), 40 ml 2N NaOH was added and the mixture was stirred for 20 h at RT. 40 ml 2N HCl was added to neutralized the mixture and the carboxylic acid started to precipitate. 150 ml water was added, stirred for 15 min and the carboxylic acid was obtained, washed with water and dried over P2O5 at 50° C. under vacuum to yield 5.6 g of solid residue. The residue was dissolved in 150 ml DCM/30 ml MeOH, filtered (10 g Chromabond XTR), pulverized and purified by flash chromatography (220 g silica; DCM/MeOH 95:5). The first fraction provided 1.2 g of the alcohol, which was once more purified by flash chromatography (DCM/0-5% MeOH). The residue was evaporated, stirred with n-pentane and a little diethyl ether, extracted, washed with pentane and dried at 50° C. under vacuum yielding 1 g of compound 315 (2.28 mmol; 14.3%). Calculated mass (C25H28ClN3O2) 437.962 g/mol. $^1$H NMR (600 MHz, DMSO-$d_6$) δ 8.55 (s, 1H), 8.33-8.27 (m, 2H), 7.53-7.45 (m, 4H), 7.15-7.09 (m, 2H), 5.18 (s, 2H), 4.49 (s, 1H), 3.57 (d, J=4.1 Hz, 2H), 2.91 (q, J=9.6, 7.7 Hz, 2H), 2.77 (t, J=5.9 Hz, 2H), 2.39-2.32 (m, 1H), 2.28 (dd, J=12.0, 7.6 Hz, 1H), 1.89 (p, J=6.7 Hz, 1H), 1.59 (dt, J=13.0, 6.4 Hz, 1H), 1.24 (q, J=7.0 Hz, 1H), 1.14-1.09 (m, 1H), 0.91 (dd, J=14.0, 6.5 Hz, 3H), M+H+ 438

(R)-4-(2-(4-(4-chlorophenethyl)phenyl)-7,8-dihydropyrido[4,3-d]pyrimidin-6(5H)-yl)-3-methylbutan-1-ol (compound 325)

Compound Mb (15.3 g; 46.7 mmol; 1 eq) was dissolved in 400 ml CDM. Pyridine (9.24 g; 117 mmol; 2.5 eq) was added under argon atmosphere and the mixture was cooled at 0° C. 51.4 ml of a solution of tirfluoromethansulfonic anhydride (1.67 g/ml;

total 14.5 g; 51.4 mmol; 1.1 eq) was added dropwise, followed by stirring for 2 h at 0° C. The volume was reduced to 200 ml and extracted twice with 75 ml 10% NH$_4$Cl solution and once with water. The organic phases were combined, washed with saturated NaCl, dried over MgSO$_4$ and evaporated giving 19.8 g tert-butyl 2-(4-(((trifluoromethyl)sulfonyl)oxy)phenyl)-7,8-dihydropyrido[4,3-d]pyrimidine-6(5H)-carboxylate (43.1 mmol; 92%).

10 g thereof (21.77 mmol; 1 eq) was dissolved in 215 ml THF. 2-(4-chlorophenethyl)-4,4,5,5-tetramethyl-1,3,2-dioxaborolane (11.6 g; 43.5 mmol; 2 eq) was added, followed by 21.5 ml water and potassium carbonated (12.03 g; 87 mmol; 4 eq). The mixture was rinsed with argon (30 min) and kept at RT overnight. The THF was evaporated and water and ethyl acetate were added. The phases were separated and the aqueous phase washed twice with ethyl acetate. The combined organic phases were washed with saturated NaCl, dried over MgSO$_4$ and evaporated giving 7.5 g tert-butyl 2-(4-(4-chlorophenethyl)phenyl)-7,8-dihydropyrido[4,3-d]pyrimidine-6(5H)-carboxylate (16.7 mmol; 77%), which was converted to the pyrimidine with TFA as described herein elsewhere.

(R)-methyl 4-(2-(4-(4-chlorophenethyl)phenyl)-7,8-dihydropyrido[4,3-d]pyrimidin-6(5H)-yl)-3-methyl-4-oxobutanoate was prepared from the pyrimidine in accordance with scheme 5: 0.5 g 2-(4-(4-chlorophenethyl)phenyl)-5,6,7,8-tetrahydropyrido[4,3-d]pyrimidine (1.43 mmol; 1 eq) was dissolved in 12.5 ml DMF. (R)-4-methoxy-2-methyl-4-oxobutanoic acid (0.209 g; 1.429 mmol; 1 eq), triethylamine (0.159 g; 1.572 mmol; 1.1. eq) and (Z)—N-(6-cyano-2-methyl-7-oxo-4,8-dioxa-2,5-diazadec-5-en-3-ylidene)-N-methylmethanaminium tetrafluoroborate (TOTU; 0.469 g; 1.429 mmo; 1 eq) were added and incubated for 2 h at RT. The DMF was evaporated, followed by flash chromatography (24 g silica, 0-60% ethylacetate in cyclohexane). The oily residue was dissolved in DCM and extracted three times with saturated NaHCO$_3$. The combined aqueous phases were washed once with DCM. The organic phases were combined, dried over MgSO$_4$ and evaporated giving (R)-methyl 4-(2-(4-(4-chlorophenethyl)phenyl)-7,8-dihydropyrido[4,3-d]pyrimidin-6(5H)-yl)-3-methyl-4-oxobutanoate with a yield of 99% (0.676 g; 1.415 mmol).

7 g (R)-methyl 4-(2-(4-(4-chlorophenethyl)phenyl)-7,8-dihydropyrido[4,3-d]pyrimidin-6(5H)-yl)-3-methyl-4-oxobutanoate (14.64 mmol; 1 eq) was dissolved in 170 ml THF. Zinc acetate (0.537 g; 2.93 mmol; 0.2 eq) and diethoxymethylsilane (9.83 g; 73.2 mmol; 5 eq) were added and heated under reflux for 7.5 h, and kept overnight at RT. This was repeated twice, once with another 537 mg zinc acetate and 9.83 diethoxymethylsilane and a second time with 265 mg zinc acetate and 4.9 diethoxymethylsilane. The mixture was evaporated and the residue extracted with water and ethylacetate. The precipitate was removed and the phases were separated. The aqueous phase was washed twice with ethylacetate. The combined organic phases were washed with water and saturated NaCl, dried over MgSO$_4$ and evaporated. A mixture of (R)-methyl 4-(2-(4-(4-chlorophenethyl)phenyl)-7,8-dihydropyrido[4,3-d]pyrimidin-6(5H)-yl)-3-methylbutanoate (41.6%), (R)-4-(2-(4-(4-chlorophenethyl)phenyl)-7,8-dihydropyrido[4,3-d]pyrimidin-6(5H)-yl)-3-methylbutanoic acid (15.17%) and compound 325 (17.62%; 1.25 g; 2.58 mmol) was obtained. These compounds were separated by chromatography (12 g silica, 0-15% MeOH in DCM). The fractions containing compounds 325 were further purified by dissolving in 30 MeOH under reflux. The precipitate is removed and the solution evaporated to 5 ml after which the precipitate is obtained giving 590 mg of compound 325.

$[\alpha]_D^{20}$=+3.8°, 1.04 mg/ml in MeOH. Calculated mass (C26H30ClN3O): 435.989; 1H NMR (600 MHz, DMSO-d$_6$) δ 8.58 (s, 1H), 8.29-8.22 (m, 2H), 7.37-7.29 (m, 4H), 7.29-7.22 (m, 2H), 4.49 (t, J=5.2 Hz, 1H), 3.63-3.53 (m, 2H), 3.54-3.41 (m, 2H), 2.98-2.88 (m, 6H), 2.77 (t, J=6.0 Hz, 2H), 2.35 (dd, J=12.0, 7.3 Hz, 1H), 2.28 (dd, J=12.0, 7.6 Hz, 1H), 1.90 (dq, J=12.1, 7.2 Hz, 1H), 1.60 (dtd, J=13.4, 7.3, 5.0 Hz, 1H), 1.24 (dddd, J=13.4, 7.9, 6.6, 5.5 Hz, 1H), 0.90 (d, J=6.6 Hz, 3H). M+H=436/438

4-(2'-(4-((4-chlorobenzyl)oxy)phenyl)-5'H-spiro[cyclobutane-1,7'-pyrido[4,3-d]pyrimidin]-6'(8'H)-yl)-3-methylbutanoic acid (compound 326)

Compound XXIVd was converted to the corresponding pyrimidine (2'444(4-chlorobenzyl)oxy)phenyl)-6',8'-dihydro-5'H-spiro[cyclobutane-1,7'-pyrido[4,3-d]pyrimidine]) with TFA as described herein elsewhere, and was subsequently substituted in accordance with scheme 5 using ethyl 3-methyl-4-oxobutanoate in the presence of sodium triacetoxyboronhydride as described herein elsewhere, e.g. for compound 244, resulting in ethyl 4-(2'-(4-((4-chlorobenzyl)oxy)phenyl)-5'H-spiro[cyclobutane-1,7'-pyrido[4,3-d]pyrimidin]-6'(8'H)-yl)-3-methylbutanoate (320 mg; 0.615 mmol; 76%).

The whole product (320 mg; 0.615 mmol; 1 eq) was converted into the corresponding carboxylic acid with 1N NaOH (6 ml; 6 mmol; 9.75 eq) as described herein elsewhere to give compound 326 with a yield of 209 mg (0.425 mmol; 69%). Calculated mass (C28H30ClN3O3) 491.20 g/mol. 1H NMR (600 MHz, DMSO-d6) δ 12.29 (s, 1H), 8.56 (s, 1H), 8.35-8.28 (m, 2H), 7.54-7.44 (m, 4H), 7.16-7.09 (m, 2H), 5.18 (s, 2H), 3.80 (d, J=2.1 Hz, 2H), 2.94 (s, 2H), 2.44-2.33 (m, 1H), 2.14-1.63 (m, 9H), 0.88 (d, J=6.3 Hz, 3H). M+H+ 492

4-(2-(4-((4-chlorobenzyl)oxy)phenyl)-7,7-dimethyl-7,8-dihydropyrido[4,3-d]pyrimidin-6(5H)-yl)-3-methylbutanoic acid (compound 329)

Compound XXIVc was converted to the corresponding pyrimidine (2-(4-((4-chlorobenzyl)oxy)phenyl)-7,7-dimethyl-5,6,7,8-tetrahydropyrido[4,3-d]pyrimidine) with TFA as described herein elsewhere, and was subsequently substituted in accordance with scheme 5 using ethyl 3-methyl-4-oxobutanoate in the presence of sodium triacetoxyboronhydride as described herein elsewhere, e.g. for compound 244, resulting in ethyl 4-(2-(4-((4-chlorobenzyl)oxy)phenyl)-7,7-dimethyl-7,8-dihydropyrido[4,3-d]pyrimidin-6(5H)-yl)-3-methylbutanoate (120 mg; 0.165 mmol; 91%).

The product was dissolved in 2 ml MeOH and 2 ml THF to give a yellow solution. NaOH (40 mg; 1.00 mmol; 6.05 eq) was added and the mixture was stirred at RT overnight. A further 0.5 ml NaOH was added and the mixture was stirred for another 24 h at RT to finish the reaction. The mixture was evaporated and the residue suspended in water and neutralized with 1 ml 2N HCl. DCM was added and after phase separation, the organic layer was evaporated. The residue was purified by flash chromatography (4 g silica gel, 0-20% MeOH in DCM) giving compound 329 with a yield of 20 mg (0.042 mmol; 25.2%). Calculated mass (C27H30ClN3O3) 479.998 g/mol. $^1$H NMR (600 MHz, DMSO-d$_6$) δ 12.20 (s, 1H), 8.58 (s, 1H), 8.34-8.28 (m, 2H), 7.56-7.45 (m, 5H), 7.18-7.10 (m, 2H), 5.18 (s, 2H), 3.84 (d, J=16.7 Hz, 1H), 3.68 (d, J=16.8 Hz, 1H), 2.80-2.69 (m, 2H), 2.44 (dd, J=12.9, 8.6 Hz, 1H), 2.32 (ddd, J=25.7, 14.1, 6.2 Hz, 2H), 2.16-2.07 (m, 1H), 1.99 (dd, J=15.3, 7.2 Hz, 1H), 1.09 (d, J=38.1 Hz, 5H), 0.90 (d, J=6.6 Hz, 3H). M+H+ 480

(R)-1-(2-(4-((4-chlorobenzyl)oxy)phenyl)-7,8-dihydropyrido[4,3-d]pyrimidin-6(5H)-yl)-4-hydroxy-3-methylbutan-1-one (compound 330)

Calculated mass (C25H26ClN3O3) 451.945 g/mol. 1H NMR (600 MHz, DMSO-d$_6$) δ 8.67 (d, J=18.6 Hz, 1H), 8.38-8.22 (m, 2H), 7.55-7.40 (m, 4H), 7.21-7.07 (m, 2H), 5.19 (s, 2H), 4.79-4.64 (m, 2H), 4.55 (dt, J=10.5, 5.3 Hz, 1H), 3.83 (p, J=6.5 Hz, 2H), 3.30-3.21 (m, 2H), 2.93 (dt, J=66.8, 6.0 Hz, 2H), 2.61-2.54 (m, 1H), 2.17 (ddd, J=15.0, 7.7, 1.9 Hz, 1H), 2.05-1.95 (m, 1H), 0.87 (dd, J=13.7, 6.8 Hz, 3H). M+H+ 452

(R)-4-(2-(4-((4-chlorobenzyl)oxy)phenyl)-7,8-dihydropyrido[4,3-d]pyrimidin-6(5H)-yl)-3-methyl-4-oxobutanoic acid (compound 332)

(R)-methyl 4-(2-(4-((4-chlorobenzyl)oxy)phenyl)-7,8-dihydropyrido[4,3-d]pyrimidin-6(5H)-yl)-3-methyl-4-oxobutanoate (prepared as described for compound 315; 96.0 mg; 0.20 mmol) was dissolved in THF/MeOH (3 ml each) and converted to the corresponding oxobutanoic acid with 2 ml 1N NaOH as described herein elsewhere giving compound 332 with a yield of 25.8% (24 mg; 0.052). Calculated mass (C25H24ClN3O4) 465.929 g/mol. $^1$H NMR (600 MHz, DMSO-$d_6$) δ 12.07 (s, 1H), 8.69 (d, J=5.3 Hz, 1H), 8.35-8.29 (m, 2H), 7.54-7.45 (m, 4H), 7.16-7.09 (m, 2H), 5.19 (s, 2H), 4.91-4.78 (m, 2H), 3.99 (dt, J=13.7, 5.6 Hz, 1H), 3.89-3.75 (m, 1H), 3.31-3.21 (m, 1H), 3.08 (ddd, J=17.4, 8.0, 5.3 Hz, 1H), 2.98 (dt, J=17.3, 5.3 Hz, 1H), 2.85 (q, J=5.5 Hz, 1H), 2.66-2.57 (m, 1H), 2.29 (dd, J=16.8, 5.0 Hz, 1H), 1.07 (d, J=7.0 Hz, 2H). M+H+ 466

General Procedure 1

A 4 mL vial was charged with a stir bar to which was added NaH (11 mg, 0.45 mmol). To this NaH was then added a solution of ethyl 4-(2-(4-hydroxyphenyl)-7,8-dihydro-pyrido[4,3-d]pyrimidin-6(5H)-yl)-3-methylbutanoate (compound XXIII with R*=ethyl 3-methylbutanoate and R"=H, prepared as described for compound 336; 35 mg; 0.10 mmol) in DMF (300 µl) at 0° C. and stirred for 30 minutes. After 30 minutes, to this mixture was added a solution of 2-(bromomethyl)-1,3-dichlorobenzene halide monomer (30 mg; 1.4 eq; 0.14 mmol) also in DMF (200 µl). This was allowed to stir at RT for 2 hours. Upon completion of the first step, to the crude material was added 500 µl of 1M LiOH and further allowed to be stirred for 1 hour at RT. The residues were dissolved in DMSO and purified by reverse phase HPLC (TFA method). Samples were purified by preparative HPLC on a Phenomenex Luna C8(2) 5 µm 100 Å AXIA column (30 mm×150 mm). A gradient of ACN (A) and 0.1% TFA in water (B) was used, at a flow rate of 50 mL/min (0-0.5 min 5% A, 0.5-8.5 min linear gradient 5-100% A, 8.7-10.7 min 100% A, 10.7-11.0 min linear gradient 100-5% A) to obtain desired compounds. Product was characterized by $^1$H NMR, MS and LC/MS.

The following compounds were prepared according to general procedure 1:

4-[2-[4-[(2,3-difluorophenyl)methoxy]phenyl]-7,8-dihydro-5H-pyrido[4,3-d]pyrimidin-6-yl]-3-methyl-butanoic acid 2,2,2-trifluoroacetic acid salt (compound 226)

Using 1-(bromomethyl)-2,3-difluorobenzene instead of 2-(bromomethyl)-1,3-dichlorobenzene. $^1$H NMR (400 MHz, Pyridine-$d_5$) δ 8.77-8.69 (m, 2H), 8.43 (s, 1H), 7.34-7.18 (m, 3H), 7.17 (t, J=2.0 Hz, 1H), 7.03 (tdd, J=8.1, 4.9, 1.6 Hz, 1H), 5.21 (d, J=1.2 Hz, 2H), 3.53 (d, J=15.2 Hz, 1H), 3.42 (d, J=15.1 Hz, 1H), 2.97 (t, J=5.9 Hz, 2H), 2.77-2.58 (m, 3H), 2.42-2.23 (m, 3H), 1.06 (d, J=6.5 Hz, 3H). MS (APCI) m/z 454.3 (M+H)+

4-[2-[4-[(2-chlorophenyl)methoxy]phenyl]-7,8-dihydro-5H-pyrido[4,3-d]pyrimidin-6-yl]-3-methyl-butanoic acid 2,2,2-trifluoroacetic acid salt (compound 229)

Using 1-(bromomethyl)-2-chlorobenzene instead of 2-(bromomethyl)-1,3-dichlorobenzene. $^1$H NMR (400 MHz, Pyridine-$d_5$) δ 8.77-8.69 (m, 2H), 8.44 (s, 1H), 8.43 (s, 1H), 7.68-7.55 (m, 1H), 7.45-7.30 (m, 1H), 7.30-7.18 (m, 4H), 5.23 (s, 2H), 3.53 (d, J=15.3 Hz, 1H), 3.42 (d, J=15.1 Hz, 1H), 2.97 (t, J=5.9 Hz, 2H), 2.77-2.58 (m, 3H), 2.53-2.23 (m, 4H), 1.06 (d, J=6.5 Hz, 3H). MS (APCI) m/z 452.3 (M+H)+

3-methyl-4-[2-[4-(o-tolylmethoxy)phenyl]-7,8-dihydro-5H-pyrido[4,3-d]pyrimidin-6-yl]butanoic acid 2,2,2-trifluoroacetic acid salt (compound 234)

Using 1-(bromomethyl)-2-methylbenzene instead of 2-(bromomethyl)-1,3-dichlorobenzene. $^1$H NMR (400 MHz, Pyridine-$d_5$) δ 8.78-8.70 (m, 2H), 8.44 (s, 1H), 8.43 (s, 1H), 7.48 (dd, J=6.7, 2.1 Hz, 1H), 7.29-7.17 (m, 4H), 5.23 (s, 2H), 3.52 (d, J=15.2 Hz, 1H), 3.42 (d, J=15.1 Hz, 1H), 2.97 (t, J=5.9 Hz, 2H), 2.77-2.61 (m, 3H), 2.48 (d, J=6.8 Hz, 1H), 2.40-2.26 (m, 3H), 2.25 (s, 3H), 1.06 (d, J=6.5 Hz, 3H). MS (APCI) m/z 432.4 (M+H)+

4-[2-[4-[(2-fluorophenyl)methoxy]phenyl]-7,8-dihydro-5H-pyrido[4,3-d]pyrimidin-6-yl]-3-methyl-butanoic acid 2,2,2-trifluoroacetic acid salt (compound 235)

Using 1-(bromomethyl)-2-fluorobenzene instead of 2-(bromomethyl)-1,3-dichlorobenzene. $^1$H NMR (400 MHz, Pyridine-$d_5$) δ 8.76-8.68 (m, 2H), 8.44 (s, 1H), 8.42 (s, 1H), 7.55 (td, J=7.5, 1.7 Hz, 1H), 7.30-7.20 (m, 3H), 7.13-7.07 (m, 2H), 5.21 (s, 2H), 3.53 (d, J=15.1 Hz, 1H), 3.40 (s, 1H), 2.97 (t, J=5.9 Hz, 2H), 2.77-2.58 (m, 3H), 2.42-2.23 (m, 3H), 1.06 (d, J=6.5 Hz, 3H). MS (APCI) m/z 436.3 (M+H)+

4-[2-[4-[(2,6-dichlorophenyl)methoxy]phenyl]-7,8-dihydro-5H-pyrido[4,3-d]pyrimidin-6-yl]-3-methyl-butanoic acid 2,2,2-trifluoroacetic acid salt (compound 243)

$^1$H NMR (400 MHz, Pyridine-$d_5$) δ 8.76 (d, J=8.9 Hz, 2H), 8.42 (s, 1H), 7.32 (dd, J=8.6, 2.1 Hz, 4H), 7.16 (s, 1H), 5.38 (s, 2H), 3.65-3.36 (m, 2H), 2.97 (d, J=5.8 Hz, 1H), 2.70 (dt, J=15.6, 5.8 Hz, 2H), 2.64-2.50 (m, 1H), 2.45-2.31 (m, 2H), 1.07 (d, 3H). MS (APCI) m/z 486.3 (M+H)+

3-methyl-4-[2-[4-[[2-methyl-3-(trifluoromethyl)phenyl]methoxy]phenyl]-7,8-dihydro-5H-pyrido[4,3-d]pyrimidin-6-yl]butanoic acid 2,2,2-trifluoroacetic acid salt (compound 246)

Using 1-(bromomethyl)-2-methyl-3-trifluoromethylbenzene instead of 2-(bromomethyl)-1,3-dichlorobenzene. $^1$H NMR (400 MHz, Pyridine-$d_5$) δ 8.80-8.71 (m, 2H), 8.44 (s, 1H), 7.68 (d, J=7.6 Hz, 1H), 7.62-7.51 (m, 1H), 7.27 (dd, J=8.3, 6.2 Hz, 3H), 5.15 (s, 2H), 3.54 (d, J=15.1 Hz, 1H), 3.43 (d, J=15.2 Hz, 1H), 2.98 (t, J=5.9 Hz, 2H), 2.69 (ddh, J=23.7, 17.8, 5.9 Hz, 3H), 2.55-2.24 (m, 7H), 1.06 (d, J=6.5 Hz, 3H). MS (APCI) m/z 500.4 (M+H)+

3-methyl-4-[2-[4-[[4-methyl-3-(trifluoromethyl)phenyl]methoxy]phenyl]-7,8-dihydro-5H-pyrido[4,3-d]pyrimidin-6-yl]butanoic acid 2,2,2-trifluoroacetic acid salt (compound 247)

Using 1-(bromomethyl)-3-trifluoromethyl-4-methyl-benzene instead of 2-(bromomethyl)-1,3-dichlorobenzene. $^1$H NMR (400 MHz, Pyridine-$d_5$) δ 8.77-8.69 (m, 2H), 8.43 (s, 1H), 7.87-7.69 (m, 1H), 7.53 (d, J=8.9 Hz, 1H), 7.23 (dd, J=15.7, 8.3 Hz, 3H), 5.12 (s, 2H), 3.54 (d, J=15.1 Hz, 1H), 3.42 (d, J=15.2 Hz, 1H), 2.98 (t, J=5.9 Hz, 2H), 2.78-2.59 (m, 3H), 2.55-2.42 (m, 1H), 2.42-2.24 (m, 6H), 1.06 (d, J=6.5 Hz, 3H). MS (APCI) m/z 500.4 (M+H)+

3-methyl-4-[2-[4-[[2-(trifluoromethyl)phenyl]methoxy]phenyl]-7,8-dihydro-5H-pyrido[4,3-d]pyrimidin-6-yl]butanoic acid 2,2,2-trifluoroacetic acid salt (compound 254)

Using 1-(bromomethyl)-2-trifluoromethylbenzene instead of 2-(bromomethyl)-1,3-dichlorobenzene. $^1$H NMR (400 MHz, Pyridine-d$_5$) δ 8.77-8.68 (m, 2H), 8.42 (s, 1H), 7.75 (d, J=7.7 Hz, 1H), 7.64 (d, J=7.5 Hz, 1H), 7.50-7.44 (m, 1H), 7.33 (t, J=7.7 Hz, 1H), 7.29-7.20 (m, 2H), 5.36 (s, 2H), 3.57-3.46 (m, 1H), 3.42 (d, J=15.2 Hz, 1H), 2.97 (t, J=5.9 Hz, 2H), 2.68 (ddh, J=23.6, 17.7, 5.9 Hz, 3H), 2.53-2.23 (m, 4H), 1.06 (d, J=6.5 Hz, 3H). MS (APCI) m/z 486.4 (M+H)+

3-methyl-4-[2-[4-[(4-methylsulfanylphenyl)methoxy]phenyl]-7,8-dihydro-5H-pyrido[4,3-d]pyrimidin-6-yl]butanoic acid 2,2,2-trifluoroacetic acid salt (compound 257)

Using 1-(bromomethyl)-4-methylsulfanylbenzene instead of 2-(bromomethyl)-1,3-dichlorobenzene. $^1$H NMR (400 MHz, Pyridine-d$_5$) δ 8.76-8.70 (m, 2H), 8.43 (d, J=4.3 Hz, 1H), 7.45-7.38 (m, 2H), 7.32-7.26 (m, 2H), 7.25-7.19 (m, 2H), 5.16 (s, 2H), 3.52 (d, J=15.2 Hz, 1H), 3.42 (d, J=15.1 Hz, 1H), 2.97 (t, J=5.9 Hz, 2H), 2.77-2.64 (m, 3H), 2.56-2.42 (m, 1H), 2.51-2.28 (m, 6H), 1.06 (d, 3H). MS (APCI) m/z 464.3 (M+H)+

4-[2-[4-[(2,3-dichlorophenyl)methoxy]phenyl]-7,8-dihydro-5H-pyrido[4,3-d]pyrimidin-6-yl]-3-methyl-butanoic acid 2,2,2-trifluoroacetic acid salt (compound 268)

Using 1-(bromomethyl)-2,3-dichlorobenzene instead of 2-(bromomethyl)-1,3-dichlorobenzene. $^1$H NMR (400 MHz, Pyridine-d$_5$) δ 8.78-8.70 (m, 2H), 8.43 (s, 1H), 7.48 (d, J=1.5 Hz, 1H), 7.40 (dd, J=8.1, 1.5 Hz, 1H), 7.28-7.23 (m, 2H), 7.15 (s, 1H), 5.23 (s, 2H), 3.53 (d, J=15.2 Hz, 1H), 3.42 (d, J=15.2 Hz, 1H), 2.97 (t, J=5.9 Hz, 2H), 2.68 (ddt, J=23.1, 11.7, 5.7 Hz, 3H), 2.42-2.23 (m, 3H), 1.06 (d, J=6.5 Hz, 3H). MS (APCI) m/z 486.3 (M+H)+

3-methyl-4-[2-[4-[[5-methyl-2-(trifluoromethyl)phenyl]methoxy]phenyl]-7,8-dihydro-5H-pyrido[4,3-d]pyrimidin-6-yl]butanoic acid 2,2,2-trifluoroacetic acid salt (compound 275)

Using 1-(bromomethyl)-2-trifluoromethyl-5-methyl-benzene instead of 2-(bromomethyl)-1,3-dichlorobenzene. $^1$H NMR (400 MHz, Pyridine-d$_5$) δ 8.78-8.69 (m, 2H), 8.44 (s, 1H), 8.42 (s, 1H), 7.54 (d, J=7.8 Hz, 2H), 7.32-7.23 (m, 2H), 7.11 (d, J=8.0 Hz, 1H), 5.34 (s, 2H), 3.53 (d, J=15.2 Hz, 1H), 3.42 (d, J=15.1 Hz, 1H), 2.97 (t, J=5.9 Hz, 2H), 2.77-2.58 (m, 3H), 2.42-2.23 (m, 3H), 2.17 (s, 3H), 1.06 (d, J=6.5 Hz, 3H). MS (APCI) m/z 500.4 (M+H)+

General Procedure 2

A 4 mL vial was charged with a stir bar to which was added NaH (10 mg, 0.27 mmol). To this NaH was then added a solution of ethyl 4-(2-(2-fluoro-4-hydroxyphenyl)-7,8-dihydropyrido[4,3-d]pyrimidin-6(5H)-yl)-3-methylbutanoate (compound XXIII with R*=ethyl 3-methylbutanoate and R"=F, prepared as described for compound 336; 30 mg; 0.09 mmol) in DMF (300 μl) at 0° C. and stirred for 30 minutes. After 30 minutes, to this mixture was added a solution of 1-(bromomethyl)-4-(trifluoromethyl) benzene halide monomer (27 mg; 1.4 eq; 0.12 mmol) also in DMF (200 μl). This was allowed to stir at RT for 2 hours. Upon completion of the first step, to the crude material was added 500 μl of 1M LiOH and further allowed to be stirred for 1 hour at RT. The residues were dissolved in DMSO and purified by reverse phase HPLC (TFA method). Samples were purified by preparative HPLC on a Phenomenex Luna C8(2) 5 μm 100 Å AXIA column (30 mm×150 mm). A gradient of ACN (A) and 0.1% TFA in water (B) was used, at a flow rate of 50 mL/min (0-0.5 min 5% A, 0.5-8.5 min linear gradient 5-100% A, 8.7-10.7 min 100% A, 10.7-11.0 min linear gradient 100-5% A) to obtain desired compounds. Product was characterized by $^1$H NMR, MS and LC/MS.

The following compounds were prepared according to general procedure 2:

4-[2-[2-fluoro-4-[[2-methyl-3-(trifluoromethyl)phenyl]methoxy]phenyl]-7,8-dihydro-5H-pyrido[4,3-d]pyrimidin-6-yl]-3-methyl-butanoic acid 2,2,2-trifluoroacetic acid salt (compound 241)

Using 2-(bromomethyl)-1,3-difluorobenzene instead of 1-(bromomethyl)-4-(trifluoromethyl) benzene. $^1$H NMR (400 MHz, Pyridine-d$_5$) δ 8.49 (s, 1H), 8.34 (t, J=8.9 Hz, 1H), 7.71 (s, 1H), 7.67 (d, J=7.6 Hz, 1H), 7.60 (d, J=7.9 Hz, 1H), 7.31 (s, 1H), 7.28 (d, J=7.8 Hz, 1H), 7.14-7.03 (m, 2H), 5.16 (s, 2H), 3.54 (d, J=15.2 Hz, 1H), 3.44 (d, J=15.3 Hz, 1H), 2.99 (t, J=5.9 Hz, 2H), 2.77-2.60 (m, 3H), 2.40 (s, 3H), 2.39-2.21 (m, 3H), 1.07 (d, J=6.6 Hz, 3H). MS (APCI) m/z 518.4 (M+H)+

4-[2-[2-fluoro-4-[[2-(trifluoromethyl)phenyl]methoxy]phenyl]-7,8-dihydro-5H-pyrido[4,3-d]pyrimidin-6-yl]-3-methyl-butanoic acid 2,2,2-trifluoroacetic acid salt (compound 260)

Using 1-(bromomethyl)-2-trifluoromethylbenzene instead of 1-(bromomethyl)-4-(trifluoromethyl) benzene. $^1$H NMR (400 MHz, Pyridine-d$_5$) δ 8.47 (s, 1H), 8.31 (t, J=8.9 Hz, 1H), 7.72 (d, J=7.8 Hz, 1H), 7.65 (d, J=7.8 Hz, 1H), 7.51 (d, J=1.0 Hz, 2H), 7.35 (t, J=7.7 Hz, 1H), 7.10 (dd, J=12.7, 2.4 Hz, 1H), 7.04 (dd, J=8.7, 2.6 Hz, 1H), 5.13 (s, 2H), 3.53 (d, J=15.2 Hz, 1H), 3.43 (d, J=15.2 Hz, 1H), 2.98 (t, J=5.9 Hz, 2H), 2.74-2.66 (m, 2H), 2.64-2.49 (m, 1H), 2.50-2.38 (m, 2H), 2.38-2.29 (m, 2H), 1.06 (d, J=6.6 Hz, 3H). MS (APCI) m/z 504.4.4 (M+H)+

4-[2-[2-fluoro-4-[[4-(trifluoromethyl)phenyl]methoxy]phenyl]-7,8-dihydro-5H-pyrido[4,3-d]pyrimidin-6-yl]-3-methyl-butanoic acid 2,2,2-trifluoroacetic acid salt (compound 263)

$^1$H NMR (400 MHz, Pyridine-d$_5$) δ 8.49 (s, 1H), 8.44 (s, 1H), 8.32 (t, J=8.8 Hz, 1H), 7.65 (d, J=8.1 Hz, 2H), 7.58 (d, J=8.1 Hz, 2H), 7.07 (dd, J=12.7, 2.4 Hz, 1H), 7.03 (dd, J=8.7, 2.6 Hz, 1H), 5.17 (s, 2H), 3.54 (d, J=15.2 Hz, 1H), 3.44 (d, J=15.3 Hz, 1H), 2.99 (t, J=5.9 Hz, 2H), 2.77-2.58 (m, 3H), 2.53-2.43 (m, 1H), 2.41-2.21 (m, 3H), 1.07 (d, J=6.4 Hz, 3H). MS (APCI) m/z 504.4.4 (M+H)+

4-[2-[4-[(3,4-dichlorophenyl)methoxy]-2-fluorophenyl]-7,8-dihydro-5H-pyrido[4,3-d]pyrimidin-6-yl]-3-methyl-butanoic acid 2,2,2-trifluoroacetic acid salt (compound 271)

Using 1-(bromomethyl)-3,4-dichlorobenzene instead of 1-(bromomethyl)-4-(trifluoromethyl) benzene. $^1$H NMR (400 MHz, Pyridine-d$_5$) δ 8.46 (d, J=18.0 Hz, 1H), 8.32 (t, J=8.8 Hz, 1H), 7.62 (d, J=2.0 Hz, 1H), 7.44 (d, J=8.2 Hz, 1H), 7.37-7.25 (m, 1H), 7.28 (d, J=2.0 Hz, 1H), 7.08 (d, J=2.5 Hz, 1H), 7.07-6.95 (m, 1H), 5.11 (s, 2H), 3.54 (d, J=15.3 Hz, 1H), 3.43 (d, J=15.4 Hz, 1H), 2.99 (t, J=5.9 Hz, 2H), 2.75-2.57 (m, 3H), 2.56-2.37 (m, 2H), 2.39-2.24 (m, 3H), 1.06 (d, J=6.6 Hz, 3H). MS (APCI) m/z 504.3 (M+H)+

4-[2-[2-fluoro-4-[[4-methyl-3-(trifluoromethyl)phenyl]methoxy]phenyl]-7,8-dihydro-5H-pyrido[4,3-d]pyrimidin-6-yl]-3-methyl-butanoic acid 2,2,2-trifluoroacetic acid salt (compound 279)

Using 1-(bromomethyl)-3-trifluoromethyl-4-methylbenzene instead of 1-(bromomethyl)-4-(trifluoromethyl) benzene. $^1$H NMR (400 MHz, Pyridine-$d_5$) δ 8.48 (s, 1H), 8.32 (t, J=8.9 Hz, 1H), 7.79 (d, J=1.7 Hz, 1H), 7.53 (d, J=8.8 Hz, 2H), 7.22 (d, J=7.8 Hz, 1H), 7.09 (dd, J=12.8, 2.4 Hz, 1H), 7.04 (dd, J=8.7, 2.6 Hz, 1H), 5.13 (s, 2H), 3.54 (d, J=15.2 Hz, 1H), 3.44 (d, J=15.3 Hz, 1H), 2.99 (t, J=5.9 Hz, 2H), 2.78-2.59 (m, 3H), 2.55-2.38 (m, 2H), 2.38-2.24 (m, 7H), 1.06 (d, J=6.5 Hz, 3H). MS (APCI) m/z 518.4 (M+H)+

4-[2-[4-[(4-tert-butylphenyl)methoxy]-2-fluoro-phenyl]-7,8-dihydro-5H-pyrido[4,3-d]pyrimidin-6-yl]-3-methyl-butanoic acid 2,2,2-trifluoroacetic acid salt (compound 283)

Using 1-(bromomethyl)-4-tert-butylbenzene instead of 1-(bromomethyl)-4-(trifluoromethyl) benzene. $^1$H NMR (400 MHz, Pyridine-$d_5$) δ 8.47 (s, 1H), 8.44 (s, 1H), 8.31 (t, J=8.9 Hz, 1H), 7.47 (d, J=8.3 Hz, 2H), 7.43-7.37 (m, 2H), 7.08-6.98 (m, 2H), 5.11 (s, 2H), 3.53 (d, J=15.2 Hz, 1H), 3.43 (d, J=15.3 Hz, 1H), 2.98 (t, J=5.9 Hz, 2H), 2.76-2.60 (m, 3H), 2.40-2.26 (m, 3H), 1.21 (s, 10H), 1.06 (d, J=6.5 Hz, 3H). MS (APCI) m/z 492.4 (M+H)+

4-[2-[4-[(2-chlorophenyl)methoxy]-2-fluoro-phenyl]-7,8-dihydro-5H-pyrido[4,3-d]pyrimidin-6-yl]-3-methyl-butanoic acid 2,2,2-trifluoroacetic acid salt (compound 284)

Using 1-(bromomethyl)-2-chlorobenzene instead of 1-(bromomethyl)-4-(trifluoromethyl) benzene. $^1$H NMR (400 MHz, Pyridine-$d_5$) δ 8.47 (s, 1H), 8.44 (s, 1H), 8.32 (t, J=8.9 Hz, 1H), 7.59-7.55 (m, 1H), 7.41-7.37 (m, 1H), 7.27-7.17 (m, 2H), 7.11 (dd, J=12.7, 2.4 Hz, 2H), 7.04 (dd, J=8.7, 2.5 Hz, 1H), 5.11 (s, 2H), 3.54 (d, J=15.3 Hz, 1H), 3.43 (d, J=15.2 Hz, 1H), 2.98 (t, J=5.9 Hz, 3H), 2.76-2.58 (m, 1H), 2.42-2.23 (m, 3H), 1.06 (d, J=6.5 Hz, 3H). MS (APCI) m/z 470.4 (M+H)+

4-[2-[2-fluoro-4-[[5-methyl-2-(trifluoromethyl)phenyl]methoxy]phenyl]-7,8-dihydro-5H-pyrido[4,3-d]pyrimidin-6-yl]-3-methyl-butanoic acid 2,2,2-trifluoroacetic acid salt (compound 290)

Using 1-(bromomethyl)-2-trifluoromethyl-5-methyl-benzene instead of 1-(bromomethyl)-4-(trifluoromethyl) benzene. $^1$H NMR (400 MHz, Pyridine-$d_5$) δ 8.45 (d, J=13.8 Hz, 1H), 8.33 (t, J=8.8 Hz, 1H), 7.55 (d, J=8.0 Hz, 2H), 7.12 (s, 2H), 7.07 (dd, J=8.7, 2.5 Hz, 1H); 5.33 (s, 2H), 3.53 (d, J=15.3 Hz, 1H), 3.43 (d, J=15.2 Hz, 1H), 2.98 (t, J=5.9 Hz, 2H), 2.80-2.58 (m, 3H), 2.43 (s, 2H), 2.43-2.28 (m, 3H), 2.19 (s, 3H), 1.06 (d, J=6.5 Hz, 3H). MS (APCI) m/z 518.4 (M+H)+

General Procedure 3

A 4 mL vial was charged with a stir bar to which was added NaH (10 mg, 0.4 mmol). To this NaH was then added a solution of ethyl 4-(2-(4-hydroxy-3-methylphenyl)-7,8-dihydropyrido[4,3-d]pyrimidin-6(5H)-yl)-3-methylbutanoate (compound XXIII with R*=ethyl 3-methylbutanoate and R"=CH$_3$, prepared as described for compound 336; 20 mg; 0.055 mmol) in DMF (200 µl) at 0° C. and stirred for 30 minutes. After 30 minutes, to this mixture was added a solution of 2-(bromomethyl)-1,3-difluorobenzene monomer (15 mg; 1.4 eq; 0.077 mmol) also in DMF (150 µl). This was allowed to stir at RT for 2 hours. Upon completion of the first step, to the crude material was added 500 µal of 1M LiOH and further allowed to be stirred for 1 hour at RT. The residues were dissolved in DMSO and purified by reverse phase HPLC (TFA method). Samples were purified by preparative HPLC on a Phenomenex Luna C8(2) 5 µm 100 Å AXIA column (30 mm×150 mm). A gradient of ACN (A) and 0.1% TFA in water (B) was used, at a flow rate of 50 mL/min (0-0.5 min 5% A, 0.5-8.5 min linear gradient 5-100% A, 8.7-10.7 min 100% A, 10.7-11.0 min linear gradient 100-5% A) to obtain desired compounds. Product was characterized by $^1$H NMR, MS and LC/MS.

The following compounds were prepared according to general procedure 3:

4-[2-[4-[(4-fluorophenyl)methoxy]-3-methyl-phenyl]-7,8-dihydro-5H-pyrido[4,3-d]pyrimidin-6-yl]-3-methyl-butanoic acid 2,2,2-trifluoroacetic acid salt (compound 269)

Using 1-(bromomethyl)-4-fluorobenzene instead of 2-(bromomethyl)-1,3-difluorobenzene. $^1$H NMR (400 MHz, Pyridine-$d_5$) δ 8.63-8.59 (m, 2H), 8.46 (s, 1H), 7.48-7.42 (m, 2H), 7.11 (dt, J=9.1, 2.1 Hz, 2H), 5.05 (s, 2H), 3.54 (d, J=15.1 Hz, 1H), 3.44 (d, J=15.1 Hz, 1H), 3.07-2.90 (m, 1H), 2.77-2.59 (m, 3H), 2.54-2.22 (m, 8H), 1.06 (d, J=6.4 Hz, 3H). MS (APCI) m/z 450.2 (M+H)+

4-[2-[4-[(2,6-dimethylphenyl)methoxy]-3-methyl-phenyl]-7,8-dihydro-5H-pyrido[4,3-d]pyrimidin-6-yl]-3-methyl-butanoic acid 2,2,2-trifluoroacetic acid salt (compound 274)

Using 2-(bromomethyl)-1,3-dimethylbenzene instead of 2-(bromomethyl)-1,3-difluorobenzene. $^1$H NMR (400 MHz, Pyridine-$d_5$) δ 8.72 (dd, J=8.6, 2.3 Hz, 2H), 8.62 (dd, J=2.2, 0.9 Hz, 2H), 8.45 (s, 1H), 7.31 (d, J=8.7 Hz, 1H), 7.11 (d, J=7.3 Hz, 1H), 7.03 (d, J=7.5 Hz, 2H), 5.10 (s, 2H), 3.53 (d, J=15.2 Hz, 1H), 3.43 (d, J=15.1 Hz, 1H), 2.76-2.58 (m, 3H), 2.48 (dq, J=13.6, 6.5 Hz, 1H), 2.42-2.23 (m, 10H), 2.19 (s, 3H), 1.06 (d, J=6.4 Hz, 3H). MS (APCI) m/z 460.3 (M+H)+

4-[2-[4-[(2,3-dimethylphenyl)methoxy]-3-methyl-phenyl]-7,8-dihydro-5H-pyrido[4,3-d]pyrimidin-6-yl]-3-methyl-butanoic acid 2,2,2-trifluoroacetic acid salt (compound 300)

Using 1-(bromomethyl)-2,3-dimethylbenzene instead of 2-(bromomethyl)-1,3-difluorobenzene. $^1$H NMR (400 MHz, Pyridine-$d_5$) δ 8.62 (d, J=2.2 Hz, 2H), 8.45 (s, 1H), 7.37 (dd, J=7.3, 1.8 Hz, 1H), 7.22 (d, J=8.6 Hz, 1H), 7.13-7.05 (m, 2H), 5.11 (s, 2H), 3.53 (d, J=15.1 Hz, 1H), 3.43 (d, J=15.1 Hz, 1H), 2.99 (t, J=5.9 Hz, 2H), 2.68 (dtt, J=22.7, 11.0, 5.9 Hz, 3H), 2.53-2.23 (m, 8H), 2.12 (d, J=6.4 Hz, 6H), 1.05 (d, J=6.5 Hz, 3H). MS (APCI) m/z 460.2 (M+H)+

3-methyl-4-[2-[3-methyl-4-(p-tolylmethoxy)phenyl]-7,8-dihydro-5H-pyrido[4,3-d]pyrimidin-6-yl]butanoic acid 2,2,2-trifluoroacetic acid salt (compound 301)

Using 1-(bromomethyl)-4-methylbenzene instead of 2-(bromomethyl)-1,3-difluorobenzene. $^1$H NMR (400 MHz, Pyridine-d$_5$) δ 8.61 (s, 2H), 8.44 (s, 1H), 7.39 (d, J=8.0 Hz, 2H), 7.12 (d, J=5.2 Hz, 2H), 5.08 (s, 2H), 3.58-3.49 (m, 1H), 3.43 (d, J=15.1 Hz, 1H), 2.98 (q, J=7.9, 6.9 Hz, 1H), 2.78-2.59 (m, 3H), 2.55-2.19 (m, 7H), 2.17 (s, 3H), 1.06 (d, J=6.5 Hz, 3H). MS (APCI) m/z 446.2 (M+H)+

3-methyl-4-[2-[3-methyl-4-[[3-(trifluoromethyl)phenyl]methoxy]phenyl]-7,8-dihydro-5H-pyrido[4,3-d]pyrimidin-6-yl]butanoic acid 2,2,2-trifluoroacetic acid salt (compound 302)

Using 1-(bromomethyl)-3-trifluoromethylbenzene instead of 2-(bromomethyl)-1,3-difluorobenzene. $^1$H NMR (400 MHz, Pyridine-d$_5$) δ 8.63 (dd, J=6.1, 2.4 Hz, 2H), 8.46 (s, 1H), 7.83 (s, 1H), 7.67 (d, J=7.7 Hz, 1H), 7.57 (d, J=7.8 Hz, 1H), 7.44 (t, J=7.7 Hz, 1H), 7.13 (s, H), 5.15 (s, 2H), 3.55 (d, J=15.1 Hz, 1H), 3.44 (d, J=15.1 Hz, 1H), 3.00 (t, J=6.0 Hz, 1H), 2.79-2.58 (m, 3H), 2.56-2.23 (m, 7H), 1.06 (d, J=6.5 Hz, 3H). MS (APCI) m/z 500.2 (M+H)+

4-[2-[4-[(2,4-dimethylphenyl)methoxy]-3-methylphenyl]-7,8-dihydro-5H-pyrido[4,3-d]pyrimidin-6-yl]-3-methyl-butanoic acid 2,2,2-trifluoroacetic acid salt (compound 305)

Using 1-(bromomethyl)-2,4-dimethylbenzene instead of 2-(bromomethyl)-1,3-difluorobenzene. $^1$H NMR (400 MHz, Pyridine-d$_5$) δ 8.64-8.58 (m, 2H), 8.45 (s, 1H), 7.38 (d, J=7.7 Hz, 1H), 7.21 (d, J=8.6 Hz, 1H), 6.99 (dd, J=7.7, 1.8 Hz, 1H), 6.93 (s, 1H), 5.07 (s, 2H), 3.54 (d, J=15.1 Hz, 1H), 3.43 (d, J=15.1 Hz, 1H), 2.99 (t, J=5.9 Hz, 1H), 2.79-2.58 (m, 3H), 2.55-2.36 (m, 2H), 2.36-2.23 (m, 8H), 2.17 (s, 3H), 1.06 (d, J=6.5 Hz, 3H). MS (APCI) m/z 460.3 (M+H)+

4-[2-[4-[(4-ethylphenyl)methoxy]-3-methyl-phenyl]-7,8-dihydro-5H-pyrido[4,3-d]pyrimidin-6-yl]-3-methyl-butanoic acid 2,2,2-trifluoroacetic acid salt (compound 306)

Using 1-(bromomethyl)-4-ethylbenzene instead of 2-(bromomethyl)-1,3-difluorobenzene. $^1$H NMR (400 MHz, Pyridine-d$_5$) δ 8.70-8.67 (m, 2H), 8.52 (s, 1H), 7.55-7.48 (m, 2H), 7.25 (d, J=7.9 Hz, 3H), 5.17 (s, 2H), 3.61 (d, J=15.1 Hz, 1H), 3.50 (d, J=15.1 Hz, 1H), 3.07 (t, J=6.0 Hz, 1H), 2.84-2.66 (m, 3H), 2.56 (q, J=7.6 Hz, 3H), 2.53-2.30 (m, 6H), 1.18-1.08 (m, 6H). MS (APCI) m/z 460.3 (M+H)+

4-[2-[4-[(2-ethylphenyl)methoxy]-3-methyl-phenyl]-7,8-dihydro-5H-pyrido[4,3-d]pyrimidin-6-yl]-3-methyl-butanoic acid 2,2,2-trifluoroacetic acid salt (compound 308)

Using 1-(bromomethyl)-2-ethylbenzene instead of 2-(bromomethyl)-1,3-difluorobenzene. $^1$H NMR (400 MHz, Pyridine-d$_5$) δ 8.72-8.69 (m, 2H), 8.52 (s, 1H), 7.61 (d, J=7.2 Hz, 1H), 7.40-7.25 (m, 4H), 5.22 (s, 2H), 3.51 (d, J=15.1 Hz, 1H), 3.06 (q, J=7.7, 6.8 Hz, 1H), 2.83-2.72 (m, 2H), 2.69 (t, J=7.6 Hz, 2H), 2.61-2.27 (m, 7H), 1.19 (t, J=7.5 Hz, 3H), 1.13 (d, J=6.5 Hz, 3H). MS (APCI) m/z 460.6 (M+H)+

3-methyl-4-[2-[3-methyl-4-[[2-(trifluoromethyl)phenyl]methoxy]phenyl]-7,8-dihydro-5H-pyrido[4,3-d]pyrimidin-6-yl]butanoic acid 2,2,2-trifluoroacetic acid salt (compound 309)

Using 1-(bromomethyl)-2-trifluoromethylbenzene instead of 2-(bromomethyl)-1,3-difluorobenzene. $^1$H NMR (400 MHz, Pyridine-d$_5$) δ 8.62 (m, 2H), 8.43 (s, 1H), 7.76 (d, J=7.8 Hz, 1H), 7.63 (d, J=7.8 Hz, 1H), 7.32 (t, J=7.6 Hz, 1H), 7.11 (s, 1H), 5.33 (d, J=8.0 Hz, 2H), 3.52 (d, J=15.1 Hz, 1H), 3.42 (d, J=15.1 Hz, 1H), 2.98 (t, J=5.9 Hz, 2H), 2.75-2.57 (m, 3H), 2.52-2.35 (m, 2H), 2.35-2.22 (m, 5H), 1.05 (d, J=6.5 Hz, 3H). MS (APCI) m/z 500.2 (M+H)+

4-[2-[4-[(4-isopropylphenyl)methoxy]-3-methylphenyl]-7,8-dihydro-5H-pyrido[4,3-d]pyrimidin-6-yl]-3-methyl-butanoic acid 2,2,2-trifluoroacetic acid salt (compound 310)

Using 1-(bromomethyl)-4-isopropylbenzene instead of 2-(bromomethyl)-1,3-difluorobenzene. $^1$H NMR (400 MHz, Pyridine-d$_5$) δ 8.69-8.65 (m, 2H), 8.51 (s, 1H), 7.51 (s, 1H), 7.33-7.26 (m, 2H), 5.17 (s, 2H), 3.60 (d, J=15.1 Hz, 1H), 3.49 (d, J=15.1 Hz, 1H), 3.06 (t, J=5.8 Hz, 2H), 2.88-2.65 (m, 4H), 2.60-2.30 (m, 7H), 1.17 (dd, J=6.9, 2.2 Hz, 6H), 1.12 (d, J=6.4 Hz, 3H). MS (APCI) m/z 474.3 (M+H)+

4-[2-[4-[(2,5-dimethylphenyl)methoxy]-3-methylphenyl]-7,8-dihydro-5H-pyrido[4,3-d]pyrimidin-6-yl]-3-methyl-butanoic acid 2,2,2-trifluoroacetic acid salt (compound 311)

Using 1-(bromomethyl)-2,5-dimethylbenzene instead of 2-(bromomethyl)-1,3-difluorobenzene. $^1$H NMR (400 MHz, Pyridine-d$_5$) δ 8.71 (m, 2H), 8.53 (s, 1H), 7.36 (d, J=1.9 Hz, 1H), 7.31 (d, J=8.6 Hz, 1H), 7.15 (d, J=7.6 Hz, 1H), 7.09 (dd, J=7.7, 1.8 Hz, 1H), 5.16 (s, 2H), 3.62 (d, J=15.1 Hz, 1H), 3.51 (d, J=15.1 Hz, 1H), 3.08 (t, J=5.9 Hz, 1H), 2.85-2.67 (m, 3H), 2.63-2.40 (m, 3H), 2.38 (d, J=4.2 Hz, 4H), 2.33 (s, 3H), 2.27 (s, 3H), 1.14 (d, J=6.5 Hz, 3H). MS (APCI) m/z 460.3 (M+H)+

3-methyl-4-[2-[3-methyl-4-[[2-methyl-5-(trifluoromethyl)phenyl]methoxy]phenyl]-7,8-dihydro-5H-pyrido[4,3-d]pyrimidin-6-yl]butanoic acid 2,2,2-trifluoroacetic acid salt (compound 314)

Using 1-(bromomethyl)-2-methyl-5-(trifluoromethylbenzene instead of 2-(bromomethyl)-1,3-difluorobenzene. $^1$H NMR (400 MHz, Pyridine-d$_5$) δ 8.63 (d, J=2.2 Hz, 2H), 8.46 (s, 1H), 7.88 (d, J=2.0 Hz, 1H), 7.48 (d, J=1.7 Hz, 1H), 7.23 (dd, J=8.3, 3.5 Hz, 2H), 5.11 (s, 2H), 3.54 (d, J=15.2 Hz, 1H), 3.44 (d, J=15.2 Hz, 1H), 2.99 (q, J=9.0, 7.5 Hz, 1H), 2.77-2.60 (m, 3H), 2.56-2.21 (m, 10H), 1.06 (d, J=6.5 Hz, 3H). MS (APCI) m/z 514.2 (M+H)+

4-[2-[4-[(2,6-difluorophenyl)methoxy]-3-methylphenyl]-7,8-dihydro-5H-pyrido[4,3-d]pyrimidin-6-yl]-3-methyl-butanoic acid 2,2,2-trifluoroacetic acid salt (compound 316)

$^1$H NMR (400 MHz, Pyridine-d$_5$) δ 8.61-8.54 (m, 1H), 8.43 (s, 1H), 7.33-7.16 (m, 4H), 6.93 (t, J=7.9 Hz, 2H), 5.24 (s, 2H), 3.53 (d, J=15.1 Hz, 1H), 3.40 (s, 1H), 2.98 (t, J=5.8 Hz, 2H), 2.77-2.58 (m, 3H), 2.53-2.23 (m, 4H), 2.22 (s, 3H), 1.05 (d, J=6.4 Hz, 3H) MS (APCI) m/z 468.2 (M+H)+.

3-methyl-4-[2-[3-methyl-4-(m-tolylmethoxy)phenyl]-7,8-dihydro-5H-pyrido[4,3-d]pyrimidin-6-yl]butanoic acid 2,2,2-trifluoroacetic acid salt (compound 320)

Using 1-(bromomethyl)-3-methylbenzene instead of 2-(bromomethyl)-1,3-difluorobenzene. $^1$H NMR (400 MHz, Pyridine-d$_5$) δ 8.60 (dt, J=4.7, 2.3 Hz, 3H), 8.43 (s, 1H), 7.34-7.27 (m, 1H), 7.27-7.20 (m, 2H), 7.05 (d, J=7.8 Hz, 1H), 5.08 (s, 2H), 3.51 (d, J=15.1 Hz, 1H), 3.43 (s, 1H), 2.97 (t, J=5.9 Hz, 2H), 2.74-2.58 (m, 3H), 2.52-2.21 (m, 8H), 2.18 (s, 3H), 1.04 (d, J=6.5 Hz, 3H). MS (APCI) m/z 446.2 (M+H)+

General Procedure 4

A 4 mL vial was charged with a stir bar to which was added NaH (10 mg, 0.4 mmol). To this NaH was then added a solution of ethyl 4-(2-(2-fluoro-4-hydroxyphenyl)-7,8-dihydropyrido[4,3-d]pyrimidin-6(5H)-yl)-3-methylbutanoate (compound XXIII with R*=ethyl 3-methylbutanoate and R"=F, prepared as described for compound 336; 20 mg; 0.055 mmol) in DMF (200 μl) at 0° C. and stirred for 30 minutes. After 30 minutes, to this mixture was added a solution of 1-(bromomethyl)-3,5-dimethylbenzene monomer (15 mg, 1.4 eq., 0.077 mmol) also in DMF (150 μl). This was allowed to stir at RT for 2 hours. Upon completion of the first step, to the crude material was added 500 μl of 1M LiOH and further allowed to be stirred for 1 hour at RT. The residues were dissolved in DMSO and purified by reverse phase HPLC (TFA method). Samples were purified by preparative HPLC on a Phenomenex Luna C8(2) 5 μm 100 Å AXIA column (30 mm×150 mm). A gradient of ACN (A) and 0.1% TFA in water (B) was used, at a flow rate of 50 mL/min (0-0.5 min 5% A, 0.5-8.5 min linear gradient 5-100% A, 8.7-10.7 min 100% A, 10.7-11.0 min linear gradient 100-5% A) to obtain desired compounds. Product was characterized by $^1$H NMR, MS and LC/MS.

The following compounds were prepared according to general procedure 4:

4-[2-[4-[(2,3-dimethylphenyl)methoxy]-2-fluorophenyl]-7,8-dihydro-5H-pyrido[4,3-d]pyrimidin-6-yl]-3-methyl-butanoic acid 2,2,2-trifluoroacetic acid salt (compound 231)

Using 1-(bromomethyl)-2,3-dimethylbenzene instead of 1-(bromomethyl)-3,5-dimethylbenzene. $^1$H NMR (400 MHz, Pyridine-d$_5$) δ 8.54 (s, 1H), 8.40 (t, J=8.9 Hz, 1H), 7.41 (dd, J=5.9, 3.2 Hz, 1H), 7.18 (d, J=3.4 Hz, 2H), 7.12 (dd, J=8.8, 2.6 Hz, 1H), 5.18 (s, 2H), 3.60 (d, J=15.2 Hz, 1H), 3.50 (d, J=15.2 Hz, 1H), 3.04 (d, J=5.9 Hz, 2H), 2.81-2.64 (m, 3H), 2.59-2.46 (m, 1H), 2.46-2.30 (m, 3H), 2.22-2.15 (m, 7H), 1.13 (d, J=6.5 Hz, 3H). MS (APCI) m/z 464.3 (M+H)+

4-[2-[4-[(2,6-difluorophenyl)methoxy]-2-fluorophenyl]-7,8-dihydro-5H-pyrido[4,3-d]pyrimidin-6-yl]-3-methyl-butanoic acid 2,2,2-trifluoroacetic acid salt (compound 240)

Using 2-(bromomethyl)-1,3-difluorobenzene instead of 1-(bromomethyl)-3,5-dimethylbenzene. $^1$H NMR (400 MHz, Pyridine-d$_5$) δ 8.46 (s, 1H), 8.30 (s, 1H), 7.28-7.18 (m, 1H), 7.08 (dd, J=17.6, 2.5 Hz, 2H), 7.04-6.89 (m, 2H), 5.25 (s, 2H), 3.53 (d, J=15.2 Hz, 1H), 3.40 (d, 1H), 2.97 (t, J=5.9 Hz, 2H), 2.74-2.58 (m, 3H), 2.47 (dt, J=13.5, 6.8 Hz, 1H), 2.40-2.23 (m, 3H), 1.06 (d, J=6.5 Hz, 3H). MS (APCI) m/z 472.3 (M+H)+

4-[2-[2-fluoro-4-[(2-fluorophenyl)methoxy]phenyl]-7,8-dihydro-5H-pyrido[4,3-d]pyrimidin-6-yl]-3-methyl-butanoic acid 2,2,2-trifluoroacetic acid salt (compound 242)

Using 1-(bromomethyl)-2-fluorobenzene instead of 1-(bromomethyl)-3,5-dimethylbenzene. $^1$H NMR (400 MHz, Pyridine-d$_5$) δ 8.47 (s, 1H), 8.30 (t, J=8.9 Hz, 1H), 7.55 (dd, J=7.4, 1.8 Hz, 1H), 7.26 (td, J=5.8, 2.6 Hz, 1H), 7.12-7.07 (m, 2H), 7.03 (dd, J=8.8, 2.5 Hz, 1H), 5.20 (s, 2H), 3.53 (d, J=15.2 Hz, 1H), 3.43 (d, J=15.3 Hz, 1H), 2.98 (t, J=5.9 Hz, 2H), 2.76-2.57 (m, 3H), 2.54-2.40 (m, 1H), 2.42-2.23 (m, 3H), 1.06 (d, J=6.4 Hz, 3H). MS (APCI) m/z 454.3 (M+H)+

4-[2-[2-fluoro-4-(m-tolylmethoxy)phenyl]-7,8-dihydro-5H-pyrido[4,3-d]pyrimidin-6-yl]-3-methyl-butanoic acid 2,2,2-trifluoroacetic acid salt (compound 264)

Using 1-(bromomethyl)-3-methylbenzene instead of 1-(bromomethyl)-3,5-dimethylbenzene. $^1$H NMR (400 MHz, Pyridine-d$_5$) δ 8.47 (s, 1H), 8.31 (t, J=8.8 Hz, 1H), 7.32-7.20 (m, 3H), 7.10-6.99 (m, 3H), 5.08 (s, 2H), 3.53 (d, J=15.3 Hz, 1H), 3.42 (d, J=15.2 Hz, 1H), 2.98 (t, J=5.9 Hz, 2H), 2.76-2.57 (m, 3H), 2.56-2.38 (m, 1H), 2.42-2.22 (m, 3H), 2.19 (s, 3H), 1.06 (d, J=6.5 Hz, 3H). MS (APCI) m/z 450.3 (M+H)+

4-[2-[2-fluoro-4-[[2-methyl-5-(trifluoromethyl)phenyl]methoxy]phenyl]-7,8-dihydro-5H-pyrido[4,3-d]pyrimidin-6-yl]-3-methyl-butanoic acid 2,2,2-trifluoroacetic acid salt (compound 272)

Using 1-(bromomethyl)-2-methyl-5-trifluoromethylbenzene instead of 1-(bromomethyl)-3,5-dimethylbenzene. $^1$H NMR (400 MHz, Pyridine-d$_5$) δ 8.48 (s, 1H), 8.34 (t, J=8.8 Hz, 1H), 7.87 (d, J=1.8 Hz, 1H), 7.23 (d, J=7.9 Hz, 1H), 7.14 (q, J=1.1 Hz, 1H), 7.07 (dd, J=8.6, 2.5 Hz, 1H), 5.13 (s, 2H), 3.54 (d, J=15.2 Hz, 1H), 3.44 (d, J=15.3 Hz, 1H), 2.99 (t, J=5.9 Hz, 2H), 2.74 (s, 1H), 2.73-2.64 (m, 2H), 2.40 (s, 1H), 2.38-2.31 (m, 2H), 1.07 (d, J=6.5 Hz, 3H). MS (APCI) m/z 486.3 (M+H)+

4-[2-[4-[(2,6-dimethylphenyl)methoxy]-2-fluorophenyl]-7,8-dihydro-5H-pyrido[4,3-d]pyrimidin-6-yl]-3-methyl-butanoic acid 2,2,2-trifluoroacetic acid salt (compound 276)

Using 2-(bromomethyl)-1,3-dimethylbenzene instead of 1-(bromomethyl)-3,5-dimethylbenzene. $^1$H NMR (400 MHz, Pyridine-d$_5$) δ 8.48 (s, 1H), 8.35 (t, J=8.9 Hz, 1H), 7.18-7.15 (m, 1H), 7.11 (d, J=2.5 Hz, 1H), 7.10-7.01 (m, 3H), 5.12 (s, 2H), 3.54 (d, J=15.3 Hz, 1H), 3.43 (d, J=15.3 Hz, 1H), 2.99 (t, J=5.8 Hz, 2H), 2.77-2.59 (m, 3H), 2.47 (dt, J=14.0, 7.2 Hz, 1H), 2.35 (td, J=8.0, 7.5, 3.9 Hz, 3H), 2.30 (s, 7H), 1.07 (d, J=6.5 Hz, 3H). MS (APCI) m/z 464.3 (M+H)+

4-[2-[2-fluoro-4-[(3-fluorophenyl)methoxy]phenyl]-7,8-dihydro-5H-pyrido[4,3-d]pyrimidin-6-yl]-3-methyl-butanoic acid 2,2,2-trifluoroacetic acid salt (compound 289)

Using 1-(bromomethyl)-3-fluorobenzene instead of 1-(bromomethyl)-3,5-dimethylbenzene. $^1$H NMR (400 MHz, Pyridine-d$_5$) δ 8.47 (s, 1H), 8.31 (t, J=8.9 Hz, 1H), 7.37-7.20 (m, 3H), 7.12-6.97 (m, 3H), 5.10 (s, 2H), 3.53 (d, J=15.2 Hz, 1H), 3.43 (d, J=15.2 Hz, 1H), 2.98 (t, J=5.8 Hz, 2H), 2.76-2.58 (m, 3H), 2.48 (qd, J=13.5, 12.1, 6.5 Hz, 1H), 2.42-2.23 (m, 2H), 1.06 (d, J=6.5 Hz, 3H). MS (APCI) m/z 454.3 (M+H)+

4-[2-[4-[(2-ethylphenyl)methoxy]-2-fluoro-phenyl]-7,8-dihydro-5H-pyrido[4,3-d]pyrimidin-6-yl]-3-methyl-butanoic acid 2,2,2-trifluoroacetic acid salt (compound 296)

Using 1-(bromomethyl)-2-ethylbenzene instead of 1-(bromomethyl)-3,5-dimethylbenzene. $^1$H NMR (400 MHz, Pyridine-$d_5$) δ 8.47 (s, 1H), 8.33 (t, J=8.9 Hz, 1H), 7.48 (d, J=1.2 Hz, 1H), 7.30 (td, J=7.4, 1.5 Hz, 1H), 7.22 (ddd, J=7.3, 3.7, 2.2 Hz, 2H), 7.13-7.02 (m, 2H), 5.14 (s, 2H), 3.53 (d, J=15.3 Hz, 1H), 3.43 (d, J=15.2 Hz, 1H), 2.98 (d, J=5.9 Hz, 2H), 2.74-2.65 (m, 3H), 2.65-2.56 (m, 3H), 2.52-2.42 (m, 1H), 2.38-2.22 (m, 3H), 1.13 (t, J=7.5 Hz, 3H), 1.07 (d, J=6.5 Hz, 3H). MS (APCI) m/z 464.3 (M+H)+

4-[2-[2-fluoro-4-[(4-fluorophenyl)methoxy]phenyl]-7,8-dihydro-5H-pyrido[4,3-d]pyrimidin-6-yl]-3-methyl-butanoic acid 2,2,2-trifluoroacetic acid salt (compound 298)

Using 1-(bromomethyl)-4-fluorobenzene instead of 1-(bromomethyl)-3,5-dimethylbenzene. $^1$H NMR (400 MHz, Pyridine-$d_5$) δ 8.48 (s, 1H), 8.31 (t, J=8.8 Hz, 1H), 7.48-7.40 (m, 2H), 7.13-7.09 (m, 1H), 7.07-6.98 (m, 2H), 5.05 (s, 2H), 3.54 (d, J=15.3 Hz, 1H), 3.43 (d, J=15.3 Hz, 1H), 2.99 (t, J=5.9 Hz, 2H), 2.5 (m, 1H); 2.77-2.58 (m, 3H), 2.42-2.23 (m, 3H), 1.07 (d, J=6.5 Hz, 3H). MS (APCI) m/z 454.3 (M+H)+

4-[2-[4-[(2,4-dimethylphenyl)methoxy]-2-fluoro-phenyl]-7,8-dihydro-5H-pyrido[4,3-d]pyrimidin-6-yl]-3-methyl-butanoic acid 2,2,2-trifluoroacetic acid salt (compound 304)

Using 1-(bromomethyl)-2,4-dimethylbenzene instead of 1-(bromomethyl)-3,5-dimethylbenzene. $^1$H NMR (400 MHz, Pyridine-$d_5$) δ 8.47 (s, 1H), 8.31 (d, J=8.9 Hz, 1H), 7.35 (d, J=7.7 Hz, 1H), 7.11-7.02 (m, 2H), 7.02-6.97 (m, 1H), 6.94 (s, 1H), 5.08 (s, 2H), 3.53 (d, J=15.3 Hz, 1H), 3.45 (d, 1H), 2.98 (t, J=5.9 Hz, 2H), 2.77-2.60 (m, 3H), 2.48 (dq, J=13.6, 6.9 Hz, 1H), 2.40-2.23 (m, 6H), 2.17 (s, 4H), 1.06 (d, J=6.5 Hz, 3H). MS (APCI) m/z 464.3 (M+H)+

4-[2-[2-fluoro-4-(p-tolylmethoxy)phenyl]-7,8-dihydro-5H-pyrido[4,3-d]pyrimidin-6-yl]-3-methyl-butanoic acid 2,2,2-trifluoroacetic acid salt (compound 307)

Using 1-(bromomethyl)-2-fluorobenzene instead of 1-(bromomethyl)-3,5-dimethylbenzene. $^1$H NMR (400 MHz, Pyridine-$d_5$) δ 8.47 (s, 1H), 8.30 (t, J=8.9 Hz, 1H), 7.37 (d, J=7.8 Hz, 2H), 7.13-7.02 (m, 2H), 5.07 (s, 2H), 3.58-3.36 (m, 2H), 2.98 (t, J=5.9 Hz, 2H), 2.76-2.67 (m, 3H), 2.67-2.56 (m, 1H), 2.48 (dq, J=13.7, 7.0 Hz, 1H), 2.45-2.33 (m, 2H), 2.29-2.20 (m, 2H), 2.18 (s, 4H), 1.06 (d, J=6.4 Hz, 3H). MS (APCI) m/z 450.3 (M+H)+

4-[2-[4-[(3,5-dimethylphenyl)methoxy]-2-fluoro-phenyl]-7,8-dihydro-5H-pyrido[4,3-d]pyrimidin-6-yl]-3-methyl-butanoic acid 2,2,2-trifluoroacetic acid salt (compound 313)

$^1$H NMR (400 MHz, Pyridine-$d_5$) δ 8.47 (s, 1H), 8.44 (s, 1H), 8.31 (s, 1H), 7.08-7.01 (m, 2H), 6.85 (s, 1H), 5.07 (s, 2H), 3.53 (d, J=15.2 Hz, 1H), 3.43 (d, J=15.2 Hz, 1H), 2.98 (t, J=5.9 Hz, 2H), 2.76-2.57 (m, 3H), 2.47 (dt, J=13.4, 6.8 Hz, 1H), 2.40-2.25 (m, 3H), 2.22-2.11 (m, 8H), 1.06 (d, J=6.5 Hz, 3H). MS (APCI) m/z 464.3 (M+H)+

4-(2-(3-(benzyloxy)cyclobutyl)-7,8-dihydropyrido[4,3-d]pyrimidin-6(5H)-yl)-3-methylbutanoic acid (compound 333)

Ethyl 4-(2-(3-(benzyloxy)cyclobutyl)-7,8-dihydropyrido[4,3-d]pyrimidin-6(5H)-yl)-3-methylbutanoate was prepared in accordance with scheme 5. 2-(3-(benzyloxy)cyclobutyl)-5,6,7,8-tetrahydropyrido[4,3-d]pyrimidine (780 mg; 2.64 mmol; 1 eq) was dissolved in 40 ml THF. Ethyl 3-methyl-4-oxobutanoate (457 mg; 3.17 mmol; 1.2 eq) was added under Argon atmosphere. The mixture was stirred for 1 h at RT and sodium triacetoxyborohydride (840 mg; 3.96 mmol; 1.5 eq) was added, followed by further stirring overnight at RT. The mixture was evaporated, extracted with water/DCM under stirring for 15 min. The organic phase was washed with water, dried over $MgSO_4$ and evaporated. The residue was dissolved in 3 ml DCM and purified by flash chromatography (24 g silica gel, EtOAc/n-heptane 2:1) giving ethyl 4-(2-(3-(benzyloxy)cyclobutyl)-7,8-dihydro-pyrido[4,3-d]pyrimidin-6(5H)-yl)-3-methylbutanoate with a yield of 88% (981 mg; 2.316 mmol). This product was converted to the corresponding methylbutanoic acid with NaOH as described herein elsewhere to give compound 333 with a yield of 42.8% (36 mg; 0.0.091 mmol). Calculated mass (C23H29N3O3): 395.495. 1H NMR (500 MHz, DMSO-$d_6$) δ 12.07 (s, 2H), 8.44 (d, J=4.7 Hz, 1H), 7.42-7.19 (m, 7H), 4.40 (d, J=5.0 Hz, 1H), 4.33 (q, J=6.8 Hz, 1H), 4.04 (dt, J=16.7, 6.7 Hz, 1H), 3.54 (s, 2H), 3.20-3.08 (m, 2H), 2.80 (dq, J=23.0, 5.9 Hz, 4H), 2.69 (dt, J=11.6, 5.9 Hz, 1H), 2.59-2.52 (m, 2H), 2.43-2.12 (m, 9H), 2.01 (dd, J=15.3, 7.5 Hz, 1H), 0.91 (dd, J=6.5, 1.4 Hz, 4H). M+H=396

1-(2-(2-(4-((4-chlorobenzyl)oxy)phenyl)-7,8-dihydropyrido[4,3-d]pyrimidin-6(5H)-yl)ethyl)cyclopropanecarboxylic acid (compound 335)

Compound 335 was prepared from 2-((4(4-chlorobenzyl)oxy)phenyl)-5,6,7,8-tetrahydropyrido[4,3-d]pyrimidine (prepared as described for compound 287) in accordance with scheme 5.

500 mg unpurified methyl 1-(2-oxoethyl)cyclopropanecarboxylate (assumed 2 mmol; 5 eq) was dissolved in THF/MeOH, 5 ml each. 2-((4(4-chlorobenzyl)oxy)phenyl)-5,6,7,8-tetrahydropyrido[4,3-d]pyrimidine (141 mg; 0.40 mmol; 1 eq) was added, 50 µl glacial acetic acid was added and this was stirred for 1 h at RT. Sodium triacetoxyborohydride (425 mg; 2.00 mmol; 5 eq) was added and stirred for another 20 h at RT. 20 ml $H_2O$ and 20 ml DCM were added and the mixture was stirred for 30 min. The organic phase was separated, washed three times with H2O, dried over $MgSO_4$ and evaporated. The residue was dissolved in 2 ml DCM and purified by flash chromatography (12 g silica gel, DCM/MeOH 95:5) giving methyl 14242444(4-chlorobenzyl)oxy)phenyl)-7,8-dihydropyrido[4,3-d]pyrimidin-6(5H)-yl)ethyl)cyclopropanecarboxylate with a yield of 96% (183 mg; 0.383 mmol).

This product was converted to the corresponding carboxylic acid with NaOH as described herein elsewhere to give compound 335 with a yield of 91% (159 mg; 0.343 mmol). Calculated mass (C26H26ClN3O3): 463.956 g/mol. 1H NMR (600 MHz, DMSO-d6) δ 12.54 (s, 1H), 8.55 (s, 1H), 8.34-8.27 (m, 2H), 7.51 (d, J=8.5 Hz, 2H), 7.51-7.44 (m, 2H), 7.16-7.09 (m, 2H), 5.18 (s, 2H), 3.64 (s, 2H), 2.92 (t, J=6.0 Hz, 2H), 2.83 (t, J=5.9 Hz, 2H), 2.70-2.63 (m, 2H), 1.75 (dt, J=9.7, 7.0 Hz, 2H), 1.05 (q, J=3.6 Hz, 2H), 0.76 (q, J=3.7 Hz, 2H). M+H=464/466

4-(2-(4-(cyclohexylmethoxy)phenyl)-7,8-dihydropyrido[4,3-d]pyrimidin-6(5H)-yl)-3-methylbutanoic acid (compound 336)

Ethyl 4-(2-(4-hydroxyphenyl)-7,8-dihydropyrido[4,3-d]pyrimidin-6(5H)-yl)-3-methylbutanoate was prepared starting from compound XXg in a palladium mediated reaction using 4-hydroxyphenylboronic acid instead of compound VI as indicated in scheme 2. Compound XXg (500 mg; 1.679 mmol; 1 eq), sodium carbonate (3.35 g; 4.20 mmol; 2.5 eq) and hydoxyphenylbonic acid (250 mg; 1.813 mmol; 1.08 eq) were dissolved in DMV (15 ml). Tetrakis(triphenylphosphine)palladium(0) (97 mg; 0.084 mmol; 0.05 eq) was added and the reaction mixture was heated for 2 h at 90° C., followed by stirring overnight at RT. The reaction mixture was evaporated. The residue was dissolved in EtOAc, washed twice with water, once with saturated NaCl solution, dried over MgSO$_4$, filtered and evaporated. The brown oily residue was purified by flash chromatography (12 g silica gel, 0-10% MeOH in DCM) giving ethyl 4-(2-(4-hydroxyphenyl)-7,8-dihydropyrido[4,3-d]pyrimidin-6(5H)-yl)-3-methylbutanoate with a yield of 36.9% (220 mg; 0.619 mmol).

50 mg thereof (0.141 mmol; 1 eq) was dissolved in 3 ml DMF. Cesium carbonate (75 mg; 0.230 mmol; 1.6 eq) and cyclohexylmethyl bromide (30 mg; 0.169 mmol; 1.2 eq) were added and the mixture was stirred overnight at RT. The mixture was evaporated and the residue dissolved in water and DCM. After phase separation, the organic layer was evaporated, and the residue was purified by flash chromatography (4 g silica gel, 0-10% MeOH in DCM) giving ethyl 44244-(cyclohexylmethoxy)phenyl)-7,8-dihydropyrido[4,3-d]pyrimidin-6(5H)-yl)-3-methylbutanoate with a yield of 28.3% (18 mg; 0.040 mmol).

This product was converted to the corresponding methylbutanoic acid with NaOH as described herein elsewhere to give compound 336 with a yield of 29.6% (5 mg; 0.012 mmol). Calculated mass (C25H33N3O3): 423.548. 1H NMR (600 MHz, Methanol-d4) δ 8.54 (s, 1H), 8.36-8.27 (m, 2H), 7.05-6.96 (m, 2H), 4.16 (d, J=15.2 Hz, 1H), 4.09 (d, J=15.5 Hz, 1H), 3.85 (d, J=6.4 Hz, 2H), 3.43 (s, 1H), 3.22-3.14 (m, 1H), 2.88 (s, 2H), 2.58-2.28 (m, 3H), 1.94-1.69 (m, 7H), 1.44-1.10 (m, 6H), 1.07 (d, J=6.6 Hz, 3H). M+H=424

TABLE 1

| No | Structure | S1P5 EC50 range # | S1P1 EC50* | S1P3 EC50* | S1P4 EC50* |
|----|-----------|-------------------|------------|------------|------------|
| 1 | 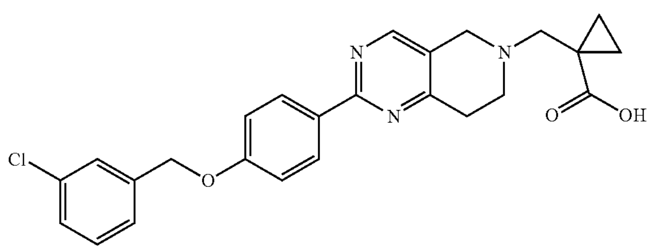 [SMILES: O=C(O)C1(CN2CCc3nc(-c4ccc(OCc5cccc(Cl)c5)cc4)ncc3C2)CC1] | C | >1 μM (1) | >1 μM (1) | >1 μM (1) |
| 2 | 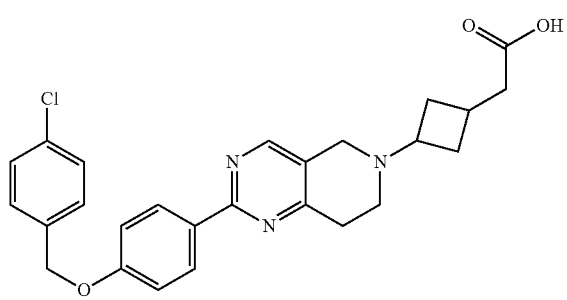 [SMILES: O=C(O)CC1CC(N2CCc3nc(-c4ccc(OCc5ccc(Cl)cc5)cc4)ncc3C2)C1] | C | >1 μM (1) | >1 μM (1) | >1 μM (1) |
| 3 | 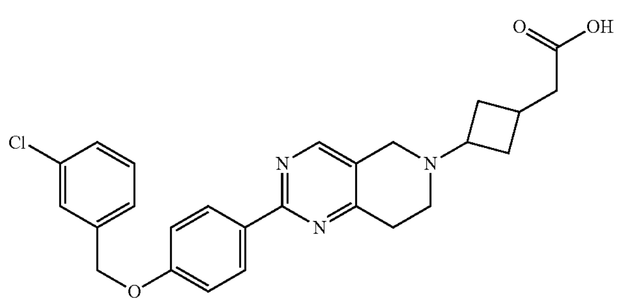 [SMILES: O=C(O)CC1CC(N2CCc3nc(-c4ccc(OCc5cccc(Cl)c5)cc4)ncc3C2)C1] | C | >1 μM (1) | >1 μM (1) | >1 μM (1) |

TABLE 1-continued

| No | Structure | S1P5 EC50 range # | S1P1 EC50* | S1P3 EC50* | S1P4 EC50* |
|---|---|---|---|---|---|
| 4 | 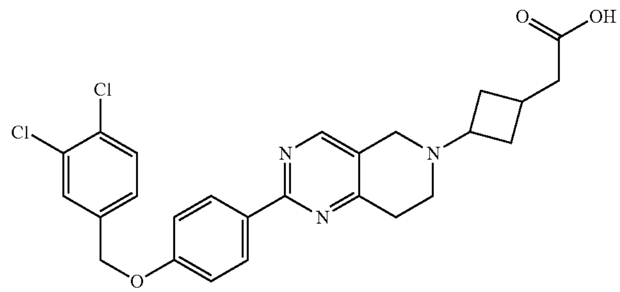 [SMILES: O=C(O)CC1CC(N2CCc3nc(-c4ccc(OCc5ccc(Cl)c(Cl)c5)cc4)ncc3C2)C1] | C | >1 μM (1) | | >1 μM (1) |
| 5 | 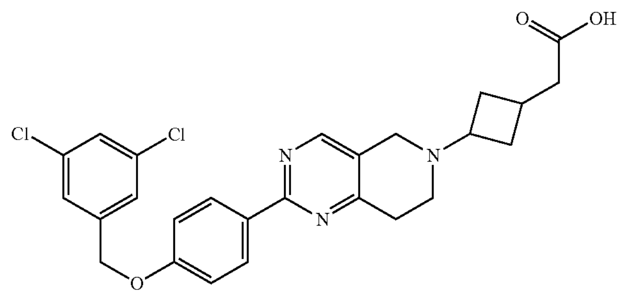 [SMILES: O=C(O)CC1CC(N2CCc3nc(-c4ccc(OCc5cc(Cl)cc(Cl)c5)cc4)ncc3C2)C1] | C | >1 μM (1) | | >1 μM (1) |
| 6 | 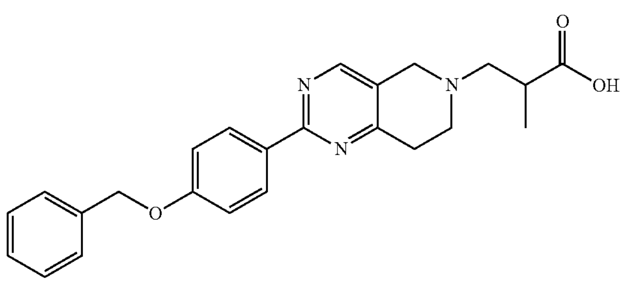 [SMILES: CC(CN1CCc2nc(-c3ccc(OCc4ccccc4)cc3)ncc2C1)C(=O)O] | F | >1 μM (2) | >1 μM (2) | |
| 7 | 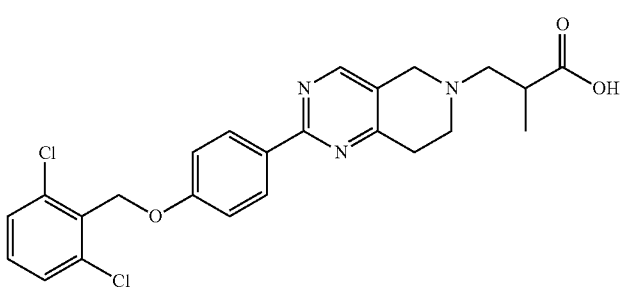 [SMILES: CC(CN1CCc2nc(-c3ccc(OCc4c(Cl)cccc4Cl)cc3)ncc2C1)C(=O)O] | F | >1 μM (2) | >1 μM (2) | |
| 8 | 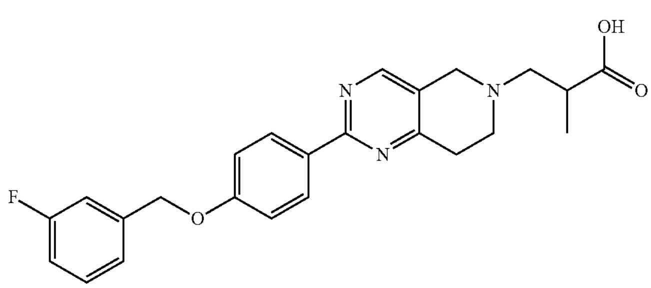 [SMILES: CC(CN1CCc2nc(-c3ccc(OCc4cccc(F)c4)cc3)ncc2C1)C(=O)O] | A | >1 μM (1) | >1 μM (1) | >1 μM (1) |

TABLE 1-continued

| No | Structure | S1P5 EC50 range # | S1P1 EC50* | S1P3 EC50* | S1P4 EC50* |
|---|---|---|---|---|---|
| 9 | 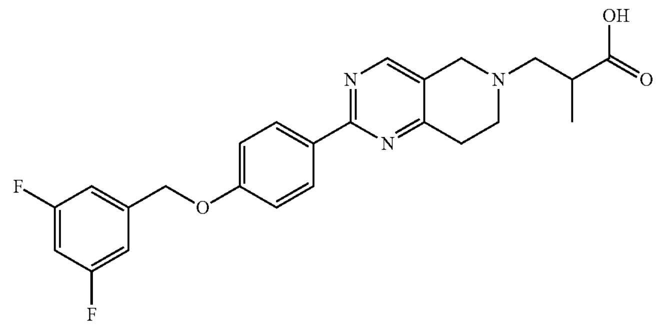 [SMILES: CC(CN1CCc2nc(-c3ccc(OCc4cc(F)cc(F)c4)cc3)ncc2C1)C(=O)O] | F | >1 μM (2) | >1 μM (2) | |
| 10 | 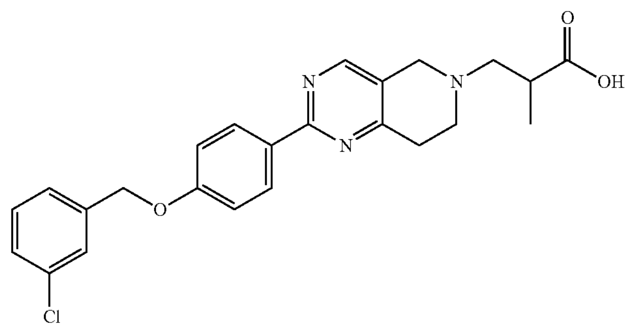 [SMILES: CC(CN1CCc2nc(-c3ccc(OCc4cccc(Cl)c4)cc3)ncc2C1)C(=O)O] | A | >1 μM (1) | >1 μM (1) | |
| 11 | 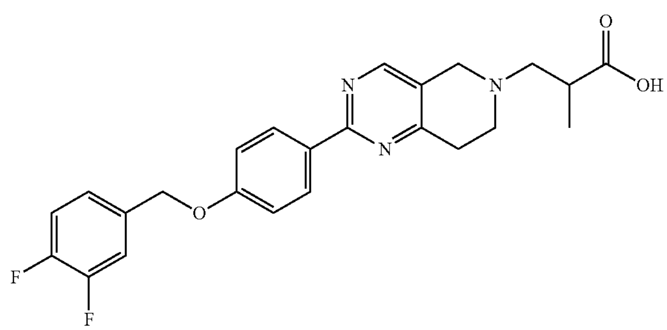 [SMILES: CC(CN1CCc2nc(-c3ccc(OCc4ccc(F)c(F)c4)cc3)ncc2C1)C(=O)O] | A | >1 μM (1) | >1 μM (1) | |
| 12 | 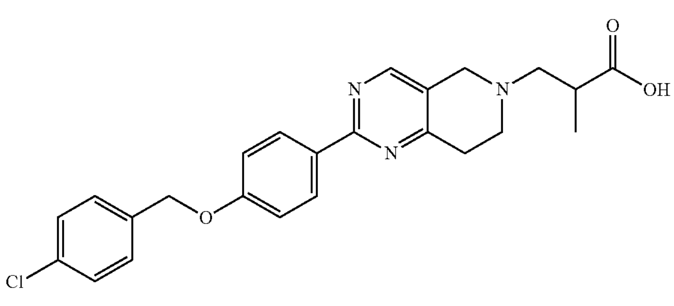 [SMILES: CC(CN1CCc2nc(-c3ccc(OCc4ccc(Cl)cc4)cc3)ncc2C1)C(=O)O] | A | >1 μM (1) | >1 μM (1) | >1 μM (1) |

TABLE 1-continued

| No | Structure | S1P5 EC50 range # | S1P1 EC50* | S1P3 EC50* | S1P4 EC50* |
|---|---|---|---|---|---|
| 14 | 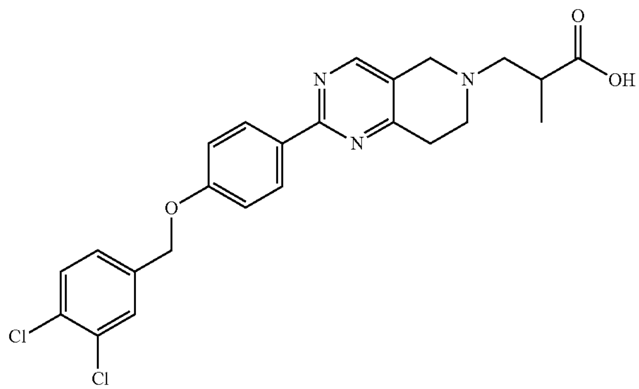 [SMILES: CC(CN1CCc2nc(-c3ccc(OCc4ccc(Cl)c(Cl)c4)cc3)ncc2C1)C(=O)O] | A | >1 μM (1) | >1 μM (1) | >1 μM (1) |
| 15 | 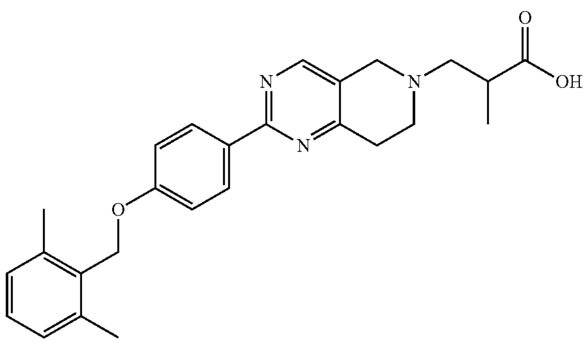 [SMILES: Cc1cccc(C)c1COc1ccc(-c2ncc3c(n2)CCN(CC(C)C(=O)O)C3)cc1] | A | <1 μM (10 | >1 μM (1) | |
| 16 | 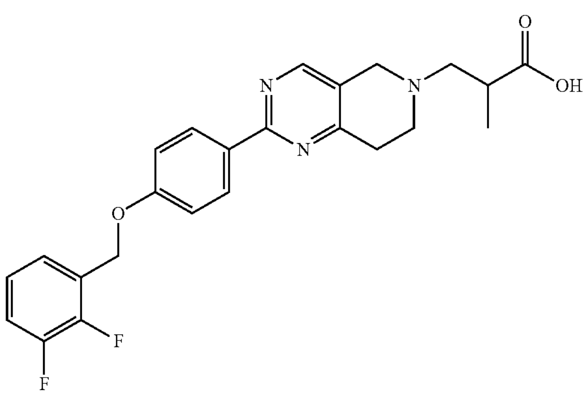 [SMILES: CC(CN1CCc2nc(-c3ccc(OCc4cccc(F)c4F)cc3)ncc2C1)C(=O)O] | A | <1 μM (10 | >1 μM (10 | |
| 17 | 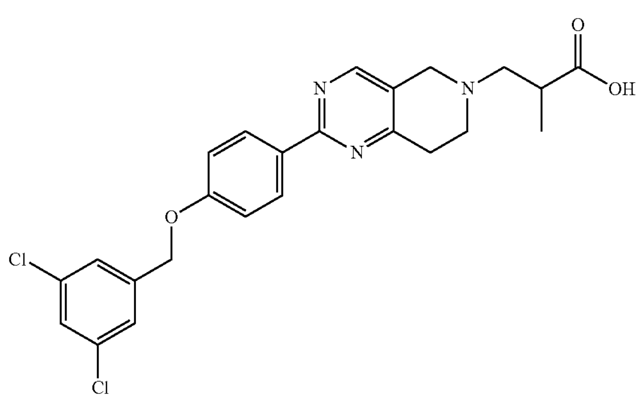 [SMILES: CC(CN1CCc2nc(-c3ccc(OCc4cc(Cl)cc(Cl)c4)cc3)ncc2C1)C(=O)O] | A | >1 μM (1) | >1 μM (1) | >1 μM (1) |

TABLE 1-continued

| No | Structure | S1P5 EC50 range # | S1P1 EC50* | S1P3 EC50* | S1P4 EC50* |
|---|---|---|---|---|---|
| 18 | 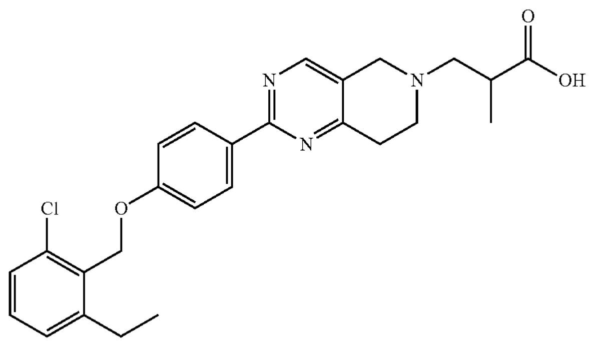 [SMILES: CCc1cccc(Cl)c1COc1ccc(-c2ncc3c(n2)CCN(CC(C)C(=O)O)C3)cc1] | B | >1 μM (1) | >1 μM (1) | <1 μM (1) |
| 19 | enantiomer 1 of compound 17 | A | >1 μM (10) | >1 μM (1) | >1 μM (1) |
| 20 | enantiomer 2 of compound 17 | B | >1 μm (1) | >1 μM (1) | >1 μM (1) |
| 21 | 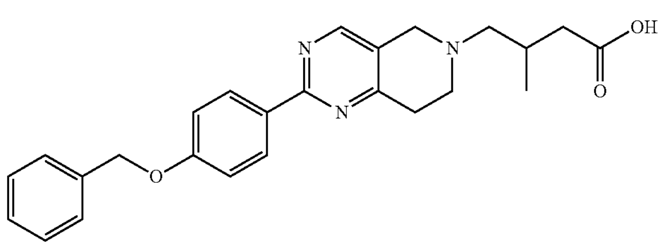 [SMILES: CC(CC(=O)O)CN1CCc2nc(-c3ccc(OCc4ccccc4)cc3)ncc2C1] | B | >1 μM (1) | >1 μM (1) | |

TABLE 1-continued
| No | Structure | S1P5 EC50 range # | S1P1 EC50* | S1P3 EC50* | S1P4 EC50* |
|---|---|---|---|---|---|
| 22 | 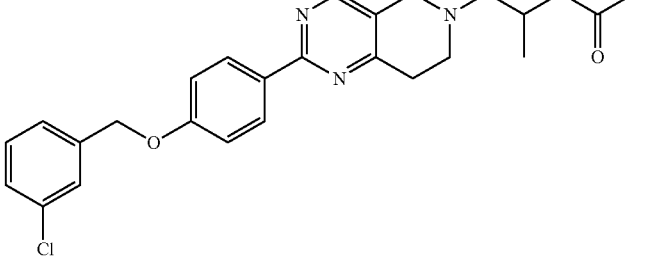 | A | >1 μM (1) | >1 μM (1) | >1 μM (1) |
| 23 | 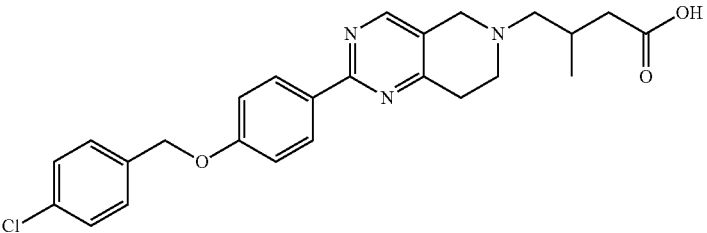 [SMILES: CC(CC(=O)O)CN1CCc2nc(-c3ccc(OCc4ccc(Cl)cc4)cc3)ncc2C1] | A | >1 μM (1) | >1 μM (1) | >1 μM (1) |
| 24 | 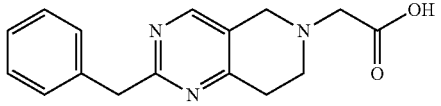 [SMILES: O=C(O)CN1CCc2nc(Cc3ccccc3)ncc2C1] | D | >1 μM (10 | >1 μM (1) | >1 μM (1) |
| 25 | 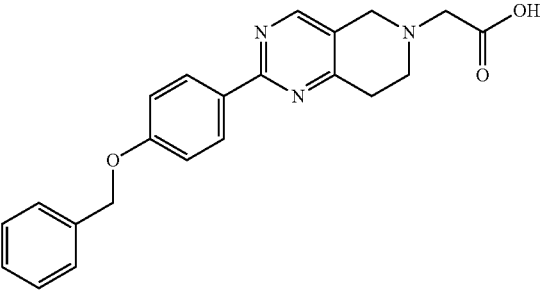 [SMILES: O=C(O)CN1CCc2nc(-c3ccc(OCc4ccccc4)cc3)ncc2C1] | C | >1 μM (1) | | >1 μM (1) |
| 26 | 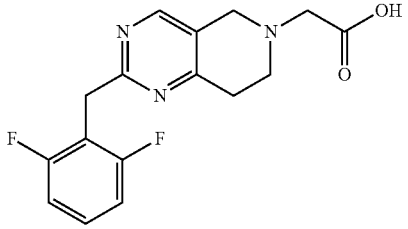 [SMILES: O=C(O)CN1CCc2nc(Cc3c(F)cccc3F)ncc2C1] | D | >1 μM (1) | | >1 μM (1) |
| 27 | 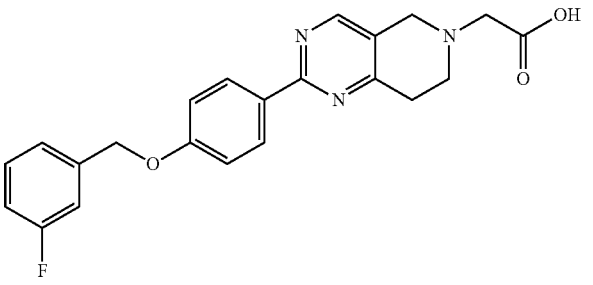 [SMILES: O=C(O)CN1CCc2nc(-c3ccc(OCc4cccc(F)c4)cc3)ncc2C1] | B | >1 μM (1) | | >1 μM (1) |

TABLE 1-continued

| No | Structure | S1P5 EC50 range # | S1P1 EC50* | S1P3 EC50* | S1P4 EC50* |
|---|---|---|---|---|---|
| 28 | (2,3-difluorobenzyloxy-phenyl tetrahydropyrido[4,3-d]pyrimidine acetic acid) | B | >1 µM (1) | | <1 µM (1) |
| 29 | (4-chlorobenzyloxy-phenyl tetrahydropyrido[4,3-d]pyrimidine acetic acid) | C | >1 µM (1) | | >1 µM (1) |
| 30 | (3,4-dichlorobenzyloxy-phenyl tetrahydropyrido[4,3-d]pyrimidine acetic acid) | B | >1 µM (1) | >1 µM (1) | >1 µM (1) |
| 31 | (3,5-difluorobenzyloxy-phenyl tetrahydropyrido[4,3-d]pyrimidine acetic acid) | C | >1 µM (1) | | >1 µM (1) |
| 32 | (3-chlorobenzyloxy-phenyl tetrahydropyrido[4,3-d]pyrimidine acetic acid) | C | >1 µM (1) | >1 µM (1) | >1 µM (1) |
| 33 | (2,6-dimethylbenzyloxy-phenyl tetrahydropyrido[4,3-d]pyrimidine acetic acid) | C | >1 µM (1) | <1 µM (1) | <1 µM (1) |

TABLE 1-continued

| No | Structure | S1P5 EC50 range # | S1P1 EC50* | S1P3 EC50* | S1P4 EC50* |
|---|---|---|---|---|---|
| 34 | 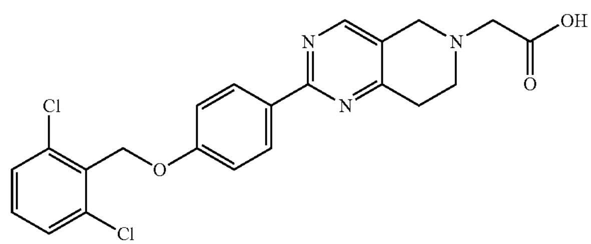 [SMILES: O=C(O)CN1CCc2nc(-c3ccc(OCc4c(Cl)cccc4Cl)cc3)ncc2C1] | C | <1 μM (1) | <1 μM (1) | <1 μM (1) |
| 35 | 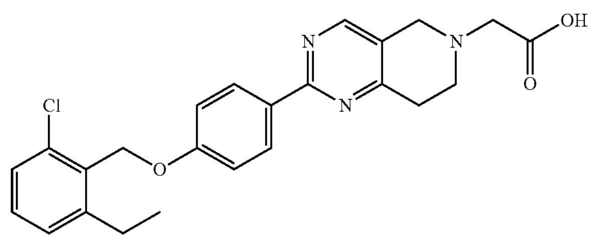 [SMILES: CCc1cccc(Cl)c1COc1ccc(-c2ncc3c(n2)CCN(CC(=O)O)C3)cc1] | C | <1 μM (1) | <1 μM (1) | <1 μM (1) |
| 36 | 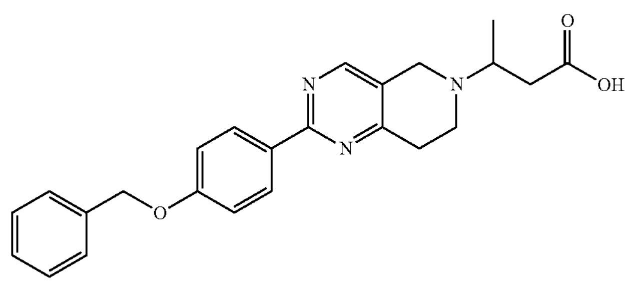 [SMILES: CC(CC(=O)O)N1CCc2nc(-c3ccc(OCc4ccccc4)cc3)ncc2C1] | C | >1 μM (1) | >1 μM (1) | |
| 37 | 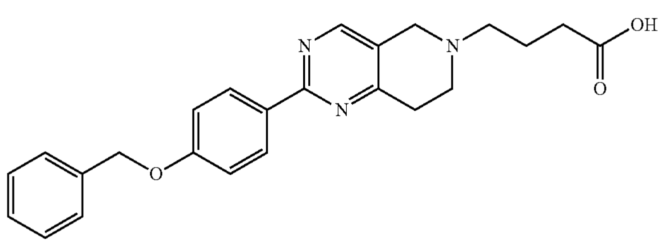 [SMILES: O=C(O)CCCN1CCc2nc(-c3ccc(OCc4ccccc4)cc3)ncc2C1] | B | >1 μM (1) | >1 μM (1) | |
| 38 | 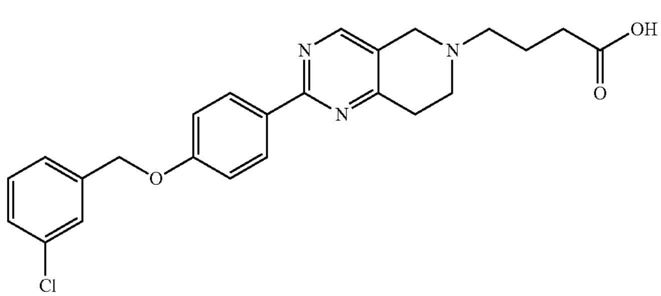 [SMILES: O=C(O)CCCN1CCc2nc(-c3ccc(OCc4cccc(Cl)c4)cc3)ncc2C1] | A | >1 μM (1) | >1 μM (1) | |

TABLE 1-continued

| No | Structure | S1P5 EC50 range # | S1P1 EC50* | S1P3 EC50* | S1P4 EC50* |
|---|---|---|---|---|---|
| 40 | 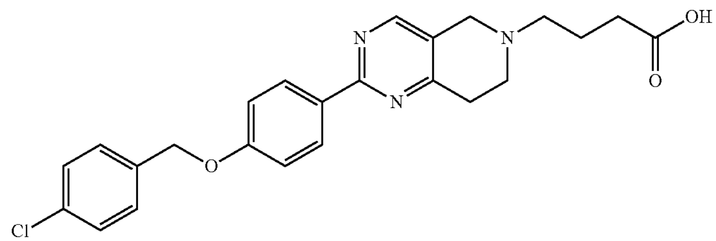 [SMILES: O=C(O)CCCN1CCc2nc(-c3ccc(OCc4ccc(Cl)cc4)cc3)ncc2C1] | A | >1 μM (1) | >1 μM (1) | >1 μM (1) |
| 41 | 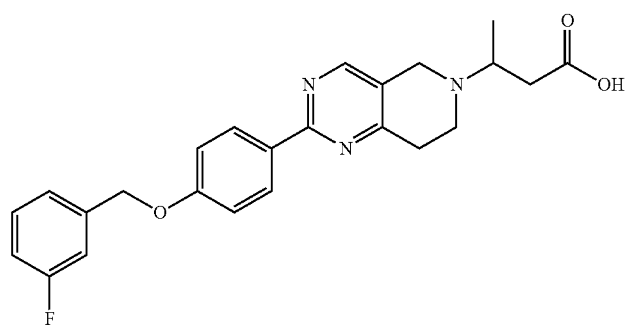 [SMILES: CC(CC(=O)O)N1CCc2nc(-c3ccc(OCc4cccc(F)c4)cc3)ncc2C1] | A | >1 μM (1) | >1 μM (1) | |
| 42 | 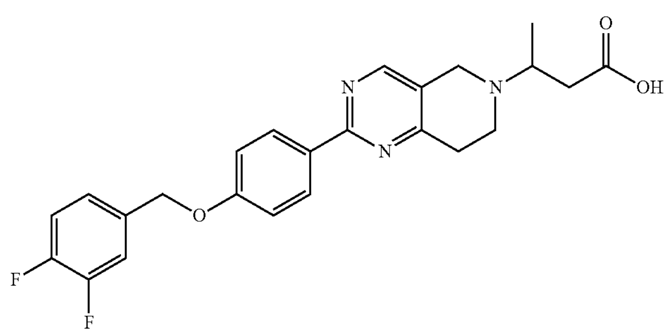 [SMILES: CC(CC(=O)O)N1CCc2nc(-c3ccc(OCc4ccc(F)c(F)c4)cc3)ncc2C1] | A | >1 μM (1) | >1 μM (1) | |
| 43 | 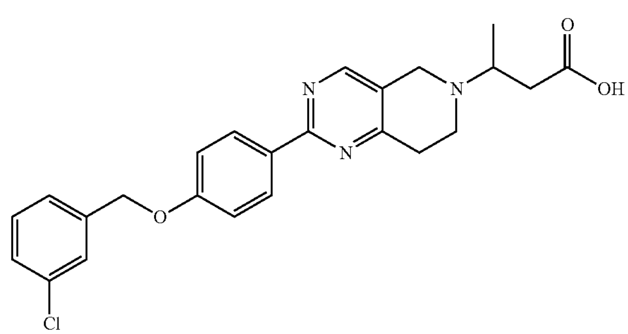 [SMILES: CC(CC(=O)O)N1CCc2nc(-c3ccc(OCc4cccc(Cl)c4)cc3)ncc2C1] | C | >1 μM (1) | >1 μM (1) | |
| 44 | 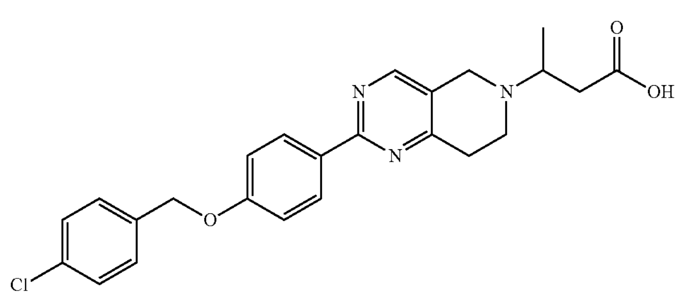 [SMILES: CC(CC(=O)O)N1CCc2nc(-c3ccc(OCc4ccc(Cl)cc4)cc3)ncc2C1] | B | >1 μM (1) | >1 μM (1) | |

TABLE 1-continued
| No | Structure | S1P5 EC50 range # | S1P1 EC50* | S1P3 EC50* | S1P4 EC50* |
|---|---|---|---|---|---|
| 45 | 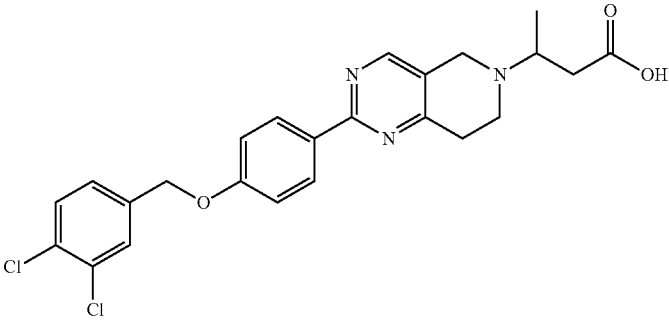 | B | >1 μM (1) | >1 μM (1) | >1 μM (1) |
| 46 | 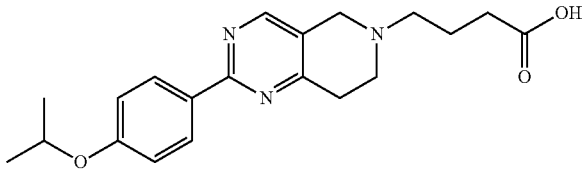 [SMILES: CC(C)Oc1ccc(-c2ncc3c(n2)CCN(CCCC(=O)O)C3)cc1] | D | >1 μM (1) | >1 μM (1) | |
| 47 | 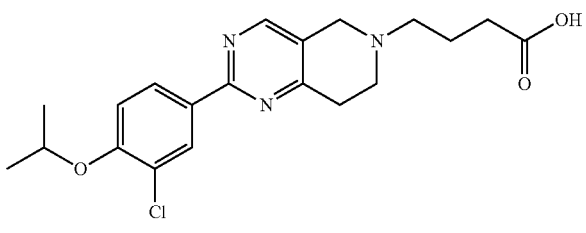 [SMILES: CC(C)Oc1ccc(-c2ncc3c(n2)CCN(CCCC(=O)O)C3)cc1Cl] | D | >1 μM (1) | >1 μM (1) | |
| 48 | 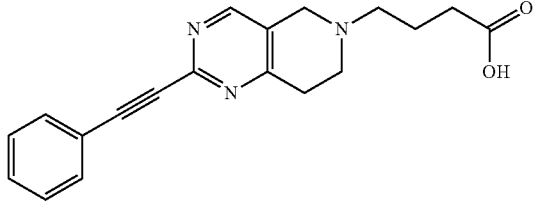 [SMILES: O=C(O)CCCN1CCc2nc(C#Cc3ccccc3)ncc2C1] | D | >1 μM (1) | >1 μM (1) | |
| 49 | 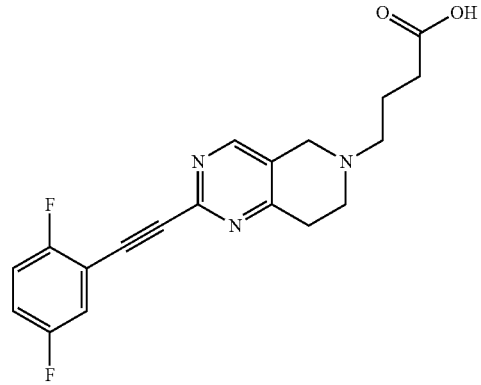 [SMILES: O=C(O)CCCN1CCc2nc(C#Cc3cc(F)ccc3F)ncc2C1] | D | >1 μM (1) | >1 μM (1) | |
| 50 | 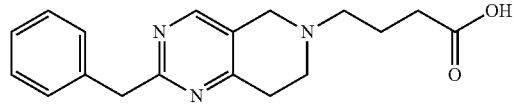 [SMILES: O=C(O)CCCN1CCc2nc(Cc3ccccc3)ncc2C1] | D | >1 μM (1) | >1 μM (1) | >1 μM (1) |

TABLE 1-continued

| No | Structure | S1P5 EC50 range # | S1P1 EC50* | S1P3 EC50* | S1P4 EC50* |
|---|---|---|---|---|---|
| 51 | 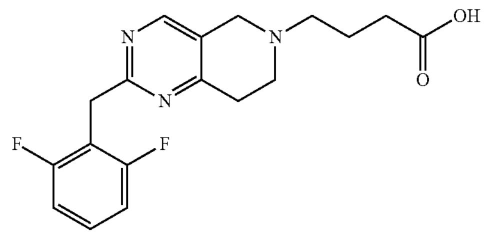 [SMILES: O=C(O)CCCN1CCc2nc(Cc3c(F)cccc3F)ncc2C1] | D | >1 μM (1) | >1 μM (1) | >1 μM (1) |
| 52 | 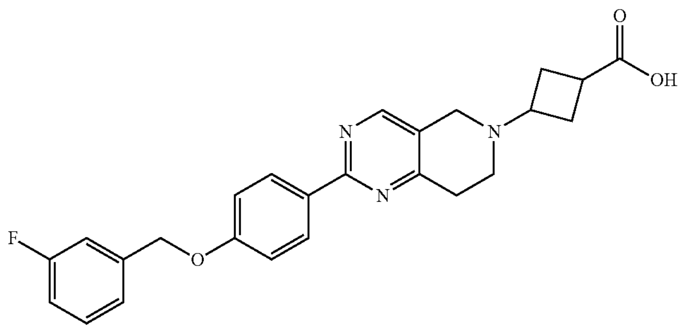 [SMILES: O=C(O)C1CC(N2CCc3nc(-c4ccc(OCc5cccc(F)c5)cc4)ncc3C2)C1] | G | >1 μM (2) | >1 μM (2) | >1 μM (1) |
| 53 | 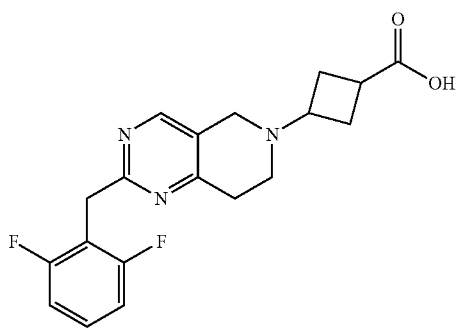 [SMILES: O=C(O)C1CC(N2CCc3nc(Cc4c(F)cccc4F)ncc3C2)C1] | D | >1 μM (1) | >1 μM (1) | >1 μM (1) |
| 54 | 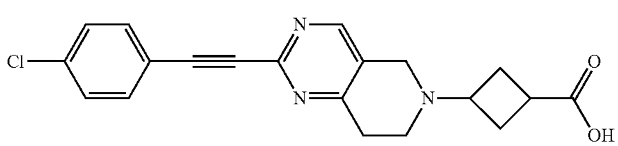 [SMILES: O=C(O)C1CC(N2CCc3nc(C#Cc4ccc(Cl)cc4)ncc3C2)C1] | D | >1 μM (1) | >1 μM (1) | >1 μM (1) |
| 55 | 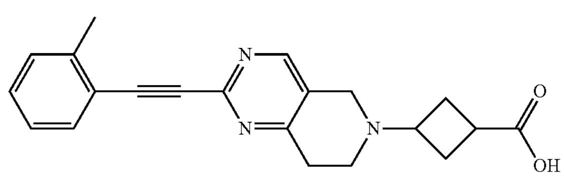 [SMILES: Cc1ccccc1C#Cc1ncc2c(n1)CCN(C1CC(C(=O)O)C1)C2] | D | >1 μM (1) | >1 μM (1) | >1 μM (1) |
| 56 | 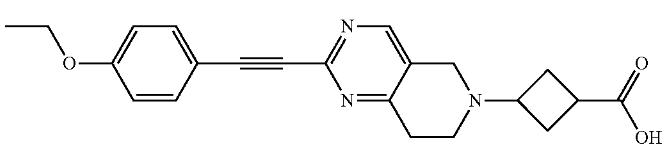 [SMILES: CCOc1ccc(C#Cc2ncc3c(n2)CCN(C2CC(C(=O)O)C2)C3)cc1] | D | >1 μM (1) | >1 μM (1) | >1 μM (1) |
| 57 | 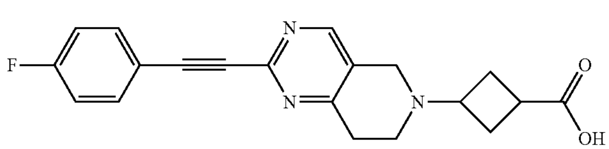 [SMILES: O=C(O)C1CC(N2CCc3nc(C#Cc4ccc(F)cc4)ncc3C2)C1] | D | >1 μM (1) | >1 μM (1) | >1 μM (1) |

TABLE 1-continued

| No | Structure | S1P5 EC50 range # | S1P1 EC50* | S1P3 EC50* | S1P4 EC50* |
|---|---|---|---|---|---|
| 58 | 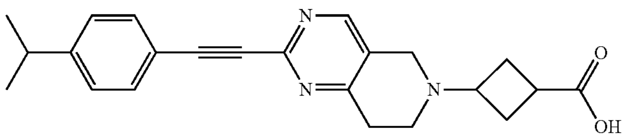 [SMILES: CC(C)c1ccc(C#Cc2ncc3c(n2)CCN(C2CC(C(=O)O)C2)C3)cc1] | D | >1 μM (1) | >1 μM (1) | >1 μM (1) |
| 59 | 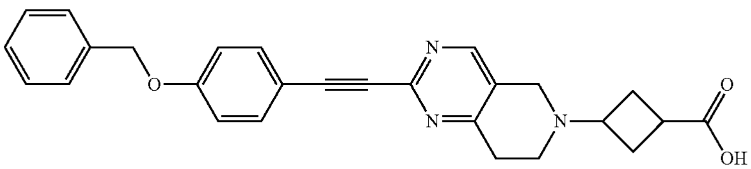 [SMILES: O=C(O)C1CC(N2CCc3nc(C#Cc4ccc(OCc5ccccc5)cc4)ncc3C2)C1] | D | >1 μM (1) | >1 μM (1) | >1 μM (1) |
| 60 | 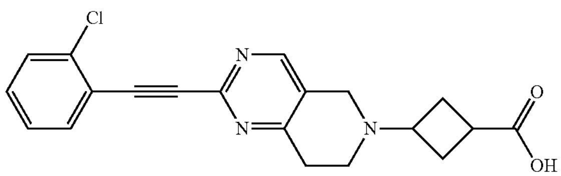 [SMILES: O=C(O)C1CC(N2CCc3nc(C#Cc4ccccc4Cl)ncc3C2)C1] | D | >1 μM (1) | >1 μM (1) | >1 μM (1) |
| 61 | 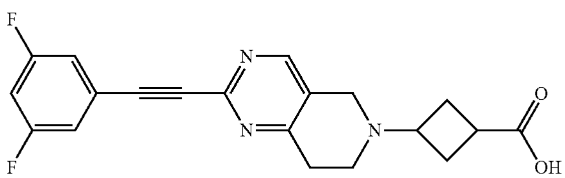 [SMILES: O=C(O)C1CC(N2CCc3nc(C#Cc4cc(F)cc(F)c4)ncc3C2)C1] | D | >1 μM (1) | >1 μM (1) | >1 μM (1) |
| 62 | 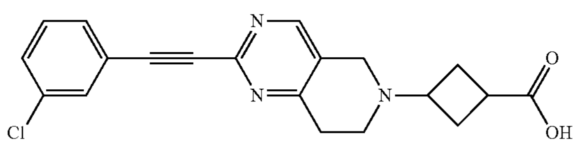 [SMILES: O=C(O)C1CC(N2CCc3nc(C#Cc4cccc(Cl)c4)ncc3C2)C1] | D | >1 μM (1) | >1 μM (1) | >1 μM (1) |
| 64 | 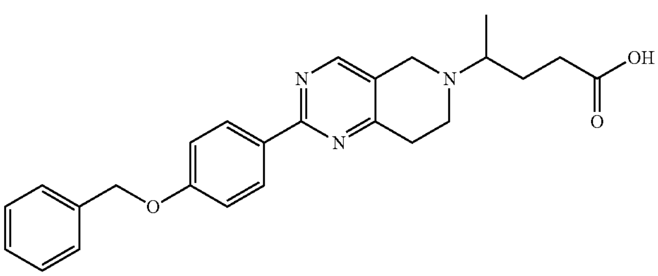 [SMILES: CC(CCC(=O)O)N1CCc2nc(-c3ccc(OCc4ccccc4)cc3)ncc2C1] | A | >1 μM (1) | >1 μM (1) | >1 μM (1) |
| 65 | 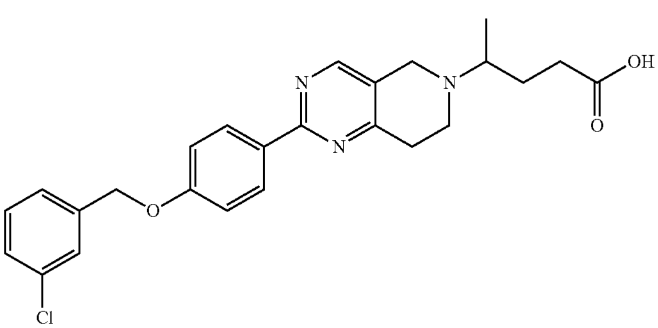 [SMILES: CC(CCC(=O)O)N1CCc2nc(-c3ccc(OCc4cccc(Cl)c4)cc3)ncc2C1] | B | >1 μM (1) | >1 μM (1) | >1 μM (1) |

TABLE 1-continued

| No | Structure | S1P5 EC50 range # | S1P1 EC50* | S1P3 EC50* | S1P4 EC50* |
|---|---|---|---|---|---|
| 66 | 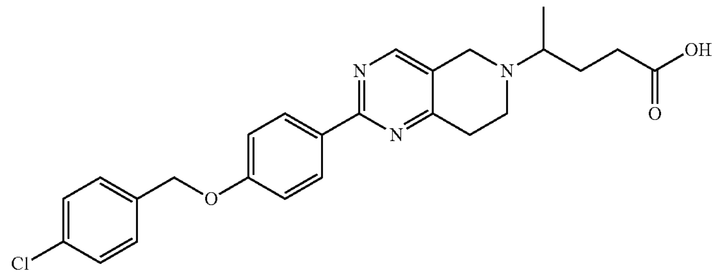 [SMILES: CC(CCC(=O)O)N1CCc2nc(-c3ccc(OCc4ccc(Cl)cc4)cc3)ncc2C1] | A | >1 μM (1) | >1 μM (1) | >1 μM (1) |
| 67 | 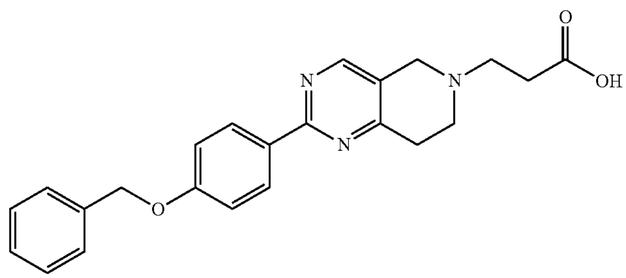 [SMILES: O=C(O)CCN1CCc2nc(-c3ccc(OCc4ccccc4)cc3)ncc2C1] | B | >1 μM (1) | >1 μM (1) | |
| 68 | 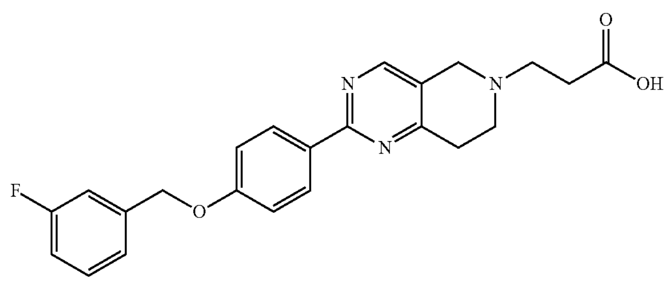 [SMILES: O=C(O)CCN1CCc2nc(-c3ccc(OCc4cccc(F)c4)cc3)ncc2C1] | B | >1 μM (1) | >1 μM (1) | |
| 69 | 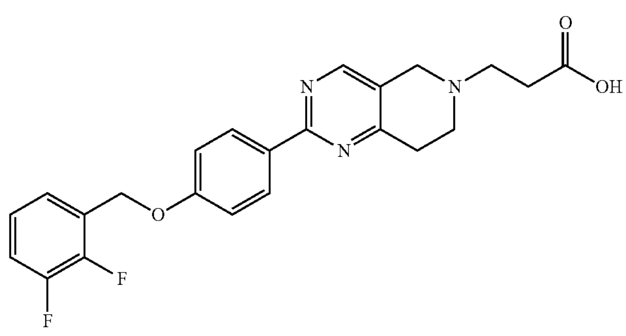 [SMILES: O=C(O)CCN1CCc2nc(-c3ccc(OCc4cccc(F)c4F)cc3)ncc2C1] | G | >1 μM (2) | >1 μM (2) | |
| 70 | 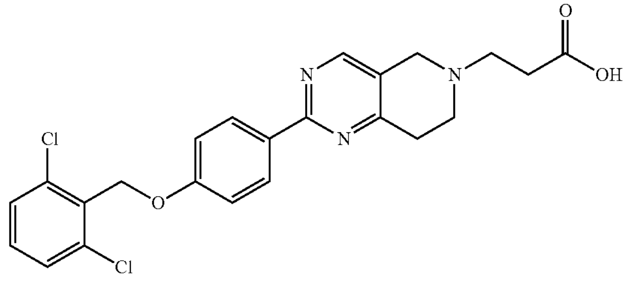 [SMILES: O=C(O)CCN1CCc2nc(-c3ccc(OCc4c(Cl)cccc4Cl)cc3)ncc2C1] | F | >1 μM (2) | >1 μM (2) | |

TABLE 1-continued

| No | Structure | S1P5 EC50 range # | S1P1 EC50* | S1P3 EC50* | S1P4 EC50* |
|----|-----------|---|---|---|---|
| 71 | 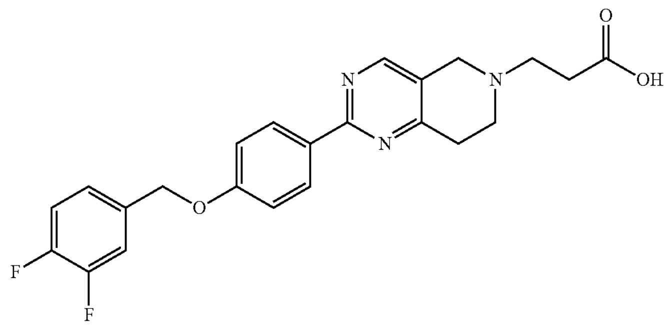 [SMILES: O=C(O)CCN1CCc2nc(-c3ccc(OCc4ccc(F)c(F)c4)cc3)ncc2C1] | A | >1 µM (1) | >1 µM (1) | |
| 72 | 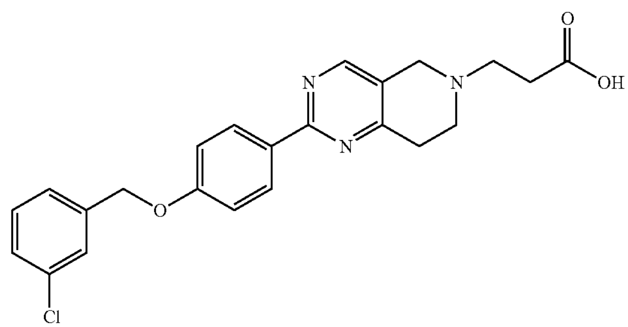 [SMILES: O=C(O)CCN1CCc2nc(-c3ccc(OCc4cccc(Cl)c4)cc3)ncc2C1] | A | >1 µM (1) | >1 µM (1) | |
| 73 | 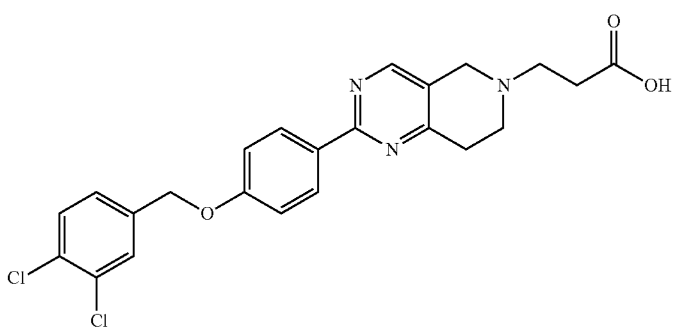 [SMILES: O=C(O)CCN1CCc2nc(-c3ccc(OCc4ccc(Cl)c(Cl)c4)cc3)ncc2C1] | A | >1 µM (1) | >1 µM (1) | |
| 74 | 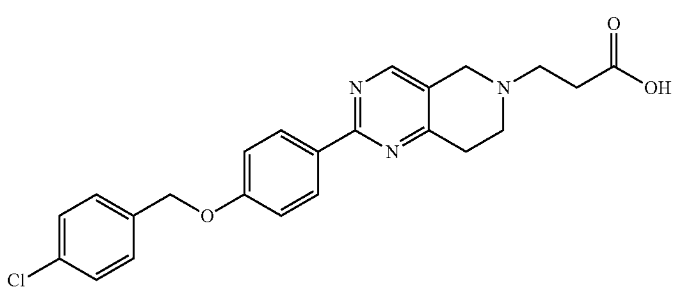 [SMILES: O=C(O)CCN1CCc2nc(-c3ccc(OCc4ccc(Cl)cc4)cc3)ncc2C1] | A | >1 µM (1) | >1 µM (1) | >1 µM (1) |
| 75 | 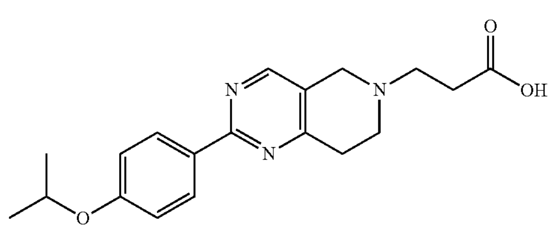 [SMILES: CC(C)Oc1ccc(-c2ncc3c(n2)CCN(CCC(=O)O)C3)cc1] | D | >1 µM (1) | >1 µM (1) | |

TABLE 1-continued

| No | Structure | S1P5 EC50 range # | S1P1 EC50* | S1P3 EC50* | S1P4 EC50* |
|----|-----------|-------------------|------------|------------|------------|
| 76 | 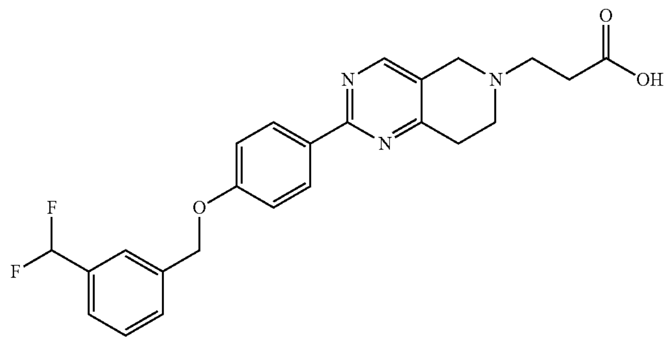 [SMILES: O=C(O)CCN1CCc2nc(-c3ccc(OCc4cccc(C(F)F)c4)cc3)ncc2C1] | A | >1 μM (1) | >1 μM (1) | |
| 77 | 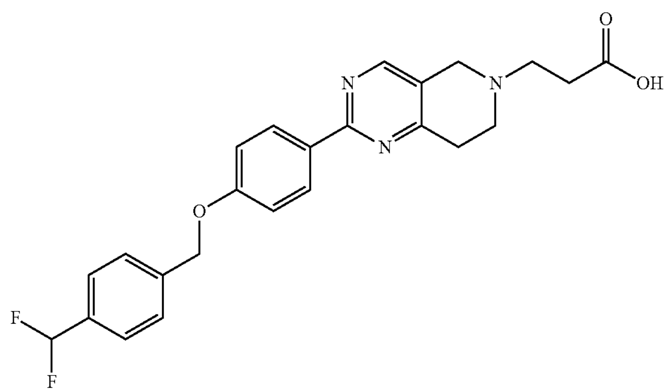 [SMILES: O=C(O)CCN1CCc2nc(-c3ccc(OCc4ccc(C(F)F)cc4)cc3)ncc2C1] | A | >1 μM (1) | >1 μM (1) | |
| 78 | 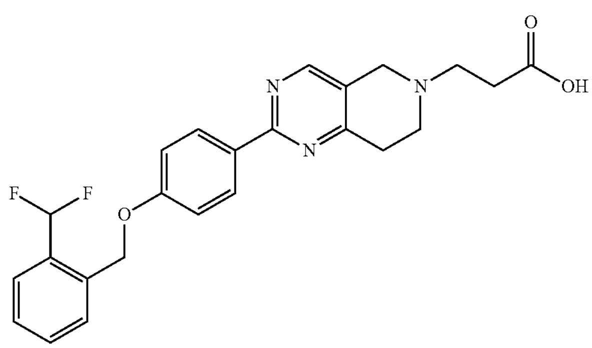 [SMILES: O=C(O)CCN1CCc2nc(-c3ccc(OCc4ccccc4C(F)F)cc3)ncc2C1] | A | >1 μM (1) | >1 μM (1) | |
| 79 | 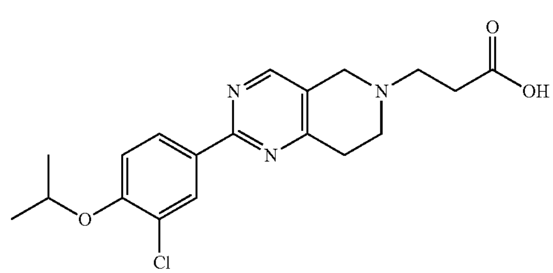 [SMILES: CC(C)Oc1ccc(-c2ncc3c(n2)CCN(CCC(=O)O)C3)cc1Cl] | D | >1 μM (1) | >1 μM (1) | |

TABLE 1-continued

| No | Structure | S1P5 EC50 range # | S1P1 EC50* | S1P3 EC50* | S1P4 EC50* |
|---|---|---|---|---|---|
| 80 | 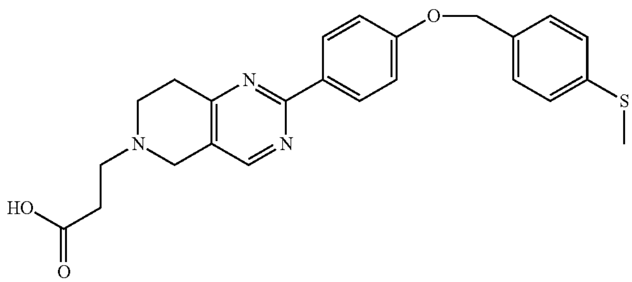 [SMILES: CSc1ccc(COc2ccc(-c3ncc4c(n3)CCN(CCC(=O)O)C4)cc2)cc1] | A | >1 μM (1) | >1 μM (1) | |
| 81 | 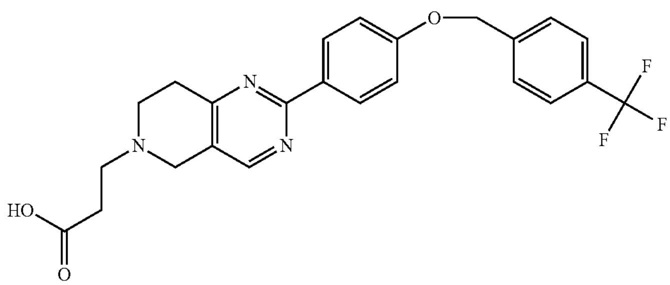 [SMILES: O=C(O)CCN1CCc2nc(-c3ccc(OCc4ccc(C(F)(F)F)cc4)cc3)ncc2C1] | A | >1 μM (1) | >1 μM (1) | |
| 82 | 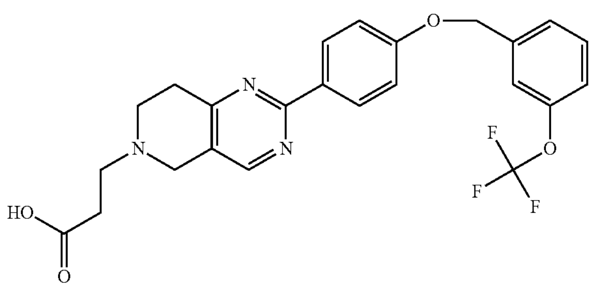 [SMILES: O=C(O)CCN1CCc2nc(-c3ccc(OCc4cccc(OC(F)(F)F)c4)cc3)ncc2C1] | A | >1 μM (1) | >1 μM (1) | >1 μM (1) |
| 83 | 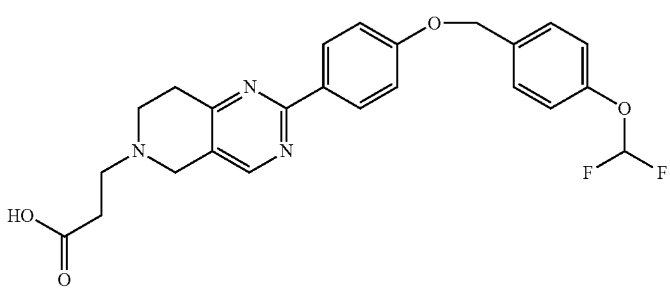 [SMILES: O=C(O)CCN1CCc2nc(-c3ccc(OCc4ccc(OC(F)F)cc4)cc3)ncc2C1] | A | >1 μM (1) | >1 μM (1) | >1 μM (1) |
| 84 | 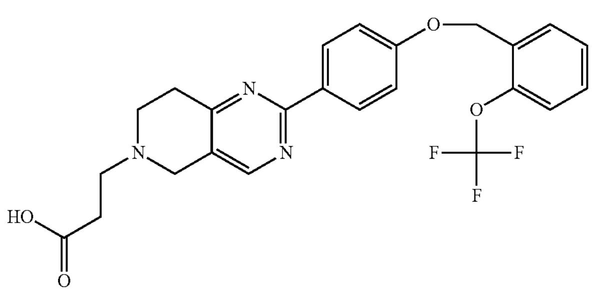 [SMILES: O=C(O)CCN1CCc2nc(-c3ccc(OCc4ccccc4OC(F)(F)F)cc3)ncc2C1] | B | >1 μM (1) | >1 μM (1) | |

TABLE 1-continued

| No | Structure | S1P5 EC50 range # | S1P1 EC50* | S1P3 EC50* | S1P4 EC50* |
|---|---|---|---|---|---|
| 85 | 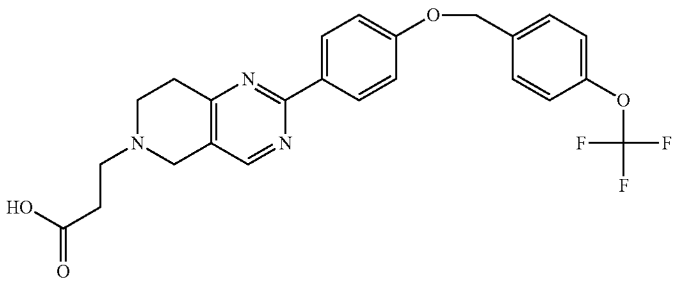 [SMILES: O=C(O)CCN1CCc2nc(-c3ccc(OCc4ccc(OC(F)(F)F)cc4)cc3)ncc2C1] | A | >1 μM (1) | >1 μM (1) | >1 μM (1) |
| 86 | 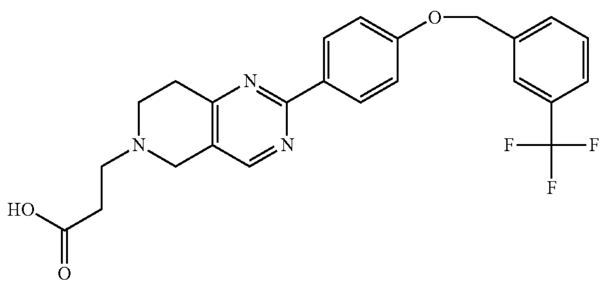 [SMILES: O=C(O)CCN1CCc2nc(-c3ccc(OCc4cccc(C(F)(F)F)c4)cc3)ncc2C1] | A | >1 μM (1) | >1 μM (1) | |
| 87 | 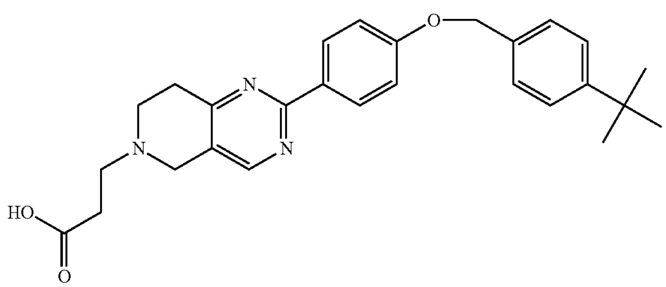 [SMILES: CC(C)(C)c1ccc(COc2ccc(-c3ncc4c(n3)CCN(CCC(=O)O)C4)cc2)cc1] | B | >1 μM (1) | >1 μM (1) | >1 μM (1) |
| 88 | 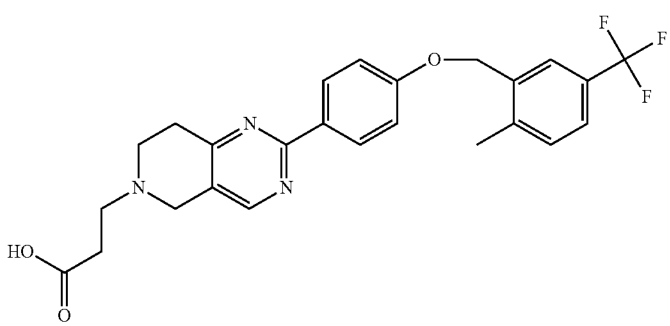 [SMILES: Cc1ccc(C(F)(F)F)cc1COc1ccc(-c2ncc3c(n2)CCN(CCC(=O)O)C3)cc1] | A | >1 μM (1) | >1 μM (1) | >1 μM (1) |
| 89 | 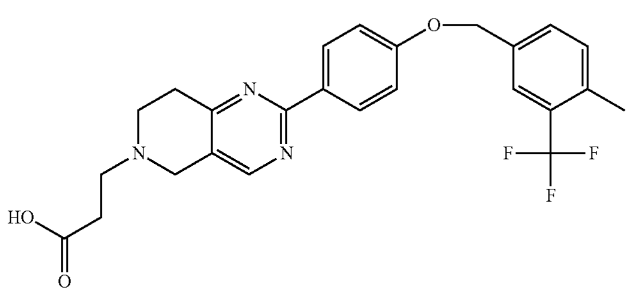 [SMILES: Cc1ccc(COc2ccc(-c3ncc4c(n3)CCN(CCC(=O)O)C4)cc2)cc1C(F)(F)F] | A | >1 μM (1) | >1 μM (1) | >1 μM (1) |

TABLE 1-continued

| No | Structure | S1P5 EC50 range # | S1P1 EC50* | S1P3 EC50* | S1P4 EC50* |
|----|-----------|-------------------|------------|------------|------------|
| 90 | 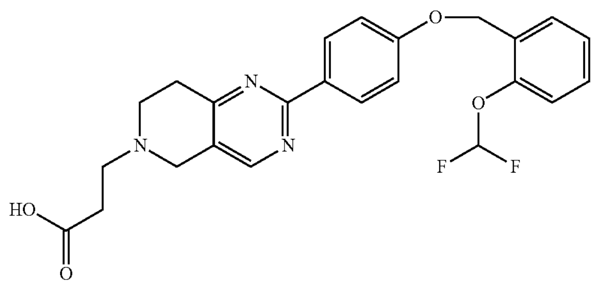 [SMILES: O=C(O)CCN1CCc2nc(-c3ccc(OCc4ccccc4OC(F)F)cc3)ncc2C1] | B | >1 μM (1) | >1 μM (1) | |
| 91 | 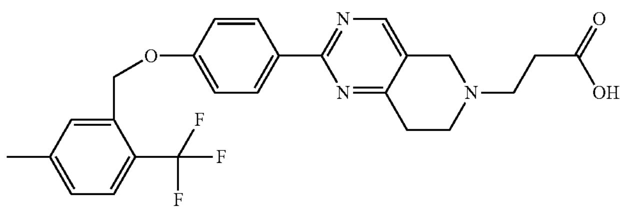 [SMILES: Cc1ccc(C(F)(F)F)c(COc2ccc(-c3ncc4c(n3)CCN(CCC(=O)O)C4)cc2)c1] | C | >1 μM (1) | >1 μM (1) | |
| 92 | 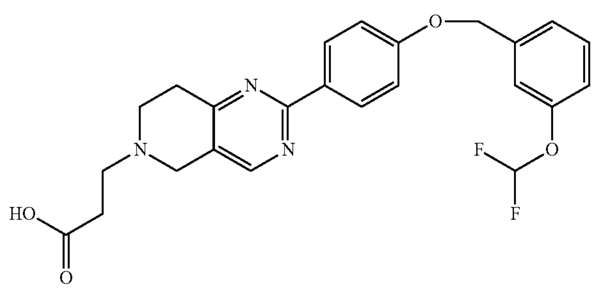 [SMILES: O=C(O)CCN1CCc2nc(-c3ccc(OCc4cccc(OC(F)F)c4)cc3)ncc2C1] | B | >1 μM (1) | >1 μM (1) | |
| 93 | 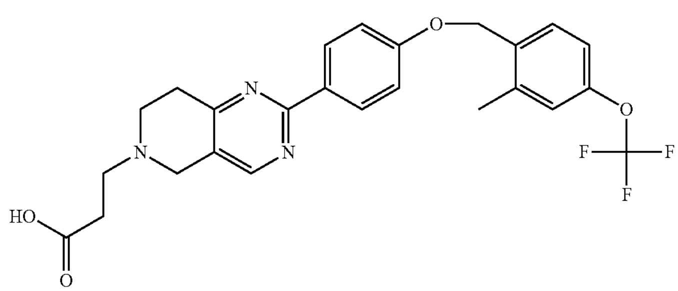 [SMILES: Cc1cc(OC(F)(F)F)ccc1COc1ccc(-c2ncc3c(n2)CCN(CCC(=O)O)C3)cc1] | A | <1 μM (1) | >1 μM (1) | |
| 94 | 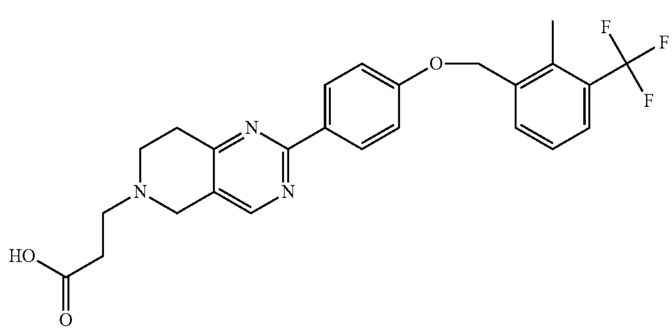 [SMILES: Cc1c(COc2ccc(-c3ncc4c(n3)CCN(CCC(=O)O)C4)cc2)cccc1C(F)(F)F] | A | <1 μM (1) | >1 μM (1) | |

TABLE 1-continued
| No | Structure | S1P5 EC50 range # | S1P1 EC50* | S1P3 EC50* | S1P4 EC50* |
|---|---|---|---|---|---|
| 95 | 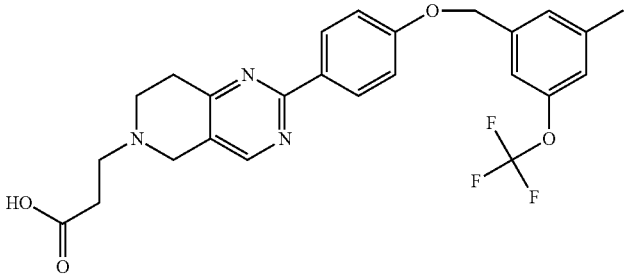 [SMILES: Cc1cc(COc2ccc(-c3ncc4c(n3)CCN(CCC(=O)O)C4)cc2)cc(OC(F)(F)F)c1] | A | <1 μM (1) | >1 μM (1) | |
| 96 | 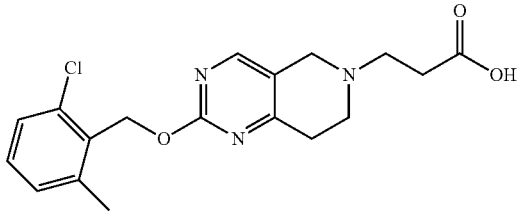 [SMILES: Cc1cccc(Cl)c1COc1ncc2c(n1)CCN(CCC(=O)O)C2] | D | >1 μM (1) | >1 μM (1) | >1 μM (1) |
| 99 | 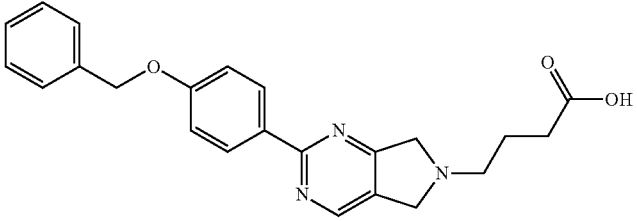 [SMILES: O=C(O)CCCN1Cc2cnc(-c3ccc(OCc4ccccc4)cc3)nc2C1] | D | >1 μM (1) | >1 μM (1) | |
| 100 | 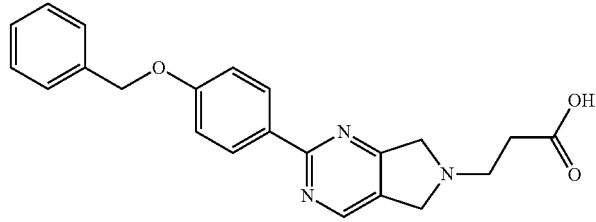 [SMILES: O=C(O)CCN1Cc2cnc(-c3ccc(OCc4ccccc4)cc3)nc2C1] | D | >1 μM (1) | >1 μM (1) | |
| 101 | 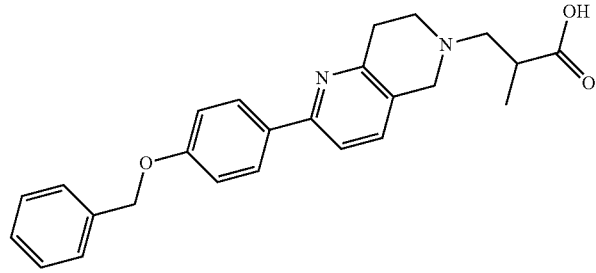 [SMILES: CC(CN1CCc2nc(-c3ccc(OCc4ccccc4)cc3)ccc2C1)C(=O)O] | F | >1 μM (2) | >1 μM (2) | |
| 102 | 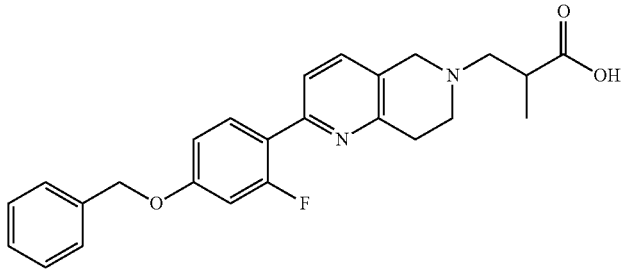 [SMILES: CC(CN1CCc2nc(-c3ccc(OCc4ccccc4)cc3F)ccc2C1)C(=O)O] | B | <1 μM (1) | >1 μM (1) | |

TABLE 1-continued

| No | Structure | S1P5 EC50 range # | S1P1 EC50* | S1P3 EC50* | S1P4 EC50* |
|---|---|---|---|---|---|
| 103 | 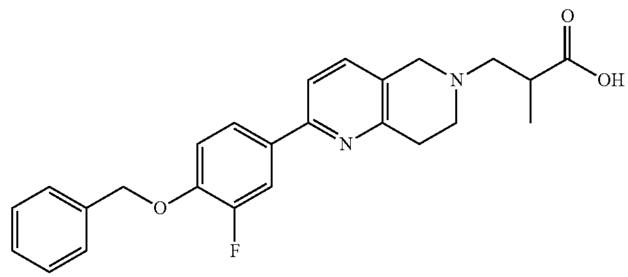 [SMILES: CC(CN1CCc2nc(-c3ccc(OCc4ccccc4)c(F)c3)ccc2C1)C(=O)O] | B | >1 µM (1) | >1 µM (1) | |
| 104 | 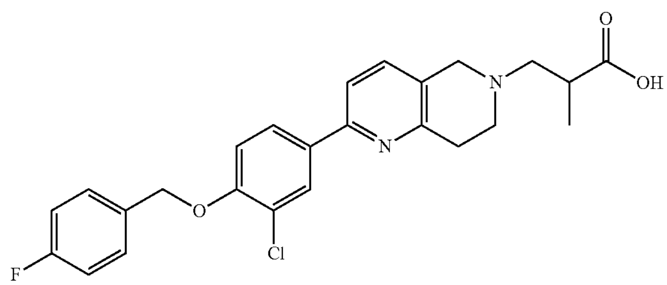 [SMILES: CC(CN1CCc2nc(-c3ccc(OCc4ccc(F)cc4)c(Cl)c3)ccc2C1)C(=O)O] | B | >1 µM (1) | >1 µM (1) | |
| 105 | 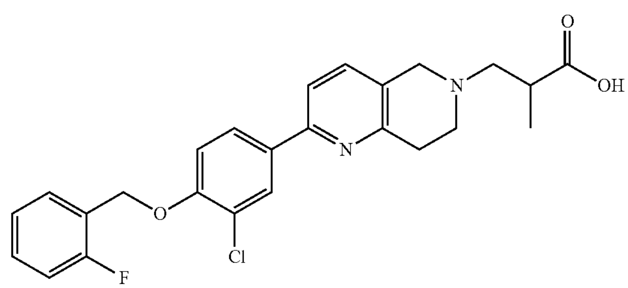 [SMILES: CC(CN1CCc2nc(-c3ccc(OCc4ccccc4F)c(Cl)c3)ccc2C1)C(=O)O] | C | >1 µM (1) | >1 µM (1) | |
| 106 | 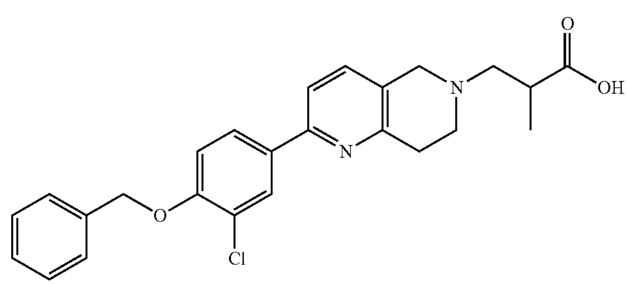 [SMILES: CC(CN1CCc2nc(-c3ccc(OCc4ccccc4)c(Cl)c3)ccc2C1)C(=O)O] | B | >1 µM (1) | >1 µM (1) | |
| 107 | 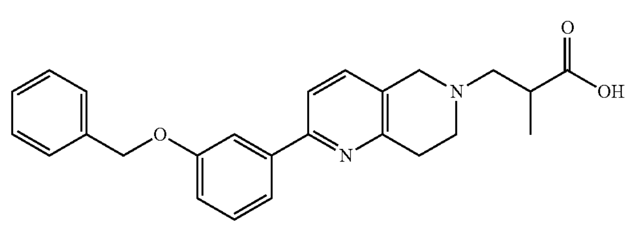 [SMILES: CC(CN1CCc2nc(-c3cccc(OCc4ccccc4)c3)ccc2C1)C(=O)O] | D | >1 µM (1) | >1 µM (1) | |

TABLE 1-continued

| No | Structure | S1P5 EC50 range # | S1P1 EC50* | S1P3 EC50* | S1P4 EC50* |
|---|---|---|---|---|---|
| 108 | 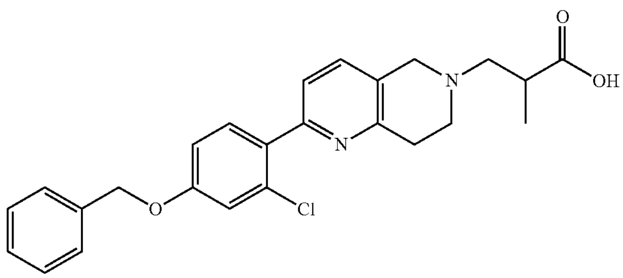 [SMILES: CC(CN1CCc2nc(-c3ccc(OCc4ccccc4)cc3Cl)ccc2C1)C(=O)O] | C | >1 μM (1) | >1 μM (1) | |
| 109 | 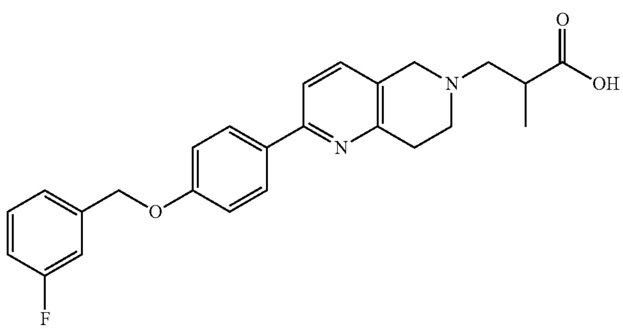 [SMILES: CC(CN1CCc2nc(-c3ccc(OCc4cccc(F)c4)cc3)ccc2C1)C(=O)O] | A | <1 μM (1) | >1 μM (1) | |
| 111 | 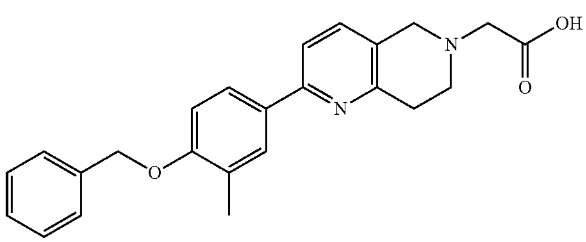 [SMILES: Cc1cc(-c2ccc3c(n2)CCN(CC(=O)O)C3)ccc1OCc1ccccc1] | C | >1 μM (1) | >1 μM (1) | |
| 112 | 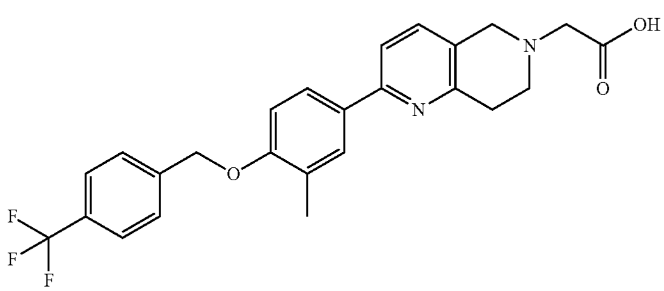 [SMILES: Cc1cc(-c2ccc3c(n2)CCN(CC(=O)O)C3)ccc1OCc1ccc(C(F)(F)F)cc1] | C | >1 μM (1) | >1 μM (1) | |
| 113 | 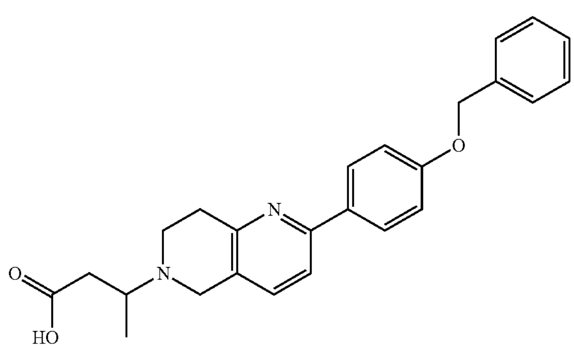 [SMILES: CC(CC(=O)O)N1CCc2nc(-c3ccc(OCc4ccccc4)cc3)ccc2C1] | G | >1 μM (2) | >1 μM (2) | |

TABLE 1-continued

| No | Structure | S1P5 EC50 range # | S1P1 EC50* | S1P3 EC50* | S1P4 EC50* |
|---|---|---|---|---|---|
| 114 | 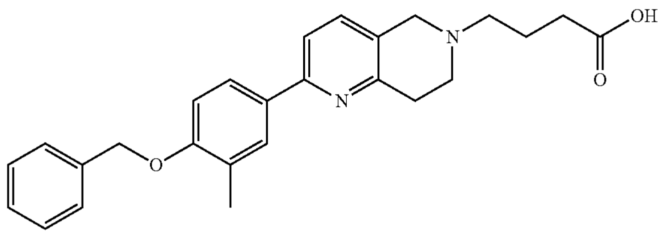 [SMILES: Cc1cc(-c2ccc3c(n2)CCN(CCCC(=O)O)C3)ccc1OCc1ccccc1] | A | >1 μM (1) | >1 μM (1) | >1 μM (1) |
| 115 | 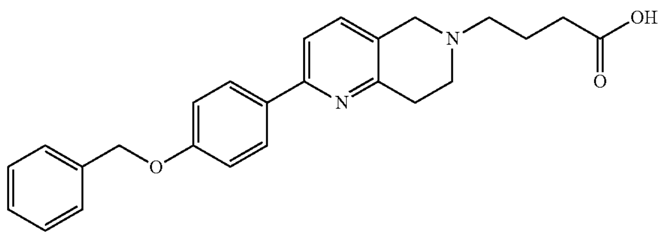 [SMILES: O=C(O)CCCN1CCc2nc(-c3ccc(OCc4ccccc4)cc3)ccc2C1] | A | >1 μM (1) | >1 μM (1) | |
| 116 | 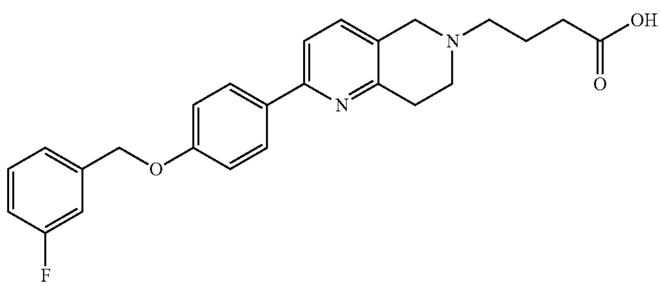 [SMILES: O=C(O)CCCN1CCc2nc(-c3ccc(OCc4cccc(F)c4)cc3)ccc2C1] | A | >1 μM (1) | >1 μM (1) | |
| 117 | 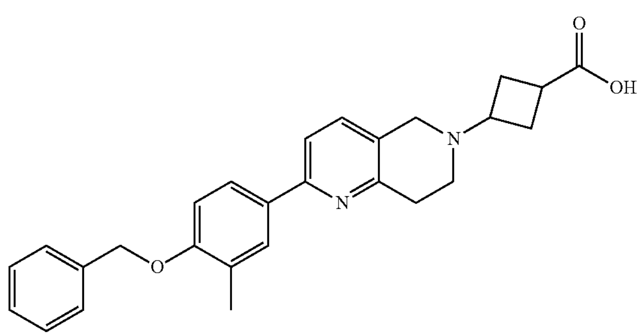 [SMILES: Cc1cc(-c2ccc3c(n2)CCN(C2CC(C(=O)O)C2)C3)ccc1OCc1ccccc1] | C | >1 μM (1) | >1 μM (1) | |
| 118 | 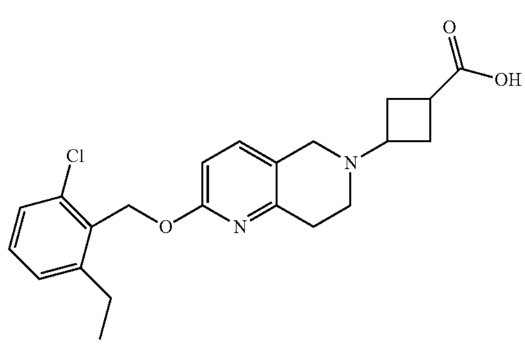 [SMILES: CCc1cccc(Cl)c1COc1ccc2c(n1)CCN(C1CC(C(=O)O)C1)C2] | A | >1 μM (1) | >1 μM (1) | >1 μM (1) |

TABLE 1-continued
| No | Structure | S1P5 EC50 range # | S1P1 EC50* | S1P3 EC50* | S1P4 EC50* |
|----|-----------|---|---|---|---|
| 119 | 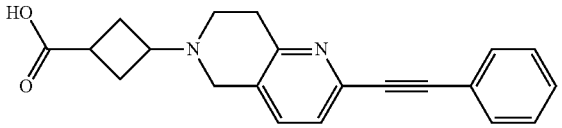 [SMILES: O=C(O)C1CC(N2CCc3nc(C#Cc4ccccc4)ccc3C2)C1] | D | >1 μM (1) | >1 μM (1) | >1 μM (1) |
| 120 | 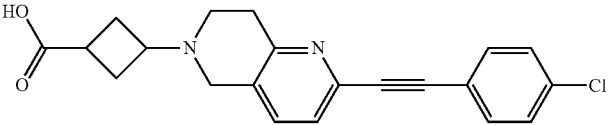 [SMILES: O=C(O)C1CC(N2CCc3nc(C#Cc4ccc(Cl)cc4)ccc3C2)C1] | D | >1 μM (1) | >1 μM (1) | >1 μM (1) |
| 121 | 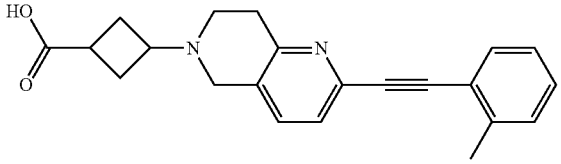 [SMILES: Cc1ccccc1C#Cc1ccc2c(n1)CCN(C1CC(C(=O)O)C1)C2] | D | >1 μM (1) | >1 μM (1) | >1 μM (1) |
| 122 | 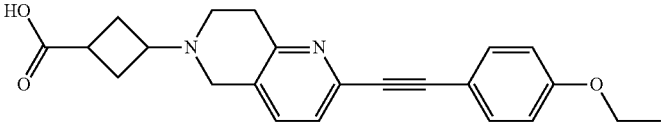 [SMILES: CCOc1ccc(C#Cc2ccc3c(n2)CCN(C2CC(C(=O)O)C2)C3)cc1] | D | >1 μM (1) | >1 μM (1) | >1 μM (1) |
| 123 | 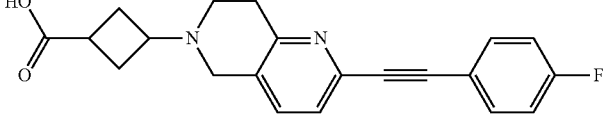 | D | >1 μM (1) | >1 μM (1) | >1 μM (1) |
| 124 | 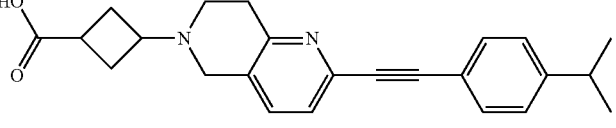 | D | >1 μM (1) | >1 μM (1) | >1 μM (1) |
| 125 | 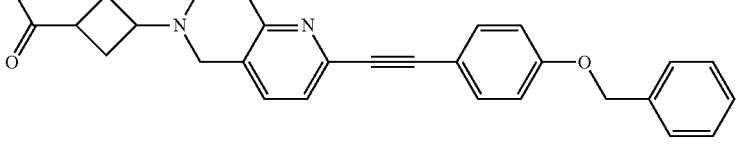 | C | >1 μM (1) | >1 μM (1) | >1 μM (1) |
| 126 | 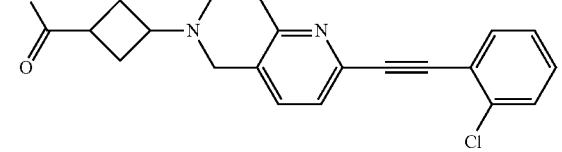 | D | >1 μM (1) | >1 μM (1) | >1 μM (1) |
| 127 | 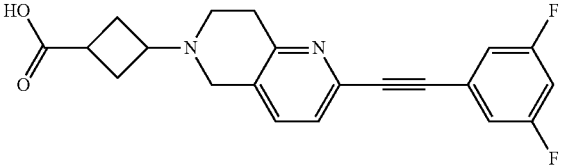 [SMILES: O=C(O)C1CC(N2CCc3nc(C#Cc4cc(F)cc(F)c4)ccc3C2)C1] | D | >1 μM (1) | >1 μM (1) | >1 μM (1) |

TABLE 1-continued

| No | Structure | S1P5 EC50 range # | S1P1 EC50* | S1P3 EC50* | S1P4 EC50* |
|---|---|---|---|---|---|
| 128 | 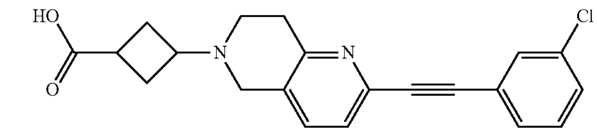 | D | >1 µM (1) | >1 µM (1) | >1 µM (1) |
| 129 | 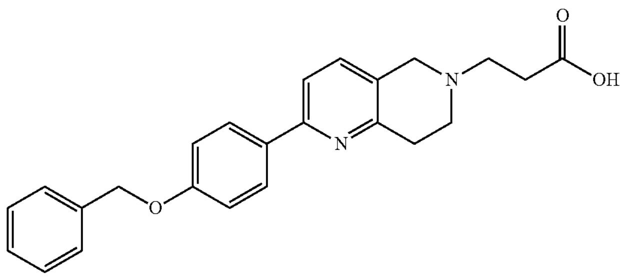 [SMILES: O=C(O)CCN1CCc2nc(-c3ccc(OCc4ccccc4)cc3)ccc2C1] | F | >1 µM (2) | >1 µM (2) | |
| 130 | 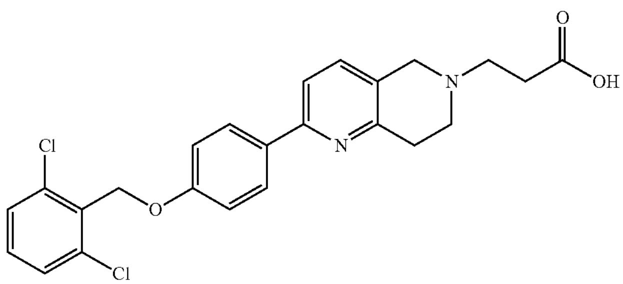 | F | >1 µM (2) | >1 µM (2) | |
| 131 | 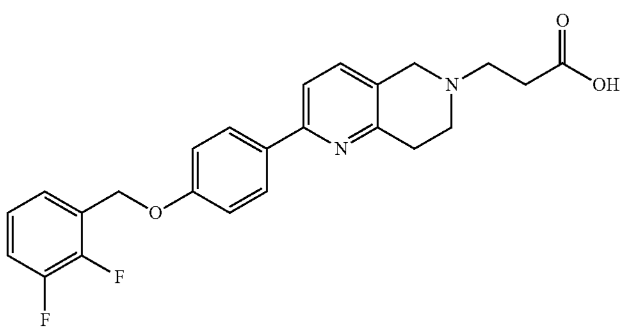 [SMILES: O=C(O)CCN1CCc2nc(-c3ccc(OCc4cccc(F)c4F)cc3)ccc2C1] | E | >1 µM (2) | >1 µM (2) | |
| 132 | 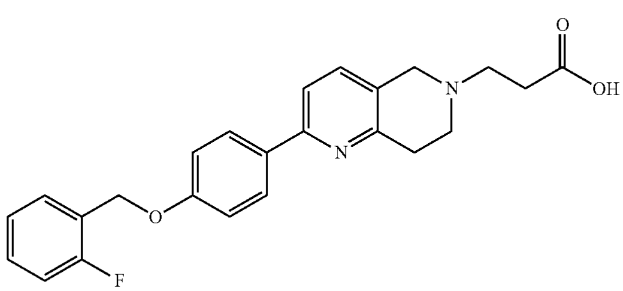 [SMILES: O=C(O)CCN1CCc2nc(-c3ccc(OCc4ccccc4F)cc3)ccc2C1] | E | >1 µM (2) | >1 µM (2) | |

TABLE 1-continued

| No | Structure | S1P5 EC50 range # | S1P1 EC50* | S1P3 EC50* | S1P4 EC50* |
|----|-----------|-------------------|------------|------------|------------|
| 133 | 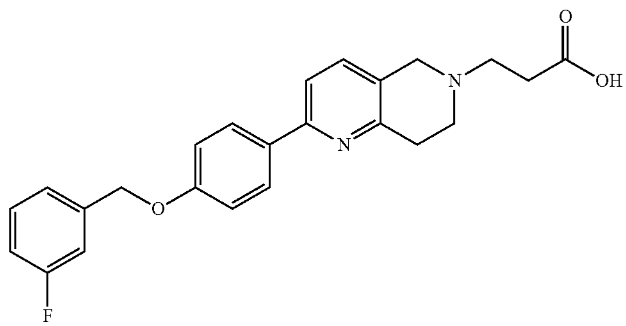 [SMILES: O=C(O)CCN1CCc2nc(-c3ccc(OCc4cccc(F)c4)cc3)ccc2C1] | A | >1 μM (1) | >1 μM (1) | >1 μM (1) |
| 134 | 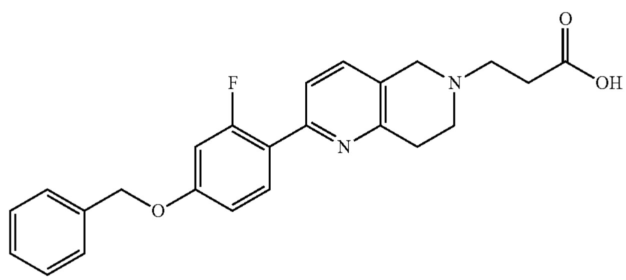 [SMILES: O=C(O)CCN1CCc2nc(-c3ccc(OCc4ccccc4)cc3F)ccc2C1] | E | >1 μM (2) | >1 μM (2) | |
| 135 | 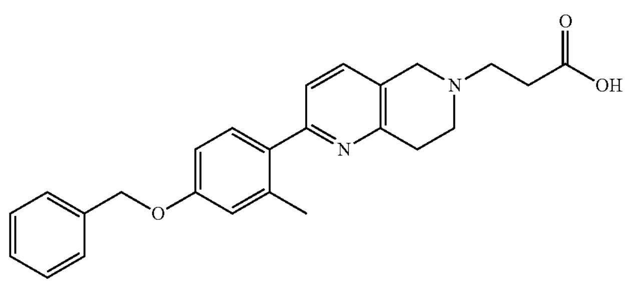 [SMILES: Cc1cc(OCc2ccccc2)ccc1-c1ccc2c(n1)CCN(CCC(=O)O)C2] | G | >1 μM (2) | >1 μM (2) | |
| 136 | 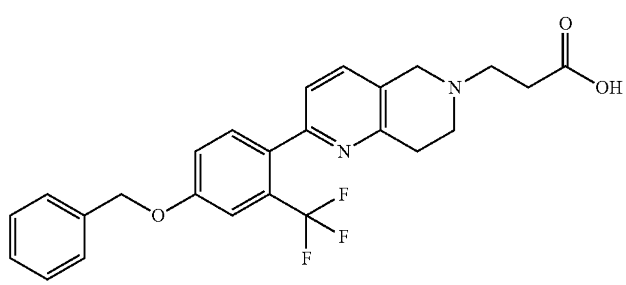 [SMILES: O=C(O)CCN1CCc2nc(-c3ccc(OCc4ccccc4)cc3C(F)(F)F)ccc2C1] | G | >1 μM (2) | >1 μM (2) | |
| 137 | 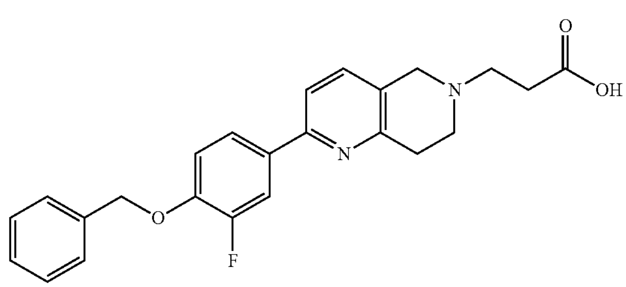 [SMILES: O=C(O)CCN1CCc2nc(-c3ccc(OCc4ccccc4)c(F)c3)ccc2C1] | F | >1 μM (2) | >1 μM (2) | |

TABLE 1-continued
| No | Structure | S1P5 EC50 range # | S1P1 EC50* | S1P3 EC50* | S1P4 EC50* |
|---|---|---|---|---|---|
| 138 | 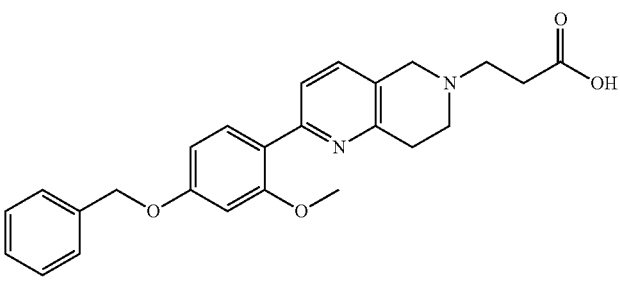 [SMILES: COc1cc(OCc2ccccc2)ccc1-c1ccc2c(n1)CCN(CCC(=O)O)C2] | G | >1 μM (2) | >1 μM (2) | |
| 139 | 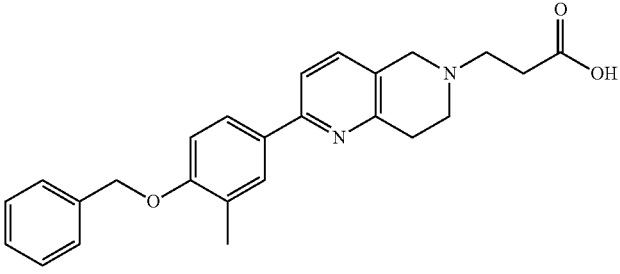 [SMILES: Cc1cc(-c2ccc3c(n2)CCN(CCC(=O)O)C3)ccc1OCc1ccccc1] | F | >1 μM (2) | >1 μM (2) | |
| 140 | 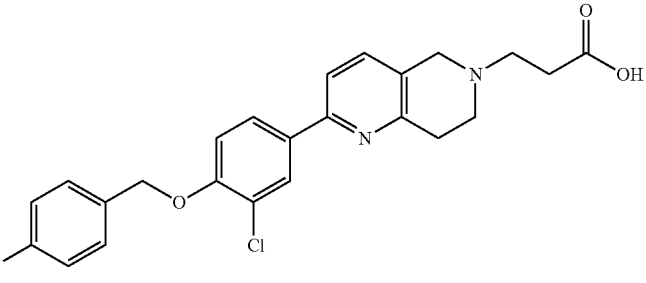 | F | >1 μM (2) | >1 μM (2) | |
| 141 | 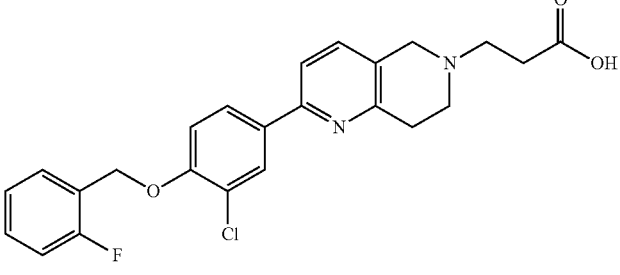 | F | >1 μM (2) | >1 μM (2) | |
| 142 | 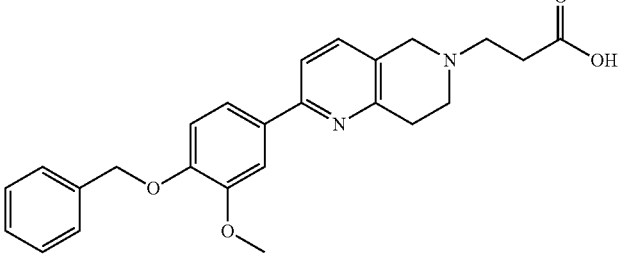 | G | >1 μM (2) | >1 μM (2) | |

TABLE 1-continued

| No | Structure | S1P5 EC50 range # | S1P1 EC50* | S1P3 EC50* | S1P4 EC50* |
|----|-----------|-------------------|------------|------------|------------|
| 143 | 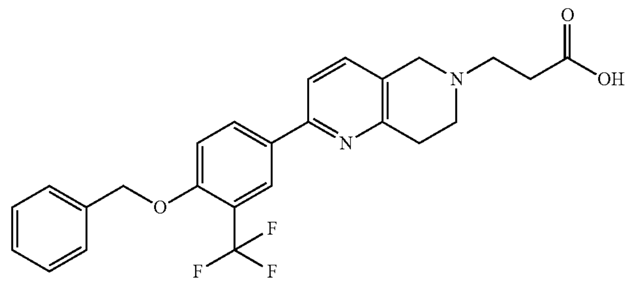 [SMILES: O=C(O)CCN1CCc2nc(-c3ccc(OCc4ccccc4)c(C(F)(F)F)c3)ccc2C1] | F | >1 μM (2) | >1 μM (2) | |
| 144 | 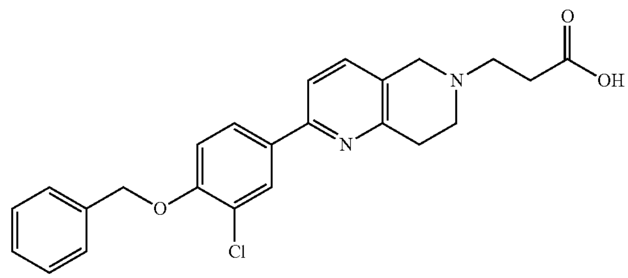 | F | >1 μM (2) | >1 μM (2) | |
| 145 | 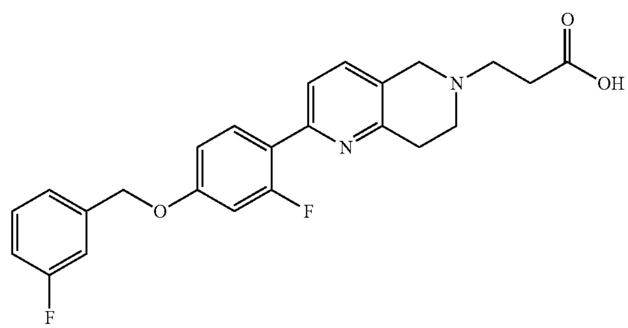 [SMILES: O=C(O)CCN1CCc2nc(-c3ccc(OCc4cccc(F)c4)cc3F)ccc2C1] | B | >1 μM (1) | >1 μM (1) | >1 μM (1) |
| 146 | 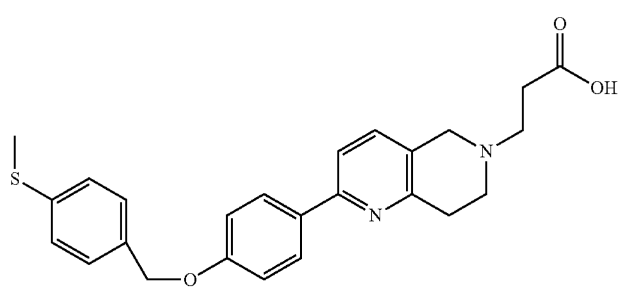 [SMILES: CSc1ccc(COc2ccc(-c3ccc4c(n3)CCN(CCC(=O)O)C4)cc2)cc1] | | | | |
| 147 | 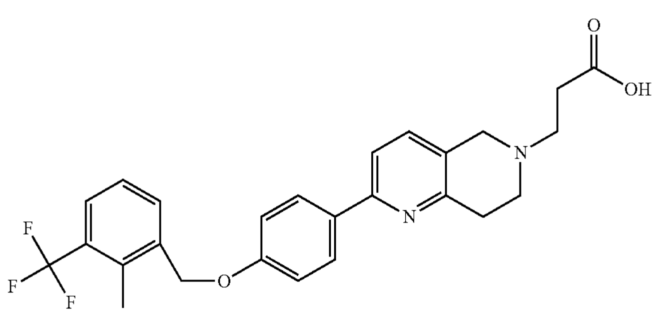 [SMILES: Cc1c(COc2ccc(-c3ccc4c(n3)CCN(CCC(=O)O)C4)cc2)cccc1C(F)(F)F] | | | | |

TABLE 1-continued

| No | Structure | S1P5 EC50 range # | S1P1 EC50* | S1P3 EC50* | S1P4 EC50* |
|---|---|---|---|---|---|
| 148 | 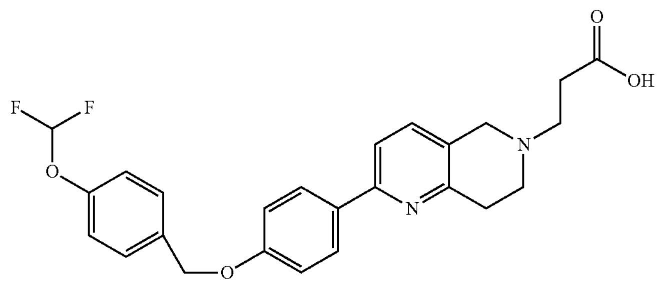 [SMILES: O=C(O)CCN1CCc2nc(-c3ccc(OCc4ccc(OC(F)F)cc4)cc3)ccc2C1] | | | | |
| 149 | 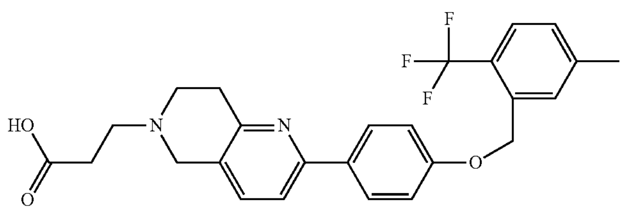 [SMILES: Cc1ccc(C(F)(F)F)c(COc2ccc(-c3ccc4c(n3)CCN(CCC(=O)O)C4)cc2)c1] | | | | |
| 150 | 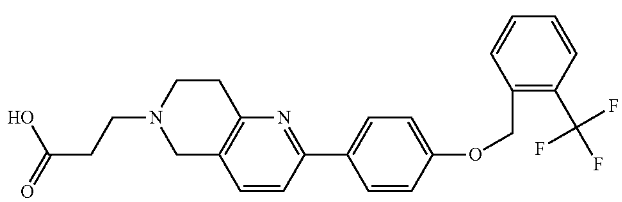 [SMILES: O=C(O)CCN1CCc2nc(-c3ccc(OCc4ccccc4C(F)(F)F)cc3)ccc2C1] | | | | |
| 151 | 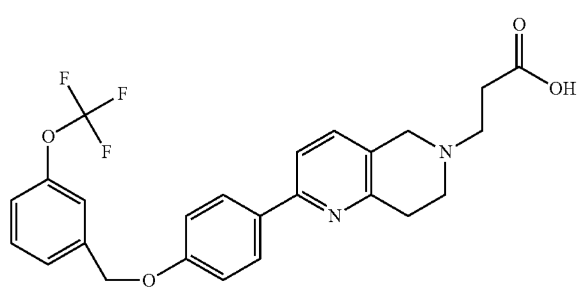 [SMILES: O=C(O)CCN1CCc2nc(-c3ccc(OCc4cccc(OC(F)(F)F)c4)cc3)ccc2C1] | A | <1 μM (1) | >1 μM (1) | |
| 152 | 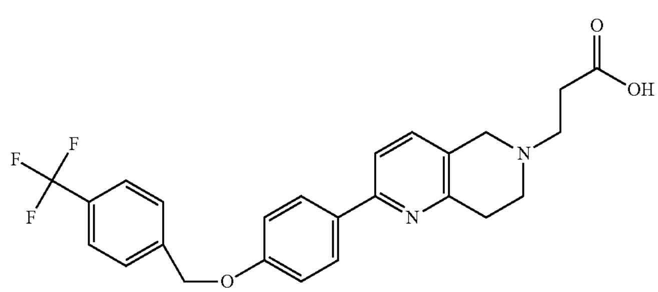 [SMILES: O=C(O)CCN1CCc2nc(-c3ccc(OCc4ccc(C(F)(F)F)cc4)cc3)ccc2C1] | A | >1 μM (1) | >1 μM (1) | |

TABLE 1-continued

| No | Structure | S1P5 EC50 range # | S1P1 EC50* | S1P3 EC50* | S1P4 EC50* |
|---|---|---|---|---|---|
| 153 | 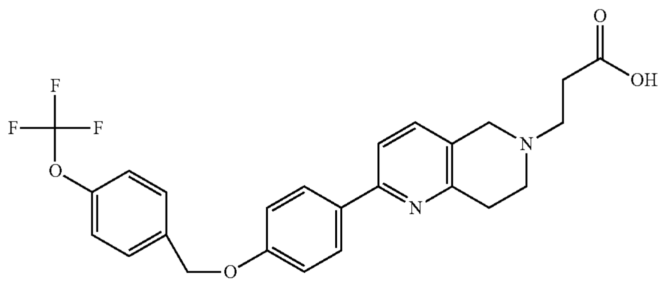 [SMILES: O=C(O)CCN1CCc2nc(-c3ccc(OCc4ccc(OC(F)(F)F)cc4)cc3)ccc2C1] | C | >1 µM (1) | >1 µM (1) | |
| 154 | 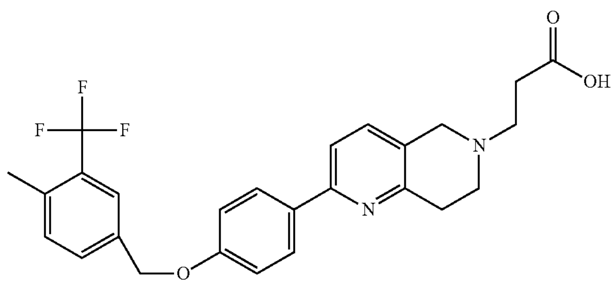 [SMILES: Cc1ccc(COc2ccc(-c3ccc4c(n3)CCN(CCC(=O)O)C4)cc2)cc1C(F)(F)F] | B | >1 µM (1) | >1 µM (1) | |
| 155 | 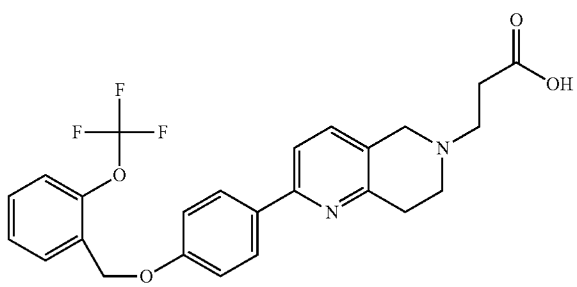 [SMILES: O=C(O)CCN1CCc2nc(-c3ccc(OCc4ccccc4OC(F)(F)F)cc3)ccc2C1] | A | >1 µM (1) | >1 µM (1) | >1 µM (1) |
| 156 | 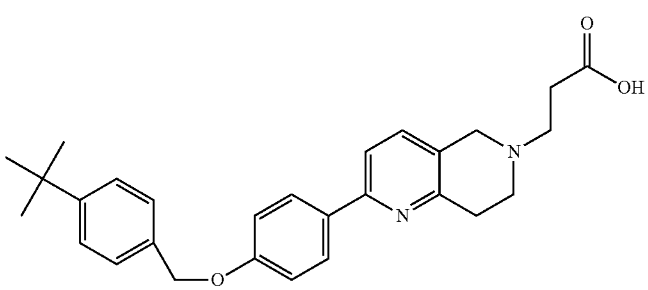 [SMILES: CC(C)(C)c1ccc(COc2ccc(-c3ccc4c(n3)CCN(CCC(=O)O)C4)cc2)cc1] | A | >1 µM (1) | >1 µM (1) | >1 µM (1) |
| 157 | 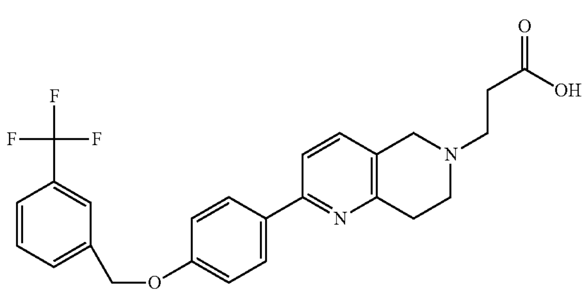 [SMILES: O=C(O)CCN1CCc2nc(-c3ccc(OCc4cccc(C(F)(F)F)c4)cc3)ccc2C1] | A | >1 µM (1) | >1 µM (1) | >1 µM (1) |

TABLE 1-continued

| No | Structure | S1P5 EC50 range # | S1P1 EC50* | S1P3 EC50* | S1P4 EC50* |
|---|---|---|---|---|---|
| 158 | 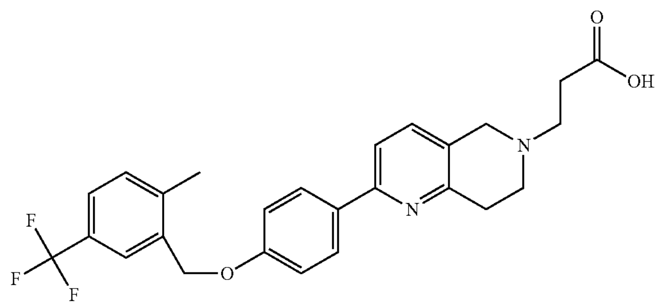 [SMILES: Cc1ccc(C(F)(F)F)cc1COc1ccc(-c2ccc3c(n2)CCN(CCC(=O)O)C3)cc1] | B | >1 μM (1) | >1 μM (1) | |
| 159 | 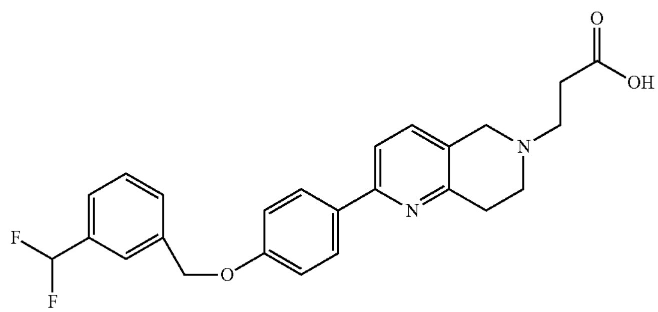 [SMILES: O=C(O)CCN1CCc2nc(-c3ccc(OCc4cccc(C(F)F)c4)cc3)ccc2C1] | A | >1 μM (1) | >1 μM (1) | >1 μM (1) |
| 160 | 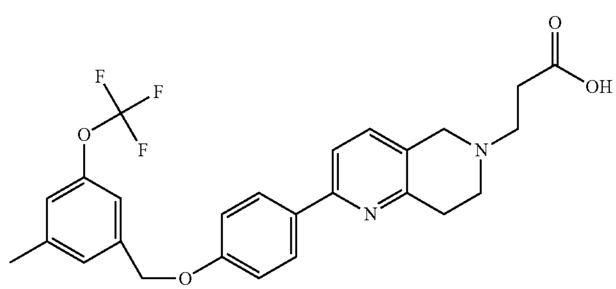 [SMILES: Cc1cc(COc2ccc(-c3ccc4c(n3)CCN(CCC(=O)O)C4)cc2)cc(OC(F)(F)F)c1] | B | >1 μM (1) | >1 μM (1) | >1 μM (1) |
| 161 | 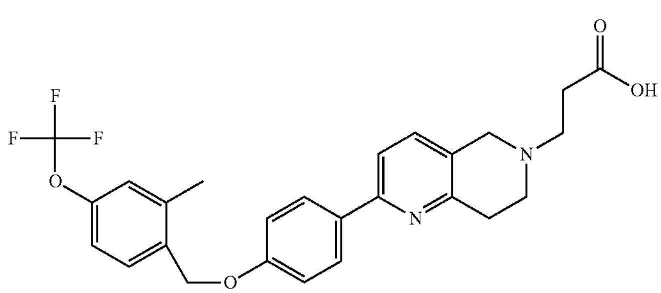 [SMILES: Cc1cc(OC(F)(F)F)ccc1COc1ccc(-c2ccc3c(n2)CCN(CCC(=O)O)C3)cc1] | A | >1 μM (1) | >1 μM (1) | >1 μM (1) |
| 162 | 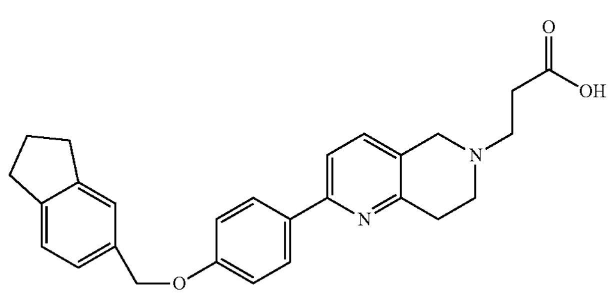 [SMILES: O=C(O)CCN1CCc2nc(-c3ccc(OCc4ccc5c(c4)CCC5)cc3)ccc2C1] | A | >1 μM (1) | >1 μM (1) | >1 μM (1) |

TABLE 1-continued

| No | Structure | S1P5 EC50 range # | S1P1 EC50* | S1P3 EC50* | S1P4 EC50* |
|---|---|---|---|---|---|
| 163 | 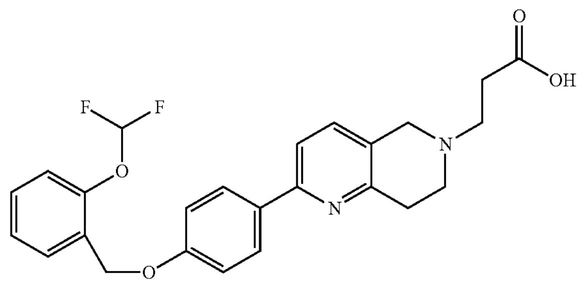 [SMILES: O=C(O)CCN1CCc2nc(-c3ccc(OCc4ccccc4OC(F)F)cc3)ccc2C1] | A | >1 μM (1) | >1 μM (1) | >1 μM (1) |
| 164 | 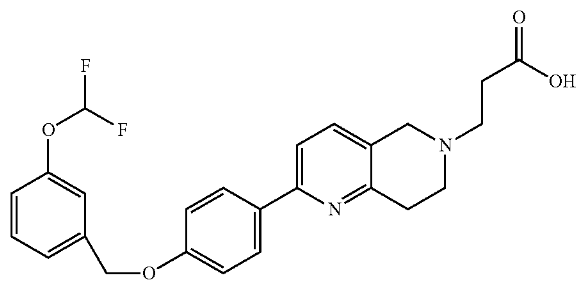 [SMILES: O=C(O)CCN1CCc2nc(-c3ccc(OCc4cccc(OC(F)F)c4)cc3)ccc2C1] | A | <1 μM (1) | >1 μM (1) | |
| 165 | 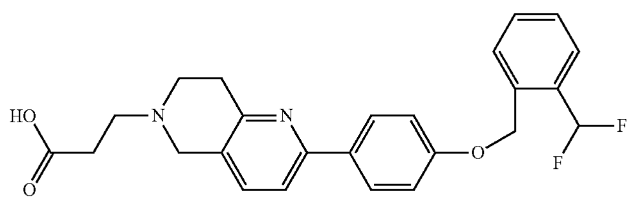 [SMILES: O=C(O)CCN1CCc2nc(-c3ccc(OCc4ccccc4C(F)F)cc3)ccc2C1] | A | >1 μM (1) | >1 μM (1) | >1 μM (1) |
| 166 | 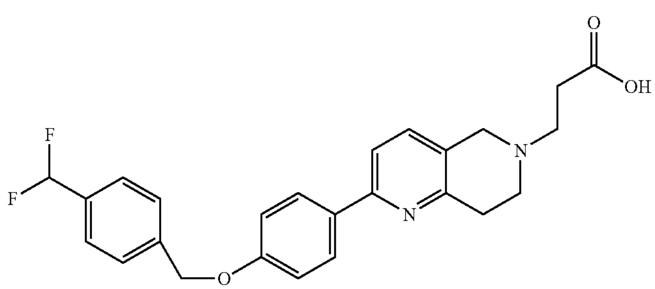 [SMILES: O=C(O)CCN1CCc2nc(-c3ccc(OCc4ccc(C(F)F)cc4)cc3)ccc2C1] | A | >1 μM (1) | >1 μM (1) | >1 μM (1) |
| 167 | 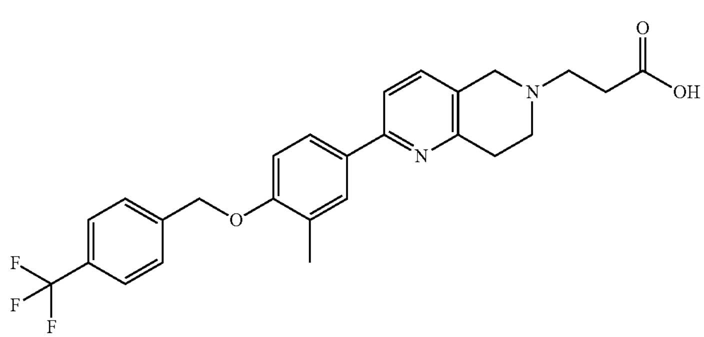 [SMILES: Cc1cc(-c2ccc3c(n2)CCN(CCC(=O)O)C3)ccc1OCc1ccc(C(F)(F)F)cc1] | A | >1 μM (1) | >1 μM (1) | >1 μM (1) |

TABLE 1-continued

| No | Structure | S1P5 EC50 range # | S1P1 EC50* | S1P3 EC50* | S1P4 EC50* |
|---|---|---|---|---|---|
| 168 | 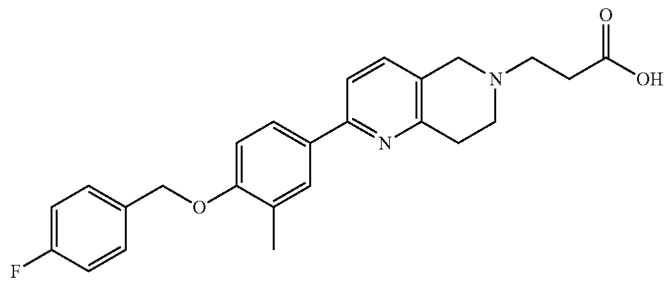 [SMILES: Cc1cc(-c2ccc3c(n2)CCN(CCC(=O)O)C3)ccc1OCc1ccc(F)cc1] | B | >1 μM (1) | >1 μM (1) | |
| 169 | 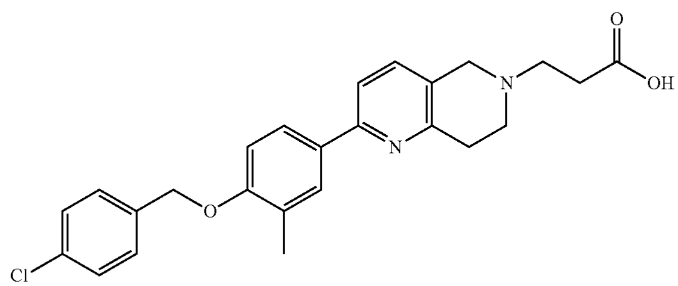 [SMILES: Cc1cc(-c2ccc3c(n2)CCN(CCC(=O)O)C3)ccc1OCc1ccc(Cl)cc1] | A | >1 μM (1) | >1 μM (1) | >1 μM (1) |
| 171 | 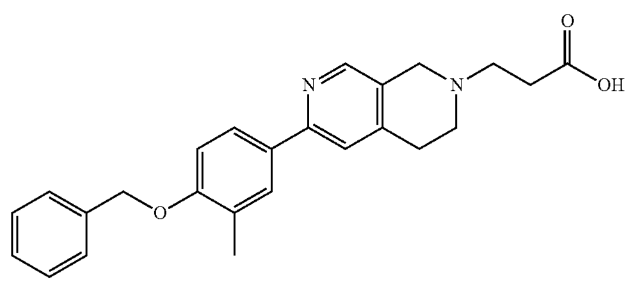 [SMILES: Cc1cc(-c2cc3c(cn2)CN(CCC(=O)O)CC3)ccc1OCc1ccccc1] | B | >1 μM (1) | >1 μM (1) | |
| 172 | 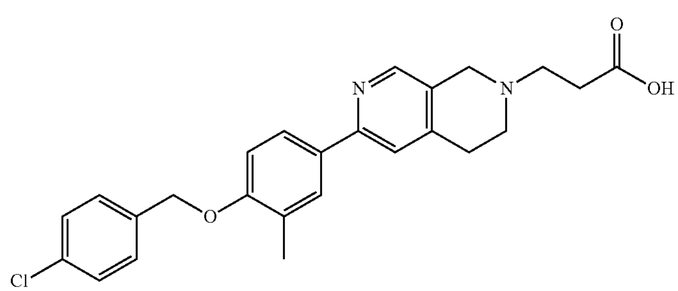 [SMILES: Cc1cc(-c2cc3c(cn2)CN(CCC(=O)O)CC3)ccc1OCc1ccc(Cl)cc1] | A | >1 μM (1) | >1 μM (1) | >1 μM (1) |
| 173 | 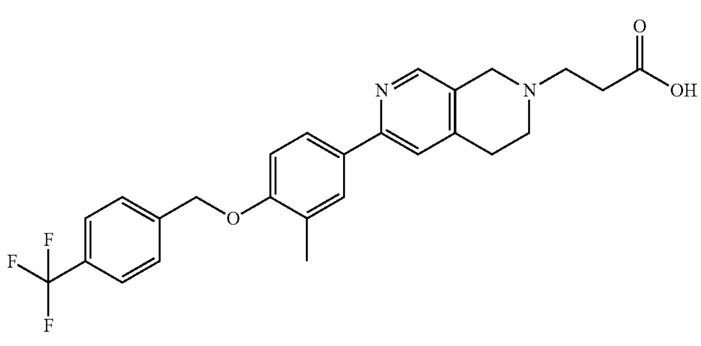 [SMILES: Cc1cc(-c2cc3c(cn2)CN(CCC(=O)O)CC3)ccc1OCc1ccc(C(F)(F)F)cc1] | A | >1 μM (1) | >1 μM (1) | >1 μM (1) |

TABLE 1-continued

| No | Structure | S1P5 EC50 range # | S1P1 EC50* | S1P3 EC50* | S1P4 EC50* |
|---|---|---|---|---|---|
| 174 | 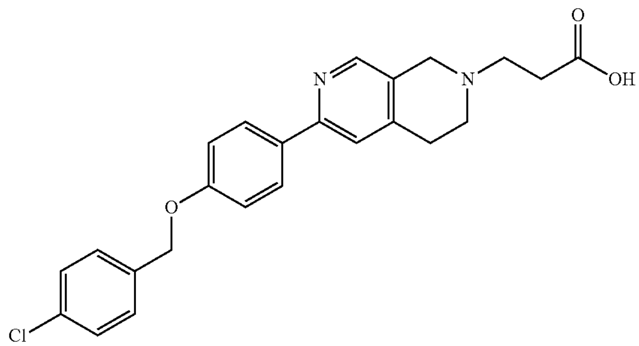 [SMILES: O=C(O)CCN1CCc2cc(-c3ccc(OCc4ccc(Cl)cc4)cc3)ncc2C1] | A | >1 μM (1) | >1 μM (1) | >1 μM (1) |
| 175 | 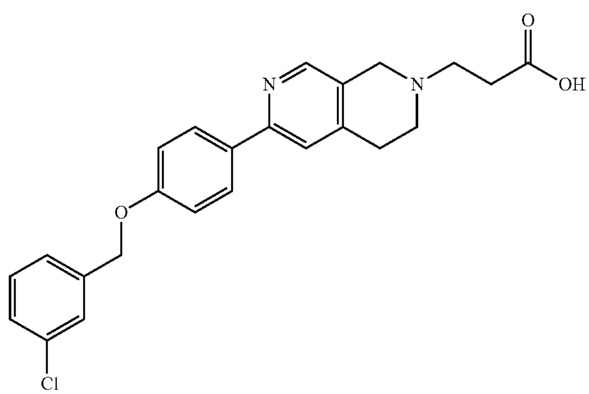 [SMILES: O=C(O)CCN1CCc2cc(-c3ccc(OCc4cccc(Cl)c4)cc3)ncc2C1] | A | >1 μM (1) | >1 μM (1) | >1 μM (1) |
| 176 | 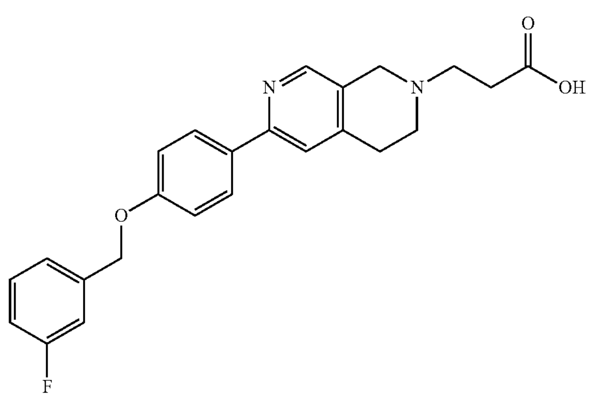 | A | >1 μM (1) | >1 μM (1) | >1 μM (1) |
| 177 | 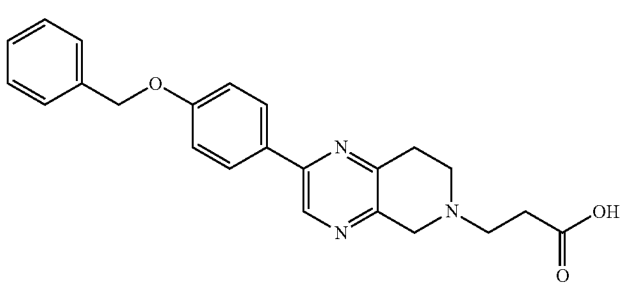 [SMILES: O=C(O)CCN1CCc2nc(-c3ccc(OCc4ccccc4)cc3)cnc2C1] | A | >1 μM (1) | >1 μM (1) | >1 μM (1) |

TABLE 1-continued

| No | Structure | S1P5 EC50 range # | S1P1 EC50* | S1P3 EC50* | S1P4 EC50* |
|---|---|---|---|---|---|
| 178 | 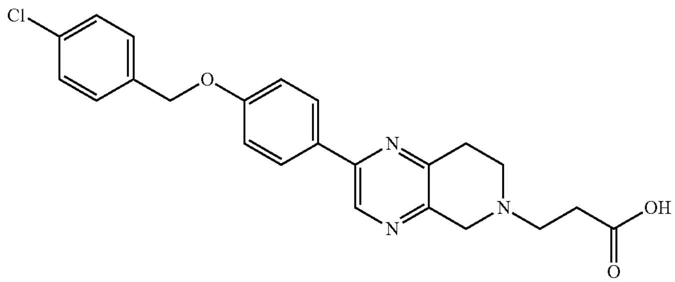 [SMILES: O=C(O)CCN1CCc2nc(-c3ccc(OCc4ccc(Cl)cc4)cc3)cnc2C1] | A | >1 μM (1) | >1 μM (1) | >1 μM (1) |
| 179 | 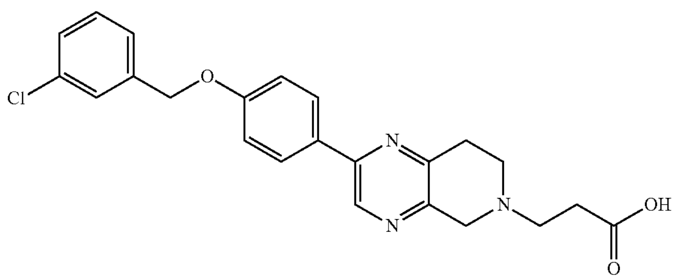 [SMILES: O=C(O)CCN1CCc2nc(-c3ccc(OCc4cccc(Cl)c4)cc3)cnc2C1] | A | >1 μM (1) | <1 μM (1) | >1 μM (1) |
| 180 | 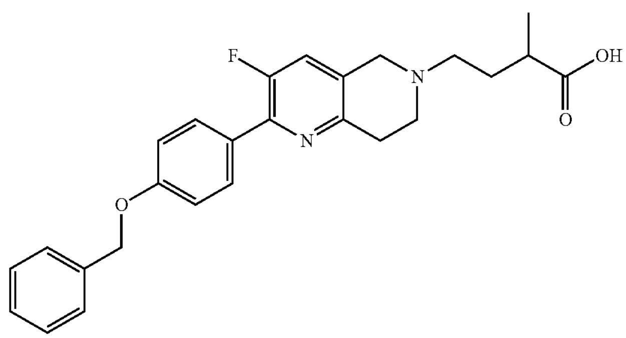 [SMILES: CC(CCN1CCc2nc(-c3ccc(OCc4ccccc4)cc3)c(F)cc2C1)C(=O)O] | A | <1 μM (1) | >1 μM (1) | >1 μM (1) |
| 181 | 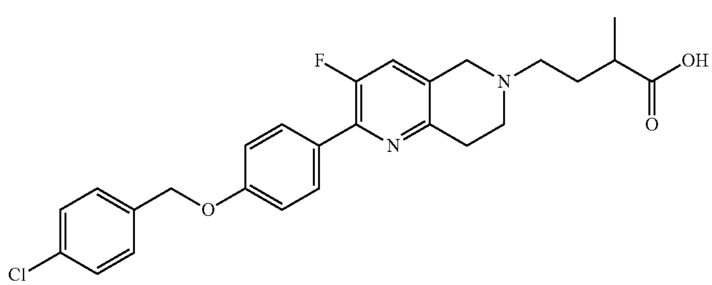 [SMILES: CC(CCN1CCc2nc(-c3ccc(OCc4ccc(Cl)cc4)cc3)c(F)cc2C1)C(=O)O] | A | <1 μM (1) | >1 μM (1) | >1 μM (1) |
| 182 | 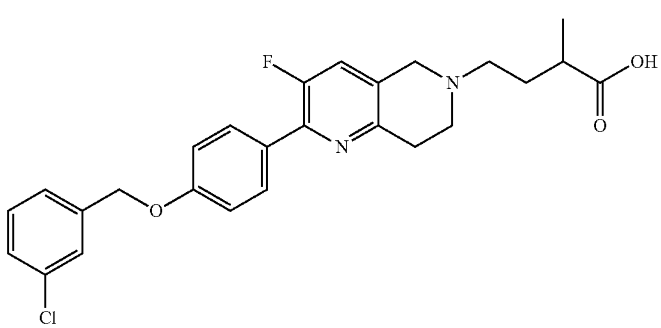 [SMILES: CC(CCN1CCc2nc(-c3ccc(OCc4cccc(Cl)c4)cc3)c(F)cc2C1)C(=O)O] | A | >1 μM (1) | >1 μM (1) | >1 μM (1) |

US 10,556,907 B2
251 252
TABLE 1-continued
| No | Structure | S1P5 EC50 range # | S1P1 EC50* | S1P3 EC50* | S1P4 EC50* |
|---|---|---|---|---|---|
| 183 | 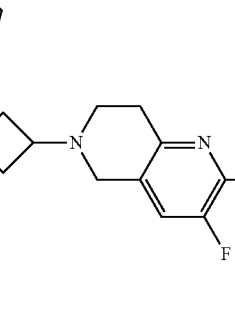 | C | >1 μM (1) | | >1 μM (1) |
| 184 | 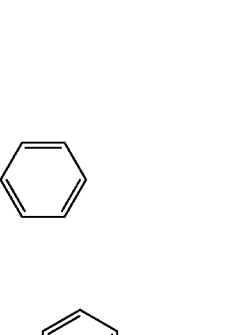 | D | >1 μM (1) | | >1 μM (1) |
| 186 | 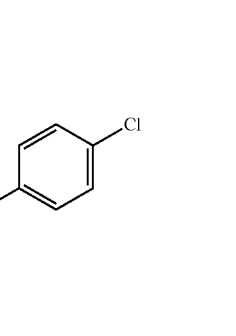 | A | >1 μM (1) | >1 μM (1) | >1 μM (1) |
| 187 | 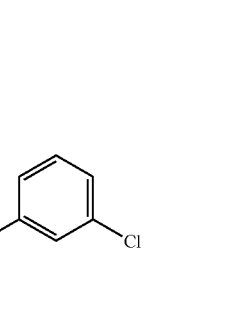 | A | <1 μM (1) | >1 μM (1) | |
| 189 | 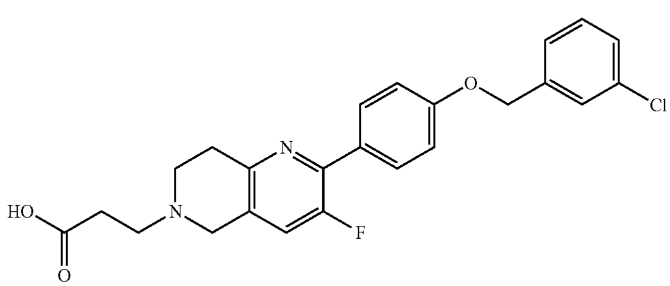 [SMILES: O=C(O)CCN1CCc2nc(-c3ccc(OCc4cccc(Cl)c4)cc3)c(F)cc2C1] | A | >1 μM (1) | >1 μM (1) | >1 μM (1) |

TABLE 1-continued

| No | Structure | S1P5 EC50 range # | S1P1 EC50* | S1P3 EC50* | S1P4 EC50* |
|---|---|---|---|---|---|
| 190 | 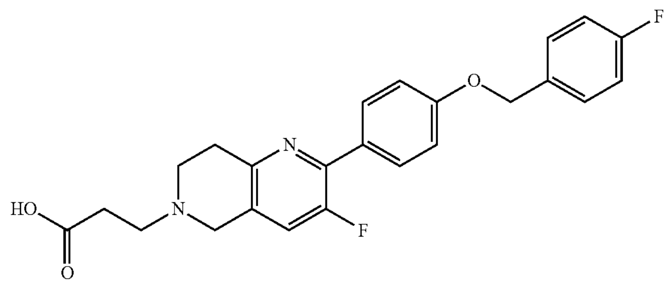 [SMILES: O=C(O)CCN1CCc2nc(-c3ccc(OCc4ccc(F)cc4)cc3)c(F)cc2C1] | A | <1 μM (1) | >1 μM (1) | |
| 191 | 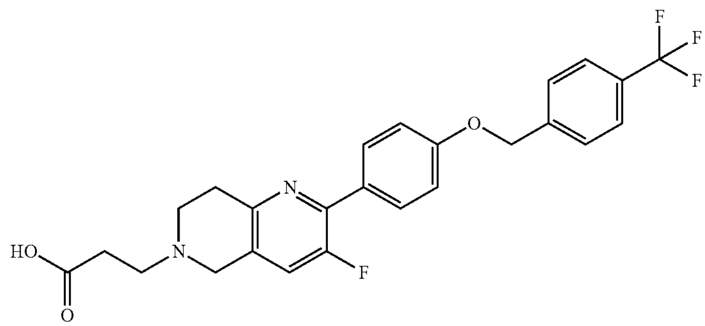 [SMILES: O=C(O)CCN1CCc2nc(-c3ccc(OCc4ccc(C(F)(F)F)cc4)cc3)c(F)cc2C1] | A | <1 μM (1) | >1 μM (1) | |
| 192 | 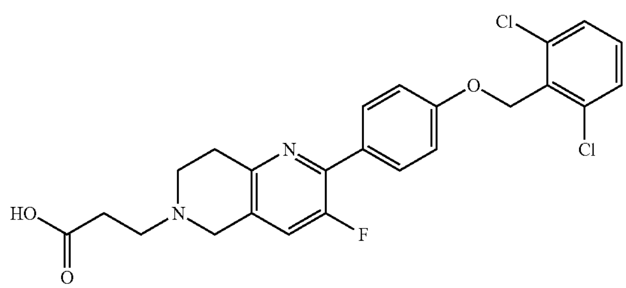 [SMILES: O=C(O)CCN1CCc2nc(-c3ccc(OCc4c(Cl)cccc4Cl)cc3)c(F)cc2C1] | A | >1 μM (1) | >1 μM (1) | >1 μM (1) |
| 193 | 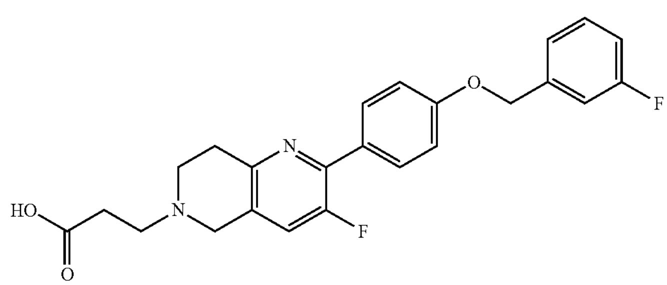 [SMILES: O=C(O)CCN1CCc2nc(-c3ccc(OCc4cccc(F)c4)cc3)c(F)cc2C1] | A | >1 μM (1) | >1 μM (1) | >1 μM (1) |
| 194 | 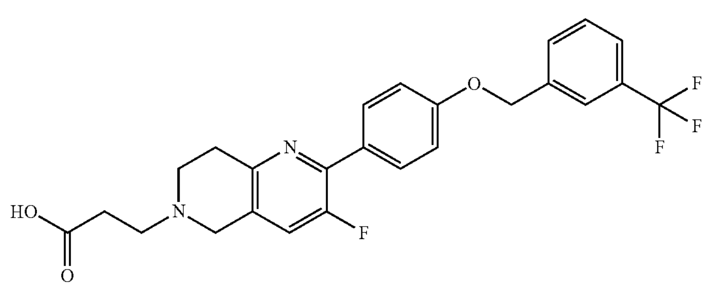 [SMILES: O=C(O)CCN1CCc2nc(-c3ccc(OCc4cccc(C(F)(F)F)c4)cc3)c(F)cc2C1] | A | >1 μM (1) | >1 μM (1) | |

TABLE 1-continued
| No | Structure | S1P5 EC50 range # | S1P1 EC50* | S1P3 EC50* | S1P4 EC50* |
|---|---|---|---|---|---|
| 196 | 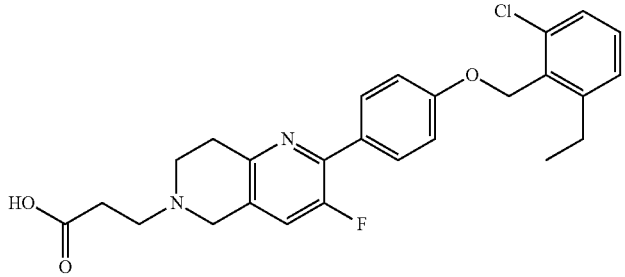 [SMILES: CCc1cccc(Cl)c1COc1ccc(-c2nc3c(cc2F)CN(CCC(=O)O)CC3)cc1] | B | >1 µM (1) | >1 µM (1) | |
| 197 | 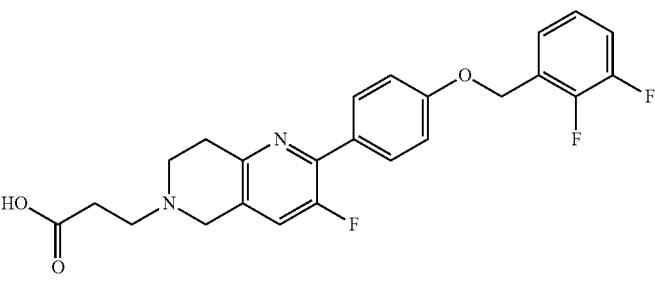 | A | <1 µM (1) | >1 µM (1) | |
| 198 | 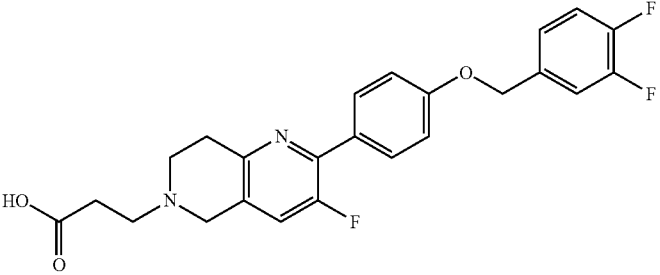 [SMILES: O=C(O)CCN1CCc2nc(-c3ccc(OCc4ccc(F)c(F)c4)cc3)c(F)cc2C1] | A | <1 µM (1) | >1 µM (1) | |
| 199 | 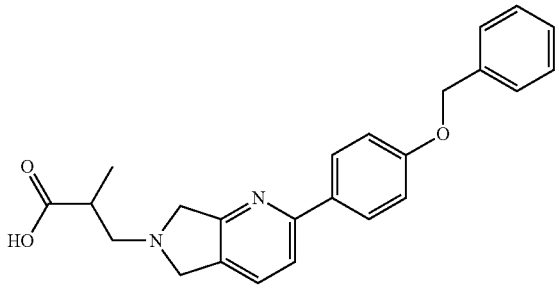 [SMILES: CC(CN1Cc2ccc(-c3ccc(OCc4ccccc4)cc3)nc2C1)C(=O)O] | G | >1 µM (2) | >1 µM (2) | |
| 200 | 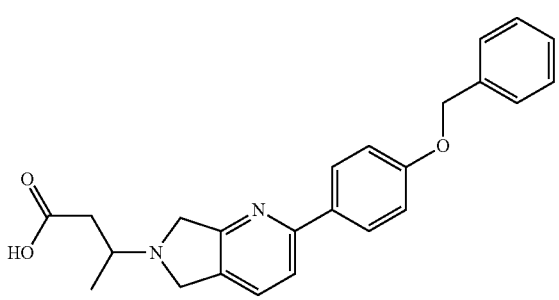 [SMILES: CC(CC(=O)O)N1Cc2ccc(-c3ccc(OCc4ccccc4)cc3)nc2C1] | G | >1 µM (2) | >1 µM (2) | |

TABLE 1-continued

| No | Structure | S1P5 EC50 range # | S1P1 EC50* | S1P3 EC50* | S1P4 EC50* |
|---|---|---|---|---|---|
| 201 | 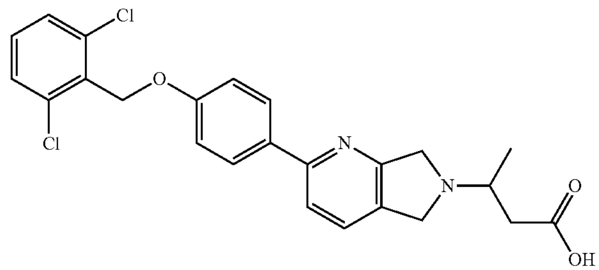 [SMILES: CC(CC(=O)O)N1Cc2ccc(-c3ccc(OCc4c(Cl)cccc4Cl)cc3)nc2C1] | D | >1 μM (1) | >1 μM (1) | |
| 202 | 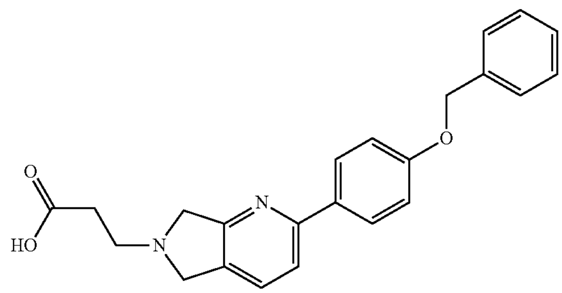 [SMILES: O=C(O)CCN1Cc2ccc(-c3ccc(OCc4ccccc4)cc3)nc2C1] | G | >1 μM (2) | >1 μM (2) | |
| 203 | 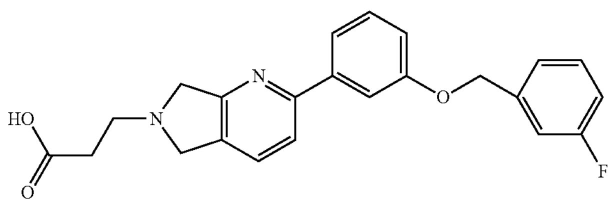 [SMILES: O=C(O)CCN1Cc2ccc(-c3cccc(OCc4cccc(F)c4)c3)nc2C1] | D | >1 μM (1) | >1 μM (1) | |
| 204 | 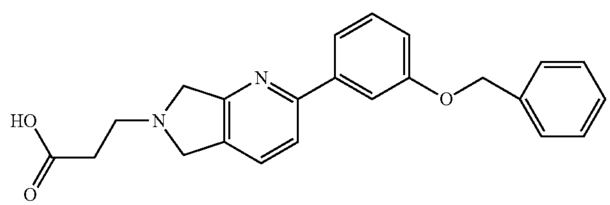 [SMILES: O=C(O)CCN1Cc2ccc(-c3cccc(OCc4ccccc4)c3)nc2C1] | D | >1 μM (1) | >1 μM (1) | |
| 205 | 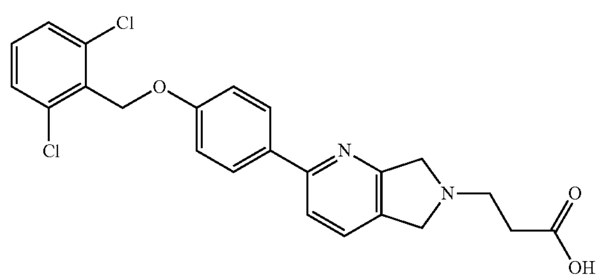 [SMILES: O=C(O)CCN1Cc2ccc(-c3ccc(OCc4c(Cl)cccc4Cl)cc3)nc2C1] | D | >1 μM (1) | >1 μM (1) | |
| 206 | 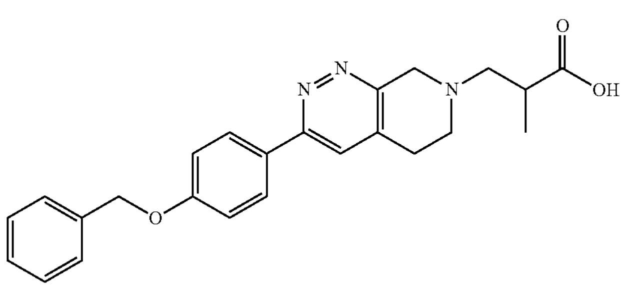 [SMILES: CC(CN1CCc2cc(-c3ccc(OCc4ccccc4)cc3)nnc2C1)C(=O)O] | F | >1 μM (2) | >1 μM (2) | |

TABLE 1-continued

| No | Structure | S1P5 EC50 range # | S1P1 EC50* | S1P3 EC50* | S1P4 EC50* |
|---|---|---|---|---|---|
| 207 | 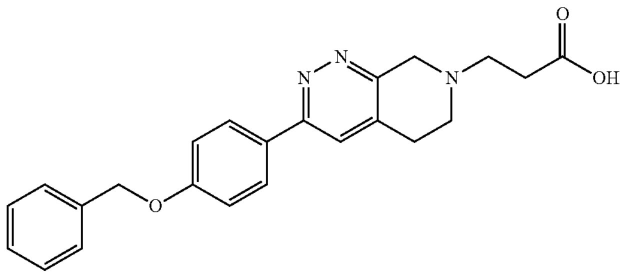 [SMILES: O=C(O)CCN1CCc2cc(-c3ccc(OCc4ccccc4)cc3)nnc2C1] | G | >1 μM (2) | >1 μM (2) | |
| 208 | 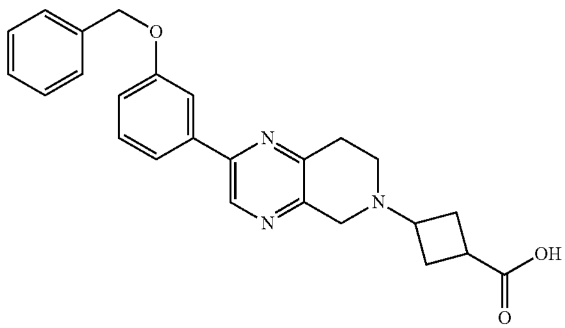 [SMILES: O=C(O)C1CC(N2CCc3nc(-c4cccc(OCc5ccccc5)c4)cnc3C2)C1] | D | >1 μM (1) | | >1 μM (1) |
| 209 | 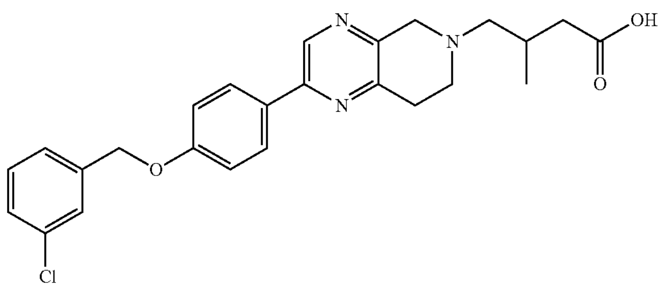 [SMILES: CC(CC(=O)O)CN1CCc2nc(-c3ccc(OCc4cccc(Cl)c4)cc3)cnc2C1] | A | >1 μM (1) | | >1 μM (1) |
| 210 | 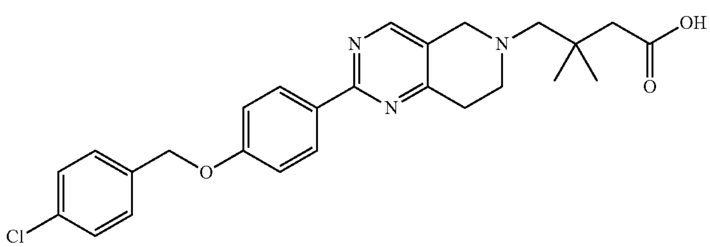 [SMILES: CC(C)(CC(=O)O)CN1CCc2nc(-c3ccc(OCc4ccc(Cl)cc4)cc3)ncc2C1] | D | >1 μM (1) | >1 μM (1) | >1 μM (1) |
| 211 | 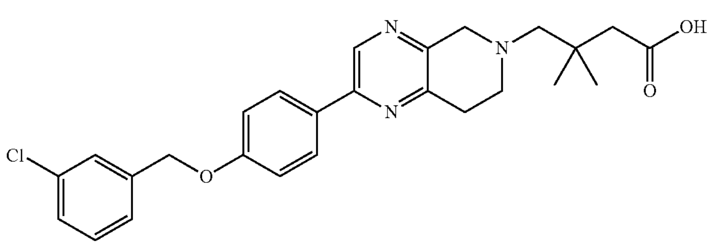 [SMILES: CC(C)(CC(=O)O)CN1CCc2nc(-c3ccc(OCc4cccc(Cl)c4)cc3)cnc2C1] | D | >1 μM (1) | | >1 μM (1) |

TABLE 1-continued

| No | Structure | S1P5 EC50 range # | S1P1 EC50* | S1P3 EC50* | S1P4 EC50* |
|---|---|---|---|---|---|
| 212 | enantiomer 1 of compound 23 | A | >1 µM (1) | >1 µM (1) | >1 µM (1) |
| 213 | enantiomer 2 of compound 23 | B | >1 µM (1) | >1 µM (1) | >1 µM (1) |
| 214 | 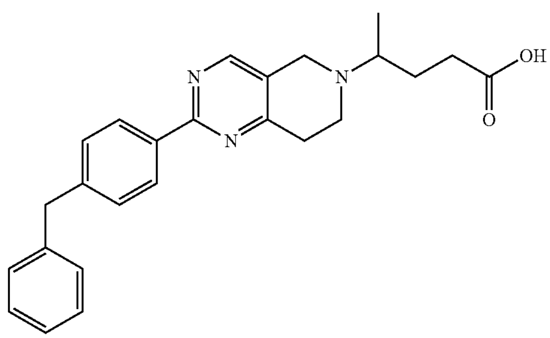 [SMILES: CC(CCC(=O)O)N1CCc2nc(-c3ccc(Cc4ccccc4)cc3)ncc2C1] | D | >1 µM (1) | >1 µM (1) | >1 µM (1) |
| 215 | 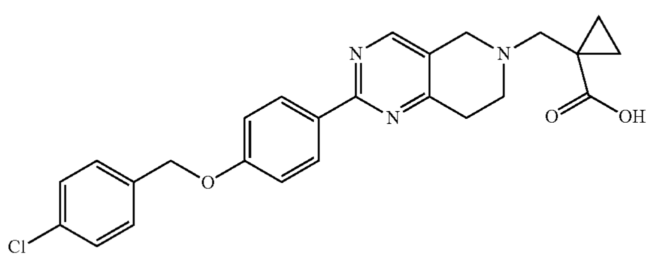 [SMILES: O=C(O)C1(CN2CCc3nc(-c4ccc(OCc5ccc(Cl)cc5)cc4)ncc3C2)CC1] | D | >1 µM (1) | >1 µM (1) | >1 µM (1) |
| 216 | 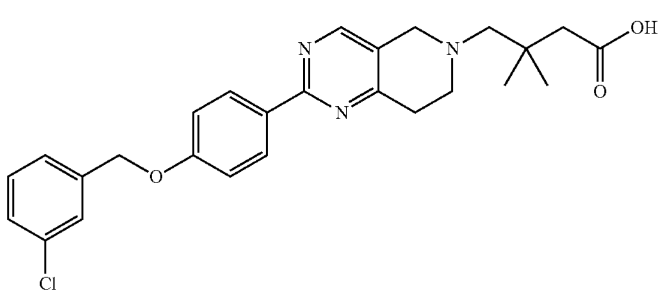 [SMILES: CC(C)(CC(=O)O)CN1CCc2nc(-c3ccc(OCc4cccc(Cl)c4)cc3)ncc2C1] | D | >1 µM (1) | | >1 µM (1) |

TABLE 1-continued

| No | Structure | S1P5 EC50 range # | S1P1 EC50* | S1P3 EC50* | S1P4 EC50* |
|---|---|---|---|---|---|
| 217 | 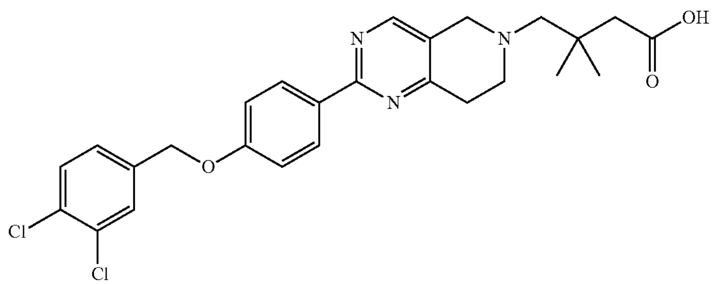 [SMILES: CC(C)(CC(=O)O)CN1CCc2nc(-c3ccc(OCc4ccc(Cl)c(Cl)c4)cc3)ncc2C1] | C | >1 μM (1) | | >1 μM (1) |
| 218 | 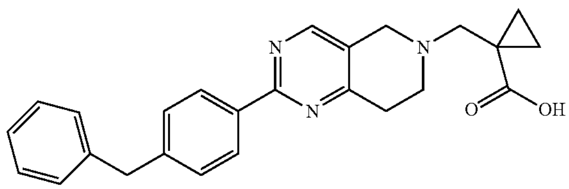 [SMILES: O=C(O)C1(CN2CCc3nc(-c4ccc(Cc5ccccc5)cc4)ncc3C2)CC1] | D | >1 μM (1) | >1 μM (1) | >1 μM (1) |
| 219 | 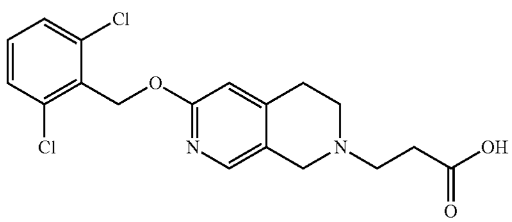 [SMILES: O=C(O)CCN1CCc2cc(OCc3c(Cl)cccc3Cl)ncc2C1] | C | >1 μM (1) | >1 μM (1) | >1 μM (1) |
| 221 | 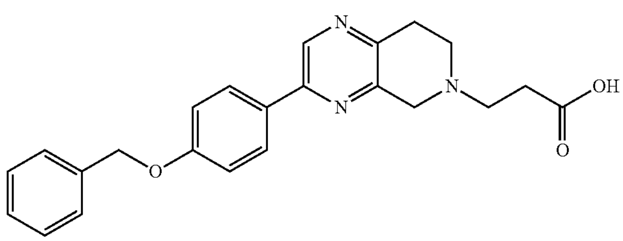 [SMILES: O=C(O)CCN1CCc2ncc(-c3ccc(OCc4ccccc4)cc3)nc2C1] | D | >1 μM (1) | >1 μM (1) | |
| 222 | 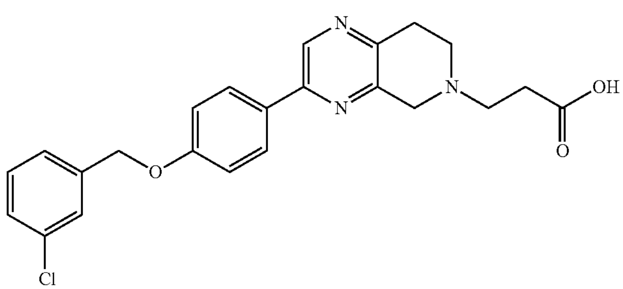 [SMILES: O=C(O)CCN1CCc2ncc(-c3ccc(OCc4cccc(Cl)c4)cc3)nc2C1] | D | >1 μM (1) | >1 μM (1) | |
| 223 | 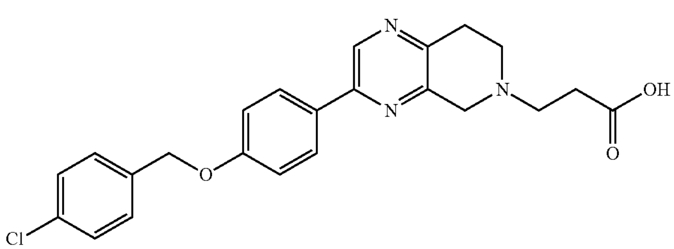 [SMILES: O=C(O)CCN1CCc2ncc(-c3ccc(OCc4ccc(Cl)cc4)cc3)nc2C1] | D | >1 μM (1) | >1 μM (1) | |

TABLE 1-continued
| No | Structure | S1P5 EC50 range # | S1P1 EC50* | S1P3 EC50* | S1P4 EC50* |
|---|---|---|---|---|---|
| 225 | 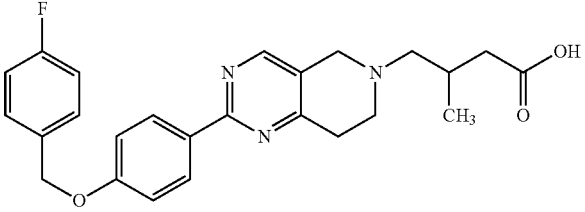 [SMILES: CC(CC(=O)O)CN1CCc2nc(-c3ccc(OCc4ccc(F)cc4)cc3)ncc2C1] | A | >1 µM (1) | >1 µM (1) | >1 µM (1) |
| 226 | 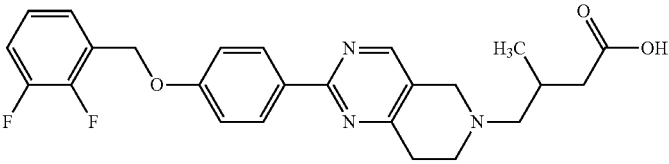 [SMILES: CC(CC(=O)O)CN1CCc2nc(-c3ccc(OCc4cccc(F)c4F)cc3)ncc2C1] | A | <1 µM (1) | >1 µM (1) | >1 µM (1) |
| 227 | 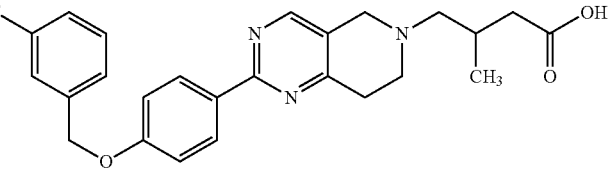 | A | >1 µM (1) | >1 µM (1) | <1 µM (1) |
| 228 | 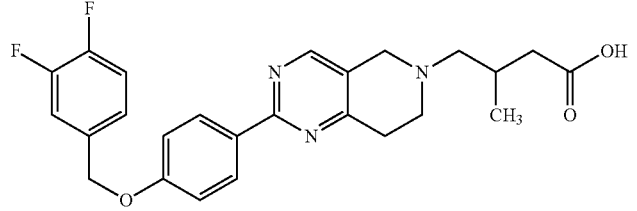 [SMILES: CC(CC(=O)O)CN1CCc2nc(-c3ccc(OCc4ccc(F)c(F)c4)cc3)ncc2C1] | A | >1 µM (1) | >1 µM (1) | >1 µM (1) |
| 229 | 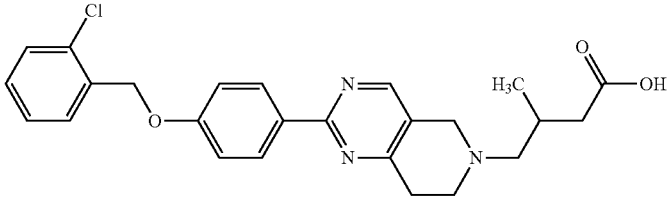 | A | <1 µM (1) | >1 µM (1) | >1 µM (1) |
| 230 | 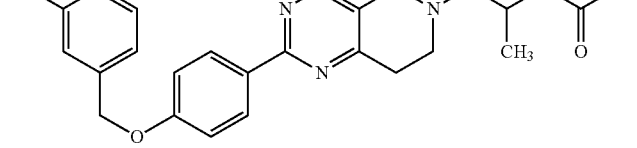 | A | <1 µM (1) | >1 µM (1) | >1 µM (1) |
| 231 | 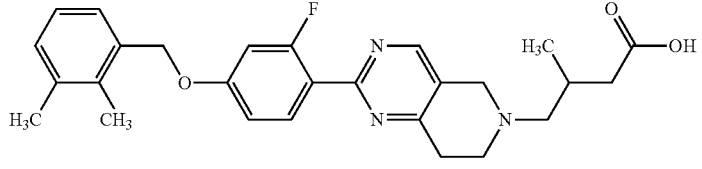 [SMILES: Cc1cccc(COc2ccc(-c3ncc4c(n3)CCN(CC(C)CC(=O)O)C4)c(F)c2)c1C] | A | >1 µM (1) | >1 µM (1) | >1 µM (1) |

TABLE 1-continued

| No | Structure | S1P5 EC50 range # | S1P1 EC50* | S1P3 EC50* | S1P4 EC50* |
|---|---|---|---|---|---|
| 232 | 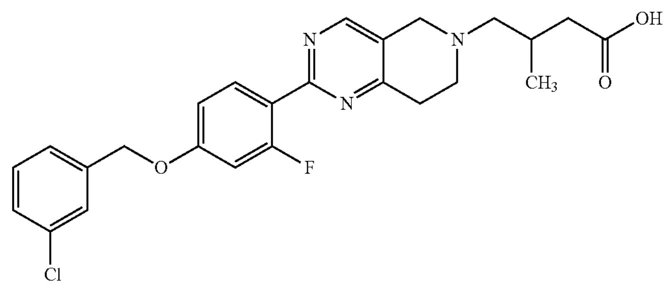 [SMILES: CC(CC(=O)O)CN1CCc2nc(-c3ccc(OCc4cccc(Cl)c4)cc3F)ncc2C1] | A | >1 μM (1) | >1 μM (1) | >1 μM (1) |
| 233 | 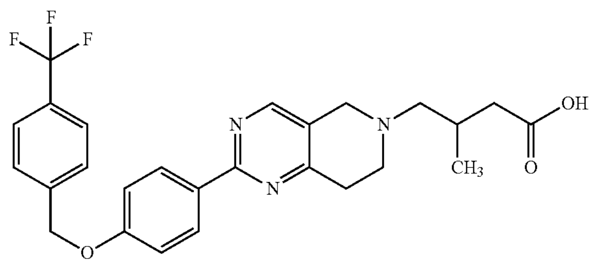 [SMILES: CC(CC(=O)O)CN1CCc2nc(-c3ccc(OCc4ccc(C(F)(F)F)cc4)cc3)ncc2C1] | A | <1 μM (1) | >1 μM (1) | <1 μM (1) |
| 234 | 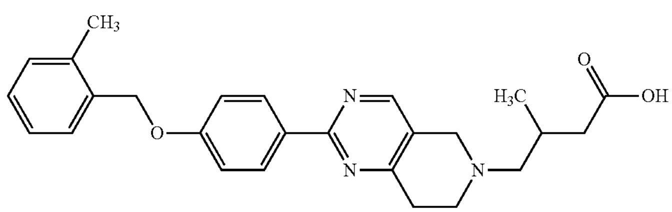 | A | <1 μM (1) | >1 μM (1) | >1 μM (1) |
| 235 | 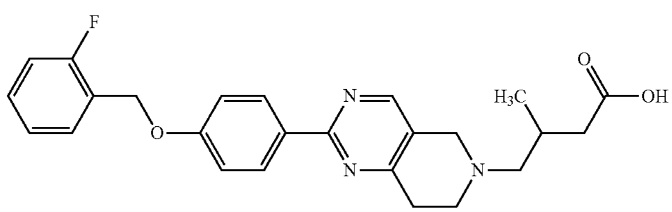 [SMILES: CC(CC(=O)O)CN1CCc2nc(-c3ccc(OCc4ccccc4F)cc3)ncc2C1] | A | <1 μM (1) | >1 μM (1) | >1 μM (1) |
| 236 | 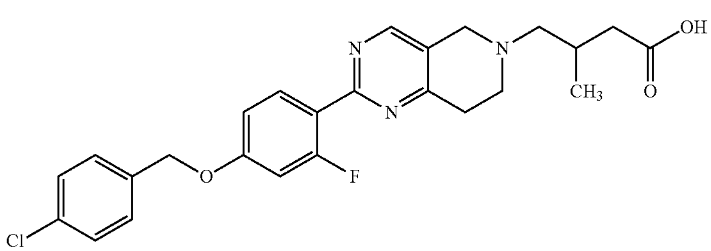 [SMILES: CC(CC(=O)O)CN1CCc2nc(-c3ccc(OCc4ccc(Cl)cc4)cc3F)ncc2C1] | A | >1 μM (1) | >1 μM (1) | >1 μM (1) |
| 237 | | A | >1 μM (1) | >1 μM (1) | >1 μM (1) | enantiomer of compound 244

TABLE 1-continued

| No | Structure | S1P5 EC50 range # | S1P1 EC50* | S1P3 EC50* | S1P4 EC50* |
|---|---|---|---|---|---|
| 238 | 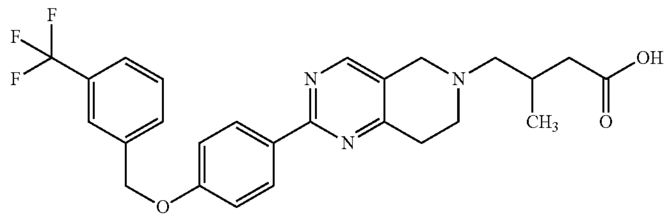 [SMILES: CC(CC(=O)O)CN1CCc2nc(-c3ccc(OCc4cccc(C(F)(F)F)c4)cc3)ncc2C1] | A | <1 µM (1) | >1 µM (1) | <1 µM (1) |
| 239 | 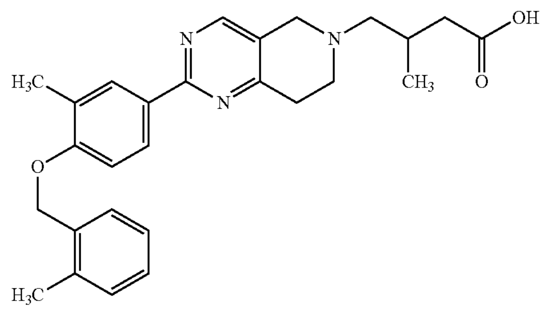 [SMILES: Cc1ccccc1COc1ccc(-c2ncc3c(n2)CCN(CC(C)CC(=O)O)C3)cc1C] | A | >1 µM (1) | >1 µM (1) | >1 µM (1) |
| 240 | 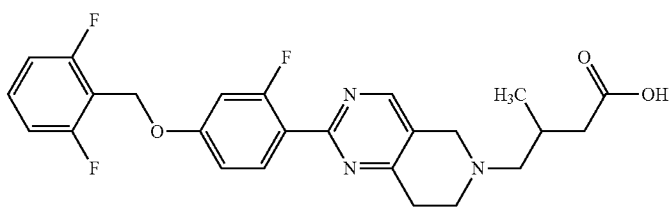 [SMILES: CC(CC(=O)O)CN1CCc2nc(-c3ccc(OCc4c(F)cccc4F)cc3F)ncc2C1] | A | >1 µM (1) | >1 µM (1) | >1 µM (1) |
| 241 | 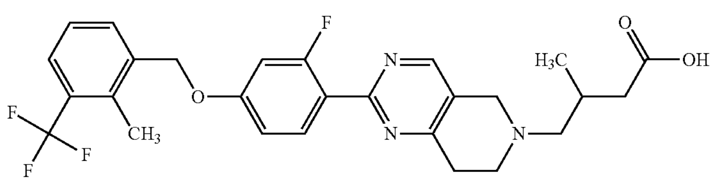 [SMILES: Cc1c(COc2ccc(-c3ncc4c(n3)CCN(CC(C)CC(=O)O)C4)c(F)c2)cccc1C(F)(F)F] | A | >1 µM (1) | >1 µM (1) | >1 µM (1) |
| 242 | 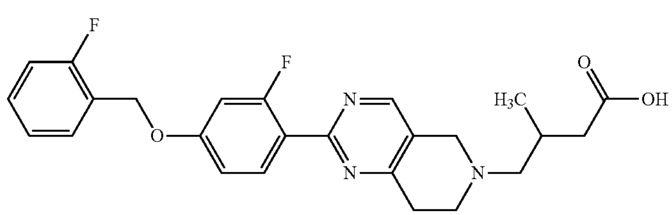 [SMILES: CC(CC(=O)O)CN1CCc2nc(-c3ccc(OCc4ccccc4F)cc3F)ncc2C1] | A | >1 µM (1) | >1 µM (1) | >1 µM (1) |
| 243 | 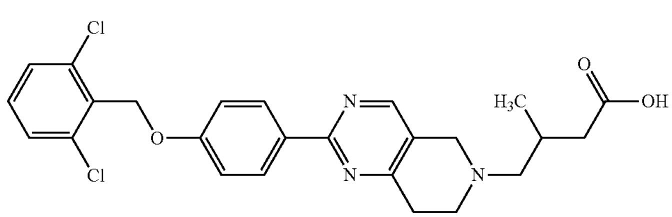 [SMILES: CC(CC(=O)O)CN1CCc2nc(-c3ccc(OCc4c(Cl)cccc4Cl)cc3)ncc2C1] | A | >1 µM (1) | >1 µM (1) | >1 µM (1) |

TABLE 1-continued

| No | Structure | S1P5 EC50 range # | S1P1 EC50* | S1P3 EC50* | S1P4 EC50* |
|---|---|---|---|---|---|
| 244 | 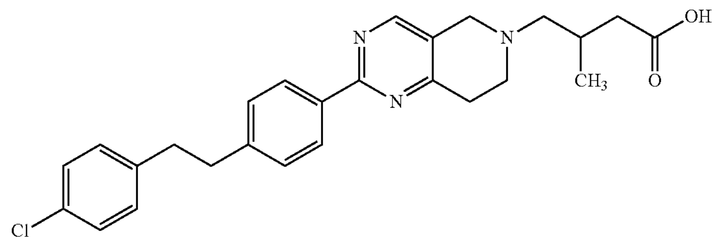 [SMILES: CC(CC(=O)O)CN1CCc2nc(-c3ccc(CCc4ccc(Cl)cc4)cc3)ncc2C1] | A | >1 μM (1) | >1 μM (1) | >1 μM (1) |
| 246 | 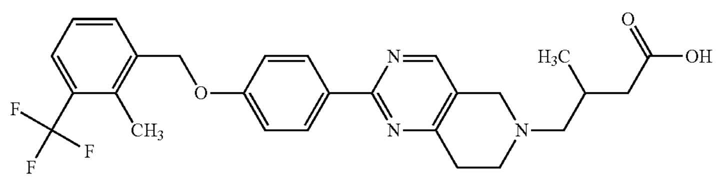 [SMILES: Cc1c(COc2ccc(-c3ncc4c(n3)CCN(CC(C)CC(=O)O)C4)cc2)cccc1C(F)(F)F] | A | >1 μM (1) | >1 μM (1) | >1 μM (1) |
| 247 | 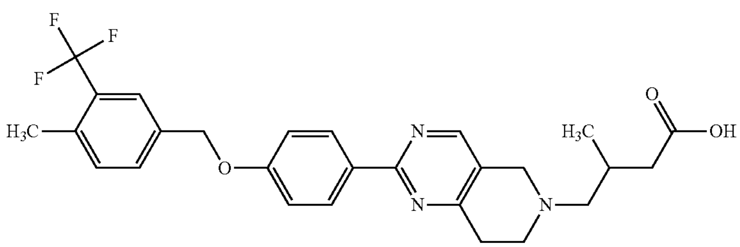 | A | >1 μM (1) | >1 μM (1) | >1 μM (1) |
| 248 | 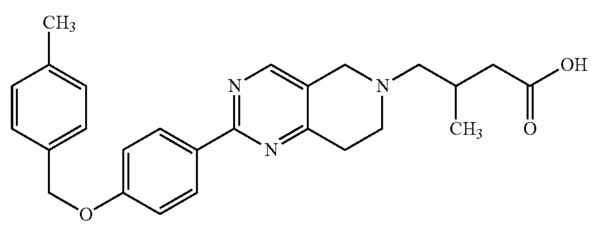 [SMILES: Cc1ccc(COc2ccc(-c3ncc4c(n3)CCN(CC(C)CC(=O)O)C4)cc2)cc1] | A | <1 μM (1) | >1 μM (1) | >1 μM (1) |
| 249 | enantiomer of compound 239 | A | >1 μM (1) | >1 μM (1) | >1 μM (1) |
| 250 | 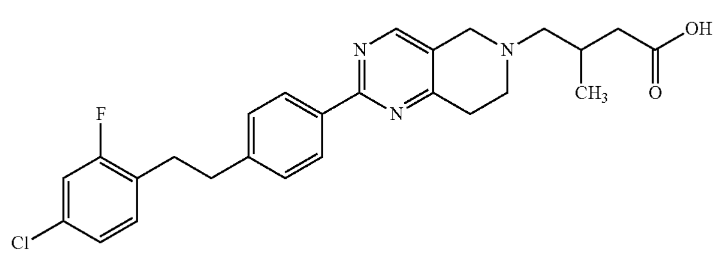 [SMILES: CC(CC(=O)O)CN1CCc2nc(-c3ccc(CCc4ccc(Cl)cc4F)cc3)ncc2C1] | A | >1 μM (1) | >1 μM (1) | >1 μM (1) |

TABLE 1-continued

| No | Structure | S1P5 EC50 range # | S1P1 EC50* | S1P3 EC50* | S1P4 EC50* |
|---|---|---|---|---|---|
| 251 | 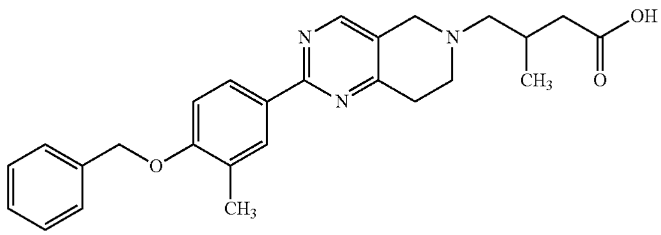 [SMILES: Cc1cc(-c2ncc3c(n2)CCN(CC(C)CC(=O)O)C3)ccc1OCc1ccccc1] | A | >1 μM (1) | >1 μM (1) | >1 μM (1) |
| 252 | 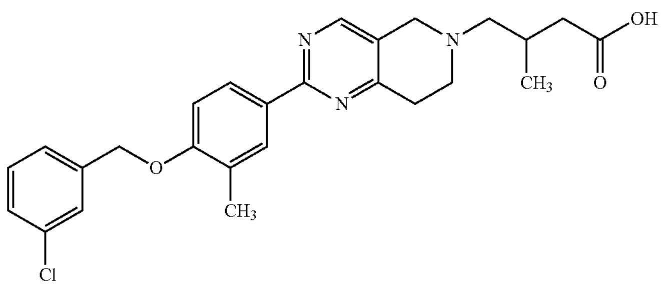 [SMILES: Cc1cc(-c2ncc3c(n2)CCN(CC(C)CC(=O)O)C3)ccc1OCc1cccc(Cl)c1] | A | >1 μM (1) | >1 μM (1) | >1 μM (1) |
| 253 | 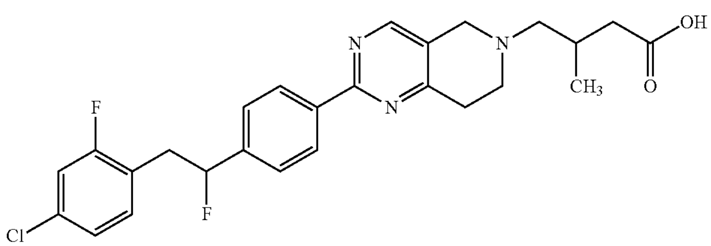 [SMILES: CC(CC(=O)O)CN1CCc2nc(-c3ccc(C(F)Cc4ccc(Cl)cc4F)cc3)ncc2C1] | A | >1 μM (1) | >1 μM (1) | >1 μM (1) |
| 254 | 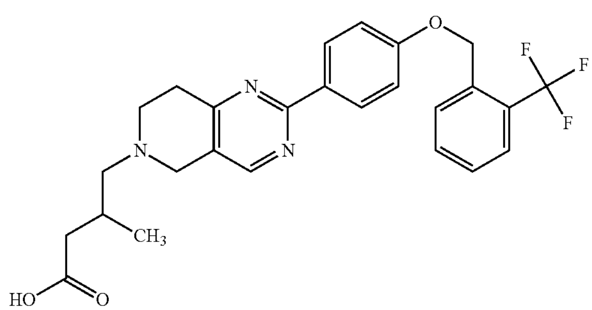 [SMILES: CC(CC(=O)O)CN1CCc2nc(-c3ccc(OCc4ccccc4C(F)(F)F)cc3)ncc2C1] | A | >1 μM (1) | >1 μM (1) | >1 μM (1) |
| 255 | 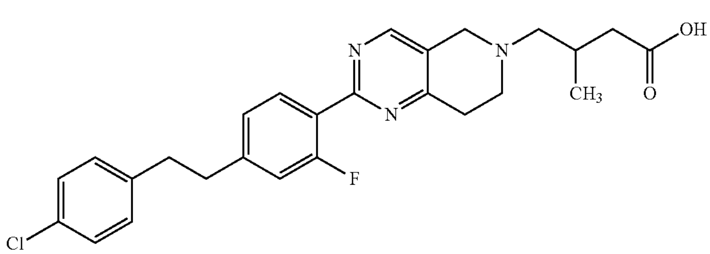 [SMILES: CC(CC(=O)O)CN1CCc2nc(-c3ccc(CCc4ccc(Cl)cc4)cc3F)ncc2C1] | A | >1 μM (1) | | >1 μM (1) |

TABLE 1-continued
| No | Structure | S1P5 EC50 range # | S1P1 EC50* | S1P3 EC50* | S1P4 EC50* |
|----|-----------|-------------------|-----------|-----------|-----------|
| 256 | 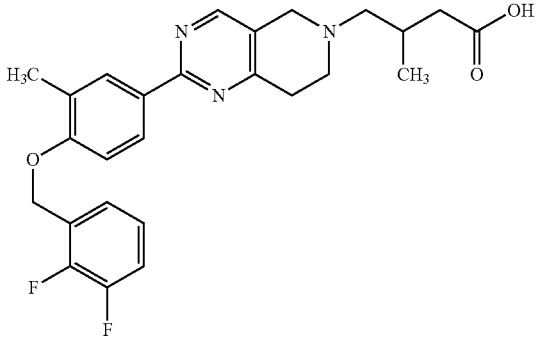 [SMILES: Cc1cc(-c2ncc3c(n2)CCN(CC(C)CC(=O)O)C3)ccc1OCc1cccc(F)c1F] | A | >1 μM (1) | | >1 μM (1) |
| 257 | 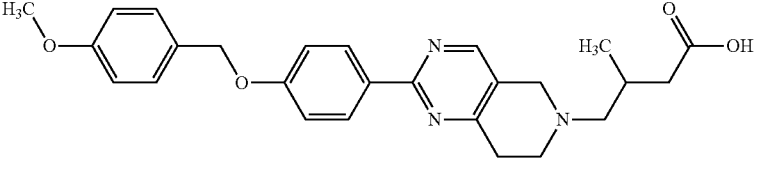 [SMILES: COc1ccc(COc2ccc(-c3ncc4c(n3)CCN(CC(C)CC(=O)O)C4)cc2)cc1] | B | >1 μM (1) | >1 μM (1) | >1 μM (1) |
| 258 | 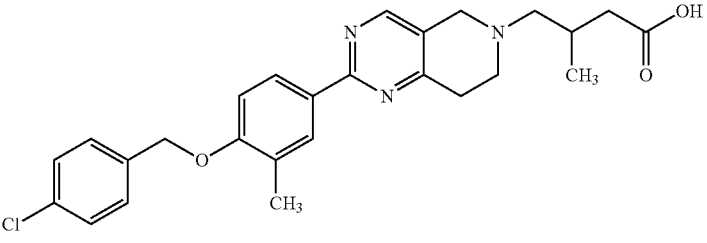 [SMILES: Cc1cc(-c2ncc3c(n2)CCN(CC(C)CC(=O)O)C3)ccc1OCc1ccc(Cl)cc1] | B | >1 μM (1) | >1 μM (1) | >1 μM (1) |
| 259 | 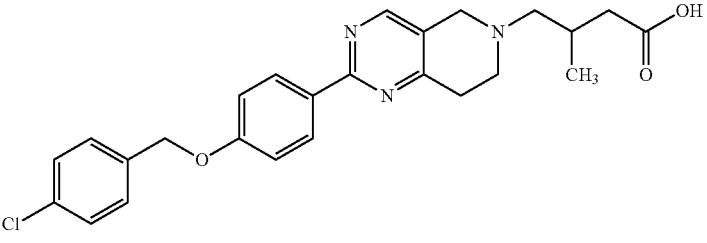 [SMILES: CC(CC(=O)O)CN1CCc2nc(-c3ccc(OCc4ccc(Cl)cc4)cc3)ncc2C1] | B | >1 μM (1) | >1 μM (1) | >1 μM (1) |
| 260 | 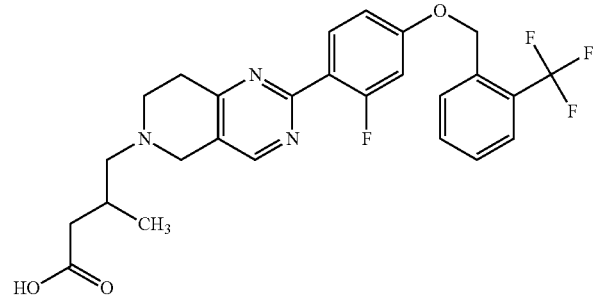 [SMILES: CC(CC(=O)O)CN1CCc2nc(-c3ccc(OCc4ccccc4C(F)(F)F)cc3F)ncc2C1] | B | >1 μM (1) | >1 μM (1) | >1 μM (1) |

TABLE 1-continued

| No | Structure | S1P5 EC50 range # | S1P1 EC50* | S1P3 EC50* | S1P4 EC50* |
|---|---|---|---|---|---|
| 261 | Enantiomer of compound 251 | B | >1 μM (1) | | >1 μM (1) |
| 262 | 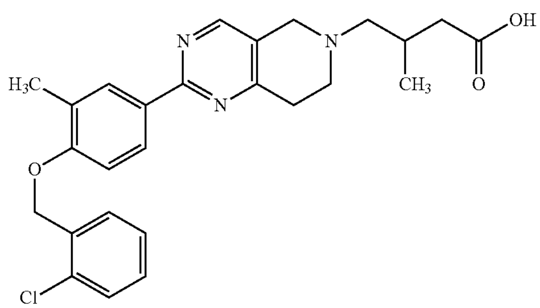 [SMILES: Cc1cc(-c2ncc3c(n2)CCN(CC(C)CC(=O)O)C3)ccc1OCc1ccccc1Cl] | B | >1 μM (1) | | >1 μM (1) |
| 263 | 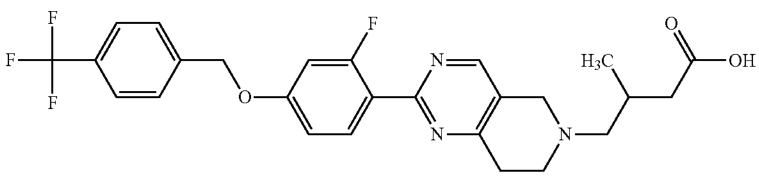 [SMILES: CC(CC(=O)O)CN1CCc2nc(-c3ccc(OCc4ccc(C(F)(F)F)cc4)cc3F)ncc2C1] | B | >1 μM (1) | >1 μM (1) | >1 μM (1) |
| 264 | 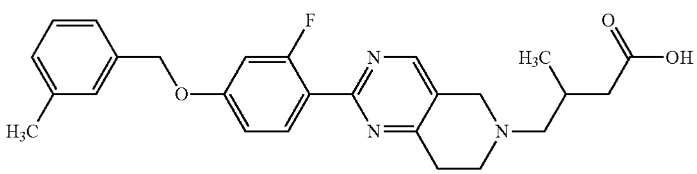 [SMILES: Cc1cccc(COc2ccc(-c3ncc4c(n3)CCN(CC(C)CC(=O)O)C4)c(F)c2)c1] | B | >1 μM (1) | | >1 μM (1) |
| 265 | 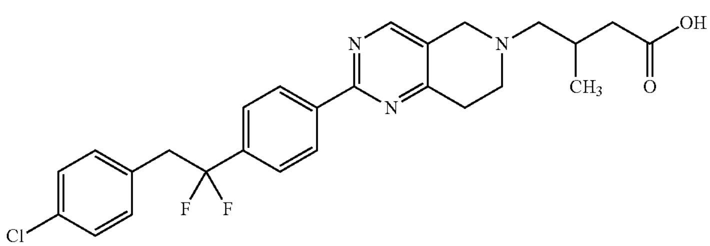 [SMILES: CC(CC(=O)O)CN1CCc2nc(-c3ccc(C(F)(F)Cc4ccc(Cl)cc4)cc3)ncc2C1] | B | >1 μM (1) | >1 μM (1) | >1 μM (1) |
| 266 | enantiomer of compound 265 | B | >1 μM (1) | >1 μM (1) | >1 μM (1) |

TABLE 1-continued

| No | Structure | S1P5 EC50 range # | S1P1 EC50* | S1P3 EC50* | S1P4 EC50* |
|---|---|---|---|---|---|
| 267 | 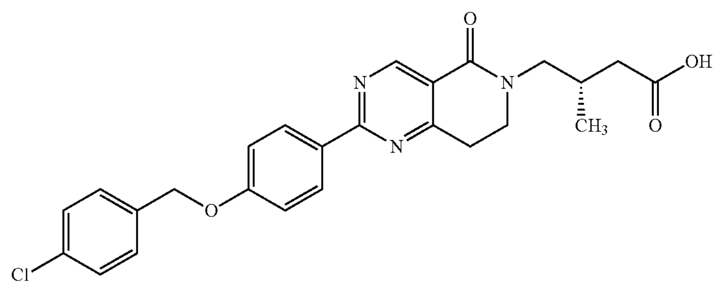 [SMILES: C[C@@H](CC(=O)O)CN1CCc2nc(-c3ccc(OCc4ccc(Cl)cc4)cc3)ncc2C1=O] | B | >1 μM (1) | >1 μM (1) | >1 μM (1) |
| 268 | 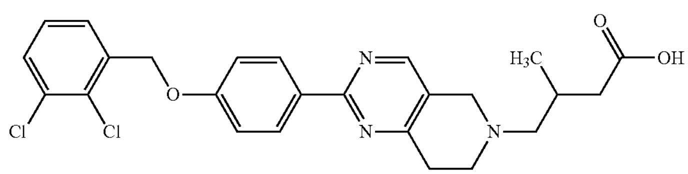 [SMILES: CC(CC(=O)O)CN1CCc2nc(-c3ccc(OCc4cccc(Cl)c4Cl)cc3)ncc2C1] | B | >1 μM (1) | >1 μM (1) | >1 μM (1) |
| 269 | 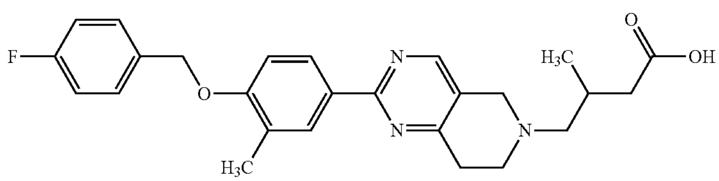 | B | >1 μM (1) | | >1 μM (1) |
| 270 | enantiomer of compound 258 | B | >1 μM (1) | | >1 μM (1) |
| 271 | 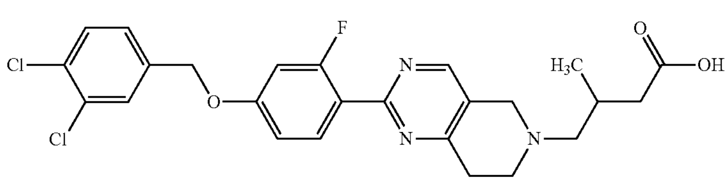 [SMILES: CC(CC(=O)O)CN1CCc2nc(-c3ccc(OCc4ccc(Cl)c(Cl)c4)cc3F)ncc2C1] | B | >1 μM (1) | >1 μM (1) | >1 μM (1) |
| 272 | 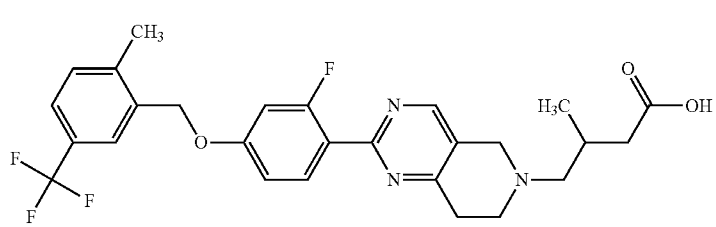 [SMILES: Cc1ccc(C(F)(F)F)cc1COc1ccc(-c2ncc3c(n2)CCN(CC(C)CC(=O)O)C3)c(F)c1] | B | >1 μM (1) | | >1 μM (1) |

TABLE 1-continued

| No | Structure | S1P5 EC50 range # | S1P1 EC50* | S1P3 EC50* | S1P4 EC50* |
|---|---|---|---|---|---|
| 273 | 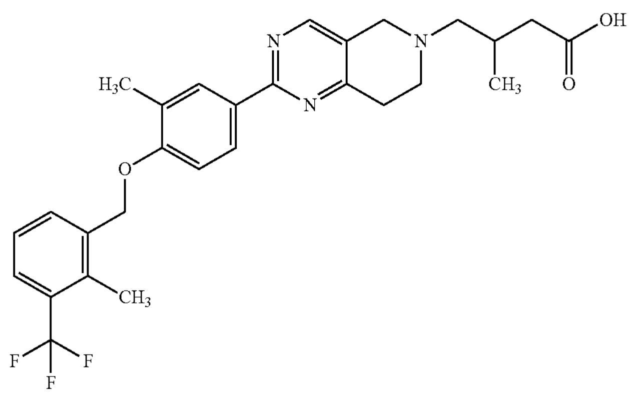 [SMILES: Cc1cc(-c2ncc3c(n2)CCN(CC(C)CC(=O)O)C3)ccc1OCc1cccc(C(F)(F)F)c1C] | B | >1 μM (1) | | >1 μM (1) |
| 274 | 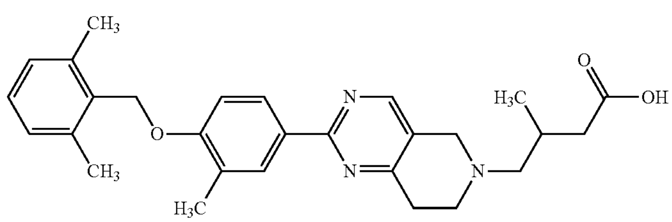 | B | >1 μM (1) | | >1 μM (1) |
| 275 | 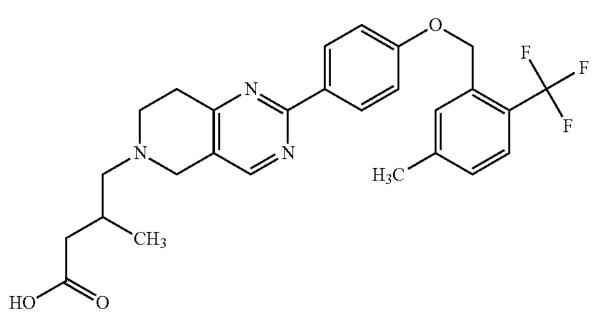 [SMILES: Cc1ccc(C(F)(F)F)c(COc2ccc(-c3ncc4c(n3)CCN(CC(C)CC(=O)O)C4)cc2)c1] | B | >1 μM (1) | >1 μM (1) | >1 μM (1) |
| 276 | 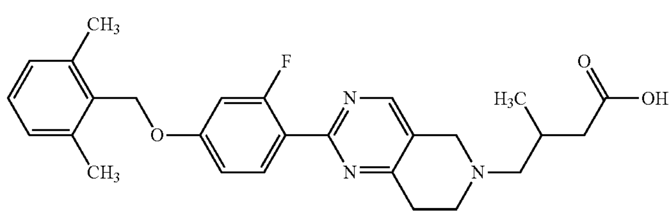 [SMILES: Cc1cccc(C)c1COc1ccc(-c2ncc3c(n2)CCN(CC(C)CC(=O)O)C3)c(F)c1] | B | >1 μM (1) | | >1 μM (1) |
| 277 | 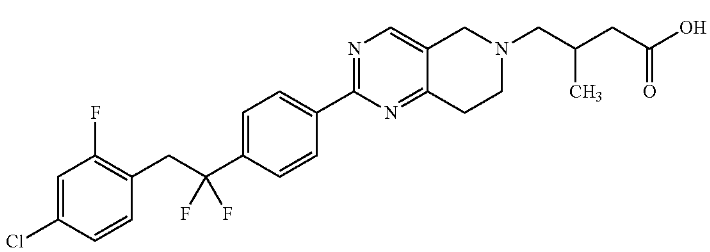 [SMILES: CC(CC(=O)O)CN1CCc2nc(-c3ccc(C(F)(F)Cc4ccc(Cl)cc4F)cc3)ncc2C1] | B | >1 μM (1) | >1 μM (1) | >1 μM (1) |

TABLE 1-continued

| No | Structure | S1P5 EC50 range # | S1P1 EC50* | S1P3 EC50* | S1P4 EC50* |
|---|---|---|---|---|---|
| 278 | enantiomer of compound 244 | B | >1 μM (1) | | >1 μM (1) |
| 279 | 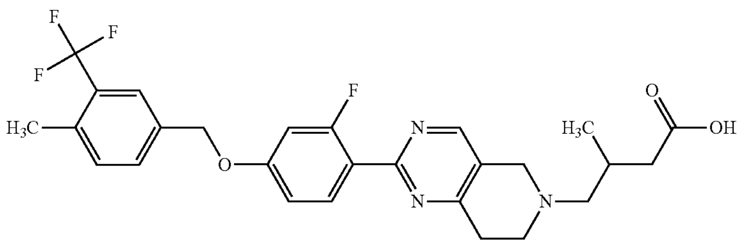 [SMILES: Cc1ccc(COc2ccc(-c3ncc4c(n3)CCN(CC(C)CC(=O)O)C4)c(F)c2)cc1C(F)(F)F] | B | >1 μM (1) | >1 μM (1) | >1 μM (1) |
| 280 | 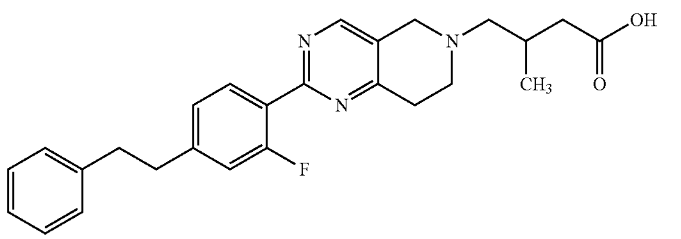 [SMILES: CC(CC(=O)O)CN1CCc2nc(-c3ccc(CCc4ccccc4)cc3F)ncc2C1] | B | >1 μM (1) | | >1 μM (1) |
| 281 | 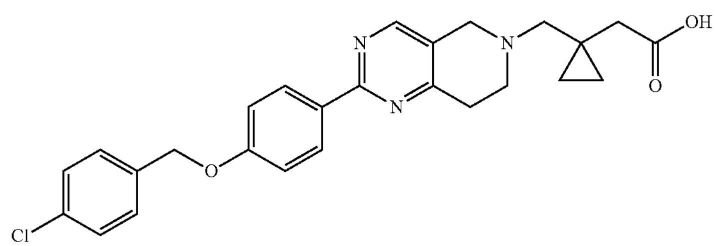 [SMILES: O=C(O)CC1(CN2CCc3nc(-c4ccc(OCc5ccc(Cl)cc5)cc4)ncc3C2)CC1] | B | >1 μM (1) | >1 μM (1) | >1 μM (1) |
| 282 | 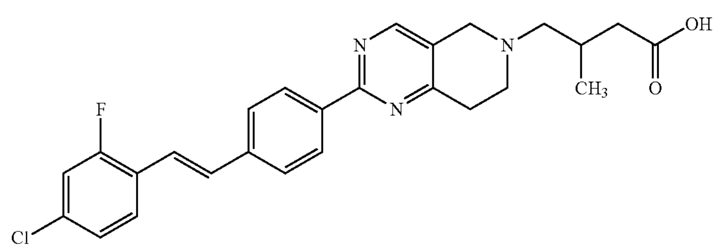 [SMILES: CC(CC(=O)O)CN1CCc2nc(-c3ccc(/C=C/c4ccc(Cl)cc4F)cc3)ncc2C1] | B | >1 μM (1) | | >1 μM (1) |
| 283 | 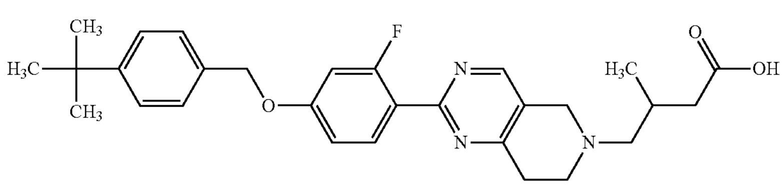 [SMILES: CC(CC(=O)O)CN1CCc2nc(-c3ccc(OCc4ccc(C(C)(C)C)cc4)cc3F)ncc2C1] | B | >1 μM (1) | >1 μM (1) | >1 μM (1) |

TABLE 1-continued

| No | Structure | S1P5 EC50 range # | S1P1 EC50* | S1P3 EC50* | S1P4 EC50* |
|---|---|---|---|---|---|
| 284 | 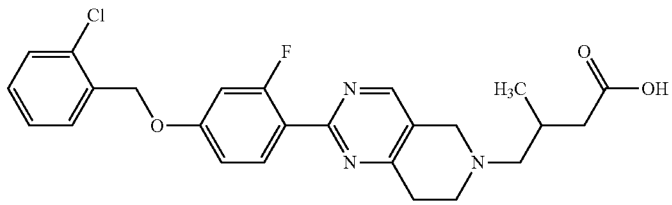 [SMILES: CC(CC(=O)O)CN1CCc2nc(-c3ccc(OCc4ccccc4Cl)cc3F)ncc2C1] | B | >1 μM (1) | >1 μM (1) | >1 μM (1) |
| 285 | 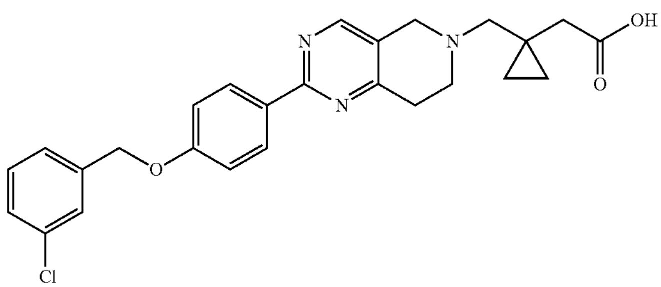 [SMILES: O=C(O)CC1(CN2CCc3nc(-c4ccc(OCc5cccc(Cl)c5)cc4)ncc3C2)CC1] | C | >1 μM (1) | >1 μM (1) | <1 μM (1) |
| 286 | 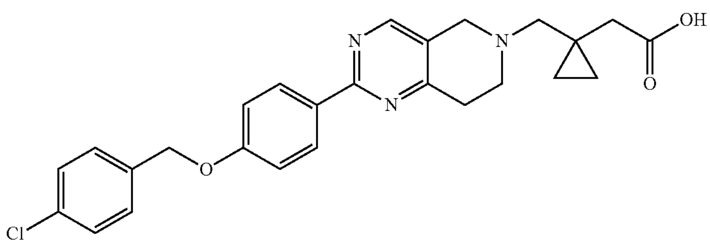 [SMILES: O=C(O)CC1(CN2CCc3nc(-c4ccc(OCc5ccc(Cl)cc5)cc4)ncc3C2)CC1] | C | >1 μM (1) | | >1 μM (1) |
| 287 | 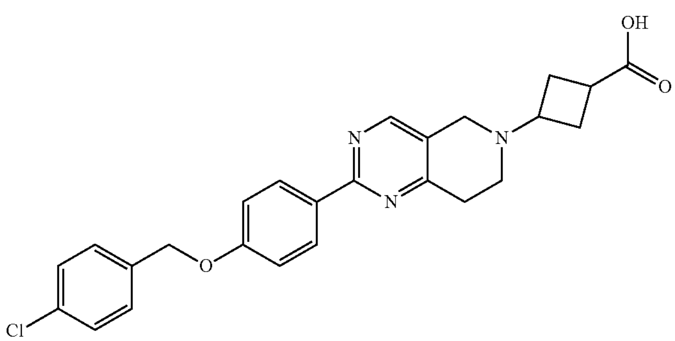 [SMILES: O=C(O)C1CC(N2CCc3nc(-c4ccc(OCc5ccc(Cl)cc5)cc4)ncc3C2)C1] | C | >1 μM (1) | | >1 μM (1) |
| 288 | 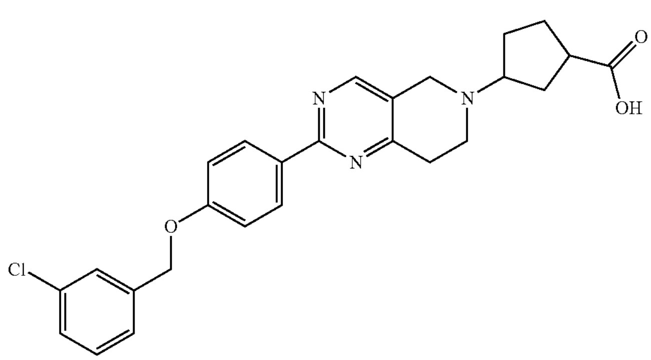 [SMILES: O=C(O)C1CCC(N2CCc3nc(-c4ccc(OCc5cccc(Cl)c5)cc4)ncc3C2)C1] | C | >1 μM (1) | | >1 μM (1) |

TABLE 1-continued

| No | Structure | S1P5 EC50 range # | S1P1 EC50* | S1P3 EC50* | S1P4 EC50* |
|---|---|---|---|---|---|
| 289 | 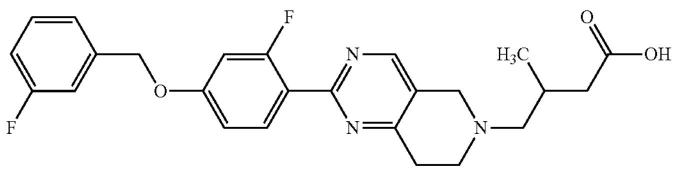 [SMILES: CC(CC(=O)O)CN1CCc2nc(-c3ccc(OCc4cccc(F)c4)cc3F)ncc2C1] | C | >1 µM (1) | | >1 µM (1) |
| 290 | 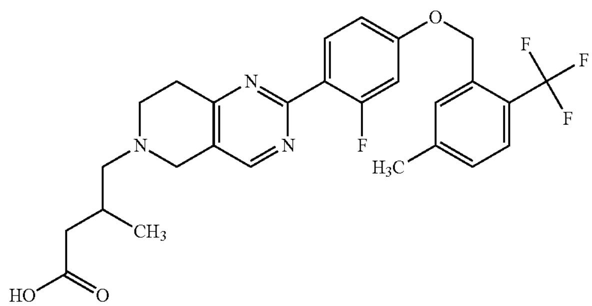 [SMILES: Cc1ccc(C(F)(F)F)c(COc2ccc(-c3ncc4c(n3)CCN(CC(C)CC(=O)O)C4)c(F)c2)c1] | C | >1 µM (1) | | >1 µM (1) |
| 291 | 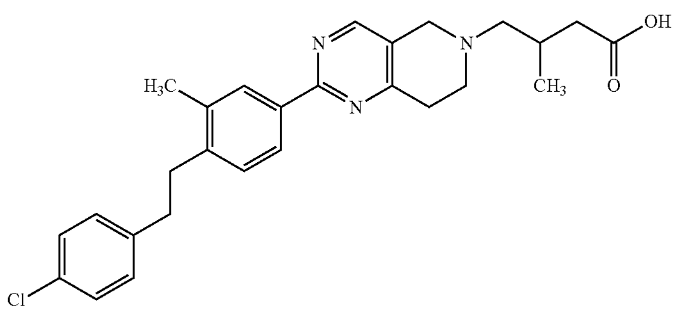 [SMILES: Cc1cc(-c2ncc3c(n2)CCN(CC(C)CC(=O)O)C3)ccc1CCc1ccc(Cl)cc1] | C | >1 µM (1) | | >1 µM (1) |
| 292 | 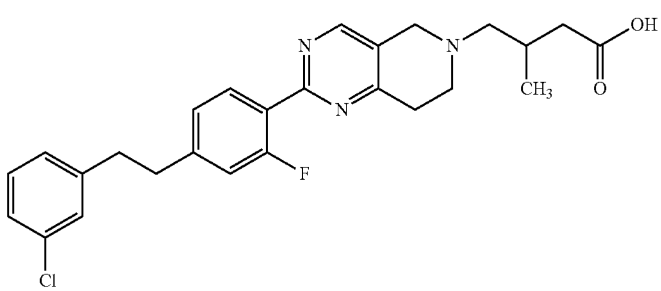 | C | >1 µM (1) | | >1 µM (1) |
| 293 | 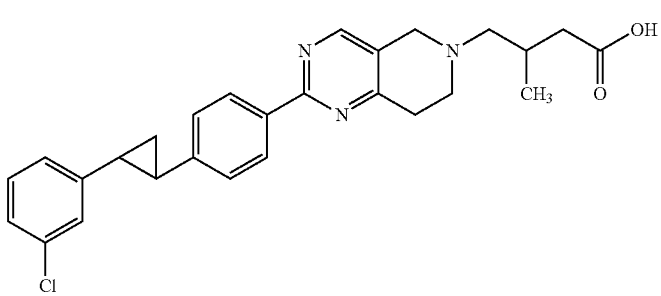 [SMILES: CC(CC(=O)O)CN1CCc2nc(-c3ccc(C4CC4c4cccc(Cl)c4)cc3)ncc2C1] | C | >1 µM (1) | | >1 µM (1) |

TABLE 1-continued
| No | Structure | S1P5 EC50 range # | S1P1 EC50* | S1P3 EC50* | S1P4 EC50* |
|---|---|---|---|---|---|
| 294 | 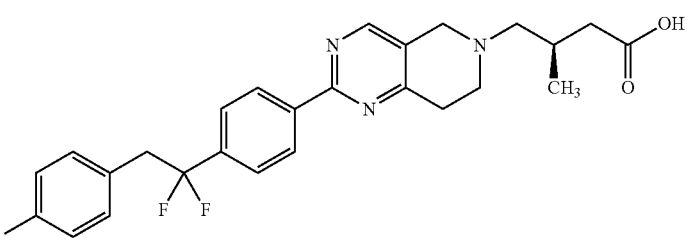 enantiomer of compound 265 | C | >1 μM (1) | | >1 μM (1) |
| 295 | 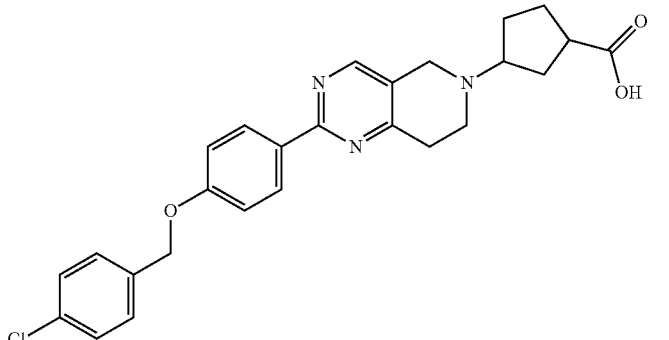 | C | >1 μM (1) | | >1 μM (1) |
| 296 | 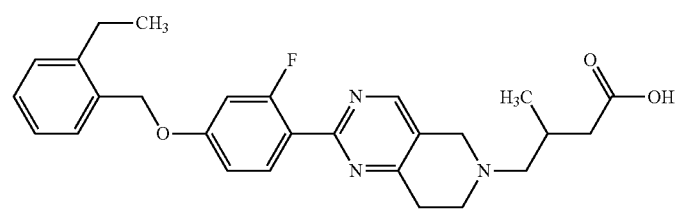 [SMILES: CCc1ccccc1COc1ccc(-c2ncc3c(n2)CCN(CC(C)CC(=O)O)C3)c(F)c1] | C | >1 μM (1) | | >1 μM (1) |
| 297 | 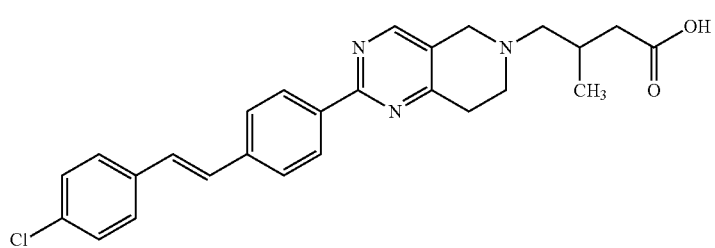 [SMILES: CC(CC(=O)O)CN1CCc2nc(-c3ccc(/C=C/c4ccc(Cl)cc4)cc3)ncc2C1] | C | >1 μM (1) | | >1 μM (1) |
| 298 | 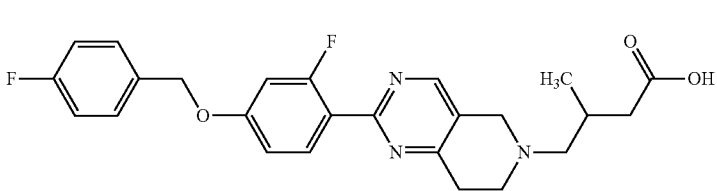 [SMILES: CC(CC(=O)O)CN1CCc2nc(-c3ccc(OCc4ccc(F)cc4)cc3F)ncc2C1] | C | >1 μM (1) | | >1 μM (1) |

TABLE 1-continued

| No | Structure | S1P5 EC50 range # | S1P1 EC50* | S1P3 EC50* | S1P4 EC50* |
|---|---|---|---|---|---|
| 299 | 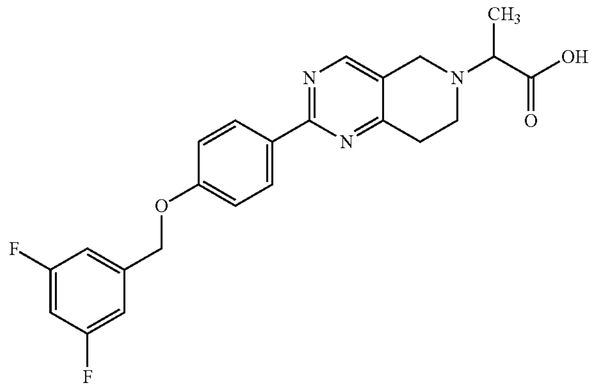 [SMILES: CC(C(=O)O)N1CCc2nc(-c3ccc(OCc4cc(F)cc(F)c4)cc3)ncc2C1] | C | >1 μM (1) | | >1 μM (1) |
| 300 | 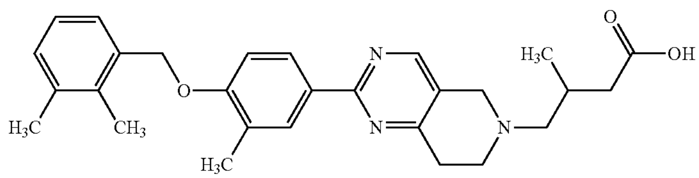 | C | >1 μM (1) | | >1 μM (1) |
| 301 | 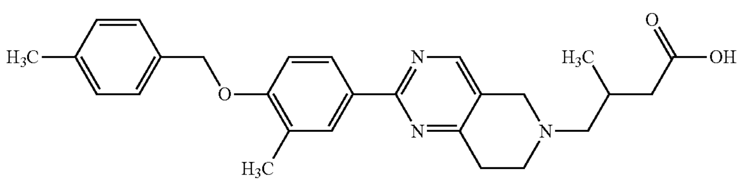 [SMILES: Cc1ccc(COc2ccc(-c3ncc4c(n3)CCN(CC(C)CC(=O)O)C4)cc2C)cc1] | C | >1 μM (1) | | >1 μM (1) |
| 302 | 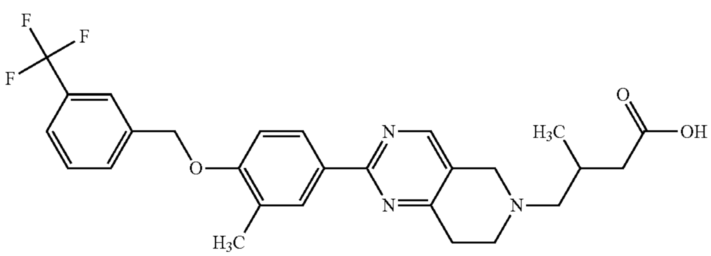 | C | >1 μM (1) | | >1 μM (1) |
| 303 | Enantiomer of compound 239 | C | >1 μM (1) | | <1 μM (1) |
| 304 | 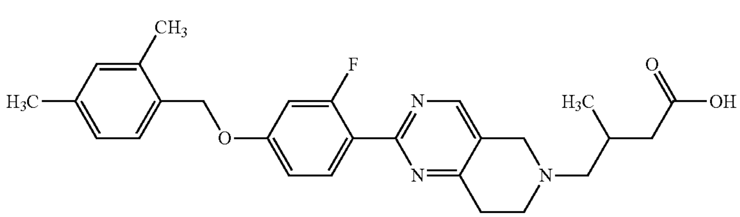 [SMILES: Cc1ccc(COc2ccc(-c3ncc4c(n3)CCN(CC(C)CC(=O)O)C4)c(F)c2)c(C)c1] | C | >1 μM (1) | | >1 μM (1) |

TABLE 1-continued

| No | Structure | S1P5 EC50 range # | S1P1 EC50* | S1P3 EC50* | S1P4 EC50* |
|---|---|---|---|---|---|
| 305 | 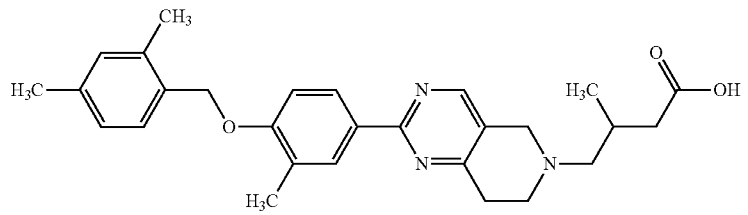 [SMILES: Cc1ccc(COc2ccc(-c3ncc4c(n3)CCN(CC(C)CC(=O)O)C4)cc2C)c(C)c1] | C | >1 μM (1) | | >1 μM (1) |
| 306 | 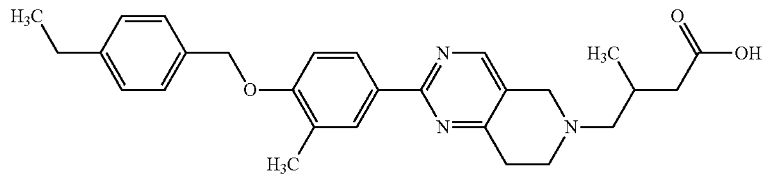 | C | >1 μM (1) | | >1 μM (1) |
| 307 | 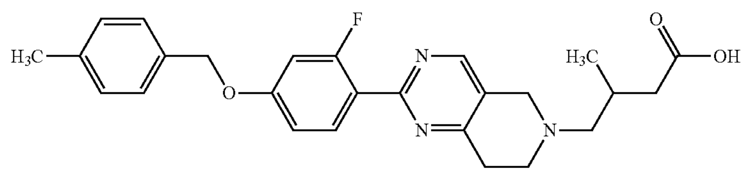 [SMILES: Cc1ccc(COc2ccc(-c3ncc4c(n3)CCN(CC(C)CC(=O)O)C4)c(F)c2)cc1] | C | >1 μM (1) | | >1 μM (1) |
| 308 | 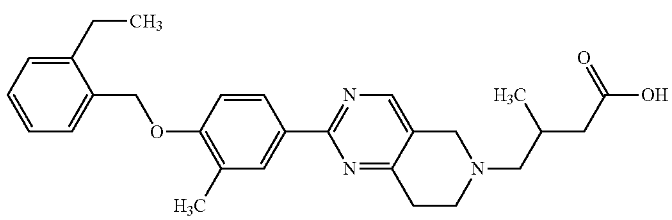 [SMILES: CCc1ccccc1COc1ccc(-c2ncc3c(n2)CCN(CC(C)CC(=O)O)C3)cc1C] | C | >1 μM (1) | | <1 μM (1) |
| 309 | 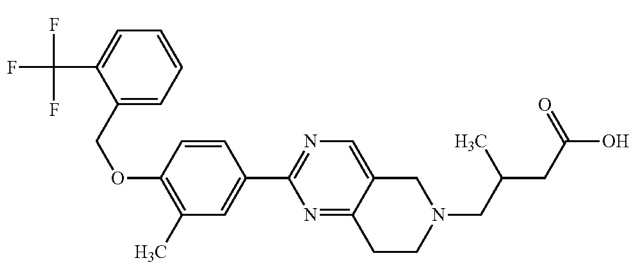 [SMILES: Cc1cc(-c2ncc3c(n2)CCN(CC(C)CC(=O)O)C3)ccc1OCc1ccccc1C(F)(F)F] | C | >1 μM (1) | | >1 μM (1) |
| 310 | 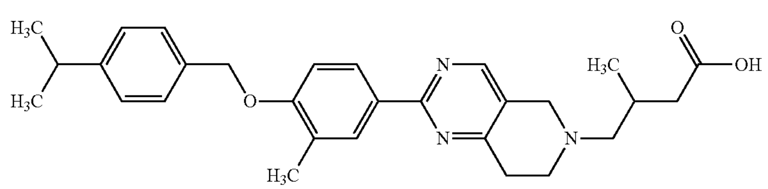 [SMILES: Cc1cc(-c2ncc3c(n2)CCN(CC(C)CC(=O)O)C3)ccc1OCc1ccc(C(C)C)cc1] | C | >1 μM (1) | | >1 μM (1) |
| 311 | 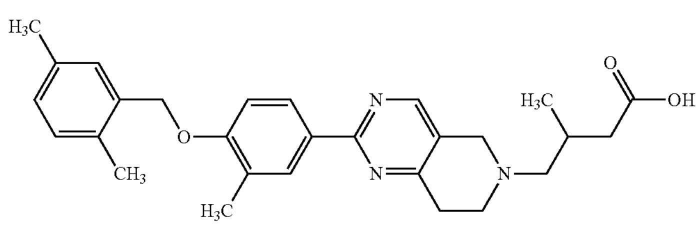 [SMILES: Cc1ccc(C)c(COc2ccc(-c3ncc4c(n3)CCN(CC(C)CC(=O)O)C4)cc2C)c1] | C | >1 μM (1) | | >1 μM (1) |

TABLE 1-continued

| No | Structure | S1P5 EC50 range # | S1P1 EC50* | S1P3 EC50* | S1P4 EC50* |
|----|-----------|-------------------|------------|------------|------------|
| 312 | 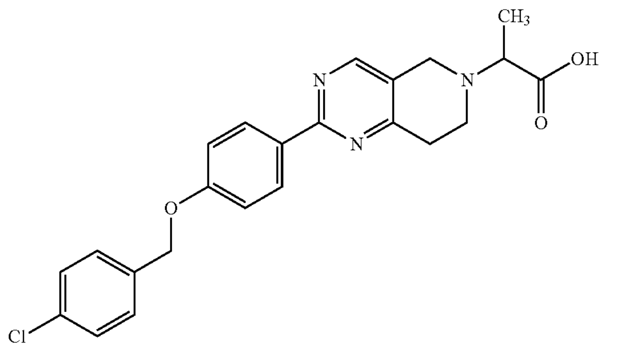 [SMILES: CC(C(=O)O)N1CCc2nc(-c3ccc(OCc4ccc(Cl)cc4)cc3)ncc2C1] | C | >1 μM (1) | | >1 μM (1) |
| 313 | 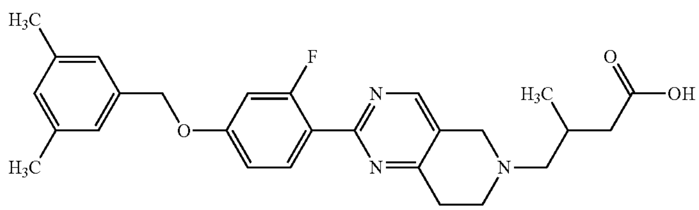 [SMILES: Cc1cc(C)cc(COc2ccc(-c3ncc4c(n3)CCN(CC(C)CC(=O)O)C4)c(F)c2)c1] | C | >1 μM (1) | | >1 μM (1) |
| 314 | 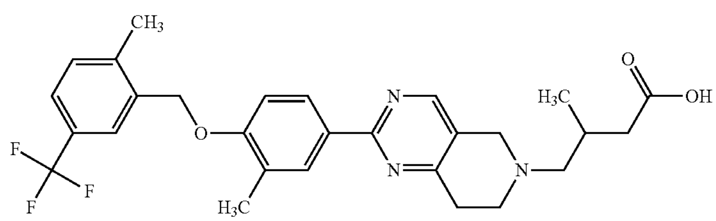 [SMILES: Cc1ccc(C(F)(F)F)cc1COc1ccc(-c2ncc3c(n2)CCN(CC(C)CC(=O)O)C3)cc1C] | C | >1 μM (1) | | >1 μM (1) |
| 315 | 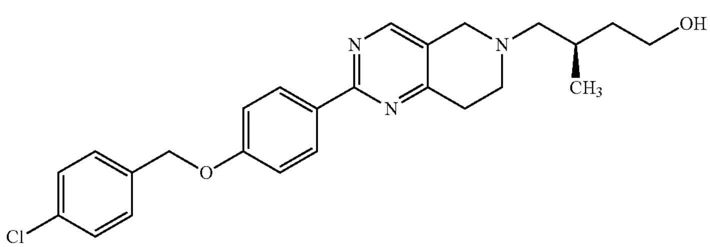 [SMILES: C[C@H](CCO)CN1CCc2nc(-c3ccc(OCc4ccc(Cl)cc4)cc3)ncc2C1] | C | >1 μM (1) | | >1 μM (1) |
| 316 | 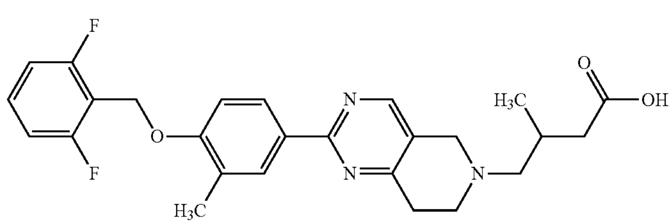 [SMILES: Cc1cc(-c2ncc3c(n2)CCN(CC(C)CC(=O)O)C3)ccc1OCc1c(F)cccc1F] | C | >1 μM (1) | | <1 μM (1) |

TABLE 1-continued

| No | Structure | S1P5 EC50 range # | S1P1 EC50* | S1P3 EC50* | S1P4 EC50* |
|---|---|---|---|---|---|
| 317 | 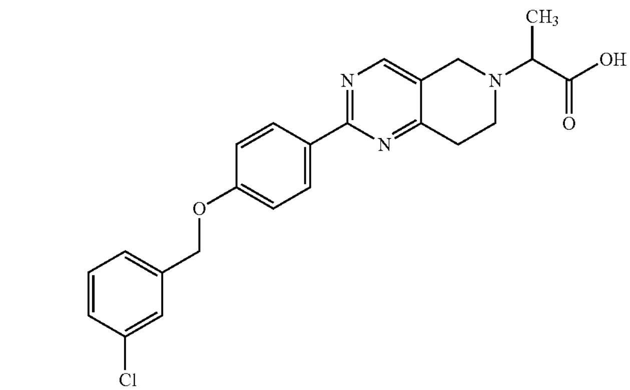 [SMILES: CC(C(=O)O)N1CCc2nc(-c3ccc(OCc4cccc(Cl)c4)cc3)ncc2C1] | C | >1 μM (1) | | >1 μM (1) |
| 318 | enantiomer of compound 258 | C | >1 μM (1) | | >1 μM (1) |
| 319 | enantiomer of compound 251 | C | >1 μM (1) | | >1 μM (1) |
| 320 | 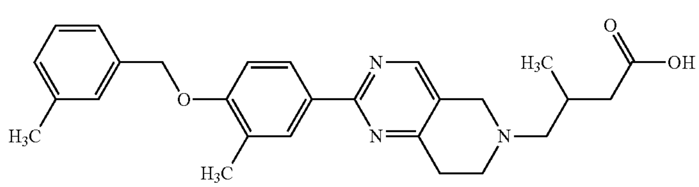 [SMILES: Cc1cccc(COc2ccc(-c3ncc4c(n3)CCN(CC(C)CC(=O)O)C4)cc2C)c1] | D | >1 μM (1) | | >1 μM (1) |
| 322 | 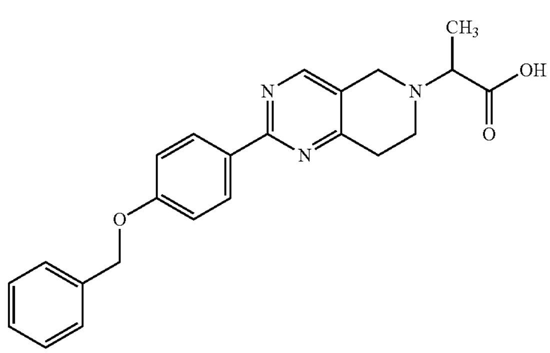 [SMILES: CC(C(=O)O)N1CCc2nc(-c3ccc(OCc4ccccc4)cc3)ncc2C1] | D | >1 μM (1) | | >1 μM (1) |

TABLE 1-continued
| No | Structure | S1P5 EC50 range # | S1P1 EC50* | S1P3 EC50* | S1P4 EC50* |
|---|---|---|---|---|---|
| 323 | 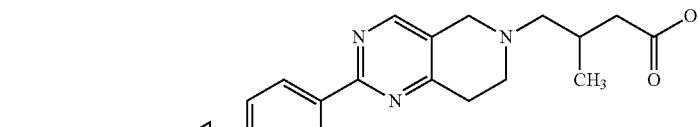 | D | >1 μM (1) | | >1 μM (1) |
| 325 | 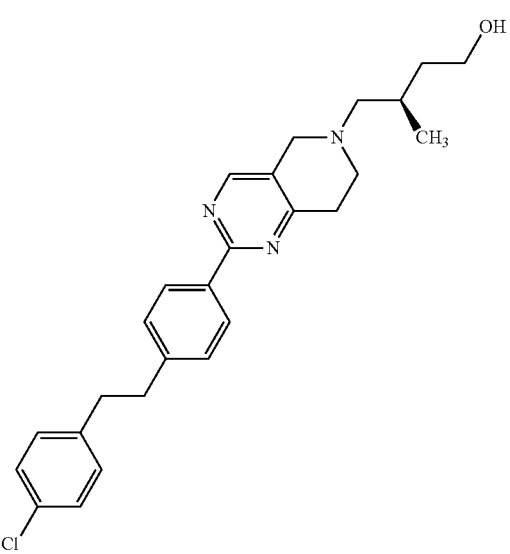 [SMILES: C[C@H](CCO)CN1CCc2nc(-c3ccc(CCc4ccc(Cl)cc4)cc3)ncc2C1] | | | | |
| 326 | 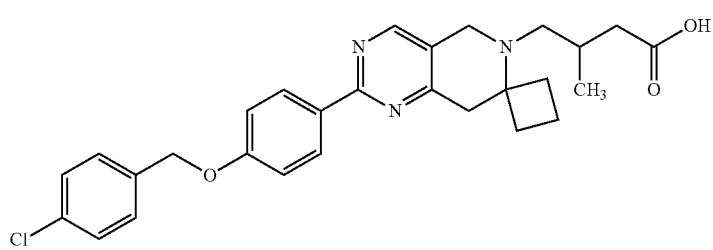 [SMILES: CC(CC(=O)O)CN1Cc2cnc(-c3ccc(OCc4ccc(Cl)cc4)cc3)nc2CC12CCC2] | | >1 μM (1) | | >1 μM (1) |
| 327 | 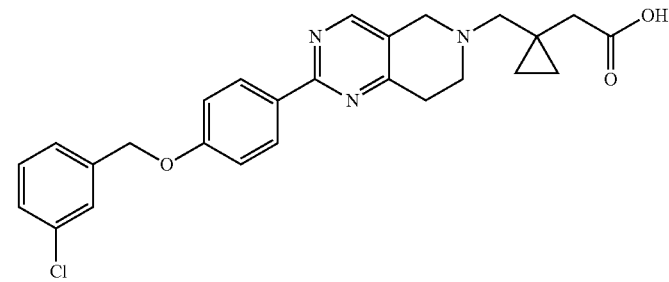 [SMILES: O=C(O)CC1(CN2CCc3nc(-c4ccc(OCc5cccc(Cl)c5)cc4)ncc3C2)CC1] | D | >1 μM (1) | | <1 μM (1) |

TABLE 1-continued

| No | Structure | S1P5 EC50 range # | S1P1 EC50* | S1P3 EC50* | S1P4 EC50* |
|---|---|---|---|---|---|
| 328 | 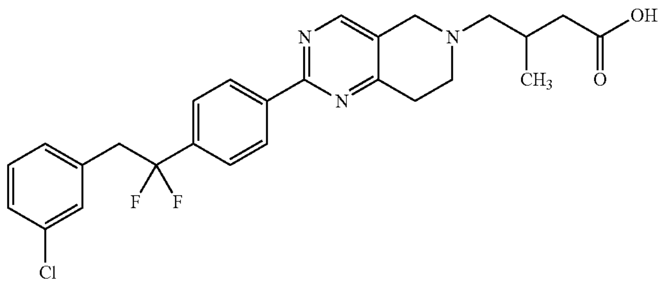 [SMILES: CC(CC(=O)O)CN1CCc2nc(-c3ccc(C(F)(F)Cc4cccc(Cl)c4)cc3)ncc2C1] | D | >1 µM (1) | | >1 µM (1) |
| 329 | 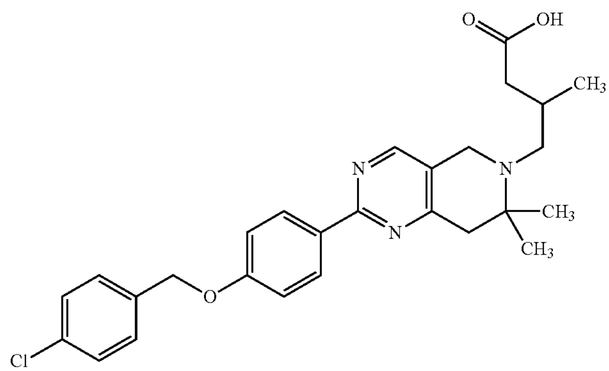 [SMILES: CC(CC(=O)O)CN1Cc2cnc(-c3ccc(OCc4ccc(Cl)cc4)cc3)nc2CC1(C)C] | D | >1 µM (1) | | >1 µM (1) |
| 331 | 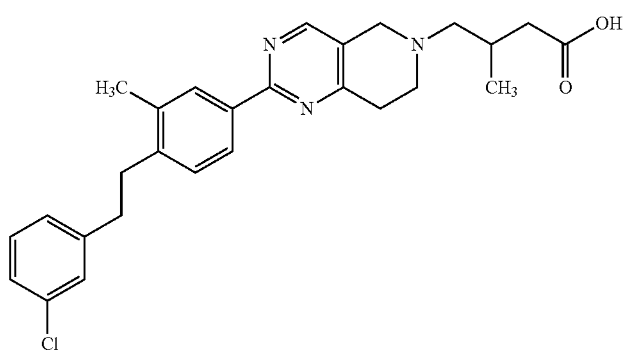 [SMILES: Cc1cc(-c2ncc3c(n2)CCN(CC(C)CC(=O)O)C3)ccc1CCc1cccc(Cl)c1] | D | >1 µM (1) | | <1 µM (1) |
| 332 | 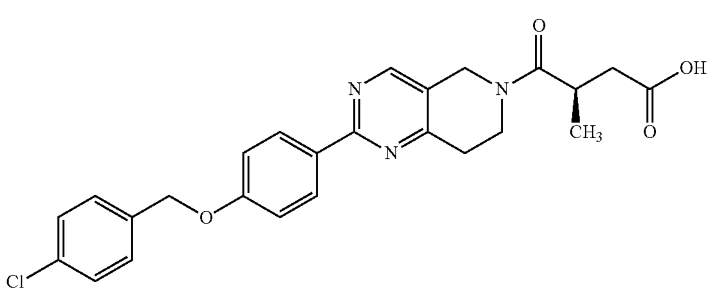 [SMILES: C[C@H](CC(=O)O)C(=O)N1CCc2nc(-c3ccc(OCc4ccc(Cl)cc4)cc3)ncc2C1] | D | >1 µM (1) | | >1 µM (1) |
| 333 | 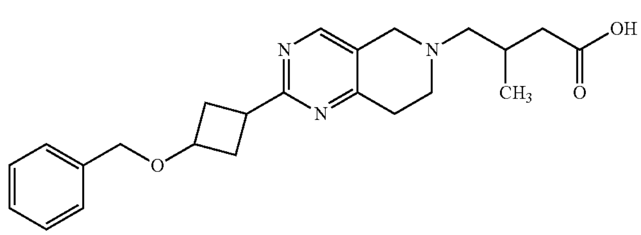 [SMILES: CC(CC(=O)O)CN1CCc2nc(C3CC(OCc4ccccc4)C3)ncc2C1] | D | >1 µM (1) | | >1 µM (1) |

TABLE 1-continued

| No | Structure | S1P5 EC50 range # | S1P1 EC50* | S1P3 EC50* | S1P4 EC50* |
|---|---|---|---|---|---|
| 335 | (structure) | C | >1 μM (1) |  | >1 μM (1) |
| 336 | (structure) | A | >1 μM (1) |  | <1 μM (1) |

\#
A: EC50 < 10 nM, determined with method 1
B: EC50 = 10 nM-100 nM, determined with method 1
C: EC50 = 100 nM-1 μM, determined with method 1
D: EC50 = 1 μM-10 μM, determined with method 1
E: EC50 < 100 nM, determined with method 2
F: EC50 = 100 nM-1 μM, determined with method 2
G: EC50 = 1 μM-10 μM, determined with method 2
*(1): determined with method 1; (2): determined with method 2.

5. Assessment of Agonist Potency

Agonistic activity was measured using two different methods, described below. The results are shown in table 1.

Method 1. Intracellular $Ca^{2+}$ Release

Agonist potency and intrinsic activity was assessed by measurement of intracellular $Ca^{2+}$ release. Recombinant CHO-K1 cells (Euroscreen, Brussels, Belgium) expressing human S1PR5, S1PR1, S1PR3 or S1PR4 receptors, aequorin, and GTP binding protein Gq/i5 were cultured using a medium containing nutrient mixture F-12 Ham (Sigma-Aldrich) with 10% FBS, and 100 μg/mL gentamicin and equilibrated at 5% $CO_2$.

15.000 cells in 20 μL medium were seeded into Biocoat poly-D-Lysine coated 384 well plates (Becton Dickinson #35-6663) and grown to 95% confluency after 24 h.

Culture medium was replaced by an assay buffer consisting of HBBS with $Ca^{2+}$ and $Mg^{2+}$ (Invitrogen #14025-050), 20 mmol/L Hepes (Sigma-Aldrich #H-3375), 2.5 mmol/L probenecid (Sigma-Aldrich #P-8761, and 0.1% BSA (Sigma-Aldrich #A-7030) pH 7.4. The Calcium 5 no-wash FLIPR assay kit (Molecular Devices #5000625) was performed as described in the kit instructions. Cells were incubated with Calcium 5 dye for 1 h at 37° C., 5% $CO_2$ in the dark. After 45 min adaptation to RT assessment of agonist stimulation of intracellular $Ca^{2+}$ release was performed by addition of test compounds at concentrations obtained by serial dilution. Phospho-fingolimod was used as positive control. Antagonists were pre-incubated for 10 min with cells before addition of the agonist (phospho-fingolimod at EC80). Measurements were performed using a fluorometric imaging plate reader FLIPR® tetra (Molecular Devices). Agonist at the human S1P receptors were characterized by deducing EC50 (potency) values from a nonlinear fit to the measured fluorescence raw data after normalization to the reference agonist (phospho-fingolimod) curve.

Method 2. Aequorin Assay

Genetically Engineered Cells

Cell clone CHO-A21-Edg1 #17 carries the transgenes human EDG1 (S1PR1) receptor (Accession number NP_001391.2), mitochondrially targeted Aequorin (active part corresponds to accession number 1SL8_A) and chimaeric $G_{aqi5}=G_{aq}$ modified with the 5 C-terminal amino-acids replaced with those of the $G_{ai}$ protein (DCGLF). CHO-A2-S1P3 Mix is a cell pool ectopically expressing human EDG3 (S1PR3) receptor (Accession number NP_005217.2) mitochondrially targeted Aequorin (active part has a sequence similar to accession number AY601106.1) and GNA16 (Accession number NP_002059.3). Cell clone CHO-A21-EDG8 #12 carries the transgenes human EDG8 (S1PR5) receptor (Accession number NP_110387.1), mitochondrially expressed Aequorin (active part corresponds to accession number 1SL8_A) and chimaeric $G_{aqi5}$ ($G_{aq}$ modified to present the 5 last amino-acids of the $G_{ai}$ protein "DCGLF"; see above). Cells are grown to mid-log phase in culture medium (HAM's F12, 10% FBS, 100 IU/mL penicillin, 100 μg/mL streptomycin, 250 μg/mL Zeocin, 400 μg/mL G418). 18 hours prior to frozen cells preparation, the medium is changed to remove the antibiotics.

Aequorin Assay 18 hours prior to the test, vials of frozen cells are quickly thawed in a 37° C. water bath, cells are recovered by centrifugation and resuspended in assay buffer (DMEM/HAM's F12 with HEPES, without phenol red+0.1% fatty acid-free BSA). Cells are gently agitated in suspension overnight at RT in presence of 5 μM of Coelenterazine h (Molecular Probes). On the day of the test, cells are diluted to their final working concentrations in assay buffer and agitated in suspension for 1 h at RT. Cells are then placed in the luminescence reader (Hamamatsu Functional Drug Screening System 6000, FDSS6000). During cells incubation, compounds are prepared in 100% DMSO, and subsequently diluted in assay buffer. Compounds are then dispensed in the assay plate (black, clear-bottom, 384-well plate). After binding of agonists to the human S1P receptor the intracellular calcium concentration increases and binding of calcium to the Aequorin/Coelenterazine complex leads to an oxidation reaction of coelenterazine, which results in the production of Aequorin, coelenteramide, $CO_2$ and light (Dmax 469 nm). The luminescent response is dependent on the agonist concentration. For agonist testing, 30 μL of cell suspension are injected on 30 μL of test compound or reference agonist in the assay plate. The resulting emission of light is recorded for 90 seconds using the FDSS6000. Dose response curves with the reference compounds are performed before testing the compounds. S1P is the reference agonist and JTE-013 the reference antagonist for S1P2.

Following an incubation of 3 min after the first injection, 30 μL of the reference agonist for a final concentration corresponding to its EC80 is injected on the 60 μL of cell suspension and test compound mixture, for antagonist testing. The resulting emission of light is recorded for 90 seconds using the FDSS6000.

Luminescence data are integrated over the reading interval for agonist and antagonist modes. To standardize the emission of recorded light (determination of the "100% signal") across plates and across different experiments, some of the wells contain 100 μM digitonin or a saturating concentration of ATP (20 μM). Plates also contain the reference agonist at a concentration equivalent to the EC80 obtained during the test validation and the $EC_{100}$. Dose-response data from test compounds were analyzed with XLfit (IDBS) software using nonlinear regression applied to a sigmoidal dose-response model and the following equation:

XL Fit fit Model 203: 4 Parameter Logistic Model
A: Bottom
B: TOP
C: LogEC50
D: Hill $$fit=(A+((B-A)/(1+(((10\hat{\ }C)/x)\hat{\ }D))))$$

$$inv=((10\hat{\ }C)/((((B-A)/(y-A))-1)\hat{\ }(1/D)))$$

$$res=(y-fit)$$

The invention claimed is:
1. A compound of formula (I):

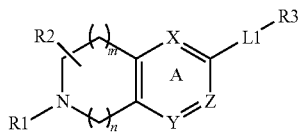

or a pharmaceutically acceptable salt thereof, wherein
X, Y and Z are independently selected from the group consisting of N and CR5, with the proviso that one or two of X, Y and Z are N and at least one of X, Y and Z is CR5, and wherein each R5 is independently selected from the group consisting of hydrogen, a halogen atom, (C1-4)alkyl and (C1-4)alkyl substituted with one or more fluoro atoms;
m is 1 and n is 1;
R1 is selected from the group consisting of
—(C1-6)alkylene-R6 wherein one or more carbon atoms in the alkylene group, each independently, are optionally substituted with one or more halogen atoms or with $(CH_2)_2$ to form a cyclopropyl moiety or with $(CH_2)_3$ to form a cyclobutyl moiety,
—(C3-6)cycloalkylene-R6 in which one carbon atom in the (C3-6)cycloalkylene can optionally be replaced by oxygen,
—(C1-3)alkylene-(C3-6)cycloalkylene-R6,
—(C3-6)cycloalkylene-(C1-3)alkylene-R6 and
—C(O)—(C1-4)alkylene-R6,
wherein R6 is selected from the group consisting of —OH, —$OPO_3H_2$, —COOH, —COO(C1-4)alkyl and tetrazol-5-yl;
R2 is absent, one or more substituents independently selected from the group consisting of a halogen atom, oxo, (C1-4)alkyl optionally substituted with one or more halogen atoms and (C1-4)alkoxy optionally substituted with one or more halogen atoms;
L1 is absent or wherein

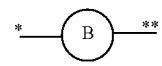

* indicates the bond to ring A and ** indicates the bond to R3; and
Ring B is selected from the group consisting of (C3-7)cycloalkyl, (C4-7)cycloalkenyl, phenyl, pyridyl, thienyl and thiazolyl, each optionally substituted with one or more substituents independently selected from the group consisting of
hydroxy,
cyano,
a halogen atom,
(C1-4)alkyl optionally substituted with one or more halogen atoms,
(C3-6)cyloalkyl optionally substituted with one or more halogen atoms,
(C1-4)alkoxy optionally substituted with one or more halogen atoms, and
phenyl optionally substituted with one or more substituents independently selected from the group consisting of a halogen atom, (C1-4)alkyl optionally substituted with one or more halogen atoms, and (C1-4)alkoxy optionally substituted with one or more halogen atoms; and
R3 is L2-R4, wherein:
L2 is absent or a group —W—$(CH_2)_p$-T- wherein:
W is attached to L1 and selected from the group consisting of a bond, —O—, —CO—, —S—, —SO—, —$SO_2$—, —CH=CH—, —$C(CF_3)$=CH—, CH=$C(CF_3)$—, —$CF_2$—$CH_2$—, —$CH_2$—$CF_2$—, —CHF—$CH_2$—, —$CH_2$—CHF—, —C≡C—, —$CH_2$—O—, —O—$CH_2$—, —O—CO—, —CO—O—, and cyclopropylene;
p is an integer from 0 to 10;
one or more C atoms of $(CH_2)p$ are optionally substituted with one or two fluoro atoms, and T is absent or attached to R4 and selected from the group consisting of a bond, —O—, —S—, —SO—, —SO$_2$—, —CO—, —CH=CH—, —C≡C—, and cyclopropylene, R4 is selected from the group consisting of:
- (C3-6)cycloalkyl, (C4-6)cycloalkenyl or an 8-10 membered bicyclic group, each optionally substituted with a substituent selected from the group consisting of a halogen atom, (C1-4)alkyl optionally substituted with one or more fluoro atoms and (C1-4)alkoxy optionally substituted with one or more fluoro atoms,
- phenyl, biphenyl or naphthyl, pyridyl, thienyl, thiazolyl optionally substituted with one or more substituents independently selected from the group consisting of:
  - a halogen atom,
  - hydroxy,
  - cyano,
  - (C1-4)alkyl optionally substituted with one or more fluoro atoms,
  - (C1-4)alkoxy optionally substituted with one or more fluoro atoms,
  - —S—(C1-4)-alkyl,
  - —SF$_5$, and
  - (C3-6)cycloalkyl optionally substituted with phenyl whereby said phenyl is optionally substituted with a substituent selected from the group consisting of (C1-4)alkyl and a halogen atom, and
- phenyl substituted with a substituent selected from the group consisting of phenoxy, benzyl, benzyloxy, phenylethyl and a monocyclic heterocycle, wherein each substituent is optionally substituted with one or more halogen atoms, (C1-4)alkyl, (C1-4)alkyl substituted with one or more fluoro atoms, (C1-4)alkoxy, or (C1-4)alkoxy substituted with one or more fluoro atoms.

2. The compound of claim 1, wherein R5 is independently selected from the group consisting of hydrogen, a fluoro atom, methyl optionally substituted with one or more fluoro atoms and ethyl optionally substituted with one or more fluoro atoms, and R2 is absent.

3. The compound of claim 1, wherein formula (I) is selected from the group consisting of:

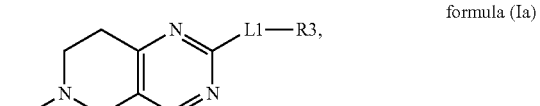

formula (Ia)

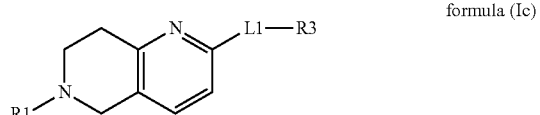

formula (Ic)

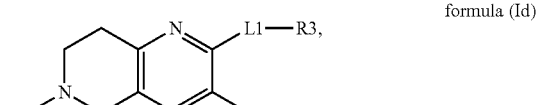

formula (Id)

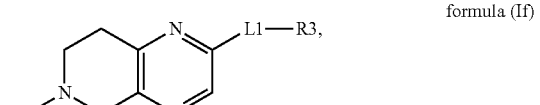

formula (If)

-continued

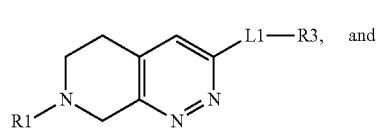

formula (Ih)

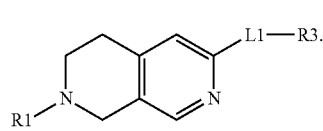

formula (Ij)

4. The compound of claim 1, wherein R1 is selected from the group consisting of —CH$_2$—COOH, —CHCH$_3$—COOH, —(CH$_2$)$_2$—COOH, —(CH$_2$)$_3$—COOH, —(CH$_2$)$_4$—COOH, —(CH$_2$)$_5$—COOH, —CH$_2$—CHCH$_3$—COOH, —CHCH$_3$—CH$_2$—COOH, —CH$_2$—C(CH$_3$)$_2$—COOH, —C(CH$_3$)$_2$—CH$_2$—COOH, —CH$_2$—CHCH$_3$—CH$_2$—COOH, —CH$_2$—C(CH$_3$)$_2$—CH$_2$—COOH, —(CH$_2$)$_2$—CHCH$_3$—COOH, —(CH$_2$)$_2$—C(CH$_3$)$_2$—COOH, —C(CH$_3$)$_2$—(CH$_2$)$_2$—COOH, —CHCH$_3$—(CH$_2$)$_2$—COOH, —CH$_2$—COO(C1-4)alkyl, —(CH$_2$)$_2$—COO(C1-4)alkyl, —(CH$_2$)$_3$—COO(C1-4)alkyl, —CH$_2$—CHCH$_3$—CH$_2$—COO(C1-4)alkyl, —CH$_2$—C(CH$_3$)$_2$—CH$_2$—COO(C1-4)alkyl, —(CH$_2$)$_2$—CHCH$_3$—COO(C1-4)alkyl, —C(CH$_3$)$_2$—(CH$_2$)$_2$—COO(C1-4)alkyl,

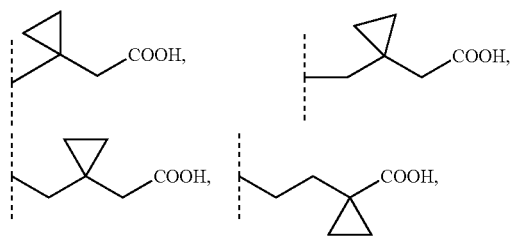

-1,3-cyclobutylene-COOH, -1,3-cyclobutylene-CH$_2$—COOH, —CH$_2$-1,3-cyclobutylene-COOH, -1,3-cyclobutylene-COO(C1-4)alkyl, -1,3-cyclobutylene-CH$_2$—COO(C1-4)alkyl and —CH$_2$-1,3-cyclobutylene-COO(C1-4)alkyl and R2 is absent.

5. The compound of claim 1, wherein L1 is absent or

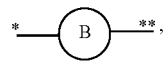

wherein Ring B is selected from the group consisting of cyclobutyl, phenyl and thienyl each optionally substituted with one or more substituents independently selected from the group consisting of
- a halogen atom,
- (C1-4)alkyl optionally substituted with one or more halogen atoms,
- (C1-4)alkoxy optionally substituted with one or more halogen atoms, and
- phenyl optionally substituted with one or more substituents independently selected from the group consisting of a halogen atom, (C1-4)alkyl optionally substituted with one or more halogen atoms; and (C1-4)alkoxy optionally substituted with one or more halogen atoms.

6. The compound of claim 1, wherein W is selected from the group consisting of a bond, —O—, —CO—, —S—, —SO—, —SO₂—, —CH═CH— and —C≡C—, p is an integer from 0-2 and T is a bond.

7. The compound of claim 1, wherein R4 is selected from the group consisting of:
(C3-6)cycloalkyl,
a (C8-10)bicyclic group, and
phenyl, optionally substituted with one or more substituents, independently selected from the group consisting of:
a halogen atom,
hydroxy,
a (C1-4)alkyl group optionally substituted with one or more fluoro atoms,
(C1-4)alkoxy optionally substituted with one or more fluoro atoms, and
—S—CH₃.

8. The compound of claim 1, wherein L2 is absent or selected from the group consisting of —O—CH₂—, —CH₂—, —CH═CH— and —C≡C— and R4 is phenyl optionally substituted with one or more substituents as defined in claim 7.

9. A compound selected from the group consisting of
1-((2-(4-((3-chlorobenzyl)oxy)phenyl)-7,8-dihydropyrido[4,3-d]pyrimidin-6(5H)-yl)methyl)cyclopropanecarboxylic acid;
2-(3-(2-(4-((4-chlorobenzyl)oxy)phenyl)-7,8-dihydropyrido[4,3-d]pyrimidin-6(5H)-yl)cyclobutyl)acetic acid;
2-(3-(2-(4-((3-chlorobenzyl)oxy)phenyl)-7,8-dihydropyrido[4,3-d]pyrimidin-6(5H)-yl)cyclobutyl)acetic acid;
2-(3-(2-(4-((3,4-dichlorobenzyl)oxy)phenyl)-7,8-dihydropyrido[4,3-d]pyrimidin-6(5H)-yl)cyclobutyl)acetic acid;
2-(3-(2-(4-((3,5-dichlorobenzyl)oxy)phenyl)-7,8-dihydropyrido[4,3-d]pyrimidin-6(5H)-yl)cyclobutyl)acetic acid;
3-(2-(4-(benzyloxy)phenyl)-7,8-dihydropyrido[4,3-d]pyrimidin-6(5H)-yl)-2-methylpropanoic acid;
3-(2-(4-(2,6-dichlorobenzyloxy)phenyl)-7,8-dihydropyrido[4,3-d]pyrimidin-6(5H)-yl)-2-methylpropanoic acid;
3-(2-(4-((3-fluorobenzyl)oxy)phenyl)-7,8-dihydropyrido[4,3-d]pyrimidin-6(5H)-yl)-2-methylpropanoic acid;
3-(2-(4-((3,5-difluorobenzyl)oxy)phenyl)-7,8-dihydropyrido[4,3-d]pyrimidin-6(5H)-yl)-2-methylpropanoic acid;
3-(2-(4-((3-chlorobenzyl)oxy)phenyl)-7,8-dihydropyrido[4,3-d]pyrimidin-6(5H)-yl)-2-methylpropanoic acid;
3-(2-(4-((3,4-difluorobenzyl)oxy)phenyl)-7,8-dihydropyrido[4,3-d]pyrimidin-6(5H)-yl)-2-methylpropanoic acid;
3-(2-(4-((4-chlorobenzyl)oxy)phenyl)-7,8-dihydropyrido[4,3-d]pyrimidin-6(5H)-yl)-2-methylpropanoic acid;
3-(2-(4-((3,4-dichlorobenzyl)oxy)phenyl)-7,8-dihydropyrido[4,3-d]pyrimidin-6(5H)-yl)-2-methylpropanoic acid;
3-(2-(4-((2,6-dimethylbenzyl)oxy)phenyl)-7,8-dihydropyrido[4,3-d]pyrimidin-6(5H)-yl)-2-methylpropanoic acid;
3-(2-(4-((2,3-difluorobenzyl)oxy)phenyl)-7,8-dihydropyrido[4,3-d]pyrimidin-6(5H)-yl)-2-methylpropanoic acid;
3-(2-(4-((3,5-dichlorobenzyl)oxy)phenyl)-7,8-dihydropyrido[4,3-d]pyrimidin-6(5H)-yl)-2-methylpropanoic acid;
(+)-3-(2-(4-((3,5-dichlorobenzyl)oxy)phenyl)-7,8-dihydropyrido[4,3-d]pyrimidin-6(5H)-yl)-2-methylpropanoic acid;
(−)-3-(2-(4-((3,5-dichlorobenzyl)oxy)phenyl)-7,8-dihydropyrido[4,3-d]pyrimidin-6(5H)-yl)-2-methylpropanoic acid;
3-(2-(4-((2-chloro-6-ethylbenzyl)oxy)phenyl)-7,8-dihydropyrido[4,3-d]pyrimidin-6(5H)-yl)-2-methylpropanoic acid;
4-(2-(4-(benzyloxy)phenyl)-7,8-dihydropyrido[4,3-d]pyrimidin-6(5H)-yl)-3-methylbutanoic acid;
4-(2-(4-((3-chlorobenzyl)oxy)phenyl)-7,8-dihydropyrido[4,3-d]pyrimidin-6(5H)-yl)-3-methylbutanoic acid;
4-(2-(4-((4-chlorobenzyl)oxy)phenyl)-7,8-dihydropyrido[4,3-d]pyrimidin-6(5H)-yl)-3-methylbutanoic acid;
(+)-4-(2-(4-((4-chlorobenzyl)oxy)phenyl)-7,8-dihydropyrido[4,3-d]pyrimidin-6(5H)-yl)-3-methylbutanoic acid;
(−)-4-(2-(4-((4-chlorobenzyl)oxy)phenyl)-7,8-dihydropyrido[4,3-d]pyrimidin-6(5H)-yl)-3-methylbutanoic acid;
2-(2-benzyl-7,8-dihydropyrido[4,3-d]pyrimidin-6(5H)-yl)acetic acid;
2-(2-(4-(benzyloxy)phenyl)-7,8-dihydropyrido[4,3-d]pyrimidin-6(5H)-yl)acetic acid;
2-(2-(2,6-difluorobenzyl)-7,8-dihydropyrido[4,3-d]pyrimidin-6(5H)-yl)acetic acid;
2-(2-(4-((3-fluorobenzyl)oxy)phenyl)-7,8-dihydropyrido[4,3-d]pyrimidin-6(5H)-yl)acetic acid;
2-(2-(4-((2,3-difluorobenzyl)oxy)phenyl)-7,8-dihydropyrido[4,3-d]pyrimidin-6(5H)-yl)acetic acid;
2-(2-(4-((4-chlorobenzyl)oxy)phenyl)-7,8-dihydropyrido[4,3-d]pyrimidin-6(5H)-yl)acetic acid;
2-(2-(4-((3,4-dichlorobenzyl)oxy)phenyl)-7,8-dihydropyrido[4,3-d]pyrimidin-6(5H)-yl)acetic acid;
2-(2-(4-((3,5-difluorobenzyl)oxy)phenyl)-7,8-dihydropyrido[4,3-d]pyrimidin-6(5H)-yl)acetic acid;
2-(2-(4-((3-chlorobenzyl)oxy)phenyl)-7,8-dihydropyrido[4,3-d]pyrimidin-6(5H)-yl)acetic acid;
2-(2-(4-((2,6-dimethylbenzyl)oxy)phenyl)-7,8-dihydropyrido[4,3-d]pyrimidin-6(5H)-yl)acetic acid;
2-(2-(4-((2,6-dichlorobenzyl)oxy)phenyl)-7,8-dihydropyrido[4,3-d]pyrimidin-6(5H)-yl)acetic acid;
2-(2-(4-((2-chloro-6-ethylbenzyl)oxy)phenyl)-7,8-dihydropyrido[4,3-d]pyrimidin-6(5H)-yl)acetic acid;
3-(2-(4-(benzyloxy)phenyl)-7,8-dihydropyrido[4,3-d]pyrimidin-6(5H)-yl)butanoic acid
4-(2-(4-(benzyloxy)phenyl)-7,8-dihydro-dihydropyrido[4,3-d]pyrimidin-6(5H)-yl)butanoic acid;
4-(2-(4-((3-chlorobenzyl)oxy)phenyl)-7,8-dihydropyrido[4,3-d]pyrimidin-6(5H)-yl)butanoic acid;
4-(2-(4-((4-chlorobenzyl)oxy)phenyl)-7,8-dihydropyrido[4,3-d]pyrimidin-6(5H)-yl)butanoic acid;
3-(2-(4-((3-fluorobenzyl)oxy)phenyl)-7,8-dihydropyrido[4,3-d]pyrimidin-6(5H)-yl)butanoic acid;
3-(2-(4-((3,4-difluorobenzyl)oxy)phenyl)-7,8-dihydropyrido[4,3-d]pyrimidin-6(5H)-yl)butanoic acid;
3-(2-(4-((3-chlorobenzyl)oxy)phenyl)-7,8-dihydropyrido[4,3-d]pyrimidin-6(5H)-yl)butanoic acid;
3-(2-(4-((4-chlorobenzyl)oxy)phenyl)-7,8-dihydropyrido[4,3-d]pyrimidin-6(5H)-yl)butanoic acid;
3-(2-(4-((3,4-dichlorobenzyl)oxy)phenyl)-7,8-dihydropyrido[4,3-d]pyrimidin-6(5H)-yl)butanoic acid;
4-(2-(4-isopropoxyphenyl)-7,8-dihydropyrido[4,3-d]pyrimidin-6(5H)-yl)butanoic acid;
4-(2-(3-chloro-4-isopropoxyphenyl)-7,8-dihydropyrido[4,3-d]pyrimidin-6(5H)-yl)butanoic acid;

4-(2-(phenylethynyl)-7,8-dihydropyrido[4,3-d]pyrimidin-6(5H)-yl)butanoic acid;

4-(2-((2,5-difluorophenyl)ethynyl)-7,8-dihydropyrido[4,3-d]pyrimidin-6(5H)-yl)butanoic acid;

4-(2-benzyl-7,8-dihydropyrido[4,3-d]pyrimidin-6(5H)-yl)butanoic acid;

4-(2-(2,6-difluorobenzyl)-7,8-dihydropyrido[4,3-d]pyrimidin-6(5H)-yl)butanoic acid;

3-(2-(4-((3-fluorobenzyl)oxy)phenyl)-7,8-dihydropyrido[4,3-d]pyrimidin-6(5H)-yl)cyclobutanecarboxylic acid;

3-(2-(2,6-difluorobenzyl)-7,8-dihydropyrido[4,3-d]pyrimidin-6(5H)-yl)cyclobutanecarboxylic acid;

3-(2-((4-chlorophenyl)ethynyl)-7,8-dihydropyrido[4,3-d]pyrimidin-6(5H)-yl)cyclobutanecarboxylic acid;

3-(2-(o-tolylethynyl)-7,8-dihydropyrido[4,3-d]pyrimidin-6(5H)-yl)cyclobutanecarboxylic acid;

3-(2-((4-ethoxyphenyl)ethynyl)-7,8-dihydropyrido[4,3-d]pyrimidin-6(5H)-yl)cyclobutanecarboxylic acid;

3-(2-((4-fluorophenyl)ethynyl)-7,8-dihydropyrido[4,3-d]pyrimidin-6(5H)-yl)cyclobutanecarboxylic acid;

3-(2-((4-isopropylphenyl)ethynyl)-7,8-dihydropyrido[4,3-d]pyrimidin-6(5H)-yl)cyclobutanecarboxylic acid;

3-(2-((4-(benzyloxy)phenyl)ethynyl)-7,8-dihydropyrido[4,3-d]pyrimidin-6(5H)-yl)cyclobutanecarboxylic acid;

3-(2-((2-chlorophenyl)ethynyl)-7,8-dihydropyrido[4,3-d]pyrimidin-6(5H)-yl)cyclobutanecarboxylic acid;

3-(2-((3,5-difluorophenyl)ethynyl)-7,8-dihydropyrido[4,3-d]pyrimidin-6(5H)-yl)cyclobutanecarboxylic acid;

3-(2-((3-chlorophenyl)ethynyl)-7,8-dihydropyrido[4,3-d]pyrimidin-6(5H)-yl)cyclobutanecarboxylic acid;

4-(2-(4-(benzyloxy)phenyl)-7,8-dihydropyrido[4,3-d]pyrimidin-6(5H)-yl)pentanoic acid;

4-(2-(4-((3-chlorobenzyl)oxy)phenyl)-7,8-dihydropyrido[4,3-d]pyrimidin-6(5H)-yl)pentanoic acid;

4-(2-(4-((4-chlorobenzyl)oxy)phenyl)-7,8-dihydropyrido[4,3-d]pyrimidin-6(5H)-yl)pentanoic acid;

3-(2-(4-(benzyloxy)phenyl)-7,8-dihydropyrido[4,3-d]pyrimidin-6(5H)-yl)propanoic acid;

3-(2-(4-((3-fluorobenzyl)oxy)phenyl)-7,8-dihydropyrido[4,3-d]pyrimidin-6(5H)-yl)propanoic acid;

3-(2-(4-((2,3-difluorobenzyl)oxy)phenyl)-7,8-dihydropyrido[4,3-d]pyrimidin-6(5H)-yl)propanoic acid;

3-(2-(4-((2,6-dichlorobenzyl)oxy)phenyl)-7,8-dihydropyrido[4,3-d]pyrimidin-6(5H)-yl)propanoic acid;

3-(2-(4-((3,4-difluorobenzyl)oxy)phenyl)-7,8-dihydropyrido[4,3-d]pyrimidin-6(5H)-yl)propanoic acid;

3-(2-(4-((3-chlorobenzyl)oxy)phenyl)-7,8-dihydropyrido[4,3-d]pyrimidin-6(5H)-yl)propanoic acid;

3-(2-(4-((3,4-dichlorobenzyl)oxy)phenyl)-7,8-dihydropyrido[4,3-d]pyrimidin-6(5H)-yl)propanoic acid;

3-(2-(4-((4-chlorobenzyl)oxy)phenyl)-7,8-dihydropyrido[4,3-d]pyrimidin-6(5H)-yl)propanoic acid;

3-(2-(4-isopropoxyphenyl)-7,8-dihydropyrido[4,3-d]pyrimidin-6(5H)-yl)propanoic acid;

3-(2-(4-((3-difluoromethylbenzyl)oxy)phenyl)-7,8-dihydropyrido[4,3-d]pyrimidin-6(5H)-yl)propanoic acid;

3-(2-(4-((4-difluoromethylbenzyl)oxy)phenyl)-7,8-dihydropyrido[4,3-d]pyrimidin-6(5H)-yl)propanoic acid;

3-(2-(4-((2-difluoromethylbenzyl)oxy)phenyl)-7,8-dihydropyrido[4,3-d]pyrimidin-6(5H)-yl)propanoic acid;

3-(2-(3-chloro-4-isopropoxyphenyl)-7,8-dihydropyrido[4,3-d]pyrimidin-6(5H)-yl)propanoic acid;

3-(2-(4-((4-(methylthio)benzyl)oxy)phenyl)-7,8-dihydropyrido[4,3-d]pyrimidin-6(5H)-yl)propanoic acid;

3-(2-(4-((4-(trifluoromethyl)benzyl)oxy)phenyl)-7,8-dihydropyrido[4,3-d]pyrimidin-6(5H)-yl)propanoic acid;

3-(2-(4-((3-(trifluoromethoxy)benzyl)oxy)phenyl)-7,8-dihydropyrido[4,3-d]pyrimidin-6(5H)-yl)propanoic acid;

3-(2-(4-((4-(difluoromethoxy)benzyl)oxy)phenyl)-7,8-dihydropyrido[4,3-d]pyrimidin-6(5H)-yl)propanoic acid;

3-(2-(4-((2-(trifluoromethoxy)benzyl)oxy)phenyl)-7,8-dihydropyrido[4,3-d]pyrimidin-6(5H)-yl)propanoic acid;

3-(2-(4-((4-(trifluoromethoxy)benzyl)oxy)phenyl)-7,8-dihydropyrido[4,3-d]pyrimidin-6(5H)-yl)propanoic acid;

3-(2-(4-((3-(trifluoromethyl)benzyl)oxy)phenyl)-7,8-dihydropyrido[4,3-d]pyrimidin-6(5H)-yl)propanoic acid;

3-(2-(4-((4-(tert-butyl)benzyl)oxy)phenyl)-7,8-dihydropyrido[4,3-d]pyrimidin-6(5H)-yl)propanoic acid;

3-(2-(4-((2-methyl-5-(trifluoromethyl)benzyl)oxy)phenyl)-7,8-dihydropyrido[4,3-d]pyrimidin-6(5H)-yl)propanoic acid;

3-(2-(4-((4-methyl-3-(trifluoromethyl)benzyl)oxy)phenyl)-7,8-dihydropyrido[4,3-d]pyrimidin-6(5H)-yl)propanoic acid;

3-(2-(4-((2-(difluoromethoxy)benzyl)oxy)phenyl)-7,8-dihydropyrido[4,3-d]pyrimidin-6(5H)-yl)propanoic acid;

3-(2-(4-((5-methyl-2-(trifluoromethyl)benzyl)oxy)phenyl)-7,8-dihydropyrido[4,3-d]pyrimidin-6(5H)-yl)propanoic acid;

3-(2-(4-((3-(difluoromethoxy)benzyl)oxy)phenyl)-7,8-dihydropyrido[4,3-d]pyrimidin-6(5H)-yl)propanoic acid;

3-(2-(4-((2-methyl-4-(trifluoromethoxy)benzyl)oxy)phenyl)-7,8-dihydropyrido[4,3-d]pyrimidin-6(5H)-yl)propanoic acid;

3-(2-(4-((2-methyl-3-(trifluoromethyl)benzyl)oxy)phenyl)-7,8-dihydropyrido[4,3-d]pyrimidin-6(5H)-yl)propanoic acid;

3-(2-(4-((3-methyl-5-(trifluoromethoxy)benzyl)oxy)phenyl)-7,8-dihydropyrido[4,3-d]pyrimidin-6(5H)-yl)propanoic acid;

3-(2-((2-chloro-6-ethylbenzyl)oxy)-7,8-dihydropyrido[4,3-d]pyrimidin-6(5H)-yl)propanoic acid;

3-(2-(4-(benzyloxy)phenyl)-7,8-dihydro-1,6-naphthyridin-6(5H)-yl)-2-methylpropanoic acid;

3-(2-(4-(benzyloxy)-2-fluorophenyl)-7,8-dihydro-1,6-naphthyridin-6(5H)-yl)-2-methylpropanoic acid;

3-(2-(4-(benzyloxy)-3-fluorophenyl)-7,8-dihydro-1,6-naphthyridin-6(5H)-yl)-2-methylpropanoic acid;

3-(2-(4-((4-fluorobenzyl)oxy)-3-chlorophenyl)-7,8-dihydro-1,6-naphthyridin-6(5H)-yl)-2-methylpropanoic acid;

3-(2-(4-((2-fluorobenzyl)oxy)-3-chlorophenyl)-7,8-dihydro-1,6-naphthyridin-6(5H)-yl)-2-methylpropanoic acid;

3-(2-(4-(benzyloxy)-3-chlorophenyl)-7,8-dihydro-1,6-naphthyridin-6(5H)-yl)-2-methylpropanoic acid;

3-(2-(4-(benzyloxyphenyl)-7,8-dihydro-1,6-naphthyridin-6(5H)-yl)-2-methylpropanoic acid;

3-(2-(4-(benzyloxy)-2-chlorophenyl)-7,8-dihydro-1,6-naphthyridin-6(5H)-yl)-2-methylpropanoic acid;

3-(2-(4-((3-fluorobenzyl)oxy)phenyl)-7,8-dihydro-1,6-naphthyridin-6(5H)-yl)-2-methylpropanoic acid;

2-(2-(4-(benzyloxy)-3-methylphenyl)-7,8-dihydro-1,6-naphthyridin-6(5H)-yl)acetic acid;

2-(2-(3-methyl-4-((4-(trifluoromethyl)benzyl)oxy)phenyl)-7,8-dihydro-1,6-naphthyridin-6(5H)-yl)acetic acid;

3-(2-(4-(benzyloxy)phenyl)-7,8-dihydro-1,6-naphthyridin-6(5H)-yl)butanoic acid;
4-(2-(4-(benzyloxy)-3-methylphenyl)-7,8-dihydro-1,6-naphthyridin-6(5H)-yl)butanoic acid;
4-(2-(4-(benzyloxy)phenyl)-7,8-dihydro-1,6-naphthyridin-6(5H)-yl)butanoic acid;
4-(2-(4-((3-fluorobenzyl)oxy)phenyl)-7,8-dihydro-1,6-naphthyridin-6(5H)-yl)butanoic acid;
3-(2-(4-(benzyloxy)-3-methylphenyl)-7,8-dihydro-1,6-naphthyridin-6(5H)-yl)cyclobutanecarboxylic acid;
3-(2-((2-chloro-6-ethylbenzyl)oxy)-7,8-dihydro-1,6-naphthyridin-6(5H)-yl)cyclobutanecarboxylic acid;
3-(2-(phenylethynyl)-7,8-dihydro-1,6-naphthyridin-6(5H)-yl)cyclobutanecarboxylic acid;
3-(2-((4-chlorophenyl)ethynyl)-7,8-dihydro-1,6-naphthyridin-6(5H)-yl)cyclobutanecarboxylic acid;
3-(2-(o-tolylethynyl)-7,8-dihydro-1,6-naphthyridin-6(5H)-yl)cyclobutanecarboxylic acid;
3-(2-((4-ethoxyphenyl)ethynyl)-7,8-dihydro-1,6-naphthyridin-6(5H)-yl)cyclobutanecarboxylic acid;
3-(2-((4-fluorophenyl)ethynyl)-7,8-dihydro-1,6-naphthyridin-6(5H)-yl)cyclobutanecarboxylic acid;
3-(2-((4-isopropylphenyl)ethynyl)-7,8-dihydro-1,6-naphthyridin-6(5H)-yl)cyclobutanecarboxylic acid;
3-(2-((4-(benzyloxy)phenyl)ethynyl)-7,8-dihydro-1,6-naphthyridin-6(5H)-yl)cyclobutanecarboxylic acid;
3-(2-((2-chlorophenyl)ethynyl)-7,8-dihydro-1,6-naphthyridin-6(5H)-yl)cyclobutanecarboxylic acid;
3-(2-((3,5-difluorophenyl)ethynyl)-7,8-dihydro-1,6-naphthyridin-6(5H)-yl)cyclobutanecarboxylic acid;
3-(2-((3-chlorophenyl)ethynyl)-7,8-dihydro-1,6-naphthyridin-6(5H)-yl)cyclobutanecarboxylic acid;
3-(2-(4-(benzyloxy)phenyl)-7,8-dihydro-1,6-naphthyridin-6(5H)-yl)propanoic acid;
3-(2-(4-((2,6-dichlorobenzyl)oxy)phenyl)-7,8-dihydro-1,6-naphthyridin-6(5H)-yl)propanoic acid;
3-(2-(4-((2,3-difluorobenzyl)oxy)phenyl)-7,8-dihydro-1,6-naphthyridin-6(5H)-yl)propanoic acid;
3-(2-(4-((2-fluorobenzyl)oxy)phenyl)-7,8-dihydro-1,6-naphthyridin-6(5H)-yl)propanoic acid;
3-(2-(4-((3-fluorobenzyl)oxy)phenyl)-7,8-dihydro-1,6-naphthyridin-6(5H)-yl)propanoic acid;
3-(2-(4-(benzyloxy)-2-fluorophenyl)-7,8-dihydro-1,6-naphthyridin-6(5H)-yl)propanoic acid;
3-(2-(4-(benzyloxy)-2-methylphenyl)-7,8-dihydro-1,6-naphthyridin-6(5H)-yl)propanoic acid;
3-(2-(4-(benzyloxy)-2-trifluoromethylphenyl)-7,8-dihydro-1,6-naphthyridin-6(5H)-yl)propanoic acid;
3-(2-(4-(benzyloxy)-3-fluorophenyl)-7,8-dihydro-1,6-naphthyridin-6(5H)-yl)propanoic acid;
3-(2-(4-(benzyloxy)-2-methoxyphenyl)-7,8-dihydro-1,6-naphthyridin-6(5H)-yl)propanoic acid;
3-(2-(4-(benzyloxy)-3-methylphenyl)-7,8-dihydro-1,6-naphthyridin-6(5H)-yl)propanoic acid;
3-(2-(3-chloro-4-((4-fluorobenzyl)oxy)phenyl)-7,8-dihydro-1,6-naphthyridin-6(5H)-yl)propanoic acid;
3-(2-(3-chloro-4-((2-fluorobenzyl)oxy)phenyl)-7,8-dihydro-1,6-naphthyridin-6(5H)-yl)propanoic acid;
3-(2-(4-(benzyloxy)-3-methoxyphenyl)-7,8-dihydro-1,6-naphthyridin-6(5H)-yl)propanoic acid;
3-(2-(4-(benzyloxy)-3-trifluoromethylphenyl)-7,8-dihydro-1,6-naphthyridin-6(5H)-yl)propanoic acid;
3-(2-(4-(benzyloxy)-3-chlorophenyl)-7,8-dihydro-1,6-naphthyridin-6(5H)-yl)propanoic acid;
3-(2-(2-fluoro-4-((3-fluorobenzyl)oxy)phenyl)-7,8-dihydro-1,6-naphthyridin-6(5H)-yl)propanoic acid;
3-(2-(4-((4-methylthiobenzyl)oxy)phenyl)-7,8-dihydro-1,6-naphthyridin-6(5H)-yl)propanoic acid;
3-(2-(4-((2-methyl-3-(trifluoromethyl)benzyl)oxy)phenyl)-7,8-dihydro-1,6-naphthyridin-6(5H)-yl)propanoic acid;
3-(2-(4-((4-difluoromethoxybenzyl)oxy)phenyl)-7,8-dihydro-1,6-naphthyridin-6(5H)-yl)propanoic acid;
3-(2-(4-((2-trifluoromethyl-5-(methyl)benzyl)oxy)phenyl)-7,8-dihydro-1,6-naphthyridin-6(5H)-yl)propanoic acid;
3-(2-(4-((2-trifluoromethylbenzyl)oxy)phenyl)-7,8-dihydro-1,6-naphthyridin-6(5H)-yl)propanoic acid;
3-(2-(4-((3-trifluoromethoxybenzyl)oxy)phenyl)-7,8-dihydro-1,6-naphthyridin-6(5H)-yl)propanoic acid;
3-(2-(4-((4-trifluoromethylbenzyl)oxy)phenyl)-7,8-dihydro-1,6-naphthyridin-6(5H)-yl)propanoic acid;
3-(2-(4-((4-trifluoromethoxybenzyl)oxy)phenyl)-7,8-dihydro-1,6-naphthyridin-6(5H)-yl)propanoic acid;
3-(2-(4-((3-trifluoromethyl-4-(methyl)benzyl)oxy)phenyl)-7,8-dihydro-1,6-naphthyridin-6(5H)-yl)propanoic acid;
3-(2-(4-((2-trifluoromethoxybenzyl)oxy)phenyl)-7,8-dihydro-1,6-naphthyridin-6(5H)-yl)propanoic acid;
3-(2-(4-((4-(tert-butyl)benzyl)oxy)phenyl)-7,8-dihydro-1,6-naphthyridin-6(5H)-yl)propanoic acid;
3-(2-(4-((3-trifluoromethylbenzyl)oxy)phenyl)-7,8-dihydro-1,6-naphthyridin-6(5H)-yl)propanoic acid;
3-(2-(4-((2-methyl-5-(trifluoromethyl)benzyl)oxy)phenyl)-7,8-dihydro-1,6-naphthyridin-6(5H)-yl)propanoic acid;
3-(2-(4-((3-difluoromethylbenzyl)oxy)phenyl)-7,8-dihydro-1,6-naphthyridin-6(5H)-yl)propanoic acid;
3-(2-(4-((3-trifluoromethoxy-5-(methyl)benzyl)oxy)phenyl)-7,8-dihydro-1,6-naphthyridin-6(5H)-yl)propanoic acid;
3-(2-(4-((2-methyl-4-(trifluoromethoxy)benzyl)oxy)phenyl)-7,8-dihydro-1,6-naphthyridin-6(5H)-yl)propanoic acid;
3-(2-(4-((5-indanyl)methoxy)phenyl)-7,8-dihydro-1,6-naphthyridin-6(5H)-yl)propanoic acid;
3-(2-(4-((2-difluoromethoxybenzyl)oxy)phenyl)-7,8-dihydro-1,6-naphthyridin-6(5H)-yl)propanoic acid;
3-(2-(4-((3-difluoromethoxybenzyl)oxy)phenyl)-7,8-dihydro-1,6-naphthyridin-6(5H)-yl)propanoic acid;
3-(2-(4-((2-difluoromethylbenzyl)oxy)phenyl)-7,8-dihydro-1,6-naphthyridin-6(5H)-yl)propanoic acid;
3-(2-(4-((4-difluoromethylbenzyl)oxy)phenyl)-7,8-dihydro-1,6-naphthyridin-6(5H)-yl)propanoic acid;
3-(2-(3-methyl-4-((4-(trifluoromethyl)benzyl)oxy)phenyl)-7,8-dihydro-1,6-naphthyridin-6(5H)-yl)propanoic acid;
3-(2-(4-((4-fluorobenzyl)oxy)-3-methylphenyl)-7,8-dihydro-1,6-naphthyridin-6(5H)-yl)propanoic acid;
3-(2-(4-((4-chlorobenzyl)oxy)-3-methylphenyl)-7,8-dihydro-1,6-naphthyridin-6(5H)-yl)propanoic acid;
tert-butyl 3-(2-(4-(benzyloxy)phenyl)-7,8-dihydro-1,6-naphthyridin-6(5H)-yl)propanoate;
3-(6-(4-(benzyloxy)-3-methylphenyl)-3,4-dihydro-2,7-naphthyridin-2(1H)-yl)propanoic acid;
3-(6-(4-((4-chlorobenzyl)oxy)-3-methylphenyl)-3,4-dihydro-2,7-naphthyridin-2(1H)-yl)propanoic acid;
3-(6-(4-((4-trifluoromethylbenzyl)oxy)-3-methylphenyl)-3,4-dihydro-2,7-naphthyridin-2(1H)-yl)propanoic acid;
3-(6-(4-((4-chlorobenzyl)oxy)phenyl)-3,4-dihydro-2,7-naphthyridin-2(1H)-yl)propanoic acid;

3-(6-(4-((3-chlorobenzyl)oxy)phenyl)-3,4-dihydro-2,7-naphthyridin-2(1H)-yl)propanoic acid;

3-(6-(4-((3-fluorobenzyl)oxy)phenyl)-3,4-dihydro-2,7-naphthyridin-2(1H)-yl)propanoic acid;

3-(2-(4-(benzyloxy)phenyl)-7,8-dihydropyrido[3,4-b]pyrazin-6(5H)-yl)propanoic acid;

3-(2-(4-((4-chlorobenzyl)oxy)phenyl)-7,8-dihydropyrido[3,4-b]pyrazin-6(5H)-yl)propanoic acid;

3-(2-(4-((3-chlorobenzyl)oxy)phenyl)-7,8-dihydropyrido[3,4-b]pyrazin-6(5H)-yl)propanoic acid;

4-(2-(4-(benzyloxy)phenyl)-3-fluoro-7,8-dihydro-1,6-naphthyridin-6(5H)-yl)-2-methylbutanoic acid;

4-(2-(4-((4-chlorobenzyl)oxy)phenyl)-3-fluoro-7,8-dihydro-1,6-naphthyridin-6(5H)-yl)-2-methylbutanoic acid;

4-(2-(4-((3-chlorobenzyl)oxy)phenyl)-3-fluoro-7,8-dihydro-1,6-naphthyridin-6(5H)-yl)-2-methylbutanoic acid;

3-(2-((2-chloro-6-ethylbenzyl)oxy)-3-fluoro-7,8-dihydro-1,6-naphthyridin-6(5H)-yl)cyclobutanecarboxylic acid;

3-(3-fluoro-2-(phenylethynyl)-7,8-dihydro-1,6-naphthyridin-6(5H)-yl)cyclobutanecarboxylic acid;

3-(2-(4-(benzyloxy)phenyl)-3-fluoro-7,8-dihydro-1,6-naphthyridin-6(5H)-yl)propanoic acid;

3-(2-(4-((4-chlorobenzyl)oxy)phenyl)-3-fluoro-7,8-dihydrro-1,6-naphthyridin-6(5H)-yl)propanoic acid;

3-(2-(4-((3-chlorobenzyl)oxy)phenyl)-3-fluoro-7,8-dihydrro-1,6-naphthyridin-6(5H)-yl)propanoic acid;

3-(2-(4-((4-fluorobenzyl)oxy)phenyl)-3-fluoro-7,8-dihydro-1,6-naphthyridin-6(5H)-yl)propanoic acid;

3-(2-(4-((4-trifluoromethylbenzyl)oxy)phenyl)-3-fluoro-7,8-dihydro-1,6-naphthyridin-6(5H)-yl)propanoic acid;

3-(2-(4-((2,6-dichlorobenzyl)oxy)phenyl)-3-fluoro-7,8-dihydro-1,6-naphthyridin-6(5H)-yl)propanoic acid 3-(2-(4-((3-fluorobenzyl)oxy)phenyl)-3-fluoro-7,8-dihydro-1,6-naphthyridin-6(5H)-yl)propanoic acid;

3-(2-(4-((3-trifluoromethylbenzyl)oxy)phenyl)-3-fluoro-7,8-dihydro-1,6-naphthyridin-6(5H)-yl)propanoic acid;

3-(2-(4-((2-chloro-6-ethylbenzyl)oxy)phenyl)-3-fluoro-7,8-dihydro-1,6-naphthyridin-6(5H)-yl)propanoic acid;

3-(2-(4-((2,3-difluorobenzyl)oxy)phenyl)-3-fluoro-7,8-dihydro-1,6-naphthyridin-6(5H)-yl)propanoic acid;

3-(2-(4-((3,4-difluorobenzyl)oxy)phenyl)-3-fluoro-7,8-dihydro-1,6-naphthyridin-6(5H)-yl)propanoic acid;

3-(3-(4-(benzyloxy)phenyl)-5,6-dihydropyrido[3,4-c]pyridazin-7(8H)-yl)-2-methylpropanoic acid;

3-(3-(4-(benzyloxy)phenyl)-5,6-dihydropyrido[3,4-c]pyridazin-7(8H)-yl)propanoic acid;

3-(2-(3-(benzyloxy)phenyl)-7,8-dihydropyrido[3,4-b]pyrazin-6(5H)-yl)cyclobutanecarboxylic acid;

4-(2-(4-((3-chlorobenzyl)oxy)phenyl)-7,8-dihydropyrido[3,4-b]pyrazin-6(5H)-yl)-3-methylbutanoic acid;

4-(2-(4-((4-chlorobenzyl)oxy)phenyl)-7,8-dihydropyrido[4,3-d]pyrimidin-6(5H)-yl)-3,3-dimethylbutanoic acid;

4-(2-(4-((3-chlorobenzyl)oxy)phenyl)-7,8-dihydropyrido[3,4-b]pyrazin-6(5H)-yl)-3,3-dimethylbutanoic acid;

4-(2-(4-benzylphenyl)-7,8-dihydropyrido[4,3-d]pyrimidin-6(5H)-yl)pentanoic acid;

1-((2-(4-((4-chlorobenzyl)oxy)phenyl)-7,8-dihydropyrido[4,3-d]pyrimidin-6(5H)-yl)methyl)cyclopropanecarboxylic acid;

4-(2-(4-((3-chlorobenzyl)oxy)phenyl)-7,8-dihydropyrido[4,3-d]pyrimidin-6(5H)-yl)-3,3-dimethylbutanoic acid;

4-(2-(4-((3,4-dichlorobenzyl)oxy)phenyl)-7,8-dihydropyrido[4,3-d]pyrimidin-6(5H)-yl)-3,3-dimethylbutanoic acid;

1-((2-(4-benzylphenyl)-7,8-dihydropyrido[4,3-d]pyrimidin-6(5H)-yl)methyl)cyclopropanecarboxylic acid;

3-(6-((2,6-dichlorobenzyl)oxy)-3,4-dihydro-2,7-naphthyridin-2(1H)-yl)propanoic acid;

4-(2-(4-((4-fluorobenzyl)oxy)phenyl)-7,8-dihydropyrido[4,3-d]pyrimidin-6(5H)-yl)-3-methylbutanoic acid;

4-[2-4-[(2,3-difluorophenyl)methoxy]phenyl]-7,8-dihydro-5H-pyrido[4,3-d]pyrimidin-6-yl]-3-methyl-butanoic acid;

4-(2-(4-((3-fluorobenzyl)oxy)phenyl)-7,8-dihydropyrido[4,3-d]pyrimidin-6(5H)-yl)-3-methylbutanoic acid;

4-(2-(4-((3,4-difluorobenzyl)oxy)phenyl)-7,8-dihydropyrido[4,3-d]pyrimidin-6(5H)-yl)-3-methylbutanoic acid;

4-[2-4-[(2-chlorophenyl)methoxy]phenyl]-7,8-dihydro-5H-pyrido[4,3-d]pyrimidin-6-yl]-3-methyl-butanoic acid;

3-methyl-4-(2-(4-((3-methylbenzyl)oxy)phenyl)-7,8-dihydropyrido[4,3-d]pyrimidin-6(5H)-yl)butanoic acid;

4-[2-4-[(2,3-dimethylphenyl)methoxy]-2-fluoro-phenyl]-7,8-dihydro-5H-pyrido[4,3-d]pyrimidin-6-yl]-3-methyl-butanoic acid;

4-(2-(4-((3-chlorobenzyl)oxy)-2-fluorophenyl)-7,8-dihydropyrido[4,3-d]pyrimidin-6(5H)-yl)-3-methylbutanoic acid;

3-methyl-4-(2-(4-((4-(trifluoromethyl)benzyl)oxy)phenyl)-7,8-dihydropyrido[4,3-d]pyrimidin-6(5H)-yl)butanoic acid;

3-methyl-4-[2-[4-(o-tolylmethoxy)phenyl]-7,8-dihydro-5H-pyrido[4,3-d]pyrimidin-6-yl]butanoic acid;

4-[2-[4-[(2-fluorophenyl)methoxy]phenyl]-7,8-dihydro-5H-pyrido[4,3-d]pyrimidin-6-yl]-3-methyl-butanoic acid;

4-(2-(4-((4-chlorobenzyl)oxy)-2-fluorophenyl)-7,8-dihydropyrido[4,3-d]pyrimidin-6(5H)-yl)-3-methylbutanoic acid;

3-methyl-4-(2-(4-((3-(trifluoromethyl)benzyl)oxy)phenyl)-7,8-dihydropyrido[4,3-d]pyrimidin-6(5H)-yl)butanoic acid;

3-methyl-4-(2-(3-methyl-4-((2-methylbenzyl)oxy)phenyl)-7,8-dihydropyrido[4,3-d]pyrimidin-6(5H)-yl)butanoic acid;

(+)-3-methyl-4-(2-(3-methyl-4-((2-methylbenzyl)oxy)phenyl)-7,8-dihydropyrido[4,3-d]pyrimidin-6(5H)-yl)butanoic acid;

(−)-3-methyl-4-(2-(3-methyl-4-((2-methylbenzyl)oxy)phenyl)-7,8-dihydropyrido[4,3-d]pyrimidin-6(5H)-yl)butanoic acid;

4-[2-[4-[(2,6-difluorophenyl)methoxy]-2-fluoro-phenyl]-7,8-dihydro-5H-pyrido[4,3-d]pyrimidin-6-yl]-3-methyl-butanoic acid;

4-[2-[2-fluoro-4-[[2-methyl-3-(trifluoromethyl)phenyl]methoxy]phenyl]-7,8-dihydro-5H-pyrido[4,3-d]pyrimidin-6-yl]-3-methyl-butanoic acid;

4-[2-[2-fluoro-4-[(2-fluorophenyl)methoxy]phenyl]-7,8-dihydro-5H-pyrido[4,3-d]pyrimidin-6-yl]-3-methyl-butanoic acid;

4-[2-[4-[(2,6-dichlorophenyl)methoxy]phenyl]-7,8-dihydro-5H-pyrido[4,3-d]pyrimidin-6-yl]-3-methyl-butanoic acid;

4-(2-(4-(4-chlorophenethyl)phenyl)-7,8-dihydropyrido[4,3-d]pyrimidin-6(5H)-yl)-3-methylbutanoic acid;

(+)-4-(2-(4-(4-chlorophenethyl)phenyl)-7,8-dihydropyrido[4,3-d]pyrimidin-6(5H)-yl)-3-methylbutanoic acid;

(−)-4-(2-(4-(4-chlorophenethyl)phenyl)-7,8-dihydropyrido[4,3-d]pyrimidin-6(5H)-yl)-3-methylbutanoic acid;

3-methyl-4-[2-[4-[[2-methyl-3-(trifluoromethyl)phenyl]methoxy]phenyl]-7,8-dihydro-5H-pyrido[4,3-d]pyrimidin-6-yl]butanoic acid;

3-methyl-4-[2-[4-[[4-methyl-3-(trifluoromethyl)phenyl]methoxy]phenyl]-7,8-dihydro-5H-pyrido[4,3-d]pyrimidin-6-yl]butanoic acid;

3-methyl-4-(2-(4-((4-methylbenzyl)oxy)phenyl)-7,8-dihydropyrido[4,3-d]pyrimidin-6(5H)-yl)butanoic acid;

4-(2-(4-(4-chloro-2-fluorophenethyl)phenyl)-7,8-dihydropyrido[4,3-d]pyrimidin-6(5H)-yl)-3-methylbutanoic acid;

4-(2-(4-(benzyloxy)-3-methylphenyl)-7,8-dihydropyrido[4,3-d]pyrimidin-6(5H)-yl)-3-methylbutanoic acid;

(+)-4-(2-(4-(benzyloxy)-3-methylphenyl)-7,8-dihydropyrido[4,3-d]pyrimidin-6(5H)-yl)-3-methylbutanoic acid;

(−)-4-(2-(4-(benzyloxy)-3-methylphenyl)-7,8-dihydropyrido[4,3-d]pyrimidin-6(5H)-yl)-3-methylbutanoic acid;

4-(2-(4-((3-chlorobenzyl)oxy)-3-methylphenyl)-7,8-dihydropyrido[4,3-d]pyrimidin-6(5H)-yl)-3-methylbutanoic acid;

4-(2-(4-(2-(4-chloro-2-fluorophenyl)-1-fluoroethyl)phenyl)-7,8-dihydropyrido[4,3-d]pyrimidin-6(5H)-yl)-3-methylbutanoic acid;

3-methyl-4-[2-[4-[[2-(trifluoromethyl)phenyl]methoxy]phenyl]-7,8-dihydro-5H-pyrido[4,3-d]pyrimidin-6-yl]butanoic acid;

4-(2-(4-(4-chlorophenethyl)-2-fluorophenyl)-7,8-dihydropyrido[4,3-d]pyrimidin-6(5H)-yl)-3-methylbutanoic acid;

4-(2-(4-((2,3-difluorobenzyl)oxy)-3-methylphenyl)-7,8-dihydropyrido[4,3-d]pyrimidin-6(5H)-yl)-3-methylbutanoic acid;

3-methyl-4-[2-[4-[(4-methylsulfanylphenyl)methoxy]phenyl]-7,8-dihydro-5H-pyrido[4,3-d]pyrimidin-6-yl]butanoic acid;

4-(2-(4-((4-chlorobenzyl)oxy)-3-methylphenyl)-7,8-dihydropyrido[4,3-d]pyrimidin-6(5H)-yl)-3-methylbutanoic acid;

(+)-4-(2-(4-((4-chlorobenzyl)oxy)-3-methylphenyl)-7,8-dihydropyrido[4,3-d]pyrimidin-6(5H)-yl)-3-methylbutanoic acid;

(−)-4-(2-(4-((4-chlorobenzyl)oxy)-3-methylphenyl)-7,8-dihydropyrido[4,3-d]pyrimidin-6(5H)-yl)-3-methylbutanoic acid;

4-(2-(4-((4-chlorobenzyl)oxy)phenyl)-7,8-dihydropyrido[4,3-d]pyrimidin-6(5H)-yl)-3-methylbutanoic acid;

4-[2-[2-fluoro-4-[[2-(trifluoromethyl)phenyl]methoxy]phenyl]-7,8-dihydro-5H-pyrido[4,3-d]pyrimidin-6-yl]-3-methyl-butanoic acid;

4-(2-(4-((2-chlorobenzyl)oxy)-3-methylphenyl)-7,8-dihydropyrido[4,3-d]pyrimidin-6(5H)-yl)-3-methylbutanoic acid;

4-[2-[2-fluoro-4-[[4-(trifluoromethyl)phenyl]methoxy]phenyl]-7,8-dihydro-5H-pyrido[4,3-d]pyrimidin-6-yl]-3-methyl-butanoic acid;

4-[2-[2-fluoro-4-(m-tolylmethoxy)phenyl]-7,8-dihydro-5H-pyrido[4,3-d]pyrimidin-6-yl]-3-methyl-butanoic acid;

4-(2-(4-(2-(4-chlorophenyl)-1,1-difluoroethyl)phenyl)-7,8-dihydropyrido[4,3-d]pyrimidin-6(5H)-yl)-3-methylbutanoic acid;

(+)-4-(2-(4-(2-(4-chlorophenyl)-1,1-difluoroethyl)phenyl)-7,8-dihydropyrido[4,3-d]pyrimidin-6(5H)-yl)-3-methylbutanoic acid;

(−)-4-(2-(4-(2-(4-chlorophenyl)-1,1-difluoroethyl)phenyl)-7,8-dihydropyrido[4,3-d]pyrimidin-6(5H)-yl)-3-methylbutanoic acid;

4-(2-(4-((4-chlorobenzyl)oxy)phenyl)-5-oxo-7,8-dihydropyrido[4,3-d]pyrimidin-6(5H)-yl)-3-methylbutanoic acid;

4-[2-[4-[(2,3-dichlorophenyl)methoxy]phenyl]-7,8-dihydro-5H-pyrido[4,3-d]pyrimidin-6-yl]-3-methyl-butanoic acid;

4-[2-[4-[(4-fluorophenyl)methoxy]-3-methyl-phenyl]-7,8-dihydro-5H-pyrido[4,3-d]pyrimidin-6-yl]-3-methyl-butanoic acid;

4-[2-[4-[(3,4-dichlorophenyl)methoxy]-2-fluoro-phenyl]-7,8-dihydro-5H-pyrido[4,3-d]pyrimidin-6-yl]-3-methyl-butanoic acid;

4-[2-[2-fluoro-4-[[2-methyl-5-(trifluoromethyl)phenyl]methoxy]phenyl]-7,8-dihydro-5H-pyrido[4,3-d]pyrimidin-6-yl]-3-methyl-butanoic acid;

3-methyl-4-(2-(3-methyl-4-((2-methyl-3-(trifluoromethyl)benzyl)oxy)phenyl)-7,8-dihydropyrido[4,3-d]pyrimidin-6(5H)-yl)butanoic acid;

4-[2-[4-[(2,6-dimethylphenyl)methoxy]-3-methyl-phenyl]-7,8-dihydro-5H-pyrido[4,3-d]pyrimidin-6-yl]-3-methyl-butanoic acid;

3-methyl-4-[2-[4-[[5-methyl-2-(trifluoromethyl)phenyl]methoxy]phenyl]-7,8-dihydro-5H-pyrido[4,3-d]pyrimidin-6-yl]butanoic acid;

4-[2-[4-[(2,6-dimethylphenyl)methoxy]-2-fluoro-phenyl]-7,8-dihydro-5H-pyrido[4,3-d]pyrimidin-6-yl]-3-methyl-butanoic acid;

4-(2-(4-(2-(4-chloro-2-fluorophenyl)-1,1-difluoroethyl)phenyl)-7,8-dihydropyrido[4,3-d]pyrimidin-6(5H)-yl)-3-methylbutanoic acid;

4-[2-[2-fluoro-4-[[4-methyl-3-(trifluoromethyl)phenyl]methoxy]phenyl]-7,8-dihydro-5H-pyrido[4,3-d]pyrimidin-6-yl]-3-methyl-butanoic acid;

4-(2-(2-fluoro-4-phenethylphenyl)-7,8-dihydropyrido[4,3-d]pyrimidin-6(5H)-yl)-3-methylbutanoic acid;

2-(1-((2-(4-((4-chlorobenzyl)oxy)phenyl)-7,8-dihydropyrido[4,3-d]pyrimidin-6(5H)-yl)methyl)cyclopropyl)acetic acid;

4-(2-(4-(4-chloro-2-fluorostyryl)phenyl)-7,8-dihydropyrido[4,3-d]pyrimidin-6(5H)-yl)-3-methylbutanoic acid;

4-[2-[4-[(4-tert-butylphenyl)methoxy]-2-fluoro-phenyl]-7,8-dihydro-5H-pyrido[4,3-d]pyrimidin-6-yl]-3-methyl-butanoic acid;

4-[2-[4-[(2-chlorophenyl)methoxy]-2-fluoro-phenyl]-7,8-dihydro-5H-pyrido[4,3-d]pyrimidin-6-yl]-3-methyl-butanoic acid;

2-(1-((2-(4-((3-chlorobenzyl)oxy)phenyl)-7,8-dihydropyrido[4,3-d]pyrimidin-6(5H)-yl)methyl)cyclopropyl)acetic acid;

2-(1-((2-(4-((4-chlorobenzyl)oxy)phenyl)-7,8-dihydropyrido[4,3-d]pyrimidin-6(5H)-yl)methyl)cyclopropyl)acetic acid;

3-(2-(4-((4-chlorobenzyl)oxy)phenyl)-7,8-dihydropyrido[4,3-d]pyrimidin-6(5H)-yl)cyclobutanecarboxylic acid;

3-(2-(4-((3-chlorobenzyl)oxy)phenyl)-7,8-dihydropyrido[4,3-d]pyrimidin-6(5H)-yl)cyclopentanecarboxylic acid;

4-[2-[2-fluoro-4-[(3-fluorophenyl)methoxy]phenyl]-7,8-dihydro-5H-pyrido[4,3-d]pyrimidin-6-yl]-3-methyl-butanoic acid;

4-[2-[2-fluoro-4-[[5-methyl-2-(trifluoromethyl)phenyl]methoxy]phenyl]-7,8-dihydro-5H-pyrido[4,3-d]pyrimidin-6-yl]-3-methyl-butanoic acid;

4-(2-(4-(4-chlorophenethyl)-3-methylphenyl)-7,8-dihydropyrido[4,3-d]pyrimidin-6(5H)-yl)-3-methylbutanoic acid;

4-(2-(4-(3-chlorophenethyl)-2-fluorophenyl)-7,8-dihydropyrido[4,3-d]pyrimidin-6(5H)-yl)-3-methylbutanoic acid;

4-(2-(4-(2-(3-chlorophenyl)cyclopropyl)phenyl)-7,8-dihydropyrido[4,3-d]pyrimidin-6(5H)-yl)-3-methylbutanoic acid;

3-(2-(4-((4-chlorobenzyl)oxy)phenyl)-7,8-dihydropyrido[4,3-d]pyrimidin-6(5H)-yl)cyclopentanecarboxylic acid;

4-[2-[4-[(2-ethylphenyl)methoxy]-2-fluoro-phenyl]-7,8-dihydro-5H-pyrido[4,3-d]pyrimidin-6-yl]-3-methyl-butanoic acid;

4-(2-(4-(4-chlorostyryl)phenyl)-7,8-dihydropyrido[4,3-d]pyrimidin-6(5H)-yl)-3-methylbutanoic acid;

4-[2-[2-fluoro-4-[(4-fluorophenyl)methoxy]phenyl]-7,8-dihydro-5H-pyrido[4,3-d]pyrimidin-6-yl]-3-methyl-butanoic acid;

2-(2-(4-((3,5-difluorobenzyl)oxy)phenyl)-7,8-dihydropyrido[4,3-d]pyrimidin-6(5H)-yl)propanoic acid;

4-[2-[4-[(2,3-dimethylphenyl)methoxy]-3-methyl-phenyl]-7,8-dihydro-5H-pyrido[4,3-d]pyrimidin-6-yl]-3-methyl-butanoic acid;

3-methyl-4-[2-[3-methyl-4-(p-tolylmethoxy)phenyl]-7,8-dihydro-5H-pyrido[4,3-d]pyrimidin-6-yl]butanoic acid;

3-methyl-4-[2-[3-methyl-4-[[3-(trifluoromethyl)phenyl]methoxy]phenyl]-7,8-dihydro-5H-pyrido[4,3-d]pyrimidin-6-yl]butanoic acid;

4-[2-[4-[(2,4-dimethylphenyl)methoxy]-2-fluoro-phenyl]-7,8-dihydro-5H-pyrido[4,3-d]pyrimidin-6-yl]-3-methyl-butanoic acid;

4-[2-[4-[(2,4-dimethylphenyl)methoxy]-3-methyl-phenyl]-7,8-dihydro-5H-pyrido[4,3-d]pyrimidin-6-yl]-3-methyl-butanoic acid;

4-[2-[4-[(4-ethylphenyl)methoxy]-3-methyl-phenyl]-7,8-dihydro-5H-pyrido[4,3-d]pyrimidin-6-yl]-3-methyl-butanoic acid;

4-[2-[2-fluoro-4-(p-tolylmethoxy)phenyl]-7,8-dihydro-5H-pyrido[4,3-d]pyrimidin-6-yl]-3-methyl-butanoic acid;

4-[2-[4-[(2-ethylphenyl)methoxy]-3-methyl-phenyl]-7,8-dihydro-5H-pyrido[4,3-d]pyrimidin-6-yl]-3-methyl-butanoic acid;

3-methyl-4-[2-[3-methyl-4-[[2-(trifluoromethyl)phenyl]methoxy]phenyl]-7,8-dihydro-5H-pyrido[4,3-d]pyrimidin-6-yl]butanoic acid;

4-[2-[4-[(4-isopropylphenyl)methoxy]-3-methyl-phenyl]-7,8-dihydro-5H-pyrido[4,3-d]pyrimidin-6-yl]-3-methyl-butanoic acid;

4-[2-[4-[(2,5-dimethylphenyl)methoxy]-3-methyl-phenyl]-7,8-dihydro-5H-pyrido[4,3-d]pyrimidin-6-yl]-3-methyl-butanoic acid;

2-(2-(4-((4-chlorobenzyl)oxy)phenyl)-7,8-dihydropyrido[4,3-d]pyrimidin-6(5H)-yl)propanoic acid;

4-[2-[4-[(3,5-dimethylphenyl)methoxy]-2-fluoro-phenyl]-7,8-dihydro-5H-pyrido[4,3-d]pyrimidin-6-yl]-3-methyl-butanoic acid;

3-methyl-4-[2-[3-methyl-4-[[2-methyl-5-(trifluoromethyl)phenyl]methoxy]phenyl]-7,8-dihydro-5H-pyrido[4,3-d]pyrimidin-6-yl]butanoic acid;

4-(2-(4-((4-chlorobenzyl)oxy)phenyl)-7,8-dihydropyrido[4,3-d]pyrimidin-6(5H)-yl)-3-methylbutan-1-ol;

4-[2-[4-[(2,6-difluorophenyl)methoxy]-3-methyl-phenyl]-7,8-dihydro-5H-pyrido[4,3-d]pyrimidin-6-yl]-3-methyl-butanoic acid;

2-(2-(4-((3-chlorobenzyl)oxy)phenyl)-7,8-dihydropyrido[4,3-d]pyrimidin-6(5H)-yl)propanoic acid;

3-methyl-4-[2-[3-methyl-4-(m-tolylmethoxy)phenyl]-7,8-dihydro-5H-pyrido[4,3-d]pyrimidin-6-yl]butanoic acid;

2-(2-(4-(benzyloxy)phenyl)-7,8-dihydropyrido[4,3-d]pyrimidin-6(5H)-yl)propanoic acid;

4-(2-(4-(2-(4-chlorophenyl)cyclopropyl)phenyl)-7,8-dihydropyrido[4,3-d]pyrimidin-6(5H)-yl)-3-methylbutanoic acid;

4-(2-(4-(4-chlorophenethyl)phenyl)-7,8-dihydropyrido[4,3-d]pyrimidin-6(5H)-yl)-3-methylbutan-1-ol;

2-(1-((2-(4-((3-chlorobenzyl)oxy)phenyl)-7,8-dihydropyrido[4,3-d]pyrimidin-6(5H)-yl)methyl)cyclopropyl)acetic acid;

4-(2-(4-(2-(3-chlorophenyl)-1,1-difluoroethyl)phenyl)-7,8-dihydropyrido[4,3-d]pyrimidin-6(5H)-yl)-3-methylbutanoic acid;

4-(2-(4-((4-chlorobenzyl)oxy)phenyl)-7,7-dimethyl-7,8-dihydropyrido[4,3-d]pyrimidin-6(5H)-yl)-3-methylbutanoic acid;

4-(2-(4-(3-chlorophenethyl)-3-methylphenyl)-7,8-dihydropyrido[4,3-d]pyrimidin-6(5H)-yl)-3-methylbutanoic acid;

4-(2-(4-((4-chlorobenzyl)oxy)phenyl)-7,8-dihydropyrido[4,3-d]pyrimidin-6(5H)-yl)-3-methyl-4-oxobutanoic acid;

4-(2-(3-(benzyloxy)cyclobutyl)-7,8-dihydropyrido[4,3-d]pyrimidin-6(5H)-yl)-3-methylbutanoic acid;

1-(2-(2-(4-((4-chlorobenzyl)oxy)phenyl)-7,8-dihydropyrido[4,3-d]pyrimidin-6(5H)-yl)ethyl)cyclopropanecarboxylic acid; and 4-(2-(4-(cyclohexylmethoxy)phenyl)-7,8-dihydropyrido[4,3-d]pyrimidin-6(5H)-yl)-3-methylbutanoic acid, or a pharmaceutically acceptable salt thereof.

10. 4-(2-(4((4-chlorobenzyl)oxy)phenyl)-7,8-dihydropyrido[4,3-d]pyrimidin-6(5H)-yl )-3-methylbutanoic acid, or a pharmaceutically acceptable salt thereof.

11. 4-(2-(4-(4-chlorophenethyl)phenyl)-7,8-dihydropyrido[4,3-d]pyrimidin-6(5H)-yl)-3-methylbutanoic acid, or a pharmaceutically acceptable salt thereof.

12. 4-[2-[4-[(2,3-difluorophenyl)methoxy]phenyl]-7,8-dihydro-5H-pyrido[4,3-d]pyrimidin-6-yl]-3-methyl-butanoic acid, or a pharmaceutically acceptable salt thereof.

* * * * *